(12) United States Patent
Birch et al.

(10) Patent No.: US 7,795,283 B2
(45) Date of Patent: *Sep. 14, 2010

(54) OXADIAZOLE DERIVATIVE AS DGAT INHIBITORS

(75) Inventors: Alan Martin Birch, Cheshire (GB); Suzanne Saxon Bowker, Cheshire (GB); Roger John Butlin, Cheshire (GB); Craig Samuel Donald, Cheshire (GB); William McCoull, Cheshire (GB); Thorsten Nowak, Cheshire (GB); Alleyn Plowright, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/792,922

(22) PCT Filed: Dec. 9, 2005

(86) PCT No.: PCT/GB2005/004726

§ 371 (c)(1),
(2), (4) Date: Jun. 13, 2007

(87) PCT Pub. No.: WO2006/064189

PCT Pub. Date: Jun. 22, 2006

(65) Prior Publication Data

US 2008/0096874 A1  Apr. 24, 2008

(30) Foreign Application Priority Data

Dec. 14, 2004 (GB) .................... 0427328.0
Apr. 13, 2005 (GB) .................... 0507403.4
Oct. 7, 2005 (GB) .................... 0520383.1

(51) Int. Cl.
*A61K 31/4245* (2006.01)
*C07D 271/113* (2006.01)

(52) U.S. Cl. ..................... 514/364; 548/143
(58) Field of Classification Search ............ 548/143; 514/364
See application file for complete search history.

(56) References Cited

U.S. PATENT DOCUMENTS

| | | | |
|---|---|---|---|
| 4,983,731 A | 1/1991 | Wagner et al. | |
| 5,491,172 A | 2/1996 | Lee et al. | |
| 6,608,185 B1 | 8/2003 | Omura et al. | |
| 6,624,185 B2 | 9/2003 | Glombik et al. | |
| 7,138,414 B2 | 11/2006 | Schoenafinger et al. | |
| 7,453,010 B2 | 11/2008 | Bovy et al. | |
| 2002/0183384 A1 | 12/2002 | Cornicelli et al. | |
| 2003/0072757 A1 | 4/2003 | Farese et al. | |
| 2004/0102432 A1* | 5/2004 | Sanganee et al. | 514/210.2 |
| 2005/0070545 A1 | 3/2005 | Fox et al. | |
| 2007/0123504 A1 | 5/2007 | Bolin et al. | |
| 2007/0155832 A1 | 7/2007 | Haeberlein et al. | |
| 2007/0249620 A1 | 10/2007 | Kurata et al. | |
| 2008/0090876 A1 | 4/2008 | Cheng et al. | |
| 2008/0306059 A1 | 12/2008 | Birch et al. | |
| 2009/0048258 A1 | 2/2009 | Ogino et al. | |
| 2009/0093497 A1 | 4/2009 | Bolin et al. | |
| 2009/0197926 A1 | 8/2009 | Birch et al. | |
| 2009/0209602 A1 | 8/2009 | Butlin et al. | |
| 2009/0215779 A1 | 8/2009 | Butlin et al. | |

FOREIGN PATENT DOCUMENTS

| | | |
|---|---|---|
| DE | 10223273 | 12/2003 |
| EP | 1236468 | 9/2002 |
| JP | 2004/067635 | 3/2004 |
| JP | 2005/206492 | 8/2005 |
| JP | 2007/131584 | 5/2007 |
| JP | 2007/191471 | 8/2007 |
| WO | WO 94/26702 | 11/1994 |
| WO | WO 00/58491 | 10/2000 |
| WO | WO 02/20484 | 3/2002 |
| WO | WO 03/099772 | 12/2003 |
| WO | WO 2004/007455 | 1/2004 |
| WO | WO 2004/047755 | 6/2004 |
| WO | WO 2004/100881 | 11/2004 |
| WO | WO 2005/013907 | 2/2005 |
| WO | WO 2005/044250 | 5/2005 |
| WO | WO 2005/046670 | 5/2005 |
| WO | WO 2005/072740 | 8/2005 |
| WO | WO 2006/004200 | 1/2006 |

(Continued)

OTHER PUBLICATIONS

RN 404032-15-1, retrieved from CAPLUS on Jul. 17, 2009.*

(Continued)

*Primary Examiner*—Rebecca L Anderson
*Assistant Examiner*—Shawquia Young
(74) *Attorney, Agent, or Firm*—Morgan Lewis & Bockius LLP

(57) ABSTRACT

Compounds of formula (I), and salts and pro-drugs thereof: Formula (I) wherein for example $R^1$ is optionally substituted aryl or heteroaryl; Y is a linking group selected from, for example, a direct bond, and a (substituted) alkyl chain; $R^2$ is an optionally substituted aryl, an optionally substituted cycloalkyl or an optionally substituted heterocyclic group; are described. Processes to make such compounds and their use as DGAT inhibitors, for example in the treatment of obesity, are also described.

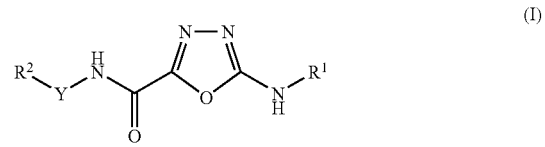

6 Claims, No Drawings

FOREIGN PATENT DOCUMENTS

| | | |
|---|---|---|
| WO | WO 2006/019020 | 2/2006 |
| WO | WO 2006/044775 | 4/2006 |
| WO | WO 2006/082010 | 8/2006 |
| WO | WO 2006/082952 | 8/2006 |
| WO | WO 2006/113919 | 10/2006 |
| WO | WO 2006/120125 | 11/2006 |
| WO | WO 2006/134317 | 12/2006 |
| WO | WO 2007/016538 | 2/2007 |
| WO | WO 2007/060140 | 5/2007 |
| WO | WO 2007/071966 | 6/2007 |
| WO | WO 2007/126957 | 11/2007 |
| WO | WO 2007/137103 | 11/2007 |
| WO | WO 2007/137107 | 11/2007 |
| WO | WO 2007/138304 | 12/2007 |
| WO | WO 2007/138311 | 12/2007 |
| WO | WO 2007/141502 | 12/2007 |
| WO | WO 2007/141517 | 12/2007 |
| WO | WO 2007/141538 | 12/2007 |
| WO | WO 2007/141545 | 12/2007 |
| WO | WO 2007/144571 | 12/2007 |
| WO | WO 2008/011130 | 1/2008 |
| WO | WO 2008/011131 | 1/2008 |
| WO | WO 2008/039007 | 4/2008 |
| WO | WO 2008/039008 | 4/2008 |
| WO | WO 2008/040651 | 4/2008 |
| WO | WO 2008/048991 | 4/2008 |
| WO | WO 2008/067257 | 6/2008 |
| WO | WO 2008/099221 | 8/2008 |
| WO | WO 2008/129319 | 10/2008 |
| WO | WO 2008/134690 | 11/2008 |
| WO | WO 2008/134693 | 11/2008 |
| WO | WO 2008/141976 | 11/2008 |
| WO | WO 2008/148840 | 12/2008 |
| WO | WO 2008/148849 | 12/2008 |
| WO | WO 2008/148851 | 12/2008 |
| WO | WO 2008/148868 | 12/2008 |
| WO | WO 2009/011285 | 1/2009 |
| WO | WO 2009/016462 | 2/2009 |
| WO | WO 2009/024821 | 2/2009 |
| WO | WO 2009/037222 | 3/2009 |
| WO | WO 2009/040410 | 4/2009 |
| WO | WO 2009/071483 | 6/2009 |
| WO | WO 2009/081195 | 7/2009 |
| WO | WO 2009/112445 | 9/2009 |

OTHER PUBLICATIONS

Adcock et al., "Electronic effect of the tricyanomethyl group by carbon-13 and fluorine-19 NMR: nature of aryl fluorine-19 NMR polar field effects in the benzene and naphthalene ring systems" Journal of Organic Chemistry 44 (17): 3004-3017 (1979).
Anderson et al. "Identification of a Form of Acyl-CoA:Cholesterol Acyltransferase Specific to Liver and Intestine in Nonhuman Primates" J Biol Chem 273(41):26747-26754 (1998).
Birch et al. "Discovery of a Potent, Selective, and Orally Efficacious Pyrimidinooxazinyl Bicyclooctaneacetic Acid Diacylglycerol Acyltransferase-1 Inhibitor" J. Med. Chem. 52(6):1558-1568 (2009).
Brown and Goldstein "Lipoprotein metabolism in the macrophage: implications for cholesterol deposition in atherosclerosis" Annu Rev Biochem. 52:223-261 (1983).
Burnett and Huff "Avasimibe Pfizer " Curr Opin Investig Drugs 3(9):1328-1333 (2002).
Cases et al. "ACAT-2, A Second Mammalian Acyl-CoA:Cholesterol Acyltransferase" J Biol Chem 273(41):26755-26764 (1998).
Cases et al. "Cloning of DGAT2, a Second Mammalian Diacylglycerol Acyltransferase, and Related Family Members" J. Biol. Chem. 276(42):38870-38876 (2001).
Cases et al. "Identification of a gene encoding an acyl CoA:diacylglycerol acyltransferase, a key enzyme in triacylglycerol synthesis" Proc Natl Acad Sci U S A. 95(22):13018-13023 (1998).
Chang et al. "Molecular cloning and functional expression of human acyl-coenzyme A:cholesterol acyltransferase cDNA in mutant Chinese hamster ovary cells" J. Biol. Chem. 268(28):20747-20755 (1993).
Chen et al. "Increased Insulin and Leptin Sensitivity in Mice Lacking ACYL COA: Diacylglycerol Acyltransferase 1" Journal of Clinical Investigation 109(8):1049-1055 (2002).
Chen et al. "Inhibition of Triglyceride Synthesis as a Treatment Strategy for Obesity: Lessons From DGAT1-Deficient Mice" Arteriosclerosis, Thrombosis, and Vascular Biology 25(3): 482-486 (2005).
Chen et al. "Obesity resistance and enhanced glucose metabolismin mice transplanted with white adipose tissue lacking acyl CoA:diacylglycerol acyltransferase 1" J. Clin. Invest. 111(11):1715-1722 (2003).
Coleman "Diacylglycerol acyltransferase and monoacylglycerol acyltransferase from liver and intestine" Methods in Enzymology 209:98-104 (1992).
Field and Salome "Effect of dietary fat saturation, cholesterol and cholestyramine on acyl-CoA: cholesterol acyltransferase activity in rabbit intestinal microsomes" Biochimica et Biophysica Acta 712(3):557-570 (1982).
Hoffman et al. "Synthesis and evaluation of 2-pyridinone derivatives as HIV-1-specific reverse transcriptase inhibitors. 4. 3-[2-(Benzoxazol-2-yl)ethyl]-5-ethyl-6-methylpyridin-2(1H)-one and analogs" Journal of Medicinal Chemistry 36(8):953-966 (1993).
Hubbard et al. "Antisense and small-molecule modulation of diacylglycerol acyltransferase" Expert Opinion on Therapeutic Patents 17(11): 1331-1339 (2007).
Insull Jr. et al. "Efficacy and short-term safety of a new ACAT inhibitor, avasimibe, on lipids, lipoproteins, and apolipoproteins, in patients with combined hyperlipidemia" Atherosclerosis 157(1):137-144 (2001).
Lehner and Kuksis "Biosynthesis of triacylglycerols" Prog Lipid Res. 35(2):169-201 (1996).
Oelkers et al. "Characterization of Two Human Genes Encoding Acyl Coenzyme A:Cholesterol Acyltransferase-related Enzymes" J Biol Chem 273(41):26765-26771 (1998).
Robertson et al. "Preclinical Safety Evaluation of Avasimibe in Beagle Dogs: An ACAT Inhibitor with Minimal Adrenal Effects" Toxicological Sciences 2001 US, 59(2):324-334 (2001).
Sawhney et al. "Synthesis of some 2-(5-substituted 1,3,4-oxadiazol-2-yl)-, 2-(5-substituted 1,3,4-thiadiazol-2-y1)- and 2-(3-mercapto-4-substituted-4H-1,2,4-triazol-5 -yl)- benzimidazoles as potential antiinflammatory agents" Indian Journal of Chemistry Section B, 30B:407-412 (1991).
Smith et al. "Obesity resistance and multiple mechanisms of triglyceride synthesis in mice lacking Dgat" Nature Genetics 25:87-90 (2000).
Yen et al. "Identification of a gene encoding MGAT1, a monoacylglycerol acyltransferase" Proc Natl Acad Sci U S A. 99(13):8512-8517 (2002).
Yen et al. "Thematic Review Series: Glycerolipids. DGAT enzymes and triacylglycerol biosynthesis" Journal of Lipid Research 49: 2283-2301 (2008).
Zammit et al. "Diacylglycerol acyltransferases: Potential roles as pharmacological targets" Pharmacology & Therapeutics 118(3):295-302 (2008).
Zhao et al. "Validation of diacyl glycerolacyltransferase I as a novel target for the treatment of obesity and dyslipidemia using a potent and selective small molecule inhibitor" J. Med. Chem. 51:380-383 (2008).

\* cited by examiner

OXADIAZOLE DERIVATIVE AS DGAT INHIBITORS

The present invention relates to compounds which inhibit acetyl CoA(acetyl coenzyme A):diacylglycerol acyltransferase (DGAT1) activity, processes for their preparation, pharmaceutical compositions containing them as the active ingredient, methods for the treatment of disease states associated with DGAT1 activity, to their use as medicaments and to their use in the manufacture of medicaments for use in the inhibition of DGAT1 in warm-blooded animals such as humans. In particular this invention relates to compounds useful for the treatment of type II diabetes, insulin resistance, impaired glucose tolerance and obesity in warm-blooded animals such as humans, more particularly to the use of these compounds in the manufacture of medicaments for use in the treatment of type II diabetes, insulin resistance, impaired glucose tolerance and obesity in warm-blooded animals such as humans.

Acyl CoA:diacylglycerol acyltransferase (DGAT) is found in the microsomal fraction of cells. It catalyzes the final reaction in the glycerol phosphate pathway, considered to be the main pathway of triglyceride synthesis in cells by facilitating the joining of a diacylglycerol with a fatty acyl CoA, resulting in the formation of triglyceride. Although it is unclear whether DGAT is rate-limiting for triglyceride synthesis, it catalyzes the only step in the pathway that is committed to producing this type of molecule [Lehner & Kuksis (1996) Biosynthesis of triacylglycerols. Prog. Lipid Res. 35: 169-201].

Two DGAT genes have been cloned and characterised. Both of the encoded proteins catalyse the same reaction although they share no sequence homology. The DGAT1 gene was identified from sequence database searches because of its similarity to acyl CoA:cholesterol acyltransferase (ACAT) genes. [Cases et al (1998) Identification of a gene encoding an acyl CoA:diacylglycerol acyltransferase, a key enzyme in triacylglycerol synthesis. Proc. Natl. Acad. Sci. USA 95: 13018-13023]. DGAT1 activity has been found in many mammalian tissues, including adipocytes.

Because of the previous lack of molecular probes, little is known about the regulation of DGAT1. DGAT1 is known to be significantly up-regulated during adipocyte differentiation.

Studies in gene knockout mice has indicated that modulators of the activity of DGAT1 would be of value in the treatment of type II diabetes and obesity. DGAT1 knockout (Dgat1$^{-/-}$) mice, are viable and capable of synthesizing triglycerides, as evidenced by normal fasting serum triglyceride levels and normal adipose tissue composition. Dgat1$^{-/-}$ mice have less adipose tissue than wild-type mice at baseline and are resistant to diet-induced obesity. Metabolic rate is ~20% higher in Dgat1$^{-/-}$ mice than in wild-type mice on both regular and high-fat diets [Smith et al (2000) Obesity resistance and multiple mechanisms of triglyceride synthesis in mice lacking DGAT. Nature Genetics 25: 87-90]. Increased physical activity in Dgat1$^{-/-}$ mice partially accounts for their increased energy expenditure. The Dgat1$^{-/-}$ mice also exhibit increased insulin sensitivity and a 20% increase in glucose disposal rate. Leptin levels are 50% decreased in the Dgat1$^{-/-}$ mice in line with the 50% decrease in fat mass.

When Dgat1$^{-/-}$ mice are crossed with ob/ob mice, these mice exhibit the ob/ob phenotype [Chen et al (2002) Increased insulin and leptin sensitivity in mice lacking acyl CoA:diacylglycerol acyltransferase J. Clin. Invest. 109:1049-1055] indicating that the Dgat1$^{-/-}$ phenotype requires an intact leptin pathway. When Dgat1$^{-/-}$ mice are crossed with Agouti mice a decrease in body weight is seen with normal glucose levels and 70% reduced insulin levels compared to wild type, agouti or ob/ob/Dgat1$^{-/-}$ mice.

Transplantation of adipose tissue from Dgat1$^{-/-}$ mice to wild type mice confers resistance to diet-induced obesity and improved glucose metabolism in these mice [Chen et al (2003) Obesity resistance and enhanced glucose metabolism in mice transplanted with white adipose tissue lacking acyl CoA:diacylglycerol acyltransferase J. Clin. Invest. 111: 1715-1722].

International Patent Applications WO2004/047755 (Tularik and Japan Tobacco) and WO2005/013907 (Japan Tobacco and Amgen) describe fused bicyclic nitrogen-containing heterocycles which are inhibitors of DGAT-1. JP2004-67635 (Otsuka Pharmaceuticals) describes thiazoleamido substituted phenyl compounds which are further substituted with alkylphosphonates and which inhibit DGAT-1. WO2004/100881 (Bayer) describes biphenylamino compounds substituted with imidazole, oxazole or thiazole which inhibit DGAT-1.

Accordingly, the present invention provides a compound of formula (I)

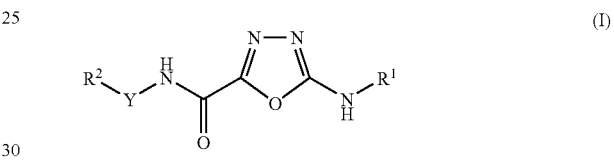

or a pharmaceutically-acceptable salt or prodrug thereof, wherein:

$R^1$ is an optionally substituted aryl or optionally substituted heteroaryl group, wherein the optional substituents are one or more groups selected from a group -$Z^a$, a group —$X^2$—$(CR^{52}R^{53})_w$$Z^a$, a group —$X^2$—$(CR^{52}$—$R^3)_a$—$X^3$-$Z^a$, a group —$(CR^{52}R^{53})_a$—$X^3$-$Z^a$ or a functional group (which is other than a group —$X^2$—$(CR^{52}R^{53})_w$-$Z^a$ or a group —$X^2$—$(CR^{52}R^{53})_a$—$X^3$-$Z^a$);

Y is a direct bond, or a group $(CR^{40}R^{41})$ or —$X^6(CR^{40}R^{41})_t$— where each $R^{40}$ and $R^{41}$ is independently selected from hydrogen, (1-4C)alkyl, hydroxy, halo, halo(1-4C)alkyl, amino, cyano, (1-4C)alkoxy, (1-4C)haloalkoxy or ((1-3C)alkyl)CONH—, s is an integer of from 1 to 6 and t is an integer of from 1 to 6, provided that the $X^6$ atom of the group —$X^6(CR^{40}R^{41})_t$— is attached to the $R^2$ group and that a single sp$^3$ hybridised carbon atom does not carry two or more bonds to a heteroatom unless the heteratom is a halo;

$R^2$ is an optionally substituted aryl, an optionally substituted cycloalkyl or an optionally substituted heterocyclic group, wherein optional substitutents are one or more groups selected from a group -Z, a group —X—$(CR^{42}R^{43})_u$-Z, a group —X—$(CR^{42}R^{43})_v$—$X^1$-Z or a group —$(CR^{42}R^{43})_v$—$X^1$-Z or a functional group (which is other than a group —X—$(CR^{42}R^{43})_u$-Z or a group —X—$(CR^{42}R^{43})_v$—$X^1$-Z);

wherein Z and $Z^a$ are independently selected from a hydrocarbyl group or a heterocyclic group or a combination thereof, wherein the group Z and $Z^a$ is optionally substituted on any available atom by one or more functional groups, or by a group —$X^7$—$(CR^{62}R^{63})_b R^{64}$;

X, $X^1$, $X^2$, $X^3$, $X^6$ and $X^7$ are linking groups independently selected from —C(O)$_x$—, —O—, —S(O)$_y$—, —NR$^{44}$—, —C(O)NR$^{44}$—, —OC(O)NR$^{44}$—, —CH═NO—, —NR$^{44}$C(O)$_x$—, —NR$^{44}$CONR$^{45}$—, —S(O)$_2$NR$^{44}$— or —NR$^{44}$S(O)$_2$— where x is an integer of 1 or 2, y is 0, 1 or 2, and R$^{44}$ and R$^{45}$ are independently selected from hydrogen or (1-6C)alkyl, u and w are independently selected from 0 or an integer of from 1 to 6;

v, a and b are independently selected from an integer of from 1 to 6;

each R$^{42}$, R$^{43}$, R$^{52}$, R$^{53}$, R$^{62}$ and R$^{63}$ is independently selected from hydrogen, (1-4C)alkyl, hydroxy, halo, halo(1-4C)alkyl, amino, cyano, (1-4C)alkoxy, (1-4C)haloalkoxy, ((1-3C)alkyl)CONH—, carboxy or a carboxylic acid mimic or bioisostere thereof, and R$^{64}$ is a functional group.

As used herein, the term "functional group" includes halo, halo(1-6C)alkyl, cyano, nitro, —C(O)$_n$R$^{20}$, a carboxylic acid mimic or bioisostere thereof, —OR$^{20}$, —S(O)$_m$R$^{20}$, —OS(O)$_2$R$^{20}$, —NR$^{21}$R$^{22}$, —C(O)NR$^{21}$R$^{22}$, —OC(O)NR$^{21}$R$^{22}$, —CH=NOR$^{20}$, —NR$^{21}$C(O)$_n$R$^{20}$ —NR$^{20}$CONR$^{21}$R$^{22}$, —N=CR$^{21}$R$^{22}$S(O)$_2$NR$^{21}$R$^{22}$, or —NR$^{21}$S(O)$_2$R$^{22}$ where R$^{20}$, R$^{21}$ and R$^{22}$ are independently selected from hydrogen or optionally substituted hydrocarbyl or optionally substituted heterocyclyl, or R$^{21}$ and R$^{22}$ together with the nitrogen atom to which they are attached form an optionally substituted ring having from 3 to 10 atoms, which optionally contains further heteroatoms such as S(O)$_m$, oxygen and nitrogen, n is an integer of 1 or 2, m is 0 or an integer of 1-2.

Suitable optional substituents for hydrocarbyl groups or heterocyclic groups R$^{20}$, R$^{21}$ and R$^{22}$ (including for rings formed by NR$^{21}$R$^{22}$) include halo, halo(1-4C)alkyl (such as trifluoromethyl, difluoromethyl or fluoromethyl), mercapto, hydroxy, alkoxy, oxo, heteroaryloxy, alkenyloxy, alkynyloxy, alkoxyalkoxy, aryloxy (where the aryl group may be substituted by halo, cyano, nitro, hydroxy(1-4C)alkyl, halo(1-4C)alkyl, amino, (1-4C)alkoxy, (1-4C)haloalkoxy, ((1-3C)alkyl)CONH—, carboxy or a carboxylic acid mimic or bioisostere thereof), cyano, nitro, amino, mono- or di-alkyl amino, alkylamido, oximino (for example hydroxyimino or alkyloxyimino), carbamoyl, carboxy or a carboxylic acid mimic or bioisostere thereof, or —S(O)$_m$R$^{23}$ where m is as defined above and R$^{23}$ is alkyl (optionally substituted by one or more groups selected from hydroxy, halo, amino, cyano, ((1-3C)alkyl)CONH—, carboxy or a carboxylic acid mimic or bioisostere thereof), (1-6C)alkoxy, (1-6C)alkoxycarbonyl, carbamoyl, N-((1-6C)alkyl)carbamoyl, halo(1-6C)alkyl (such as trifluoromethyl), (1-6C)alkylsulphonyl, (1-6C) alkylsulphinyl. Heterocyclic groups R$^{20}$, R$^{21}$ and R$^{22}$ may also be optionally substituted by one or more hydrocarbyl groups such as (1-4C)alkyl.

In this specification the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1-10 carbon atoms, suitably from 1-6 carbon atoms, preferably 1-4 carbon atoms.

In this specification the term "alkoxy" means an alkyl group as defined hereinbefore linked to an oxygen atom.

It is to be understood that optional substituents on any group may be attached to any available atom as appropriate unless otherwise specified, including heteroatoms provided that they are not thereby quaternised.

In this specification the term "heteroatom" refers to non-carbon atoms such as oxygen, nitrogen or sulphur atoms. In addition, where the heteroatom may have a single valency, it may comprise a halo. The terms "alkenyl" and "alkynyl" refer to unsaturated straight or branched structures, which unless specified otherwise, contain for example from 2 to 10, preferably from 2 to 6 carbon atoms. Cyclic moieties such as cycloalkyl and cycloalkenyl are similar in nature but have at least 3 carbon atoms. Examples of alkyl, alkenyl and cycloalkyl groups are given hereinafter, such as examples of (1-6C)alkyl, (3-8C)cycloalkyl etc.

References to aryl groups include aromatic carbocylic groups such as phenyl and naphthyl, as well as partially aromatic groups such as indenyl and indanyl. The term "aralkyl" refers to aryl substituted alkyl groups such as benzyl.

The term "heterocyclyl" or "heterocyclic" includes saturated or unsaturated rings, which may be aromatic, non-aromatic rings or partially aromatic, for example containing from 3 to 20, suitably from 4 to 10 ring atoms, at least one of which is a heteroatom such as oxygen, sulphur or nitrogen. They may be mono- or bicyclic ring systems, wherein one or both rings may be saturated or unsaturated, for example they may be aromatic. In particular, bicyclic ring systems will comprise fused 5,6-membered or 6,6-membered rings.

"Heteroaryl" refers to those heterocyclic groups described above which have an aromatic character. Where "heteroaryl" is a bi-cyclic ring system, then at least one ring is aromatic and one or both rings contain ring heteroatoms.

In general, examples of heterocyclyl rings include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, indolyl, quinolinyl, isoquinolinyl, quinoxalinyl, benzthiazolyl, benzoxazolyl, benzothienyl and benzofuryl. Further examples include thiadiazolyl, oxadiazolyl and isothiazolyl, morpholino, piperazinyl and piperidinyl. Further examples of monocyclic heteroaryl rings are those listed hereinafter as suitable examples of HET-1$^{a-f}$. Further examples of bicyclic heterocyclic rings are those listed hereinafter as suitable examples of HET-2$^{a-b}$. Further examples of monocyclic heterocyclic (non heteroaryl) rings are those listed hereinafter as suitable examples of HET-3$^{b,c,e}$. Suitable examples of bicyclic heteroaryl rings include indolyl, quinolinyl, isoquinolinyl, quinoxalinyl, benzthiazolyl, benzoxazolyl, benzothienyl, benzofuryl, benzimidazolyl, benzodioxolanyl, pyrrolopyridyl, quinazolinyl and naphthyridinyl. It will be understood that structures such as 2-oxo-2,3-dihydro-1H-benzimidazolyl and oxothiadiazolyl which fall within the definition of the term heteroaryl, retain their aromatic characteristics in both rings by virtue of tautomerism.

Other expressions used in the specification include "hydrocarbyl" which refers to any structure comprising carbon and hydrogen atoms. These may be arranged in rings or chains or combinations in which rings are joined to chains or to further rings, or a fused to further rings. Generally, hydrocarbyl groups will contain from 1 to 20, for instance from 1-12 carbon atoms. These may be alkyl, alkenyl, alkynyl, aryl, aralkyl, aralkenyl, aralkynyl, cycloalkyl or cycloalkenyl, wherein any cyclic moiety such as aryl, aralkyl, cycloalkyl or cycloalkenyl are optionally substituted with alkyl, alkenyl, alkynyl and/or with further cyclic moieties, and where any alkyl, alkenyl or alkynyl groups are optionally substituted with cycloalkyl, or cycloalkenyl. The term cycloalkyl also includes bi- and tri-cycloalkyl rings, such as adamantyl and bicyclo[2.2.2]octanyl Suitable combinations of rings and chains which are comprised by the term hydrocarbyl include a) cycloalkyl linked to a (1-6C)alkyl group (in particular cyclohexylmethyl, cyclopentylmethyl, cyclobutylmethyl, cyclohexylethyl), or to two (1-6C)alkyl groups (for example methylcyclobutylmethyl);

b) cyclohexyl linked to a second cyclohexyl or a cyclopentyl group by a direct bond, or with a (1-6C)alkyl group linker;

c) a phenyl group linked to a second phenyl group by a direct bond, or with a (1-6C)alkyl group linker;

d) a (3-8C)cycloalkylgroup (such as cyclohexyl or cyclopentyl) linked to a phenyl group by a direct bond or with a (1-6C)alkyl linker;

e) a benzyl or methylphenyl (such as tolyl) group.

References to a "combination" of hydrocarbyl and heterocyclic groups refer to moieties which contain one or more heterocyclic groups joined together, or one or more heterocyclic groups joined to one or more hydrocarbyl groups.

Suitable combinations of hydrocarbyl and heterocyclic groups include a heterocyclyl group (such as pyridyl, morpholino, thiomorpholino, piperazinyl or piperidinyl) linked to (or substituted by) a hydrocarbyl group (such as a (1-6C)alkyl group and/or a (3-8C)cycloalkyl group; in particular a (1-6C) alkyl group). For example methylpyridyl (wherein the methyl may be further substituted by a functional group such as carboxy), benzylpiperazine, (methyl)oxopyridazine, (methyl)oxothiadiazole, (optionally carboxy substituted)methylpiperidyl, (optionally carboxy substituted)methylpiperidylmethyl, (optionally carboxy substituted)dimethylpiperidyl, (optionally carboxy substituted)ethylpiperidyl and (cyclopropylmethyl)piperazinyl.

Unless specified otherwise, the expression "haloalkyl" refers to alkyl groups which carry at least one halo substitutent. This includes perhalo groups where all hydrogen atoms are replaced by halo such as fluoro.

It is to be understood that optional substituents on any group may be attached to any available atom as appropriate unless otherwise specified, including heteroatoms provided that they are not thereby quaternised.

Within this specification composite terms are used to describe groups comprising more than one functionality such as -(1-6C)alkylNHSO$_2$(1-6C)alkyl. Such terms are to be interpreted in accordance with the meaning which is understood by a person skilled in the art for each component part. For example -(1-6)alkylNHSO$_2$(1-6C)alkyl includes -methylaminosulfonylmethyl, -methylaminosulfonylethyl, -ethylaminosulfonylmethyl, and -propylaminosulfonylbutyl.

Where optional substituents are chosen from "0, 1, 2 or 3" groups it is to be understood that this definition includes all substituents being chosen from one of the specified groups or the substituents being chosen from two or more of the specified groups. An analogous convention applies to substituents chosen from "0, 1 or 2" groups and "1 or 2" and any other analogous groups.

Substituents may be present at any suitable position on, for example, an alkyl group. Therefore, hydroxy substituted (1-6C)alkyl includes hydroxymethyl, 1-hydroxyethyl, 2-hydroxyethyl and 3-hydroxypropyl.

Examples of (1-4C)alkyl include methyl, ethyl, propyl and isopropyl; examples of (1-6C)alkyl include methyl, ethyl, propyl, isopropyl, t-butyl, pentyl, iso-pentyl, 1-2-dimethylpropyl and hexyl; examples of (2-6C)alkenyl include ethenyl, propenyl, isopropenyl, 2-pentenyl, 3-pentenyl, 4-pentenyl, 2-methylpropenyl and hexenyl; examples of (2-6C)alkynyl include ethynyl, propynyl, 2-pentynyl, 3-pentynyl, 4-pentynyl and hexynyl; examples of (1-4C)alkoxy include methoxy, ethoxy, propoxy, isopropoxy and tert-butoxy; examples of (1-6C)alkoxy include methoxy, ethoxy, propoxy, isopropoxy, tert-butoxy and pentoxy; examples of (1-6C)alkoxy(1-6C)alkyl include methoxymethyl, ethoxymethyl, methoxyethyl, propoxymethyl, isopropoxymethyl, pentoxyethyl, methoxyhexyl and tert-butoxybutyl; examples of (3-8C)cycloalkyl include (3-6C)cycloalkyl (cyclopropyl, cyclobutyl, cyclopentyl, cyclohexyl), cycloheptyl and cyclooctyl; examples of (3-8C)cycloalkoxy include cyclopropoxy, cyclobutoxy, cyclopentoxy, cyclohexyloxy, cyclopentyloxy and cyclooctyloxy; examples of (3-8C)cycloalkyl(1-6C)alkyl include cyclopropylmethyl, cyclopropylethyl, cyclopropylbutyl, cyclobutylmethyl, cyclopentylmethyl, cyclohexylmethyl, cyclopentylethyl and cyclooctylpropyl; examples of (3-6C) cycloalkoxy(1-6C)alkyl include cyclopropoxymethyl, cyclopropoxyethyl, cyclopropoxybutyl, cyclobutoxymethyl, cyclopentoxymethyl, cyclohexyloxymethyl, cyclopentoxyethyl and cyclooctyloxypropyl; examples of (3-8C)cycloalkoxy(1-6C)alkoxy include cyclopropoxymethoxy, cyclopropoxyethoxy, cyclopropoxybutoxy, cyclobutoxymethoxy, cyclopentoxymethoxy, cyclohexyloxymethoxy cyclopentoxyethoxy and cyclooctyloxypropoxy; examples of (3-8C)cycloalkoxy(1-6C)alkoxy(1-6C)alkyl include cyclopropoxymethoxymethyl, cyclopropoxyethoxymethyl, cyclopropoxybutoxymethyl, cyclobutoxymethoxyethyl, cyclopentoxymethoxypropyl, cyclohexyloxymethoxymethyl cyclopentoxyethoxymethyl and cyclooctyloxypropoxymethyl; examples of halo are chloro, bromo, iodo and fluoro; examples of halo(1-6C)alkyl include halo(1-4C)alkyl such as chloromethyl, fluoroethyl, fluoromethyl, fluoropropyl, fluorobutyl, dichloromethyl, difluoromethyl, 1,2-difluoroethyl and 1,1-difluoroethyl as well as perhalo(1-6C)alkyl (including perhalo(1-4C)alkyl) such as trifluoromethyl, pentafluoroethyl, and heptafluoropropyl; examples of halo(1-6C)alkoxy include halo(1-4C)alkoxy such as chloromethoxy, fluoroethoxy and fluoromethoxy, difluoromethoxy, as well as perhaloalkoxy such as pentafluoroethoxy, trifluoromethoxy and heptafluoropropoxy; examples of hydroxy(1-6C)alkyl include hydroxy(1-4C)alkyl such as hydroxy methyl, 1-hydroxyethyl, 2-hydroxyethyl and 3-hydroxybutyl; example of carboxy(1-6C)alkyl include carboxy (1-4C)alkyl, such as carboxymethyl, carboxyethyl, carboxypropyl and carboxybutyl; examples of amino(1-6C)alkyl include aminomethyl, aminoethyl, 2-aminopropyl, 3-aminopropyl, 2-aminoiso-propyl, aminobutyl and 2-aminotert-butyl; examples of (1-6C)alkylamino include (1-4C)alkylamino such as methylamino, ethylamino and propylamino; examples of di-((1-6C)alkyl)amino include di-(1-4C)alkylamino such as dimethylamino, N-ethyl-N-methylamino, diethylamino, N-methyl-N-propylamino and di-isopropylamino; examples of (1-6C)alkylcarbonyl include (1-4C) alkylcarbonyl such as methylcarbonyl, ethylcarbonyl, propylcarbonyl, iso-propylcarbonyl and tert-butylcarbonyl; examples of (1-6C)alkylcarbonyloxy include (1-4C)alkylcarbonyloxy such as methylcarbonyloxy, ethylcarbonyloxy, propylcarbonyloxy, iso-propylcarbonyloxy and tert-butylcarbonyloxy; examples of (1-6C)alkoxycarbonyl (N-(1-6C) alkylcarbamoyl) include (1-4C)alkoxycarbonyl such as methoxycarbonyl, ethoxycarbonyl, propoxycarbonyl, iso-propoxycarbonyl and tert-butoxycarbonyl; examples of (1-6C)alkoxycarbonylamino include (1-4C)alkoxycarbonylamino such as methoxycarbonylamino, ethoxycarbonylamino, propoxycarbonylamino, iso-propoxycarbonylamino and tert-butoxycarbonylamino; examples of (1-6C)alkoxycarbonyl(N-methyl)amino include (1-4C)alkoxycarbonyl(N-methyl)amino such as methoxycarbonyl(N-methyl)amino, ethoxycarbonyl(N-methyl)amino, propoxycarbonyl(N-methyl)amino, iso-propoxycarbonyl(N-methyl)amino and tert-butoxycarbonyl(N-methyl)amino; examples of (1-6C)alkylthio include methylthio, ethylthio, propylthio, isopropylthio and butylthio; examples of (1-6C)alkylsulfinyl include methylsulfinyl, ethylsulfinyl, propylsulfinyl, isopropylsulfinyl and butylsulfinyl; examples of (1-6C)alkylsulfonyl include methylsulfonyl, ethylsulfonyl, propylsulfonyl, isopropylsulfonyl and butylsulfonyl; examples of (1-6C)alkoxysulfonyl include methoxysulfonyl, ethoxysulfonyl, propoxysulfonyl, isopropoxysulfonyl and butoxysulfonyl; examples of (1-6C)alkylcarbonylamino include (1-4C)alkylcarbonylamino such as (1-3C)alkylCONH) (methylcarbonylamino, ethylcarbonylamino, propylcarbonylamino, iso-propylcarbonylamino) and tert-butylcarbonylamino; examples of (1-6C)alkylaminocarbonyl include (1-4C)alkylaminocarbonyl such as methylaminocarbonyl, ethylaminocarbonyl, propylaminocarbonyl, iso-propylaminocarbonyl and tert-butylaminocarbonyl; examples of di(1-6C)alkylaminocarbonyl include di(1-4C)alkylaminocarbonyl such as dimethylaminocarbonyl, N-methyl-N-ethylaminocarbonyl, diethylaminocarbonyl, N-methyl-N-propylaminocarbonyl and di-isopropylaminocarbonyl; examples of (1-6C) alkylaminocarbonyloxy include (1-4C) alkylaminocarbonyloxy such as methylaminocarbonyloxy, ethylaminocarbonyloxy, propylaminocarbonyloxy, iso-propylaminocarbonyloxy and tert-butylaminocarbonyloxy; examples of —S(O)$_p$(1-4C)alkyl (wherein p is 0, 1 or 2) include (1-6C)alkylthio, (1-6C)alkylsulfinyl and (1-6C)alkylsulfonyl; examples of (1-6C)alkylaminosulfonyl include —SO$_2$NH(1-4C)alkyl such as methylaminosulfonyl, ethylaminosulfonyl, propylaminosulfonyl, iso-propylaminosulfonyl and tert-butylaminosulfonyl; examples of di(1-6C) alkylaminosulfonyl include di(1-4C)alkylaminosulfonyl such as dimethylaminosulfonyl, N-methyl-N-ethylaminosulfonyl, diethylaminosulfonyl, N-methyl-N-propylaminosulfonyl and di-isopropylaminosulfonyl; examples of (1-6C) alkylsulfonylamino include (1-4C)alkylsulfonylamino such as methylsulfonylamino, ethylsulfonylamino, propylsulfonylamino, iso-propylsulfonylamino and tert-butylsulfonylamino.

Particular values of variable groups in compounds of formula (I) are as follows. Such values may be used where appropriate with any of the other values, definitions, claims or embodiments defined hereinbefore or hereinafter.

In a particular embodiment, $R^1$ is an optionally substituted aryl group such as optionally substituted phenyl or napthyl. $R^1$ as an optionally substituted aryl group may also be indanyl. It will be understood that when $R^1$ is a partially saturated aryl group, such as indanyl, it is the aromatic ring portion of $R^1$ which is directly attached to the linking nitrogen atom.

Alternatively, $R^1$ is an optionally substituted heteroaryl group, and in particular is an optionally substituted monocyclic heteroaryl group such as pyridyl. Suitable values for $R^1$ as a heteroaryl ring include pyrimidinyl, pyridyl, pyrazolyl, pyrazinyl, thiazolyl, oxadiazolyl, isoxazolyl and thiadiazolyl.

It will be understood that when $R^1$ is a partially saturated bicyclic heteroaryl group, such as benzodioxolanyl, it is the aromatic ring portion of $R^1$ which is directly attached to the linking nitrogen atom.

Suitable values for $R^1$ as a bicyclic heteroaryl ring include pyrrolopyridyl, benzodioxolanyl, benzthiazolyl, benzimidazolyl and quinolyl.

More suitable values for $R^1$ include phenyl, naphthyl, indanyl, pyrimidinyl, pyridyl, pyrazolyl, pyrazinyl, thiazolyl, oxadiazolyl, isoxazolyl, thiadiazolyl, pyrrolopyridyl, 1,3-benzodioxan-5-yl, benzthiazolyl, benzimidazolyl and quinolyl.

In one embodiment, $R^1$ may not be pyrrolo[1,2-b]pyridazine.

Preferred optional substituents for $R^1$ include functional groups or (1-6C)alkyl groups such as methyl. Particular functional groups for substituents on $R^1$ include halo, —C(O)$_n$R$^{20}$ or —OR$^{20}$, where R$^{20}$ is as defined above, and in particular is an aryl or aralkyl group.

Suitable functional groups as substituents on $R^1$ include halo, —OR$^{20}$ (wherein R$^{20}$ is hydrogen, phenyl or (1-4C) alkyl, optionally substituted by one or more halo, such that for example R$^{20}$ is difluoromethyl or trifluoromethyl, or optionally substituted by (1-4C)alkoxy), cyano, halo(1-4C)alkyl, —S(O)$_m$R$^{20}$ (wherein R$^{20}$ is phenyl or (1-4C)alkyl, particularly methyl or ethyl, m is 0, 1 or 2, particularly 0 or 2), trifluoromethylthio, —NR$^{20}$CONR$^{21}$R$^{22}$ (wherein R$^{20}$, R$^{21}$ and R$^{22}$ are suitably all hydrogen), —C(O)$_n$R$^{20}$ (wherein n is 1 or 2, particularly 2 and R$^{20}$ is (1-4C)alkyl or phenyl), —OSO$_2$R$^{20}$ (wherein R$^{20}$ is suitably (1-4C)alkyl), —SO$_2$NR$^{21}$R$^{22}$ (wherein R$^{21}$ and R$^{22}$ are suitably both hydrogen), —NR$^{21}$C(O)$_n$R$^{20}$ (wherein n is 1 or 2, particularly 1, R$^{21}$ is suitably hydrogen and R$^{20}$ is suitably phenyl or (1-4C)alkyl), and —CONR$^{21}$R$^{22}$ (wherein R$^{21}$ and R$^{22}$ are suitably hydrogen).

Suitable values for $Z^a$ include phenyl (optionally substituted by a functional group as hereinbefore defined, for example by —CO$_2$Me, or carboxy), benzyl, cyclohexyl, pyridyl, pyrimidinyl (optionally substituted by (1-4C)alkyl), triazolyl, morpholino, (2-4C)alkynyl (for example ethynyl) and (1-4C)alkyl (optionally substituted by a substituent selected from —CO$_2$Me, carboxy, methoxy, hydroxy and cyano).

Where $R^1$ is substituted by a group —X$^2$—(CR$^{52}$R$^{53}$)$_w$-Z$^a$, suitably w is 0 or 1; $Z^a$ is selected from the suitable values given above, particularly hydrocarbyl (such as optionally substituted alkyl, phenyl or benzyl) or pyridyl, and is more suitably optionally substituted phenyl; X$^2$ is suitably —SO$_2$—, —CO—, NHCO—, —NH—, —O—, and R$^{52}$ and R$^{53}$ are suitably both hydrogen.

In another aspect, preferred optional substituents on $R^1$ are 1, 2 or 3 substituents independently selected from alkyl (for example (1-6C)alkyl such as methyl or ethyl), halo, haloalkyl (such as halo(1-6C)alkyl, such as halomethyl, for example trifluoromethyl), haloalkoxy (such as halo(1-6C)alkoxy, such as halomethoxy, for example trifluoromethoxy) and cyano.

In another aspect, preferred optional substituents on $R^1$ are 1, 2 or 3 substituents independently selected from halo, halo (1-4C)alkyl, (1-4C)alkoxy, halo(1-4C)alkoxy, cyano, (1-4C) alkyl, (2-4C)alkynyl, Ph(CH$_2$)$_{0-1}$O— (wherein the phenyl group is optionally substituted by halo), phenyl, benzoyl and anilino.

In another aspect, preferred optional substituents on $R^1$ are 1, 2 or 3 substituents independently selected from fluoro, chloro, bromo, trifluoromethyl, methoxy, difluoromethoxy, trifluoromethoxy, cyano, methyl, ethyl, ethynyl, benzyloxy, 3-chlorobenzyloxy, phenoxy, 4-chlorophenoxy, phenyl, benzoyl and anilino.

In one aspect, $R^1$ is mono-substituted in the 3-position relative to the bond to NH; in another aspect $R^1$ is mono-substituted in the 4-position. In a further aspect $R^1$ is 2,4-di-substituted, 2,6-di-substituted, 3,4-di-substituted, 2,4-di-substituted, or 2,5-di-substituted by any of the possible substituents hereinbefore or hereinafter, but particularly those preferred optional substituents above, and more particularly di-halo, for example di-fluoro. In a further aspect $R^1$ is trisubstituted, for example 2,4,5-trisubstituted, such as 2,4, 5-trihalo (for example 2,4,5-trifluoro).

When $R^1$ is di- or tri-substituted, the substituents are suitably independently selected from a functional group, $Z^a$ and —X$^2$—(CR$^{52}$R$^{53}$)$_w$-Z$^a$, for example any of those values given herein for these groups. For example, $R^1$ may be substituted by di-halo (such as difluoro, dichloro, mono-fluoro mono-chloro and mono-chloro mono-bromo), tri-halo (such as trifluoro), mono-halo mono-alkyl (such as mono-methyl, mono-chloro), mono-halo (such as fluoro or chloro) mono-trifluoromethyl, mono-alkyl (such as methyl) mono-cyano, di-methoxy, mono-chloro mono-methoxy, di-halo mono-hydroxy (such as 2-F, 4-Cl, 5-OH), or may be for example di-halo mono —O-$Z^a$(such as —OCH$_2$CO$_2$Me). When $R^1$ is di-substituted, in one aspect at least one of the substituents is selected from halo, (1-4C)alkyl, (1-4C)alkoxy, trifluoromethyl and cyano. When $R^1$ is tri-substituted, in one aspect at least one, for example at least two, of the substituents are selected from halo, (1-4C)alkyl, (1-4C)alkoxy, trifluoromethyl and cyano.

Where $R^1$ is substituted by a group —$X^2$—(CR$^{52}$R$^{53}$)$_w$-$Z^a$, a group —$X^2$—(CR$^{52}$R$^{53}$)$_a$—$X^3$- $Z^a$ or a group —(CR$^{52}$R$^{53}$)$_c$$X^3$-$Z^a$, $R^{52}$ and $R^{53}$ are suitably hydrogen.

When $R^1$ is substituted by $Z^a$, wherein $Z^a$ is a heterocyclyl ring, such as a morpholino ring, preferably $Z^a$ is not attached to the carbon atom of $R^1$ which is in an ortho position to the bond to the linking nitrogen atom.

In one embodiment, $R^1$ is selected from phenyl, naphthyl, indanyl, pyrimidinyl, pyridyl, pyrazolyl, pyrazinyl, thiazolyl, oxadiazolyl, isoxazolyl, thiadiazolyl, pyrrolopyridyl, 1,3-benzodioxan-5-yl, benzthiazolyl, benzimidazolyl and quinolyl; optionally substituted with 1, 2 or 3 substituents independently selected from halo, (1-4C)alkyl, ethynyl, (1-4C)alkoxy, hydroxy, (1-4C)alkoxy(1-4C)alkoxy, methoxymethyl, cyanomethyl, hydroxy(1-4C)alkyl, trifluoromethyl, difluoromethoxy, trifluoromethoxy, trifluoromethylthio, cyano, methylthio, methylsulfonyloxy, methylsulfonyl, ethylsulfonyl, aminocarbonylamino, methoxycarbonylamino, methylcarbonylamino, (1-4C)alkoxycarbonyl, methoxycarbonylmethoxy, benzyloxy, pyridylmethoxy, phenoxy (optionally substituted by methoxy or halo), phenyl (optionally substituted by methoxycarbonyl or carboxy), benzyl, anilino, anilinocarbonyl, aminocarbonyl, benzoyl, benzoylamino, phenylsulfonyl, aminosulfonyl, cyclohexyl, methylpyrimidinyl, triazolyl and morpholino.

In a preferred embodiment, Y is a direct bond.

Where Y is a group —$X^6$(CR$^{40}$R$^{41}$)$_t$, $X^6$ is suitably oxygen and t is preferably an integer of from 2 to 6.

Alternatively, Y is a group (CH$_2$)$_s$ or more preferably —O(CH$_2$)$_t$— where s is an integer of from 1 to 6 and t is an integer of from 2 to 6, and in particular s or t are 3.

When $R^2$ is unsubstituted aryl or unsubstituted cycloalkyl, Y is preferably other than a direct bond.

$R^2$ is a suitably a substituted phenyl or a substituted heteroaryl group (for example any of those heteroaryl groups listed hereinbefore). Suitable examples of $R^2$ include phenyl, pyridyl, pyrimidinyl, indanyl, cyclohexyl, piperidinyl and benzthiazolyl.

When $R^2$ is an optionally substituted cycloalkyl group, it is preferably a monocyclic group such as (3-8C)cycloalkyl or (3-6C)cycloalkyl.

When $R^2$ is a substituted group, it is suitably substituted by at least one and optionally more than one substituent group -Z, a group —X—(CR$^{42}$R$^{43}$)$_u$-Z, a group —X—(CR$^{42}$R$^{43}$)$_v$—$X^1$-Z or a group —(CR$^{42}$R$^{43}$)$_v$$X^1$-Z, where one or more further substituents may be selected from halo, cyano, nitro, amino, hydroxy or halo(1-6C)alkyl. Preferably $R^2$ is substituted by 1 or 2 groups independently selected from those defined hereinbefore or hereinafter, more preferably by 1 group. When $R^2$ is substituted by 2 groups, preferably one is a functional group as hereinbefore defined, such as halo, —CO$_2$R$^{20}$ (wherein $R^{20}$ is hydrogen, (1-4C)alkyl or allyl) or cyano, or one substituent is (1-4C)alkyl.

Particular examples of groups Z or $Z^a$ include groups of sub formula (x), (y) or (z).

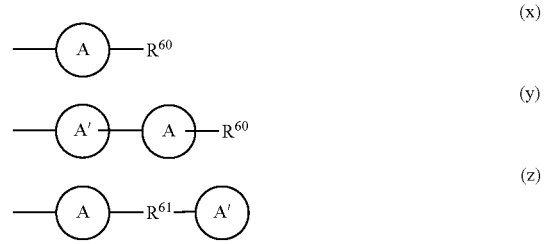

wherein each ring A or A' is independently selected from an optionally substituted heterocyclic ring, an optionally substituted cycloalkyl ring or an optionally substituted aryl ring, each $R^{60}$ is an optionally substituted (1-6C)alkyl, an optionally substituted (2-6C)alkenyl or an optionally substituted (2-6C)alkynyl, and $R^{61}$ is an optionally substituted (1-6C) alkylene, an optionally substituted (2-6C)alkenylene or an optionally substituted (2-6C)alkynylene.

Suitably optional substituents for groups A, A', $R^{60}$ and $R^{61}$ are functional groups.

A further particular example of groups Z or $Z^a$ includes groups of sub formula (zz), wherein A, $R^{60}$ and $R^{61}$, and suitable optional substituents therein are as defined above for sub formulae (x), (y) and (z).

In a particularly preferred embodiment, Z is a group of sub-formula (x) above. In one embodiment, $R^2$ is a 5- or 6-membered aromatic ring of sub-structure (a):

$Z^1$, $Z^2$, $Z^3$ and $Z^4$ are independently selected from —CH—, —CR$^6$— or a heteroatom selected from —O—, —S—, —N(R$^{50}$)$_r$—, where r is 0 or 1 depending upon the requirements of the aromatic ring, and $R^{50}$ is hydrogen or (1-6C) alkyl, and $Z^4$ may additionally be a direct bond;

$R^4$ is a group -Z, a group —X—(CR$^{42}$R$^{41}$)$_u$-Z, a group —X—(CR$^{43}$R$^{43}$)$_v$—$X^1$-Z or a group —(CR$^{42}$R$^{43}$)$_v$$X^1$-Z, wherein Z, X, $X^1$, $R^{42}$, $R^{43}$, u and v are as defined above;

each $R^6$ is independently selected from halo, cyano, nitro, amino, hydroxy, haloC$_{1-6}$alkyl, a group -Z, a group —X— (CR$^{42}$R$^{43}$)$_u$-Z, a group —X—(CR$^{42}$R$^{43}$)$_v$—$X^1$-Z or a group —(CR$^{42}$R$^{43}$)$_v$$X^1$-Z, wherein Z, X, $X^1$ $R^{42}$, $R^{43}$, u and v are as defined above.

Suitably, when $Z^4$ is a direct bond, one of $Z^1$ or $Z^2$ is a heteroatom, in particular oxygen or sulphur.

Preferably $Z^4$ is other than a direct bond.

Suitably in this case, $Z^2$ and $Z^3$ are independently selected from —CH—, —CR$^{24}$— or a nitrogen atom.

Suitably $Z^1$ is a —CH— group.
Preferred groups $R^6$ are listed below as $R^{6a}$.
Suitably, $Z^1$, $Z^2$, $Z^3$ and $Z^4$ are —CH—.
Suitably $R^{42}$ and $R^{43}$ are hydrogen.
Where one of $Z^1$ to $Z^4$ is $N(R^{50})_r$, preferably it is $Z^2$ or $Z^3$.
Where one of $Z^1$ to $Z^4$ is —$CR^6$, preferably it is $Z^2$ or $Z^3$.

In an alternative embodiment, $R^2$ is a cycloalkyl group such as cyclohexyl of sub-formula (b)

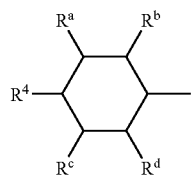

(b)

where $R^4$ is as defined above, and $R^a$, $R^b$, $R^c$ and $R^d$ are independently selected from hydrogen or a group $R^6$ as defined above.

In yet a further embodiment, $R^2$ is a bicyclic ring, which may be a bicyclic aryl ring or a bicyclic heterocyclic ring. For instance, $R^2$ comprises fused 6,6-membered rings, or fused 5,6-membered rings, one or both of said rings may be unsaturated. Examples of such rings include benzimidazole (preferably linked to the group-Y—NH— by way of the benzene ring), indanyl, indenyl. Particularly suitable bicyclic rings are partially unsaturated, such that the ring linked to the group-Y—NH— is saturated and this is fused to an aromatic ring. Particular examples of such rings are indanyl rings, such as 2-indanyl. In one embodiment, $R^2$ may not be pyrrolo[1,2-b]pyridazine.

In particular, $R^4$ is a group Z.

Suitably Z is an aryl, heterocyclyl or cycloalkyl group, any of which are optionally substituted by a functional group or an (1-6C)alkyl, (2-6C)alkenyl or (2-6C)alkynyl group.

Preferably Z is substituted by a functional group or by a (1-6C)alkyl group which is substituted by a functional group. Particular examples of such functional groups include —C(O)$_2R^{20}$ or a carboxylic acid mimic or bioisostere thereof, —C(O)NR$^{21}$R$^{22}$ and —NR$^{21}$C(O)$_n$R$^{20}$, where $R^{20}$, $R^{21}$ and $R^{22}$ are as defined above.

In another embodiment, $R^2$ is substituted by Z and Z is an optionally substituted heterocyclyl group. Suitable examples of Z as an optionally substituted heterocyclyl group include any of the suitable values for heterocyclyl given hereinbefore and in particular include pyrrolidinyl, piperazinyl, piperidinyl, pyridyl, morpholino, thiomorpholino, homopiperazinyl, thiadiazolyl, (oxo)pyridazinyl and (oxo)thiadiazolyl.

In another embodiment, $R^2$ is substituted by Z and Z is an optionally substituted hydrocarbyl group. Suitable examples of Z as an optionally substituted hydrocarbyl group include (all optionally substituted) (1-6C)alkyl (such as (1-4C)alkyl), phenyl, cycloalkyl (such as adamantyl, cyclobutyl, cyclopentyl and cyclohexyl), cycloalkyl combined with (1-4C)alkyl (such as methylcyclohexyl, ethylcyclohexyl, isopropylcyclohexyl, cyclohexylmethyl, ethylcyclobutyl, cyclobutylmethyl and methylcyclopentyl) and phenyl combined with (1-4C) alkyl (such as benzyl and methylphenyl (such as tolyl)).

In another embodiment, $R^2$ is substituted by Z and Z is an optionally substituted combination of hydrocarbyl and heterocyclyl groups. Suitable examples of Z as an optionally substituted combination of hydrocarbyl and heterocyclyl groups include non aromatic heterocycles such as piperazinyl or piperidyl substituted by (1-4C)alkyl (for example methyl, ethyl and isopropyl), benzyl or cycloalkyl(1-4C)alkyl (for example cyclopropylmethyl); oxidised heterocycles such as oxopyridazine or oxothiadiazine substituted by one or two (1-4C)alkyl (such as methyl); aromatic heterocycles (such as pyridyl) substituted by one or two (1-4C)alkyl (such as methyl). For example pyridylmethyl (wherein the methyl may be further substituted by a functional group such as carboxy), benzylpiperazinyl, (methyl)oxopyridazinyl, (methyl)oxothiadiazolyl, (optionally carboxy substituted)methylpiperidyl, (optionally carboxy substituted)methylpiperidylmethyl, (optionally carboxy substituted) dimethylpiperidyl, (optionally carboxy substituted) ethylpiperidyl and (cyclopropylmethyl)piperazinyl.

In another embodiment $R^2$ is substituted by Z and Z is an optionally substituted combination of two heterocyclyl groups, for example pyridyl in combination with piperazinyl.

Suitable substituents on a group Z include halo, hydroxy, carboxy, —CO$_n$R$^{20}$ [wherein $R^{20}$ is hydrogen, optionally substituted hydrocarbyl (such as (1-4C)alkyl, benzyl, phenyl, methylphenyl, phenethyl) or optionally substituted heterocyclyl (such as pyridyl) and wherein n is 1 or 2], —CONH$_2$, —CONHR$^{21}$ (wherein $R^{21}$ is selected from hydrogen, alkyl and benzyl), cyano, amino, —NHCO$_2$(1-4C)alkyl, and —CONR$^{21}$R$^{22}$ (wherein NR$^{21}$R$^{22}$ forms an optionally substituted heterocyclyl ring).

Suitably a ring formed by NR$^{21}$R$^{22}$ contains 0 or 1 further heteroatom selected from O, N and S and may be for example piperidinyl, piperazinyl, pyrrolidinyl or morpholino. A ring formed by NR$^{21}$R$^{22}$ may also be fused to another ring, for example thereby comprise a pyrrolidinyl ring fused with dioxolan.

In general, suitably $R^{20}$ is hydrogen or is selected from (all optionally substituted) (1-4C)alkyl, phenyl, pyridyl, benzyl, phenethyl, methylphenyl and allyl.

In general, $R^{21}$ and $R^{22}$ are suitably are each independently hydrogen or are selected from (optionally substituted) phenyl, (1-4C)alkyl, and benzyl.

Suitably $R^{20}$, $R^{21}$ and $R^{22}$ (and rings formed by NR$^{21}$R$^{22}$) are unsubstituted or are substituted by 1 or 2 substituents. Suitable optional substitutents for $R^{20}$, $R^{21}$ and $R^{22}$ include halo, cyano, hydroxy, (1-4C)alkoxy, carboxy and —CO$_2$(1-4C)alkyl. A particular substituent for $R^{21}$ and $R^{22}$ is hydroxy. Particular substituents for rings formed by NR$^{21}$R$^{22}$ are hydroxy, carboxy and —CO$_2$(1-4C)alkyl.

In another embodiment W is substituted by —X—(CR$^{42}$R$^{43}$)$_u$Z, wherein X is preferably O, —NH—, —NMe-, or —SO$_2$NH—, u is 0, 1 or 2, $R^{42}$ and $R^{43}$ are each hydrogen and Z is selected from any of the values mentioned hereinbefore, particularly morpholino or optionally substituted phenyl (such as methoxyphenyl) or methylphenyl.

In another embodiment, $R^2$ is substituted only by a functional group as hereinbefore defined. In particular, the functional group may be selected from (1-4C)alkoxy, (1-4C)alkylthio and (1-4C)alkylsulfonyl, wherein the aforementioned (1-4C)alkyl groups may optionally be substituted by carboxy or (1-4C)alkoxycarbonyl.

In one aspect, $R^2$—Y is selected from:
4-(piperazino)phenyl (substituted on the available piperazine nitrogen by a substituent selected from (1-4C)alkyl, acyl, benzyl, ethoxycarbonyl, tert-butoxycarbonyl, pyridyl, cyclopropylmethyl and methoxyethyl),
4-(piperazino)-3-methyl-phenyl (substituted on the available piperazine nitrogen by a substituent selected from acyl and tert-butoxycarbonyl),
4-(piperazino)pyridyl (substituted on the available piperazine nitrogen by a substituent selected from (1-4C)alkyl, acyl, ethoxycarbonyl, tert-butoxycarbonyl, benzoyl, fluorobenzoyl, cyanobenzoyl, methylbenzoyl, pyridylcarbonyl, methylsulfonyl, methoxymethylcarbonyl, phenethylcarbonyl, anilinocarbonyl, benzylaminocarbonyl, phenoxycarbonyl, benzyloxycarbonyl and aminocarbonyl), 4-piperidinophenyl, benzyloxyphenyl, (1-4C)alkylphenyl, pyridylmethoxyphenyl, N-methylanilinophenyl, biphenyl, (chloro)biphenyl, (methoxycarbonyl)biphenyl, (ethoxycarbonylmethyl)biphenyl, (carboxy)biphenyl, morpholinophenyl, dimethylmorpholinophenyl, (morpholino)(chloro)phenyl, (morpholino)(dichloro)phenyl (morpholino)(bromo)phenyl, (morpholino)(methyl)phenyl, (morpholino)(fluoro)phenyl, (morpholino)(cyano)phenyl, (morpholino)(allyloxycarbonyl)phenyl, (morpholinoethoxy)phenyl, morpholinopyridyl, (morpholino)(chloro)pyridyl, (morpholino)(fluoro)pyridyl, phenxoypyridyl, anilinopyridyl, methoxypyridyl, butoxypyridyl, pyridyloxypyridyl, hydroxybutylpyridyl, thiomorpholinopyridyl, phenoxypropyl, (fluoro)(trifluoromethyl)phenyl, (N-acyl)homopiperazinophenyl, (N-acyl)piperazinopyrimidinyl, methylbenzthiazolyl, butylthiophenyl, (methoxythiadiazolyl)aminosulfonylphenyl, (difluorophenoxy)phenyl, (dimethyl-oxo-pyridazinyl)phenyl, (methyl-oxo-thiadiazinyl)phenyl, methoxycarbonylpropylphenyl, (methoxycarbonyl)methylthiophenyl, (methoxycarbonyl)adamantyl, carboxyadamantyl, (methoxycarbonylmethyl)bi-cyclohexyl, (carboxy)bi-cyclohexyl, (ethoxycarbonylethyl)indanyl, (carboxyethyl)indanyl, (methoxycarbonyl)phenoxypropyl, (carboxy)phenoxypropyl, (carboxypropyl)phenyl, dicarboxybutylphenyl, carboxybutylphenyl, propylsulfonylphenyl, (carboxy)isopropylsulfonylphenyl, phenoxyphenyl, (methoxyphenoxy)phenyl, methylphenoxyphenyl, hydroxypropoxyphenyl, ethoxyethoxyphenyl, (dimethylaminocarbonyl)isopropoxyphenyl, (carboxymethyl)piperidinophenyl, (methoxycarbonylmethyl)piperidinopyridyl, (carboxymethyl)piperidinopyridyl, (carboxy)piperidinopyridyl, (methoxycarbonyl)piperidinopyridyl, (carboxy)(methyl)piperidinopyridyl, (methoxycarbonyl)(methyl)piperidinopyridyl, (carboxymethyl)(methyl)piperidinopyridyl, (methoxycarbonyl)piperidyl[(methyl)pyridyl], (carboxy)piperidyl[(methyl)pyridyl], (methoxycarbonylmethyl)piperidyl [(methyl)pyridyl], (carboxymethyl)piperidyl[(methyl)pyridyl], (carboxyethyl)piperidyl[(methyl)pyridyl], (ethoxycarbonylethyl)piperidyl[(methyl)pyridyl], [(methoxycarbonyl)piperidinocarbonylmethyl]cyclohexylphenyl, [(carboxy)piperidinocarbonylmethyl]cyclohexylphenyl, [(methoxycarbonyl)isopropylaminocarbonylmethyl]cyclohexylphenyl, [(carboxy)isopropylaminocarbonylmethyl]cyclohexylphenyl, [(methoxycarbonyl)pyrrolidinylcarbonylmethyl]cyclohexylphenyl, [(carboxy)pyrrolidinylcarbonylmethyl]cyclohexylphenyl, [(methoxycarbonyl)(hydroxy)pyrrolidinylcarbonylmethyl]cyclohexylphenyl, [(carboxy)(hydroxy)pyrrolidinylcarbonylmethyl]cyclohexylphenyl, (hydroxyisobutylaminocarbonylmethyl)cyclohexylphenyl, [(tetrahydrodioxolopyrrolyl)carbonyl]methylcyclohexylphenyl, (methoxycarbonylpyridyl)piperidino, (carboxypyridyl)piperidino, (aminocarbonylpyridyl)piperidino, (carboxymethylpyridyl)piperidino, (ethoxycarbonylmethyl)cyclohexylphenyl, (methoxycarbonylmethyl)cyclohexylphenyl, cyclohexylphenyl, (carboxymethyl)cyclohexylphenyl, (hydroxyethyl)cyclohexylphenyl, (aminocarbonylmethyl)cyclohexylphenyl, (cyanomethyl)cyclohexylphenyl, carboxycyclohexylphenyl, (dimethylaminocarbonylmethyl)cyclohexylphenyl, [(N-hydroxyethyl-N-methylaminocarbonylmethyl]cyclohexylphenyl, [N-(dihydroxypropyl)aminocarbonylmethyl]cyclohexylphenyl, (aminomethyl)cyclohexylphenyl, (tertbutoxycarbonylaminomethyl)cyclohexylphenyl, (methoxycarbonyl)cyclohexyloxyphenyl, (ethoxycarbonyl)cyclohexyloxyphenyl, carboxycyclohexyloxyphenyl, (methoxycarbonyl)cyclopentylphenyl, (ethoxycarbonylmethyl)cyclopentylphenyl, (carboxy)cyclopentylphenyl (carboxymethyl)cyclopentylphenyl, (methoxycarbonyl)cyclobutylphenyl, (ethoxycarbonyl)cyclobutylmethylphenyl, (carboxy)cyclobutylphenyl, (carboxy)cyclobutylmethylphenyl, (carboxyethyl)cyclobutylphenyl, (ethoxycarbonylethyl)cyclobutylphenyl, (carboxymethyl)phenylcyclohexyl, 1-(ethoxycarbonyl)ethylcyclohexylphenyl, 1-carboxyethylcyclohexylphenyl, (2-methoxycarbonyl)isopropy-2-ylcyclohexyl, (2-carboxy)isoprop-2-ylcyclohexyl, pyrrolidinylphenyl, (methoxycarbonylmethyl)cyclohexylpyridyl and (carboxymethyl)cyclohexylpyridyl.

As used herein, the reference to carboxylic acid mimic or bioisostere includes groups as defined in The Practice of Medicinal Chemistry, Wermuth C. G. Ed.: Academic Press: New York, 1996, p 203. Particular examples of such groups include —SO$_3$H, S(O)$_2$NHR$^{13}$, S(O)$_2$NHC(O)R$^{13}$, —CH$_2$S(O)$_2$R$^{13}$, —C(O)NHS(O)$_2$R$^{13}$, —C(O)NHOH, —C(O)NHCN, —CH(CF$_3$)OH, C(CF$_3$)$_2$OH, —P(O)(OH)$_2$ and groups of sub-formula (a-(i') below

(a)

(b)

(c)

(d)

(e)

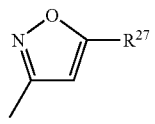

(f)

(g)

-continued
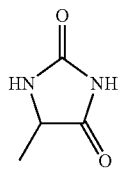 (h)
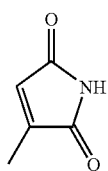 (i)
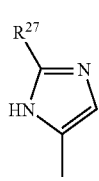 (j)
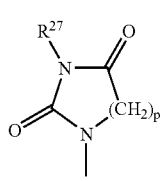 (k)
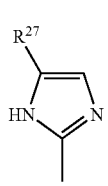 (l)
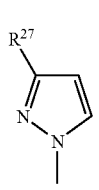 (m)
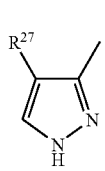 (n)
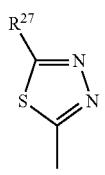 (o)
 (p)
-continued
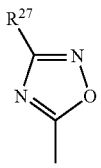 (q)
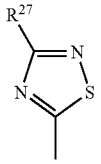 (r)
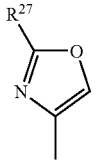 (s)
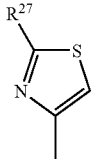 (t)
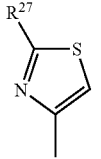 (u)
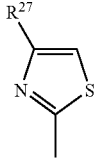 (v)
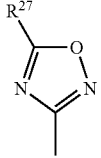 (w)
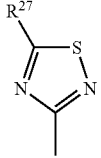 (x)
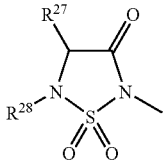 (y)

-continued

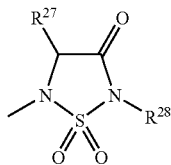
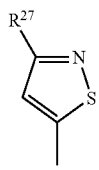
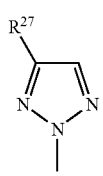
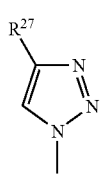
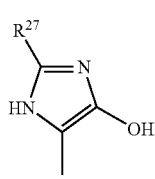
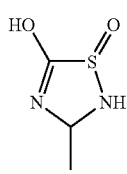
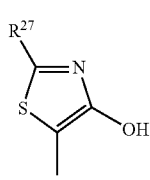
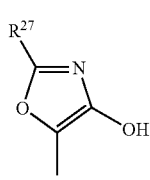
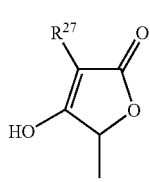

-continued

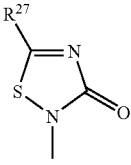

where p is 1 or 2, $R^{27}$ and $R^{28}$ are independently selected from hydrogen, hydroxy, (1-6C)alkoxy, thiol, (1-6C)alkylthio, —C(O)$R^{29}$, —S(O)$R^{30}$, —SO$_2$$R^{31}$, —N$R^{32}$$R^{33}$, —NHCN, halogen and trihalomethyl, where $R^{29}$, $R^{30}$ and $R^{31}$ are —O$R^{34}$, (1-6C)alkyl, —N$R^{32}$$R^{33}$ or trihalomethyl, $R^{32}$ and $R^{33}$ are independently selected from hydrogen, (1-6C)alkyl, —SO$_2$$R^{34}$ and —CO$R^{35}$, where $R^{35}$ is (1-6C)alkyl or trihalomethyl, and $R^{34}$ is hydrogen, (1-6C)alkyl or trihalomethyl.

Particular examples of $R^{27}$ or $R^{28}$ are hydroxy.

In a further aspect of the invention, there is provided a compound of formula (IZA), or a pharmaceutically-acceptable salt or pro-drug thereof,

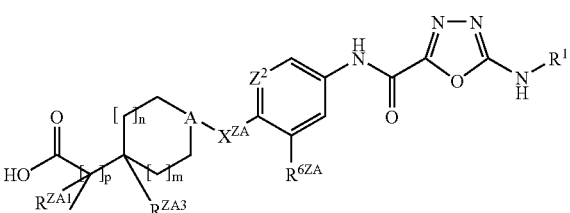

wherein $R^1$ is selected from phenyl (optionally substituted with 1, 2 or 3 substituents independently selected from fluoro, chloro, bromo, trifluoromethyl, methoxy, difluoromethoxy, trifluoromethoxy, cyano, methyl, ethyl, ethynyl, benzyloxy, 3-chlorobenzyloxy, phenoxy, 4-chlorophenoxy, phenyl, benzoyl and anilino), 2-pyridyl (optionally substituted by chlorophenoxy, chlorobenzyloxy or methoxyphenoxy, and/or substituted with a substituent selected from halo, trifluoromethyl, (1-4C)alkyl, (1-4C)alkoxy and cyano), 3-pyridyl (optionally substituted as for 2-pyridyl), halopyrimidinyl and trifluoromethylthiazolyl;

$Z^2$ is N or CH;

$R^{ZA1}$ and $R^{ZA2}$ are each independently hydrogen or methyl;

$R^{ZA3}$ is hydrogen or methyl;

$R^{6ZA}$ is hydrogen, fluoro, chloro or methyl;

A is N or CH;

$X^{ZA}$ is a direct bond, —CH$_2$— or —O— (except when A is N);

m is 0, 1 or 2;

n is 0 or 1;

provided that m+n=0, 1 or 2;

p is 0 or 1.

In another aspect of this embodiment, in the compound of formula (IZA), $R^1$ is phenyl, optionally substituted as defined above.

In a farther aspect of this embodiment, in the compound of formula (IZA), $R^1$ is phenyl, optionally substituted with 1, 2 or 3 substituents independently selected from fluoro, chloro, trifluoromethyl, trifluoromethoxy, cyano, methyl and ethyl.

In a further aspect of this embodiment, in the compound of formula (IZA), $R^1$ is phenyl, optionally substituted with 1, 2 or 3 substituents independently selected from fluoro, chloro, trifluoromethyl, trifluoromethoxy, cyano, methyl and ethyl;

$Z^2$ is CH;

$R^{ZA1}$ and $R^{ZA2}$ are each independently hydrogen or methyl;

$R^{ZA3}$ is hydrogen;

$R^{6ZA}$ is hydrogen, chloro, fluoro or methyl, particularly hydrogen;

A is CH;

$X^{ZA}$ is a direct bond or —$CH_2$—;

m is 0, 1 or 2;

n is 0 or 1;

provided that m+n=0, 1 or 2;

p is 0 or 1.

In a further aspect of this embodiment, in the compound of formula (IZA), $R^1$ is phenyl, optionally substituted with 1, 2 or 3 substituents independently selected from fluoro, chloro, trifluoromethyl, trifluoromethoxy, cyano, methyl and ethyl;

$Z^2$ is N;

$R^{ZA1}$ and $R^{ZA2}$ are each independently hydrogen or methyl;

$R^{ZA3}$ is hydrogen;

$R^{6ZA}$ is hydrogen, chloro, fluoro or methyl, particularly hydrogen;

A is CH;

$X^{ZA}$ is a direct bond or —$CH_2$—;

m is 0, 1 or 2;

n is 0 or 1;

provided that m+n=0, 1 or 2;

p is 0 or 1.

In a further aspect of this embodiment, in the compound of formula (IZA), $R^1$ is phenyl, optionally substituted with 1, 2 or 3 substituents independently selected from fluoro, chloro, trifluoromethyl, trifluoromethoxy, cyano, methyl and ethyl;

$Z^2$ is CH;

$R^{ZA1}$ and $R^{ZA2}$ are each independently hydrogen or methyl;

$R^{ZA3}$ is hydrogen;

$R^{6ZA}$ is hydrogen, chloro, fluoro or methyl, particularly hydrogen;

A is N;

$X^{ZA}$ is a direct bond or —$CH_2$—;

m is 0, 1 or 2;

n is 0 or 1;

provided that m+n=0, 1 or 2;

p is 0 or 1.

In a further aspect of this embodiment, in the compound of formula (IZA), $R^1$ is phenyl, optionally substituted with 1, 2 or 3 substituents independently selected from fluoro, chloro, trifluoromethyl, trifluoromethoxy, cyano, methyl and ethyl;

$Z^2$ is N;

$R^{ZA1}$ and $R^{ZA2}$ are each independently hydrogen or methyl;

$R^{ZA3}$ is hydrogen;

$R^{6ZA}$ is hydrogen, chloro, fluoro or methyl, particularly hydrogen;

A is N;

$X^{ZA}$ is a direct bond or —$CH_2$—;

m is 0, 1 or 2;

n is 0 or 1;

provided that m+n=0, 1 or 2;

p is 0 or 1.

In a further aspect of this embodiment, in the compound of formula (IZA), $R^1$ is phenyl, optionally substituted with 1, 2 or 3 substituents independently selected from fluoro, chloro, trifluoromethyl, trifluoromethoxy, cyano, methyl and ethyl;

$Z^2$ is N;

$R^{ZA3}$ is methyl;

$R^{6ZA}$ is hydrogen, chloro, fluoro or methyl, particularly hydrogen;

A is N;

$X^{ZA}$ is a direct bond or —$CH_2$—;

m is 1;

n is 1;

p is 0.

In a further aspect of this embodiment, in the compound of formula (IZA), $R^1$ is phenyl, optionally substituted with 1, 2 or 3 substituents independently selected from fluoro, chloro, trifluoromethyl, trifluoromethoxy, cyano, methyl and ethyl;

$Z^2$ is CH;

$R^{ZA1}$ and $R^{ZA2}$ are each independently hydrogen or methyl;

$R^{ZA3}$ is hydrogen;

$R^{6ZA}$ is hydrogen, chloro, fluoro or methyl, particularly hydrogen;

A is CH;

$X^{ZA}$ is —O;

m is 0, or 2;

n is 0 or 1;

provided that m+n=0, 1 or 2;

p is 0 or 1.

In a further aspect of this embodiment, in the compound of formula (IZA),

R¹ is phenyl, optionally substituted with 1, 2 or 3 substituents independently selected from fluoro, chloro, trifluoromethyl, trifluoromethoxy, cyano, methyl and ethyl;

$Z^2$ is N;

$R^{ZA1}$ and $R^{ZA2}$ are each independently hydrogen or methyl;

$R^{ZA3}$ is hydrogen;

$R^{6ZA}$ is hydrogen, chloro, fluoro or methyl, particularly hydrogen;

A is CH;

$X^{ZA}$ is —O—;

m is 0, 1 or 2;

n is 0 or 1;

provided that m+n=0, 1 or 2;

p is 0 or 1.

In one aspect, for a compound of formula (IZA), wherein A is —CH—, the substituents on the ring containing A (ie the $X^{ZA}$-pyridyl/phenyl group and the carboxy(alkyl) group) are trans relative to each other.

In one aspect, for a compound of formula (IZA), wherein A is —CH—, the substituents on the ring containing A (ie the $X^{ZA}$-pyridyl/phenyl group and the carboxy(alkyl) group) are cis relative to each other.

In a further aspect of the invention, there is provided a compound of formula (IZB), or a pharmaceutically-acceptable salt or pro-drug thereof,

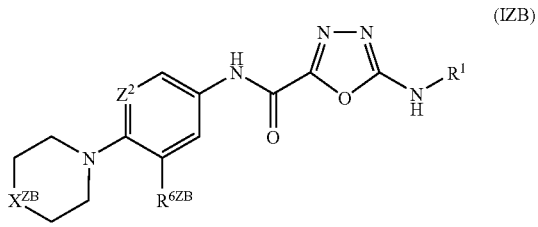

(IZB)

wherein R¹ is selected from phenyl (optionally substituted with 1, 2 or 3 substituents independently selected from fluoro, chloro, bromo, trifluoromethyl, methoxy, difluoromethoxy, trifluoromethoxy, cyano, methyl, ethyl, ethynyl, benzyloxy, 3-chlorobenzyloxy, phenoxy, 4-chlorophenoxy, phenyl, benzoyl and anilino), 2-pyridyl (optionally substituted by chlorophenoxy, chlorobenzyloxy or methoxyphenoxy, and/or substituted with a substituent selected from halo, trifluoromethyl, (1-4C)alkyl, (1-4C)alkoxy and cyano), 3-pyridyl (optionally substitued as for 2-pyridyl), halopyrimidinyl and trifluoromethylthiazolyl;

$Z^2$ is N or CH;

$R^{6B}$ is hydrogen, fluoro, chloro or methyl;

$X^{ZB}$ is O or S, particularly O.

In another aspect of this embodiment, in the compound of formula (IZB), R¹ is phenyl, optionally substitued as defined above.

In a further aspect of this embodiment, in the compound of formula (IZB), R¹ is phenyl, optionally substituted with 1, 2 or 3 substituents independently selected from fluoro, chloro, trifluoromethyl, trifluoromethoxy, cyano, methyl and ethyl.

In a further aspect of the invention, there is provided a compound of formula (IZC), or a pharmaceutically-acceptable salt or pro-drug thereof,

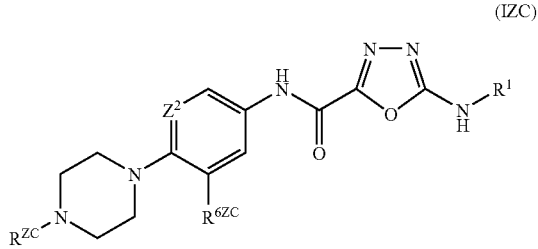

(IZC)

wherein R¹ is selected from phenyl (optionally substituted with 1, 2 or 3 substituents independently selected from fluoro, chloro, bromo, trifluoromethyl, methoxy, difluoromethoxy, trifluoromethoxy, cyano, methyl, ethyl, ethynyl, benzyloxy, 3-chlorobenzyloxy, phenoxy, 4-chlorophenoxy, phenyl, benzoyl and anilino), 2-pyridyl (optionally substituted by chlorophenoxy, chlorobenzyloxy or methoxyphenoxy, and/or substituted with a substituent selected from halo, trifluoromethyl, (1-4C)alkyl, (1-4C)alkoxy and cyano), 3-pyridyl (optionally substitued as for 2-pyridyl), halopyrimidinyl and trifluoromethylthiazolyl;

Z is N or CH;

$R^{6C}$ is hydrogen, fluoro, chloro or methyl;

$R^{ZC}$ is selected from (1-4C)alkyl, acyl, benzyl, ethoxycarbonyl, tert-butoxycarbonyl, pyridyl, cyclopropylmethyl, methoxyethyl, benzoyl, fluorobenzoyl, cyanobenzoyl, methylbenzoyl, pyridylcarbonyl, methylsulfonyl, methoxymethylcarbonyl, phenethylcarbonyl, anilinocarbonyl, benzylaminocarbonyl, phenoxycarbonyl, benzyloxycarbonyl and aminocarbonyl, In another aspect of this embodiment, in the compound of formula (IZC), R¹ is phenyl, optionally substitued as defined above.

In a further aspect of this embodiment, in the compound of formula (IZC), R¹ is phenyl, optionally substituted with 1, 2 or 3 substituents independently selected from fluoro, chloro, trifluoromethyl, trifluoromethoxy, cyano, methyl and ethyl.

In particular, the present invention provides a compound of formula (IA) or a pharmaceutically-acceptable salt or pro-drug thereof,

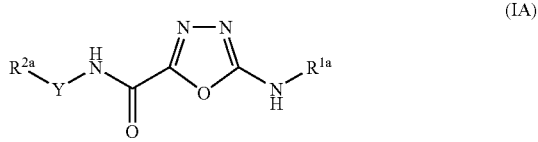

(IA)

wherein:

$R^{1a}$ is selected from $AR^{1a}$, $HET-1^a$ and $HET-2^a$; wherein $R^{1a}$ is optionally substituted by 1, 2, 3 or 4 groups independently selected from $R^3$;

$R^3$ is selected from halo, $R^{8a}$, $R^{8a}O$—, $R^{8a}OCO$—, $R^{8a}COO$, $R^{8a}CO$—, $R^{8a}NHCO$—, $R^{8a}CONH$, $R^{8a}OCONH$—, $R^{8a}OCON(Me)$—, $R^{8a}(1-6C)alkyl$-, halo(1-6C)alkyl, halo(1-6C)alkoxy, (1-6C)alkylthio, di(1-6C)alkylaminocarbonyl, (3-8C)cycloalkyloxy(1-6C)alkyl, (3-8C)cycloalkyl(1-6C)alkoxy, (3-8C)cycloalkyl(1-6C)alkoxy(1-6C)alkyl, phenyl, HET-1$^b$, AR1$^b$-(1-6C)alkoxy, HET-1$^b$-(1-6C)alkoxy, HET-3$^b$-(1-6C)alkoxy, AR1$^b$-oxy, HET-1$^b$-oxy, HET-3$^b$-oxy, AR1$^b$-oxy(1-6C)alkyl, HET-1$^b$-oxy(1-6C)alkyl, HET-3$^b$-oxy(1-6C)alkyl, AR1$^b$-(1-6C)alkoxy(1-6C)alkyl, HET-1$^b$-(1-6C)alkoxy(1-6C)alkyl, and HET-3$^b$-(1-6C)alkoxy(1-6C)alkyl;

wherein any phenyl, AR1$^b$, HET-1$^b$, HET-3$^b$ or cycloalkyl ring in any of the above values for R$^3$ may optionally be substituted by up to 4 substituents independently selected from R$^{7a}$;

and wherein any R$^{8a}$, (3-8C)cycloalkyl, or (1-6C)alkyl group in any of the above definitions for R$^3$ may optionally be substituted by 1, 2 or 3 substituents independently selected from halo, (1-6C)alkyl, (1-6C)alkoxy, (2-6C)alkenyl, (2-6C)alkynyl, hydroxy, cyano, carboxy, aminocarbonyl, haloC$_{1-6}$alkyl, amino, (1-6C)alkylamino, di(1-6C)alkylamino, (1-6C)alkylthio, (1-6C)alkylsulfinyl, (1-6C)alkylsulfonyl, aminosulfonyl, (1-6C)alkylaminosulfonyl, di(1-6C)alkylaminosulfonyl, (1-6C)alkylsulfonylamino, aminocarbonyl, (1-6C)alkylaminocarbonyl, di(1-6C)alkylaminocarbonyl, (1-6C)alkylcarbonylamino, (1-6C)alkoxycarbonylamino, (1-6C)alkoxycarbonyl(N-methyl)amino and (1-6C)alkylaminocarbonyloxy;

Y is a direct bond, or a group (CH$_2$), or —O(CH$_2$)$_t$— where s is an integer of from 1 to 6 and t is an integer of from 2 to 6, provided that the oxygen atom of the group —O(CH$_2$)$_t$— is attached to the R$^{2a}$ group;

R$^{2a}$ is:

a) a 6-membered ring selected from (i), (ii) or (iii)

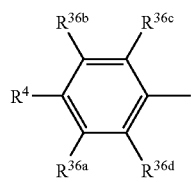

(i)

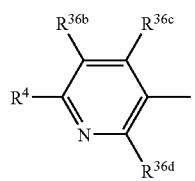

(ii)

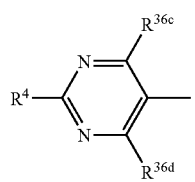

(iii)

wherein R$^{36a}$, R$^{36b}$, R$^{36c}$ and R$^{36d}$ are independently selected from hydrogen or a group R$^{6a}$ as defined hereinafter; or b) a 5-membered heteroaryl ring of sub-formula (iv)

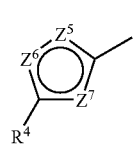

(iv)

wherein Z$^5$, Z$^6$ and Z$^7$ are independently selected from a heteroatom (O, N or S) or CR$^{37}$, where each R$^{37}$ is hydrogen or a group R$^{6b}$ as defined hereinafter, and provided that at least one of Z$^5$, Z$^6$ and Z$^7$ is a heteroatom and there are no O—O, S—S or O—S bonds); or c) a group HET-2$^b$ which is optionally substituted by 1 or 2 groups independently selected from R$^4$ or R$^6$;

d) an optionally substituted cycloalkyl group or an optionally substituted bicyclic aryl group (such as indanyl) wherein optional substituents are selected from groups R$^4$ and R$^{6a}$ as hereinafter defined;

R$^4$ is selected from:

a) phenyl;

b) HET-3$^c$ (wherein any available nitrogen atom is substituted by R$^5$ provided it is not thereby quaternised;

c) HET-1$^c$;

d) phenoxy, HET-1$^c$-oxy, R$^{8b}$O—, R$^{8b}$S(O)$_q$—, phenyl(1-6C)alkoxy and HET-1$^c$-(1-6C)alkoxy, where q is 0, 1 or 2;

e) R$^{8b}$, R$^{8b}$O(1-6C)alkyl, amino(1-6C)alkyl, hydroxy(1-6C)alkyl, phenoxy(1-6C)alkyl, HET-1$^c$-oxy(1-6C)alkyl; and f) phenylamino, phenyl(1-6C)alkylamino, HET-1$^c$-amino, HET-1$^c$-(1-6C)alkylamino, (1-6C)alkylamino, N-phenyl-N-(1-6C)alkylamino, N-phenyl(1-6C)alkyl-N-(1-6C)alkylamino, N-(HET-1$^c$)-N-(1-6C)alkylamino, N-(HET-1$^c$(1-6C)alkyl)-N-(1-6C)alkylamino, and di(1-6C)alkylamino;

wherein any alkyl, R$^{8b}$, phenyl (including phenoxy), HET-1$^c$ or HET-3$^c$ ring in any of the definitions a) to f) for R$^4$ may optionally be substituted by 1, 2, 3 or 4 substituents independently selected from R$^{7b}$;

R$^5$ is selected from a group R$^{8c}$, phenyl, HET-1$^d$, R$^{8c}$CO—, R$^{8c}$OC(O)—, phenylcarbonyl, HET-1$^d$-carbonyl, (1-6C)alkoxycarbonyl, H$_2$NCO, R$^{8c}$NHCO—, phenylNHCO—, (1-6C)alkoxysulfonyl, (1-6C)alkylaminosulfonyl, (1-6C)alkylsulfinyl and (1-6C)alkylsulfonyl;

wherein any (1-6C)alkyl or (3-8C)cycloalkyl groups in any of the definitions of R$^5$ including R$^{8c}$ may optionally be substituted by a substituent selected from a group R$^{15}$, amino, (1-6C)alkylamino, hydroxy, carboxy, (2-6C)alkenyl, (2-6C)alkynyl, phenyl (optionally substituted with up to four groups selected from R$^{15a}$ and HET-1$^f$;

and wherein any phenyl or HET-1$^d$ groups in any of the definitions of R$^5$ are optionally substituted by up to four groups selected from R$^{15b}$, where R$^{15}$, R$^{15a}$ and R$^{15b}$ are independently selected from halo, cyano, C$_{1-6}$alkoxy, haloC$_{1-6}$alkyl, haloC$_{1-6}$alkoxy, (1-6C)alkylS(O)p'- (wherein p' is 0, 1 or 2), R$^{6a}$ and R$^{6b}$ are independently selected from R$^{8a}$R$^{8d}$O—, R$^{8d}$OCO—, R$^{8d}$COO—, halo, cyano, halo(1-6C)alkyl, (1-6C)alkoxy(1-6C)alkyl, (1-6C)alkoxy(1-6C)alkoxy, (1-6C)alkylcarbonyl, (1-6C)alkylS(O)p- (wherein p is 0, 1 or 2), (1-6C)alkylaminocarbonyl, di(1-6C)alkylaminocarbonyl, (1-6C)alkylcarbonylamino, (1-6C)alkylaminosulfonyl, di(1-6C)alkylaminosulfonyl, (1-6C)alkylsulfonylamino, AR1$^e$(1-6C)alkoxy, HET-1$^e$(1-6C)alkoxy, HET-3$^e$-(1-6C)alkoxy, AR1$^e$-oxy(1-6C)alkyl, HET-1$^e$-oxy(1-6C)alkyl, HET-3-oxy (1-6C)alkyl, AR1$^e$-(1-6C)alkoxy(1-6C)alkyl, HET-1$^e$-(1-6C)alkoxy(1-6C)alkyl, and HET-3$^e$-(1-6C)alkoxy(1-6C)alkyl;

wherein any alkyl, R$^{8d}$, phenyl, AR1$^e$, HET-1$^e$, HET-3$^e$ or cycloalkyl ring in any of the above values for R$^{6a}$ or R$^{6b}$ may optionally be substituted by 1, 2 or 3 substituents independently selected from R$^{7c}$, each R$^{7a}$, R$^{7b}$ and R$^{7c}$ is independently selected from R$^{8e}$, R$^{8e}$O(CR$^{13}$R$^{14}$)$_{n'}$—, R$^{8e}$OCO(CR$^{13}$R$^{14}$)$_{n'}$—, R$^{8e}$COO (CR$^{13}$R$^{14}$)$_{n'}$—, HCOO(CR$^{13}$R$^{14}$)$_{n'}$—, R$^{8e}$CO(CR$^{13}$R$^{14}$)$_{n'}$—, HCO(CR$^{13}$R$^{14}$)$_{n'}$—, R$^{8e}$NHCO(CR$^{13}$R$^{14}$)$_{n'}$, H$_2$NCO (CR$^{13}$R$^{14}$)$_{n'}$—, (R$^{10}$R$^{11}$)NCO(CH$_2$)$_{n'}$—, R$^{8e}$CONH (CR$^{13}$R$^{14}$)$_{n'}$, HCONH(CR$^{13}$R$^{14}$)$_{n'}$, HCONR$^{8e}$ (CR$^{13}$R$^{14}$)$_{n'}$, $_R$$^{8e}$CONR$^{8f}$(CR$^{13}$R$^{14}$)$_{n'}$, R$^{8e}$OCONH(CR$^{13}$R$^{14}$)$_{n'}$—, HCONR$^{8e}$(CR$^{13}$R$^{14}$)$_{n'}$, R$^{8e}$OCON(R$^{8f}$) (CR$^{13}$R$^{14}$)$_{n'}$—, ROCON(H)(CR$^{13}$R$^{14}$)$_{n'}$—, HOCON(R$^{8e}$) (CR$^{13}$R$^{14}$)$_{n'}$—, R$^{8e}$(1-6C)alkyl-, halo, cyano, R$^{12}$, R$^{12}$(1-6C) alkyl, hydroxy, oxo, aminocarbonyl, halo(1-6C)alkyl, halo(1-6C)alkoxy, R$^{8e}$S(O)p"- (wherein p" is 0, 1 or 2), amino, amino(1-6C)alkyl, R$^{8e}$NH(1-6C)alkyl, (R$^{8e}$R$^{8f}$)N(1-6C)alkyl, R$^{8e}$NHSO$_2$—, (R$^{10}$R$^{11}$)NSO$_2$—, and R$^{8e}$SO$_2$NH—, where n' is 0 or an integer of from 1 to 6;

R$^{12}$ is carboxy or a carboxylic acid mimic or bioisostere of carboxy;

R$^{13}$ is selected from hydrogen, (1-6C)alkyl, hydroxy, halo, amino, cyano, ((1-3C)alkyl)CONH—, carboxy, (1-6C)alkoxy, (1-6C)alkoxycarbonyl, carbamoyl, N-((1-6C)alkyl) carbamoyl, halo((1-6C)alkyl) (such as trifluoromethyl), (1-6C)alkylsulphonyl or (1-6C)alkylsulphinyl;

R$^{14}$ is hydrogen, (1-6C)alkyl or halo(1-6C)alkyl;

and wherein any alkyl group or R$^{8e}$, R$^{8f}$, R$^{10}$ or R$^{11}$ group within a group R$^{7a}$, R$^{7b}$ or R$^{7c}$ is optionally substituted by 1, 2 or 3 groups independently selected from R$^9$;

each R$^{8a}$, R$^{8b}$, R$^{8c}$, R$^{8d}$, R$^{8e}$ and R$^{8f}$ is independently selected from (1-6C)alkyl, (2-6C)alkenyl, (2-6C)alkynyl and (3-8C)cycloalkyl;

R$^{10}$ and R$^{11}$ are independently selected from selected from (1-6C)alkyl, (2-6C)alkenyl, (2-6C)alkynyl and (3-8C)cycloalkyl; or R$^{10}$ and R$^{11}$ together with the nitrogen atom to which they are attached form a 4-7 membered heterocyclic ring, which optionally contains one or more further heteroatoms selected from O, N and S, and which is optionally substituted by from 1, 2 or 3 groups selected from hydroxy, (1-6C)alkyl, (1-6C)haloalkyl, carboxy or a carboxylic acid mimic or bioisostere thereof;

R$^9$ is selected from hydroxy, halo, amino, cyano, ((1-3C)alkyl)CONH—, carboxy, (1-6C)alkoxy, (1-6C)alkoxycarbonyl, carbamoyl, N-((1-6C)alkyl)carbamoyl, halo((1-6C)alkyl) (such as trifluoromethyl), (1-6C)alkylsulphonyl, (1-6C)alkylsulphinyl, AR1$^a$, AR1$^b$ and AR1$^e$ are independently selected from phenyl or a 6,5-, or 6,6-bicyclic fused ring system, wherein both rings are carbocyclic and wherein at least the ring attached to the linking nitrogen atom is fully aromatic;

HET-1$^a$, HET-1$^b$, HET-1$^c$, HET-1$^d$, HET-1$^e$ and HET-1$^f$ are independently selected from a 5- or 6-membered heteroaryl ring containing 1, 2, or 3 heteroatoms independently selected from O, N and S (provided there are no O—O, S—S or O—S bonds), wherein any sulfur atom may optionally be oxidised to an SO or SO$_2$ group, and wherein any carbon atom may optionally be oxidised to a carbonyl group;

HET-2$^a$ and HET-2$^b$ are independently selected from a 5,5-, 5,6-6,5- or 6,6-fused bicyclic, aromatic or partially unsaturated heterocyclic ring system, containing 1, 2, 3 or 4 heteroatoms independently selected from O, N and S (provided there are no O—O, S—S or O—S bonds), in which the ring directly attached to the linking nitrogen atom is aromatic, and either ring of the bicyclic ring system may be carbocyclic;

HET-3$^b$, HET-3$^c$, HET-3$^e$ are independently selected from a partially or fully unsaturated 4-, 5-, 6- or 7 membered heterocyclic ring containing 1, 2, or 3 heteroatoms independently selected from O, N and S (provided there are no O—O, S—S or O—S bonds), wherein any sulfur atom may optionally be oxidised to an SO or SO$_2$ group, and wherein any carbon atom may optionally be oxidised to a carbonyl group; except that HET-3$^b$ and HET-3$^c$ are not 3-oxomorpholin-4-yl.

In a particular embodiment, the present invention provides a compound of formula (IB) or a pharmaceutically-acceptable salt thereof,

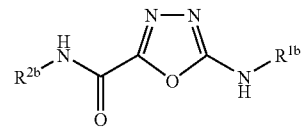

(IB)

wherein:

R$^{1b}$ is selected from AR1$^a$, HET-1$^a$ and HET-2$^a$; wherein R$^{1b}$ is optionally substituted by 1, 2, 3 or 4 groups independently selected from R$^{3a}$;

R$^{3a}$ is selected from halo, R$^{8a}$, R$^{8a}$O—, R$^{8a}$OCO—, R$^{8a}$COO—, R$^{8a}$CO—, R$^{8a}$NHCO—, R$^{8a}$CONH, R$^{8a}$OCONH—, R$^{8a}$OCON(Me)—, R$^{8a}$(1-6C)alkyl-, —C$_6$H$_{(13-a)}$F$_a$ (wherein a is 1 to 13), —OC$_6$H$_{(13-a)}$F$_a$ (wherein a is 1 to 13), (1-6C)alkylthio, di(1-6C)alkylaminocarbonyl, (3-8C)cycloalkyloxy(1-6C)alkyl, (3-8C)cycloalkyl(1-6C)alkoxy, (3-8C)cycloalkyl(1-6C)alkoxy(1-6C) alkyl, phenyl, HET-1$^b$, AR1$^b$-(1-6C)alkoxy, HET-1$^b$-(1-6C) alkoxy, HET-3$^b$-(1-6C)alkoxy, AR1$^b$-oxy(1-6C)alkyl, HET-1$^b$ oxy(1-6C)alkyl, HET-3$^b$-oxy(1-6C)alkyl, AR1$^b$-(1-6C) alkoxy(1-6C)alkyl, HET-1$^b$-(1-6C)alkoxy(1-6C)alkyl, and HET-3 b-(1-6C)alkoxy(1-6C)alkyl;

wherein any phenyl, AR1$^b$, HET-1$^b$, HET-3$^b$ or cycloalkyl ring in any of the above values for R$^{3a}$ may optionally be substituted by 1 or 2 substituents independently selected from R$^{7d}$;

and wherein any R$^{8a}$, (3-8C)cycloalkyl, or (1-6C)alkyl group in any of the above definitions for R$^{3a}$ may optionally be substituted by 1 or 2 substituents independently selected from (1-6C)alkyl, (1-6C)alkoxy, (2-6C)alkenyl, (2-6C)alkynyl, hydroxy, cyano, carboxy, aminocarbonyl, —C$_6$H$_{(13-a)}$F$_a$ (wherein a is 1 to 13), amino, (1-6C)alkylamino, di(1-6C) alkylamino, (1-6C)alkylthio, (1-6C)alkylsulfinyl, (1-6C)alkylsulfonyl, aminosulfonyl, (1-6C)alkylaminosulfonyl, di(1-6C)alkylaminosulfonyl, (1-6C)alkylsulfonylamino, aminocarbonyl, (1-6C)alkylaminocarbonyl, di(1-6C)alkylaminocarbonyl, (1-6C)alkylcarbonylamino, (1-6C)alkoxycarbonylamino, (1-6C)alkoxycarbonyl, (1-6C)alkoxycarbonyl(N-methyl)amino and (1-6C)alkylaminocarbonyloxy; and/or any $R^{8a}$, (3-8C)cycloalkyl, or (1-6C)alkyl group in any of the above definitions for $R^{3a}$ may optionally be substituted by 1, 2 or 3 halo;

$R^{2b}$ is:

a) a 6-membered ring selected from phenyl, 3-pyridyl and 3,5-pyrimidinyl; substituted in the position which is para to the linkage with the group —Y—NH— by a group selected from $R^{4a}$ and optionally additionally substituted on a carbon atom in one or both of the meta-positions to the linkage with the group —Y—NH— (where possible) by 1 or 2 groups independently selected from $R^{6c}$; or b) a 5-membered heteroaryl ring containing 1, 2, or 3 heteroatoms independently selected from O, N and S (provided there are no O—O, S—S or O—S bonds); substituted on a carbon atom in a position which is not adjacent the linkage to the group —Y—NH—, by a group selected from $R^{4a}$ and optionally additionally substituted on carbon (where available) by 1 or 2 groups independently selected from $R^{6d}$;

$R^{4a}$ is selected from:

a) phenyl;

b) HET-$3^c$ (wherein any available nitrogen atom is substituted by $R^{5a}$ provided it is not thereby quaternised);

c) HET-$1^c$;

d) phenoxy, HET-$1^c$-oxy, $R^{8b}$O—, phenyl(1-6C)alkoxy and HET-$1^c$-(1-6C)alkoxy;

e) $R^{8b}$, $R^{8b}$O(1-6C)alkyl, amino(1-6C)alkyl, hydroxy(1-6C)alkyl, phenoxy(1-6C)alkyl, HET-$1^c$-oxy(1-6C)alkyl; and f) phenylamino, phenyl(1-6C)alkylamino, HET-$1_c$-amino, HET-$1_c$-(1-6C)alkylamino, (1-6C)alkylamino, N-phenyl-N-(1-6C)alkylamino, N-phenyl(1-6C)alkyl-N-(1-6C)alkylamino, N-(HET-$1^c$)-N-(1-6C)alkylamino, N-(HET-1' (1-6C)alkyl)-N-(1-6C)alkylamino, and di(1-6C)alkylamino;

wherein any alkyl, $R^{8b}$, phenyl, HET-$1^c$ or HET-$3^c$ ring in any of the definitions a) to f) for $R^{4a}$ may optionally be substituted by 1 or 2 substituents independently selected from $R^{7e}$;

$R^{5a}$ is selected from (1-6C)alkyl, (3-8C)cycloalkyl, phenyl (optionally substituted with 1 or 2 halo), HET-$1^d$, $R^{8c}$CO—, phenylcarbonyl (wherein the phenyl is optionally substituted with 1 or 2 halo), HET-$1^d$-carbonyl, (1-6C)alkoxycarbonyl, $R^{8c}$NHCO—, (1-6C)alkoxysulfonyl, (1-6C)alkylaminosulfonyl, (1-6C)alkylsulfinyl and (1-6C)alkylsulfonyl; wherein any (1-6C)alkyl group in any of the definitions of $R^{5a}$ may optionally be substituted by a substituent selected from (1-6C)alkoxy, (1-6C)alkylS(O)p'- (wherein p' is 0, 1 or 2), amino, (1-6C)alkylamino, hydroxy, carboxy, (2-6C)alkenyl, (2-6C)alkynyl, phenyl (optionally substituted with 1 or 2 halo) and HET-$1^f$;

$R^{6c}$ and $R^{6d}$ are independently selected from $R^{8d}$, $R^{8d}$O—, $R^{8d}$OCO—, $R^{8d}$COO—, halo, cyano, halo(1-6C)alkyl, dihalo(1-6C)alkyl, (1-6C)alkoxy(1-6C)alkyl, (1-6C)alkoxy(1-6C)alkoxy, (1-6C)alkylcarbonyl, (1-6C)alkylS(O)p- (wherein p is 0, 1 or 2), (1-6C)alkylaminocarbonyl, di(1-6C)alkylaminocarbonyl, (1-6C)alkylcarbonylamino, (1-6C)alkylaminosulfonyl, di(1-6C)alkylaminosulfonyl, (1-6C)alkylsulfonylamino, AR$1^e$-(1-6C)alkoxy, HET-$1^e$-(1-6C)alkoxy, HET-$3^e$-(1-6C)alkoxy, AR$1^e$-oxy(1-6C)alkyl, HET-$1^e$-oxy(1-6C)alkyl, HET-$3^e$-oxy(1-6C)alkyl, AR$1^e$-(1-6C)alkoxy(1-6C)alkyl, HET-$1^e$-(1-6C)alkoxy(1-6C)alkyl, and HET-$3^e$-(1-6C)alkoxy(1-6C)alkyl;

wherein any alkyl, $R^{8d}$, phenyl, AR$1^e$, HET-$1^e$, HET-$3^e$ or cycloalkyl ring in any of the above values for $R^{6c}$ or $R^{6d}$ may optionally be substituted by 1, 2 or 3 substituents independently selected from $R^{7f}$;

$R^{7d}$, $R^{7e}$ and $R^{7f}$ are independently selected from $R^{8e}$ (optionally substituted with 1, 2 or 3 halo or with hydroxy), $R^{8e}$O— (optionally substituted with 1, 2 or 3 halo), $R^{8e}$OCO—, $R^{8e}$COO—, $R^{8e}$CO—, $R^{8e}$NHCO—, $(R^{8e})_2$NCO, $R^{8e}$CONH, $R^{8e}$OCONH—, $R^{8e}$OCON(Me)—, $R^{8e}$(1-6C)alkyl-, halo, cyano, carboxy, carboxy(1-6C)alkyl, hydroxy, aminocarbonyl, —$C_6H_{(13-a)}F_a$ (wherein a is 1 to 13), —$OC_6H_{(13-a)}F_a$ (wherein a is 1 to 13), $R^{8e}$S(O)p"- (wherein p" is 0, 1 or 2), amino(1-6C)alkyl, $R^{8e}$NH(1-6C)alkyl, $(R^{8e})_2$N(1-6C)alkyl, $R^{8e}$NHSO$_2$—, $(R^{8e})_2$NSO$_2$—, and $R^{8e}$SO$_2$NH—;

each $R^{8a}$, $R^{8b}$, $R^{8c}$, $R^{8d}$, $R^{8e}$ and $R^{8f}$ is selected from (1-6C)alkyl, (2-6C)alkenyl, (2-6C)alkynyl and (3-8C)cycloalkyl;

AR$1^a$, AR$1^b$ or AR$1^e$ are independently selected from phenyl or a 6,5-, or 6,6-bicyclic fused ring system, wherein both rings are carbocyclic and wherein at least the ring attached to the linking nitrogen atom is fully aromatic;

HET-$1^a$, HET-$1^b$, HET-$1^c$, HET-$1^d$, HET-$1^e$ and HET-$1^f$ are independently selected from a 5- or 6-membered heteroaryl ring containing 1, 2, or 3 heteroatoms independently selected from O, N and S (provided there are no O—O, S—S or O—S bonds), wherein any sulfur atom may optionally be oxidised to an SO or SO$_2$ group, and wherein any carbon atom may optionally be oxidised to a carbonyl group;

HET-$2^a$ and HET-$2^b$ are independently selected from a 5,5-, 5,6-6,5- or 6,6-fused bicyclic, aromatic or partially unsaturated heterocyclic ring system, containing 1, 2, 3 or 4 heteroatoms independently selected from O, N and S (provided there are no O—O, S—S or O—S bonds), in which the ring directly attached to the linking nitrogen atom is aromatic, and either ring of the bicyclic ring system may be carbocyclic;

HET-$3^b$, HET-$3^c$, HET-$3^e$ are independently selected from a partially or fully unsaturated 4-, 5-, 6- or 7 membered heterocyclic ring containing 1, 2, or 3 heteroatoms independently selected from O, N and S (provided there are no O—O, S—S or O—S bonds), wherein any sulfur atom may optionally be oxidised to an SO or SO$_2$ group, and wherein any carbon atom may optionally be oxidised to a carbonyl group; except that HET-$3^b$ and HET-$3^c$ are not 3-oxomorpholin-4-yl.

It will be understood that the definition of $R^{2b}$ in relation to formula (IB) as a 6-membered ring selected from phenyl, 3-pyridyl and 3,5-pyrimidinyl; substituted in the position which is para to the linkage with the group —Y—NH— with a group $R^{4a}$ and optionally additionally substituted on a carbon atom in one or both positions which are meta to the linkage with the group —Y—NH— (where possible) by 1 or 2 groups independently selected from $R^{6c}$; encompasses the following structures, for every definition of substituent $R^{6c}$:

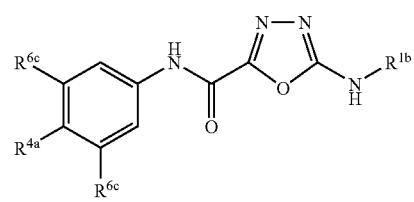

-continued

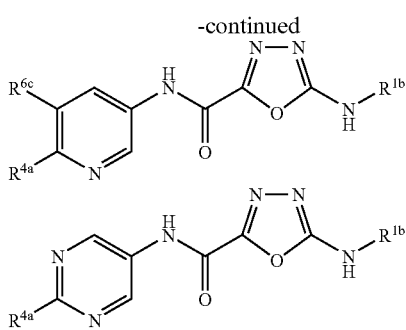

Similarly, it will be understood that the definition of $R^{2b}$ as a 5-membered heteroaryl ring containing 1, 2, or 3 heteroatoms independently selected from O, N and S (provided there are no O—O, S—S or O—S bonds); substituted on a carbon atom in a position which is not directly adjacent the linkage to the group —Y—NH— by a group selected from $R^{4a}$ and optionally additionally substituted on carbon (where available) by 1 or 2 groups independently selected from $R^{6d}$; encompasses the following structures:

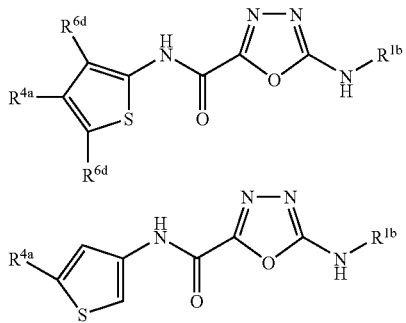

For the avoidance of doubt it is to be understood that where in this specification a group is qualified by 'hereinbefore defined' or 'defined hereinbefore' the said group encompasses the first occurring and broadest definition as well as each and all of the particular definitions for that group.

It is to be understood that where substituents contain two substituents on an alkyl chain, in which both are linked by a heteroatom (for example two alkoxy substituents), then these two substituents are not substituents on the same carbon atom of the alkyl chain.

Examples of $AR1^a$, $AR1^b$ and $AR1^e$ are phenyl, naphthyl, indenyl and dihydroindenyl.

Examples of $AR1^a$(1-6C)alkyl, $AR1^b$(1-6C)alkyl or $AR^{e1}$(1-6C)alkyl are benzyl, phenethyl, naphthylmethyl and naphthylethyl.

Examples of $AR1^a$-oxy, $AR1^b$-oxy or $AR1^b$-oxy are phenoxy and naphthyloxy.

Examples of $AR1^a$-oxy(1-6C)alkyl, $AR1^b$-oxy(1-6C)alkyl or $AR1^e$-oxy(1-6C)alkyl are phenoxymethyl and naphthyloxyethyl. Examples of $AR1^a$-(1-6C)alkoxy, $AR1^b$-(1-6C)alkoxy or $AR1^e$-(1-6C)alkoxy are any value of $AR1^a$, $AR1^b$ or $AR1^e$ bonded to any value of (1-6C)alkoxy, for example benzyloxy and naphthyloxy. The same convention applies wherever $AR1^a$, $AR1^b$ or $AR1^e$ is linked to another group.

Examples of HET-$1^a$, HET-$1^b$, HET-$1^c$, HET-$1^d$, HET-$1^e$ or HET-$1^f$ are oxazolyl, oxadiazolyl, pyridyl, pyrimidinyl, imidazolyl, triazolyl, pyrazinyl, pyridazinyl, pyrrolyl, thienyl and furyl.

Further examples of NET-$1^a$, HET-$1^b$, HET-$1^c$, HET-$1^d$, HET-$1^e$ or HET-$1^f$ include thiazolyl, tetrazolyl, isoxazolyl, pyrazolyl, triazinyl thiadiazolyl, oxadiazolyl and isothiazolyl.

Examples of HET-$1^a$-oxy, HET-$1^b$-oxy, HET-$1^c$-oxy, HET-$1^d$-oxy, HET-$1^e$-oxy or HET-$1^f$-oxy are oxazolyl-2-oxy, 1,2,4-oxadiazolyl-3-oxy, pyridyl-2-oxy, and pyrimidinyl-4-oxy. The convention illustrated above for $AR1^a$, $AR1^b$ and $AR1^c$ applies to HET-$1^a$, HET-$1^b$, HET-$1^c$, HET-$1^d$, HET-$1^e$ or HET-$1^f$ linked to any other group.

Examples of HET-$2^a$ or HET-$2^b$ are 1,3-benzodioxol-5-yl, quinazolinyl, purinyl, indolyl, benzofuryl, benzothienyl, chromanyl, isochromanyl, quinolinyl and isoquinolinyl. Further examples of HET-$2^a$ or HET-$2^b$ include quinoxalinyl, benzthiazolyl and benzoxazolyl.

Examples of HET-$3^b$, HET-$3^c$ or HET-$3^e$ are morpholinyl, thiomorpholinyl, piperazinyl, piperidinyl, 2-oxopiperidinyl, pyrrolidinyl, 2-oxopyrrolidinyl, tetrahydropyranyl, dihydropyranyl, tetrahydrothienyl, azetidinyl, homomorpholinyl, diazepinyl and azepinyl.

Particular examples of HET-$3^b$, HET-$3^c$ or HET-$3^e$ are morpholinyl, thiomorpholinyl, piperazinyl and piperidinyl.

Examples of HET-$3^b$-oxy, HET-3'-oxy or HET-$3^e$-oxy are morpholinyloxy, thiomorpholinyloxy, piperazinyloxy, piperidinyloxy, 2-oxopiperidinyloxy, pyrrolidinyloxy, 2-oxopyrrolidinyloxy, tetrahydropyranyloxy, dihydropyranyloxy, tetrahydrothienyloxy, azetidinyloxy, homomorpholinyloxy, diazepinyloxy and azepinyloxy. The convention illustrated above for $AR1^a$, $AR1^b$ and $AR1^e$ applies to HET-3 b, HET-$3^c$ or HET-$3^e$ linked to any other group.

If not stated elsewhere, suitable optional substituents for a particular group are those as stated for similar groups herein.

A compound of formula (I) may form stable acid or basic salts, and in such cases administration of a compound as a salt may be appropriate, and pharmaceutically acceptable salts may be made by conventional methods such as those described following.

Suitable pharmaceutically-acceptable salts include acid addition salts such as methanesulfonate, tosylate, α-glycerophosphate, fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

Within the present invention it is to be understood that a compound of the formula (I) or a salt thereof may exhibit the phenomenon of tautomerism and that the formulae drawings within this specification can represent only one of the possible tautomeric forms. It is to be understood that the invention encompasses any tautomeric form which inhibits DGAT1 activity and is not to be limited merely to any one tautomeric form utilised within the formulae drawings.

Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, Advanced Drug Delivery Reviews, 8, 1-38 (1992);
d) H. Bundgaard, et al., Journal of Pharmaceutical Sciences, 77, 285 (1988); and
e) N. Kakeya, et al., Chem Pharm Bull, 32, 692 (1984).

Examples of such prodrugs are in vivo cleavable esters of a compound of the invention. An in vivo cleavable ester of a compound of the invention containing a carboxy group is, for example, a pharmaceutically-acceptable ester which is cleaved in the human or animal body to produce the parent acid. Suitable pharmaceutically-acceptable esters for carboxy include (1-6C)alkyl esters, for example methyl or ethyl; (1-6C)alkoxymethyl esters, for example methoxymethyl; (1-6C)alkanoyloxymethyl esters, for example pivaloyloxymethyl; phthalidyl esters; (3-8C)cycloalkoxycarbonyloxy(1-6C)alkyl esters, for example 1-cyclohexylcarbonyloxyethyl; 1,3-dioxolan-2-ylmethyl esters, for example 5-methyl-1,3-dioxolan-2-ylmethyl; (1-6C)alkoxycarbonyloxyethyl esters, for example 1-methoxycarbonyloxyethyl; aminocarbonylmethyl esters and mono- or di-N-((1-6C)alkyl) versions thereof, for example N,N-dimethylaminocarbonylmethyl esters and N-ethylaminocarbonylmethyl esters; and may be formed at any carboxy group in the compounds of this invention. An in vivo cleavable ester of a compound of the invention containing a hydroxy group is, for example, a pharmaceutically-acceptable ester which is cleaved in the human or animal body to produce the parent hydroxy group. Suitable pharmaceutically acceptable esters for hydroxy include (1-6C)alkanoyl esters, for example acetyl esters; and benzoyl esters wherein the phenyl group may be substituted with aminomethyl or N-substituted mono- or di-(1-6C)alkyl aminomethyl, for example 4-aminomethylbenzoyl esters and 4-N,N-dimethylaminomethylbenzoyl esters.

It will be appreciated by those skilled in the art that certain compounds of formula (I) contain asymmetrically substituted carbon and/or sulfur atoms, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the inhibition of DGAT1 activity, it being well known in the art how to prepare optically-active forms (for example, by resolution of the racemic form by recrystallization techniques, by synthesis from optically-active starting materials, by chiral synthesis, by enzymatic resolution, by biotransformation, or by chromatographic separation using a chiral stationary phase) and how to determine efficacy for the inhibition of DGAT1 activity by the standard tests described hereinafter.

It is also to be understood that certain compounds of the formula (I) and salts thereof can exist in solvated as well as unsolvated forms such as, for example, hydrated forms. It is to be understood that the invention encompasses all such solvated forms which inhibit DGAT1 activity.

As stated before, we have discovered a range of compounds that have good DGAT1 inhibitory activity. They have good physical and/or pharmacokinetic properties in general.

The following compounds possess preferred pharmaceutical and/or physical and/or pharmacokinetic properties.

Particular aspects of the invention comprise a compound of formula (I), or a pharmaceutically-acceptable salt thereof, wherein the substituents AR, HET, $R^1$ to $R^8$ and other substituents mentioned above have values defined hereinbefore, or any of the following values (which may be used where appropriate with any of the definitions and embodiments disclosed hereinbefore or hereinafter):

In one embodiment of the invention there are provided compounds of formula (I), in an alternative embodiment there are provided pharmaceutically-acceptable salts of compounds of formula (I). In a further embodiment, there are provided pro-drugs, particularly in-vivo cleavable esters, of compounds of formula (I). In a further embodiment, there are provided pharmaceutically-acceptable salts of pro-drugs of compounds of formula (I). Reference herein to a compound of formula (I) should in general be taken to apply also to compounds of formulae (IA), (IB), (IZA), (IZB) and (IZC).

Particular values of variable groups in compounds of formulae (I), (IA) and (IB) are as follows. Such values may be used where appropriate with any of the other values, definitions, claims or embodiments defined hereinbefore or hereinafter.

1) $R^1$, $R^{1a}$ or $R^{1b}$ is $AR^{1a}$
2) $R^1$, $R^{1a}$ or $R^{1b}$ is HET-$1^a$
3) $R^1$, $R^{1a}$ or $R^{1b}$ is HET-$2^a$
4) $R^1$, $R^{1a}$ or $R^{1b}$ is unsubstituted
5) $R^1$ or $R^{1a}$ is substituted by 1 group selected from $R^3$ or $R^{1b}$ is substituted by 1 group selected from $R^{3a}$
6) $R^1$ or $R^{1a}$ is substituted by 2 groups independently selected from $R^3$ or $R^{1b}$ is substituted by 2 groups independently selected from $R^{3a}$
7) $R^1$ or $R^{1a}$ is substituted by 3 groups independently selected from $R^3$ or $R^{1b}$ is substituted by 3 groups independently selected from $R^{3a}$
8) $R^1$ or $R^{1a}$ is substituted by 4 groups independently selected from $R^3$ or $R^{1b}$ is substituted by 4 groups independently selected from $R^{3a}$
9) $R^3$ or $R^{3a}$ is halo
10) $R^3$ or $R^{3a}$ is selected from $R^{8a}$, $R^{8a}$O—, $R^{8a}$OCO—, $R^{8a}$COO— and $R^{8a}$CO—
11) $R^3$ or $R^{3a}$ is selected from $R^{8a}$, $R^{8a}$O— and $R^{8a}$OCO—
12) $R^3$ or $R^{3a}$ is selected from $R^{8a}$NHCO—, $R^{8a}$CONH, $R^{8a}$OCONH— and $R^{8a}$OCON(Me)-
13) $R^3$ or $R^{3a}$ is selected from $R^{8a}$(1-6C)alkyl-, halo$C_{1-6}$alkyl or halo$C_{1-6}$alkoxy
14) $R^3$ or $R^{3a}$ is selected from $R^{8a}$(1-6C)alkyl-, —$C_6H_{(13-a)}F_a$ (wherein a is 1 to 14), —O$C_6H_{(13-a)}F_a$ (wherein a is 1 to 14)
15) $R^3$ or $R^{3a}$ is selected from (1-6C)alkylthio, alkylcarbonyl and di(1-6C)alkylaminocarbonyl
16) $R^3$ or $R^{3a}$ is selected from (3-8C)cycloalkyloxy(1-6C)alkyl, (3-8C)cycloalkyl(1-6C)alkoxy, and (3-8C)cycloalkyl(1-6C)alkoxy(1-6C)alkyl
17) $R^3$ or $R^{3a}$ is selected from halo, $R^{8a}$, $R^{8a}$O—, $R^{8a}$OCO—, $R^{8a}$COO—$R^{8a}$CO—, $R^{8a}$NHCO—, $R^{8a}$CONH, $R^{8a}$OCONH—, $R^{8a}$OCON(Me)—, $R^{8a}$(1-6C)alkyl-, halo(1-6C)alkyl (such as —$C_6H_{(13-a)}F_a$ (wherein a is 1 to 13), halo(1-6C)alkoxy (such as —O$C_6H_{(13-a)}F_a$ (wherein a is 1 to 13), (1-6C)alkylthio, di(1-6C)alkylaminocarbonyl, (3-8C)cycloalkyloxy(1-6C)alkyl, (3-8C)cycloalkyl(1-6C)alkoxy, (3-8C)cycloalkyl(1-6C)alkoxy(1-6C)alkyl, $AR_1^b$-(1-6C)alkoxy, HET-$1^b$-(1-6C)alkoxy, HET-$3^b$-(1-6C)alkoxy, $AR1^b$-oxy(1-6C)alkyl, HET-$1^b$-oxy(1-6C)alkyl, HET-3 b-oxy(1-6C)alkyl, AR$^{1b}$— (1-6C)alkoxy(1-6C)alkyl, HET-1$^b$-(1-6C)alkoxy(1-6C)alkyl, and HET-3$^b$-(1-6C)alkoxy(1-6C)alkyl 18) R$^3$ or R$^{3a}$ is selected from plenyl and HET-1$^b$
19) R$^3$ or R$^{3a}$ is phenyl
20) R$^3$ or R$^{3a}$ is selected from AR$^{1b}$-(1-6C)alkoxy, and HET-1$^b$-(1-6C)alkoxy, HET-3$^b$-(1-6C)alkoxy
21) R$^3$ or R$^{3a}$ is selected from AR1$^b$-oxy(1-6C)alkyl, HET-1$^b$-oxy(1-6C)alkyl, HET-3 b-oxy(1-6C)alkyl, AR1$^b$(1-6C)alkoxy(1-6C)alkyl, HET-1$^b$-(1-6C)alkoxy(1-6C)alkyl, and HET-3$^b$-(1-6C)alkoxy(1-6C)alkyl
22) a phenyl, AR1$^b$, HET-1$^b$, HET-3$^b$ or cycloalkyl ring in any value for R$^3$ is substituted by 1 or 2 substituents independently selected from R$^{7a}$, and a phenyl, AR1$^b$, HET-1$^b$, HET-3$^b$ or cycloalkyl ring in any value for R$^{3a}$ is substituted by 1 or 2 substituents independently selected from R$^{7d}$
23) a phenyl, AR1$^b$, HET-1$^b$, HET-3$^b$- or cycloalkyl ring in any value for R$^3$ or R$^{3a}$ is unsubstituted
24) an R$^{8a}$, (3-8C)cycloalkyl, or (1-6C)alkyl group in any definitions for R$^3$ or R$^{3a}$ is unsubstituted
25) an R$^{8a}$ (3-8C)cycloalkyl, or (1-6C)alkyl group in any definitions for R$^3$ or R$^{3a}$ is substituted by 1 or 2 substituents independently selected from (1-6C)alkyl, (1-6C)alkoxy, (2-6C)alkenyl, (2-6C)alkynyl, hydroxy, cyano, carboxy, aminocarbonyl, —C$_6$H$_{(14-a)}$F$_a$ (wherein a is 1 to 14), amino, (1-6C)alkylamino, di(1-6C)alkylamino, (1-6C)alkylthio, (1-6C)alkylsulfinyl, (1-6C)alkylsulfonyl, aminosulfonyl, (1-6C)alkylaminosulfonyl, di(1-6C)alkylaminosulfonyl, (1-6C)alkylsulfonylamino, aminocarbonyl, (1-6C)alkylaminocarbonyl, di(1-6C)alkylaminocarbonyl, (1-6C)alkylcarbonylamino, (1-6C)alkoxycarbonylamino, (1-6C)alkoxycarbonyl(N-methyl)amino and (1-6C)alkylaminocarbonyloxy; and/or substituted by 1, 2 or 3 halo;
26) R$^2$ or R$^{2a}$ is a 6-membered ring selected from phenyl, 3-pyridyl, 5-pyridyl and 3,5-pyrimidinyl; substituted in the 4-position by a group selected from R$^4$ and optionally additionally substituted on a carbon atom in one or both meta-positions relative to the linkage to the group —Y—NH— (where possible) by 1 or 2 groups independently selected from R$^{6a}$; or
27) R$^{2b}$ is a 6-membered ring selected from phenyl, 3-pyridyl, 5-pyridyl and 3,5-pyrimidinyl; substituted in the 4-position by a group selected from R$^{4a}$ and optionally additionally substituted on a carbon atom in one or both meta-positions relative to the linkage to the group —Y—NH— (where possible) by 1 or 2 groups independently selected from R$^{6c}$;
28) R$^2$, R$^{2a}$ or R$^{2b}$ is phenyl
29) R$^2$, lea or R$^{1b}$ is 3-pyridyl
30) R$^2$, R$^{1e}$ or R$^{2b}$ is phenyl or 3-pyridyl
31) R$^2$ or R$^{2a}$ is a six-membered ring substituted in the position which is para to the linkage with the group —Y—NH— by a group selected from R$^4$; or a group R$^{2b}$ is a six-membered ring substituted in the position which is para to the linkage with the group —Y—NH— by a group selected from R$^{4a}$
32) R$^2$ or R$^{2a}$ is a six-membered ring substituted in the position which is para to the linkage with the group —Y—NH— by a group selected from R$^4$ and additionally substituted on a carbon atom in a 3-position by R$^{6a}$; or R$^{2b}$ is a six-membered ring substituted in the position which is para to the linkage with the group —Y—NH— by a group selected from R$^{4a}$ and additionally substituted on a carbon atom in a 3-position by R$^{6c}$;
33) R$^2$ or R$^{2a}$ is a group or sub-formula (Iv) as defined above; or R$^{2b}$ is a 5-membered heteroaryl ring containing 1, 2, or 3 heteroatoms independently selected from O, N and S (provided there are no O—O, S—S or O—S bonds); substituted on a carbon atom in a position which is not adjacent the linkage to the group —Y—NH— by a group selected from R$^{4a}$ and optionally additionally substituted on carbon (where available) by 1 or 2 groups independently selected from R$^{6d}$
34) R$^2$ or R$^{2e}$ is a group HET-2$^b$ optionally substituted with methyl
35) R$^4$ or R$^{4a}$ is phenyl
36) R$^4$ or R$^{4a}$ is HET-3$^c$ (wherein any available nitrogen atom is substituted by R$^5$ provided it is not thereby quaternised)
37) R$^4$ or R$^{4a}$ is HET-1$^c$
38) R$^4$ or R$^{4a}$ is selected from phenoxy, HET-1r-oxy, R$^{8b}$O—, phenyl(1-6C)alkoxy and HET-1$^c$-(1-6C)alkoxy
39) R$^4$ or R$^{4a}$ is selected from R$^{8b}$, R$^{8b}$O(1-6C)alkyl, amino(1-6C)alkyl, hydroxy(1-6C)alkyl, phenoxy(1-6C)alkyl and HET-1-oxy(1-6C)alkyl
40) R$^4$ or R$^{4a}$ is selected from R$^{8b}$ and hydroxy(1-6C)alkyl
41) R$^4$ or R$^{4a}$ is selected from phenylamino, phenyl(1-6C)alkylamino, HET-1$^c$-amino, HET-1$^c$-(1-6C)alkylamino, (1-6C)alkylamino, N-phenyl-N-(1-6C)alkylamino, N-phenyl(1-6C)alkyl-N-(1-6C)alkylamino, N-(HET-1$^c$)-N-(1-6C)alkylamino, N-(HET-1$^c$-(1-6C)alkyl)-N-(1-6C)alkylamino, and di(1-6C)alkylamino
42) R$^4$ or R$^{4a}$ is selected from phenylamino, N-phenyl-N-(1-6C)alkylamino
43) R$^4$ or R$^{4a}$ is selected from phenyl, HET-3$^c$, phenoxy, HET-1-oxy, R$^{8b}$O—, phenyl(1-6C)alkoxy, HET-1-(1-6C)alkoxy, R$^{86}$, hydroxy(1-6C)alkyl, phenylamino and N-phenyl-N-(1-6C)alkylamino
44) an alkyl, R$^{8b}$, phenyl, HET-1$^c$ or HET-3$^c$ ring in any of the definitions for R$^4$ is substituted by 1 or 2 substituents independently selected from R$^{7b}$; or an alkyl, R$^{8b}$, phenyl, HET-1$^c$ or HET-3$^c$ ring in any of the definitions for R$^{4a}$ is substituted by 1 or 2 substituents independently selected from R$^{7c}$
45) an alkyl, R$^{8b}$, phenyl, HET-1$^c$ or HET-3$^c$ ring in any of the definitions for R$^4$ or R$^{4a}$ is unsubstituted
46) R$^5$ or R$^{5a}$ is selected from (1-6C)alkyl and (3-8C)cycloalkyl
47) R$^5$ or R$^{5a}$ is R$^{8c}$CO—
48) R$^5$ or R$^{5a}$ is phenyl (optionally substituted) or HET-1$^d$
49) R$^5$ or R$^{5a}$ is phenylcarbonyl (optionally substituted) or HET-1$^d$-carbonyl
50) R$^5$ or R$^{5a}$ is selected from carboxy, (1-6C)alkoxycarbonyl, R$^{8c}$NHCO—, (1-6C)alkoxysulfonyl, (1-6C)alkylaminosulfonyl, (1-6C)alkylsulfinyl and (1-6C)alkylsulfonyl
51) R$^5$ or R$^{5a}$ is selected from (1-6C)alkoxycarbonyl and (1-6C)alkylsulfonyl
52) R$^5$ or R$^{5a}$ is selected from (1-6C)alkyl, HET-1, R$^{8c}$CO—, (1-6C)alkoxycarbonyl and (1-6C)alkylsulfonyl
53) any (1-6C)alkyl group in any of the definitions of R$^5$ or R$^{5a}$ is substituted by a substituent selected from (1-6C)alkoxy, (1-6C)alkylS(O)p- (wherein p is 0, 1 or 2), amino, (1-6C)alkylamino, hydroxy, carboxy, (2-6C)alkenyl, (2-6C)alkynyl, phenyl (optionally substituted) and HET-1$^d$
54) any (1-6C)alkyl group in any of the definitions of R$^5$ or R$^{5a}$ is unsubstituted
55) R$^{6a}$, R$^{6b}$, R$^{6c}$ or R$^{6d}$ is selected from R$^{8d}$, R$^{8d}$O—, R$^{8d}$OCO— and R$^{8d}$COO—
56) R$^{6a}$, R$^{6b}$, R$^{6c}$ or R$^{6d}$ is selected from halo and cyano
57) R$^{6a}$, R$^{6b}$, R$^{6c}$ or R$^{6d}$ is selected from halo(1-6C)alkyl, dihalo(1-6C)alkyl
58) R$^{6a}$, R$^{6b}$, R$^{6c}$ or R$^{6d}$ is selected from (1-6C)alkoxy(1-6C)alkyl and (1-6C)alkoxy(1-6C)alkoxy 59) $R^{6a}$, $R^{6b}$, $R^{6c}$ or $R^{6d}$ is selected from (1-6C)alkylcarbonyl and (1-6C)alkylS(O)p- (wherein p is 0, 1 or 2)
60) $R^{6a}$, $R^{6b}$, $R^{6c}$ or $R^{6d}$ is selected from (1-6C)alkylaminocarbonyl, di(1-6C)alkylaminocarbonyl, (1-6C)alkylcarbonylamino, (1-6C)alkylaminosulfonyl, di(1-6C)alkylaminosulfonyl and (1-6C)alkylsulfonylamino
61) $R^{6a}$, $R^{6b}$, $R^{6c}$ or $R^{6d}$ is selected from $AR^{11}$—(1-6C)alkoxy, HET-1'-(1-6C)alkoxy, HET-$3^e$-(1-6C)alkoxy, $AR1^e$-oxy(1-6C)alkyl, HET-1'-oxy(1-6C)alkyl, HET-$3^e$-oxy(1-6C)alkyl, $AR1^e$-(1-6C)alkoxy(1-6C)alkyl, HET-1'-(1-6C)alkoxy(1-6C)alkyl, and HET-$3^e$-(1-6C)alkoxy(1-6C)alkyl
62) any alkyl, $R^{8d}$, phenyl, $AR1^e$, HET-$1^e$, HET-$3^e$ or cycloalkyl ring in any value for $R^{6a}$, $R^{6b}$ is substituted by 1, 2 or 3 substituents independently selected from $R^{7c}$, or in any value for $R^{6c}$ or $R^{6d}$ is substituted by 1, 2 or 3 substituents independently selected from $R^{7f}$
63) any alkyl, $R^{8d}$, phenyl, $AR1^e$, HET-$1^e$, HET-$3^e$ or cycloalkyl ring in any value for $R^{6a}$, $R^{6b}$, $R^{6c}$ or $R^{6d}$ is unsubstituted
64) $R^{7a}$, $R^{7b}$, $R^{7c}$, $R^{7d}$, $R^{7e}$ or $R^{7f}$ is $R^{8e}$ (optionally substituted with 1, 2 or 3 halo or with hydroxy)
65) $R^{7a}$, $R^{7b}$, $R^{7C}$, $R^{7d}$, $R^{7e}$ or $R^{7f}$ is $R^{8e}O$— (optionally substituted with 1, 2 or 3 halo)
66) $R^{7a}$, $R^{7b}$ or $R^{7c}$ is selected from $R^{8e}OCO$, $R^{8e}COO$—, $R^{8e}NHCO$—, $R^{10}R^{11}NCO$, $R^{8e}CONH$, $R^{8e}OCONH$— and $R^{8e}OCON(Me)$—
67) $R^{7d}$, $R^{7e}$ or $R^{7f}$ is selected from $R^{8e}OCO$—, $R^{8e}COO$—, $R^{8e}CO$—, $R^{8e}NHCO$—, $(R^{8e})_2NCO$, $R^{8e}CONH$, $R^{8e}OCONH$— and $R^{8e}OCON(Me)$—
68) $R^{7a}$, $R^{7b}$ or $R^{7c}$ is selected from $R^{8e}$(1-6C)alkyl-, halo, cyano, carboxy, carboxy(1-6C)alkyl, hydroxy, aminocarbonyl, halo(1-6C)alkyl, halo(1-6C)alkoxy
69) $R^{7d}$, $R^{7e}$ or $R^{7f}$ is selected from $R^{8e}$ (1-6C)alkyl-, halo, cyano, carboxy, carboxy(1-6C)alkyl, hydroxy, aminocarbonyl, $-C_6H_{(13-a)}F_a$ (wherein a is 1 to 13), $-OC_6H_{(14-a)}F_a$ (wherein a is 1 to 13)
70) $R^{7a}$, $R^{7b}$ or $R^{7c}$ is selected from $R^{8e}S(O)p$- (wherein p is 0, 1 or 2), amino(1-6C)alkyl, $R^{8e}NH$(1-6C)alkyl, $R^{11}R^{10}N$(1-6C)alkyl, $R^{8e}NHSO_2$—, $R^{11}R^{10}NSO_2$—, and $R^{8e}SO_2NH$—
71) $R^{7d}$, $R^{7e}$ or $R^{7f}$ is selected from $R^{8e}S(O)p$- (wherein p is 0, 1 or 2), amino(1-6C)alkyl, $R^{8e}NH$(1-6C)alkyl, $(R^{8e})_2N$(1-6C)alkyl, $R^{8e}NHSO_2$—, $(R^{8e})_2NSO_2$—, and $R^{8e}SO_2NH$—
72) $R^{8a}$, $R^{8b}$, $R^{8c}$, $R^{8d}$, $R^{8e}$ or $R^8$ is selected from (1-6C)alkyl, (2-6C)alkenyl, (2-6C)alkynyl, (3-8C)cycloalkyl
73) $R^{8a}$, $R^{8b}$, $R^{8c}$, $R^{8d}$, $R^{8e}$ or $R^{8f}$ is selected from (1-6C)alkyl and (3-8C)cycloalkyl
74) $R^{8a}$, $R^{8b}$, $R^{8c}$, $R^{8d}$, $R^{8e}$ or $R^{8f}$ is selected from (1-6C)alkyl
75) $AR1^a$, $AR1^b$ or $AR1^e$ is phenyl
76) $AR1^a$, $AR1^b$ or $AR1^e$ is a 6,5-, or 6,6-bicyclic fused ring system,
77) $AR1^a$, $AR1^b$ or $AR1^e$ is naphthyl
78) $AR1^a$, $AR1^b$ or $AR1^e$ is phenyl, dihydroindenyl or naphthyl
79) HET-$1^a$, HET-$1^b$, HET-$1^c$, HET-$1^d$, HET-$1^e$ or HET-$1^f$ is 5-membered heteroaryl ring
80) HET-$1^a$, HET-$1^b$, HET-$1^c$, HET-$1^d$, HET-$1^e$ or HET-$1^f$ is a 6-membered heteroaryl ring
81) HET-$2^a$ or HET-$2^b$ is a 5,5- or 6,6-fused bicyclic heterocyclic ring system
82) HET-$2^a$ or HET-$2_b$ is a 5,6-6,5-fused bicyclic heterocyclic ring system
83) HET-$3^b$, HET-$3^c$ or HET-$3^e$ is a 5-membered ring
84) HET-$3^b$, HET-$3^c$ or HET-$3^e$ is a 6-membered ring
85) HET-$3^b$, HET-$3^c$ or HET-$3^e$ is a 7-membered ring
86) HET-$3^b$, HET-$3^c$ or HET-$3^e$ is a 4-membered ring
87) s is suitably 0

In yet further preferred compounds:
88) $R^4$ is a group $R^{8b}$ where $R^{8b}$ is (3-8C)cycloalkyl such as cyclohexyl
89) $R^4$ is a group $R^{8b}$ where $R^{8b}$ is substituted by a substituent $R^{7b}$
90) $R^{7b}$ is $H_2NCO(CR^{13}R^{14})_n$— or $(R^{10}R^{11})NCO(CH_2)_n$
91) $R^{7b}$ is $HCONH(CR^{13}R^{14})_n$, $HCONR^{8e}(CR^{13}R^{14})_n$, $R^{8e}CONR^{8f}(CR^{13}R^{14})_n$
92) $R^{7b}$ is $R^{12}$ or $R^{12}$(1-6C)alkyl,
93) $R^2$ or $R^{2a}$ is a cyclohexyl group.

In a further aspect of the invention there is provided a compound of the formula (IB') or a pharmaceutically-acceptable salt thereof, which is a compound of the formula (IB) as shown above, wherein:

$R^{1b}$ is selected from $AR1^a$, HET-$1^a$ and HET-$2^a$; wherein $R^{1b}$ is optionally substituted by 1, or 2 groups independently selected from $R^{3a}$;

$R^{3a}$ is selected from halo, $R^{8a}$, $R^{8a}O$—, $R^{8a}OCO$—, $R^{8a}COO$—, $R^{8a}CO$—, $R^{8a}NHCO$—, $R^{8a}CONH$, $R^{8a}OCONH$—, $R^{8a}OCON(Me)$—, $R^{8a}$(1-6C)alkyl-, $-C_6H_{(13-a)}F_a$ (wherein a is 1 to 13), $-OC_6H_{(13-a)}F_a$ (wherein a is 1 to 13), (1-6C)alkylthio, di(1-6C)alkylaminocarbonyl, phenyl, HET-$1^b$, $AR1^b$-(1-6C)alkoxy, HET-$1^b$-(1-6C)alkoxy, HET-$3^b$-(1-6C)alkoxy, $AR1^b$-oxy(1-6C)alkyl, HET-$1^b$-oxy(1-6C)alkyl, HET-$3^b$-oxy(1-6C)alkyl, $AR1^b$-(1-6C)alkoxy(1-6C)alkyl, HET-$1^b$-(1-6C)alkoxy(1-6C)alkyl, and HET-$3^b$-(1-6C)alkoxy(1-6C)alkyl;

wherein any phenyl, $AR^b$, HET-$1^b$, HET-$3^b$ or cycloalkyl ring in any of the above values for $R^{3a}$ may optionally be substituted by 1 or 2 substituents independently selected from $R^{7d}$;

and wherein any $R^{8a}$, or (1-6C)alkyl group in any of the above definitions for $R^{3a}$ may optionally be substituted by 1 or 2 substituents independently selected from (1-6C)alkyl, (1-6C)alkoxy, hydroxy, carboxy, $-C_6H_{(13-a)}F_a$ (wherein a is 1 to 13), (1-6C)alkylamino, di(1-6C)alkylamino, (1-6C)alkylsulfonyl, (1-6C)alkylaminosulfonyl, di(1-6C)alkylaminosulfonyl, (1-6C)alkylsulfonylamino, aminocarbonyl, (1-6C)alkylaminocarbonyl, di(1-6C)alkylaminocarbonyl, (1-6C)alkylcarbonylamino, (1-6C)alkoxycarbonylamino; and/or any $R^{8a}$, or (1-6C)alkyl group in any of the above definitions for $R^{3a}$ may optionally be substituted by 1, 2 or 3 halo;

$R^{2b}$ is:

a) a 6-membered ring selected from phenyl, 3-pyridyl and 3,5-pyrimidinyl; substituted in the which is para to the linkage of the group —Y—NH— by a group selected from $R^{4a}$ and optionally additionally substituted on a carbon atom in one or both 3-positions (where possible) by 1 or 2 groups independently selected from $R^{6a}$;

$R^{4a}$ is selected from:

a) phenyl;

b) HET-$3^c$ (wherein any available nitrogen atom is substituted by $R^{5a}$ provided it is not thereby quaternised);

c) HET-$1^c$;

d) phenoxy, HET-$1^c$-oxy, $R^{8b}O$—, phenyl(1-6C)alkoxy and HET-$1^c$-(1-6C)alkoxy;

e) $R^{8b}$, $R^{8b}O$(1-6C)alkyl, amino(1-6C)alkyl, hydroxy(1-6C)alkyl, phenoxy(1-6C)alkyl, HET-1'-oxy(1-6C)alkyl; and f) phenylamino, phenyl(1-6C)alkylamino, HET-$1^c$ amino, HET-$1^c$-(1-6C)alkylamino, (1-6C)alkylamino, N-phenyl-N-(1-6C)alkylamino, N-phenyl(1-6C)alkyl-N-(1-6C)alkylamin o, N-(HET-1$_c$)-N-(1-6C)alkylamino, N-(HET-1$^c$-(1-6C)alkyl)-N-(1-6C)alkylamino, and di(1-6C)alkylamino;

wherein any alkyl, R$^{8b}$, phenyl, HET-1$^c$ or HET-3$^c$ ring in any of the definitions a) to f) for R$^{4a}$ may optionally be substituted by 1 or 2 substituents independently selected from R$^{7e}$;

R$^{5a}$ is selected from (1-6C)alkyl, (3-8C)cycloalkyl, phenyl (optionally substituted with 1 or 2 halo), HET-1$^d$, R$^{8c}$CO—, phenylcarbonyl (wherein the phenyl is optionally substituted with 1 or 2 halo), HET-1$^d$-carbonyl, (1-6C)alkoxycarbonyl, R$^{8c}$NHCO—, (1-6C)alkoxysulfonyl, (1-6C)alkylaminosulfonyl, (1-6C)alkylsulfinyl and (1-6C)alkylsulfonyl; wherein any (1-6C)alkyl group in any of the definitions of R$^{5a}$ may optionally be substituted by a substituent selected from (1-6C)alkoxy, (1-6C)alkylS(O)p- (wherein p' is 0, 1 or 2), amino, (1-6C)alkylamino, hydroxy, carboxy, phenyl (optionally substituted with 1 or 2 halo) and HET-1$^f$;

R$^{6c}$ and R$^{6d}$ are independently selected from R$^{8d}$, R$^{8d}$O—, R$^{8d}$OCO—, R$^{8d}$COO—, halo, cyano, halo(1-6C)alkyl, dihalo(1-6C)alkyl, (1-6C)alkoxy(1-6C)alkyl, (1-6C)alkoxy (1-6C)alkoxy, (1-6C)alkylcarbonyl and (1-6C)alkylS (O)p- (wherein p is 0, 1 or 2), wherein any alkyl or R$^{8d}$ in any of the above values for R$^{6c}$ or R$^{6d}$ may optionally be substituted by 1, 2 or 3 substituents independently selected from R$^{7f}$;

R$^{7d}$, R$^{7e}$ and R$^{7f}$ are independently selected from R$^{8e}$ (optionally substituted with 1, 2 or 3 halo or with hydroxy), R$^{8e}$O— (optionally substituted with 1, 2 or 3 halo), halo, cyano, carboxy, carboxy(1-6C)alkyl, hydroxy, aminocarbonyl, —C$_6$H$_{(13-a)}$F$_a$ (wherein a is 1 to 13), —OC$_6$H$_{(13-a)}$F$_a$ (wherein a is 1 to 13), R$^{8e}$S(O)p"- (wherein p" is 0, 1 or 2);

each R$^{8a}$, R$^{8b}$, R$^{8c}$, R$^{8d}$, R$^{8e}$ or R$^{5f}$ is selected from (1-6C)alkyl;

each AR$^a$, AR1$^b$ or AR1$^e$ is phenyl or a 6,5-, or 6,6-bicyclic fused ring system, wherein both rings are carbocyclic and wherein at least the ring attached to the linking nitrogen atom is fully aromatic;

each HET-1$^a$, HET-1$^b$, HET-1$^c$, HET-1$^d$, HET-1$^e$ or HET-1$^f$ is 5- or 6-membered heteroaryl ring containing 1, 2, or 3 heteroatoms independently selected from O, N and S (provided there are no O—O, S—S or O—S bonds), wherein any sulfur atom may optionally be oxidised to an SO or SO$_2$ group, and wherein any carbon atom may optionally be oxidised to a carbonyl group;

each HET-2$^a$ or HET-2$^b$ is a 5,5-, 5,6-6,5- or 6,6-fused bicyclic, aromatic or partially saturated heterocyclic ring system, containing 1, 2, 3 or 4 heteroatoms independently selected from O, N and S (provided there are no O—O, S—S or O—S bonds), in which the ring directly attached to the linking nitrogen atom is aromatic, and either ring of the bicyclic ring system may be carbocyclic;

HET-3$^b$, HET-3$^c$ or HET-3$^e$ is independently selected from a partially or fully saturated 4-, 5-, 6- or 7 membered heterocyclic ring containing 1, 2, or 3 heteroatoms independently selected from O, N and S (provided there are no O—O, S—S or O—S bonds), wherein any sulfur atom may optionally be oxidised to an SO or SO$_2$ group, and wherein any carbon atom may optionally be oxidised to a carbonyl group; except that HET-3 HET-3$^c$ or HET-3$^e$ is not 3-oxomorpholin-4-yl.

In a further aspect of the invention there is provided a compound of the formula (IB") or a pharmaceutically-acceptable salt thereof, which is a compound of the formula (IB) as shown above, wherein:

R$^{1b}$ is selected from AR1$^a$, HET-1$^a$ and HET-2$^a$; wherein R$^{1b}$ is optionally substituted by 1, or 2 groups independently selected from R$^{3a}$;

R$^{3a}$ is selected from halo, R$^{8a}$, R$^{8a}$O—, R$^{8a}$OCO—, R$^{8a}$COO—, R$^{8a}$CO—, —C$_6$H$_{(13-a)}$F$_a$ (wherein a is 1 to 13), —OC$_6$H$_{(13-a)}$F$_a$ (wherein a is 1 to 13), (1-6C)alkylthio, di(1-6C)alkylaminocarbonyl, phenyl, HET-1$^b$, AR1$^b$-(1-6C)alkoxy, HET-1$^b$-(1-6C)alkoxy, wherein any R$^{8a}$, or (1-6C)alkyl group in any of the above definitions for R$^{3a}$ may optionally be substituted by 1 or 2 substituents independently selected from (1-6C)alkoxy, hydroxy, carboxy, —C$_6$H$_{(13-a)}$F$_a$ (wherein a is 1 to 13); and/or by 1, 2 or 3 halo;

R$^{2b}$ is phenyl or 3-pyridyl; substituted in the position which is para to the linkage with the group Y—NH— by a group selected from R$^{4a}$ and optionally additionally substituted on a carbon atom in one or both meta positions with respect to the linkage with the group —Y—NH— (where possible) by 1 or 2 groups independently selected from R$^{6d}$;

R$^{4a}$ is selected from:

a) phenyl;

b) HET-3$^c$ (wherein any available nitrogen atom is substituted by R$^a$ provided it is not thereby quaternised);

d) phenoxy, HET-1$^c$-oxy, R$^{8b}$O—, phenyl(1-6C)alkoxy and HET-1$^c$-(1-6C)alkoxy;

e) R$^{8b}$, R$^{8b}$O(1-6C)alkyl, hydroxy(1-6C)alkyl; and f) phenylamino, phenyl(1-6C)alkylamino, HET-1$^c$-amino, HET-1$^c$-(1-6C)alkylamino, (1-6C)alkylamino, N-phenyl-N-(1-6C)alkylamino and di(1-6C)alkylamino;

R$^{5a}$ is selected from (1-6C)alkyl, phenyl (optionally substituted with 1 or 2 halo), HET-1$^d$, R$^{8c}$CO—, phenylcarbonyl (wherein the phenyl is optionally substituted with 1 or 2 halo), HET-1$^d$-carbonyl, (1-6C)alkoxycarbonyl, R$^{8c}$NHCO—, (1-6C)alkoxysulfonyl, (1-6C)alkylaminosulfonyl, and (1-6C)alkylsulfonyl; wherein any (1-6C)alkyl group in any of the definitions of R$^{5a}$ may optionally be substituted by a substituent selected from (1-6C)alkoxy, (1-6C)alkylS(O)p- (wherein p' is 0, 1 or 2), amino, (1-6C)alkylamino, hydroxy, carboxy, phenyl (optionally substituted with 1 or 2 halo) and HET-1$^f$;

R$^{6d}$ is selected from R$^{8d}$, halo and cyano;

R$^{8a}$, R$^{8b}$, R$^{8c}$ or R$^{8d}$ is (1-6C)alkyl;

AR1$^a$ or AR1$^b$ is phenyl or a 6,5-, or 6,6-bicyclic fused ring system, wherein both rings are carbocyclic and wherein at least the ring attached to the linking nitrogen atom is fully aromatic;

HET-1$^a$, HET-1$^b$, HET-1$^b$, HET-1$^d$ or HET-1$^f$ is 5- or 6-membered heteroaryl ring containing 1, 2, or 3 heteroatoms independently selected from O, N and S (provided there are no O—O, S—S or O—S bonds), wherein any sulfur atom may optionally be oxidised to an SO or SO$_2$ group, and wherein any carbon atom may optionally be oxidised to a carbonyl group;

HET-2$^a$ is a 5,5-, 5,6-6,5- or 6,6-fused bicyclic, aromatic or partially saturated heterocyclic ring system, containing 1, 2, 3 or 4 heteroatoms independently selected from O, N and S (provided there are no O—O, S—S or O—S bonds), in which the ring directly attached to the linking nitrogen atom is aromatic, and either ring of the bicyclic ring system may be carbocyclic;

HET-3$^c$ is a partially or fully saturated 5- or 6-membered heterocyclic ring containing 1, 2, or 3 heteroatoms independently selected from O, N and S (provided there are no O—O, S—S or O—S bonds), wherein any sulfur atom may optionally be oxidised to an SO or SO$_2$ group, and wherein any carbon atom may optionally be oxidised to a carbonyl group; except that HET-3 is not 3-oxomorpholin-4-yl.

In a further aspect of the invention there is provided a compound of the formula (IB''') or a pharmaceutically-acceptable salt thereof, which is a compound of the formula (IB) as shown above, wherein:

$R^{1b}$ is selected from AR1$^a$ and HET-2$^a$; wherein $R^{1b}$ is optionally substituted by 1 or 2 groups independently selected from $R^{3a}$;

$R^{3a}$ is selected from halo, $R^{8a}$, $R^{8a}O$—, $R^{8a}OCO$—, —$C_6H_{(13-a)}F_a$ (wherein a is 1 to 13), and (1-6C)alkylthio;

$R^{2b}$ is phenyl or 3-pyridyl; substituted in the position which is para to the linkage with the group —Y—NH— by a group selected from $R^{4a}$ and optionally additionally substituted on a carbon atom in one or both of the positions which are meta to the linkage with the group —Y—NH— (where possible) by 1 or 2 groups independently selected from $R^{6c}$;

$R^{4a}$ is selected from:

a) phenyl;

b) HET-3$^c$ (wherein any available nitrogen atom is substituted by $R^{5a}$ provided it is not thereby quaternised);

d) phenoxy, HET-1'-oxy, $R^{8b}O$—, phenyl(1-6C)alkoxy and HET-1$^c$-(1-6C)alkoxy;

e) $R^{8b}$ and hydroxy(1-6C)alkyl; and f) phenylamino and N-phenyl-N-(1-6C)alkylamino;

$R^{5a}$ is selected from (1-6C)alkyl, benzyl, HET-1$^d$, $R^{8c}CO$—, phenylcarbonyl (wherein the phenyl is optionally substituted with 1 or 2 halo), HET-1$^d$-carbonyl, (1-6C)alkoxycarbonyl and (1-6C)alkylsulfonyl;

$R^{6e}$ is selected from $R^{8d}$, halo and cyano;

$R^{8a}$, $R^{8b}$, $R^{8c}$ and $R^{8d}$ are independently selected from (1-6C)alkyl, AR1$^a$ is selected from phenyl, naphthyl, indenyl and dihydroindenyl;

HET-1$^c$ or HET-1$^d$ is pyridyl;

HET-2$^a$ is 1,3-benzodioxolyl; HET-3' is selected from morpholino, morpholinyl, piperazinyl and piperidinyl.

In a further aspect of the invention there is provided a compound of the formula (IB'''), or a pharmaceutically-acceptable salt thereof, which is a compound of the formula (IB) as shown above, wherein $R^{1b}$ is selected from phenyl, 1-naphthyl and 2-napthyl, optionally selected with 1, 2 or 3 fluoro;

$R^{2b}$ is phenyl or pyridyl; substituted as described by a group $R^{4a}$ and a group $R^{6c}$ $R^{6c}$ is halo, preferably fluoro or chloro;

$R^{4a}$ is morpholino, acylpiperazinyl or phenyl.

In a further aspect of the invention there is provided a compound of the formula (IB''''), or a pharmaceutically-acceptable salt thereof, which is a compound of the formula (IB) as shown above, wherein $R^{1b}$ is selected from phenyl, 1-naphthyl and 2-napthyl, optionally substituted with 1, 2 or 3 fluoro;

$R^{2b}$ is phenyl or pyridyl; substituted as described by a group $R^{4a}$ and a group $R^{6c}$ $R^{6c}$ is halo, preferably fluoro or chloro;

$R^{4a}$ is morpholino or acylpiperazinyl.

Preferred compounds of the invention are any one of the following, or their pharmaceutical acceptable salts and/or pro-drugs thereof:

N-[4-(4-morpholinyl)phenyl]-5-[[3-(phenylmethoxy)phenyl]amino]-1,3,4-oxadiazole-2-carboxamide;

5-[(4-chloro-3-methylphenyl)amino]-N-[4-(4-morpholinyl)phenyl]-1,3,4-oxadiazole-2-carboxamide;

5-[(4-chlorophenyl)amino]-N-[4-(4-morpholinyl)phenyl]-1,3,4-oxadiazole-2-carboxamide;

5-[(2,3-dihydro-1H-inden-5-yl)amino]-N-[4-(4-morpholinyl)phenyl]-1,3,4-oxadiazole-2-carboxamide;

5-[(3-methylphenyl)amino]-N-[4-(4-morpholinyl)phenyl]-1,3,4-oxadiazole-2-carboxamide;

N-[4-(4-morpholinyl)phenyl]-5-(1-naphthalenylamino)-1,3,4-oxadiazole-2-carboxamide;

5-[(3,4-difluorophenyl)amino]-N-[4-(4-morpholinyl)phenyl]-1,3,4-oxadiazole-2-carboxamide;

3-[[5-[[[4-(4-morpholinyl)phenyl]amino]carbonyl]-1,3,4-oxadiazol-2-yl]amino]-benzoic acid, ethyl ester;

5-[(3-ethylphenyl)amino]-N-[4-(4-morpholinyl)phenyl]-1,3,4-oxadiazole-2-carboxamide;

5-[(3-chlorophenyl)amino]-N-[4-(4-morpholinyl)phenyl]-1,3,4-oxadiazole-2-carboxamide;

N-[4-(4-morpholinyl)phenyl]-5-(2-naphthalenylamino)-1,3,4-oxadiazole-2-carboxamide;

5-[(3-bromophenyl)amino]-N-[4-(4-morpholinyl)phenyl]-1,3,4-oxadiazole-2-carboxamide;

5-[(3,4-dimethylphenyl)amino]-N-[4-(4-morpholinyl)phenyl]-1,3,4-oxadiazole-2-carboxamide;

5-[(3-chloro-4-methylphenyl)amino]-N-[4-(4-morpholinyl)phenyl]-1,3,4-oxadiazole-2-carboxamide, 5-[[3-(methylthio)phenyl]amino]-N-[4-(4-morpholinyl)phenyl]-1,3,4-oxadiazole-2-carboxamide, 5-[(4-fluoro-3-methylphenyl)amino]-N-[4-(4-morpholinyl)phenyl]-1,3,4-oxadiazole-2-carboxamide, 5-[(3,5-dimethylphenyl)amino]-N-[4-(4-morpholinyl)phenyl]-1,3,4-oxadiazole-2-carboxamide, 5-[(2,5-difluorophenyl)amino]-N-[4-(4-morpholinyl)phenyl]-1,3,4-oxadiazole-2-carboxamide, 5-[(2,3-difluorophenyl)amino]-N-[4-(4-morpholinyl)phenyl]-1,3,4-oxadiazole-2-carboxamide, 5-[(2,4-difluorophenyl)amino]-N-[4-(4-morpholinyl)phenyl]-1,3,4-oxadiazole-2-carboxamide;

5-[[4-(1-dimethylethyl)phenyl]amino]-N-[4-(4-morpholinyl)phenyl]-1,3,4-oxadiazole-2-carboxamide;

5-[(4-methylphenyl)amino]-N-[4-(4-morpholinyl)phenyl]-1,3,4-oxadiazole-2-carboxamide;

N-[4-(4-morpholinyl)phenyl]-5-(phenylamino)-1,3,4-oxadiazole-2-carboxamide;

N-[4-(4-morpholinyl)phenyl]-5-[[3-(trifluoromethyl)phenyl]amino]-1,3,4-oxadiazole-2-carboxamide;

5-[(4-fluorophenyl)amino]-N-[4-(4-morpholinyl)phenyl]-1,3,4-oxadiazole-2-carboxamide;

5-[(2-chlorophenyl)amino]-N-[4-(4-morpholinyl)phenyl]-1,3,4-oxadiazole-2-carboxamide;

5-[(2-chloro-4-methylphenyl)amino]-N-[4-(4-morpholinyl)phenyl]-1,3,4-oxadiazole-2-carboxamide;

5-[(2,3-dimethylphenyl)amino]-N-[4-(4-morpholinyl)phenyl]-1,3,4-oxadiazole-2-carboxamide;

5-[(2-fluorophenyl)amino]-N-[4-(4-morpholinyl)phenyl]-1,3,4-oxadiazole-2-carboxamide;

5-[(2-methylphenyl)amino]-N-[4-(4-morpholinyl)phenyl]-1,3,4-oxadiazole-2-carboxamide;

5-[(3-fluorophenyl)amino]-N-[4-(4-morpholinyl)phenyl]-1,3,4-oxadiazole-2-carboxamide;

5-[[2-(1-methylethyl)phenyl]amino]-N-[4-(4-morpholinyl)phenyl]-1,3,4-oxadiazole-2-carboxamide;

5-[(4-methoxyphenyl)amino]-N-[4-(4-morpholinyl)phenyl]-1,3,4-oxadiazole-2-carboxamide;

5-(1,3-benzodioxol-5-ylamino)-N-[4-(4-morpholinyl)phenyl]-1,3,4-oxadiazole-2-carboxamide;

5-[(2-iodophenyl)amino]-N-[4-(4-morpholinyl)phenyl]-1,3,4-oxadiazole-2-carboxamide;
N-[3-chloro-4-(4-morpholinyl)phenyl]-5-[(3-methylphenyl)amino]-1,3,4-oxadiazole-2-carboxamide;
N-[3-fluoro-4-(4-morpholinyl)phenyl]-5-(1-naphthalenylamino)-1,3,4-oxadiazole-2-carboxamide;
N-[3-chloro-4-(4-morpholinyl)phenyl]-5-(1-naphthalenylamino)-1,3,4-oxadiazole-2-carboxamide;
5-[(3,4-difluorophenyl)amino]-N-[3-methyl-4-(4-morpholinyl)phenyl]-1,3,4-oxadiazole-2-carboxamide;
N-[3-methyl-4-(4-morpholinyl)phenyl]-5-[(3-methylphenyl)amino]-1,3,4-oxadiazole-2-carboxamide;
N-[3-fluoro-4-(4-morpholinyl)phenyl]-5-[(3-methylphenyl)amino]-1,3,4-oxadiazole-2-carboxamide,
N-[3-chloro-4-(4-morpholinyl)phenyl]-5-[(2-fluorophenyl)amino]-1,3,4-oxadiazole-2-carboxamide,
N-[3-fluoro-4-(4-morpholinyl)phenyl]-5-[(2-fluorophenyl)amino]-1,3,4-oxadiazole-2-carboxamide;
5-[(2-fluorophenyl)amino]-N-[3-methyl-4-(4-morpholinyl)phenyl]-1,3,4-oxadiazole-2-carboxamide;
N-[3-cyano-4-(4-morpholinyl)phenyl]-5-(1-naphthalenylamino)-1,3,4-oxadiazole-2-carboxamide;
5-[(2,5-difluorophenyl)amino]-N-[6-(4-morpholinyl)-3-pyridinyl]-1,3,4-oxadiazole-2-carboxamide;
N-[6-(4-morpholinyl)-3-pyridinyl]-5-(1-naphthalenylamino)-1,3,4-oxadiazole-2-carboxamide;
5-[(2-fluorophenyl)amino]-N-[6-(4-morpholinyl)-3-pyridinyl]-1,3,4-oxadiazole-2-carboxamide;
5-[(3-fluorophenyl)amino]-N-[6-(4-morpholinyl)-3-pyridinyl]-1,3,4-oxadiazole-2-carboxamide;
5-[(3-methylphenyl)amino]-N-[6-(4-morpholinyl)-3-pyridinyl]-1,3,4-oxadiazole-2-carboxamide;
5-[[4-(1,1-dimethylethyl)phenyl]amino]-N-[6-(4-morpholinyl)-3-pyridinyl]-1,3,4-oxadiazole-2-carboxamide;
5-[(3-chlorophenyl)amino]-N-[6-(4-morpholinyl)-3-pyridinyl]-1,3,4-oxadiazole-2-carboxamide;
N-[6-(4-morpholinyl)-3-pyridinyl]-5-(2-naphthalenylamino)-1,3,4-oxadiazole-2-carboxamide;
N-[5-chloro-6-(4-morpholinyl)-3-pyridinyl]-5-[(3,4-difluorophenyl)amino]-1,3,4-oxadiazole-2-carboxamide;
5-[(4-chlorophenyl)amino]-N-[6-(4-morpholinyl)-3-pyridinyl]-1,3,4-oxadiazole-2-carboxamide;
N-[5-chloro-6-(4-morpholinyl)-3-pyridinyl]-5-[(2-fluorophenyl)amino]-1,3,4-oxadiazole-2-carboxamide;
5-[(3,4-difluorophenyl)amino]-N-[6-(4-morpholinyl)-3-pyridinyl]-1,3,4-oxadiazole-2-carboxamide;
5-[(3-bromophenyl)amino]-N-[6-(4-morpholinyl)-3-pyridinyl]-1,3,4-oxadiazole-2-carboxamide;
5-[(2,3-difluorophenyl)amino]-N-[6-(4-morpholinyl)-3-pyridinyl]-1,3,4-oxadiazole-2-carboxamide;
N-[5-chloro-6-(4-morpholinyl)-3-pyridinyl]-5-[(3-methylphenyl)amino]-1,3,4-oxadiazole-2-carboxamide;
5-[(4-methylphenyl)amino]-N-[6-(4-morpholinyl)-3-pyridinyl]-1,3,4-oxadiazole-2-carboxamide;
5-[(4-fluorophenyl)amino]-N-[6-(4-morpholinyl)-3-pyridinyl]-1,3,4-oxadiazole-2-carboxamide;
N-[6-(4-morpholinyl)-3-pyridinyl]-5-(phenylamino)-1,3,4-oxadiazole-2-carboxamide;
5-(1,3-benzodioxol-5-ylamino)-N-[6-(4-morpholinyl)-3-pyridinyl]-1,3,4-oxadiazole-2-carboxamide;
5-[(3-methoxyphenyl)amino]-N-[6-(4-morpholinyl)-3-pyridinyl]-1,3,4-oxadiazole-2-carboxamide;
5-[(2,4-difluorophenyl)amino]-N-[6-(4-morpholinyl)-3-pyridinyl]-1,3,4-oxadiazole-2-carboxamide;
N-[4-(4-acetyl-1-piperazinyl)phenyl]-5-[(3-methylphenyl)amino]-1,3,4-oxadiazole-2-carboxamide;
N-[4-(4-acetyl-1-piperazinyl)phenyl]-5-(1-naphthalenylamino)-1,3,4-oxadiazole-2-carboxamide;
N-[4-(4-methyl-1-piperazinyl)phenyl]-5-(1-naphthalenylamino)-1,3,4-oxadiazole-2-carboxamide;
N-[4-(4-acetyl-1-piperazinyl)phenyl]-5-[(2-fluorophenyl)amino]-1,3,4-oxadiazole-2-carboxamide;
N-[4-(4-acetyl-1-piperazinyl)-3-methylphenyl]-5-[(3,4-difluorophenyl)amino]-1,3,4-oxadiazole-2-carboxamide;
5-[(2-fluorophenyl)amino]-N-[4-[4-(1-methylethyl)-1-piperazinyl]phenyl]-1,3,4-oxadiazole-2-carboxamide;
5-[(3-methylphenyl)amino]-N-[4-(4-methyl-1-piperazinyl)phenyl]-1,3,4-oxadiazole-2-carboxamide;
N-[4-(4-acetyl-1-piperazinyl)-3-methylphenyl]-5-[(3-methylphenyl)amino]-1,3,4-oxadiazole-2-carboxamide;
4-[2-fluoro-4-[[[5-(1-naphthalenylamino)-1,3,4-oxadiazol-2-yl]carbonyl]amino]phenyl]-1-piperazinecarboxylic acid, 1,1-dimethylethyl ester;
5-[(2-fluorophenyl)amino]-N-[4-[4-(phenylmethyl)-1-piperazinyl]phenyl]-1,3,4-oxadiazole-2-carboxamide;
N-[4-(4-acetyl-1-piperazinyl)-3-methylphenyl]-5-[(2-fluorophenyl)amino]-1,3,4-oxadiazole-2-carboxamide;
4-[2-fluoro-4-[[[5-[(2-fluorophenyl)amino]-1,3,4-oxadiazol-2-yl]carbonyl]amino]phenyl]-1-piperazinecarboxylic acid, 1,1-dimethylethyl ester;
5-[(2-fluorophenyl)amino]-N-[4-(4-methyl-1-piperazinyl)phenyl]-1,3,4-oxadiazole-2-carboxamide;
4-[4-[[[5-[(2-fluorophenyl)amino]-1,3,4-oxadiazol-2-yl]carbonyl]amino]phenyl]-1-piperazinecarboxylic acid, 1,1-dimethylethyl ester;
5-[(2-fluorophenyl)amino]-N-[4-[4-(4-pyridinyl)-1-piperazinyl]phenyl]-1,3,4-oxadiazole-2-carboxamide;
5-(1-naphthalenylamino)-N-[4-(1-piperidinyl)phenyl]-1,3,4-oxadiazole-2-carboxamide;
5-[(3-methylphenyl)amino]-N-[4-(1-piperidinyl)phenyl]-1,3,4-oxadiazole-2-carboxamide;
5-[(2-fluorophenyl)amino]-N-[4-(1-piperidinyl)phenyl]-1,3,4-oxadiazole-2-carboxamide;
N-[6-(4-methyl-1-piperazinyl)-3-pyridinyl]-5-(1-naphthalenylamino)-1,3,4-oxadiazole-2-carboxamide;
5-[(3-methylphenyl)amino]-N-[6-(4-methyl-1-piperazinyl)-3-pyridinyl]-1,3,4-oxadiazole-2-carboxamide;
N-[6-(4-benzoyl-1-piperazinyl)-3-pyridinyl]-5-[(2-fluorophenyl)amino]-1,3,4-oxadiazole-2-carboxamide;
N-[6-[4-(3-fluorobenzoyl)-1-piperazinyl]-3-pyridinyl]-5-[(2-fluorophenyl)amino]-1,3,4-oxadiazole-2-carboxamide;
5-[(2-fluorophenyl)amino]-N-[6-[4-(methylsulfonyl)-1-piperazinyl]-3-pyridinyl]-1,3,4-oxadiazole-2-carboxamide;
N-[6-[4-(4-fluorobenzoyl)-1-piperazinyl]-3-pyridinyl]-5-[(2-fluorophenyl)amino]1,3,4-oxadiazole-2-carboxamide;
5-[(2-fluorophenyl)amino]-N-[6-(4-methyl-1-piperazinyl)-3-pyridinyl]-1,3,4-oxadiazole-2-carboxamide;
4-[5-[[[5-[(2-fluorophenyl)amino]-1,3,4-oxadiazol-2-yl]carbonyl]amino]-2-pyridinyl]-1-piperazinecarboxylic acid, 1,1-dimethylethyl ester;
N-[6-(4-acetyl-1-piperazinyl)-3-pyridinyl]-5-[(2-fluorophenyl)amino]-1,3,4-oxadiazole-2-carboxamide;
5-[(2-fluorophenyl)amino]-N-[6-[4-(4-pyridinylcarbonyl)-1-piperazinyl]-3-pyridinyl]-1,3,4-oxadiazole-2-carboxamide;
5-[(2-fluorophenyl)amino]-N-(6-phenoxy-3-pyridinyl)-1,3,4-oxadiazole-2-carboxamide;
5-[(2-fluorophenyl)amino]-N-[6-(phenylamino)-3-pyridinyl]-1,3,4-oxadiazole-2-carboxamide;
N-(6-butoxy-3-pyridinyl)-5-[(2-fluorophenyl)amino]-1,3,4-oxadiazole-2-carboxamide;

5-[(2-fluorophenyl)amino]-N-[6-(3-pyridinyloxy)-3-pyridinyl]-1,3,4-oxadiazole-2-carboxamide;
5-[(2-fluorophenyl)amino]-N-[6-(4-hydroxybutyl)-3-pyridinyl]-1,3,4-oxadiazole-2-carboxamide;
5-[(2-fluorophenyl)amino]-N-[4-(phenylmethoxy)phenyl]-1,3,4-oxadiazole-2-carboxamide;
N-(4-butylphenyl)-5-[(2-fluorophenyl)amino]-1,3,4-oxadiazole-2-carboxamide;
5-[(2-fluorophenyl)amino]-N-[4-(2-pyridinylmethoxy)phenyl]-1,3,4-oxadiazole-2-carboxamide;
5-[(2-fluorophenyl)amino]-N-[4-(methylphenylamino)phenyl]-1,3,4-oxadiazole-2-carboxamide;
N-[1,1'-biphenyl]-4-yl-5-[(2-fluorophenyl)amino]-1,3,4-oxadiazole-2-carboxamide; and/or methyl {trans-4-[4-({[5-(pyridin-2-ylamino)-1,3,4-oxadiazol-2-yl]carbonyl}amino)phenyl]cyclohexyl}acetate;
methyl (trans-4-{4-[({5-[(3-ethoxyphenyl)amino]-1,3,4-oxadiazol-2-yl}carbonyl)amino]phenyl}cyclohexyl)acetate;
methyl [trans-4-(4-{[(5-{[3-(benzyloxy)phenyl]amino}-1,3,4-oxadiazol-2-yl)carbonyl]amino}phenyl)cyclohexyl]acetate;
methyl (trans-4-{4-[({5-[(4-chlorophenyl)amino]-1,3,4-oxadiazol-2-yl}carbonyl)amino]phenyl}cyclohexyl)acetate;
methyl (trans-4-{4-[({5-[(2,4,5-trifluorophenyl)amino]-1,3,4-oxadiazol-2-yl}carbonyl)amino]phenyl}cyclohexyl)acetate;
methyl trans-4-{-4-[({5-[(2-fluorophenyl)amino]-1,3,4-oxadiazol-2-yl}carbonyl)amino]phenyl}cyclohexanecarboxylate;
methyl (trans-4-{4-[({5-[(2-fluorophenyl)amino]-1,3,4-oxadiazol-2-yl}carbonyl)amino]phenyl}cyclohexyl)acetate;
{trans-4-[4-({[5-(pyridin-2-ylamino)-1,3,4-oxadiazol-2-yl]carbonyl}amino)phenyl]cyclohexyl}acetic acid;
(trans-4-{4-[({5-[(3-ethoxyphenyl)amino]-1,3,4-oxadiazol-2-yl}carbonyl)amino]phenyl}cyclohexyl)acetic acid;
[trans-4-(4-{[(5-{[3-(benzyloxy)phenyl]amino}-1,3,4-oxadiazol-2-yl)carbonyl]amino}phenyl)cyclohexyl]acetic acid;
(trans-4-{4-[({5-[(4-chlorophenyl)amino]-1,3,4-oxadiazol-2-yl}carbonyl)amino]phenyl}cyclohexyl)acetic acid;
sodium (trans-4-{4-[({5-[(2,4,5-trifluorophenyl)amino]-1,3,4-oxadiazol-2-yl}carbonyl)amino]phenyl}cyclohexyl)acetate;
trans-4-{4-[({5-[(2-fluorophenyl)amino]-1,3,4-oxadiazol-2-yl}carbonyl)amino]phenyl}cyclohexanecarboxylic acid;
(trans-4-{4-[({5-[(2-fluorophenyl)amino]-1,3,4-oxadiazol-2-yl}carbonyl)amino]phenyl}cyclohexyl)acetic acid;
5-[(2-fluorophenyl)amino]-N-{4-[4-(2-hydroxyethyl)cyclohexyl]phenyl}-1,3,4-oxadiazole-2-carboxamide;
N-{4-[trans-4-(2-amino-2-oxoethyl)cyclohexyl]phenyl}-5-[(3-ethoxyphenyl)amino]-1,3,4-oxadiazole-2-carboxamide;
5-[(2-fluorophenyl)amino]-N-(3-phenoxypropyl)-1,3,4-oxadiazole-2-carboxamide;
5-[(3-methylphenyl)amino]-N-(3-phenoxypropyl)-1,3,4-oxadiazole-2-carboxamide;
5-{[3-(benzyloxy)phenyl]amino}-N-(3-phenoxypropyl)-1,3,4-oxadiazole-2-carboxamide;
N-(4-cyclohexylphenyl)-5-[(2-fluorophenyl)amino]-1,3,4-oxadiazole-2-carboxamide;
N-(4-cyclohexylphenyl)-5-[(3,4-difluorophenyl)amino]-1,3,4-oxadiazole-2-carboxamide;
5-{[3-(benzyloxy)phenyl]amino}-N-(4-cyclohexylphenyl)-1,3,4-oxadiazole-2-carboxamide;
N-[4-(4-acetylpiperazin-1-yl)phenyl]-5-[(3-isopropoxyphenyl)amino]-1,3,4-oxadiazole-2-carboxamide;
N-[4-(4-acetylpiperazin-1-yl)phenyl]-5-{[4-(methylthio)phenyl]amino}-1,3,4-oxadiazole-2-carboxamide;
N-[4-(4-acetylpiperazin-1-yl)phenyl]-5-{[4-(benzyloxy)phenyl]amino}-1,3,4-oxadiazole-2-carboxamide;
5-[(5-bromo-2,4-difluorophenyl)amino]-N-(4-morpholin-4-ylphenyl)-1,3,4-oxadiazole-2-carboxamide;
5-{[2,4-difluoro-5-(trifluoromethyl)phenyl]amino}-N-(6-morpholin-4-ylpyridin-3-yl)-1,3,4-oxadiazole-2-carboxamide;
N-(6-morpholin-4-ylpyridin-3-yl)-5-{[3-(trifluoromethyl)phenyl]amino}-1,3,4-oxadiazole-2-carboxamide;
5-[(4-methylpyridin-2-yl)amino]-N-(6-morpholin-4-ylpyridin-3-yl)-1,3,4-oxadiazole-2-carboxamide;
5-{[2-fluoro-5-(trifluoromethyl)phenyl]amino}-N-(4-morpholin-4-ylphenyl)-1,3,4-oxadiazole-2-carboxamide;
5-{[4-fluoro-3-(trifluoromethyl)phenyl]amino}-N-(4-morpholin-4-ylphenyl)-1,3,4-oxadiazole-2-carboxamide;
5-[(3-isopropoxyphenyl)amino]-N-(6-morpholin-4-ylpyridin-3-yl)-1,3,4-oxadiazole-2-carboxamide;
N-(6-morpholin-4-ylpyridin-3-yl)-5-[(3-phenoxyphenyl)amino]-1,3,4-oxadiazole-2-carboxamide;
N-(6-morpholin-4-ylpyridin-3-yl)-5-{[3-(trifluoromethoxy)phenyl]amino}-1,3,4-oxadiazole-2-carboxamide;
N-(6-morpholin-4-ylpyridin-3-yl)-5-{[3-(pyridin-2-ylmethoxy)phenyl]amino}-1,3,4-oxadiazole-2-carboxamide;
5-[(3-ethoxyphenyl)amino]-N-(6-morpholin-4-ylpyridin-3-yl)-1,3,4-oxadiazole-2-carboxamide;
N-[4-(4-acetylpiperazin-1-yl)phenyl]-5-[(3-ethoxyphenyl)amino]-1,3,4-oxadiazole-2-carboxamide;
5-(biphenyl-3-ylamino)-N-(6-morpholin-4-ylpyridin-3-yl)-1,3,4-oxadiazole-2-carboxamide;
5-{[3-(benzyloxy)phenyl]amino}-N-(6-morpholin-4-ylpyridin-3-yl)-1,3,4-oxadiazole-2-carboxamide;
ethyl 3-[(5-{[(6-morpholin-4-ylpyridin-3-yl)amino]carbonyl}-1,3,4-oxadiazol-2-yl)amino]benzoate;
tert-butyl 3-[(5-{[(6-morpholin-4-ylpyridin-3-yl)amino]carbonyl})-1,3,4-oxadiazol-2-yl)amino]benzoate;
5-[(3-iodophenyl)amino]-N-(6-morpholin-4-ylpyridin-3-yl)-1,3,4-oxadiazole-2-carboxamide;
N-(6-methoxypyridin-3-yl)-5-(1-naphthylamino)-1,3,4-oxadiazole-2-carboxamide;
N-(3-fluoro-4-morpholin-4-ylphenyl)-5-[(4-fluorophenyl)amino]-1,3,4-oxadiazole-2-carboxamide;
5-[(2,5-difluorophenyl)amino]-N-(3-fluoro-4-morpholin-4-ylphenyl)-1,3,4-oxadiazole-2-carboxamide;
5-anilino-N-(3-fluoro-4-morpholin-4-ylphenyl)-1,3,4-oxadiazole-2-carboxamide;
N-(3-fluoro-4-morpholin-4-ylphenyl)-5-[(3-fluorophenyl)amino]-1,3,4-oxadiazole-2-carboxamide;
N-(3-fluoro-4-morpholin-4-ylphenyl)-5-[(4-methylphenyl)amino]-1,3,4-oxadiazole-2-carboxamide;
5-[(2,4-difluorophenyl)amino]-N-(3-fluoro-4-morpholin-4-ylphenyl)-1,3,4-oxadiazole-2-carboxamide;
5-[(3-bromophenyl)amino]-N-(3-fluoro-4-morpholin-4-ylphenyl)-1,3,4-oxadiazole-2-carboxamide;
5-[(4-chlorophenyl)amino]-N-(3-fluoro-4-morpholin-4-ylphenyl)-1,3,4-oxadiazole-2-carboxamide;
N-(3-fluoro-4-morpholin-4-ylphenyl)-5-(2-naphthylamino)-1,3,4-oxadiazole-2-carboxamide;
5-[(3,4-difluorophenyl)amino]-N-(3-fluoro-4-morpholin-4-ylphenyl)-1,3,4-oxadiazole-2-carboxamide;
5-[(2,3-difluorophenyl)amino]-N-(3-fluoro-4-morpholin-4-ylphenyl)-1,3,4-oxadiazole-2-carboxamide;

ethyl 3-[(5-{[(3-fluoro-4-morpholin-4-ylphenyl)amino]carbonyl}-1,3,4-oxadiazol-2-yl)amino]benzoate;
N-(5-chloro-6-morpholin-4-ylpyridin-3-yl)-5-[(4-fluorophenyl)amino]-1,3,4-oxadiazole-2-carboxamide;
N-(5-chloro-6-morpholin-4-ylpyridin-3-yl)-5-[(2-methylphenyl)amino]-1,3,4-oxadiazole-2-carboxamide;
N-(5-chloro-6-morpholin-4-ylpyridin-3-yl)-5-[(3-chlorophenyl)amino]-1,3,4-oxadiazole-2-carboxamide;
N-(5-chloro-6-morpholin-4-ylpyridin-3-yl)-5-[(2-methoxyphenyl)amino]-1,3,4-oxadiazole-2-carboxamide;
N-(5-chloro-6-morpholin-4-ylpyridin-3-yl)-5-[(4-methoxyphenyl)amino]1,3,4-oxadiazole-2-carboxamide;
N-(5-chloro-6-morpholin-4-ylpyridin-3-yl)-5-[(2,5-difluorophenyl)amino]-1,3,4-oxadiazole-2-carboxamide;
5-anilino-N-(5-chloro-6-morpholin-4-ylpyridin-3-yl)-1,3,4-oxadiazole-2-carboxamide;
5-[(3-bromophenyl)amino]-N-(5-chloro-6-morpholin-4-ylpyridin-3-yl)-1,3,4-oxadiazole-2-carboxamide;
N-(5-chloro-6-morpholin-4-ylpyridin-3-yl)-5-[(3-fluorophenyl)amino]-1,3,4-oxadiazole-2-carboxamide;
N-(5-chloro-6-morpholin-4-ylpyridin-3-yl)-5-[(4-methylphenyl)amino]-1,3,4-oxadiazole-2-carboxamide;
N-(5-chloro-6-morpholin-4-ylpyridin-3-yl)-5-[(2,6-difluorophenyl)amino]-1,3,4-oxadiazole-2-carboxamide;
N-(5-chloro-6-morpholin-4-ylpyridin-3-yl)-5-[(2-chlorophenyl)amino]-1,3,4-oxadiazole-2-carboxamide;
N-(5-chloro-6-morpholin-4-ylpyridin-3-yl)-5-[(4-chlorophenyl)amino]-1,3,4-oxadiazole-2-carboxamide;
N-(5-chloro-6-morpholin-4-ylpyridin-3-yl)-5-(2-naphthylamino)-1,3,4-oxadiazole-2-carboxamide;
N-(5-chloro-6-morpholin-4-ylpyridin-3-yl)-5-[(3-methoxyphenyl)amino]-1,3,4-oxadiazole-2-carboxamide;
5-[(4-tert-butylphenyl)amino]-N-(5-chloro-6-morpholin-4-ylpyridin-3-yl)-1,3,4-oxadiazole-2-carboxamide;
N-(5-chloro-6-morpholin-4-ylpyridin-3-yl)-5-[(2,3-difluorophenyl)amino]-1,3,4-oxadiazole-2-carboxamide;
ethyl 3-[(5-{[(5-chloro-6-morpholin-4-ylpyridin-3-yl)amino]carbonyl}-1,3,4-oxadiazol-2-yl)amino]benzoate;
N-(5-chloro-6-morpholin-4-ylpyridin-3-yl)-5-(1-naphthylamino)-1,3,4-oxadiazole-2-carboxamide;
N-{4-[cis-2,6-dimethylmorpholin-4-yl]phenyl}-5-[(3-methylphenyl)amino]-1,3,4-oxadiazole-2-carboxamide;
5-[(3,4-difluorophenyl)amino]-N-{4-[cis-2,6-dimethylmorpholin-4-yl]phenyl}-1,3,4-oxadiazole-2-carboxamide;
N-[4-(4-acetyl-1,4-diazepan-1-yl)phenyl]-5-[(2-fluorophenyl)amino]-1,3,4-oxadiazole-2-carboxamide;
N-[4-(4-acetyl-1,4-diazepan-1-yl)phenyl]-5-[(3-methylphenyl)amino]-1,3,4-oxadiazole-2-carboxamide;
N-[4-(4-acetyl-1,4-diazepan-1-yl)phenyl]-5-[(3,4-difluorophenyl)amino]-1,3,4-oxadiazole-2-carboxamide;
N-[4-(4-acetyl-1,4-diazepan-1-yl)phenyl]-5-{[3-(benzyloxy)phenyl]amino}-1,3,4-oxadiazole-2-carboxamide;
N-[4-(4-acetyl-1,4-diazepan-1-yl)phenyl]-5-(1-naphthylamino)-1,3,4-oxadiazole-2-carboxamide;
N-[4-(4-acetyl-1,4-diazepan-1-yl)phenyl]-5-[(2,4,5-trifluorophenyl)amino]-1,3,4-oxadiazole-2-carboxamide;
N-[4-(4-acetyl-1,4-diazepan-1-yl)phenyl]-5-[(2,5-difluorophenyl)amino]-1,3,4-oxadiazole-2-carboxamide;
N-[2-(4-acetylpiperazin-1-yl)pyrimidin-5-yl]-5-{[3-(benzyloxy)phenyl]amino}-1,3,4-oxadiazole-2-carboxamide;
N-(2-methyl-1,3-benzothiazol-5-yl)-5-(1-naphthylamino)-1,3,4-oxadiazole-2-carboxamide;
N-[6-(4-acetylpiperazin-1-yl)pyridin-3-yl]-5-[(4-fluorophenyl)amino]-1,3,4-oxadiazole-2-carboxamide;
N-[6-(4-acetylpiperazin-1-yl)pyridin-3-yl]-5-[(3-chlorophenyl)amino]-1,3,4-oxadiazole-2-carboxamide;
N-[6-(4-acetylpiperazin-1-yl)pyridin-3-yl]-5-[(2,5-difluorophenyl)amino]-1,3,4-oxadiazole-2-carboxamide;
N-[6-(4-acetylpiperazin-1-yl)pyridin-3-yl]-5-anilino-1,3,4-oxadiazole-2-carboxamide;
N-[6-(4-acetylpiperazin-1-yl)pyridin-3-yl]-5-[(3-bromophenyl)amino]-1,3,4-oxadiazole-2-carboxamide;
N-[6-(4-acetylpiperazin-1-yl)pyridin-3-yl]-5-[(3-fluorophenyl)amino]-1,3,4-oxadiazole-2-carboxamide;
N-[6-(4-acetylpiperazin-1-yl)pyridin-3-yl]-5-[(4-methylphenyl)amino]-1,3,4-oxadiazole-2-carboxamide;
N-[6-(4-acetylpiperazin-1-yl)pyridin-3-yl]-5-[(2-chlorophenyl)amino]-1,3,4-oxadiazole-2-carboxamide;
N-[6-(4-acetylpiperazin-1-yl)pyridin-3-yl]-5-[(4-chlorophenyl)amino]-1,3,4-oxadiazole-2-carboxamide;
N-[6-(4-acetylpiperazin-1-yl)pyridin-3-yl]-5-(2-naphthylamino)-1,3,4-oxadiazole-2-carboxamide;
N-[6-(4-acetylpiperazin-1-yl)pyridin-3-yl]-5-(pyridin-2-ylamino)-1,3,4-oxadiazole-2-carboxamide;
ethyl 4-{[5-({[6-(4-acetylpiperazin-1-yl)pyridin-3-yl]amino}carbonyl)-1,3,4-oxadiazol-2-yl]amino}benzoate;
N-[6-(4-acetylpiperazin-1-yl)pyridin-3-yl]-5-(1,3-benzodioxol-5-ylamino)-1,3,4-oxadiazole-2-carboxamide;
N-[6-(4-acetylpiperazin-1-yl)pyridin-3-yl]-5-[(2,4-difluorophenyl)amino]-1,3,4-oxadiazole-2-carboxamide;
ethyl 3-{[5-({[6-(4-acetylpiperazin-1-yl)pyridin-3-yl]amino}carbonyl)-1,3,4-oxadiazol-2-yl]amino}benzoate;
N-[6-(4-acetylpiperazin-1-yl)pyridin-3-yl]-5-[(4-tert-butylphenyl)amino]-1,3,4-oxadiazole-2-carboxamide;
N-[6-(4-acetylpiperazin-1-yl)pyridin-3-yl]-5-[(3,4-difluorophenyl)amino]-1,3,4-oxadiazole-2-carboxamide;
N-[6-(4-acetylpiperazin-1-yl)pyridin-3-yl]-5-[(2,3-difluorophenyl)amino]-1,3,4-oxadiazole-2-carboxamide;
N-[6-(4-acetylpiperazin-1-yl)pyridin-3-yl]-5-[(3-methylphenyl)amino]-1,3,4-oxadiazole-2-carboxamide;
N-[6-(4-acetylpiperazin-1-yl)pyridin-3-yl]-5-{[3-(benzyloxy)phenyl]amino}-1,3,4-oxadiazole-2-carboxamide;
N-[6-(4-acetylpiperazin-1-yl)pyridin-3-yl]-5-[(3,5-difluorophenyl)amino]-1,3,4-oxadiazole-2-carboxamide;
N-[6-(4-acetylpiperazin-1-yl)pyridin-3-yl]-5-(1-naphthylamino)-1,3,4-oxadiazole-2-carboxamide;
N-[6-(4-acetylpiperazin-1-yl)pyridin-3-yl]-5-[(2,4,5-trifluorophenyl)amino]-1,3,4-oxadiazole-2-carboxamide;
N-[4-(4-acetylpiperazin-1-yl)phenyl]-5-[(4-fluorophenyl)amino]-1,3,4-oxadiazole-2-carboxamide;
N-[4-(4-acetylpiperazin-1-yl)phenyl]-5-[(3-chlorophenyl)amino]-1,3,4-oxadiazole-2-carboxamide;
N-[4-(4-acetylpiperazin-1-yl)phenyl]-5-[(2,5-difluorophenyl)amino]-1,3,4-oxadiazole-2-carboxamide;
N-[4-(4-acetylpiperazin-1-yl)phenyl]-5-anilino-1,3,4-oxadiazole-2-carboxamide;
N-[4-(4-acetylpiperazin-1-yl)phenyl]-5-[(3-bromophenyl)amino]-1,3,4-oxadiazole-2-carboxamide;
N-[4-(4-acetylpiperazin-1-yl)phenyl]-5-[(3-fluorophenyl)amino]-1,3,4-oxadiazole-2-carboxamide;
N-[4-(4-acetylpiperazin-1-yl)phenyl]-5-[(4-methylphenyl)amino]-1,3,4-oxadiazole-2-carboxamide;
N-[4-(4-acetylpiperazin-1-yl)phenyl]-5-[(2-chlorophenyl)amino]-1,3,4-oxadiazole-2-carboxamide;
N-[4-(4-acetylpiperazin-1-yl)phenyl]-5-[(4-chlorophenyl)amino]-1,3,4-oxadiazole-2-carboxamide;
N-[4-(4-acetylpiperazin-1-yl)phenyl]-5-(2-naphthylamino)-1,3,4-oxadiazole-2-carboxamide;
N-[4-(4-acetylpiperazin-1-yl)phenyl]-5-(1,3-benzodioxol-5-ylamino)-1,3,4-oxadiazole-2-carboxamide;
N-[4-(4-acetylpiperazin-1-yl)phenyl]-5-[(2,4-difluorophenyl)amino]-1,3,4-oxadiazole-2-carboxamide;

ethyl 3-{[5-({[4-(4-acetylpiperazin-1-yl)phenyl]amino}carbonyl)-1,3,4-oxadiazol-2-yl]amino}benzoate;
N-[4-(4-acetylpiperazin-1-yl)phenyl]-5-[(4-tert-butylphenyl)amino]-1,3,4-oxadiazole-2-carboxamide;
N-[4-(4-acetylpiperazin-1-yl)phenyl]-5-[(3,4-difluorophenyl)amino]-1,3,4-oxadiazole-2-carboxamide;
N-[4-(4-acetylpiperazin-1-yl)phenyl]-5-[(2,3-difluorophenyl)amino]-1,3,4-oxadiazole-2-carboxamide;
N-[4-(4-acetylpiperazin-1-yl)phenyl]-5-{[3-(benzyloxy)phenyl]amino}-1,3,4-oxadiazole-2-carboxamide;
N-[4-(4-acetylpiperazin-1-yl)phenyl]-5-[(3,5-difluorophenyl)amino]-1,3,4-oxadiazole-2-carboxamide;
N-[4-(4-acetylpiperazin-1-yl)phenyl]-5-[(2,4,5-trifluorophenyl)amino]-1,3,4-oxadiazole-2-carboxamide;
N-[4-(4-acetylpiperazin-1-yl)phenyl]-5-[(3-methoxyphenyl)amino]-1,3,4-oxadiazole-2-carboxamide;
N-[4-(4-acetylpiperazin-1-yl)phenyl]-5-[(4-methoxyphenyl)amino]-1,3,4-oxadiazole-2-carboxamide;
5-anilino-N-{6-[4-(methylsulfonyl)piperazin-1-yl]pyridin-3-yl}-1,3,4-oxadiazole-2-carboxamide;
5-[(4-chlorophenyl)amino]-N-{6-[4-(methylsulfonyl)piperazin-1-yl]pyridin-3-yl}-1,3,4-oxadiazole-2-carboxamide;
5-[(2,3-difluorophenyl)amino]-N-{6-[4-(methylsulfonyl)piperazin-1-yl]pyridin-3-yl}-1,3,4-oxadiazole-2-carboxamide;
5-{[3-(benzyloxy)phenyl]amino}-N-{6-[4-(methylsulfonyl)piperazin-1-yl]pyridin-3-yl}-1,3,4-oxadiazole-2-carboxamide;
5-[(2,4-difluorophenyl)amino]-N-{6-[4-(methylsulfonyl)piperazin-1-yl]pyridin-3-yl}-1,3,4-oxadiazole-2-carboxamide;
5-[(2,5-difluorophenyl)amino]-N-{6-[4-(methylsulfonyl)piperazin-1-yl]pyridin-3-yl}-1,3,4-oxadiazole-2-carboxamide;
5-[(3,5-difluorophenyl)amino]-N-{6-[4-(methylsulfonyl)piperazin-1-yl]pyridin-3-yl}-1,3,4-oxadiazole-2-carboxamide;
N-{6-[4-(methylsulfonyl)piperazin-1-yl]pyridin-3-yl}-5-(1-naphthylamino)-1,3,4-oxadiazole-2-carboxamide;
N-{6-[4-(methylsulfonyl)piperazin-1-yl]pyridin-3-yl}-5-(2-naphthylamino)-1,3,4-oxadiazole-2-carboxamide;
N-{6-[4-(methylsulfonyl)piperazin-1-yl]pyridin-3-yl}-5-[(2,4,5-trifluorophenyl)amino]-1,3,4-oxadiazole-2-carboxamide;
5-[(4-tert-butylphenyl)amino]-N-{6-[4-(methylsulfonyl)piperazin-1-yl]pyridin-3-yl}-1,3,4-oxadiazole-2-carboxamide;
ethyl 3-({5-[({6-[4-(methylsulfonyl)piperazin-1-yl]pyridin-3-yl}amino)carbonyl]-1,3,4-oxadiazol-2-yl}amino)benzoate;
N-{6-[4-(methylsulfonyl)piperazin-1-yl]pyridin-3-yl}-5-(pyridin-2-ylamino)-1,3,4-oxadiazole-2-carboxamide;
5-[(2,6-difluorophenyl)amino]-N-{6-[4-(methylsulfonyl)piperazin-1-yl]pyridin-3-yl}-1,3,4-oxadiazole-2-carboxamide;
5-anilino-N-(6-thiomorpholin-4-ylpyridin-3-yl)-1,3,4-oxadiazole-2-carboxamide;
5-[(2-methylphenyl)amino]-N-(6-thiomorpholin-4-ylpyridin-3-yl)-1,3,4-oxadiazole-2-carboxamide;
5-[(4-methylphenyl)amino]-N-(6-thiomorpholin-4-ylpyridin-3-yl)-1,3,4-oxadiazole-2-carboxamide;
5-[(3-fluorophenyl)amino]-N-(6-thiomorpholin-4-ylpyridin-3-yl)-1,3,4-oxadiazole-2-carboxamide;
5-[(4-fluorophenyl)amino]-N-(6-thiomorpholin-4-ylpyridin-3-yl)-1,3,4-oxadiazole-2-carboxamide;
5-[(2-methoxyphenyl)amino]-N-(6-thiomorpholin-4-ylpyridin-3-yl)-1,3,4-oxadiazole-2-carboxamide;
5-[(3-methoxyphenyl)amino]-N-(6-thiomorpholin-4-ylpyridin-3-yl)-1,3,4-oxadiazole-2-carboxamide;
5-[(4-methoxyphenyl)amino]-N-(6-thiomorpholin-4-ylpyridin-3-yl)-1,3,4-oxadiazole-2-carboxamide;
5-[(2-chlorophenyl)amino]-N-(6-thiomorpholin-4-ylpyridin-3-yl)-1,3,4-oxadiazole-2-carboxamide;
5-[(3-chlorophenyl)amino]-N-(6-thiomorpholin-4-ylpyridin-3-yl)-1,3,4-oxadiazole-2-carboxamide;
5-[(4-chlorophenyl)amino]-N-(6-thiomorpholin-4-ylpyridin-3-yl)-1,3,4-oxadiazole-2-carboxamide;
5-[(2,3-difluorophenyl)amino]-N-(6-thiomorpholin-4-ylpyridin-3-yl)-1,3,4-oxadiazole-2-carboxamide;
5-[(2,4-difluorophenyl)amino]-N-(6-thiomorpholin-4-ylpyridin-3-yl)-1,3,4-oxadiazole-2-carboxamide;
5-[(2,5-difluorophenyl)amino]-N-(6-thiomorpholin-4-ylpyridin-3-yl)-1,3,4-oxadiazole-2-carboxamide;
5-[(3,5-difluorophenyl)amino]-N-(6-thiomorpholin-4-ylpyridin-3-yl)-1,3,4-oxadiazole-2-carboxamide;
5-(1,3-benzodioxol-5-ylamino)-N-(6-thiomorpholin-4-ylpyridin-3-yl)-1,3,4-oxadiazole-2-carboxamide;
5-(1-naphthylamino)-N-(6-thiomorpholin-4-ylpyridin-3-yl)-1,3,4-oxadiazole-2-carboxamide;
5-(2-naphthylamino)-N-(6-thiomorpholin-4-ylpyridin-3-yl)-1,3,4-oxadiazole-2-carboxamide;
N-(6-thiomorpholin-4-ylpyridin-3-yl)-5-[(2,4,5-trifluorophenyl)amino]-1,3,4-oxadiazole-2-carboxamide;
5-[(4-tert-butylphenyl)amino]-N-(6-thiomorpholin-4-ylpyridin-3-yl)-1,3,4-oxadiazole-2-carboxamide;
5-[(3-bromophenyl)amino]-N-(6-thiomorpholin-4-ylpyridin-3-yl)-1,3,4-oxadiazole-2-carboxamide;
5-(pyridin-2-ylamino)-N-(6-thiomorpholin-4-ylpyridin-3-yl)-1,3,4-oxadiazole-2-carboxamide;
5-{[3-(benzyloxy)phenyl]amino}-N-(6-thiomorpholin-4-ylpyridin-3-yl)-1,3,4-oxadiazole-2-carboxamide;
ethyl 3-[(5-{[(6-thiomorpholin-4-ylpyridin-3-yl)amino]carbonyl}-1,3,4-oxadiazol-2-yl)amino]benzoate;
5-[(2-fluorophenyl)amino]-N-(6-thiomorpholin-4-ylpyridin-3-yl)-1,3,4-oxadiazole-2-carboxamide;
5-[(3,4-difluorophenyl)amino]-N-(6-thiomorpholin-4-ylpyridin-3-yl)-1,3,4-oxadiazole-2-carboxamide;
5-[(3-methylphenyl)amino]-N-(6-thiomorpholin-4-ylpyridin-3-yl)-1,3,4-oxadiazole-2-carboxamide;
5-[(4-fluorophenyl)amino]-N-[6-(4-methylpiperazin-1-yl)pyridin-3-yl]-1,3,4-oxadiazole-2-carboxamide;
5-[(3-chlorophenyl)amino]-N-[6-(4-methylpiperazin-1-yl)pyridin-3-yl]-1,3,4-oxadiazole-2-carboxamide;
5-[(2-methoxyphenyl)amino]-N-[6-(4-methylpiperazin-1-yl)pyridin-3-yl]-1,3,4-oxadiazole-2-carboxamide;
5-[(2,5-difluorophenyl)amino]-N-[6-(4-methylpiperazin-1-yl)pyridin-3-yl]-1,3,4-oxadiazole-2-carboxamide;
5-anilino-N-[6-(4-methylpiperazin-1-yl)pyridin-3-yl]-1,3,4-oxadiazole-2-carboxamide;
5-[(3-bromophenyl)amino]-N-[6-(4-methylpiperazin-1-yl)pyridin-3-yl]-1,3,4-oxadiazole-2-carboxamide;
5-[(3-fluorophenyl)amino]-N-[6-(4-methylpiperazin-1-yl)pyridin-3-yl]-1,3,4-oxadiazole-2-carboxamide;
5-[(4-methylphenyl)amino]-N-[6-(4-methylpiperazin-1-yl)pyridin-3-yl]-1,3,4-oxadiazole-2-carboxamide;
5-[(2,6-difluorophenyl)amino]-N-[6-(4-methylpiperazin-1-yl)pyridin-3-yl]-1,3,4-oxadiazole-2-carboxamide;
5-[(2-chlorophenyl)amino]-N-[6-(4-methylpiperazin-1-yl)pyridin-3-yl]-1,3,4-oxadiazole-2-carboxamide;
5-[(4-chlorophenyl)amino]-N-[6-(4-methylpiperazin-1-yl)pyridin-3-yl]-1,3,4-oxadiazole-2-carboxamide;
N-[6-(4-methylpiperazin-1-yl)pyridin-3-yl]-5-(2-naphthylamino)-1,3,4-oxadiazole-2-carboxamide;

N-[6-(4-methylpiperazin-1-yl)pyridin-3-yl]-5-(pyridin-2-ylamino)-1,3,4-oxadiazole-2-carboxamide;
5-[(3-methoxyphenyl)amino]-N-[6-(4-methylpiperazin-1-yl)pyridin-3-yl]-1,3,4-oxadiazole-2-carboxamide;
5-(1,3-benzodioxol-5-ylamino)-N-[6-(4-methylpiperazin-1-yl)pyridin-3-yl]-1,3,4-oxadiazole-2-carboxamide;
5-[(2,4-difluorophenyl)amino]-N-[6-(4-methylpiperazin-1-yl)pyridin-3-yl]-1,3,4-oxadiazole-2-carboxamide;
5-[(2,3-difluorophenyl)amino]-N-[6-(4-methylpiperazin-1-yl)pyridin-3-yl]-1,3,4-oxadiazole-2-carboxamide;
N-(3-bromo-4-morpholin-4-ylphenyl)-5-[(2-fluorophenyl)amino]-1,3,4-oxadiazole-2-carboxamide;
N-(3-bromo-4-morpholin-4-ylphenyl)-5-[(3,4-difluorophenyl)amino]-1,3,4-oxadiazole-2-carboxamide;
N-(3-bromo-4-morpholin-4-ylphenyl)-5-[(3-methylphenyl)amino]-1,3,4-oxadiazole-2-carboxamide;
allyl 5-[({5-[(3,4-difluorophenyl)amino]-1,3,4-oxadiazol-2-yl}carbonyl)amino]-2-morpholin-4-ylbenzoate;
allyl 5-[({5-[(2-fluorophenyl)amino]-1,3,4-oxadiazol-2-yl}carbonyl)amino]-2-morpholin-4-ylbenzoate;
5-[(2-fluorophenyl)amino]-N-{6-[4-(methoxyacetyl)piperazin-1-yl]pyridin-3-yl}-1,3,4-oxadiazole-2-carboxamide;
5-[(2-fluorophenyl)amino]-N-{6-[4-(3-phenylpropanoyl)piperazin-1-yl]pyridin-3-yl}-1,3,4-oxadiazole-2-carboxamide;
N-{6-[4-(2-fluorobenzoyl)piperazin-1-yl]pyridin-3-yl}-5-[(2-fluorophenyl)amino]-1,3,4-oxadiazole-2-carboxamide;
N-{6-[4-(4-cyanobenzoyl)piperazin-1-yl]pyridin-3-yl}-5-[(2-fluorophenyl)amino]-1,3,4-oxadiazole-2-carboxamide;
5-[(2-fluorophenyl)amino]-N-{6-[4-(4-methylbenzoyl)piperazin-1-yl]pyridin-3-yl}-1,3,4-oxadiazole-2-carboxamide;
5-[(2-fluorophenyl)amino]-N-{6-[4-(2-methylbenzoyl)piperazin-1-yl]pyridin-3-yl}-1,3,4-oxadiazole-2-carboxamide;
5-[(2-fluorophenyl)amino]-N-{6-[4-(3-methylbenzoyl)piperazin-1-yl]pyridin-3-yl}-1,3,4-oxadiazole-2-carboxamide;
5-[(2-fluorophenyl)amino]-N-{6-[4-(pyridin-3-ylcarbonyl)piperazin-1-yl]pyridin-3-yl}-1,3,4-oxadiazole-2-carboxamide;
5-[(2-fluorophenyl)amino]-N-[6-(4-glycoloylpiperazin-1-yl)pyridin-3-yl]-1,3,4-oxadiazole-2-carboxamide;
4-{5-[({5-[(2-fluorophenyl)amino]-1,3,4-oxadiazol-2-yl}carbonyl)amino]pyridin-2-yl}piperazine-1-carboxamide;
4-{5-[({5-[(2-fluorophenyl)amino]-1,3,4-oxadiazol-2-yl}carbonyl)amino]pyridin-2-yl}-N-phenylpiperazine-1-carboxamide;
N-benzyl-4-{5-[({5-[(2-fluorophenyl)amino]-1,3,4-oxadiazol-2-yl}carbonyl)amino]pyridin-2-yl}piperazine-1-carboxamide;
phenyl 4-{5-[({5-[(2-fluorophenyl)amino]-1,3,4-oxadiazol-2-yl}carbonyl)amino]pyridin-2-yl}piperazine-1-carboxylate;
ethyl 4-{4-[({5-[(2-fluorophenyl)amino]-1,3,4-oxadiazol-2-yl}carbonyl)amino]phenyl}piperazine-1-carboxylate;
benzyl 4-{5-[({5-[(2-fluorophenyl)amino]-1,3,4-oxadiazol-2-yl}carbonyl)amino]pyridin-2-yl}piperazine-1-carboxylate;
ethyl 4-{5-[({5-[(2-fluorophenyl)amino]-1,3,4-oxadiazol-2-yl}carbonyl)amino]pyridin-2-yl}piperazine-1-carboxylate;
N-[4-(butylthio)phenyl]-5-[(2-fluorophenyl)amino]-1,3,4-oxadiazole-2-carboxamide;
5-[(2-fluorophenyl)amino]-N-(4-{[(5-methoxy-1,3,4-thiadiazol-2-yl)amino]sulfonyl}phenyl)-1,3,4-oxadiazole-2-carboxamide;
N-[4-(2,4-difluorophenoxy)phenyl]-5-[(2-fluorophenyl)amino]-1,3,4-oxadiazole-2-carboxamide;
N-[4-(1,4-dimethyl-6-oxo-1,4,5,6-tetrahydropyridazine-3-yl)phenyl]-5-[(2-fluorophenyl)amino]-1,3,4-oxadiazole-2-carboxamide;
5-[(2-fluorophenyl)amino]-N-[4-(6-methyl-2-oxo-3,6-dihydro-2H-1,3,4-thiadiazin-5-yl)phenyl]-1,3,4-oxadiazole-2-carboxamide; and
N-(4'-chlorobiphenyl-4-yl)-5-[(2-fluorophenyl)amino]-1,3,4-oxadiazole-2-carboxamide; and/or
N-cyclohexyl-5-{[3-(methylthio)phenyl]amino}-1,3,4-oxadiazole-2-carboxamide;
N-cyclohexyl-5-[(4-ethoxyphenyl)amino]-1,3,4-oxadiazole-2-carboxamide;
ethyl 4-[({5-[(3-bromophenyl)amino]-1,3,4-oxadiazol-2-yl}carbonyl)amino]piperidine-1-carboxylate;
N-(1-benzylpiperidin-4-yl)-5-[(2-fluorophenyl)amino]-1,3,4-oxadiazole-2-carboxamide;
N-(2,3-dihydro-1H-inden-2-yl)-5-{[3-(2-oxo-1,3-oxazolidin-3-yl)phenyl]amino}-1,3,4-oxadiazole-2-carboxamide;
N-(2,3-dihydro-1H-inden-2-yl)-5-{[2-(2-oxo-1,3-oxazolidin-3-yl)phenyl]amino}-1,3,4-oxadiazole-2-carboxamide;
ethyl 4-[({5-[(2-fluorophenyl)amino]-1,3,4-oxadiazol-2-yl}carbonyl)amino]piperidine-1-carboxylate;
ethyl 4-{[(5-{[4-(ethoxycarbonyl)phenyl]amino}-1,3,4-oxadiazol-2-yl)carbonyl]amino}piperidine-1-carboxylate;
ethyl 4-({[5-(1-naphthylamino)-1,3,4-oxadiazol-2-yl]carbonyl}amino)piperidine-1-carboxylate;
tert-butyl 4-[({5-[(2-fluorophenyl)amino]-1,3,4-oxadiazol-2-yl}carbonyl)amino]piperidine-1-carboxylate; and
N-(1-benzoylpiperidin-4-yl)-5-[(2-fluorophenyl)amino]-1,3,4-oxadiazole-2-carboxamide; and/or
methyl (1-{5-[({5-[(2,4,5-trifluorophenyl)amino]-1,3,4-oxadiazol-2-yl}carbonyl)amino]pyridin-2-yl}piperidin-4-yl)acetate;
(1-{5-[({5-[(2,4,5-trifluorophenyl)amino]-1,3,4-oxadiazol-2-yl}carbonyl)amino]pyridin-2-yl}piperidin-4-yl)acetic acid;
methyl (trans-4-{4-[({5-[(4-ethylphenyl)amino]-1,3,4-oxadiazol-2-yl}carbonyl)amino]phenyl}cyclohexyl)acetate;
methyl (trans-4-{4-[({5-[(4-methoxyphenyl)amino]-1,3,4-oxadiazol-2-yl}carbonyl)amino]phenyl}cyclohexyl)acetate;
methyl [trans-4-(4-{[(5-{[3-(trifluoromethyl)phenyl]amino}-1,3,4-oxadiazol-2-yl)carbonyl]amino}phenyl)cyclohexyl]acetate;
methyl (trans-4-{4-[({5-[(3-cyanophenyl)amino]-1,3,4-oxadiazol-2-yl}carbonyl)amino]phenyl}cyclohexyl)acetate;
methyl (trans-4-{4-[({5-[(2-ethylphenyl)amino]-1,3,4-oxadiazol-2-yl}carbonyl)amino]phenyl}cyclohexyl)acetate;
methyl (trans-4-{4-[({5-[(2-isopropylphenyl)amino]-1,3,4-oxadiazol-2-yl}carbonyl)amino]phenyl}cyclohexyl)acetate;
methyl [trans-4-(4-{[(5-{[4-(benzyloxy)phenyl]amino}-1,3,4-oxadiazol-2-yl)carbonyl]amino}phenyl)cyclohexyl]acetate;
methyl (trans-4-{4-[({5-[(3-methylphenyl)amino]-1,3,4-oxadiazol-2-yl}carbonyl)amino]phenyl}cyclohexyl)acetate;
methyl (trans-4-{4-[({5-[(4-isopropylphenyl)amino]-1,3,4-oxadiazol-9-yl}carbonyl)amino]phenyl}cyclohexyl)acetate;

methyl [trans-4-(4-{[(5-{[2-(trifluoromethyl)phenyl]amino}-1,3,4-oxadiazol-2-yl)carbonyl]amino}phenyl)cyclohexyl]acetate;

methyl [trans-4-(4-{[(5-{[4-(trifluoromethyl)phenyl]amino}-1,3,4-oxadiazol-2-yl)carbonyl]amino}phenyl)cyclohexyl]acetate;

methyl (trans-4-{4-[({5-[(4-cyanophenyl)amino]-1,3,4-oxadiazol-2-yl}carbonyl)amino]phenyl}cyclohexyl)acetate;

methyl [trans-4-(4-{[(5-{[4-(trifluoromethoxy)phenyl]amino}-1,3,4-oxadiazol-2-yl)carbonyl]amino}phenyl)cyclohexyl]acetate;

methyl [trans-4-(4-{1-[(5-{[2-(trifluoromethoxy)phenyl]amino}-1,3,4-oxadiazol-2-yl)carbonyl]amino}phenyl)cyclohexyl]acetate;

methyl (trans-4-{4-[({5-[(3-ethylphenyl)amino]-1,3,4-oxadiazol-2-yl}carbonyl)amino]phenyl}cyclohexyl)acetate;

methyl (trans-4-{4-[({5-[(2-methoxyphenyl)amino]-1,3,4-oxadiazol-2-yl}carbonyl)amino]phenyl}cyclohexyl)acetate;

methyl (trans-4-{4-[({5-[(3-anilinophenyl)amino]-1,3,4-oxadiazol-2-yl}carbonyl)amino]phenyl}cyclohexyl)acetate;

methyl [trans-4-(4-{[(5-{[3-(aminocarbonyl)phenyl]amino}-1,3,4-oxadiazol-2-yl)carbonyl]amino}phenyl)cyclohexyl]acetate;

methyl (trans-4-{4-[({5-[(3-benzoylphenyl)amino]-1,3,4-oxadiazol-2-yl}carbonyl)amino]phenyl}cyclohexyl)acetate;

methyl [trans-4-(4-{[(5-{[3-(trifluoromethoxy)phenyl]amino}-1,3,4-oxadiazol-2-yl)carbonyl]amino}phenyl)cyclohexyl]acetate;

methyl (trans-4-{4-[({5-[(3-phenoxyphenyl)amino]-1,3,4-oxadiazol-2-yl}carbonyl)amino]phenyl}cyclohexyl)acetate;

methyl [trans-4-(4-{[(5-{[2-(benzyloxy)phenyl]amino}-1,3,4-oxadiazol-2-yl)carbonyl]amino}phenyl)cyclohexyl]acetate;

methyl [trans-4-(4-{[(5-{[3-(benzoylamino)phenyl]amino}-1,3,4-oxadiazol-2-yl)carbonyl]amino}phenyl)cyclohexyl]acetate;

methyl {trans-4-[4-({[5-({4-[(methylsulfonyl)oxy]phenyl}amino)-1,3,4-oxadiazol-2-yl]carbonyl}amino)phenyl]cyclohexyl}acetate;

methyl [trans-4-(4-{[(5-{[3-(phenylsulfonyl)phenyl]amino}-1,3,4-oxadiazol-2-yl)carbonyl]amino}phenyl)cyclohexyl]acetate;

methyl {trans-4-[4-({[5-({3-[(methylsulfonyl)oxy]phenyl}amino)-1,3,4-oxadiazol-2-yl]carbonyl}amino)phenyl]cyclohexyl}acetate;

methyl {trans-4-[4-({[5-({2-[(methylsulfonyl)oxy]phenyl}amino)-1,3,4-oxadiazol-2-yl]carbonyl}amino)phenyl]cyclohexyl}acetate;

methyl {trans-4-[4-({[5-({3-[(aminocarbonyl)amino]phenyl}amino)-1,3,4-oxadiazol-2-yl]carbonyl}amino)phenyl]cyclohexyl}acetate;

methyl {trans-4-[4-({[5-({3-[(methoxycarbonyl)amino]phenyl}amino)-1,3,4-oxadiazol-2-yl]carbonyl}amino)phenyl]cyclohexyl}acetate;

methyl (trans-4-{4-[({5-[(4-morpholin-4-ylphenyl)amino]-1,3,4-oxadiazol-2-yl}carbonyl)amino]phenyl}cyclohexyl)acetate;

methyl (trans-4-{4-[({5-[(2-cyanophenyl)amino]-1,3,4-oxadiazol-2-yl}carbonyl)amino]phenyl}cyclohexyl)acetate;

methyl (trans-4-{4-[({5-[(4-anilinophenyl)amino]-1,3,4-oxadiazol-2-yl}carbonyl)amino]phenyl}cyclohexyl)acetate;

methyl [trans-4-(4-{[(5-{[4-(phenylsulfonyl)phenyl]amino}-1,3,4-oxadiazol-2-yl)carbonyl]amino}phenyl)cyclohexyl]acetate;

methyl [trans-4-(4-{[(5-{[2-(phenylsulfonyl)phenyl]amino}-1,3,4-oxadiazol-2-yl)carbonyl]amino}phenyl)cyclohexyl]acetate;

methyl [trans-4-(4-{[(5-{[4-(ethylsulfonyl)phenyl]amino})-1,3,4-oxadiazol-2-yl)carbonyl]amino}phenyl)cyclohexyl]acetate;

(trans-4-{4-[({5-[(4-ethylphenyl)amino]-1,3,4-oxadiazol-2-yl}carbonyl)amino]phenyl}cyclohexyl)acetic acid;

(trans-4-{4-[({5-[(4-methoxyphenyl)amino]-1,3,4-oxadiazol-2-yl}carbonyl)amino]phenyl}cyclohexyl)acetic acid;

[trans-4-(4-{[(5-{[3-(trifluoromethyl)phenyl]amino}-1,3,4-oxadiazol-2-yl)carbonyl]amino}phenyl)cyclohexyl]acetic acid;

(trans-4-{4-[({5-[(3-cyanophenyl)amino]-1,3,4-oxadiazol-2-yl}carbonyl)amino]phenyl}cyclohexyl)acetic acid;

(trans-4-{4-[({5-[(2-ethylphenyl)amino]-1,3,4-oxadiazol-2-yl}carbonyl)amino]phenyl}cyclohexyl)acetic acid;

(trans-4-{4-[({5-[(2-isopropylphenyl)amino]-1,3,4-oxadiazol-2-yl}carbonyl)amino]phenyl}cyclohexyl)acetic acid;

[trans-4-(4-{[(5-{[4-(benzyloxy)phenyl]amino}-1,3,4-oxadiazol-2-yl)carbonyl]amino}phenyl)cyclohexyl]acetic acid;

(trans-4-{4-[({5-[(3-methylphenyl)amino]-1,3,4-oxadiazol-2-yl}carbonyl)amino]phenyl}cyclohexyl)acetic acid;

(trans-4-{4-[({5-[(4-isopropylphenyl)amino]-1,3,4-oxadiazol-2-yl}carbonyl)amino]phenyl}cyclohexyl)acetic acid;

[trans-4-(4-{[(5-{[2-(trifluoromethyl)phenyl]amino}-1,3,4-oxadiazol-2-yl)carbonyl]amino}phenyl)cyclohexyl]acetic acid;

[trans-4-(4-{1-[(5-{[4-(trifluoromethyl)phenyl]amino}-1,3,4-oxadiazol-2-yl)carbonyl]amino}phenyl)cyclohexyl]acetic acid;

(trans-4-{4-[({5-[(4-cyanophenyl)amino]-1,3,4-oxadiazol-2-yl}carbonyl)amino]phenyl}cyclohexyl)acetic acid;

[trans-4-(4-{[(5-{[4-(trifluoromethoxy)phenyl]amino}-1,3,4-oxadiazol-2-yl)carbonyl]amino}phenyl)cyclohexyl]acetic acid;

[trans-4-(4-{[(5-{[2-(trifluoromethoxy)phenyl]amino}-1,3,4-oxadiazol-2-yl)carbonyl]amino}phenyl)cyclohexyl]acetic acid;

(trans-4-{4-[({5-[(3-ethylphenyl)amino]-1,3,4-oxadiazol-2-yl}carbonyl)amino]phenyl}cyclohexyl)acetic acid;

[trans-4-(4-{[(5-{[3-(aminocarbonyl)phenyl]amino}-1,3,4-oxadiazol-2-yl)carbonyl]amino}phenyl)cyclohexyl]acetic acid;

(trans-4-{4-[({5-[(3-benzoylphenyl)amino]-1,3,4-oxadiazol-2-yl}carbonyl)amino]phenyl}cyclohexyl)acetic acid;

[trans-4-(4-{[(5-{[3-(trifluoromethoxy)phenyl]amino}-1,3,4-oxadiazol-2-yl)carbonyl]amino}phenyl)cyclohexyl]acetic acid;

(trans-4-{4-[({5-[(3-phenoxyphenyl)amino]-1,3,4-oxadiazol-2-yl}carbonyl)amino]phenyl}cyclohexyl)acetic acid;

[trans-4-(4-{[(5-{[2-(benzyloxy)phenyl]amino}-1,3,4-oxadiazol-2-yl)carbonyl]amino}phenyl)cyclohexyl]acetic acid;

[trans-4-(4-{[(5-{[3-(benzoylamino)phenyl]amino}-1,3,4-oxadiazol-2-yl)carbonyl]amino}phenyl)cyclohexyl]acetic acid;

{trans-4-[4-({[5-({4-[(methylsulfonyl)oxy]phenyl}amino)-1,3,4-oxadiazol-2-yl]carbonyl}amino)phenyl]cyclohexyl}acetic acid;

[trans-4-(4-{[(5-{[3-(phenylsulfonyl)phenyl]amino}-1,3,4-oxadiazol-2-yl)carbonyl]amino}phenyl)cyclohexyl]acetic acid;

{trans-4-[4-({[5-({3-[(methylsulfonyl)oxy]phenyl}amino)-1,3,4-oxadiazol-2-yl]carbonyl}amino)phenyl]cyclohexyl}acetic acid;
{trans-4-[4-({[5-({2-[(methylsulfonyl)oxy]phenyl}amino)-1,3,4-oxadiazol-2-yl]carbonyl}amino)phenyl]cyclohexyl}acetic acid;
(trans-4-{4-[({5-[(2-methoxyphenyl)amino]-1,3,4-oxadiazol-2-yl}carbonyl)amino]phenyl}cyclohexyl)acetic acid;
{trans-4-[4-({[5-({3-[(aminocarbonyl)amino]phenyl}amino)-1,3,4-oxadiazol-2-yl]carbonyl}amino)phenyl]cyclohexyl}acetic acid;
(trans-4-[4-({[5-((3-[(methoxycarbonyl)amino]phenyl)amino)-1,3,4-oxadiazol-2-yl}carbonyl}amino)phenyl]cyclohexyl)acetic acid;
(trans-4-{4-[({5-[(4-morpholin-4-ylphenyl)amino]-1,3,4-oxadiazol-2-yl}carbonyl)amino]phenyl}cyclohexyl)acetic acid;
[trans-4-(4-{[(5-{[4-(phenylsulfonyl)phenyl]amino}-1,3,4-oxadiazol-2-yl)carbonyl]amino}phenyl)cyclohexyl]acetic acid;
[trans-4-(4-{[(5-{[2-(phenylsulfonyl)phenyl]amino}-1,3,4-oxadiazol-2-yl}carbonyl]amino}phenyl)cyclohexyl]acetic acid;
(trans-4-{4-[({5-[(2-cyanophenyl)amino]-1,3,4-oxadiazol-2-yl}carbonyl)amino]phenyl}cyclohexyl)acetic acid;
(trans-4-{4-[({5-[(4-anilinophenyl)amino]-1,3,4-oxadiazol-2-yl}carbonyl)amino]phenyl}cyclohexyl)acetic acid;
(trans-4-{4-[({5-[(3-anilinophenyl)amino]-1,3,4-oxadiazol-2-yl}carbonyl)amino]phenyl}cyclohexyl)acetic acid; and
[trans-4-(4-{[(5-{[4-(ethylsulfonyl)phenyl]amino}-1,3,4-oxadiazol-2-yl)carbonyl]amino}phenyl)cyclohexyl]acetic acid; and/or
methyl 1-[(trans-4-{4-[({5-[(2-fluorophenyl)amino]-1,3,4-oxadiazol-2-yl}carbonyl)amino]phenyl}cyclohexyl)acetyl]piperidine-4-carboxylate;
methyl N-[(trans-4-{4-[({5-[(2-fluorophenyl)amino]-1,3,4-oxadiazol-2-yl}carbonyl)amino]phenyl}cyclohexyl)acetyl]-2-methylalaninate;
methyl 1-[(trans-4-{4-[({5-[(2-fluorophenyl)amino]-1,3,4-oxadiazol-2-yl}carbonyl)amino]phenyl}cyclohexyl)acetyl]-L-prolinate;
methyl 1-[(trans-4-{4-[({5-[(2-fluorophenyl)amino]-1,3,4-oxadiazol-2-yl}carbonyl)amino]phenyl}cyclohexyl)acetyl]-D-prolinate;
methyl (4R)-1-[(trans-4-{4-[({5-[(2-fluorophenyl)amino]-1,3,4-oxadiazol-2-yl}carbonyl)amino]phenyl}cyclohexyl)acetyl]-4-hydroxy-L-prolinate;
5-[(2-fluorophenyl)amino]-N-[4-(trans-4-{2-[(2-hydroxy-1,1-dimethylethyl)amino]-2-oxoethyl}cyclohexyl)phenyl]-1,3,4-oxadiazole-2-carboxamide;
5-[(2-fluorophenyl)amino]-N-[4-(trans-4-{2-oxo-2-[(3aR,6aS)-tetrahydro-5H-[1,3]dioxolo[4,5-c]pyrrol-5-yl]ethyl}cyclohexyl)phenyl]-1,3,4-oxadiazole-2-carboxamide;
N-(4-{trans-4-[2-(dimethylamino)-2-oxoethyl]cyclohexyl}phenyl)-5-[(2-fluorophenyl)amino]-1,3,4-oxadiazole-2-carboxamide;
5-[(2-fluorophenyl)amino]-N-[4-(trans-4-{2-[(2-hydroxyethyl)(methyl)amino]-2-oxoethyl}cyclohexyl)phenyl]-1,3,4-oxadiazole-2-carboxamide;
N-[4-(trans-4-{2-[(2,3-dihydroxypropyl)amino]-2-oxoethyl}cyclohexyl)phenyl]-5-[(2-fluorophenyl)amino]-1,3,4-oxadiazole-2-carboxamide;
1-[(trans-4-{4-[({5-[(2-fluorophenyl)amino]-1,3,4-oxadiazol-2-yl}carbonyl)amino]phenyl}cyclohexyl)acetyl]piperidine-4-carboxylic acid;
N-[(trans-4-{4-[({5-[(2-fluorophenyl)amino]-1,3,4-oxadiazol-2-yl}carbonyl)amino]phenyl}cyclohexyl)acetyl]-2-methylalanine;
1-[(trans-4-{4-[({5-[(2-fluorophenyl)amino]-1,3,4-oxadiazol-2-yl}carbonyl)amino]phenyl}cyclohexyl)acetyl]-L-proline;
1-[(trans-4-{4-[({5-[(2-fluorophenyl)amino]-1,3,4-oxadiazol-2-yl}carbonyl)amino]phenyl}cyclohexyl)acetyl]-D-proline;
(4R)-1-[(trans-4-{4-[({5-[(2-fluorophenyl)amino]-1,3,4-oxadiazol-2-yl}carbonyl)amino]phenyl}cyclohexyl)acetyl]-4-hydroxy-L-proline;
methyl (trans-4-{5-[({5-[(2,4,5-trifluorophenyl)amino]-1,3,4-oxadiazol-2-yl}carbonyl)amino]pyridin-2-yl}cyclohexyl)acetate;
(trans-4-{5-[({5-[(2,4,5-trifluorophenyl)amino]-1,3,4-oxadiazol-2-yl}carbonyl)amino]pyridin-2-yl}cyclohexyl)acetic acid;
[trans-4-(4-{[(5-{[4-(2-hydroxyethyl)phenyl]amino}-1,3,4-oxadiazol-2-yl)carbonyl]amino}phenyl)cyclohexyl]acetic acid;
(trans-4-{4-[({5-[(3-ethynylphenyl)amino]-1,3,4-oxadiazol-2-yl}carbonyl)amino]phenyl}cyclohexyl)acetic acid;
[trans-4-(4-{[(5-{[4-(cyanomethyl)phenyl]amino}-1,3,4-oxadiazol-2-yl)carbonyl]amino}phenyl)cyclohexyl]acetic acid;
{trans-4-[4-({[5-(biphenyl-2-ylamino)-1,3,4-oxadiazol-2-yl]carbonyl}amino)phenyl]cyclohexyl}acetic acid;
(trans-4-{4-[({5-[(4-tert-butoxyphenyl)amino]-1,3,4-oxadiazol-2-yl}carbonyl)amino]phenyl}cyclohexyl)acetic acid;
(trans-4-{4-[({5-[(4-phenoxyphenyl)amino]-1,3,4-oxadiazol-2-yl}carbonyl)amino]phenyl}cyclohexyl)acetic acid;
[trans-4-(4-{1-[(5-{[4-(1H-1,2,4-triazol-1-yl)phenyl]amino}-1,3,4-oxadiazol-2-yl)carbonyl]amino}phenyl)cyclohexyl]acetic acid;
(trans-4-{4-[({5-[(4-benzylphenyl)amino]-1,3,4-oxadiazol-2-yl}carbonyl)amino]phenyl}cyclohexyl)acetic acid;
[trans-4-(4-{[(5-{[3-(acetylamino)phenyl]amino}-1,3,4-oxadiazol-2-yl)carbonyl]amino}phenyl)cyclohexyl]acetic acid;
(trans-4-{4-[({5-[(3-chlorophenyl)amino]-1,3,4-oxadiazol-2-yl}carbonyl)amino]phenyl}cyclohexyl)acetic acid;
(trans-4-{4-[({5-[(4-ethynylphenyl)amino]-1,3,4-oxadiazol-2-yl}carbonyl)amino]phenyl}cyclohexyl)acetic acid;
(trans-4-{4-[({5-[(3-bromophenyl)amino]-1,3,4-oxadiazol-2-yl}carbonyl)amino]phenyl}cyclohexyl)acetic acid;
[trans-4-(4-{[(5-{[3-(difluoromethoxy)phenyl]amino}-1,3,4-oxadiazol-2-yl)carbonyl]amino}phenyl)cyclohexyl]acetic acid;
[trans-4-(4-{[(5-{[3-(methoxymethyl)phenyl]amino}-1,3,4-oxadiazol-2-yl)carbonyl]amino}phenyl)cyclohexyl]acetic acid;
[trans-4-(4-{[(5-{[3-(2-methylpyrimidin-4-yl)phenyl]amino}-1,3,4-oxadiazol-2-yl)carbonyl]amino}phenyl)cyclohexyl]acetic acid;
(trans-4-{4-[({5-[(4-cyclohexylphenyl)amino]-1,3,4-oxadiazol-2-yl}carbonyl)amino]phenyl}cyclohexyl)acetic acid;
methyl {trans-4-[4-({[5-(pyrimidin-4-ylamino)-1,3,4-oxadiazol-2-yl]carbonyl}amino)phenyl]cyclohexyl}acetate;
methyl (trans-4-{4-[({5-[(1-methyl-1H-pyrazol-3-yl)amino]-1,3,4-oxadiazol-2-yl}carbonyl)amino]phenyl}cyclohexyl)acetate;
methyl {trans-4-[4-({[5-(pyridin-3-ylamino)-1,3,4-oxadiazol-2-yl]carbonyl}amino)phenyl]cyclohexyl}acetate;

methyl {trans-4-[4-({[5-(pyridin-4-ylamino)-1,3,4-oxadiazol-2-yl]carbonyl}amino)phenyl]cyclohexyl}acetate;

methyl {trans-4-[4-({[5-(pyrazin-2-ylamino)-1,3,4-oxadiazol-2-yl]carbonyl}amino)phenyl]cyclohexyl}acetate;

methyl {trans-4-[4-({[5-(1,3-thiazol-2-ylamino)-1,3,4-oxadiazol-2-yl]carbonyl}amino)phenyl]cyclohexyl}acetate;

{trans-4-[4-({[5-(pyrimidin-4-ylamino)-1,3,4-oxadiazol-2-yl]carbonyl}amino)phenyl]cyclohexyl}acetic acid;

(trans-4-{4-[({5-[(1-methyl-1H-pyrazol-3-yl)amino]-1,3,4-oxadiazol-2-yl}carbonyl)amino]phenyl}cyclohexyl)acetic acid;

{trans-4-[4-({[5-(pyridin-3-ylamino)-1,3,4-oxadiazol-2-yl]carbonyl}amino)phenyl]cyclohexyl}acetic acid;

{trans-4-[4-({[5-(pyridin-4-ylamino)-1,3,4-oxadiazol-2-yl]carbonyl}amino)phenyl]cyclohexyl}acetic acid;

{trans-4-[4-({[5-(pyrazin-2-ylamino)-1,3,4-oxadiazol-2-yl]carbonyl}amino)phenyl]cyclohexyl}acetic acid;

{trans-4-[4-({[5-(1,3-thiazol-2-ylamino)-1,3,4-oxadiazol-2-yl]carbonyl}amino)phenyl]cyclohexyl}acetic acid;

(trans-4-{4-[({5-[(1-methyl-1H-pyrazol-5-yl)amino]-1,3,4-oxadiazol-2-yl}carbonyl)amino]phenyl}cyclohexyl)acetic acid;

{trans-4-[4-({[5-(pyrimidin-2-ylamino)-1,3,4-oxadiazol-2-yl]carbonyl}amino)phenyl]cyclohexy}acetic acid;

trans-4-{4-[({5-[(2-methoxyphenyl)amino]-1,3,4-oxadiazol-2-yl}carbonyl)amino]phenyl}cyclohexanecarboxylic acid;

trans-4-(4-{[(5-{[3-(hydroxymethyl)phenyl]amino}-1,3,4-oxadiazol-2-yl)carbonyl]amino}phenyl)cyclohexanecarboxylic acid;

trans-4-(4-{[(5-{[2-(trifluoromethyl)phenyl]amino}-1,3,4-oxadiazol-2-yl)carbonyl]amino}phenyl)cyclohexanecarboxylic acid;

trans-4-(4-{[(5-{[2-(trifluoromethoxy)phenyl]amino}1,3,4-oxadiazol-2-yl)carbonyl]amino}phenyl)cyclohexanecarboxylic acid;

trans-4-(4-{[(5-{[3-(trifluoromethyl)phenyl]amino}-1,3,4-oxadiazol-2-yl)carbonyl]amino}phenyl)cyclohexanecarboxylic acid;

trans-4-{4-[({5-[(4-methoxyphenyl)amino]-1,3,4-oxadiazol-2-yl}carbonyl)amino]phenyl}cyclohexanecarboxylic acid;

trans-4-(4-{[(5-{[4-(trifluoromethoxy)phenyl]amino}-1,3,4-oxadiazol-2-yl)carbonyl]amino}phenyl)cyclohexanecarboxylic acid;

trans-4-(4-{[(5-{[4-(trifluoromethyl)phenyl]amino}-1,3,4-oxadiazol-2-yl)carbonyl]amino}phenyl)cyclohexanecarboxylic acid;

trans-4-(4-{[(5-{[2-(benzyloxy)phenyl]amino}-1,3,4-oxadiazol-2-yl)carbonyl]amino}phenyl)cyclohexanecarboxylic acid;

trans-4-(4-{[(5-{[3-(trifluoromethoxy)phenyl]amino}-1,3,4-oxadiazol-2-yl)carbonyl]amino}phenyl)cyclohexanecarboxylic acid;

trans-4-(4-{[(5-{[3-(methoxymethyl)phenyl]amino}-1,3,4-oxadiazol-2-yl)carbonyl]amino}phenyl)cyclohexanecarboxylic acid;

trans-4-(4-{[(5-{[3-(phenylsulfonyl)phenyl]amino}-1,3,4-oxadiazol-2-yl)carbonyl]amino}phenyl)cyclohexanecarboxylic acid;

trans-4-[({5-[(3-anilinophenyl)amino]-1,3,4-oxadiazol-2-yl}carbonyl)amino]phenyl)cyclohexanecarboxylic acid;

trans-4-{4-[({5-[(4-anilinophenyl)amino]-1,3,4-oxadiazol-2-yl}carbonyl)amino]phenyl}cyclohexanecarboxylic acid;

trans-4-[4-({[5-({2-[(methylsulfonyl)oxy]phenyl}amino)-1,3,4-oxadiazol-2-yl]carbonyl]amino)phenyl}cyclohexanecarboxylic acid;

trans-4-[4-({[5-({3-[(methylsulfonyl)oxy]phenyl}amino)-1,3,4-oxadiazol-2-yl]carbonyl}amino)phenyl]cyclohexanecarboxylic acid;

trans-4-[4-({[5-({4-[(methylsulfonyl)oxy]phenyl}amino)-1,3,4-oxadiazol-2-yl]carbonyl}amino)phenyl]cyclohexanecarboxylic acid;

ethyl trans-4-{4-[({5-[(2,4,5-trifluorophenyl)amino]-1,3,4-oxadiazol-2-yl}carbonyl)amino]phenoxy}cyclohexanecarboxylate;

trans-4-{4-[({5-[(2,4,5-trifluorophenyl)amino]-1,3,4-oxadiazol-2-yl}carbonyl)amino]phenoxy}cyclohexanecarboxylic acid;

methyl (trans-4-{4-[({5-[(3-fluorophenyl)amino]-1,3,4-oxadiazol-2-yl}carbonyl)amino]phenyl}cyclohexyl)acetate;

methyl (trans-4-{4-[({5-[(4-fluorophenyl)amino]-1,3,4-oxadiazol-2-yl}carbonyl)amino]phenyl}cyclohexyl)acetate;

methyl (trans-4-{4-[({5-[(2,4-difluorophenyl)amino]-1,3,4-oxadiazol-2-yl}carbonyl)amino]phenyl}cyclohexyl)acetate;

methyl (trans-4-{4-[({5-[(2,6-difluorophenyl)amino]-1,3,4-oxadiazol-2-yl}carbonyl)amino]phenyl}cyclohexyl)acetate;

methyl (trans-4-{4-[({5-[(2,5-difluorophenyl)amino]-1,3,4-oxadiazol-2-yl}carbonyl)amino]phenyl}cyclohexyl)acetate;

methyl (trans-4-{4-[({5-[(2,3-difluorophenyl)amino]-1,3,4-oxadiazol-2-yl}carbonyl)amino]phenyl}cyclohexyl)acetate;

methyl (trans-4-{4-[({5-[(2,4,6-trifluorophenyl)amino]-1,3,4-oxadiazol-2-yl}carbonyl)amino]phenyl}cyclohexyl)acetate;

methyl (trans-4-{4-[({5-[(3,4-dimethoxyphenyl)amino]-1,3,4-oxadiazol-2-yl}carbonyl)amino]phenyl}cyclohexyl)acetate;

methyl {trans-4-[4-({[5-({3-[(1R)-2-methoxy-1-methylethoxy]phenyl}amino)-1,3,4-oxadiazol-2-yl]carbonyl}amino)phenyl]cyclohexyl}acetate;

methyl {trans-4-[4-({[5-({3-[(1S)-2-methoxy-1-methylethoxy]phenyl}amino)-1,3,4-oxadiazol-2-yl]carbonyl}amino)phenyl]cyclohexyl}acetate;

methyl (trans-4-{4-[({5-[(4-fluoro-3-methoxyphenyl)amino]-1,3,4-oxadiazol-2-yl}carbonyl)amino]phenyl}cyclohexyl)acetate;

(trans-4-{4-[({5-[(3-fluorophenyl)amino]-1,3,4-oxadiazol-2-yl}carbonyl)amino]phenyl}cyclohexyl)acetic acid;

(trans-4-f{4-[({5-[(4-fluorophenyl)amino]-1,3,4-oxadiazol-2-yl}carbonyl)amino]phenyl}cyclohexyl)acetic acid;

(trans-4-{4-[({5-[(2,4-difluorophenyl)amino]-1,3,4-oxadiazol-2-yl}carbonyl)amino]phenyl}cyclohexyl)acetic acid;

(trans-4-{4-[({5-[(2,6-difluorophenyl)amino]-1,3,4-oxadiazol-2-yl}carbonyl)amino]phenyl}cyclohexyl)acetic acid;

(trans-4-f{4-[({5-[(2,5-difluorophenyl)amino]-1,3,4-oxadiazol-2-yl}carbonyl)amino]phenyl}cyclohexyl)acetic acid;

(trans-4-{4-[({5-[(2,3-difluorophenyl)amino]-1,3,4-oxadiazol-2-yl}carbonyl)amino]phenyl}cyclohexyl)acetic acid;

(trans-4-{4-[({5-[(2,4,6-trifluorophenyl)amino]-1,3,4-oxadiazol-2-yl}carbonyl)amino]phenyl}cyclohexyl)acetic acid;

(trans-4-{4-[({5-[(3,4-dimethoxyphenyl)amino]-1,3,4-oxadiazol-2-yl}carbonyl)amino]phenyl}cyclohexyl)acetic acid;

{trans-4-[4-({[5-({3-[(1S)-2-methoxy-1-methylethoxy]phenyl}amino)-1,3,4-oxadiazol-2-yl]carbonyl}amino)phenyl]cyclohexyl}acetic acid;
{trans-4-[4-({[5-({3-[(1R)-2-methoxy-1-methylethoxy]phenyl}amino)-1,3,4-oxadiazol-2-yl]carbonyl}amino)phenyl]cyclohexyl}acetic acid;
(trans-4-{4-[({5-[(4-fluoro-3-methoxyphenyl)amino]-1,3,4-oxadiazol-2-yl}carbonyl)amino]phenyl}cyclohexyl)acetic acid;
1-{5-[({5-[(2-fluorophenyl)amino]-1,3,4-oxadiazol-2-yl}carbonyl)amino]pyridin-2-yl}piperidine-4-carboxylic acid;
1-{5-[({5-[(2,4,5-trifluorophenyl)amino]-1,3,4-oxadiazol-2-yl}carbonyl)amino]pyridin-2-yl}piperidine-4-carboxylic acid;
1-{5-[({5-[(3,4-difluorophenyl)amino]-1,3,4-oxadiazol-2-yl}carbonyl)amino]pyridin-2-yl}piperidine-4-carboxylic acid;
1-{5-[({5-[(4-fluorophenyl)amino]-1,3,4-oxadiazol-2-yl}carbonyl)amino]pyridin-2-yl}piperidine-4-carboxylic acid;
methyl 4-{4-[({5-[(2-fluorophenyl)amino]-1,3,4-oxadiazol-2-yl}carbonyl)amino]phenyl}butanoate;
methyl ({4-[({5-[(2-fluorophenyl)amino]-1,3,4-oxadiazol-2-yl}carbonyl)amino]phenyl}thio)acetate;
methyl 3-{4-[({5-[(2-fluorophenyl)amino]-1,3,4-oxadiazol-2-yl}carbonyl)amino]phenyl}adamantane-1-carboxylate;
methyl 3-{4-[({5-[(2-fluorophenyl)amino]-1,3,4-oxadiazol-2-yl}carbonyl)amino]phenyl}cyclopentanecarboxylate;
methyl 4'-[({5-[(2-fluorophenyl)amino]-1,3,4-oxadiazol-2-yl}carbonyl)amino]biphenyl-4-carboxylate;
ethyl {4'-[({5-[(2-fluorophenyl)amino]-1,3,4-oxadiazol-2-yl}carbonyl)amino]biphenyl-3-yl}acetate;
methyl [(1,4-trans-)-4'-[({5-[(2-fluorophenyl)amino]-1,3,4-oxadiazol-2-yl}carbonyl)amino]-1,1'-bi(cyclohexyl)-4-yl]acetate;
ethyl 3-{2-[({5-[(3,4-difluorophenyl)amino]-1,3,4-oxadiazol-2-yl}carbonyl)amino]-2,3-dihydro-1H-inden-5-yl}propanoate;
ethyl ((1R,3R)-3-{4-[({5-[(3,4-difluorophenyl)amino]-1,3,4-oxadiazol-2-yl}carbonyl)amino]phenyl}cyclohexyl)acetate;
ethyl (3-{4-[({5-[(3,4-difluorophenyl)amino]-1,3,4-oxadiazol-2-yl}carbonyl)amino]phenyl}cyclopentyl)acetate;
methyl 4-{3-[({5-[(3,4-difluorophenyl)amino]-1,3,4-oxadiazol-2-yl}carbonyl)amino]propoxy}benzoate;
methyl 3-{3-[({5-[(3,4-difluorophenyl)amino]-1,3,4-oxadiazol-2-yl}carbonyl)amino]propoxy}benzoate;
methyl cis-3-{4-[({5-[(3,4-difluorophenyl)amino]-1,3,4-oxadiazol-2-yl}carbonyl)amino]phenyl}cyclobutanecarboxylate;
ethyl cis-3-{4-[({5-[(3,4-difluorophenyl)amino]-1,3,4-oxadiazol-2-yl}carbonyl)amino]benzyl}cyclobutanecarboxylate;
4-{4-[({5-[(2-fluorophenyl)amino]-1,3,4-oxadiazol-2-yl}carbonyl)amino]phenyl}butanoic acid;
3-{4-[({5-[(2-fluorophenyl)amino]-1,3,4-oxadiazol-2-yl}carbonyl)amino]phenyl}adamantane-1-carboxylic acid;
3-{4-[({5-[(2-fluorophenyl)amino]-1,3,4-oxadiazol-2-yl}carbonyl)amino]phenyl}cyclopentanecarboxylic acid;
4'-[({5-[(2-fluorophenyl)amino]-1,3,4-oxadiazol-2-yl}carbonyl)amino]biphenyl-4-carboxylic acid;
{4'-[({5-[(2-fluorophenyl)amino]-1,3,4-oxadiazol-2-yl}carbonyl)amino]biphenyl-4-yl}acetic acid;
{4'-[({5-[(2-fluorophenyl)amino]-1,3,4-oxadiazol-2-yl}carbonyl)amino]biphenyl-3-yl}acetic acid;
[(1,4-trans-)-4'-[({5-[(2-fluorophenyl)amino]-1,3,4-oxadiazol-2-yl}carbonyl)amino]-1,1'-bi(cyclohexyl)-4-yl]acetic acid;
3-{2-[({5-[(3,4-difluorophenyl)amino]-1,3,4-oxadiazol-2-yl}carbonyl)amino]-2,3-dihydro-1H-inden-5-yl}propanoic acid;
(3-{4-[({5-[(3,4-difluorophenyl)amino]-1,3,4-oxadiazol-2-yl}carbonyl)amino]phenyl}propyl)malonic acid;
(4-{4-[({5-[(2-fluorophenyl)amino]-1,3,4-oxadiazol-2-yl}carbonyl)amino]cyclohexyl}phenyl)acetic acid;
(3-{4-[({5-[(3,4-difluorophenyl)amino]-1,3,4-oxadiazol-2-yl}carbonyl)amino]phenyl}cyclohexyl)acetic acid;
((3R)-3-{4-[({5-[(3,4-difluorophenyl)amino]-1,3,4-oxadiazol-2-yl}carbonyl)amino]phenyl}cyclopentyl)acetic acid;
((3S)-3-{4-[({5-[(3,4-difluorophenyl)amino]-1,3,4-oxadiazol-2-yl}carbonyl)amino]phenyl}cyclopentyl)acetic acid;
4-{3-[({5-[(3,4-difluorophenyl)amino]-1,3,4-oxadiazol-2-yl}carbonyl)amino]propoxy}benzoic acid;
3-{3-[({5-[(3,4-difluorophenyl)amino]-1,3,4-oxadiazol-2-yl}carbonyl)amino]propoxy}benzoic acid;
3-{4-[({5-[(3,4-difluorophenyl)amino]-1,3,4-oxadiazol-2-yl}carbonyl)amino]phenyl}cyclobutanecarboxylic acid;
3-{4-[({5-[(3,4-difluorophenyl)amino]-1,3,4-oxadiazol-2-yl}carbonyl)amino]benzyl}cyclobutanecarboxylic acid;
5-{4-[({5-[(3,4-difluorophenyl)amino]-1,3,4-oxadiazol-2-yl}carbonyl)amino]phenyl}pentanoic acid;
N-{4-[trans-4-(2-amino-2-oxoethyl)cyclohexyl]phenyl}-5-[(2-fluorophenyl)amino]-1,3,4-oxadiazole-2-carboxamide;
N-{4-[trans-4-(cyanomethyl)cyclohexyl]phenyl}-5-[(2-fluorophenyl)amino]-1,3,4-oxadiazole-2-carboxamide;
5-[(2-fluorophenyl)amino]-N-[4-(propylsulfonyl)phenyl]-1,3,4-oxadiazole-2-carboxamide;
methyl 4'-{[5-({[4-(4-acetylpiperazin-1-yl)phenyl]amino}carbonyl)-1,3,4-oxadiazol-2-yl]amino}biphenyl-4-carboxylate;
N-[4-(4-acetylpiperazin-1-yl)phenyl]-5-[(4-chloro-2-fluoro-5-hydroxyphenyl)amino]-1,3,4-oxadiazole-2-carboxamide;
ethyl (5-{[5-({[4-(4-acetylpiperazin-1-yl)phenyl]amino}carbonyl)-1,3,4-oxadiazol-2-yl]amino}-2-chloro-4-fluorophenoxy)acetate;
methyl 3'-{[5-({[4-(4-acetylpiperazin-1-yl)phenyl]amino}carbonyl)-1,3,4-oxadiazol-2-yl]amino}biphenyl-4-carboxylate;
3'-{[5-({[4-(4-acetylpiperazin-1-yl)phenyl]amino}carbonyl)-1,3,4-oxadiazol-2-yl]amino}biphenyl-4-carboxylic acid;
2-({4-[({5-[(2-fluorophenyl)amino]-1,3,4-oxadiazol-2-yl}carbonyl)amino]phenyl}sulfonyl)-2-methylpropanoic acid;
(trans-4-{4-[({5-[(3-methylisoxazol-5-yl)amino]-1,3,4-oxadiazol-2-yl}carbonyl)amino]phenyl}cyclohexyl)acetic acid;
{trans-4-[4-({[5-(1,3,4-thiadiazol-2-ylamino)-1,3,4-oxadiazol-2-yl]carbonyl}amino)phenyl]cyclohexyl}acetic acid;
(trans-4-{4-[({5-[(2,5-dimethylpyridin-4-yl)amino]-1,3,4-oxadiazol-2-yl}carbonyl)amino]phenyl}cyclohexyl)acetic acid;
(trans-4-{4-[({5-[(5,6-dimethylpyrazin-2-yl)amino]-1,3,4-oxadiazol-2-yl}carbonyl)amino]phenyl}cyclohexyl)acetic acid;
(trans-4-{4-[({5-[(3-methylpyrazin-2-yl)amino]-1,3,4-oxadiazol-2-yl}carbonyl)amino]phenyl}cyclohexyl)acetic acid;

(trans-4-{4-[({5-[(5-bromopyrazin-2-yl)amino]-1,3,4-oxadiazol-2-yl}carbonyl)amino]phenyl}cyclohexyl)acetic acid;
(trans-4-{4-[({5-[(2-methoxypyrimidin-5-yl)amino]-1,3,4-oxadiazol-2-yl}carbonyl)amino]phenyl}cyclohexyl)acetic acid;
(trans-4-{4-[({5-[(5-benzyl-1,3,4-oxadiazol-2-yl)amino]-1,3,4-oxadiazol-2-yl}carbonyl)amino]phenyl}cyclohexyl)acetic acid;
(trans-4-{4-[({5-[(3-methyl-1,2,4-thiadiazol-5-yl)amino]-1,3,4-oxadiazol-2-yl}carbonyl)amino]phenyl}cyclohexyl)acetic acid;
(trans-4-{4-[({5-[(3-ethyl-1,2,4-thiadiazol-5-yl)amino]-1,3,4-oxadiazol-2-yl}carbonyl)amino]phenyl}cyclohexyl)acetic acid;
(trans-4-{4-[({5-[(2,6-dimethylpyrimidin-4-yl)amino]-1,3,4-oxadiazol-2-yl}carbonyl)amino]phenyl}cyclohexyl)acetic acid;
(trans-4-{4-[({5-[(1,3-dimethyl-1H-pyrazol-5-yl)amino]-1,3,4-oxadiazol-2-yl}carbonyl)amino]phenyl}cyclohexyl)acetic acid;
(trans-4-{4-[({5-[(6-chloropyrazin-2-yl)amino]-1,3,4-oxadiazol-2-yl}carbonyl)amino]phenyl}cyclohexyl)acetic acid;
(trans-4-{4-[({5-[(3,5-dimethylpyrazin-2-yl)amino]-1,3,4-oxadiazol-2-yl}carbonyl)amino]phenyl}cyclohexyl)acetic acid;
[trans-4-(4-{[(5-{[4-(trifluoromethyl)-1,3-thiazol-2-yl]amino}-1,3,4-oxadiazol-2-yl)carbonyl]amino}phenyl)cyclohexyl]acetic acid;
methyl (trans-4-{4-[({5-[(3,4-difluorophenyl)amino]-1,3,4-oxadiazol-2-yl}carbonyl)amino]phenyl}cyclohexyl)acetate;
(trans-4-{4-[({5-[(3,4-difluorophenyl)amino]-1,3,4-oxadiazol-2-yl}carbonyl)amino]phenyl}cyclohexyl)acetic acid;
methyl (trans-4-{4-[({5-[(3-chloro-4-cyanophenyl)amino]-1,3,4-oxadiazol-2-yl}carbonyl)amino]phenyl}cyclohexyl)acetate;
methyl [trans-4-(4-{[(5-{4-cyano-3-(trifluoromethyl)phenyl]amino}-1,3,4-oxadiazol-2-yl)carbonyl]amino}phenyl)cyclohexyl)acetate;
methyl (trans-4-{4-[({5-[(3,4-dicyanophenyl)amino]-1,3,4-oxadiazol-2-yl}carbonyl)amino]phenyl}cyclohexyl)acetate;
methyl (trans-4-{4-[({5-[(4-cyano-3-methylphenyl)amino]-1,3,4-oxadiazol-2-yl}carbonyl)amino]phenyl}cyclohexyl)acetate;
methyl [trans-4-(4-{[(5-{[4-cyano-3-(methylthio)phenyl]amino}-1,3,4-oxadiazol-2-yl)carbonyl]amino}phenyl)cyclohexyl]acetate;
(trans-4-{4-[({5-[(3-chloro-4-cyanophenyl)amino]-1,3,4-oxadiazol-2-yl}carbonyl)amino]phenyl}cyclohexyl)acetic acid;
[trans-4-(4-{[(5-{[4-cyano-3-(trifluoromethyl)phenyl]amino}-1,3,4-oxadiazol-2-yl)carbonyl]amino}phenyl)cyclohexyl]acetic acid;
(trans-4-{4-[({5-[(3,4-dicyanophenyl)amino]-1,3,4-oxadiazol-2-yl}carbonyl)amino]phenyl}cyclohexyl)acetic acid;
(trans-4-{4-[({5-[(4-cyano-3-methylphenyl)amino]-1,3,4-oxadiazol-2-yl}carbonyl)amino]phenyl}cyclohexyl)acetic acid;
[trans-4-(4-{[(5-{[4-cyano-3-(methylthio)phenyl]amino}-1,3,4-oxadiazol-2-yl)carbonyl]amino}phenyl]cyclohexyl]acetic acid;
(trans-4-{4-[({5-[(3-chloro-4-fluorophenyl)amino]-1,3,4-oxadiazol-2-yl}carbonyl)amino]phenyl}cyclohexyl)acetic acid;

(trans-4-{4-[({5-[(3,5-dimethylphenyl)amino]-1,3,4-oxadiazol-2-yl}carbonyl)amino]phenyl}cyclohexyl)acetic acid;
[trans-4-(4-{[(5-{[4-fluoro-3-(trifluoromethyl)phenyl]amino}1,3,4-oxadiazol-2-yl)carbonyl]amino}phenyl)cyclohexyl]acetic acid;
[trans-4-(4-{[(5-{[3-fluoro-5-(trifluoromethyl)phenyl]amino}-1,3,4-oxadiazol-2-yl)carbonyl]amino}phenyl)cyclohexyl]acetic acid;
(trans-4-{4-[({5-[(2-methyl-1,3-benzothiazol-6-yl)amino]-1,3,4-oxadiazol-2-yl}carbonyl)amino]phenyl}cyclohexyl)acetic acid;
(trans-4-{4-[({5-[(3-cyano-4-methylphenyl)amino]-1,3,4-oxadiazol-2-yl}carbonyl)amino]phenyl}cyclohexyl)acetic acid;
(trans-4-{4-[({5-[(3-cyano-4-fluorophenyl)amino]-1,3,4-oxadiazol-2-yl}carbonyl)amino]phenyl}cyclohexyl)acetic acid;
(trans-4-{4-[({5-[(5-chloro-2-fluorophenyl)amino]-1,3,4-oxadiazol-2-yl}carbonyl)amino]phenyl}cyclohexyl)acetic acid;
[trans-4-(4-{[(5-{[4-methoxy-3-(trifluoromethyl)phenyl]amino}-1,3,4-oxadiazol-2-yl)carbonyl]amino}phenyl)cyclohexyl]acetic acid;
(trans-4-{4-[({5-[(4-chloro-3-cyanophenyl)amino]-1,3,4-oxadiazol-2-yl}carbonyl)amino]phenyl}cyclohexyl)acetic acid;
(trans-4-{4-[({5-[(4-chloro-3-methoxyphenyl)amino]-1,3,4-oxadiazol-2-yl}carbonyl)amino]phenyl}cyclohexyl)acetic acid;
[trans-4-(4-{[(5-{[3-methoxy-5-(trifluoromethyl)phenyl]aminol}-1,3,4-oxadiazol-2-yl)carbonyl]amino}phenyl)cyclohexyl]acetic acid;
(trans-4-{4-[({5-[(4-chloro-3-fluorophenyl)amino]-1,3,4-oxadiazol-2-yl}carbonyl)amino]phenyl}cyclohexyl)acetic acid;
(trans-4-{4-[({5-[(4-cyano-2-fluorophenyl)amino]-1,3,4-oxadiazol-2-yl}carbonyl)amino]phenyl}cyclohexyl)acetic acid;
(trans-4-{4-[({5-[(3-fluoro-4-methoxyphenyl)amino]-1,3,4-oxadiazol-2-yl}carbonyl)amino]phenyl}cyclohexyl)acetic acid;
(trans-4-{4-[({5-[(2-methyl-1,3-benzothiazol-5-yl)amino]-1,3,4-oxadiazol-2-yl}carbonyl)amino]phenyl}cyclohexyl)acetic acid;
(trans-4-{4-[({5-[(2-oxo-2,3-dihydro-1H-benzimidazol-5-yl)amino]-1,3,4-oxadiazol-2-yl}carbonyl)amino]phenyl}cyclohexyl)acetic acid;
(trans-4-{4-[({5-[(2-methyl-1H-benzimidazol-6-yl)amino]-1,3,4-oxadiazol-2-yl}carbonyl)amino]phenyl}cyclohexyl)acetic acid;
{trans-4-[4-({[5-(quinolin-3-ylamino)-1,3,4-oxadiazol-2-yl]carbonyl}amino)phenyl]cyclohexyl}acetic acid;
[trans-4-(4-{[(5-{[6-(4-chlorophenoxy)pyridin-3-yl]amino}-1,3,4-oxadiazol-2-yl)carbonyl]amino}phenyl)cyclohexyl]acetic acid;
(trans-4-{4-[({5-[(6-methoxypyridin-3-yl)amino]-1,3,4-oxadiazol-2-yl}carbonyl)amino]phenyl}cyclohexyl)acetic acid;
(trans-4-{4-[({5-[(4-methylpyridin-2-yl)amino]-1,3,4-oxadiazol-2-yl}carbonyl)amino]phenyl}cyclohexyl)acetic acid;
(trans-4-f{4-[({f{5-[(5-methylpyridin-2-yl)amino]-1,3,4-oxadiazol-2-yl}carbonyl)amino]phenyl}cyclohexyl)acetic acid;

(trans-4-{4-[({5-[(2-methoxypyridin-3-yl)amino]-1,3,4-oxadiazol-2-yl}carbonyl)amino]phenyl}cyclohexyl)acetic acid;
(trans-4-{4-[({5-[(5-fluoropyridin-2-yl)amino]-1,3,4-oxadiazol-2-yl}carbonyl)amino]phenyl}cyclohexyl)acetic acid;
[trans-4-(4-{[(5-{[6-(4-methoxyphenoxy)pyridin-3-yl]amino}-1,3,4-oxadiazol-2-yl)carbonyl]amino}phenyl)cyclohexyl]acetic acid;
{trans-4-[4-({[5-({6-[(3-chlorobenzyl)oxy]pyridin-3-yl}amino)-1,3,4-oxadiazol-2-yl]carbonyl}amino)phenyl]cyclohexyl}acetic acid;
{trans-4-[4-({[5-(1H-pyrrolo[2,3-b]pyridin-5-ylamino)-1,3,4-oxadiazol-2-yl]carbonyl}amino)phenyl]cyclohexyl}acetic acid;
(trans-4-{4-[({5-[(6-cyanopyridin-3-yl)amino]-1,3,4-oxadiazol-2-yl}carbonyl)amino]phenyl}cyclohexyl)acetic acid;
(trans-4-{4-[({5-[(5-cyanopyridin-2-yl)amino]-1,3,4-oxadiazol-2-yl}carbonyl)amino]phenyl}cyclohexyl)acetic acid;
rac-ethyl 2-(trans-4-{4-[({5-[(2,4,5-trifluorophenyl)amino]-1,3,4-oxadiazol-2-yl}carbonyl)amino]phenyl}cyclohexyl)propanoate;
rac-ethyl 2-(trans-4-{4-[({5-[(4-cyanophenyl)amino]-1,3,4-oxadiazol-2-yl}carbonyl)amino]phenyl}cyclohexyl)propanoate;
rac-ethyl 2-(trans-4-{4-[({5-[(3,4-difluorophenyl)amino]-1,3,4-oxadiazol-2-yl}carbonyl)amino]phenyl}cyclohexyl)propanoate;
rac-2-(trans-4-{4-[({5-[(2,4,5-trifluorophenyl)amino]-1,3,4-oxadiazol-2-yl}carbonyl)amino]phenyl}cyclohexyl)propanoic acid;
rac-2-(trans-4-{4-[({5-[(3,4-difluorophenyl)amino]-1,3,4-oxadiazol-2-yl}carbonyl)amino]phenyl}cyclohexyl)propanoic acid;
rac-2-(trans-4-{4-[({5-[(4-cyanophenyl)amino]-1,3,4-oxadiazol-2-yl}carbonyl)amino]phenyl}cyclohexyl)propanoic acid;
(trans-4-{4-[({5-[(4-methylphenyl)amino]-1,3,4-oxadiazol-2-yl}carbonyl)amino]phenyl}cyclohexyl)acetic acid;
(trans-4-{4-[({5-[(4-bromophenyl)amino]-1,3,4-oxadiazol-2-yl}carbonyl)amino]phenyl}cyclohexyl)acetic acid;
(trans-4-{4-[({5-[(4-ethoxyphenyl)amino]-1,3,4-oxadiazol-2-yl}carbonyl)amino]phenyl}cyclohexyl)acetic acid;
(trans-4-{4-[({5-[(4-tert-butylphenyl)amino]-1,3,4-oxadiazol-2-yl}carbonyl)amino]phenyl}cyclohexyl)acetic acid;
(trans-4-{4-[({5-[(2-ethoxyphenyl)amino]-1,3,4-oxadiazol-2-yl}carbonyl)amino]phenyl}cyclohexyl)acetic acid;
(trans-4-{4-[({5-[(2-methylphenyl)amino]-1,3,4-oxadiazol-2-yl}carbonyl)amino]phenyl}cyclohexyl)acetic acid;
[trans-4-(4-{[(5-{[4-(aminosulfonyl)phenyl]amino}-1,3,4-oxadiazol-2-yl)carbonyl]amino}phenyl)cyclohexyl]acetic acid;
(trans-4-{4-[({5-[(2-chlorophenyl)amino]-1,3,4-oxadiazol-2-yl}carbonyl)amino]phenyl}cyclohexyl)acetic acid;
(trans-4-{4-[({5-[(3-methoxyphenyl)amino]-1,3,4-oxadiazol-2-yl}carbonyl)amino]phenyl}cyclohexyl)acetic acid;
{trans-4-[4-({[5-({4-[(trifluoromethyl)thio]phenyl}amino)-1,3,4-oxadiazol-2-yl]carbonyl}amino)phenyl]cyclohexyl}acetic acid;
5-[(3,4-difluorophenyl)amino]-N-(4-phenoxyphenyl)-1,3,4-oxadiazole-2-carboxamide;
5-[(3,4-difluorophenyl)amino]-N-[4-(2-methoxyphenoxy)phenyl]-1,3,4-oxadiazole-2-carboxamide;
5-[(3,4-difluorophenyl)amino]-N-[4-(4-methylphenoxy)phenyl]-1,3,4-oxadiazole-2-carboxamide;
5-[(3,4-difluorophenyl)amino]-N-[4-(3-methoxyphenoxy)phenyl]-1,3,4-oxadiazole-2-carboxamide;
N-(3,5-dichloro-4-morpholin-4-ylphenyl)-5-[(3-methylphenyl)amino]-1,3,4-oxadiazole-2-carboxamide;
N-{6-[4-(cyclopropylmethyl)piperazin-1-yl]pyridin-3-yl}-5-[(2-fluorophenyl)amino]-1,3,4-oxadiazole-2-carboxamide;
5-[(2-fluorophenyl)amino]-N-{6-[4-(2-methoxyethyl)piperazin-1-yl]pyridin-3-yl}-1,3,4-oxadiazole-2-carboxamide;
5-[(2-fluorophenyl)amino]-N-[4-(2-morpholin-4-ylethoxy)phenyl]-1,3,4-oxadiazole-2-carboxamide;
5-[(2-fluorophenyl)amino]-N-[4-(3-hydroxypropoxy)phenyl]-1,3,4-oxadiazole-2-carboxamide;
N-[4-(2-ethoxyethoxy)phenyl]-5-[(2-fluorophenyl)amino]-1,3,4-oxadiazole-2-carboxamide;
N-{4-[2-(diethylamino)-1,1-dimethyl-2-oxoethoxy]phenyl}-5-[(2-fluorophenyl)amino]-1,3,4-oxadiazole-2-carboxamide;
5-[(2-fluorophenyl)amino]-N-(4-pyrrolidin-1-ylphenyl)-1,3,4-oxadiazole-2-carboxamide;
methyl trans-4-{4-[({5-[(2,4,5-trifluorophenyl)amino]-1,3,4-oxadiazol-2-yl}carbonyl)amino]phenyl}cyclohexanecarboxylate;
trans-4-{4-[({5-[(2,4,5-trifluorophenyl)amino]-1,3,4-oxadiazol-2-yl}carbonyl)amino]phenyl}cyclohexanecarboxylic acid;
methyl 6-{4-[({5-[(2-fluorophenyl)amino]-1,3,4-oxadiazol-2-yl}carbonyl)amino]piperidin-1-yl}nicotinate;
6-{4-[({5-[(2-fluorophenyl)amino]-1,3,4-oxadiazol-2-yl}carbonyl)amino]piperidin-1-yl}nicotinic acid;
6-{4-[({5-[(2-fluorophenyl)amino]-1,3,4-oxadiazol-2-yl}carbonyl)amino]piperidin-1-yl}nicotinamide;
(6-{4-[({5-[(2-fluorophenyl)amino]-1,3,4-oxadiazol-2-yl}carbonyl)amino]piperidin-1-yl}pyridin-3-yl)acetic acid;
5-{[3-(anilinocarbonyl)phenyl]amino}-N-(6-morpholin-4-ylpyridin-3-yl)-1,3,4-oxadiazole-2-carboxamide;
N-{4-[trans-4-(aminomethyl)cyclohexyl]phenyl}-5-[(2-fluorophenyl)amino]-1,3,4-oxadiazole-2-carboxamide;
tert-butyl [(trans-4-{4-[({5-[(2-fluorophenyl)amino]-1,3,4-oxadiazol-2-yl}carbonyl)amino]phenyl}cyclohexyl)methyl]carbamate;
methyl (1-{5-[({5-[(3,4-difluorophenyl)amino]-1,3,4-oxadiazol-2-yl}carbonyl)amino]pyridin-2-yl}piperidin-4-yl)acetate;
(1-{5-[({5-[(3,4-difluorophenyl)amino]-1,3,4-oxadiazol-2-yl}carbonyl)amino]pyridin-2-yl}piperidin-4-yl)acetic acid;
methyl [1-(5-{[(5-{[4-(trifluoromethoxy)phenyl]amino}-1,3,4-oxadiazol-2-yl)carbonyl]amino}pyridin-2-yl)piperidin-4-yl]acetate;
[1-(5-{[(5-{[4-(trifluoromethoxy)phenyl]amino}-1,3,4-oxadiazol-2-yl)carbonyl]amino}pyridin-2-yl)piperidin-4-yl]acetic acid;
(2R)-2-(trans-4-{4-[({5-[(2,4,5-trifluorophenyl)amino]-1,3,4-oxadiazol-2-yl}carbonyl)amino]phenyl}cyclohexyl)propanoic acid;
(2S)-2-(trans-4-{4-[({5-[(2,4,5-trifluorophenyl)amino]-1,3,4-oxadiazol-2-yl}carbonyl)amino]phenyl}cyclohexyl)propanoic acid;
(2R)-2-(trans-4-{4-[({5-[(3,4-difluorophenyl)amino]-1,3,4-oxadiazol-2-yl}carbonyl)amino]phenyl}cyclohexyl)propanoic acid;
(2S)-2-(trans-4-{4-[({5-[(3,4-difluorophenyl)amino]-1,3,4-oxadiazol-2-yl}carbonyl)amino-phenyl}cyclohexyl)propanoic acid;

(2R)-2-(trans-4-{4-[({5-[(4-cyanophenyl)amino]-1,3,4-oxadiazol-2-yl}carbonyl)amino]phenyl}cyclohexyl)-propanoic acid;

(2S)-2-(trans-4-{4-[({5-[(4-cyanophenyl)amino]-1,3,4-oxadiazol-2-yl}carbonyl)amino]phenyl}cyclohexyl)-propanoic acid; and/or ethyl (2R)-2-(trans-4-{4-[({5-[(2,4,5-trifluorophenyl)amino]-1,3,4-oxadiazol-2-yl}carbonyl)amino]phenyl}cyclohexyl)propanoate;

ethyl (2S)-2-(trans-4-{4-[({5-[(2,4,5-trifluorophenyl)amino]-1,3,4-oxadiazol-2-yl}carbonyl)amino]phenyl}cyclohexyl)propanoate;

ethyl (2R)-2-(trans-4-f{4-[({5-[(3,4-difluorophenyl)amino]-1,3,4-oxadiazol-2-yl}carbonyl)amino]phenyl}cyclohexyl)propanoate;

ethyl (2S)-2-(trans-4-{4-[({5-[(3,4-difluorophenyl)amino]-1,3,4-oxadiazol-2-yl}carbonyl)amino]phenyl}cyclohexyl)propanoate;

ethyl (2R)-2-(trans-4-{4-[({5-[(4-cyanophenyl)amino]-1,3,4-oxadiazol-2-yl}carbonyl)amino]phenyl}cyclohexyl)propanoate;

ethyl (2S)-2-(trans-4-{4-[({5-[(4-cyanophenyl)amino]-1,3,4-oxadiazol-2-yl}carbonyl)amino]phenyl}cyclohexyl)propanoate; and/or methyl 2-methyl-2-(trans-4-{4-[({5-[(2,4,5-trifluorophenyl)amino]-1,3,4-oxadiazol-2-yl}carbonyl)amino]phenyl}cyclohexyl)propanoate;

2-methyl-2-(trans-4-{4-[({5-[(2,4,5-trifluorophenyl)amino]-1,3,4-oxadiazol-2-yl}carbonyl)amino]phenyl}cyclohexyl)propanoic acid;

1-{5-[({5-[(3,4-difluorophenyl)amino]-1,3,4-oxadiazol-2-yl}carbonyl)amino]pyridin-2-yl}-4-methylpiperidine-4-carboxylic acid;

1-{5-[({5-[(4-ethylphenyl)amino]-1,3,4-oxadiazol-2-yl}carbonyl)amino]pyridin-2-yl}-4-methylpiperidine-4-carboxylic acid;

4-methyl-1-(5-{[(5-{[4-(trifluoromethoxy)phenyl]amino}-1,3,4-oxadiazol-2-yl)carbonyl]amino}pyridin-2-yl)piperidine-4-carboxylic acid;

4-methyl-1-{5-[({5-[(2,4,5-trifluorophenyl)amino]-1,3,4-oxadiazol-2-yl}carbonyl)amino]pyridin-2-yl}piperidine-4-carboxylic acid;

4-methyl-1-(5-{[(5-{[4-(trifluoromethyl)phenyl]amino}-1,3,4-oxadiazol-2-yl)carbonyl]amino}pyridin-2-yl)piperidine-4-carboxylic acid;

1-(5-{[(5-{[4-(4-chlorophenoxy)phenyl]amino}-1,3,4-oxadiazol-2-yl)carbonyl]amino}pyridin-2-yl)-4-methylpiperidine-4-carboxylic acid;

methyl 1-{5-[({5-[(3,4-difluorophenyl)amino]-1,3,4-oxadiazol-2-yl}carbonyl)amino]pyridin-2-yl}-4-methylpiperidine-4-carboxylate;

methyl 1-{5-[({5-[(4-ethylphenyl)amino]-1,3,4-oxadiazol-2-yl}carbonyl)amino]pyridin-2-yl}-4-methylpiperidine-4-carboxylate;

methyl 4-methyl-1-(5-{[(5-{[4-(trifluoromethoxy)phenyl]amino}-1,3,4-oxadiazol-2-yl)carbonyl]amino}pyridin-2-yl)piperidine-4-carboxylate;

methyl 4-methyl-1-{5-[({5-[(2,4,5-trifluorophenyl)amino]-1,3,4-oxadiazol-2-yl}carbonyl)amino]pyridin-2-yl}piperidine-4-carboxylate;

methyl 4-methyl-1-(5-{[(5-{[4-(trifluoromethyl)phenyl]amino}-1,3,4-oxadiazol-2-yl)carbonyl]amino}pyridin-2-yl)piperidine-4-carboxylate;

methyl 1-(5-{[(5-{[4-(4-chlorophenoxy)phenyl]amino}-1,3,4-oxadiazol-2-yl)carbonyl]amino}pyridin-2-yl)-4-methylpiperidine-4-carboxylate;

1-(5-{[(5-{[4-(4-chlorophenoxy)phenyl]amino}-1,3,4-oxadiazol-2-yl)carbonyl]amino}pyridin-2-yl)piperidine-4-carboxylic acid;

methyl 1-(5-{[(5-{[4-(4-chlorophenoxy)phenyl]amino}-1,3,4-oxadiazol-2-yl)carbonyl]amino}pyridin-2-yl)piperidine-4-carboxylate;

[1-(5-{[(5-{[4-(4-chlorophenoxy)phenyl]amino}-1,3,4-oxadiazol-2-yl)carbonyl]amino}pyridin-2-yl)piperidin-4-yl]acetic acid;

methyl [1-(5-{[(5-{[4-(4-chlorophenoxy)phenyl]amino}-1,3,4-oxadiazol-2-yl)carbonyl]amino}pyridin-2-yl)piperidin-4-yl]acetate; rac-ethyl 2-(trans-4-{2-chloro-4-[({5-[(2,4,5-trifluorophenyl)amino]-1,3,4-oxadiazol-2-yl}carbonyl)amino]phenyl}cyclohexyl)propanoate;

rac-ethyl 2-(trans-4-{3-chloro-4-[({5-[(2,4,5-trifluorophenyl)amino]-1,3,4-oxadiazol-2-yl}carbonyl)amino]phenyl}cyclohexyl)propanoate;

rac-2-(trans-4-{2-chloro-4-[({5-[(2,4,5-trifluorophenyl)amino]-1,3,4-oxadiazol-2-yl}carbonyl)amino]phenyl}cyclohexyl)propanoic acid;

rac-2-(trans-4-{3-chloro-4-[({5-[(2,4,5-trifluorophenyl)amino]-1,3,4-oxadiazol-2-yl}carbonyl)amino]phenyl}cyclohexyl)propanoic acid;

ethyl cis-4-{4-[({5-[(2,4,5-trifluorophenyl)amino]-1,3,4-oxadiazol-2-yl}carbonyl)amino]-phenoxy}cyclohexanecarboxylate;

cis-4-{4-[({5-[(2,4,5-trifluorophenyl)amino]-1,3,4-oxadiazol-2-yl}carbonyl)amino]-phenoxy}cyclohexanecarboxylic acid;

(1-{5-[({5-[(4-ethylphenyl)amino]-1,3,4-oxadiazol-2-yl}carbonyl)amino]pyridin-2-yl}piperidin-4-yl)acetic acid;

[1-(5-{[(5-{[4-(trifluoromethyl)phenyl]amino}-1,3,4-oxadiazol-2-yl)carbonyl]amino}pyridin-2-yl)piperidin-4-yl]acetic acid;

methyl (1-{5-[({5-[(4-ethylphenyl)amino]-1,3,4-oxadiazol-2-yl}carbonyl)amino]pyridin-2-yl}piperidin-4-yl)acetate;

methyl [1-(5-{[(5-{[4-(trifluoromethyl)phenyl]amino}-1,3,4-oxadiazol-2-yl)carbonyl]amino}pyridin-2-yl)piperidin-4-yl]acetate;

1-{5-[({5-[(4-ethylphenyl)amino]-1,3,4-oxadiazol-2-yl}carbonyl)amino]pyridin-2-yl}piperidine-4-carboxylic acid;

1-(5-{[(5-{[4-(trifluoromethoxy)phenyl]amino}-1,3,4-oxadiazol-2-yl)carbonyl]amino}pyridin-2-yl)piperidine-4-carboxylic acid;

1-(5-{[(5-{[4-(trifluoromethyl)phenyl]amino}-1,3,4-oxadiazol-2-yl)carbonyl]amino}pyridin-2-yl)piperidine-4-carboxylic acid;

methyl 1-{5-[({5-[(4-ethylphenyl)amino]-1,3,4-oxadiazol-2-yl}carbonyl)amino]pyridin-2-yl}piperidine-4-carboxylate;

methyl 1-(5-{[(5-{[4-(trifluoromethoxy)phenyl]amino}-1,3,4-oxadiazol-2-yl)carbonyl]amino}pyridin-2-yl)piperidine-4-carboxylate;

methyl 1-(5-{[(5-{[4-(trifluoromethyl)phenyl]amino}-1,3,4-oxadiazol-2-yl)carbonyl]amino}pyridin-2-yl)piperidine-4-carboxylate;

(trans-4-{4-[({5-[(2-chloro-4-methylphenyl)amino]-1,3,4-oxadiazol-2-yl}carbonyl)amino]phenyl}cyclohexyl)acetic acid;

(trans-4-{4-[({5-[(4-methoxy-2-methylphenyl)amino]-1,3,4-oxadiazol-2-yl}carbonyl)amino]phenyl}cyclohexyl)acetic acid;

(trans-4-{4-[({5-[(4-fluoro-2-methylphenyl)amino]-1,3,4-oxadiazol-2-yl}carbonyl)amino]phenyl}cyclohexyl)acetic acid;

[trans-4-(4-{[(5-{[4-fluoro-2-(trifluoromethyl)phenyl]amino}-1,3,4-oxadiazol-2-yl)carbonyl]amino}phenyl)cyclohexyl]acetic acid;

(trans-4-{4-[({5-[(2,4-dichlorophenyl)amino]-1,3,4-oxadiazol-2-yl}carbonyl)amino]phenyl}cyclohexyl)acetic acid;

(trans-4-{4-[({5-[(2-chloro-4-cyanophenyl)amino]-1,3,4-oxadiazol-2-yl}carbonyl)amino]phenyl}cyclohexyl)acetic acid;

(trans-4-{4-[({5-[(4-cyano-2-methylphenyl)amino]-1,3,4-oxadiazol-2-yl}carbonyl)amino]phenyl}cyclohexyl)acetic acid;

(trans-4-{4-[({5-[(4-chloro-2,5-dimethylphenyl)amino]-1,3,4-oxadiazol-2-yl}carbonyl)amino]phenyl}cyclohexyl)acetic acid;

(trans-4-{4-[({5-[(4-cyano-2-ethylphenyl)amino]-1,3,4-oxadiazol-2-yl}carbonyl)amino]phenyl}cyclohexyl)acetic acid;

(trans-4-{4-[({5-[(2-chloro-4-fluorophenyl)amino]-1,3,4-oxadiazol-2-yl}carbonyl)amino]phenyl}cyclohexyl)acetic acid;

(trans-4-{4-[({5-[(4-chloro-2-methylphenyl)amino]-1,3,4-oxadiazol-2-yl}carbonyl)amino]phenyl}cyclohexyl)acetic acid;

(trans-4-{4-[({5-[(2,3-dichlorophenyl)amino]-1,3,4-oxadiazol-2-yl}carbonyl)amino]phenyl}cyclohexyl)acetic acid;

(trans-4-{4-[({5-[(2,5-dichlorophenyl)amino]-1,3,4-oxadiazol-2-yl}carbonyl)amino]phenyl}cyclohexyl)acetic acid;

(trans-4-{4-[({5-[(2-bromo-4-methylphenyl)amino]-1,3,4-oxadiazol-2-yl}carbonyl)amino]phenyl}cyclohexyl)acetic acid;

[trans-4-(4-{[(5-{[2-chloro-5-(trifluoromethyl)phenyl]amino}-1,3,4-oxadiazol-2-yl)carbonyl]amino}phenyl)cyclohexyl]acetic acid;

[trans-4-(4-{[(5-{[2-bromo-4-(trifluoromethyl)phenyl]amino}-1,3,4-oxadiazol-2-yl)carbonyl]amino}phenyl)cyclohexyl]acetic acid;

[trans-4-(4-{[(5-{[2-chloro-4-(trifluoromethyl)phenyl]amino}-1,3,4-oxadiazol-2-yl)carbonyl]amino}phenyl)cyclohexyl]acetic acid;

(trans-4-{4-[({5-[(4-bromo-2-chlorophenyl)amino]-1,3,4-oxadiazol-2-yl}carbonyl)amino]phenyl}cyclohexyl)acetic acid;

(trans-4-{4-[({5-[(3-chloro-2-methylphenyl)amino]-1,3,4-oxadiazol-2-yl}carbonyl)amino]phenyl}cyclohexyl)acetic acid;

(trans-4-{4-[({5-[(5-bromo-2-methylphenyl)amino]-1,3,4-oxadiazol-2-yl}carbonyl)amino]phenyl}cyclohexyl)acetic acid;

(trans-4-{4-[({5-[(2-chloro-5-fluorophenyl)amino]-1,3,4-oxadiazol-2-yl}carbonyl)amino]phenyl}cyclohexyl)acetic acid;

(trans-4-{4-[({5-[(2-chloro-5-methylphenyl)amino]-1,3,4-oxadiazol-2-yl}carbonyl)amino]phenyl}cyclohexyl)acetic acid;

(trans-4-{4-[({5-[(5-chloro-2-methylphenyl)amino]-1,3,4-oxadiazol-2-yl}carbonyl)amino]phenyl}cyclohexyl)acetic acid;

ethyl 2-(3-{4-[({5-[(3,4-difluorophenyl)amino]-1,3,4-oxadiazol-2-yl}carbonyl)amino]phenyl}cyclobutyl)propanoate;

2-(3-{4-[({5-[(3,4-difluorophenyl)amino]-1,3,4-oxadiazol-2-yl}carbonyl)amino]phenyl}cyclobutyl)propanoic acid;

methyl 1-{5-[({5-[(3,4-difluorophenyl)amino]-1,3,4-oxadiazol-2-yl}carbonyl)amino]-3-methylpyridin-2-yl}piperidine-4-carboxylate;

methyl 1-(3-methyl-5-{[(5-{[4-trifluoromethoxy)phenyl]amino}-1,3,4-oxadiazol-2-yl)carbonyl]amino}pyridin-2-yl)piperidine-4-carboxylate;

methyl 1-(3-methyl-5-{[(5-{[4-trifluoromethyl)phenyl]amino}-1,3,4-oxadiazol-2-yl)carbonyl]amino}pyridin-2-yl)piperidine-4-carboxylate;

methyl 1-{5-[({5-[(4-ethylphenyl)amino]-1,3,4-oxadiazol-2-yl}carbonyl)amino]-3-methylpyridin-2-yl}piperidine-4-carboxylate;

methyl (1-{5-[({5-[(3,4-difluorophenyl)amino]-1,3,4-oxadiazol-2-yl}carbonyl)amino]-3-methylpyridin-2-yl}piperidin-4-yl)acetate;

methyl [1-(3-methyl-5-{[(5-{[4-trifluoromethyl)phenyl]amino}-1,3,4-oxadiazol-2-yl)carbonyl]amino}pyridin-2-yl)piperidin-4-yl]acetate;

methyl [1-(3-methyl-5-{[(5-{[4-trifluoromethyl)phenyl]amino}-1,3,4-oxadiazol-2-yl)carbonyl]amino}pyridin-2-yl)piperidin-4-yl]acetate;

methyl (1-{5-[({5-[(4-ethylphenyl)amino]-1,3,4-oxadiazol-2-yl}carbonyl)amino]-3-methylpyridin-2-yl}piperidin-4-yl)acetate;

ethyl 2-(1-{5-[({5-[(3,4-difluorophenyl)amino]-1,3,4-oxadiazol-2-yl}carbonyl)amino]-3-methylpyridin-2-yl}piperidin-4-yl)propanoate;

ethyl 2-[1-(3-methyl-5-{-[(5-{[4-trifluoromethyl)phenyl]amino}-1,3,4-oxadiazol-2-yl)carbonyl]amino}pyridin-2-yl)piperidin-4-yl]propanoate;

ethyl 2-(1-{3-methyl-5-[({5-[(2,4,5-trifluorophenyl)amino]-1,3,4-oxadiazol-2-yl}carbonyl)amino]pyridine-2-yl}piperidin-4-yl)propanoate;

ethyl 2-(1-{5-[({5-[(4-ethylphenyl)amino]-1,3,4-oxadiazol-2-yl}carbonyl)amino]-3-methylpyridin-2-yl}piperidin-4-yl)propanoate;

(1-{5-[({5-[(3,4-difluorophenyl)amino]-1,3,4-oxadiazol-2-yl}carbonyl)amino]-3-methylpyridin-2-yl}piperidin-4-yl)acetic acid;

[1-(3-methyl-5-{[(5-{[4-(trifluoromethoxy)phenyl]amino}-1,3,4-oxadiazol-2-yl)carbonyl]amino}pyridin-2-yl)piperidin-4-yl]acetic acid;

[1-(3-methyl-5-{[(5-{[4-(trifluoromethyl)phenyl]amino}-1,3,4-oxadiazol-2-yl)carbonyl]amino}pyridin-2-yl)piperidin-4-yl]acetic acid;

(1-{5-[({5-[(4-ethylphenyl)amino]-1,3,4-oxadiazol-2-yl}carbonyl)amino]-3-methylpyridin-2-yl}piperidin-4-yl)acetic acid;

1-{5-[({5-[(3,4-difluorophenyl)amino]-1,3,4-oxadiazol-2-yl}carbonyl)amino]-3-methylpyridin-2-yl}piperidine-4-carboxylic acid;

1-(3-methyl-5-{[(5-{[4-(trifluoromethoxy)phenyl]amino}-1,3,4-oxadiazol-2-yl)carbonyl]amino}pyridin-2-yl)piperidine-4-carboxylic acid;

1-(3-methyl-5-{[(5-{[4-(trifluoromethyl)phenyl]amino}-1,3,4-oxadiazol-2-yl)carbonyl]amino}pyridin-2-yl)piperidine-4-carboxylic acid;

1-{5-[({5-[(4-ethylphenyl)amino]-1,3,4-oxadiazol-2-yl}carbonyl)amino]-3-methylpyridin-2-yl}piperidine-4-carboxylic acid;

2-(1-{3-methyl-5-[({5-[(2,4,5-trifluorophenyl)amino]-1,3,4-oxadiazol-2-yl}carbonyl)amino]pyridin-2-yl}piperidin-4-yl)propanoic acid;

methyl (1-{5-[({5-[(3,4-difluorophenyl)amino]-1,3,4-oxadiazol-9-yl}carbonyl)amino]pyridin-2-yl}-4-methylpiperidin-4-yl)acetate;

1-(5-{[(5-{[4-(4-fluorophenoxy)phenyl]amino}-1,3,4-oxadiazol-2-yl)carbonyl]amino}pyridin-2-yl)piperidine-4-carboxylic acid;

1-(5-{[(5-{[4-(4-fluorophenoxy)phenyl]amino}-1,3,4-oxadiazol-2-yl)carbonyl]amino}pyridin-2-yl)-4-methylpiperidine-4-carboxylic acid;
[1-(5-{[(5-{[4-(4-fluorophenoxy)phenyl]amino}-1,3,4-oxadiazol-2-yl)carbonyl]amino}pyridin-2-yl)piperidin-4-yl] acetic acid;
methyl 1-(5-{[(5-{[4-(4-fluorophenoxy)phenyl]amino}-1,3,4-oxadiazol-2-yl)carbonyl]amino}pyridin-2-yl)piperidine-4-carboxylate;
methyl [1-(5-{[(5-{[4-(4-fluorophenoxy)phenyl]amino}-1,3,4-oxadiazol-2-yl)carbonyl]amino}pyridin-2-yl)piperidin-4-yl]acetate;
methyl 1-(5-{[(5-{[4-(4-fluorophenoxy)phenyl]amino}-1,3,4-oxadiazol-2-yl)carbonyl]amino}pyridin-2-yl)-4-methylpiperidine-4-carboxylate;
(1-{5-[({5-[(3,4-difluorophenyl)amino]-1,3,4-oxadiazol-2-yl}carbonyl)amino]pyridin-2-yl}-4-methylpiperidin-4-yl)acetic acid;
(4-methyl-1-{5-[({5-[(2,4,5-trifluorophenyl)amino]-1,3,4-oxadiazol-2-yl}carbonyl)amino]pyridin-2-yl}piperidin-4-yl)acetic acid;
[4-methyl-1-(5-{[(5-{[4-(trifluoromethyl)phenyl]amino}-1,3,4-oxadiazol-2-yl)carbonyl]amino}pyridin-2-yl)piperidin-4-yl]acetic acid; and/or
[1-(5-{[(5-{[4-(4-fluorophenoxy)phenyl]amino}-1,3,4-oxadiazol-2-yl)carbonyl]amino}pyridin-2-yl)-4-methylpiperidin-4-yl]acetic acid.

In a further aspect of the invention, there is provided any one or more of the following compounds, or pharmaceutically-acceptable salts or pro-drugs thereof:
N-[4-(4-morpholinyl)phenyl]-5-[[3-(phenylmethoxy)phenyl]amino]-1,3,4-oxadiazole-2-carboxamide;
5-[(3,4-difluorophenyl)amino]-N-[4-(4-morpholinyl)phenyl]-1,3,4-oxadiazole-2-carboxamide;
5-[(2,4-difluorophenyl)amino]-N-[4-(4-morpholinyl)phenyl]-1,3,4-oxadiazole-2-carboxamide;
5-[(2-fluorophenyl)amino]-N-[4-(4-morpholinyl)phenyl]-1,3,4-oxadiazole-2-carboxamide; and
5-[(2-fluorophenyl)amino]-N-[6-(4-morpholinyl)-3-pyridinyl]-1,3,4-oxadiazole-2-carboxamide.

In a further aspect of the invention, there is provided any one or more of the following compounds, or pharmaceutically-acceptable salts or pro-drugs thereof:
N-[4-(4-acetylpiperazin-1-yl)phenyl]-5-[(2,4-difluorophenyl)amino]-1,3,4-oxadiazole-2-carboxamide;
N-[4-(4-acetylpiperazin-1-yl)phenyl]-5-[(4-chlorophenyl)amino]-1,3,4-oxadiazole-2-carboxamide;
N-[4-(4-acetylpiperazin-1-yl)phenyl]-5-[(3-chlorophenyl)amino]-1,3,4-oxadiazole-2-carboxamide;
N-[4-(4-acetylpiperazin-1-yl)phenyl]-5-[(2,4,5-trifluorophenyl)amino]-1,3,4-oxadiazole-2-carboxamide;
N-[4-(4-acetyl-1-piperazinyl)phenyl]-5-[(2-fluorophenyl)amino]-1,3,4-oxadiazole-2-carboxamide;
N-[6-(4-acetyl-1-piperazinyl)-3-pyridinyl]-5-[(2-fluorophenyl)amino]-1,3,4-oxadiazole-2-carboxamide; and
5-[(2-fluorophenyl)amino]-N-{6-[4-(pyridin-3-ylcarbonyl)piperazin-1-yl]pyridin-3-yl}-1,3,4-oxadiazole-2-carboxamide.

In a further aspect of the invention, there is provided any one or more of the following compounds, or pharmaceutically-acceptable salts or pro-drugs thereof:
sodium (trans-4-{4-[({5-[(2,4,5-trifluorophenyl)amino]1,3,4-oxadiazol-2-yl}carbonyl)amino]phenyl}cyclohexyl)acetate;
{trans-4-[4-({[5-(pyridin-2-ylamino)-1,3,4-oxadiazol-2-yl]carbonyl}amino)phenyl]cyclohexyl}acetic acid;
(trans-4-{4-[({5-[(3,4-difluorophenyl)amino]-1,3,4-oxadiazol-2-yl}carbonyl)amino]phenyl}cyclohexyl)acetic acid;
(trans-4-{4-[({5-[(2,4,6-trifluorophenyl)amino]-1,3,4-oxadiazol-2-yl}carbonyl)amino]phenyl}cyclohexyl)acetic acid;
[trans-4-(4-{[(5-{[4-(trifluoromethyl)phenyl]amino}-1,3,4-oxadiazol-2-yl)carbonyl]amino}phenyl)cyclohexyl]acetic acid;
(trans-4-{4-[({5-[(4-cyanophenyl)amino]-1,3,4-oxadiazol-2-yl}carbonyl)amino]phenyl}cyclohexyl)acetic acid;
[trans-4-(4-{[(5-{[4-(trifluoromethoxy)phenyl]amino}-1,3,4-oxadiazol-2-yl)carbonyl]amino}phenyl)cyclohexyl]acetic acid;
(trans-4-{5-[({5-[(2,4,5-trifluorophenyl)amino]1,3,4-oxadiazol-2-yl}carbonyl)amino]pyridin-2-yl}cyclohexyl)acetic acid;
trans-4-{4-[({5-[(2,4,5-trifluorophenyl)amino]-1,3,4-oxadiazol-2-yl}carbonyl)amino]phenyl}cyclohexanecarboxylic acid;
(2R)-2-(trans-4-{4-[({5-[(2,4,5-trifluorophenyl)amino]-1,3,4-oxadiazol-2-yl}carbonyl)amino]phenyl}cyclohexyl)-propanoic acid;
(2S)-2-(trans-4-{4-[({5-[(2,4,5-trifluorophenyl)amino]-1,3,4-oxadiazol-2-yl}carbonyl)amino]phenyl}cyclohexyl) propanoic acid;
(2R)-2-(trans-4-{4-[({5-[(3,4-difluorophenyl)amino]-1,3,4-oxadiazol-2-yl}carbonyl)amino]phenyl}cyclohexyl)propanoic acid;
(2S)-2-(trans-4-{4-[({5-[(3,4-difluorophenyl)amino]-1,3,4-oxadiazol-2-yl}carbonyl)amino]-phenyl}cyclohexyl)propanoic acid;
trans-4-{4-[({5-[(2,4,5-trifluorophenyl)amino]-1,3,4-oxadiazol-2-yl}carbonyl)amino]phenoxy}cyclohexanecarboxylic acid;
1-{5-[({5-[(2,4,5-trifluorophenyl)amino]-1,3,4-oxadiazol-2-yl}carbonyl)amino]pyridin-2-yl}piperidine-4-carboxylic acid;
(1-{5-[({5-[(2,4,5-trifluorophenyl)amino]-1,3,4-oxadiazol-2-yl}carbonyl)amino]pyridin-2-yl}piperidin-4-yl)acetic acid;
methyl (1-{5-[({5-[(3,4-difluorophenyl)amino]-1,3,4-oxadiazol-2-yl}carbonyl)amino]pyridin-2-yl}piperidin-4-yl)acetate;
((3S)-3-{4-[({5-[(3,4-difluorophenyl)amino]-1,3,4-oxadiazol-2-yl}carbonyl)amino]phenyl}cyclopentyl)acetic acid;
((3R)-3-{4-[({5-[(3,4-difluorophenyl)amino]-1,3,4-oxadiazol-2-yl}carbonyl)amino]phenyl}cyclopentyl)acetic acid;
3-{4-[({5-[(3,4-difluorophenyl)amino]-1,3,4-oxadiazol-2-yl}carbonyl)amino]benzyl}cyclobutanecarboxylic acid;
[trans-4-(4-{[(5-{[6-(4-chlorophenoxy)pyridin-3-yl]amino}-1,3,4-oxadiazol-2-yl)carbonyl]amino}phenyl)cyclohexyl]acetic acid;
[trans-4-(4-{[(5-{[6-(4-methoxyphenoxy)pyridin-3-yl]amino}-1,3,4-oxadiazol-2-yl)carbonyl]amino}phenyl)cyclohexyl]acetic acid;
{trans-4-[4-({[5-(quinolin-3-ylamino)-1,3,4-oxadiazol-2-yl]carbonyl}amino)phenyl]cyclohexyl}acetic acid;
(trans-4-{4-[({5-[(5-bromopyrazin-2-yl)amino]-1,3,4-oxadiazol-2-yl}carbonyl)amino]phenyl}cyclohexyl)acetic acid;
{trans-4-[4-({[5-(pyridin-3-ylamino)-1,3,4-oxadiazol-2-yl]carbonyl}amino)phenyl]cyclohexyl}acetic acid;
(trans-4-{4-[({5-[(6-methoxypyridin-3-yl)amino]-1,3,4-oxadiazol-2-yl}carbonyl)amino]phenyl}cyclohexyl)acetic acid;

[trans-4-(4-{[(5-{[4-cyano-3-(trifluoromethyl)phenyl]amino}-1,3,4-oxadiazol-2-yl)carbonyl]amino}phenyl)cyclohexyl]acetic acid; and/or selected from 2-methyl-2-(trans-4-{4-[({5-[(2,4,5-trifluorophenyl)amino]-1,3,4-oxadiazol-2-yl}carbonyl)amino]phenyl}cyclohexyl)propanoic acid;

1-{5-[({5-[(3,4-difluorophenyl)amino]-1,3,4-oxadiazol-2-yl}carbonyl)amino]pyridin-2-yl}-4-methylpiperidine-4-carboxylic acid;

1-{5-[({5-[(4-ethylphenyl)amino]-1,3,4-oxadiazol-2-yl}carbonyl)amino]pyridin-2-yl}-4-methylpiperidine-4-carboxylic acid;

4-methyl-1-(5-{[(5-{[4-(trifluoromethoxy)phenyl]amino)1,3,4-oxadiazol-2-yl}carbonyl]amino}pyridin-2-yl)piperidine-4-carboxylic acid;

4-methyl-1-{5-[({5-[(2,4,5-trifluorophenyl)amino]-1,3,4-oxadiazol-2-yl}carbonyl)amino]pyridin-2-yl}piperidine-4-carboxylic acid;

4-methyl-1-(5-{[(5-{[4-(trifluoromethyl)phenyl]amino}-1,3,4-oxadiazol-2-yl)carbonyl]amino}pyridin-2-yl)piperidine-4-carboxylic acid;

1-(5-{[(5-{[4-(4-chlorophenoxy)phenyl]amino}-1,3,4-oxadiazol-2-yl)carbonyl]amino}pyridin-2-yl)-4-methylpiperidine-4-carboxylic acid;

1-(5-{[(5-{[4-(4-chlorophenoxy)phenyl]amino)-1,3,4-oxadiazol-2-yl}carbonyl]amino}pyridin-2-yl)piperidine-4-carboxylic acid;

[1-(5-{[(5-{[4-(4-chlorophenoxy)phenyl]amino}-1,3,4-oxadiazol-2-yl)carbonyl]amino}pyridin-2-yl)piperidin-4-yl]acetic acid;

rac-2-(trans-4-{2-chloro-4-[({5-[(2,4,5-trifluorophenyl)amino]-1,3,4-oxadiazol-2-yl}carbonyl)amino]phenyl}cyclohexyl)propanoic acid;

rac-2-(trans-4-{3-chloro-4-[({5-[(2,4,5-trifluorophenyl)amino]-1,3,4-oxadiazol-2-yl}carbonyl)amino]phenyl}cyclohexyl)propanoic acid;

cis-4-{4-[({5-[(2,4,5-trifluorophenyl)amino]-1,3,4-oxadiazol-2-yl}carbonyl)amino]-phenoxy}cyclohexanecarboxylic acid;

(1-{5-[({5-[(4-ethylphenyl)amino]-1,3,4-oxadiazol-2-yl}carbonyl)amino]pyridin-2-yl}piperidin-4-yl)acetic acid;

[1-(5-{[(5-{[4-(trifluoromethyl)phenyl]amino}-1,3,4-oxadiazol-2-yl)carbonyl]amino}pyridin-2-yl)piperidin-4-yl]acetic acid;

1-{5-[({5-[(4-ethylphenyl)amino]-1,3,4-oxadiazol-2-yl}carbonyl)amino]pyridin-2-yl}piperidine-4-carboxylic acid;

1-(5-{[(5-{[4-(trifluoromethoxy)phenyl]amino}-1,3,4-oxadiazol-2-yl)carbonyl]amino}pyridin-2-yl)piperidine-4-carboxylic acid;

1-(5-{[(5-{[4-(trifluoromethyl)phenyl]amino}-1,3,4-oxadiazol-2-yl)carbonyl]amino}pyridin-2-yl)piperidine-4-carboxylic acid;

(trans-4-{4-[({5-[(2-chloro-4-methylphenyl)amino]-1,3,4-oxadiazol-2-yl}carbonyl)amino]phenyl}cyclohexyl)acetic acid;

(trans-4-{4-[({5-[(4-methoxy-2-methylphenyl)amino]-1,3,4-oxadiazol-2-yl}carbonyl)amino]phenyl}cyclohexyl)acetic acid;

(trans-4-{4-[({5-[(4-fluoro-2-methylphenyl)amino]-1,3,4-oxadiazol-2-yl}carbonyl)amino]phenyl}cyclohexyl)acetic acid;

[trans-4-(4-{[(5-{[4-fluoro-2-(trifluoromethyl)phenyl]amino}-1,3,4-oxadiazol-2-yl)carbonyl]amino}phenyl)cyclohexyl]acetic acid;

(trans-4-{4-[({5-[(2,4-dichlorophenyl)amino]-1,3,4-oxadiazol-2-yl}carbonyl)amino]phenyl}cyclohexyl)acetic acid;

(trans-4-{4-[({5-[(2-chloro-4-cyanophenyl)amino]-1,3,4-oxadiazol-2-yl}carbonyl)amino]phenyl}cyclohexyl)acetic acid;

(trans-4-{4-[({5-[(4-cyano-2-methylphenyl)amino]-1,3,4-oxadiazol-2-yl}carbonyl)amino]phenyl}cyclohexyl)acetic acid;

(trans-4-{4-[({5-[(4-chloro-2,5-dimethylphenyl)amino]-1,3,4-oxadiazol-2-yl}carbonyl)amino]phenyl}cyclohexyl)acetic acid;

(trans-4-{4-[({5-[(4-cyano-2-ethylphenyl)amino]-1,3,4-oxadiazol-2-yl}carbonyl)amino]phenyl}cyclohexyl)acetic acid;

(trans-4-{4-[({5-[(2-chloro-4-fluorophenyl)amino]-1,3,4-oxadiazol-2-yl}carbonyl)amino]phenyl}cyclohexyl)acetic acid;

(trans-4-{4-[({5-[(4-chloro-2-methylphenyl)amino]-1,3,4-oxadiazol-2-yl}carbonyl)amino]phenyl}cyclohexyl)acetic acid;

(trans-4-{4-[({5-[(2,3-dichlorophenyl)amino]-1,3,4-oxadiazol-2-yl}carbonyl)amino]phenyl}cyclohexyl)acetic acid;

(trans-4-{4-[({5-[(2,5-dichlorophenyl)amino]-1,3,4-oxadiazol-2-yl}carbonyl)amino]phenyl}cyclohexyl)acetic acid;

(trans-4-{4-[({5-[(2-bromo-4-methylphenyl)amino]-1,3,4-oxadiazol-2-yl}carbonyl)amino]phenyl}cyclohexyl)acetic acid;

[trans-4-(4-{[(5-{[2-chloro-5-(trifluoromethyl)phenyl]amino}-1,3,4-oxadiazol-2-yl)carbonyl]amino}phenyl)cyclohexyl]acetic acid;

[trans-4-(4-{[(5-{[2-bromo-4-(trifluoromethyl)phenyl]amino}-1,3,4-oxadiazol-2-yl)carbonyl]amino}phenyl)cyclohexyl]acetic acid;

[trans-4-(4-{[(5-{[2-chloro-4-(trifluoromethyl)phenyl]amino}-1,3,4-oxadiazol-2-yl)carbonyl]amino}phenyl)cyclohexyl]acetic acid;

(trans-4-{4-[({5-[(4-bromo-2-chlorophenyl)amino]-1,3,4-oxadiazol-2-yl}carbonyl)amino]phenyl}cyclohexyl)acetic acid;

(trans-4-{4-[({5-[(3-chloro-2-methylphenyl)amino]-1,3,4-oxadiazol-2-yl}carbonyl)amino]phenyl}cyclohexyl)acetic acid;

(trans-4-{4-[({5-[(5-bromo-2-methylphenyl)amino]-1,3,4-oxadiazol-2-yl}carbonyl)amino]phenyl}cyclohexyl)acetic acid;

(trans-4-{4-[({5-[(2-chloro-5-fluorophenyl)amino]-1,3,4-oxadiazol-2-yl}carbonyl)amino]phenyl}cyclohexyl)acetic acid;

(trans-4-{4-[({5-[(2-chloro-5-methylphenyl)amino]-1,3,4-oxadiazol-2-yl}carbonyl)amino]phenyl}cyclohexyl)acetic acid;

(trans-4-{4-[({5-[(5-chloro-2-methylphenyl)amino]-1,3,4-oxadiazol-2-yl}carbonyl)amino]phenyl}cyclohexyl)acetic acid;

2-(3-{4-[({5-[(3,4-difluorophenyl)amino]-1,3,4-oxadiazol-2-yl}carbonyl)amino]phenyl}cyclobutyl)propanoic acid;

(1-{5-[({5-[(3,4-difluorophenyl)amino]-1,3,4-oxadiazol-2-yl}carbonyl)amino]-3-methylpyridin-2-yl}piperidin-4-yl)acetic acid;

[1-(3-methyl-5-{[(5-{[4-(trifluoromethoxy)phenyl]amino}-1,3,4-oxadiazol-2-yl)carbonyl]amino}pyridin-2-yl)piperidin-4-yl]acetic acid;

[1-(3-methyl-5-{[(5-{[4-(trifluoromethyl)phenyl]amino}-1,3,4-oxadiazol-2-yl)carbonyl]amino}pyridin-2-yl)piperidin-4-yl]acetic acid;

(1-{5-[({5-[(4-ethylphenyl)amino]-1,3,4-oxadiazol-2-yl}carbonyl)amino]-3-methylpyridin-2-yl}piperidin-4-yl)acetic acid;

1-{5-[({5-[(3,4-difluorophenyl)amino]-1,3,4-oxadiazol-2-yl}carbonyl)amino]-3-methylpyridin-2-yl}piperidine-4-carboxylic acid;

1-(3-methyl-5-{[(5-{[4-(trifluoromethoxy)phenyl]amino}-1,3,4-oxadiazol-2-yl)carbonyl]amino}pyridin-2-yl)piperidine-4-carboxylic acid;

1-(3-methyl-5-{[(5-{[4-(trifluoromethyl)phenyl]amino}-1,3,4-oxadiazol-2-yl)carbonyl]amino}pyridin-2-yl)piperidine-4-carboxylic acid;

1-{5-[({5-[(4-ethylphenyl)amino]-1,3,4-oxadiazol-2-yl}carbonyl)amino]-3-methylpyridin-2-yl}piperidine-4-carboxylic acid;

2-(1-{3-methyl-5-[({5-[(2,4,5-trifluorophenyl)amino]-1,3,4-oxadiazol-2-yl}carbonyl)amino]pyridin-2-yl}piperidin-4-yl)propanoic acid;

1-(5-{[(5-{[4-(4-fluorophenoxy)phenyl]amino}-1,3,4-oxadiazol-2-yl)carbonyl]amino}pyridin-2-yl)piperidine-4-carboxylic acid;

1-(5-{[(5-{[4-(4-fluorophenoxy)phenyl]amino}-1,3,4-oxadiazol-2-yl)carbonyl]amino}pyridin-2-yl)-4-methylpiperidine-4-carboxylic acid;

[1-(5-{[(5-{[4-(4-fluorophenoxy)phenyl]amino}-1,3,4-oxadiazol-2-yl)carbonyl]amino}pyridin-2-yl)piperidin-4-yl]acetic acid;

(1-{5-[({5-[(3,4-difluorophenyl)amino]-1,3,4-oxadiazol-2-yl}carbonyl)amino]pyridin-2-yl}-4-methylpiperidin-4-yl)acetic acid;

(4-methyl-1-{5-[({5-[(2,4,5-trifluorophenyl)amino]-1,3,4-oxadiazol-2-yl}carbonyl)amino]pyridin-2-yl}piperidin-4-yl)acetic acid;

[4-methyl-1-(5-{[(5-{[4-(trifluoromethyl)phenyl]amino}-1,3,4-oxadiazol-2-yl)carbonyl]amino}pyridin-2-yl)piperidin-4-yl]acetic acid; and/or

[1-(5-{[(5-{[4-(4-fluorophenoxy)phenyl]amino}-1,3,4-oxadiazol-2-yl)carbonyl]amino}pyridin-2-yl)-4-methylpiperidin-4-yl]acetic acid.

In a further aspect of the invention, there is provided any one or more of the following compounds, or pharmaceutically-acceptable salts or pro-drugs thereof:

sodium (trans-4-{4-[({5-[(2,4,5-trifluorophenyl)amino]-1,3,4-oxadiazol-2-yl}carbonyl)amino]phenyl}cyclohexyl)acetate;

(trans-4-{4-[({5-[(3,4-difluorophenyl)amino]-1,3,4-oxadiazol-2-yl}carbonyl)amino]phenyl}cyclohexyl)acetic acid;

(trans-4-{4-[({5-[(2,4,6-trifluorophenyl)amino]-1,3,4-oxadiazol-2-yl}carbonyl)amino]phenyl}cyclohexyl)acetic acid;

[trans-4-(4-{[(5-{[4-(trifluoromethyl)phenyl]amino}-1,3,4-oxadiazol-2-yl)carbonyl]amino}phenyl)cyclohexyl]acetic acid;

[trans-4-(4-{[(5-{[4-(trifluoromethoxy)phenyl]amino}-1,3,4-oxadiazol-2-yl)carbonyl]amino}phenyl)cyclohexyl]acetic acid;

(trans-4-{5-[({5-[(2,4,5-trifluorophenyl)amino]-1,3,4-oxadiazol-2-yl}carbonyl)amino]pyridin-2-yl}cyclohexyl)acetic acid;

(2R)-2-(trans-4-{4-[({5-[(2,4,5-trifluorophenyl)amino]-1,3,4-oxadiazol-2-yl}carbonyl)amino]phenyl}cyclohexyl)-propanoic acid;

(2S)-2-(trans-4-{4-[({5-[(2,4,5-trifluorophenyl)amino]-1,3,4-oxadiazol-2-yl}carbonyl)amino]phenyl}cyclohexyl) propanoic acid;

(2R)-2-(trans-4-{4-[({5-[(3,4-difluorophenyl)amino]-1,3,4-oxadiazol-2-yl}carbonyl)amino]phenyl}cyclohexyl)propanoic acid;

(2S)-2-(trans-4-{4-[({5-[(3,4-difluorophenyl)amino]-1,3,4-oxadiazol-2-yl}carbonyl)amino]-phenyl}cyclohexyl)propanoic acid;

((3S)-3-{4-[({5-[(3,4-difluorophenyl)amino]-1,3,4-oxadiazol-2-yl}carbonyl)amino]phenyl}cyclopentyl)acetic acid;

((3R)-3-{4-[({5-[(3,4-difluorophenyl)amino]-1,3,4-oxadiazol-2-yl}carbonyl)amino]phenyl}cyclopentyl)acetic acid;

3-{4-[({5-[(3,4-difluorophenyl)amino]-1,3,4-oxadiazol-2-yl}carbonyl)amino]benzyl}cyclobutanecarboxylic acid;

[trans-4-(4-{[(5-{[4-cyano-3-(trifluoromethyl)phenyl]amino)-1,3,4-oxadiazol-2-yl}carbonyl]amino}phenyl)cyclohexyl]acetic acid;

2-methyl-2-(trans-4-{4-[({5-[(2,4,5-trifluorophenyl)amino]-1,3,4-oxadiazol-2-yl}carbonyl)amino]phenyl}cyclohexyl)propanoic acid;

rac-2-(trans-4-{2-chloro-4-[({5-[(2,4,5-trifluorophenyl)amino]-1,3,4-oxadiazol-2-yl}carbonyl)amino]phenyl}cyclohexyl)propanoic acid;

rac-2-(trans-4-{3-chloro-4-[({5-[(2,4,5-trifluorophenyl)amino]-1,3,4-oxadiazol-2-yl}carbonyl)amino]phenyl}cyclohexyl)propanoic acid;

cis-4-{4-[({5-[(2,4,5-trifluorophenyl)amino]-1,3,4-oxadiazol-2-yl}carbonyl)amino]-phenoxy}cyclohexanecarboxylic acid;

(trans-4-{4-[({5-[(2-chloro-4-methylphenyl)amino]-1,3,4-oxadiazol-2-yl}carbonyl)amino]phenyl}cyclohexyl)acetic acid;

(trans-4-{4-[({5-[(4-methoxy-2-methylphenyl)amino]-1,3,4-oxadiazol-2-yl}carbonyl)amino]phenyl}cyclohexyl) acetic acid;

(trans-4-{4-[({5-[(4-fluoro-2-methylphenyl)amino]-1,3,4-oxadiazol-2-yl}carbonyl)amino]phenyl}cyclohexyl)acetic acid;

[trans-4-(4-{[(5-{[4-fluoro-2-(trifluoromethyl)phenyl]amino}-1,3,4-oxadiazol-2-yl)carbonyl]amino}phenyl)cyclohexyl]acetic acid;

(trans-4-{4-[({5-[(2,4-dichlorophenyl)amino]-1,3,4-oxadiazol-2-yl}carbonyl)amino]phenyl}cyclohexyl)acetic acid;

(trans-4-{4-[({5-[(2-chloro-4-cyanophenyl)amino]-1,3,4-oxadiazol-2-yl}carbonyl)amino]phenyl}cyclohexyl)acetic acid;

(trans-4-{4-[({5-[(4-cyano-2-methylphenyl)amino]-1,3,4-oxadiazol-2-yl}carbonyl)amino]phenyl}cyclohexyl)acetic acid;

(trans-4-{4-[({5-[(4-chloro-2,5-dimethylphenyl)amino]-1,3,4-oxadiazol-2-yl}carbonyl)amino]phenyl}cyclohexyl) acetic acid;

(trans-4-{4-[({5-[(4-cyano-2-ethylphenyl)amino]-1,3,4-oxadiazol-2-yl}carbonyl)amino]phenyl}cyclohexyl)acetic acid;

(trans-4-{4-[({5-[(2-chloro-4-fluorophenyl)amino]-1,3,4-oxadiazol-2-yl}carbonyl)amino]phenyl}cyclohexyl)acetic acid;

(trans-4-{4-[({5-[(4-chloro-2-methylphenyl)amino]-1,3,4-oxadiazol-2-yl}carbonyl)amino]phenyl}cyclohexyl)acetic acid;

(trans-4-f{4-[({5-[(2,3-dichlorophenyl)amino]-1,3,4-oxadiazol-2-yl}carbonyl)amino]phenyl}cyclohexyl)acetic acid;

(trans-4-{4-[({5-[(2,5-dichlorophenyl)amino]-1,3,4-oxadiazol-2-yl}carbonyl)amino]phenyl}cyclohexyl)acetic acid;

(trans-4-{4-[({5-[(2-bromo-4-methylphenyl)amino]-1,3,4-oxadiazol-2-yl}carbonyl)amino]phenyl}cyclohexyl)acetic acid;

[trans-4-(4-{[(5-{[2-chloro-5-(trifluoromethyl)phenyl]amino}-1,3,4-oxadiazol-2-yl)carbonyl]amino}phenyl)cyclohexyl]acetic acid;

[trans-4-(4-{[(5-{[2-bromo-4-(trifluoromethyl)phenyl]amino}-1,3,4-oxadiazol-2-yl)carbonyl]amino}phenyl)cyclohexyl]acetic acid;

[trans-4-(4-{[(5-{[2-chloro-4-(trifluoromethyl)phenyl]amino}-1,3,4-oxadiazol-2-yl)carbonyl]amino}phenyl)cyclohexyl]acetic acid;

(trans-4-{4-[({5-[(4-bromo-2-chlorophenyl)amino]-1,3,4-oxadiazol-2-yl}carbonyl)amino]phenyl}cyclohexyl)acetic acid;

(trans-4-{4-[({5-[(3-chloro-2-methylphenyl)amino]-1,3,4-oxadiazol-2-yl}carbonyl)amino]phenyl}cyclohexyl)acetic acid;

(trans-4-{4-[({5-[(5-bromo-2-methylphenyl)amino]-1,3,4-oxadiazol-2-yl}carbonyl)amino]phenyl}cyclohexyl)acetic acid;

(trans-4-{4-[({5-[(2-chloro-5-fluorophenyl)amino]-1,3,4-oxadiazol-2-yl}carbonyl)amino]phenyl}cyclohexyl)acetic acid;

(trans-4-{4-[({5-[(2-chloro-5-methylphenyl)amino]-1,3,4-oxadiazol-2-yl}carbonyl)amino]phenyl}cyclohexyl)acetic acid;

(trans-4-{4-[({5-[(5-chloro-2-methylphenyl)amino]-1,3,4-oxadiazol-2-yl}carbonyl)amino]phenyl}cyclohexyl)acetic acid; and 2-(3-{4-[({5-[(3,4-difluorophenyl)amino]-1,3,4-oxadiazol-2-yl}carbonyl)amino]phenyl}cyclobutyl)propanoic acid.

In a further aspect of the invention, there is provided any one or more of the following compounds, or pharmaceutically-acceptable salts or pro-drugs thereof:

[trans-4-(4-{[(5-{[6-(4-chlorophenoxy)pyridin-3-yl]amino}-1,3,4-oxadiazol-2-yl)carbonyl]amino}phenyl)cyclohexyl]acetic acid;

[trans-4-(4-{[(5-{[6-(4-methoxyphenoxy)pyridin-3-yl]amino}-1,3,4-oxadiazol-2-yl)carbonyl]amino}phenyl)cyclohexyl]acetic acid;

{trans-4-[4-({[5-(quinolin-3-ylamino)-1,3,4-oxadiazol-2-yl]carbonyl}amino)phenyl]cyclohexyl}acetic acid;

(trans-4-{4-[({5-[(5-bromopyrazin-2-yl)amino]-1,3,4-oxadiazol-2-yl}carbonyl)amino]phenyl}cyclohexyl)acetic acid;

{trans-4-[4-({[5-(pyridin-3-ylamino)-1,3,4-oxadiazol-2-yl]carbonyl}amino)phenyl]cyclohexyl}acetic acid;

(trans-4-{4-[({5-[(6-methoxypyridin-3-yl)amino]1,3,4-oxadiazol-2-yl}carbonyl)amino]phenyl}cyclohexyl)acetic acid.

In a further aspect of the invention, there is provided any one or more of the following compounds, or pharmaceutically-acceptable salts or pro-drugs thereof:

1-{5-[({5-[(2,4,5-trifluorophenyl)amino]-1,3,4-oxadiazol-2-yl}carbonyl)amino]pyridin-2-yl}piperidine-4-carboxylic acid;

(1-{5-[{5-[(2,4,5-trifluorophenyl)amino]-1,3,4-oxadiazol-2-yl}carbonyl)amino]pyridin-2-yl}piperidin-4-yl)acetic acid;

1-{5-[({5-[(3,4-difluorophenyl)amino]-1,3,4-oxadiazol-2-yl}carbonyl)amino]pyridin-2-yl}-4-methylpiperidine-4-carboxylic acid;

1-{5-[({5-[(4-ethylphenyl)amino]-1,3,4-oxadiazol-2-yl}carbonyl)amino]pyridin-2-yl}-4-methylpiperidine-4-carboxylic acid;

4-methyl-1-(5-{[(5-{[4-(trifluoromethoxy)phenyl]amino}-1,3,4-oxadiazol-2-yl)carbonyl]amino}pyridin-2-yl)piperidine-4-carboxylic acid;

4-methyl-1-{5-[({5-[(2,4,5-trifluorophenyl)amino]-1,3,4-oxadiazol-2-yl}carbonyl)amino]pyridin-2-yl}piperidine-4-carboxylic acid;

4-methyl-1-(5-{[(5-{[4-(trifluoromethyl)phenyl]amino}-1,3,4-oxadiazol-2-yl)carbonyl]amino}pyridin-2-yl)piperidine-4-carboxylic acid;

1-(5-{[(5-{[4-(4-chlorophenoxy)phenyl]amino}-1,3,4-oxadiazol-2-yl)carbonyl]amino}pyridin-2-yl)-4-methylpiperidine-4-carboxylic acid;

1-(5-{[(5-{[4-(4-chlorophenoxy)phenyl]amino}-1,3,4-oxadiazol-2-yl)carbonyl]amino}pyridin-2-yl)piperidine-4-carboxylic acid;

[1-(5-{[(5-{[4-(4-chlorophenoxy)phenyl]amino}-1,3,4-oxadiazol-2-yl)carbonyl]amino}pyridin-2-yl)piperidin-4-yl]acetic acid;

(1-{5-[({5-[(4-ethylphenyl)amino]-1,3,4-oxadiazol-2-yl}carbonyl)amino]pyridin-2-yl}piperidin-4-yl)acetic acid;

[1-(5-{[(5-{[4-(trifluoromethyl)phenyl]amino}-1,3,4-oxadiazol-2-yl)carbonyl]amino}pyridin-2-yl)piperidin-4-yl]acetic acid;

1-{5-[({5-[(4-ethylphenyl)amino]-1,3,4-oxadiazol-2-yl}carbonyl)amino]pyridin-2-yl}piperidine-4-carboxylic acid;

1-(5-{[(5-{[4-(trifluoromethoxy)phenyl]amino}-1,3,4-oxadiazol-2-yl) carbonyl]amino}pyridin-2-yl)piperidine-4-carboxylic acid;

1-(5-{[(5-{[4-(trifluoromethyl)phenyl]amino}-1,3,4-oxadiazol-2-yl)carbonyl]amino}pyridin-2-yl)piperidine-4-carboxylic acid;

(1-{5-[({5-[(3,4-difluorophenyl)amino]-1,3,4-oxadiazol-2-yl}carbonyl)amino]-3-methylpyridin-2-yl}piperidin-4-yl)acetic acid;

[1-(3-methyl-5-{[(5-{[4-(trifluoromethoxy)phenyl]amino}-1,3,4-oxadiazol-2-yl)carbonyl]amino}pyridin-2-yl)piperidin-4-yl]acetic acid;

[1-(3-methyl-5-{[(5-{[4-(trifluoromethyl)phenyl]amino}-1,3,4-oxadiazol-2-yl)carbonyl]amino}pyridin-2-yl)piperidin-4-yl]acetic acid;

(1-{5-[({5-[(4-ethylphenyl)amino]-1,3,4-oxadiazol-2-yl}carbonyl)amino]-3-methylpyridin-2-yl}piperidin-4-yl)acetic acid;

1-{5-[({5-[(3,4-difluorophenyl)amino]-1,3,4-oxadiazol-1-yl}carbonyl)amino]-3-methylpyridin-2-yl}piperidine-4-carboxylic acid;

1-(3-methyl-5-{[(5-{[4-(trifluoromethoxy)phenyl]amino}-1,3,4-oxadiazol-2-yl)carbonyl]amino}pyridin-2-yl)piperidine-4-carboxylic acid;

1-(3-methyl-5-{[(5-{[4-(trifluoromethyl)phenyl]amino}-1,3,4-oxadiazol-2-yl)carbonyl]amino}pyridin-2-yl)piperidine-4-carboxylic acid;

1-{5-[({5-[(4-ethylphenyl)amino]-1,3,4-oxadiazol-2-yl}carbonyl)amino]-3-methylpyridin-2-yl}piperidine-4-carboxylic acid;

2-(1-{3-methyl-5-[({5-[(2,4,5-trifluorophenyl)amino]-1,3,4-oxadiazol-2-yl}carbonyl)amino]pyridin-2-yl}piperidin-4-yl)propanoic acid;

1-(5-{[(5-{[4-(4-fluorophenoxy)phenyl]amino}-1,3,4-oxadiazol-2-yl)carbonyl]amino}pyridin-2-yl)piperidine-4-carboxylic acid;

1-(5-{[(5-{[4-(4-fluorophenoxy)phenyl]amino}-1,3,4-oxadiazol-2-yl)carbonyl]amino}pyridin-2-yl)-4-methylpiperidine-4-carboxylic acid;

[1-(5-{[(5-{[4-(4-fluorophenoxy)phenyl]amino}-1,3,4-oxadiazol-2-yl)carbonyl]amino}pyridin-2-yl)piperidin-4-yl]acetic acid;

(1-{5-[({5-[(3,4-difluorophenyl)amino]-1,3,4-oxadiazol-2-yl}carbonyl)amino]pyridin-2-yl}-4-methylpiperidin-4-yl)acetic acid;

(4-methyl-1-{5-[({5-[(2,4,5-trifluorophenyl)amino]-1,3,4-oxadiazol-2-yl}carbonyl)amino]pyridin-2-yl}piperidin-4-yl)acetic acid;

[4-methyl-1-(5-{[(5-{[4-(trifluoromethyl)phenyl]amino}-1,3,4-oxadiazol-2-yl)carbonyl]amino}pyridin-2-yl)piperidin-4-yl]acetic acid; and

[1-(5-{[(5-{[4-(4-fluorophenoxy)phenyl]amino}-1,3,4-oxadiazol-2-yl)carbonyl]amino}pyridin-2-yl)-4-methylpiperidin-4-yl]acetic acid.

Further preferred compounds of the invention are each of the Examples, each of which provides a further independent aspect of the invention. In further aspects, the present invention also comprises any two or more compounds of the Examples.

Process

A compound of formula (I) and its pharmaceutically-acceptable salts may be prepared by any process known to be applicable to the preparation of chemically related compounds. Such processes, when used to prepare a compound of the formula (I), or a pharmaceutically-acceptable salt thereof, are provided as a further feature of the invention.

In a further aspect the present invention also provides that the compounds of the formula (I) and pharmaceutically-acceptable salts or prodrugs thereof, can be prepared by a process a) to g) as follows (wherein all variables are as hereinbefore defined for a compound of formula (I) unless otherwise stated):

a) reaction of a compound of formula (I) to form another compound of formula (I);

b) reaction of an amine of formula (2) with a carboxylate salt of formula (3);

(2)

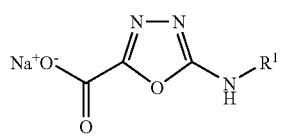
(3)

c) cyclisation of a compound of formula (4) (where X is S or O);

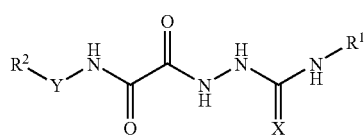
(4)

d) when $R^2$ is substituted by piperazinyl, by reaction of the piperazine nitrogen with $R^5$-LG wherein LG is a suitable leaving group such as halo, and $R^5$ is hydrocarbyl or a suitable functional group such as acyl, for example:

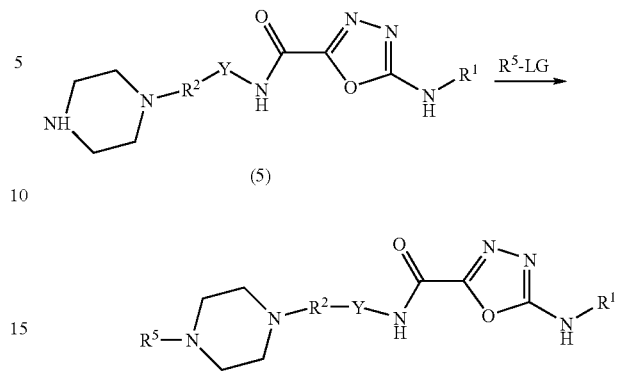
(5)

e) when $R^2$ is aryl and is substituted by aryl, by transition metal catalysed aromatic substitution, for example:

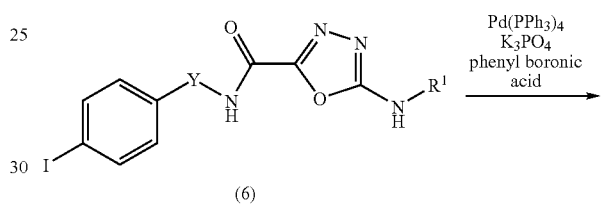
(6)

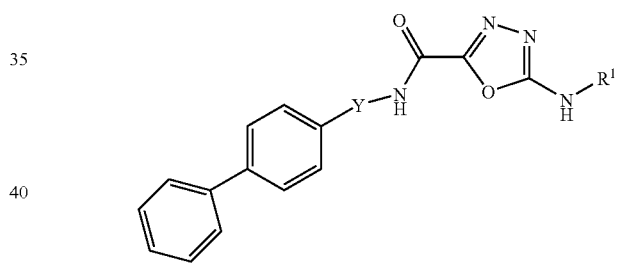

f) when $R^2$ is substituted by piperazinyl, by reductive alkylation of the piperazine nitrogen with $R^5$—CHO (wherein $R^5$ is for example hydrocarbyl), for example:

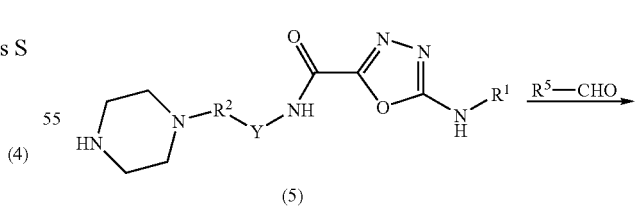
(5)

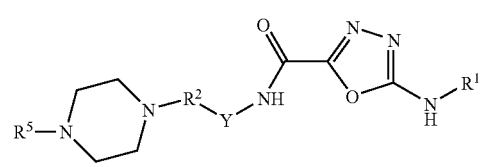

g) reaction of halogenated (for example with iodo) $R^2$ with an amide of formula (7) followed by subsequent removal of protecting group $P^1$, wherein $P^1$ is for example benzyl or trimethylsilylethoxymethyl (SEM), for example;

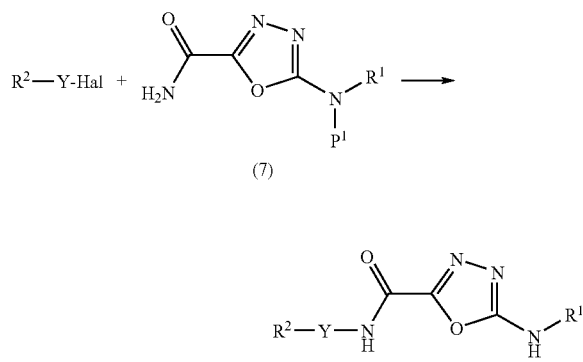

wherein Hal is halogen;

and thereafter if necessary, removing any protecting groups, and/or forming a pharmaceutically-acceptable salt or prodrug thereof.

In the above schemes, R, $R^1$, Y and $R^5$ are defined above. Suitably in the above schemes, $R^1$ is a group $R^{1a}$ and $R^2$ is a group $R^{2a}$ as defined above so that they can be used to prepare a compound of formula (IA). Furthermore, the group $R^1$ may be a group $R^{1b}$ and $R^2$ may be a group $R^{2b}$ in order to produce a compound of formula (IB). In the latter case, Y is a direct bond. It will be understood that, where Y is a direct bond, processes a,b,d, and g apply to compounds of formula (IZA), processes a, b, c and g apply to compounds of formula (IZB) and processes a, b, c, d, f and g apply to compounds of formula (IZC).

Process a)

Examples of conversions of a compound of formula (I) into another compound of Formula (I), well known to those skilled in the art, include functional group interconversions such as hydrolysis (in particular ester hydrolysis), oxidation or reduction (such as the reduction of an acid to an alcohol, or removal of an N protecting group), and/or further functionalisation by standard reactions such as amide or metal-catalysed coupling, or nucleophilic displacement reactions.

Process b)

Compounds of formula (2) where Y is not a direct bond or where $R^2$ is not aromatic, may be made by application of standard synthetic methods well known in the art. For example, reductive alkylation of ammonia (or a suitable amine such as a benzylamine or N,N-dibenzylamine) with a ketone or aldehyde $R^2Y=O$ (followed by deprotection as appropriate) provides $R^2$—Y—$NH_2$. Alternatively, alkylation of an amine or amine equivalent (such as a Gabriel reagent or a guanidine) with a halide $R^2$—Y—X (where X is a halide) (followed by N-deprotection or hydrolysis as appropriate) provides the required compounds of formula (2).

Compounds of formula (2) for other definitions of Y or $R^2$ may be made by metal catalysed couplings or nucleophilic displacement reactions among other methods. In particular, compounds of formula (2) may be prepared by reduction of a compound of formula (2A).

$$R^2—Y—NO_2 \tag{2A}$$

Compounds of formula (2A) may be made by metal catalysed couplings or nucleophilic displacement reactions depending upon the nature of the $R^2$ group and Y. For example, production of a compound of formula (2A) may be represented as follows:

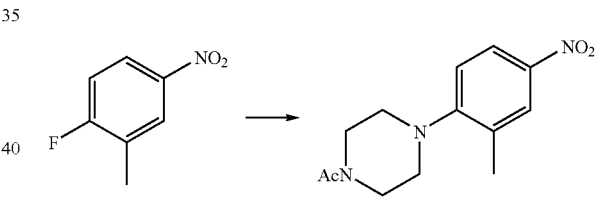

Examples of process (b) where Y is a direct bond are shown in Schemes 1 to 3 (wherein $R^6$ represents optional substituent on $R^2$, including those defined hereinbefore for $R^{6a-d}$):

Scheme 1

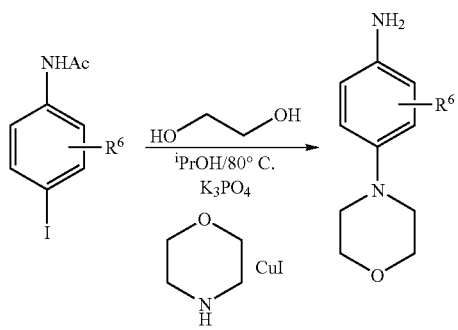

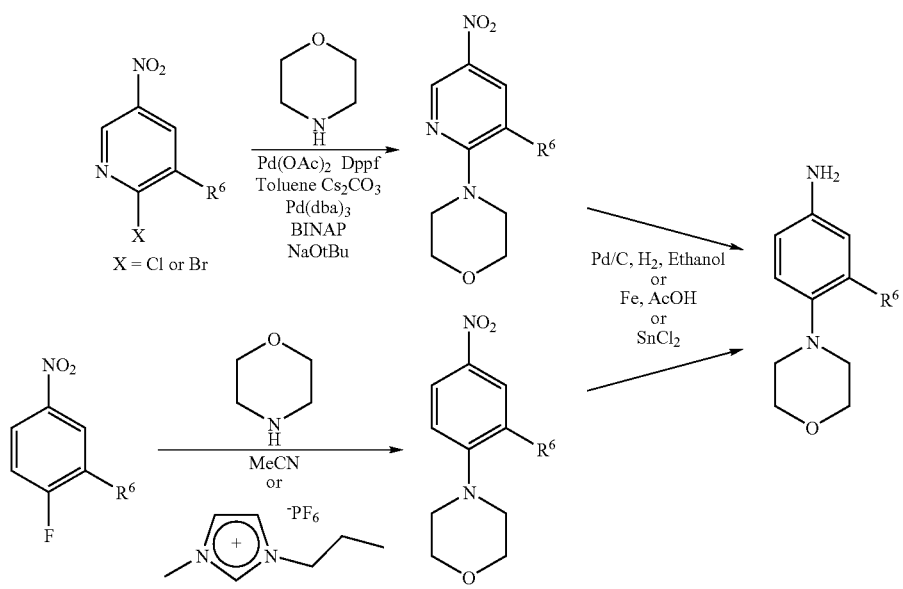
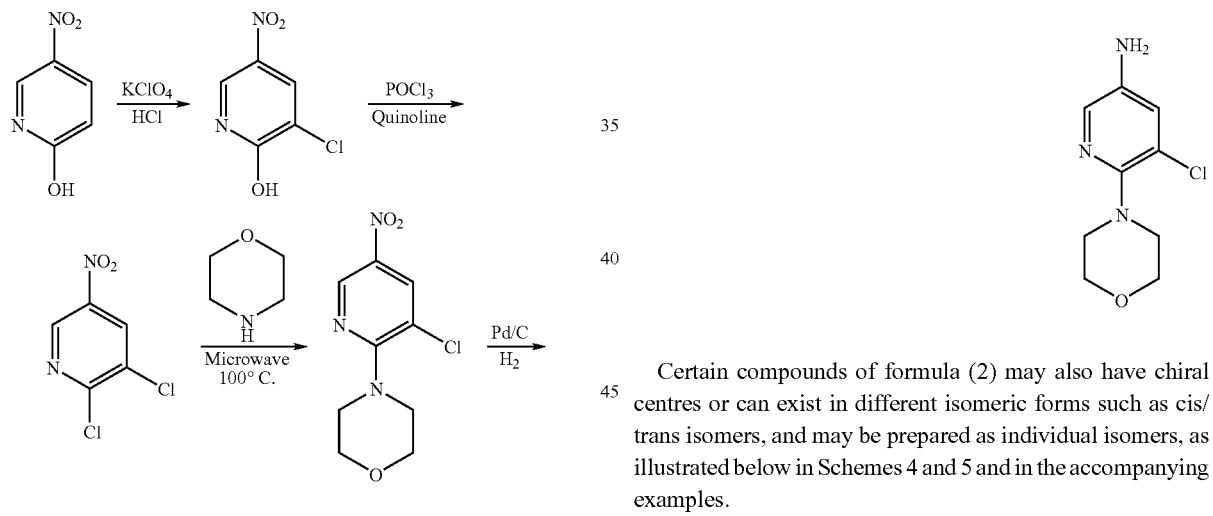
Certain compounds of formula (2) may also have chiral centres or can exist in different isomeric forms such as cis/trans isomers, and may be prepared as individual isomers, as illustrated below in Schemes 4 and 5 and in the accompanying examples.
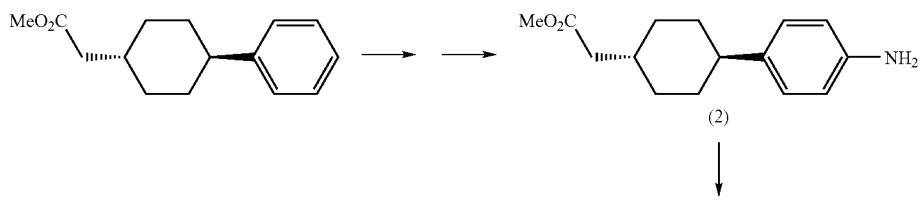

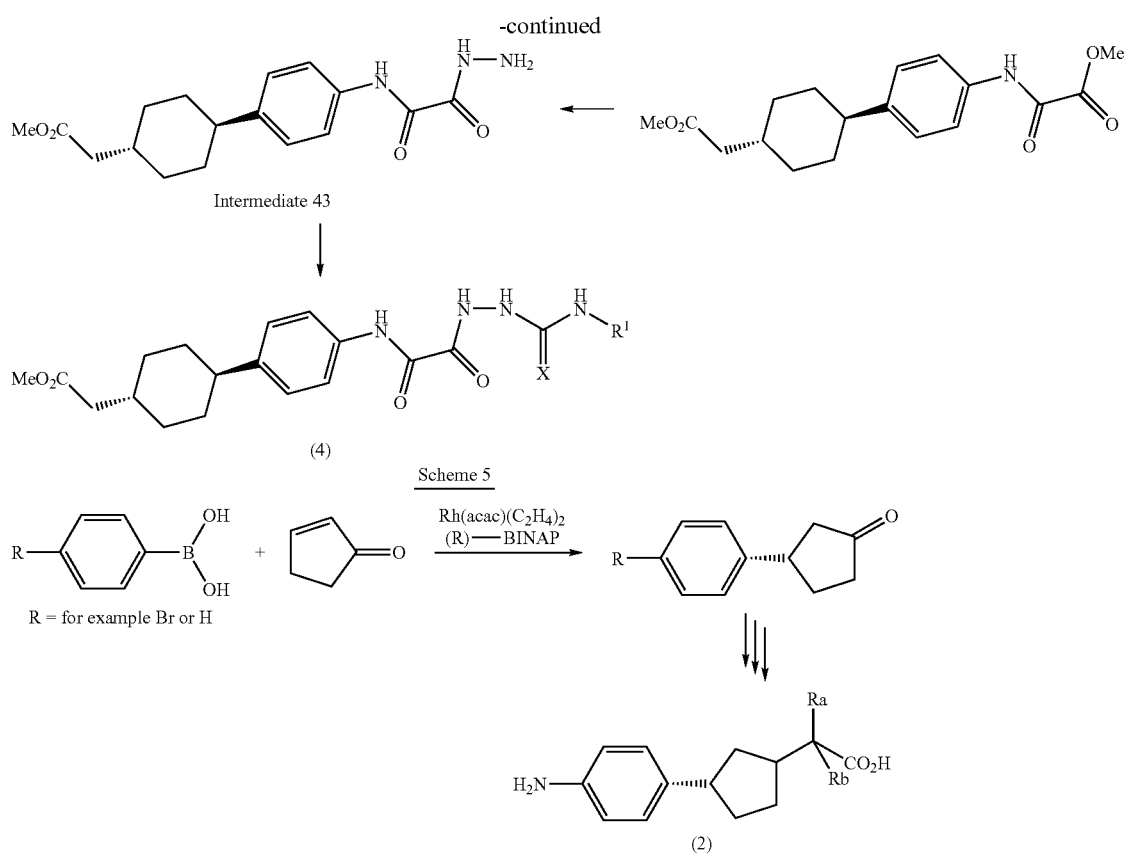

The process illustrated in Scheme 5 may also be used with cyclohexenone as a starting material. The opposite stereochemistry may be obtained by using known alternative chiral catalysts and/or chiral ligands. Elaboration of the bicyclic ketone intermediate may be carried out by processes known in the art, for example by Wittig or enolate/enol ether chemistry, optionally followed by functionalisation (such as alkylation) and functional group interconversion as desired to give the compound of formula (2) (wherein Ra and Rb may each for example be hydrogen or (optionally substituted) alkyl groups). Mixtures of diastereoisomers may be separated by standard procedures.

$S_NAr$ chemistry may be used (under conditions well known in the art) to make certain compounds of formula (2), as illustrated in Scheme 6 (in which R is for example an alkyl group, X is for example Br or Cl, n is for example 0 to 4, group A may be a (hetero)aryl ring, a saturated ring or an alkyl chain).

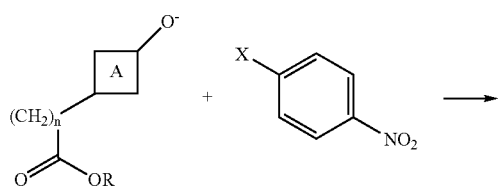

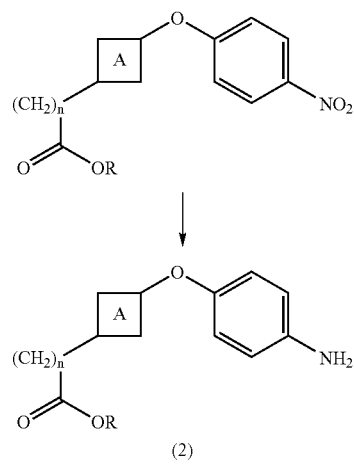

Compounds of formula (3) may be made by alkaline hydrolysis of ester (8a) as prepared using a published procedure (J. Het. Chem. 1977, 14, 1385-1388). Ester (8a) may be made by cyclisation of a compound of formula (8b) (where X is O or S) in a similar manner as described in process c) for compounds of formula (4).

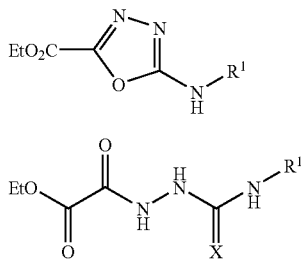

An alternative method for making compounds of formula (8a) is illustrated below:

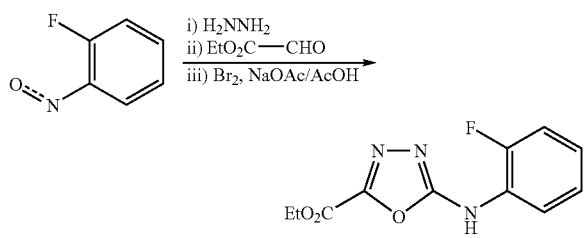

Compounds of formula (2) may be coupled with compounds of formula (3) under standard conditions for formation of amide bonds. For example using an appropriate coupling reaction, such as a carbodiimide coupling reaction performed with EDAC, optionally in the presence of DMAP, in a suitable solvent such as DCM, chloroform or DMF at room temperature.

For compounds of formula (2) other than when $R^2$ is aromatic and Y is a direct bond (ie other than compounds such as anilino compounds), an ester derivative of formula (8a) (or equivalent) may be used instead of the compound of formula (3) to couple with the compound of formula (2). Such a reaction may be carried out by any method known in the art such as by heating (thermally or by microwave) in a suitable solvent.

Process c)

Compounds of formula (4) and (8b) where X is S may be made by reaction of an aminocarbonyl acylhydrazine or ethoxycarbonyl acylhydrazine with a thioisocyanate or thioisocyanate equivalent such as aminothiocarbonylimidazole in a suitable solvent such as DMF or MeCN at a temperature between 0 and 100° C. The preparation of aminocarbonyl acylhydrazines from anilines and of ethoxycarbonyl acylhydrazines is well known in the art. For example reaction of an aniline with methyl chlorooxoacetate in the presence of pyridine in a suitable solvent such as DCM followed by reaction with hydrazine in a suitable solvent such as ethanol at a temperature between 0 and 100° C.

The compound of formula (4) may then be cyclised using, for example agents such as carbonyldiimidazole, or tosyl chloride and a suitable base (such as triethylamine), under conditions known in the art.

An example of process c) is shown in Scheme 7 (wherein $R^3$ represents a substituent on $R^1$ as hereinbefore defined, $R^6$ represents an optional substituent on $R^2$, including those defined hereinbefore as $R^{6a-d}$):

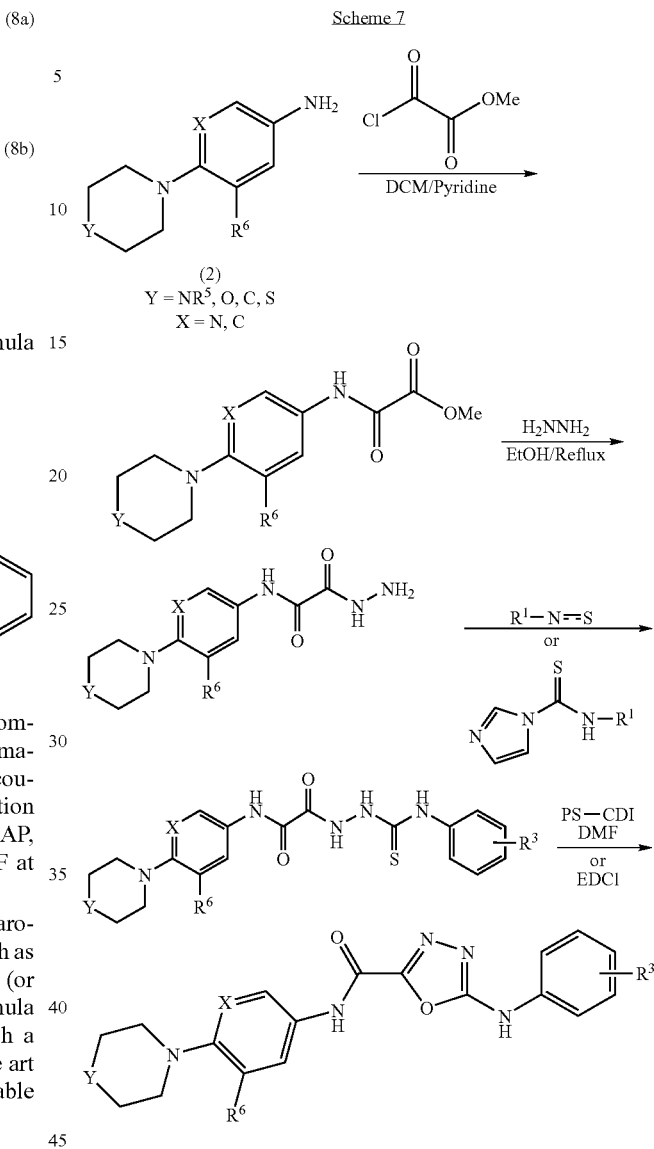

Iso(thio)cyanates $R^1$—NCX (where X is O or S) are commercially available or may be made by reaction of the acid chlorides $R^1$—NH$_2$ with for example (thio)phosgene or a (thio)phosgene equivalent followed by a suitable base (such as triethylamine).

Compounds of formula (4) may be made from compounds of formula (2) (wherein $R^2$ and Y are as defined for a compound of formula (I)) as illustrated above in Scheme 7.

Process d)

Compounds of formula (5) can be reacted with an acid chloride or sulfonyl chloride in the presence of a base such as triethylamine or pyridine in a suitable solvent such as DMF.

Process e)

Compounds of formula (6) can be reacted with aryl boronic acids in the presence of a suitable catalyst such as tetrakis (triphenyl phosphine)palladium(0) and a suitable base such as potassium phosphate in a suitable solvent such as DME-water (2:1) under microwave heating at 0 to 110° C.

Process f)

Compounds of formula (5) can be reacted with aldehydes in the presence of a suitable acid such as acetic acid, and a reducing agent such as sodium borohydride in a suitable solvent such as DCM.

Process g)

Compounds of formula (7) can be reacted with arylbromides, aryliodides, heteroarylbromides or heteroaryliodides in the presence of a suitable catalyst such as copper(i) iodide, a suitable diamine ligand such as trans-N,N'-dimethyl-1,2-cyclohexyldiamine and a suitable base such as potassium phosphate in a suitable solvent such as DMF or dioxane heating at 80-110° C.

It will be appreciated that certain of the various ring substituents in the compounds of the present invention, for example Z, Za, and/or $R^3$, may be introduced by standard aromatic substitution reactions or generated by conventional functional group modifications either prior to or immediately following the processes mentioned above, and as such are included in the process aspect of the invention. Such reactions may convert one compound of the formula (I) into another compound of the formula (I). Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkanesulfinyl or alkanesulfonyl.

If not commercially available, the necessary starting materials for the procedures such as those described above may be made by procedures which are selected from standard organic chemical techniques, techniques which are analogous to the synthesis of known, structurally similar compounds, techniques which are described or illustrated in the references given above, or techniques which are analogous to the above described procedure or the procedures described in the examples. The reader is further referred to Advanced Organic Chemistry, $5^{th}$ Edition, by Jerry March and Michael Smith, published by John Wiley & Sons 2001, for general guidance on reaction conditions and reagents.

It will be appreciated that some intermediates to compounds of the formula (I) are also novel and these are provided as separate independent aspects of the invention.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, Protective Groups in Organic Synthesis, John Wiley and Sons, 1991).

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

Examples of a suitable protecting group for a hydroxy group is, for example, an acyl group, for example an alkanoyl group such as acetyl, an aroyl group, for example benzoyl, a silyl group such as trimethylsilyl or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl or SEM may be removed, for example, by fluoride or by aqueous acid; or an arylmethyl group such as a benzyl group may be removed, for example, by hydrogenation in the presence of a catalyst such as palladium-on-carbon.

A suitable protecting group for an amino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine or 2-hydroxyethylamine, or with hydrazine.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art, or they may be removed during a later reaction step or work-up.

The skilled organic chemist will be able to use and adapt the information contained and referenced within the above references, and accompanying Examples therein and also the examples herein, to obtain necessary starting materials, and products.

The removal of any protecting groups and the formation of a pharmaceutically-acceptable salt are within the skill of an ordinary organic chemist using standard techniques. Furthermore, details on the these steps has been provided hereinbefore.

When an optically active form of a compound of the invention is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the invention is required, it may be obtained by carrying out one of the above procedures using a pure regioisomer as a starting material, or by resolution of a mixture of the regioisomers or intermediates using a standard procedure.

According to a further aspect of the invention there is provided a pharmaceutical composition which comprises a compound of formula (I), (IA), (IB), (IZA), (IZB) and (IZC) as defined hereinbefore or a pharmaceutically-acceptable salt thereof, in association with a pharmaceutically-acceptable excipient or carrier.

Certain intermediates used in the processes described above are novel, and these form a further aspect of the invention. In particular, compounds of formula (4) form a further aspect of the invention.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

According to a further aspect of the present invention there is provided a compound of formula (I) or a pharmaceutically acceptable salt thereof as defined hereinbefore for use in a method of treatment of the human or animal body by therapy.

Reference herein to a compound of formula (I) should be understood to refer equally to compounds of formulae (I), (IA), (IB) (and sub-formulae thereof), (IZA), (IZB) and/or (IZC).

We have found that compounds of the present invention inhibit DGAT1 activity and are therefore of interest for their blood glucose-lowering effects.

A further feature of the present invention is a compound of formula (I) or a pharmaceutically-acceptable salt thereof for use as a medicament.

Conveniently this is a compound of formula (I), or a pharmaceutically-acceptable salt thereof, for use as a medicament for producing an inhibition of DGAT1 activity in a warm-blooded animal such as a human being.

Particularly this is a compound of formula (I), or a pharmaceutically-acceptable salt thereof, for use as a medicament for treating diabetes mellitus and/or obesity in a warm-blooded animal such as a human being.

Thus according to a further aspect of the invention there is provided the use of a compound of formula (I), or a pharmaceutically-acceptable salt thereof in the manufacture of a medicament for use in the production of an inhibition of DGAT1 activity in a warm-blooded animal such as a human being.

Thus according to a further aspect of the invention there is provided the use of a compound of formula (I), or a pharmaceutically-acceptable salt thereof in the manufacture of a medicament for use in the treatment of diabetes mellitus and/or obesity in a warm-blooded animal such as a human being.

According to a further aspect of the invention there is provided a pharmaceutical composition which comprises a compound of formula (I) as defined hereinbefore or a pharmaceutically-acceptable salt thereof, in association with a pharmaceutically-acceptable excipient or carrier for use in producing an inhibition of DGAT1 activity in an warm-blooded animal, such as a human being.

According to a further aspect of the invention there is provided a pharmaceutical composition which comprises a compound of formula (I) as defined hereinbefore or a pharmaceutically-acceptable salt thereof, in association with a pharmaceutically-acceptable excipient or carrier for use in the treatment of diabetes mellitus and/or obesity in an warm-blooded animal, such as a human being.

According to a further feature of the invention there is provided a method for producing an inhibition of DGAT1 activity in a warm-blooded animal, such as a human being, in need of such treatment which comprises administering to said animal an effective amount of a compound of formula (I) or a pharmaceutically-acceptable salt thereof as defined hereinbefore.

According to a further feature of the invention there is provided a method of treating diabetes mellitus and/or obesity in a warm-blooded animal, such as a human being, in need of such treatment which comprises administering to said animal an effective amount of a compound of formula (I) or a pharmaceutically-acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

As stated above compounds defined in the present invention are of interest for their ability to inhibit the activity of DGAT1. A compound of the invention may therefore be useful for the prevention, delay or treatment of a range of disease states including diabetes mellitus, more specifically type 2 diabetes mellitus (T2DM) and complications arising there from (for example retinopathy, neuropathy and nephropathy), impaired glucose tolerance (IGT), conditions of impaired fasting glucose, metabolic acidosis, ketosis, dysmetabolic syndrome, arthritis, osteoporosis, obesity and obesity related disorders, (which include peripheral vascular disease, (including intermittent claudication), cardiac failure and certain cardiac myopathies, myocardial ischaemia, cerebral ischaemia and reperfusion, hyperlipidaemias, atherosclerosis, infertility and polycystic ovary syndrome); the compounds of the invention may also be useful for muscle weakness, diseases of the skin such as acne, Alzheimer's disease, various immunomodulatory diseases (such as psoriasis), HIV infection, inflammatory bowel syndrome and inflammatory bowel disease such as Crohn's disease and ulcerative colitis.

In particular, the compounds of the present invention are of interest for the prevention, delay or treatment of diabetes mellitus and/or obesity and/or obesity related disorders. In one aspect, the compounds of the invention are used for prevention, delay or treatment of diabetes mellitus. In another aspect, the compounds of the invention are used for prevention, delay or treatment of obesity. In a further aspect, the compounds of the invention are used for prevention, delay or treatment of obesity related disorders.

In a further aspect of the invention, compounds of the invention are used for the treatment of Alzheimer's disease.

The inhibition of DGAT1 activity described herein may be applied as a sole therapy or in combination with one or more other substances and/or treatments for the indication being treated. Such conjoint treatment may be achieved by way of the simultaneous, sequential or separate administration of the individual components of the treatment. Simultaneous treatment may be in a single tablet or in separate tablets. For example such conjoint treatment may be beneficial in the treatment of metabolic syndrome [defined as abdominal obesity (as measured by waist circumference against ethnic and gender specific cut-points) plus any two of the following: hypertriglyceridemia (>150 mg/dl; 1.7 mmol/l); low HDLc (<40 mg/dl or <1.03 mmol/l for men and <50 mg/dl or 1.29 mmol/l for women) or on treatment for low HDL (high density lipoprotein); hypertension (SBP ≧130 mmHg DBP ≧85 mmHg) or on treatment for hypertension; and hyperglycemia (fasting plasma glucose ≧100 mg/dl or 5.6 mmol/l or impaired glucose tolerance or pre-existing diabetes mellitus)—International Diabetes Federation & input from IAS/NCEP].

Such conjoint treatments may include the following main categories:
1) Anti-obesity therapies such as those that cause weight loss by effects on food intake, nutrient absorption or energy expenditure, such as orlistat, sibutramine and the like.
2) Insulin secretagogues including sulphonylureas (for example glibenclamide, glipizide), prandial glucose regulators (for example repaglinide, nateglinide);
3) Agents that improve incretin action (for example dipeptidyl peptidase IV inhibitors, and GLP-1 agonists);
4) Insulin sensitising agents including PPARgamma agonists (for example pioglitazone and rosiglitazone), and agents with combined PPARalpha and gamma activity;
5) Agents that modulate hepatic glucose balance (for example metformin, fructose 1, 6 bisphosphatase inhibitors, glycogen phopsphorylase inhibitors, glycogen synthase kinase inhibitors, glucokinase activators);
6) Agents designed to reduce the absorption of glucose from the intestine (for example acarbose);
7) Agents that prevent the reabsorption of glucose by the kidney (SGLT inhibitors);
8) Agents designed to treat the complications of prolonged hyperglycaemia (for example aldose reductase inhibitors);
9) Anti-dyslipidaemia agents such as, HMG-CoA reductase inhibitors (eg statins); PPARα-agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
10) Antihypertensive agents such as, β-blockers (eg atenolol, inderal); ACE inhibitors (eg lisinopril); Calcium antagonists (eg. nifedipine); Angiotensin receptor antagonists (eg candesartan), α antagonists and diuretic agents (eg. furosemide, benzthiazide);
11) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin;
12) Agents which antagonise the actions of glucagon; and
13) Anti-inflammatory agents, such as non-steroidal anti-inflammatory drugs (eg. aspirin) and steroidal anti-inflammatory agents (eg. cortisone).

In addition to their use in therapeutic medicine, compounds of formula (I) and their pharmaceutically-acceptable salts are also useful as pharmacological tools in the development and standardisation of in vitro and in vivo test systems for the evaluation of the effects of inhibitors of DGAT1 activity in laboratory animals such as cats, dogs, rabbits, monkeys, rats and mice, as part of the search for new therapeutic agents.

As indicated above, all of the compounds, and their corresponding pharmaceutically-acceptable salts, are useful in inhibiting DGAT1. The ability of the compounds of formula (I), and their corresponding pharmaceutically-acceptable acid addition salts, to inhibit DGAT1 may be demonstrated employing the following enzyme assay:

Human Enzyme Assay

The in vitro assay to identify DGAT1 inhibitors uses human DGAT1 expressed in insect cell membranes as the enzyme source (Proc. Natl. Acad. Sci. 1998, 95, 13018-13023). Briefly, sf9 cells were infected with recombinant baculovirus containing human DGAT1 coding sequences and harvested after 48 h. Cells were lysed by sonication and membranes isolated by centrifuging at 28000 rpm for 1 h at 4° C. on a 41% sucrose gradient. The membrane fraction at the interphase was collected, washed, and stored in liquid nitrogen.

DGAT1 activity was assayed by a modification of the method described by Coleman (Methods in Enzymology 1992, 209, 98-102). Compound at 1-10 μM was incubated with 0.4 μg membrane protein, 5 mM $MgCl_2$, and 10 0 μM 1, 2 dioleoyl-sn-glycerol in a total assay volume of 200 μl in plastic tubes. The reaction was started by adding $^{14}C$ oleoyl coenzyme A (30 μM final concentration) and incubated at room temperature for 30 minutes. The reaction was stopped by adding 1.5 mL 2-propanol:heptane:water (80:20:2). Radioactive triolein product was separated into the organic phase by adding 1 mL heptane and 0.5 mL 0.1 M carbonate buffer pH 9.5. DGAT1 activity was quantified by counting aliquots of the upper heptane layer by liquid scintillography.

Using this assay the compounds generally show activity with $IC_{50}$<10 mM, preferably <1 μM. Example 48 showed an $IC_{50}$=0.12 μM.

The ability of the compounds of formula (I), and their corresponding pharmaceutically-acceptable acid salts, to inhibit DGAT1 may further be demonstrated employing the following whole cell assays 1) and 2):

1) Measurement of Triglyceride Synthesis in 3T3 Cells

Mouse adipocyte 3T3 cells were cultured to confluency in 6 well plates in new born calf serum containing media. Differentiation of the cells was induced by incubating in medium containing 10% foetal calf serum, 1 μg/mL insulin, 0.25 μM dexamethasone and 0.5 mM isobutylmethyl xanthine. After 48 h the cells were maintained in medium containing 10% foetal calf serum and 1 μg/mL insulin for a further 4-6 days. For the experiment, the medium was changed to serum-free medium and the cells pre-incubated with compound solubilised in DMSO (final concentration 0.1%) for 30 minutes. De novo lipogenesis was measured by the addition of 0.25 mM sodium acetate plus 1 μCi/mL $^{14}C$-sodium acetate to each well for a further 2 h (J. Biol. Chem., 1976, 251, 6462-6464). The cells were washed in phosphate buffered saline and solubilised in 1% sodium dodecyl sulfate. An aliquot was removed for protein determination using a protein estimation kit (Perbio) based on the method of Lowry (J. Biol. Chem., 1951, 193, 265-275). The lipids were extracted into the organic phase using a heptane:propan-2-ol:water (80:20:2) mixture followed by aliquots of water and heptane according to the method of Coleman (Methods in Enzymology, 1992, 209, 98-104). The organic phase was collected and the solvent evaporated under a stream of nitrogen. The extracts solubilised in iso-hexane:acetic acid (99:1) and lipids separated via normal phase high performance liquid chromatography (HPLC) using a Lichrospher diol-5, 4×250 mm column and a gradient solvent system of iso-hexane:acetic acid (99:1) and iso-hexane:propan-2-ol:acetic acid (85:15:1), flow rate of 1 mL/minute according to the method of Silversand and Haux (1997). Incorporation of radiolabel into the triglyceride fraction was analysed using a Radiomatic Flo-one Detector (Packard) connected to the HPLC machine.

2) Measurement of Triglyceride Synthesis in MCF7 Cells

Human mammary epithelial (MCF7) cells were cultured to confluency in 6 well plates in foetal calf serum containing media. For the experiment, the medium was changed to serum-free medium and the cells pre-incubated with compound solubilised in DMSO (final concentration 0.1%) for 30 minutes. De novo lipogenesis was measured by the addition of 50 µM sodium acetate plus 3 µCi/mL 14C-sodium acetate to each well for a further 3 h (J. Biol. Chem., 1976, 251, 6462-6464). The cells were washed in phosphate buffered saline and solubilised in 1% sodium dodecyl sulfate. An aliquot was removed for protein determination using a protein estimation kit (Perbio) based on the method of Lowry (J. Biol. Chem., 1951, 193, 265-275). The lipids were extracted into the organic phase using a heptane:propan-2-ol:water (80:20:2) mixture followed by aliquots of water and heptane according to the method of Coleman (Methods in Enzymology, 1992, 209, 98-104). The organic phase was collected and the solvent evaporated under a stream of nitrogen. The extracts solubilised in iso-hexane:acetic acid (99:1) and lipids separated via normal phase high performance liquid chromatography (HPLC) using a Lichrospher diol-5, 4×250 mm column and a gradient solvent system of iso-hexane:acetic acid (99:1) and iso-hexane:propan-2-ol:acetic acid (85:15:1), flow rate of 1 mL/minute according to the method of Silversand and Haux (J. Chromat. B, 1997, 703, 7-14). Incorporation of radiolabel into the triglyceride fraction was analysed using a Radiomatic Flo-one Detector (Packard) connected to the HPLC machine.

In the above other pharmaceutical composition, process, method, use and medicament manufacture features, the alternative and preferred embodiments of the compounds of the invention described herein also apply.

EXAMPLES

The invention will now be illustrated by the following Examples in which, unless stated otherwise:
(i) temperatures are given in degrees Celsius (° C.); operations were carried out at room or ambient temperature, that is, at a temperature in the range of 18-25° C. and under an atmosphere of an inert gas such as argon;
(ii) organic solutions were dried over anhydrous magnesium sulfate; evaporation of solvent was carried out using a rotary evaporator under reduced pressure (600-4000 Pa; 4.5-30 mmHg) with a bath temperature of up to 60° C.;
(iii) chromatography means flash chromatography on silica gel; where a Biotage cartridge is referred to this means a cartridge containing KP-SIL™ silica, 60 Å, particle size 32-63 mM, supplied by Biotage, a division of Dyax Corp., 1500 Avon Street Extended, Charlottesville, Va. 22902, USA;
(iv) in general, the course of reactions was followed by TLC and reaction times are given for illustration only;
(v) yields are given for illustration only and are not necessarily those which can be obtained by diligent process development; preparations were repeated if more material was required;
(vi) where given, NMR data ($^1$H) is in the form of delta values for major diagnostic protons, given in parts per million (ppm) relative to tetramethylsilane (TMS), determined at 300 or 400 MHz (unless otherwise stated) using perdeuterio dimethyl sulfoxide (DMSO-$d_6$) as solvent, unless otherwise stated; peak multiplicities are shown thus: s, singlet; d, doublet; dd, doublet of doublets; dt, doublet of triplets; dm, doublet of multiplets; t, triplet, q, quartet; m, multiplet; br, broad;
(vii) chemical symbols have their usual meanings; SI units and symbols are used;
(viii) solvent ratios are given in volume:volume (v/v) terms;
(ix) mass spectra (MS) (loop) were recorded on a Micromass Platform LC equipped with HP 1100 detector; unless otherwise stated the mass ion quoted is (MH$^+$);
(x) LCMS (liquid chromatography-mass spectrometry) were recorded on a system comprising Waters 2790 LC equipped with a Waters 996 Photodiode array detector and Micromass ZMD MS, using a Phenomenex(Gemini 5u C18 110A 50×2 mm column and eluting with a flow rate of 1.1 ml/min with 5% (Water/Acetonitrile (1:1)+1% formic acid) and a gradient increasing from 0-95% of acetonitrile over the first 4 minutes, the balance (95-0%) being water and where HPLC Retention Times are reported these are in minutes in this system unless otherwise stated; unless otherwise stated the mass ion quoted is (MH$^+$);
(xi) where phase separation cartridges are stated then ISOLUTE Phase Separator 70 ml columns, supplied by Argonaut Technologies, New Road, Hengoed, Mid Glamorgan, CF82 8AU, United Kingdom, were used;
(xii) where a SiliCycle cartridge is referred to this means a cartridge containing Ultra Pure Silica Gel particle size 230-400 mesh, 40-63 um pore size, supplied by SiliCycle Chemical Division, 1200 Ave St-Jean-Baptiste, Suite 114, Quebec City, Quebec, G2E,5E8, CANADA;
(xiii) where an Isco Companion is referred to then a Combiflash companion chromatography instrument, supplied by ISOC Inc. Address Teledyne ISOC Inc, 4700 Superior Street, Lincoln, Nebr. 68504, USA, was used;
(xiv) where a microwave is referred to this means a Biotage Initiator sixty or Smith Creator microwave, supplied by Biotage, a division of Dyax Corp., 1500 Avon Street Extended, Charlottesville, Va. 22902, USA;
(xv) where GCMS is referred to then a Gas Chromatography—Mass Spectrometry analysis was carried out on a QP-2010 GC-MS system fitted with an AOC 20i autosampler and controlled by 'GCMS solutions' software, version 2.0, supplied by Shimadzu, Milton Keynes, MK12 5RE, UK; the GC column was a DB-5MS of length 25 m, 0.32 mm i.d. with a film thickness of 0.52µm supplied by J & W Scientific, Folsom, Calif., USA;
(xvi) where a centrifuge is referred to this means a Genevac EZ-2plus, supplied by Genevac Limited, The Soveriegn Centre, Farthing Road, Ipswich, IPI 5AP, UK;
(xvii) where chiral chromatography is referred to this is carried generally out using a 20 µm Merck 50 mm Chiralpak AD column, (Chiral Stationary Phase supplied by Chiral Technologies Europe, Parc d'Innovation, Bd. Gonthier d'Andernach, 67404 Illkirch Cedex, France), using MeCN/2-propanol/AcOH (90/10/0.1) as eluent, flow rate 80 mL/min, wavelength 300 nm, using a Gilson prep HPLC instrument (200 ml heads);
(xviii) melting points were determined using a Buchi 530 apparatus and are uncorrected;
(xix) The following abbreviations may be used below or in the process section hereinbefore:
Et$_2$O or ether diethyl ether
DMF dimethylformamide
DCM dichloromethane
DME 1,2-dimethoxyethane
MeOH methanol
EtOH ethanol
H$_2$O water
TFA trifluoroacetic acid
THF tetrahydrofuran
DMSO dimethylsulfoxide HOBt 1-hydroxybenzotriazole
EDCI (EDAC) 1-ethyl-3-(3-dimethylaminopropyl)carbodi-imide hydrochloride
DIPEA diisopropylethylamine
DEAD diethyl azodicarboxylate
EtOAc ethyl acetate
NaHCO₃ sodium bicarbonate/sodium hydrogencarbonate
K₃PO₄ potassium phosphate
PS polymer supported
BINAP 2,2'-bis(diphenylphosphino)-1,1'binaphthyl
Dppf 1,1'-bis(diphenylphosphino)ferrocene
dba dibenzylidineacetone
PS-CDI polymer supported carbonyldiimidazole
CH₃CN or MeCN acetonitrile
h hour
min minute
HATU O-(7-Azabenzotriazol-1-yl)-N,N,N',N'-tetramethyluronium hexofluorophosphate
NaOH sodium hydroxide
AcOH acetic acid
DMA dimethyl acetamide
nBuLi n-butyl lithium
MgSO₄ magnesium sulfate
Na₂SO₄ sodium sulfate
CDCl₃ deutero chloroform
CD₃OD per-deuterated methanol
Boc tert-butoxycarbonyl All compound names were derived using ACD NAME computer package.

Example 1

5-[(2-Fluorophenyl)amino]-N-(4-morpholin-4-ylphenyl)-1,3,4-oxadiazole-2-carboxamide

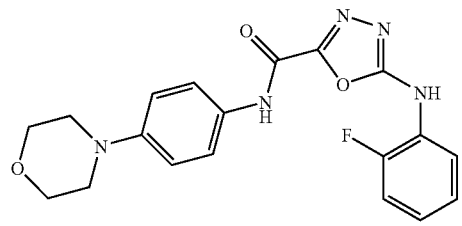

2-Fluorophenylisothiocyanate (92 µL, 0.75 mmol) was added to a stirred suspension of 2-hydrazino-N-(4-morpholin-4-ylphenyl)-2-oxoacetamide (Intermediate 16, 160 mg, 0.6 mmol) in DMF (10 mL) and stirred at 50° C. until a clear solution was obtained. PS-Carbodiimide (909 mg, 1.2 mmol) was added and the reaction was heated at 80° C. for a further 4 h. The reaction was filtered and the resin washed with DMF (5 mL). The combined DMF solutions were concentrated in vacuo and the residue triturated with diethyl ether to give the title compound as a yellow powder (190 mg, 82%):

$^1$H NMR δ 10.83 (1H, s), 10.77 (1H, s), 8.05 (1H, t), 7.66 (2H, d), 7.30 (2H, m), 6.95 (2H, d), 3.80-3.65 (4H, m), 3.11-3.01 (4H, m); MS m/e MH⁺ 384.

Examples 2-66

The following examples were prepared by the general procedure of Example 1, using Intermediates 23 to 28 and commercially available isothiocyanates.

| Example | R⁶ | R¹ | ¹HNMR δ | MS m/e MH⁺ |
|---|---|---|---|---|
| 2 | H | 3-OBn-phenyl | 11.01 (1H, s), 10.86 (1H, s), 7.67 (2H, d), 7.51-7.45 (2H, m), 7.41 (1H, t), 7.37-7.25 (4H, m), 7.15 (1H, d), 6.95 (2H, d), 6.74 (1H, d), 5.15 (2H, s), 3.79-3.69 (4H, m), 3.15-3.03 (4H, m) | 472 |
| 3 | H | 4-methyl-3-chloro-phenyl | 11.10 (1H, s), 10.88 (1H, s), 7.68 (2H, d), 7.57-7.39 (3H, m), 6.96 (2H, d), 3.87-3.67 (4H, m), 3.20-3.03 (4H, m), 2.41 (3H, s) | 414 |

-continued

| Example | R⁶ | R¹ | ¹HNMR δ | MS m/e MH⁺ |
|---|---|---|---|---|
| 4 | H | 4-chlorophenyl | 11.10 (1H, s), 10.82 (1H, s), 7.62 (4H, dd), 7.39 (2H, d), 6.93 (2H, d), 3.81-3.65 (4H, m), 3.11-3.01 (4H, m) | 400 |
| 5 | H | 2,3-dihydro-1H-inden-5-yl | 10.82-10.76 (2H, m), 7.67 (2H, d), 7.51 (1H, s), 7.35 (1H, d), 7.22 (1H, d), 6.95 (2H, d), 3.79-3.70 (4H, m), 3.14-3.05 (4H, m), 2.93-2.79 (4H, m), 2.09-1.98 (2H, m) | 406 |
| 6 | H | 3-methylphenyl | 10.80 (2H, s), 7.7 (2H, d), 7.45 (1H, m), 7.4 (1H, s), 7.3 (1H, m), 6.96 (2H, d) 6.9 (1H, d), 3.80-3.64 (4H, m), 3.11-3.00 (4H, m) | 380 |
| 7 | H | naphthalen-1-yl | 10.80 (1H, s), 10.70 (1H, s), 8.30 (1H, d), 8.02 (1H, d), 7.95 (1H, d), 7.75 (1H, d), 7.70 (2H, d), 7.58 (3H, m), 6.95 (2H, d), 3.80-3.65 (4H, m), 3.12-3.01 (4H, m) | 416 |
| 8 | H | 3,4-difluorophenyl | 11.27 (1H, s), 10.94 (1H, s), 7.49 (1H, q), 7.69 (3H, m), 7.35 (1H, m), 6.95 (2H, d), 3.80-3.66 (4H, m), 3.11-3.00 (4H, m) | 402 |
| 9 | H | 3-ethylphenyl | 10.89 (1H, s), 10.82 (1H, s), 7.67 (2H, d), 7.50-7.40 (2H, m), 7.30 (1H, t), 7.00-6.89 (3H, m), 3.80-3.70 (4H, m), 3.16-3.04 (4H, m), 2.62 (2H, q), 1.20 (3H, t) | 394 |
| 10 | H | 3-(ethoxycarbonyl)phenyl | 11.22 (1H, s), 10.87 (1H, s), 8.30 (1H, s), 7.87 (1H, d), 7.71-7.62 (3H, m), 7.56 (2H, t), 6.95 (2H, d), 4.35 (2H, q), 3.80-3.69 (4H, m), 3.15-3.04 (4H, m), 1.34 (3H, t) | 438 |
| 11 | H | 3-chlorophenyl | 11.20 (1H, s), 10.82 (1H, s), 7.72 (1H, s), 7.69 (2H, d), 7.50 (1H, d), 7.41 (1H, dd), 7.1 (1H, d), 6.95 (2H, d), 3.79-3.64 (4H, m), 3.10-3.01 (4H, m) | 400 |

-continued

| Example | R⁶ | R¹ | ¹HNMR δ | MS m/e MH⁺ |
|---|---|---|---|---|
| 12 | H | 2-naphthyl | 10.95 (1H, s), 10.64 (1H, s), 8.0 (1H, s), 7.73 (1H, s), 7.63 (2H, m), 7.44 (3H, m), 7.25 (1H, m), 7.16 (1H, m), 6.75 (2H, d), 3.60- 3.50 (4H, m), 2.93-2.84 (4H, m) | 416 |
| 13 | H | 3-bromophenyl | 11.15 (1H, s), 10.81 (1H, s), 7.85 (1H, d), 7.70 (2H, d), 7.52 (1H, d), 7.31 (1H, t), 7.20 (1H, d), 6.93 (2H, d), 3.80-3.69 (4H, m), 3.12-3.01 (4H, m) | 446 |
| 14 | H | 3,4-dimethylphenyl | 10.81 (1H, s), 10.75 (1H, s), 7.67 (2H, d), 7.39-7.30 (2H, m), 7.14 (1H, d), 6.95 (2H, d), 3.79-3.69 (4H, m), 3.13-3.04 (4H, m), 2.27 (3H, s), 2.16 (3H, s) | 394 |
| 15 | H | 3-chloro-4-methylphenyl | 11.12 (1H, s), 10.87 (1H, s), 7.73 (1H, d), 7.66 (2H, d), 7.45-7.33 (2H, m), 6.95 (2H, d), 3.80-3.70 (4H, m), 3.14-3.05 (4H, m), 2.32 (3H, s) | 414 |
| 16 | H | 3-(methylthio)phenyl | 11.01 (1H, s), 10.85 (1H, s), 7.66 (2H, d), 7.59 (1H, s), 7.40-7.29 (2H, m), 7.00-6.90 (3H, m), 3.80-3.70 (4H, m), 3.28 (3H, s), 3.14-3.04 (4H, m) | 412 |
| 17 | H | 4-fluoro-3-methylphenyl | 10.90 (1H, s), 10.82 (1H, s), 7.66 (2H, d), 7.51-7.40 (2H, m), 7.17 (1H, t), 6.95 (2H, d), 3.80-3.70 (4H, m), 3.15-3.01 (4H, m), 2.29 (3H, s) | 398 |
| 18 | H | 3,5-dimethylphenyl | 10.77 (2H, d), 7.65 (2H, d), 7.25 (2H, s), 6.95 (2H, d), 6.73 (1H, s), 3.80-3.70 (4H, m), 3.13-3.04 (4H, m), 2.31 (6H, s) | 394 |
| 19 | H | 2,5-difluorophenyl | 11.07 (1H, s), 10.80 (1H, s), 7.98 (1H, m), 7.68 (2H, d), 7.30 (1H, m), 6.95 (3H, d), 3.79-3.62 (4H, m), 3.11-3.02 (4H, m) | 402 |

-continued
| Example | R⁶ | R¹ | ¹HNMR δ | MS m/e MH⁺ |
|---|---|---|---|---|
| 20 | H | 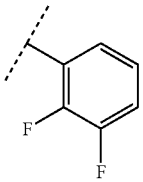 | 11.05 (1H, s), 10.80 (1H, s), 7.91 (1H, t), 7.70 (2H, d), 7.23 (1H, m), 7.15 (1H, m), 6.95 (2H, d), 3.80-3.65 (4H, m), 3.11-3.02 (4H, m) | 402 |
| 21 | H | 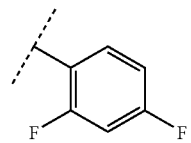 | 10.80 (1H, s), 10.69 (1H, m), 8.0 (2H, m), 7.60 (2H, d), 7.35 (1H, m), 7.16 (1H, m), 6.90 (2H, d), 3.79-3.63 (4H, m), 3.11-3.01 (4H, m) | 402 |
| 22 | H | 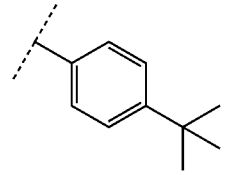 | 10.80 (2H, s), 7.72 (2H, d), 7.55 (2H, d), 7.40 (2H, d), 6.95 (2H, d), 3.77-3.65 (4H, m), 3.15-3.03(4H, d), 1.25 (9H, s) | 422 |
| 23 | H | 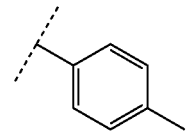 | 10.78 (2H, s), 7.70 (2H, d), 7.45 (2H, d), 7.18 (2H, d), 6.91 (2H, d), 3.78-3.64 (4H, m), 3.11-3.02 (4H, m), 2.22 (3H, s) | 380 |
| 24 | H | 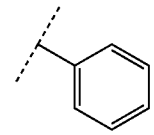 | 10.93 (1H, s), 10.83 (1H, s), 7.65 (2H, d), 7.59 (2H, d), 7.38 (1H, t), 7.06 (1H, t), 6.93 (2H, d), 3.77-3.69 (4H, m), 3.11-3.02 (4H, m) | 366 |
| 25 | H | 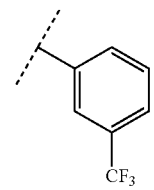 | 11.38 (1H, s), 10.89 (1H, s), 8.04 (1H, s), 7.86 (1H, d), 7.71-7.59 (3H, m), 7.41 (1H, d), 6.95 (2H, d), 3.79-3.71 (4H, m), 3.14-3.04 (4H, m) | 434 |
| 26 | H | 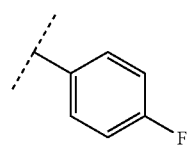 | 11.00 (1H, s), 10.84 (1H, s), 7.71-7.58 (4H, m), 7.25 (2H, t), 6.95 (2H, d), 3.79-3.70 (4H, m), 3.14-3.05 (4H, m) | 384 |
| 27 | H | 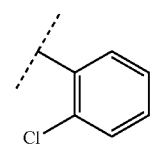 | 10.83 (1H, s), 10.35 (1H, s), 7.95 (1H, m), 7.65 (2H, d), 7.56 (1H, d), 7.45 (1H, m), 7.20 (1H, m), 6.95 (2H, d), 3.80-3.66 (4H, m), 3.10-3.01 (4H, m) | 400 |
| 28 | H | 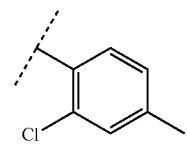 | 10.78 (1H, s), 10.21 (1H, s), 7.78 (1H, d), 7.65 (2H, d), 7.36 (1H, s), 7.23 (1H, d), 6.95 (2H, d), 3.79-3.65 (4H, m), 3.11-3.02 (4H, m), 2.27 (3H, s) | 414 |

-continued

| Example | R⁶ | R¹ | ¹HNMR δ | MS m/e MH⁺ |
|---|---|---|---|---|
| 29 | H | 2,3-dimethylphenyl | 10.78 (1H, s), 10.00 (1H, s), 7.64 (2H, d), 7.46 (1H, d), 7.18-7.09 (2H, m), 7.04 (1H, d), 6.94 (2H, d), 3.78-3.70 (4H, m), 3.14-3.04 (4H, m), 2.31 (3H, s), 2.16 (3H, s) | 394 |
| 30 | H | 2-methylphenyl | 10.70 (1H, s), 9.90 (1H, s), 7.68 (1H, d), 7.58 (2H, d), 7.30 (2H, m), 7.05 (1H, m), 6.89 (2H, d), 3.69-3.59 (4H, m), 3.10-3.02 (4H, m), 2.21 (3H, s) | 380 |
| 31 | H | 3-fluorophenyl | 11.25 (1H, s), 10.89 (1H, s), 7.66 (2H, d), 7.58-7.50 (1H, m), 7.47-7.32 (2H, m), 6.95 (2H, d), 6.92-6.85 (1H, m), 3.79-3.70 (4H, m), 3.13-3.05 (4H, m) | 384 |
| 32 | H | 2-isopropylphenyl | 10.68 (1H, s), 9.95 (1H, s), 7.60 (2H, d), 7.51 (1H, d), 7.40 (1H, d), 7.15 (2H, m), 6.86 (2H, d), 3.79-3.65 (4H, m), 3.30-3.20 (1H, m), 3.00 (4H, m), 1.10 (6H, d) | 408 |
| 33 | H | 4-methoxyphenyl | 10.80 (1H, s), 10.70 (1H, s), 7.70 (2H, d), 7.55 (2H, d), 7.00 (4H, dd), 3.82-3.67 (7H, m), 3.15-3.05 (4H, m) | 396 |
| 34 | H | benzo[1,3]dioxol-5-yl | 10.80 (2H, s), 7.65 (2H, d), 7.23 (1H, s), 7.00 (1H, d), 6.93 (3H, m), 6.00 (2H, s), 3.80-3.65 (4H, m), 3.11-3.02 (4H, s) | 410 |
| 35 | H | 2-iodophenyl | 10.75 (1H, s), 10.15 (1H, s), 7.97 (2H, d), 7.70 (3H, m), 7.50 (1H, m), 7.05 (1H, m), 6.95 (2H, d), 3.79-3.63 (4H, m), 3.15-3.03 (4H, m) | 492. |
| 36 | Cl | 3-methylphenyl | 11.07 (1H, s), 10.89 (1H, s), 7.94 (1H, s), 7.68-7.76 (1H, m), 7.44 (1H, d), 7.38 (1H, s), 7.25 (1H, t), 7.18 (1H, d), 6.86 (1H, d), 3.70-3.78 (4H, m), 2.99-2.92 (4H, m), 2.32 (3H, s) | 414 |

-continued
| Example | R⁶ | R¹ | ¹HNMR δ | MS m/e MH⁺ |
|---|---|---|---|---|
| 37 | F | 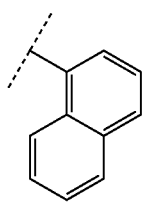 | 11.08 (1H, s), 10.80 (1H, s), 8.35-8.26 (1H, m), 8.08-7.95 (2H, m), 7.78 (1H, d), 7.69 (1H, dd), 7.53-7.64 (4H, m), 7.06 (1H, t), 3.75 (4H, t), 2.99 (4H, t) | 434 |
| 38 | Cl | 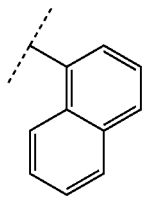 | 11.17 (1H, s), 10.86 (1H, s), 8.33-8.25 (1H, m), 8.08-7.94 (3H, m), 7.80-7.72 (2H, m), 7.62-7.55 (3H, m), 7.20 (1H, d), 3.79-3.70 (4H, m), 2.99-2.92 (4H, m) | 450 |
| 39 | Me | 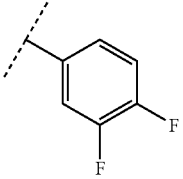 | 11.21 (1H, bs), 10.85 (1H, s), 7.74-7.39 (4H, m), 7.37-7.28 (1H, m), 7.01 (1H, d), 3.77-3.67 (4H, m), 2.85-2.75 (4H, m), 2.25 (3H, s) | 416 |
| 40 | Me | 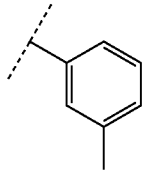 | 10.88-10.77 (2H, m), 7.60 (1H, s), 7.55 (1H, d), 7.42 (1H, d), 7.37 (1H, s), 7.25 (1H, t), 7.01 (1H, d), 6.86 (1H, d), 3.72 (4H, t), 2.80 (4H, t), 2.31 (3H, s), 2.31 (3H, s) | 394 |
| 41 | F | 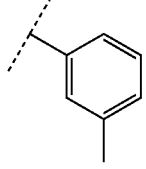 | 11.06 (1H, s), 10.89 (1H, s), 7.68 (1H, d), 7.57 (1H, d), 7.44 (1H, d), 7.39 (1H, s), 7.28 (1H, t), 7.05 (1H, t), 6.89 (1H, d), 3.75 (4H, t), 2.99 (4H, t), 2.33 (3H, s) | 398 |
| 42 | Cl | 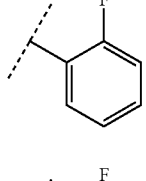 | 11.10 (1H, s), 10.79 (1H, s), 8.05 (1H, t), 7.96 (1H, s), 7.73 (1H, d), 7.38-7.25 (2H, m), 7.22-7.13 (2H, m), 3.80-3.72 (4H, m), 3.02-2.94 (4H, m) | 418 |
| 43 | F | 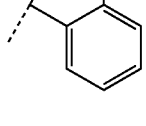 | 11.08 (1H, s), 10.79 (1H, s), 8.10-7.99 (1H, m), 7.68 (1H, dd), 7.61-7.52 (1H, m), 7.36-7.23 (2H, m), 7.21-7.13 (1H, m), 7.05 (1H, t), 3.79-3.71 (4H, t), 3.02-2.94 (4H, t) | 402 |
| 44 | Me | 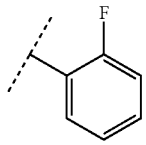 | 10.82 (1H, s), 10.73 (1H, s), 8.07-7.98 (1H, m), 7.67-7.50 (2H, m), 7.34-7.20 (2H, m), 7.19-7.09 (1H, m), 7.01 (1H, d), 3.77-3.68 (4H, m), 2.80 (4H, t), 2.25 (3H, s) | 398 |

| Example | R⁶ | R¹ | ¹HNMR δ | MS m/e MH⁺ |
|---|---|---|---|---|
| 45 | CN | 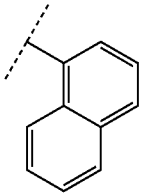 | 11.22 (1H, s), 10.82 (1H, s), 8.32-8.26 (1H, m), 8.15 (1H, d), 8.05-7.96 (3H, m), 7.78 (1H, d), 7.63-7.54 (3H, m), 7.24 (1H, d), 3.78 (4H, t), 3.13 (4H, t) | 441 |
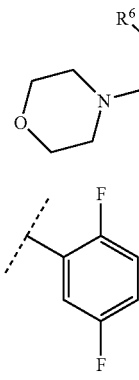
| Example | R⁶ | R¹ | ¹HNMR δ | MS m/e MH⁺ |
|---|---|---|---|---|
| 46 | H | 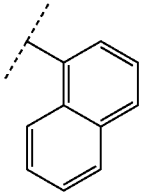 | 11.09 (1H, s), 11.00 (1H, s), 8.52 (1H, d), 8.03-7.93 (2H, m), 7.41-7.33 (1H, m), 7.01-6.94 (1H, m), 6.88 (1H, d), 3.71 (4H, t), 3.42 (4H, t) | 402 |
| 47 | H | 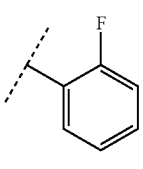 | 10.93 (1H, s), 10.75 (1H, s), 8.51 (1H, s), 8.31-8.22 (1H, m), 8.05-7.91 (3H, m), 7.78 (1H, d), 7.61-7.50 (3H, m), 6.87 (1H, d), 3.74-3.65 (4H, m), 3.44-3.35 (4H, m) | 417 |
| 48 | H | 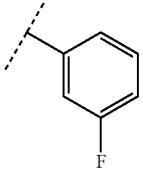 | 10.96 (1H, s), 10.75 (1H, s), 8.52 (1H, s), 8.04 (1H, t), 7.95 (1H, d), 7.35-7.23 (2H, m), 7.20-7.11 (1H, m), 6.88 (1H, d), 3.74-3.66 (4H, m), 3.45-3.37 (4H, m). | 385 |
| 49 | H | 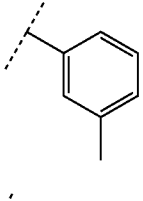 | 11.23 (1H, s), 10.98 (1H, s), 8.52 (1H, d), 7.96 (1H, dd), 7.53 (1H, dt), 7.43 (1H, dd), 7.38-7.34 (1H, m), 6.93-6.85 (2H, m), 3.71 (4H, t), 3.42 (4H, t) | 385 |
| 50 | H | 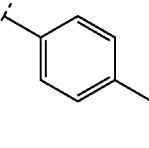 | 10.91 (1H, s), 10.85 (1H, s), 8.51 (1H, s), 7.98-7.90 (1H, m), 7.42 (1H, d), 7.38 (1H, s), 7.25 (1H, t), 6.90-6.83 (2H, m), 3.74-3.64 (4H, m), 3.45-3.37 (4H, m), 2.32 (3H, s). | 381 |
| 51 | H | | 10.92 (1H, s), 10.83 (1H, s), 8.52 (1H, d), 7.98-7.93 (1H, m), 7.54-7.50 (2H, m), 7.43-7.39 (2H, m), 6.87 (1H, d), 3.71 (4H, t), 3.42 (4H, t), 2.51 (9H, s) | 423 |

-continued

| Example | R⁶ | R¹ | ¹HNMR δ | MS m/e MH⁺ |
|---|---|---|---|---|
| 52 | H | 3-chlorophenyl | 11.22 (1H, s), 10.98 (1H, s), 8.52 (1H, d,), 7.98-7.94 (1H, m), 7.74 (1H, t), 7.54-7.50 (1H, m), 7.43 (1H, t), 7.14-7.10 (1H, m), 6.88 (1H, 4), 3.71 (4H, t), 3.42 (4H, t) | 401 |
| 53 | H | naphthalen-2-yl | 11.19 (1H, s), 10.96 (1H, s), 8.54 (1H, d,), 8.21 (1H, s), 7.99-7.93 (2H, m), 7.90-7.85 (2H, m), 7.67-7.63 (1H, m), 7.51 (1H, t), 7.42 (1H, t), 6.88 (1H, d), 3.72 (4H, t), 3.43 (4H, t) | 417 |
| 54 | Cl | 3,4-difluorophenyl | 11.27 (2H, bs), 8.61 (1H, d), 8.25 (1H, d), 7.67 (1H, ddd), 7.47 (1H, dd), 7.37-7.29 (1H, m), 3.77-3.69 (4H, m), 3.24-3.17 (4H, m) | 437 |
| 55 | H | 4-chlorophenyl | 11.13 (1H, s), 11.01 (1H, s), 8.52 (1H, d), 7.96 (1H, dd), 7.63 (2H, d), 7.46 (2H, d), 6.87 (1H, d), 3.71 (4H, t), 3.42 (4H, t) | 401 |
| 56 | Cl | 2-fluorophenyl | 11.26 (1H, broad s), 10.79 (1H, broad s), 8.61 (1H, d), 8.24 (1H, d), 8.01 (1H, t), 7.34-7.11 (3H, m), 3.73 (4H, t), 3.21 (4H, t) | 419 |
| 57 | H | 3,4-difluorophenyl | 11.23 (1H, s), 10.97 (1H, s), 8.52 (1H, d), 7.97-7.93 (1H, m), 7.70 (1H, ddd), 7.49 (1H, dd), 7.38-7.33 (1H, m), 6.87 (1H, d), 3.71 (4H, t), 3.42 (4H, t) | 403 |
| 58 | H | 3-bromophenyl | 11.19 (1H, s), 10.97 (1H, s), 8.52 (1H, d), 7.98-7.94 (2H, m), 7.59-7.55 (1H, m), 7.36 (1H, t), 7.27-7.24 (1H, m), 6.88 (1H, d), 3.71 (4H, t), 3.42 (4H, t) | 446 and 447 |
| 59 | H | 2,3-difluorophenyl | 11.07 (1H, broad s), 10.97 (1H, s), 8.52 (1H, d), 7.98-7.86 (2H, m), 7.32-7.14 (2H, m), 6.87 (1H, d), 3.71 (4H, t), 3.42 (4H, t) | 403 |

-continued

| Example | R⁶ | R¹ | ¹HNMR δ | MS m/e MH⁺ |
|---|---|---|---|---|
| 60 | Cl | 3-methylphenyl | 11.24 (1H, s), 10.91 (1H, s), 8.62 (1H, d), 8.27 (1H, dd), 7.47-7.34 (2H, m), 7.26 (1H, t), 6.87 (1H, d), 3.73 (4H, t), 3.21 (4H, t), 2.31 (3H, s) | 415 |
| 61 | H | 4-methylphenyl | 10.92 (1H, s), 10.83 (1H, s), 8.52 (1H, d), 7.95 (1H, dd), 7.49 (2H, d), 7.20 (2H, d), 6.87 (1H, d), 3.71 (4H, t), 3.42 (4H, t), 2.28 (3H, s) | 381 |
| 62 | H | 4-fluorophenyl | 10.99 (1H, s), 10.94 (1H, s), 8.52 (1H, d), 7.95 (1H, dd), 7.62 (2H, dd), 7.25 (2H, t), 6.87 (1H, d), 3.71 (4H, t), 3.42 (4H, t) | 385 |
| 63 | H | phenyl | 10.95 (2H, bs), 8.52 (1H, d), 7.96 (1H, dd), 7.61 (2H, d), 7.40 (2H, t), 7.07 (1H, t), 6.87 (1H, d), 3.71 (4H, t), 3.42 (4H, t) | 367 |
| 64 | H | benzo[1,3]dioxol-5-yl | 10.92 (1H, s), 10.81 (1H, s), 8.52 (1H, d), 7.95 (1H, dd), 7.26-7.24 (1H, m), 7.02 (1H, dd), 6.94 (1H, d), 6.87 (1H, d), 6.02 (2H, s), 3.71 (4H, t), 3.42 (4H, t) | 411 |
| 65 | H | 4-methoxyphenyl | 10.96 (1H, s), 10.94 (1H, s), 8.52 (1H, d), 7.96 (1H, dd), 7.33-7.25 (2H, m), 7.18-7.13 (1H, m), 6.87 (1H, d), 6.66 (1H, dd), 3.78 (3H, s), 3.71 (4H, t), 3.42 (4H, t) | 397 |
| 66 | H | 2,4-difluorophenyl | 10.94 (1H, s), 10.73 (1H, s), 8.51 (1H, d), 8.05-7.92 (2H, m), 7.40 (1H, ddd), 7.21-7.15 (1H, m), 6.87 (1H, d), 3.71 (4H, t), 3.42 (4H, t) | 403 |

Example 72

5-[(2-Fluorophenyl)amino]-N-[4-(4-isopropylpiperazin-1-yl)phenyl]-1,3,4-oxadiazole-2-carboxamide

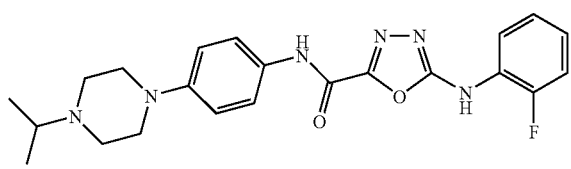

Ethyl 5-[(2-fluorophenyl)amino]-1,3,4-oxadiazole-2-carboxylate (Intermediate 40, 94 mg, 0.37 mmol) was stirred in water (1 mL). Sodium hydroxide (37 mg, 0.925 mmol) was dissolved in water (0.5 mL) and added to the reaction mixture. After stirring for 1 h the reaction was concentrated in vacuo to give a yellow solid which was dissolved in DMF (1 mL). [4-(4-Isopropylpiperazin-1-yl)phenyl]amine (WO02/057261) (89 mg, 0.41 mmol) dissolved in DMF (1 mL), HOBt (100 mg, 0.74 mmol), and EDAC (142 mg, 0.74 mmol) were added. The reaction was allowed to stir for 3 h then water (20 mL) was added and the reaction mixture thoroughly shaken to give a precipitate. After filtration and drying under in vacuo the title compound was obtained as a cream solid (69 mg, 44%):

$^1$H NMR δ 10.78 (1H, s), 8.0 (1H, t), 7.6 (2H, d), 7.20-7.35 (2H, m), 7.10-7.20 (1H, m), 6.9 (2H, d), 3.1 (4H, s), 2.6 (4H, s), 1.0 (6H, d);

MS m/e MH+ 425.38

Examples 67-71 and 73-84

The following examples were prepared by the general procedure of Example 1 (method A) using intermediates 19-22, 29-30 or the general procedure of Example 72 (method B) using intermediate 40 and 4-(4-benzylpiperazin-1-yl)aniline or 4-(4-pyridin-4-ylpiperazin-1-5 yl)aniline (J. Med. Chem., 2003; 46, 1803-1806).

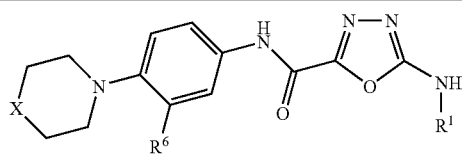

| Ex | X | R⁶ | R¹ | ¹HNMR δ | MS m/e MH+ | Method |
|----|-----|-----|-----|---------|------------|--------|
| 67 | NAc | H | 3-methylphenyl | 10.84 (1H, s), 10.80 (1H, s), 7.65 (2H, d), 7.42 (1H, d), 7.38 (1H, s), 7.25 (1 h, t), 6.95 (2H, d), 6.90 (1H, d) 3.60 (4H, s), 3.10 (4H, d), 2.00 (3H, s) | 421 | A |
| 68 | NAc | H | 1-naphthyl | 10.84 (1H, s), 10.74 (1H, s), 8.22-8.35 (1H, m), 7.9-8.05 (2H, m), 7.80 (1H, d), 7.70 (2H, d), 7.50-7.60 (3H, m), 6.95 (2H, d), 3.60-3.90 (4H, m), 3.10 (4H, d), 2.00 (3H, s) | 457 | A |
| 69 | NMe | H | 1-naphthyl | 10.80 (1H, s), 10.72 (1H, s), 8.25-8.35 (1H, m), 8.01 (1H, d), 7.95-8.0 (1H, m), 7.75 (1H, d), 7.70 (2H, d), 7.55-7.65 (3H, m), 6.95 (2H, d), 3.10 (4H, s), 2.40 (4H, s), 2.21 (3H, s) | 429 | A |
| 70 | NAc | H | 2-fluorophenyl | 10.82 (1H, s), 10.72 (1H, s), 8.05 (1H, t), 7.90 (1H, s), 7.60 (2H, d), 7.20-7.35 (2H, m), 7.10-7.20 (1H, m), 6.95 (2H, d), 3.6 (4H, s), 3.05 (4H, d), 2.00 (3H, s) | 425 | A |
| 71 | NAc | Me | 3,4-difluorophenyl | 11.21 (1H, s), 10.86 (1H, s), 7.68 (1H, ddd), 7.62 (1H, s), 7.58-7.50 (1H, m), 7.50-7.40 (1H, m), 7.37-7.29 (1H, m), 7.00 (1H, d), 3.61-3.51 (4H, m), 2.85-2.72 (4H, m), 2.27 (3H, s), 2.03 (3H, s) | 457 | A |
| 73 | NMe | H | 3-methylphenyl | 10.84 (1H, s), 10.79 (1H, s), 7.70 (2H, d), 7.45 (2H, d), 7.40 (1H, s), 7.25 (1H, t), 6.85-6.95 (3H, m), 3.10 (4H, s), 2.45 (4H, s), 2.25 (3H, s) | 393 | A |

-continued

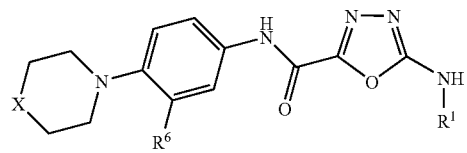

| Ex | X | R6 | R1 | 1HNMR δ | MS m/e MH+ | Method |
|---|---|---|---|---|---|---|
| 74 | NAc | Me | 3-methylbenzyl | 10.86 (1H, s), 10.81 (1H, s), 7.62 (1H, s), 7.54 (1H, d), 7.42 (1H, d), 7.37 (1H, s), 7.25 (1H, t), 7.00 (1H, d), 6.86 (1H, d), 3.62-3.50 (4H, m), 2.85-2.70 (4H, m), 2.31 (3H, s), 2.27 (3H, s), 2.03 (3H, s) | 435 | A |
| 75 | NBoc | F | 1-naphthylmethyl | 11.09 (1H, s), 10.79 (1H, broad s), 8.32-8.26 (1H, m), 8.05-7.96 (2H, m), 7.78 (1H, d), 7.70 (1H, dd), 7.63-7.54 (4H, m), 7.07 (1H, t), 3.53-3.44 (4H, m), 2.98-2.91 (4H, m), 2.51 (9H, s) | 531 (M−H)− | A |
| 76 | NBn | H | 2-fluorobenzyl | 10.78 (1H, s), 10.70 (1H, broad s), 8.00 (1H, t), 7.65 (2H, d), 7.1-7.3 (7H, m), 6.90 (2H, d), 3.30 (4H, s), 3.10 (4H, s) | 473 | B |
| 77 | NAc | Me | 2-fluorobenzyl | 10.84 (1H, s), 10.74 (1H, s), 8.03 (1H, t), 7.61 (1H, s), 7.54 (1H, d), 7.35-7.21 (2H, m), 7.20-7.10 (1H, m), 7.00 (1H, d), 3.61-3.51 (4H, m), 2.85-2.71 (4H, m), 2.27 (3H, s), 2.03 (3H, s) | 439 | A |
| 78 | NBoc | F | 2-fluorobenzyl | 11.07 (1H, s), 10.76 (1H, s), 8.02 (1H, t), 7.76-7.50 (2H, m), 7.34-7.10 (3H, m), 7.05 (1H, t), 3.50-3.40 (4H, m), 2.96-2.89 (4H, m), 2.49 (9H, s) | 499 (M−H)− | A |
| 79 | NMe | H | 2-fluorobenzyl | 10.80 (1H, s), 8.05 (1H, t), 7.66 (2H, d), 7.20-7.35 (2H, m), 7.1-7.2 (1H, m), 6.95 (H, d), 3.10 (4H, s), 2.40 (4H, s), 2.30 (2H, s) | 397 | A |
| 80 | NBoc | H | 2-fluorobenzyl | 10.82 (1H, s), 10.72 (1H, s), 8.05 (1H, t), 7.60 (2H, d), 7.20-7.30 (2H, m), 7.10-7.20 (1H, m), 6.95 (2H, d), 3.40-3.48 (4H, m), 3.05-3.10 (4H, m), 1.40 (9H, s) | 427 [MH−C4H8]+ | A |

-continued

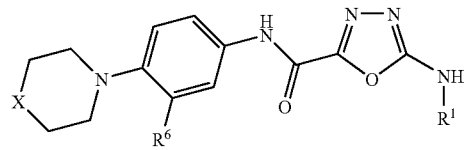

| Ex | X | R⁶ | R¹ | ¹HNMR δ | MS m/e MH⁺ | Method |
|---|---|---|---|---|---|---|
| 81 | 4-pyridinyl-N | H | 2-fluorophenyl | | 460 | B |
| 82 | CH₂ | H | 1-naphthyl | 10.78 (1H, s), 10.72 (1H, s), 8.25-8.35 (1H, m), 8.05 (1H, d), 7.95-8.0 (1H, m), 7.80 (1H, d), 7.55-7.65 (5H, m), 6.95 (2H, d), 3.05-3.15 (4H, m), 1.45-1.65 (6H, m) | 414 | A |
| 83 | CH₂ | H | 3-methylphenyl | 10.84 (1H, s), 10.75 (1H, s), 7.60 (1H, d), 7.45 (1H, d), 7.40 (1H, s), 7.25 (1H, t), 6.85-6.95 (3H, m), 3.05-3.15 (4H, m), 1.45-1.65 (6H, m) | 378 | A |
| 84 | CH₂ | H | 2-fluorophenyl | 10.78 (1H, s), 10.72 (1H, s), 8.05 (1H, t), 7.60 (2H, d), 7.20-7.35 (2H, m), 7.10-7.20 (1H, m), 6.95 (2H, d), 3.05-3.15 (4H, m), 1.45-1.65 (6H, m) | 382 | A |

Example 87

N-[6-(4-Benzoyl-1-piperazinyl)-3-pyridinyl]-5-[(2-fluorophenyl)amino]-1,3,4-oxadiazole-2-carboxamide

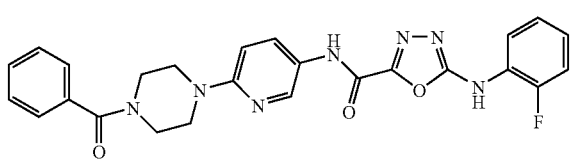

5-[(2-Fluorophenyl)amino]-N-(6-piperazin-1-ylpyridin-3-yl)-1,3,4-oxadiazole-2-carboxamide (intermediate 41, 150 mg, 0.39 mmol), was stirred in DMF (4 mL) and pyridine (1 mL). Benzoyl chloride (60 mg, 0.43 mmol) was added and the reaction stirred for 18 h. Water (20 mL) was added and the reaction mixture thoroughly mixed. The resulting precipitate was filtered, washed with water (2×10 mL) then ether (2×10 mL) and dried in vacuo to give the title compound (130 mg) as a pale purple solid:

¹H NMR δ 10.94 (1H, s), 10.74 (1H, s), 8.50 (1H, s), 8.00 (1H, t), 7.95 (1H, d), 7.40 (4H, s), 7.20-7.35 (2H, m), 7.10-7.20 (1H, m), 6.90 (2H, d), 3.42-3.83 (8H, m); MS m/e MH⁺ 488.

Examples 85, 86 and 88-94A

The following examples were prepared by the general procedure of Example 1 (method A) using Intermediates 31-33, or the general procedure of Example 72 (method B) using Intermediate 40 and the appropriate aniline, for example N²-phenylpyridine-2,5-diamine (J. Med. Chem. 1994, 37, 18-25), [4-pyridin-2-ylmethoxy)phenyl]amine (DE 3607382), N-methyl-N-phenylbenzene-1,4-diamine (WO 03059905), 6-butoxypyridin-3-amine (J. Am. Chem. Soc., 1947, 69, 1204), or the general procedure of Example 87 (method C) using Intermediate 41 and the appropriate acid chloride.

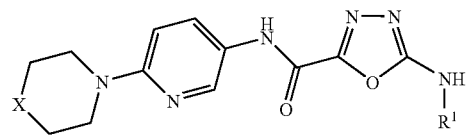

| Ex | X | R¹ | ¹H NMR (DMSO-d₆) δ | MS m/e MH⁺ | Method |
|---|---|---|---|---|---|
| 85 | NMe | naphthalen-1-ylmethyl | 10.90 (1H, s), 10.76 (1H, s), 8.45-8.50 (1H, m), 8.25-8.35 (1H, m), 7.90-8.05 (3H, m), 7.80 (1H, d), 7.55-7.65 (3H, m), 6.80 (2H, d), 3.40-3.50 (4H, m), 2.35-2.45 (4H, m), 2.20 (3H, s) | 430 | A |
| 86 | NMe | 3-methylbenzyl | 10.88 (1H, s), 10.84 (1H, s), 8.50 (1H, s), 7.90 (1H, d), 7.45 (1H, d), 7.40 (s, 1H), 7.30 (1H, t), 6.95 (2H, t), 3.40-3.45 (4H, m), 2.35-2.45 (4H, m), 2.20 (3H, s) | 394 | A |
| 88 | N-C(O)-(3-fluorophenyl) | 2-fluorobenzyl | 10.94 (1H, s), 10.73 (1H, s), 8.50 (1H, s), 8.00 (1H, t), 7.90 (1H, d), 7.50 (1H, q), 7.20-7.35 (5H, m), 7.10-7.20 (1H, m), 6.90 (1H, d), 3.47-3.81 (8H, bd) | 506 | C |
| 89 | NSO₂Me | 2-fluorobenzyl | 10.95 (1H, s), 8.50 (1H, s), 8.00 (1H, t), 7.90 (1H, d), 7.20-7.35 (2H, m), 7.10-7.20 (1H, m), 6.90 (1H, d), 3.55-3.65 (4H, m), 3.15-3.25 (4H, m), 2.90 (3H, s) | 462 | B |
| 90 | N-C(O)-(4-fluorophenyl) | 2-fluorobenzyl | 10.94 (1H, s), 10.73 (1H, s), 8.50 (1H, s), 8.00 (1H, t), 7.90-8.00 (1H, m), 7.45-7.55 (2H, m), 7.20-7.35 (4H, m), 7.10-7.20 (1H, m), 6.90 (1H, d), 3.40-3.80 (8H, bs) | 506 | C |
| 91 | NMe | 2-fluorobenzyl | 10.90 (1H, s), 10.70 (1H, s), 8.50 (1H, s), 8.05 (1H, t), 7.90-7.95 (1H, m), 7.20-7.35 (2H, m), 7.10-7.20 (1H, m), 6.95 (2H, d), 3.40-3.50 (4H, m), 2.35-2.45 (4H, m), 2.20 (3H, s) | 398 | A |
| 92 | NBoc | 2-fluorobenzyl | 10.93 (1H, s), 10.73 (1H, s), 8.50 (1H, s), 8.05 (1H, t), 7.90-8.00 (1H, m), 7.20-7.35 (2H, m), 7.10-7.20 (1H, m), 6.95 (2H, d), 3.40 (8H, d), 1.40 (9H, s) | 484 | A |
| 93 | NAc | 2-fluorobenzyl | 10.94 (1H, s), 10.74 (1H, s), 8.50 (1H, s), 8.05 (1H, t), 7.90-8.00 (1H, m), 7.20-7.35 (2H, m), 7.10-7.20 (1H, m), 6.95 (2H, d), 3.50 (6H, m), 3.40-3.50 (2H, m), 2.00 (3H, s) | 424 | A |

-continued

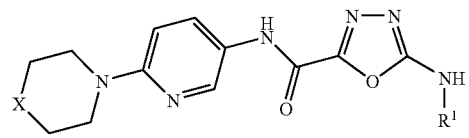

| Ex | X | R¹ | ¹H NMR (DMSO-d₆) δ | MS m/e MH⁺ | Method |
|---|---|---|---|---|---|
| 94 | ![N-C(=O)-pyridyl] | F-phenyl | 10.95 (1H, s), 10.74 (1H, s), 8.70 (2H, s), 8.50 (1H, s), 8.00 (1H, t), 7.90-8.00 (1H, m), 7.50 (2H, d), 7.20-7.35 (2H, m), 7.10-7.20 (1H, m), 6.90 (1H, d), 3.70 (2H, s), 3.60 (2H, s), 3.50 (2H, s) | 489 | C |
| 94 A | NMe | 2-pyridyl | | 381 | A |

Examples 95-103

The following examples were prepared by the general procedure of Example 72 (method B) using Intermediate 40 and the appropriate aniline, for example Intermediate 42.

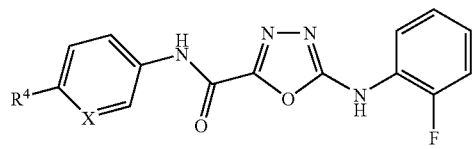

| Example | R⁴ | X | ¹H NMR δ | MS m/e MH⁺ |
|---|---|---|---|---|
| 95 | OPh | N | 11.22 (1H, s), 10.78 (1H, s), 8.50 (1H, s), 8.20 (1H, d), 8.00 (1H, t), 7.40 (2H, t), 7.10-7.30 (7H, m) | 392 |
| 96 | NPh | N | 10.98 (1H, s), 9.00 (1H, s), 8.50 (1H, s), 8.05 (1H, t), 7.95 (1H, d), 7.70 (2H, d), 7.10-7.30 (5H, m), 6.80-6.90 (2H, m) | 391 |
| 97 | O-nBu | N | | 372 |
| 98 | 3-pyridyl-O- | N | 11.26 (1H, s), 8.70 (1H, s), 8.60-8.70 (2H, m), 8.30 (1H, d), 8.00 (1H, t), 7.60 (1H, d), 7.50 (1H, m), 7.10-7.30 (4H, m) | 393 |
| 99 | —(CH₂)₄OH | N | 11.18 (1H, s), 8.90 (1H, s), 8.00-8.10 (2H, m), 7.20-7.35 (4H, m), 7.10-7.20 (1H, m), 4.40 (1H, d), 3.40 (2H, s), 2.70 (2H, t), 1.60-1.70 (2H, m), 1.35-1.45 (2H, m) | 372 |

-continued

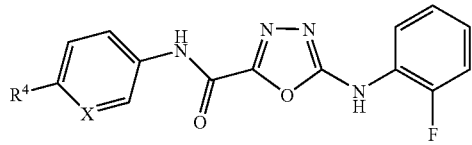

| Example | R⁴ | X | ¹H NMR δ | MS m/e MH⁺ |
|---|---|---|---|---|
| 100 | OBn | C | 10.80 (1H, s), 10.76 (1H, s), 8.00 (1H, t), 7.50 (1H, s), 7.20-7.40 (9H, m), 6.80 (1H, d), 5.10 (2H, s) | 405 |
| 101 | nBu | C | 10.92 (1H, s), 10.75 (1H, s), 8.00 (1H, t), 7.70 (2H, d), 7.20-7.35 (2H, m), 7.10-7.20 (3H, d), 2.50 (2H, t), 1.50-1.60 (2H, m), 1.20-1.40 (2H, m), 0.90 (3H, t) | 355 |
| 102 | 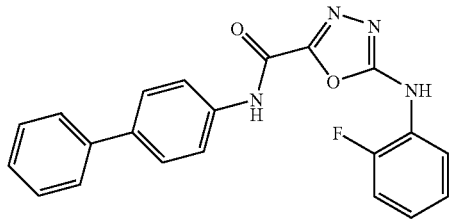 | C | 11.07 (1H, s), 8.60 (1H, d), 7.95-8.05 (2H, m), 7.90 (1H, t), 7.70 (1H, d), 7.50 (1H, d), 7.20-7.40 (4H, m), 7.10-7.20 (1H, m), 5.20 (2H, s) | 440 |
| 103 | N(Me)Ph | C | | 404 |

Example 104

N-Biphenyl-4-yl-5-[(2-fluorophenyl)amino]-1,3,4-oxadiazole-2-carboxamide

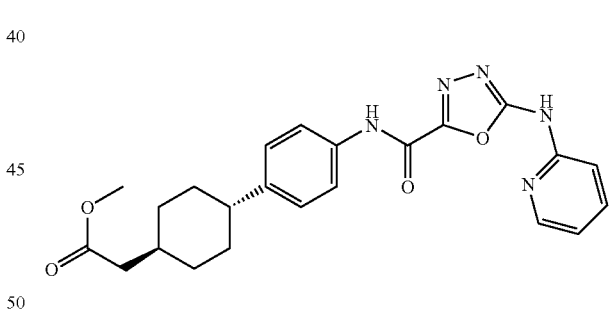

N-(4-Iodophenyl)-5-[(2-fluorophenyl)amino]-1,3,4-oxadiazole-2-carboxamide (Intermediate 35), 150 mg, 0.36 mmol), phenyl boronic acid (35 mg, 0.29 mmol), potassium phosphate (230 mg, 1.44 mmol), and tetrakis(triphenyl phosphine)palladium(0) (22 mg, 0.02 mmol) were stirred in DME (1.2 mL) and water (0.6 mL), in a microwave tube, and heated at 110° C. for 3 h. The reaction mixture was partitioned between ethyl acetate (10 mL) and water (10 mL), and extracted with ethyl acetate (2×10 mL). The organics were combined, and dried by passing through a Varian Chem elut column. The filtrate was concentrated in vacuo and purified by preparative HPLC to afford the title compound as a cream solid (25 mg, 19%):

¹H NMR δ 11.20 (1H, s), 10.78 (1H, s), 8.10 (1H, t), 7.90 (2H, d), 7.65-7.75 (4H, m), 7.50 (2H, t), 7.20-7.35 (3H, m), 7.10-7.20 (1H, m); MS m/e MH⁺ 375.

Example 105

Methyl {trans-4-[4-({[5-(pyridin-2-ylamino)-1,3,4-oxadiazol-2-yl]carbonyl}amino)phenyl]cyclohexyl}acetate 2-Isothiocyanatopyridine (163 mg) was added to a stirred suspension of methyl [trans-4-(4-{[hydrazino(oxo)acetyl]amino}phenyl)cyclohexyl]acetate (Intermediate 43) (333 mg) in DMF (3 mL) and the mixture was heated to 40° C. and stirred for 60 minutes. EDAC (230 mg) was added and the resulting mixture was heated to 85° C. and stirred for 16 hours. Water (3 mL) was added. The precipitate was filtered off and washed with water, Et₂O then dried under vacuum overnight to give the title compound (333 mg) as a solid; ¹H NMR δ 11.60 (1H, bs), 10.93 (1H, s), 8.30 (1H, m), 7.88 (2H, m), 7.70 (2H, d), 7.23 (2H, d), 7.07 (1H, m), 3.61 (3H, s), 2.45 (1H+DMSO, m), 2.25 (2H, d), 1.80 (5H, m), 1.46 (2H, m), 1.13 (2H, m); MS m/e MH⁺ 436.

Examples 106-111

Using an analogous procedure to that described for Example 105 with the appropriate starting material (SM) and using the requisite isothiocyanate the following Examples were prepared:

| Ex. | SM | Name | ¹H NMR | MS m/e M + H⁺ |
|---|---|---|---|---|
| 106[1] | Int. 43 | methyl (trans-4-{4-[({5-[(3-ethoxyphenyl)amino]-1,3,4-oxadiazol-2-yl}carbonyl)amino]phenyl}cyclohexyl)acetate | 10.94 (1H, s), 10.92 (1H, s), 7.69 (2H, d), 7.30-7.19 (4H, m), 7.13 (1H, d), 6.63 (1H, d), 4.05 (2H, quartet), 3.61 (3H, s), 2.45 (1H + DMSO, m), 2.25 (2H, d), 1.79 (5H, m), 1.45 (2H, m), 1.35 (3H, t), 1.13 (2H, m). | 479 |
| 107 | Int. 43 | methyl [trans-4-(4-{[(5-{[3-(benzyloxy)phenyl]amino}-1,3,4-oxadiazol-2-yl)carbonyl]amino}phenyl)cyclohexyl]acetate | 10.97 (1H, s), 10.93 (1H, s), 7.69 (2H, d), 7.48 (2H, d), 7.41 (2H, t), 7.36-7.28 (3H, m), 7.22 (2H, d), 7.16 (1H, d), 6.73 (1H, d), 5.12 (1H, s), 3.60 (3H, s), 2.45 (1H + DMSO, m), 2.25 (2H, d), 1.80 (5H, m), 1.47 (2H, m), 1.15 (2H, m) | 541 |
| 108[2,3] | Int. 43' | methyl (trans-4-{4-[({5-[(4-chlorophenyl)amino]-1,3,4-oxadiazol-2-yl}carbonyl)amino]phenyl}cyclohexyl)acetate | | 469 |
| 109[2,4] | Int. 43' | methyl (trans-4-{4-[({5-[(2,4,5-trifluorophenyl)amino]-1,3,4-oxadiazol-2-yl}carbonyl)amino]phenyl}cyclohexyl)acetate | | 489 |
| 110 | Int. 44 | methyl trans-4-{4-[({5-[(2-fluorophenyl)amino]-1,3,4-oxadiazol-2-yl}carbonyl)amino]phenyl}cyclohexanecarboxylate | 10.94 (1H, s), 10.75 (1H, s), 8.04 (1H, t), 7.69 (2H, d), 7.34-7.14 (5H, m), 3.62 (3H, s), 2.60-2.33 (2H + DMSO, m), 2.01 (2H, m), 1.84 (2H, m), 1.49 (4H, m) | 439 |
| 111 | Int. 43 | methyl (trans-4-{4-[({5-[2-fluorophenyl)amino]-1,3,4-oxadiazol-2-yl}carbonyl)amino]phenyl}cyclohexyl)acetate | 10.49 (1H, br.s), 8.02 (1H, t), 7.67 (2H, d), 7.28 (2H, d), 7.1-6.98 (2H, m), 6.79 (1H, br.s), 3.60 (3H, s), 2.42 (1H, m), 2.23 (2H, d), 1.87-1.67 (5H, m), 1.45 (2H, m), 1.12 (2H, m) | 453 |

[1]O-(pentafluorophenyl) (3-ethoxyphenyl)thiocarbamate (Intermediate 48) was used instead of the corresponding isothiocyanate.
[2]Prepared in similar manner to Example 105 except a mixture of methyl trans-4-(4-{[(hydrazino(oxo)acetyl]amino}phenyl)cyclohexyl]acetate and ethyl [trans-4-(4-{[hydrazino(oxo)acetyl]amino}phenyl)cyclohexyl]acetate used.
[3]Contains 17% ethyl (trans-4-{4-[({5-[(4-chlorophenyl)amino]-1,3,4-oxadiazol-2-yl}carbonyl)amino]phenyl}cyclohexyl)acetate by LCMS; MS m/e MH⁺ 483.
[4]Contains 26% ethyl (trans-4-{4-[({5-[(2,4,5-trifluorophenyl)amino]-1,3,4-oxadiazol-2-yl}carbonyl)amino]phenyl}cyclohexyl)acetate by LCMS; MS m/e MH⁺ 503.

Example 112

{trans-4-[4-({[5-(Pyridin-2-ylamino)-1,3,4-oxadiazol-2-yl]carbonyl}amino)phenyl]cyclohexyl}acetic acid

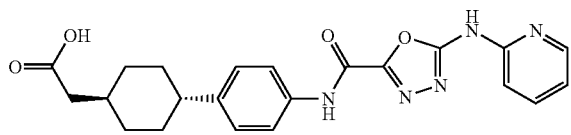

Lithium hydroxide monohydrate (60 mg) in water (2 mL) was added to a stirred suspension of methyl {trans-4-[4-({[5-(pyridin-2-ylamino)-1,3,4-oxadiazol-2-yl]carbonyl}amino)phenyl]cyclohexyl}acetate (Example 105, 309 mg) in THF (7 mL). After 16 hours the solution was heated to 40° C. and stirred for a further 5 hours then allowed to cool to ambient temperature. The THF was removed in vacuo and the residue was acidified with 2M HCl. The precipitate was filtered off, washed with ether, warm DCM and warm ether then dried overnight. The resultant solid was purified by HPLC using a gradient of 5-25% MeCN in water with 1% ammonia as the eluent to give the title compound (119 mg) as a solid; ¹H NMR δ 10.80 (1H, bs), 10.91 (1H, s), 8.31 (1H, d), 7.86 (2H, m), 7.69 (2H, d), 7.23 (2H, d), 7.05 (1H, m), 2.45 (1H+ DMSO, m), 2.14 (2H, d), 1.82 (5H, m), 1.47 (2H, m), 1.13 (2H, m); MS m/e MH⁺ 422.

Examples 113-117

The following examples were prepared by the general procedure of Example 112 using the appropriate starting material selected from Examples 106-110.

| Example | Name | ¹H NMR | MS m/e M + H⁺ |
|---|---|---|---|
| 113[1,5] | (trans-4-{4-[({5-[(3-ethoxyphenyl)amino]-1,3,4-oxadiazol-2-yl}carbonyl)amino]phenyl}cyclohexyl)acetic acid | 11.98 (1H, s), 10.94 (1H, s), 10.92 (1H, s), 7.69 (2H, d), 7.30-7.22 (4H, m), 7.13 (1H, d), 6.64 (1H, d), 4.04 (2H, quartet), 2.45 (1H + DMSO, m), 2.15 (2H, d), 1.82 (5H, m), 1.46 (2H, m), 1.35 (3H, t), 1.13 (2H, m). | 464 |
| 114[1,6] | [trans-4-(4-{[(5-{[3-(benzyloxy)phenyl]amino}-1,3,4-oxadiazol-2-yl)carbonyl]amino}phenyl)cyclohexyl]acetic acid | 11.98 (1H, bs), 10.98 (1H, s), 10.93 (1H, s), 7.69 (2H, d), 7.48 (2H, d), 7.41 (2H, m), 7.36-7.27 (3H, m), 7.22 (2H, d), 7.16 (1H, d), 6.74 (1H, dd), 5.12 (2H, s), 2.45 (1H + DMSO, m), 2.15 (2H, d), 1.81 (5H, m), 1.46 (2H, m), 1.15 (2H, m). | 527 |
| 115[2,4] | (trans-4-{4-[({5-[(4-chlorophenyl)amino]-1,3,4-oxadiazol-2-yl}carbonyl)amino]phenyl}cyclohexyl)acetic acid | 11.98 (1H, s), 11.13 (1H, s), 10.94 (1H, s), 7.70 (2H, d), 7.63 (2H, d), 7.46 (2H, d), 7.23 (2H, d), 2.45 (1H + DMSO, m), 2.15 (2H, d), 1.80 (5H, m), 1.45 (2H, m), 1.13 (2H, m) | 455 |
| 116[3,4] | Sodium (trans-4-{4-[({5-[(2,4,5-trifluorophenyl)amino]-1,3,4-oxadiazol-2-yl}carbonyl)amino]phenyl}cyclohexyl)acetate | 10.24 (1H, s), 8.16 (1H, m), 7.67 (2H, d), 7.15 (2H, d), 7.08 (1H, m), 2.43 (1H + DMSO, m), 1.90-1.60 (7H, m), 1.40 (2H, m), 1.00 (2H, m). | 475 |
| 117 | trans-4-{4-[({5-[(2-fluorophenyl)amino]-1,3,4-oxadiazol-2-yl}carbonyl)amino]phenyl}cyclohexanecarboxylic acid | 12.00 (1H, s), 10.94 (1H, s), 10.76 (1H, s), 8.04 (1H, t), 7.70 (2H, d), 7.35-7.13 (5H, m), 2.50 (1H + DMSO, m), 2.28 (1H, m), 2.00 (2H, m), 1.85 (2h, m), 1.48 (4H, m) | 425 |

[1]Final compound did not require HPLC purification
[2]HPLC Purification used an acidic modifier, 0.2% TFA, in place of 1% ammonia
[3]The crude material was partitioned between EtOAc and saturated aqueous Na₂CO₃ solution. A precipitate was filtered off, dried under vacuum to give title compound.
[4]Prepared from a mixture of methyl and ethyl esters of appropriate starting material via Intermediate 43'.
[5]Reaction carried in EtOH at ambient temperature for 16 hours, then 5 hours at 40° C. Worked up in usual manner. Crude material was then hydrolysed further in THF for 16 hours.
[6]Stirred for 64 hours at ambient temperature.

Example 118

(trans-4-{4-[({5-[(2-Fluorophenyl)amino]-1,3,4-oxadiazol-2-yl}carbonyl)amino]phenyl}cyclohexyl)acetic acid

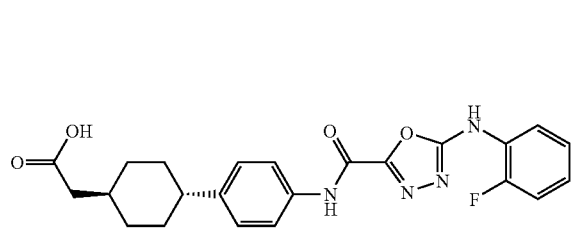

Lithium hydroxide monohydrate (45 mg, 1.06 mmol) was added to a solution of Example 111 (240 mg, 0.53 mmol) in MeOH/H₂O (1:1) (10 mL) and the reaction mixture was stirred for 18 hours. The mixture was then filtered, cooled in an ice bath and acidified to pH 5 with 2M HCl. The resulting precipitate was filtered off and dried under high vacuum to give the title compound as a solid (127 mg, 55%); ¹H NMR δ 11.90 (1H, br.s), 10.85 (s, 1H), 10.69 (1H, s), 7.97 (1H, t), 7.60 (2H, d), 7.30-7.03 (5H, m), 2.38 (1H, m), 2.09 (2H, d), 1.80-1.60 (5H, m), 1.38 (2H, m), 1.04 (2H, m); MS m/e MH⁺ 439.

Example 119

5-[(2-Fluorophenyl)amino]-N-{4-[4-(2-hydroxyethyl)cyclohexyl]phenyl}-1,3,4-oxadiazole-2-carboxamide

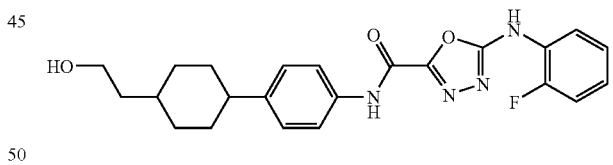

Borane (1 mL of a 1M solution in THF) was added to a stirred solution of (4-{4-[({5-[(2-fluorophenyl)amino]-1,3,4-oxadiazol-2-yl}carbonyl)amino]phenyl}cyclohexyl)acetic acid (Intermediate 45, 79 mg) in THF (2 mL). The reaction mixture was stirred for 16 hours. The mixture was evaporated and the residue dissolved in DCM (10 mL) then washed with brine (10 mL), dried and concentrated in vacuo to give a solid. This solid was purified by HPLC eluting with a gradient of acetonitrile/water containing 0.2% TFA to give the title compound (35 mg) as a solid, a ca. 2:1 trans:cis isomeric mixture; ¹H NMR δ 10.90 (1H, s), 10.72 (1H, s), 8.01 (1H, t), 7.65 (2H, m), 7.33-7.12 (5H, m), 4.28 (1H, m), 3.46 (2H, bs), 2.58-2.40 (1H+ DMSO, m), 1.80 (3H, bs), 1.68-1.50 (4H, m), 1.49-1.31 (3H, m), 1.05 (1H, m); MS m/e MH⁺ 425.

Example 120

N-{4-[trans-4-(2-Amino-2-oxoethyl)cyclohexyl]phenyl}-5-[(3-ethoxyphenyl)amino]-1,3,4-oxadiazole-2-carboxamide

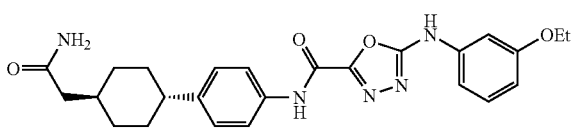

Ammonia (0.06 mL of a 28-30% wt % solution in water) was added to a stirred mixture of (trans-4-{4-[({5-[(3-ethoxyphenyl)amino]-1,3,4-oxadiazol-2-yl}carbonyl)amino]phenyl}cyclohexyl)acetic acid (Example 113, 65 mg), EDAC (32 mg), and HOBt (23 mg) in DMF (1 mL). The mixture was stirred for 16 h then was diluted with DMF (2 mL) and heated to 100° C. for 30 minutes in an Emrys Optimizer™ microwave. The crude mixture was purified directly by HPLC using a gradient of 25-75% acetonitrile/water with 1% ammonia as the eluent to give the title compound (10 mg) as a solid; $^1$H NMR δ 10.82 (2H, bs), 7.68 (2H, d), 7.22 (5H, m), 7.08 (1H, 1H), 6.67 (1H, s), 6.56 (1H, m), 4.00 (2H, quartet), 2.50 (1H+DMSO, m), 1.96 (2H, d), 1.83-1.66 (5H, m), 1.42 (2H, m), 1.33(3H, t), 1.08 (2H, m); MS m/e MH$^+$ 474.

Examples 121-126

The following examples were prepared by the general procedure of Example 105, using the indicated Intermediates as Starting Materials and commercially available isothiocyanates:

Example 127

N-[4-(4-Acetylpiperazin-1-yl)phenyl]-5-[(3-isopropoxyphenyl)amino]-1,3,4-oxadiazole-2-carboxamide

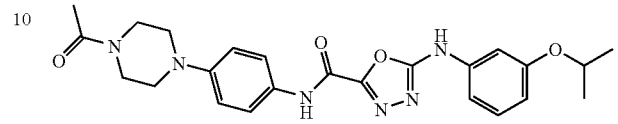

Thiophosgene (46 µL, 0.60 mmol) was added dropwise to a stirred solution of 3-isopropoxy aniline (82 mg, 0.543 mmol) and calcium carbonate (272 mg, 2.72 mmol) in DCM/H$_2$O (1:1) (4 mL). This was stirred at room temperature for 1 h. The phases were separated and the organic layer was dried and concentrated in vacuo. The residue was dissolved in DMF (3 mL) and added to a stirred solution of N-[4-(4-acetylpiperazin-1-yl)phenyl]-2-hydrazino-2-oxoacetamide (Intermediate 21, 100 mg, 0.33 mmol) in DMF at 85° C. This mixture was stirred at 85° C. for 1 h then EDAC (105 mg, 0.54 mmol) was added. The mixture was stirred at 100° C. for a further 1 h then allowed to cool and treated with H$_2$O (10 mL). The resulting precipitate was filtered and washed sequentially with DMSO/MeCN/H$_2$O (7:2:1) (5 mL) and ether (5 mL) to give the title compound as a white solid (12 mg, 8%); $^1$H NMR δ 10.90 (1H, s), 10.82 (s, 1H), 7.67 (2H, d), 7.25 (2H, d), 7.10 (1H, d), 6.97 (2H, d), 6.63 (1H, d), 4.59 (1H, m), 3.58 (4H, br. s), 3.15 (2H, m), 3.09 (2H, m), 2.04 (3H, s), 1.32 (3H, s), 1.30 (3H, s); MS m/e MH$^+$ 465.

| Ex. | SM | Name | $^1$H NMR | MS MH$^+$ |
|---|---|---|---|---|
| 121 | Int. 46 | [(2-fluorophenyl)amino]-N-(3-phenoxypropyl)-1,3,4-oxadiazole-2-carboxamide | 10.68 (1H, s), 9.14 (1H, m), 8.02 (1H, t), 7.30 (4H, m), 7.16 (1H, m), 6.95 (3H, m), 4.03 (2H, t), 3.43 (2H, m), 2.00 (2H, m) | 357 |
| 122 | Int. 46 | 5-[(3-methylphenyl)amino]-N-(3-phenoxypropyl)-1,3,4-oxadiazole-2-carboxamide | 10.75 (1H, s), 9.10 (1H, m), 7.41 (2H, m), 7.28 (3H, m), 6.93 (3H, m), 6.86 (2H, d), 4.03 (2H, t), 3.44 (2H, m), 2.31 (3H, s), 1.99 (2H, m) | 353 |
| 123 | Int. 46 | 5-{[3-(benzyloxy)phenyl]amino}-N-(3-phenoxypropyl)-1,3,4-oxadiazole-2-carboxamide | 10.88 (1H, s), 9.13 (1H, t), 7.53-7.25 (9H, m), 7.13 (1H, d), 6.93 (3H, m), 6.70 (1H, d), 5.10 (2H, s), 4.02 (2H, t), 3.42 (2H, m), 2.00 (2H, m) | 445 |
| 124 | Int. 47 | N-(4-cyclohexylphenyl)-5-[(2-fluorophenyl)amino]-1,3,4-oxadiazole-2-carboxamide | 10.92 (1H, s), 10.73 (1H, s), 8.05 (1H, t), 7.20 (1H, d), 7.37-7.10 (5H, m), 2.50 (1H + DMSO, bs), 1.88-1.67 (5H, m), 1.48-1.17 (5H, m) | 381 |
| 125 | Int. 47 | N-(4-cyclohexylphenyl)-5-[(3,4-difluorophenyl)amino]-1,3,4-oxadiazole-2-carboxamide | 11.25 (1H, s), 10.96 (1H, s), 7.70 (3H, m), 7.49 (1H, m), 7.37 (1H, m), 7.23 (2H, d), 2.50 | 399 |
| 126 | Int. 47 | 5-{[3-(benzyloxy)phenyl]amino}-N-(4-cyclohexylphenyl)-1,3,4-oxadiazole-2-carboxamide | 10.96 (2H, d), 7.70 (2H, d), 7.50-7.26 (7H, m), 7.20 (2H, d), 7.15 (1H, d), 6.23 (1H, d), 5.12 (2H, s), 2.50 (1H + DMSO, bs), 1.88-1.67 (5H, m), 1.48-1.20 (5H, m) | 469 |

Examples 128-129

The following examples were prepared by the general procedure of Example 105 using Intermediate 21 and the appropriate isothiocyanate

Example 128

N-[4-(4-Acetylpiperazin-1-yl)phenyl]-5-{[4-(methylthio)phenyl]amino}-1,3,4-oxadiazole-2-carboxamide

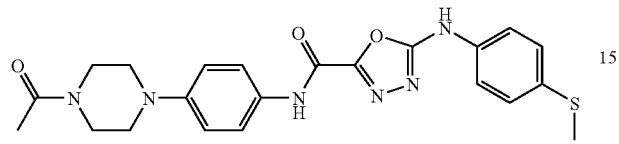

$^1$H NMR δ 10.95 (1H, s), 10.81 (1H, s), 7.66 (2H, d), 7.57 (2H, d), 7.34 (2H, d), 6.97 (2H, d), 3.58 (4H, br. s), 3.28 (3H, s), 3.14 (2H, m), 3.07 (2H, m), 2.05 (3H, s); MS m/e MH$^+$ 453.

Example 129

N-[4-(4-Acetylpiperazin-1-yl)phenyl]-5-[(4-benzyloxyphenyl)amino]-1,3,4-oxadiazole-2-carboxamide

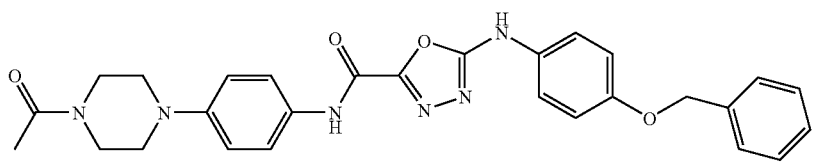

$^1$H NMR at 373 K δ 10.25 (2H, s), 7.62 (2H, d), 7.48 (2H, d), 7.44 (2H, m), 7.39 (2H, t), 7.32 (1H, m), 7.04 (2H, d), 6.94 (2H, d), 5.10 (2H, s), 3.60 (4H, m), 3.15 (4H, m), 2.03 (3H, s); MS m/e MH$^+$ 513.

Example 130

5-[(5-Bromo-2,4-difluorophenyl)amino]-N-(4-morpholin-4-ylphenyl)-1,3,4-oxadiazole-2-carboxamide

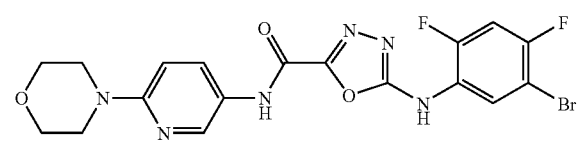

2,4-Difluoro-5-bromoaniline (208 mg, 1.04 mmol) was added to a solution of thiocarbonyldiimidazole (185 mg 1.04 mmol) in DMF (10 mL) and the mixture was stirred for 16 h. 2-Hydrazino-N-(4-morpholin-4-ylphenyl)-2 oxoacetamide (Intermediate 27, 211 mg, 0.8 mmol) was added and the mixture was stirred at 80° C. until a clear solution was obtained. EDAC (306 mg, 1.6 mmol) was added and stirring was continued for a further 1 h. The mixture was cooled then diluted with water (25 mL) and the resulting precipitate was filtered and dried to give the title compound the title compound (135 mg) as a solid;

$^1$H NMR δ 11.09 (1H, s), 10.88 (1H, s), 8.45-8.33 (1H, m), 7.74-7.57 (3H, m), 6.95 (2H, d), 3.83-3.68 (5H, m), 3.15-2.99 (5H, m); MS m/e MH$^+$ 482.

Examples 131-140

The following examples were prepared by the general procedure of Example 130 using either Intermediate 27 (for X=N) or Intermediate 18 (for X=CH) and the appropriate aniline.

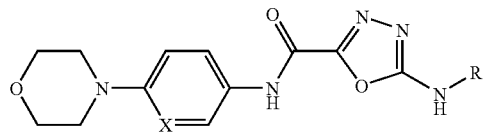
| Example | X | R | ¹H NMR | MS m/e M+H |
|---|---|---|---|---|
| 131 | N | 2,5-difluoro-4-(trifluoromethyl)phenyl | 11.15 (1H, s), 10.95 (1H, s), 8.58-8.48 (2H, m), 7.97-7.90 (1H, dd), 7.78 (1H, t), 6.87 (1H, d), 3.77-3.63 (4H, m), 3.48-3.38 (4H, m) | 471 |
| 132 | N | 3-(trifluoromethyl)phenyl | 11.39 (1H, s), 11.00 (1H, s), 8.52 (1H, d), 8.03 (1H, s), 7.99-7.93 (1H, m), 7.86 (1H, d), 7.65 (1H, t), 7.42 (1H, d), 6.87 (1H, d), 3.77-3.64 (4H, m), 3.52-3.35 (4H, m) | 435 |
| 133 | N | 4-methylpyridin-2-yl | 11.90 (1H, s), 11.00 (1H, s), 8.51 (1H, d), 8.14 (1H, d), 7.95 (1H, d), 7.71 (1H, s), 6.92-6.84 (2H, m), 3.76-3.62 (4H, m), 3.50-3.38 (4H, m), 2.40 (3H, s) | 382 |
| 134 | CH | 4-fluoro-3-(trifluoromethyl)phenyl | 11.25 (1H, s), 10.89 (1H, s), 8.63-8.52 (1H, m), 7.67 (2H, d), 7.60-7.49 (2H, m), 6.95 (2H, d), 3.84-3.66 (4H, m), 3.13-3.04 (4H, m) | 452 |
| 135 | CH | 4-fluoro-3-(trifluoromethyl)phenyl (isomer) | 11.37 (1H, s), 10.89 (1H, s), 8.08-7.98 (1H, m), 7.93-7.84 (1H, m), 7.68 (2H, d), 7.58 (1H, t), 6.95 (2H, d), 3.82-3.70 (4H, m), 3.13-3.04 (4H, m) | 452 |
| 136 | N | 3-isopropoxyphenyl-CH(CH3)- | 10.96 (1H, s), 10.88 (1H, s), 8.53 (1H, d), 7.99-7.91 (1H, m), 7.31-7.20 (2H, m), 7.13-7.07 (1H, m), 6.87 (1H, d), 6.66-6.60 (1H, m), 4.65-4.54 (1H, m), 3.75-3.66 (4H, m), 3.46-3.37 (4H, m), 1.30 (6H, d) | 425 |

-continued

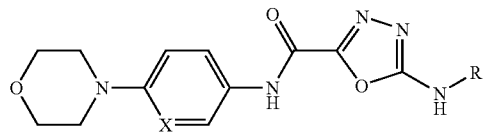

| Example | X | R | ¹H NMR | MS m/e M+H |
|---|---|---|---|---|
| 137 | N | 3-phenoxyphenyl-CH< | 11.10 (1H, s), 10.96 (1H, s), 8.52 (1H, d), 7.98-7.92 (1H, m), 7.45-7.27 (6H, m), 7.18 (1H, t), 7.07 (2H, d), 6.87 (1H, d), 3.74-3.67 (4H, m), 3.45-3.38 (4H, m) | 459 |
| 138 | N | 3-(trifluoromethoxy)phenyl-CH< | 11.36 (1H, s), 11.09 (1H, s), 8.53 (1H, d, J = 10.1Hz), 8.07-8.01 (1H, m), 7.72 (1H, s), 7.59-7.50 (m2H, m), 7.08-6.99 (2H, m), 3.75-3.69 (4H, m), 3.49-3.44 (4H, m) | 451 |
| 139 | N | 3-(pyridin-2-ylmethoxy)phenyl-CH< | 11.05 (1H, s), 10.98 (1H, s), 8.66-8.63 (1H, m), 8.53 (1H, d, 8.05-8.01 (1H, m), 7.99-7.93 (1H, m), 7.62 (1H, d), 7.48-7.44 (1H, m), 7.36 (1H, t), 7.32 (1H, t), 7.21-7.17 (1H, m), 6.99 (1H, d), 6.78-6.73 (1H, m), 5.25 (2H, s), 3.75-3.70 (4H, m), 3.48-3.43 (4H, m) | 474 |
| 140 | N | 3-ethoxyphenyl-CH< | 10.98 (2H, s), 8.52 (1H, d, 7.98-7.93 (1H, m), 7.29 (1H, d), 7.27-7.23 (1H, m), 7.16-7.11 (1H, m), 6.87 (1H, d), 6.67-6.61 (1H, m), 4.04 (2H, q), 3.75-3.67 (4H, m), 3.45-3.38 (4H, m), 1.35 (3H, t) | 411 |

Example 141

N-[4-(4-Acetylpiperazin-1-yl)phenyl]-5-[(3-ethoxyphenyl)amino]-1,3,4-oxadiazole-2-carboxamide

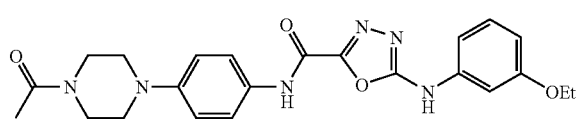

N-[4-(4-Acetylpiperazin-1-yl)phenyl]-2-hydrazino-2-oxoacetamide (Intermediate 21, 153 mg, 0.5 mmol) was added to a solution of O-(pentafluorophenyl) (3-ethoxyphenyl)thiocarbamate (Intermediate 48, 182 mg 0.5 mmol) in DMF (7 mL). The mixture was stirred at 60° C. for 30 min then PS-CDI (500 mg 1.0 mmol) was added and stirring was continued for a further 2 hours. The mixture was allowed to cool then filtered to remove the resin, which was washed with a further 2×10 mL DMF. The combined filtrates were concentrated by evaporation to give a solid that was then triturated with 1:1 acetonitrile:water to give the title compound (220 mg) as a solid; ¹H NMR δ 10.95 (1H, s), 10.85 (1H, s), 7.67 (2H, d), 7.33-7.22 (2H, m), 7.12 (1H, d), 6.97 (2H, d), 6.64 (1H, d), 4.04 (2H, q), 3.65-3.51 (4H, m), 3.11 (4H, d), 2.07 (3H, s), 1.35 (3H, t); MS m/e MH+ 451.

Example 142

5-(Biphenyl-3-ylamino)-N-(6-morpholin-4-ylpyridin-3-yl)-1,3,4-oxadiazole-2-carboxamide

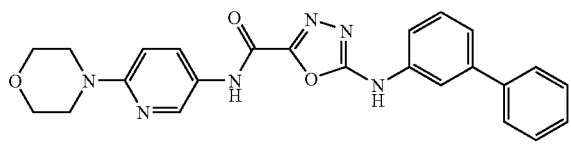

Anisole (0.14 mL, 1.30 mmol) and a mixture of TFA:water (9:1) (3 mL) was added to (5-(biphenyl-3-yl{[2-(trimethylsilyl)ethoxy]methyl}amino)-N-(6-morpholin-4-ylpyridin-3-yl)-N-{[2-(trimethylsilyl)ethoxy]methyl}-1,3,4-oxadiazole-2-carboxamide (Intermediate 49, 180 mg, 0.28 mmol). After 30 minutes the mixture was by diluted with DCM (40 mL) and washed with 1M aqueous NaHCO₃ (20 mL). The DCM layer was separated and MeOH (5 mL) was added. The aqueous was again extracted with MeOH:DCM (1:9) (4×10 mL). DMF (5 mL) was added to the aqueous and the aqueous was extracted with MeOH:DCM (1:9) (2×10 mL). All organics were combined, dried, filtered and evaporated to give a solid which was triturated with hot Et₂O (10 mL) and washed with Et₂O (2×5 mL) then hexane (2×5 mL). Chromatography through silica using 0-100% DCM/EtOAc then 10% MeOH/DCM as eluent gave the title compound (30 mg, 24%) as a solid; ¹H NMR δ 11.10 (1H, s), 10.98 (1H, s), 8.53 (1H, d), 7.99-0.93 (1H, m), 7.91 (1H, s), 77.67-7.61 (3H, m), 7.54-7.47 (3H, m), 7.41 (1H, t), 7.35 (1H, d), 6.88 (1H, d), 3.74-3.69), (4H, m), 3.45-3.40 (4H, m); MS m/e MH+ 443.

Examples 143-147

The following examples were prepared by the general procedure of Example 1 using the indicated Intermediates and commercially available isothiocyanates:

| Ex. | R | Int. | ¹H NMR | MS m/e M+H |
|---|---|---|---|---|
| 143 | 3-(benzyloxy)phenyl | 27 | 11.00 (2H, s), 8.53 (1H, d), 7.99-7.93 (1H, m), 7.51-7.26 (7H, m), 7.19-7.13 (1H, m), 6.87 (1H, d), 6.76-6.72 (1H, m), 5.13 (2H, s), 3.73-.68 (4H, m), 3.44-3.40 (4H, m) | 473 |
| 144 | 3-(ethoxycarbonyl)phenyl | 27 | 11.18 (1H, s), 10.95 (1H, s), 8.52 (1H, d), 8.31-8.26 (1H, m), 7.98-7.93 (1H, m), 7.89-7.85 (1H, m), 7.64 (1H, d), 7.55 (1H, t), 6.87 (1H, d), 4.33 (2H, q), 3.73-3.66 (4H, m), 3.44-3.39 (4H, m), 1.33 (3H, t) | 439 |
| 145 | 3-(tert-butoxycarbonyl)phenyl | 27 | 11.16 (1H, s), 10.97 (1H, s), 8.53 (1H, d), 8.25-8.23 (1H, m 7.98-7.93 (1H, m), 7.84-7.81 (1H, m), 7.60 (1H, d), 7.51 (1H, t), 6.87 (1H, d), 3.73-3.68 (4H, m), 3.44-3.39 (4H, m), 1.56 (9H, s) | 467 |

-continued

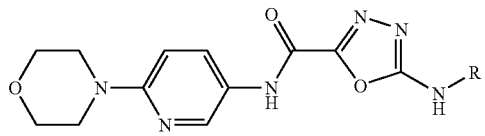

| Ex. | R | Int. | ¹H NMR | MS m/e M+H |
|---|---|---|---|---|
| 146 | (3-iodophenyl) | 27 | 11.14 (1H, s), 10.98 (1H, s), 8.52 (1H, d), 8.02 (1H, t), 7.98-7.93 (1H, m), 7.62-7.57 (1H, m), 7.42 (1H, d), 7.20 (1H, t), 6.87 (1H, d), 3.74-3.68 (4H, m), 3.45-3.38 (4H, m) | 493 |

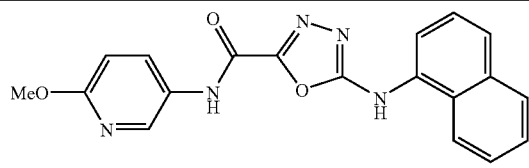

| Example | SM | ¹H NMR | MS m/e M+H |
|---|---|---|---|
| 147 | Int. 58 | 11.07 (1H, s), 10.76 (1H, s), 8.59-8.57 (1H, m), 8.24-8.20 (1H, m), 8.10-7.90 (3H, m), 7.75 (1H, d), 7.60-7.50 (3H, m), 6.8 (1H, d), 3.8 (3H, s) | 362 |

Examples 148-296

The following examples were prepared by the general procedure of Example 1, using the indicated Intermediate as starting material (SM) in conjunction with the appropriate commercially available isothiocyanate.

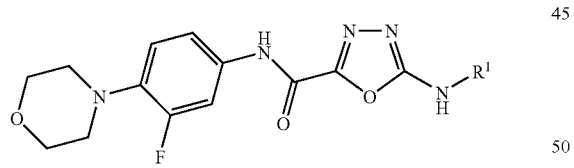

Starting material=Intermediate 24:

| Example | R¹ | ¹H NMR δ | MS m/e MH⁺ |
|---|---|---|---|
| 148 | (4-fluorophenyl) | 11.07 (1H, s), 11.03 (1H, brs), 7.71-7.55 (4H, m), 7.28-7.21 (2H, m), 7.05 (1H, t), 3.77-3.72 (4H, m), 3.01-2.97 (4H, m) | 402 |

-continued
| Example | R¹ | ¹H NMR δ | MS m/e MH⁺ |
|---|---|---|---|
| 149 | 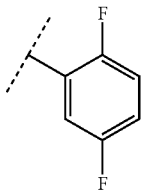 | 11.12 (2H, s), 8.03-7.97 (1H, m), 7.68 (1H, dd), 7.57 (1H, dd), 7.37 (1H, ddd), 7.06 (1H, t), 7.01-6.94 (1H, m), 3.77-3.73 (4H, m), 3.02-2.97 (4H, m) | 420 |
| 150 | 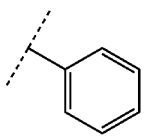 | 11.07 (1H, s), 11.07 (1H, br s), 7.71-7.55 (4H, m), 7.43-7.37 (2H, m), 7.10-7.03 (2H, m), 3.77-3.73 (4H, m), 3.01-2.97 (4H, m) | 384 |
| 151 | 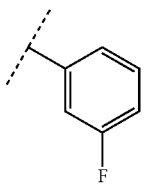 | 11.25 (1H, brs), 11.10 (1H, s), 7.68 (1H, dd), 7.59-7.50 (2H, m), 7.47-7.40 (1H, m), 7.38-7.34 (1H, m), 7.06 (1H, t), 6.89 (1H, td), 3.77-3.72 (4H, m), 3.02-2.97 (4H, m) | 402 |
| 152 | 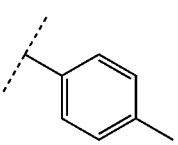 | 11.03 (1H, s), 10.22 (1H, br s), 7.75-7.64 (2H, m), 7.56 (1H, dd), 7.28-7.23 (2H, m), 7.13-7.02 (2H, m), 3.77-3.72 (4H, m), 3.01-2.96 (4H, m), 2.30 (3H, s) | 398 |
| 153 | 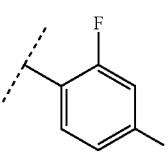 | 11.07 (1H, s), 11.07 (1H, br s), 8.06-7.95 (1H, m), 7.67 (1H, dd), 7.56 (1H, dd), 7.43-7.36 (1H, m), 7.22-7.15 (1H, m), 7.05 (1H, t), 3.77-3.72 (4H, m), 3.02-2.96 (4H, m) | 420 |
| 154 | 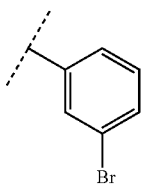 | 11.10 (2H, brs), 7.89-7.86 (1H, m), 7.68 (1H, dd), 7.59-7.55 (2H, m), 7.36 (1H, t), 7.28-7.23 (1H, m), 7.06 (1H, t), 3.77-3.72 (4H, m), 3.02-2.96 (4H, m) | 462 and 464 |
| 155 | 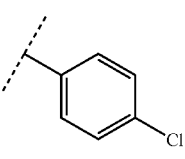 | 11.07 (2H, br s), 7.71-7.60 (3H, m), 7.57 (1H, dd), 7.49-7.44 (2H, m), 7.05 (1H, t), 3.77-3.72 (4H, m), 3.01-2.97 (4H, m) | 418 and 420 |
| 156 | 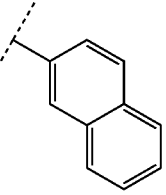 | 11.09 (2H, br s), 8.21 (1H, d), 7.95 (1H, d), 7.87 (2H, dd), 7.73-7.63 (2H, m), 7.58 (1H, dd), 7.54-7.48 (1H, m), 7.42 (1H, dd), 7.07 (1H, t), 3.78-3.73 (4H, m), 3.02-2.97 (4H, m) | 434 |

-continued

| Example | R¹ | ¹H NMR δ | MS m/e MH⁺ |
|---|---|---|---|
| 157 | 3,4-difluorophenyl | 11.09 (2H, s), 7.92-7.86 (1H, m), 7.68 (1H, dd), 7.56 (1H, dd), 7.31-7.24 (1H, m), 7.22-7.14 (1H, m), 7.06 (1H, t), 3.77-3.72 (4H, m), 3.01-2.97 (4H, m) | 420 |
| 158 | 2,3-difluorophenyl | 11.25 (1H, brs), 11.25 (1H, s), 7.73-7.65 (2H, m), 7.57 (1H, dd), 7.52-7.44 (1H, m), 7.37-7.32 (1H, m), 7.05 (1H, t), 3.77-3.72 (4H, m), 3.02-2.97 (4H, m) | 420 |
| 159 | 3-(CO₂Et)phenyl | 11.21 (1H, br s), 11.09 (1H, s), 8.29-8.26 (1H, m), 7.87 (1H, ddd), 7.72-7.63 (2H, m), 7.59-7.53 (2H, m), 7.06 (1H, t), 4.35 (2H, q), 3.77-3.72 (4H, m), 3.02-2.96 (4H, m), 1.34 (3H, t) | 456 |

Starting material=Intermediate 28:

| Example | R² | MS m/e MH⁺ |
|---|---|---|
| 160 | 4-fluorophenyl | 419 |
| 161 | 2-methylphenyl | 415 |
| 162 | 3-chlorophenyl | 435 |
| 163 | 2-methoxyphenyl | 431 |
| 164 | 4-methoxyphenyl | 431 |
| 165 | 2,5-difluorophenyl | 437 |
| 166 | phenyl | 401 |

-continued
| Example | R² | MS m/e MH⁺ |
|---|---|---|
| 167 | 3-bromophenyl | 479 and 481 |
| 168 | 3-fluorophenyl | 419 |
| 169 | 4-methylphenyl | 415 |
| 170 | 2,6-difluorophenyl | 437 |
| 171 | 2-chlorophenyl | 435 |
| 172 | 4-chlorophenyl | 435 |
| 173 | 2-naphthyl | 451 |
-continued
| Example | R² | MS m/e MH⁺ |
|---|---|---|
| 174 | 3-methoxyphenyl | 431 |
| 175 | 4-tert-butylphenyl | 457 |
| 176 | 2,3-difluorophenyl | 437 |
| 177 | 3-(ethoxycarbonyl)phenyl | 473 |
| 178 | 1-naphthyl | 451 |
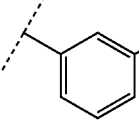
Starting material=Intermediate 59
| Example | R¹ | ¹H NMR δ | MS m/e MH⁺ |
|---|---|---|---|
| 179 | 3-methylphenyl | 10.85 (1H, br s), 10.77 (1H, s), 7.63 (2H, d), 7.45-7.35 (2H, m), 7.25 (1H, t), 6.96-6.82 (3H, m), 3.74-3.61 (2H, m), 3.58-3.49 (2H, m), 2.31 (3H, s), 2.23 (2H, t), 1.14 (6H, d) | 408 |

| Example | R¹ | ¹H NMR δ | MS m/e MH⁺ |
|---|---|---|---|
| 180 | 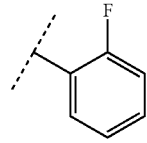 3,4-difluorophenyl | 11.20 (1H, br s), 10.81 (1H, s), 7.73-7.59 (3H, m), 7.51-7.39 (1H, m)7.36-7.28 (1H, m), 6.92 (2H, d), 3.74-3.62 (2H, m), 3.57-3.49 (2H, m), 2.23 (2H, t), 1.14 (6H, d) | 430 |
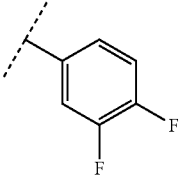
Starting material=Intermediate 60:
| Example | R² | ¹H NMR δ | MS m/e MH⁺ |
|---|---|---|---|
| 181 | 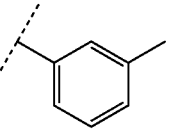 2-fluorophenyl | 10.69 (2H, s), 8.02 (1H, t), 7.56 (2H, dd), 7.33-7.09 (3H, m), 6.72 (2H, dd), 3.68-3.45 (6H, m), 3.35-3.24 (2H, m), 1.98-1.72 (5H, m) | 4.39 |
| 182 | 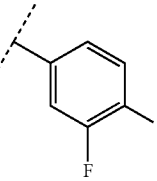 3-methylphenyl | 10.80 (1H, s), 10.66 (1H, s), 7.57 (2H, dd), 7.44-7.34 (2H, m), 7.23 (1H, t), 6.86 (1H, d), 6.72 (2H, dd), 3.68-3.45 (6H, m), 3.35-3.23 (2H, m), 2.30 (3H, s), 1.98-1.72 (5H, m) | 435 |
| 183 | 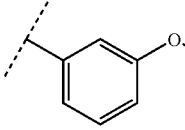 3,4-difluorophenyl | 11.17 (1H, s), 11.17 (1H, s), 7.68 (1H, ddd), 7.57 (2H, dd), 7.52-7.39 (1H, m), 7.36-7.28 (1H, m), 6.72 (2H, dd), 3.68-3.44 (6H, m), 3.35-3.23 (2H, m), 1.98-1.72 (5H, m) | 457 |
| 184 | 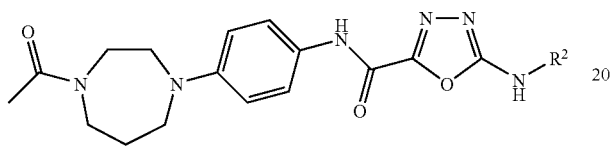 3-(phenylmethoxy)phenyl | 10.91 (1H, s), 10.68 (1H, s), 7.57 (2H, dd), 7.48-7.23 (7H, m), 7.16-7.10 (1H, m), 6.76-6.68 (3H, m), 5.09 (2H, s), 3.68-3.45 (6H, m), 3.35-3.24 (2H, m), 1.98-1.73 (5H, m) | 527 |
| 185 | 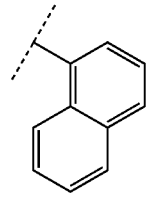 1-naphthyl | 10.71 (1H, s), 10.69 (1H, s), 8.30-8.24 (1H, m), 8.03-7.95 (2H, m), 7.75 (1H, d), 7.65-7.50 (5H, m), 6.73 (2H, d), 3.70-3.47 (6H, m), 3.37-3.25 (2H, m), 1.98-1.73 (5H, m) | 471 |

| Example | R² | ¹H NMR δ | MS m/e MH⁺ |
|---|---|---|---|
| 186 | 2,4,5-trifluorophenylmethyl | 10.99 (1H, s), 10.71 (1H, s), 8.21-8.09 (1H, m), 7.75-7.63 (1H, m), 7.65 (2H, dd), 6.72 (2H, dd), 3.68-3.46 (6H, m), 3.35-3.25 (2H, m), 1.98-1.74 (5H, m) | 475 |
| 187 | 2,5-difluorophenylmethyl | 11.02 (1H, s), 10.73 (1H, s), 8.02-7.93 (1H, m), 7.57 (2H, dd), 7.35 (1H, ddd), 6.98-6.90 (1H, m), 6.74 (2H, dd), 3.69-3.44 (6H, m), 3.34-3.25 (2H, m), 1.98-1.75 (5H, m) | 457 |

Example 189

| Example | SM | ¹H NMR δ | MS m/e MH⁺ |
|---|---|---|---|
| 188 | Int. 61 | 11.01 (1H, s), 10.96 (1H, s), 8.70 (2H, s), 7.48-7.23 (7H, m), 7.17-7.11 (1H, m), 6.72 (1H, dd), 5.09 (2H, s), 3.79-3.64 (4H, m), 3.55-3.47 (4H, m), 2.03 (3H, s) | 515 |
| 189 | Int. 62 | 11.15 (1H, s), 10.72 (1H, s), 8.38 (1H, s), 8.22 (1H, d), 7.99-7.90 (3H, m), 7.78 (1H, d), 7.70 (1H, d), 7.55-7.45 (3H, m), 2.72 (3H, s). | 402 |

Starting material=Intermediate 32

| Example | R² | ¹H NMR δ | MS m/e MH⁺ |
|---|---|---|---|
| 190 | 4-fluorophenylmethyl | 10.97 (1H, s), 10.92 (1H, s), 8.5 (1H, s), 7.95 (1H, d), 7.65-7.55 (2H, m), 7.20(2H, t), 6.95 (1H, d), 3.60 (6H, m), 3.30-3.20 (2H, m), 2.00 (3H, s) | 426 |
| 191 | 3-chlorophenylmethyl | 11.20 (1H, s), 10.80 (1H, s), 8.5 (1H, s), 7.95 (1H, d), 7.70 (1H, s), 7.50 (1H, d), 7.40(1H, t), 7.10 (1H, d), 6.95 (1H, d), 3.60 (6H, m), 3.50-3.40 (2H, m), 2.00 (3H, s) | 442 |

-continued

| Example | R² | ¹H NMR δ | MS m/e MH⁺ |
|---|---|---|---|
| 192 | 2,5-difluorophenyl | 11.07 (1H, s), 10.97 (1H, s), 8.5 (1H, s), 8.01-7.95 (2H, m), 7.40-7.30 (1H, m), 7.00-6.95 (1H, m), 6.95 (1H, d), 3.60 (6H, m), 3.50-3.40 (2H, m), 2.00 (3H, s) | 444 |
| 193 | phenyl | 10.95-10.91 (2H, d), 8.5 (1H, s), 7.95 (1H, d), 7.60 (2H, d), 7.40 (1H, t), 7.05 (1H, t), 6.95 (1H, d), 3.60 (6H, m), 3.50-3.40 (2H, m), 2.00 (3H, s) | 408 |
| 194 | 3-bromophenyl | 11.17 (1H, s), 10.97 (1H, s), 8.5 (1H, s), 7.95 (1H, d), 7.90 (1H, s), 7.65 (1H, d), 7.35 (1H, t), 7.20 (1H, d), 6.95 (1H, d), 3.60 (6H, m), 3.50-3.40 (2H, m), 2.00 (3H, s) | 488 |
| 195 | 3-fluorophenyl | 11.21 (1H, s), 10.97 (1H, s), 8.5 (1H, s), 7.95 (1H, d), 7.55-7.30 (3H, m), 6.95 (2H, d), 3.60 (6H, m), 3.50-3.40 (2H, m), 2.00 (3H, s) | 426 |
| 196 | 4-methylphenyl | 10.90 (1H, s), 10.81 (1H, s), 8.5 (1H, s), 7.95 (1H, d), 7.45 (2H, d), 7.20 (2H, d), 6.95 (1H, d), 3.60 (6H, m), 3.50-3.40 (2H, m), 2.20 (3H, s), 2.00 (3H, s) | 422 |
| 197 | 2-chlorophenyl | 10.92 (1H, d), 10.38 (1H, s), 8.5 (1H, s), 7.95-7.90 (2H, m), 7.55 (1H, d), 7.40 (1H, t), 7.20 (1H, t), 6.95 (1H, d), 3.60 (6H, m), 3.50-3.40 (2H, m), 2.00 (3H, s) | 442 |
| 198 | 4-chlorophenyl | 11.10 (1H, s), 10.93 (1H, s), 8.5 (1H, s), 7.95 (1H, d), 7.60 (2H, d), 7.40 (2H, d), 6.95 (1H, d), 3.60 (6H, m), 3.50-3.40 (2H, m), 2.00 (3H, s) | 442 |
| 199 | 2-naphthyl | 11.18 (1H, s), 10.95 (1H, s), 8.5 (1H, s), 8.20 (1H, s), 8.0-7.90 (2H, m), 7.80 (2H, d), 7.65 (1H, d), 7.50 (1H, t), 7.40 (1H, t), 6.95 (1H, d), 3.60 (6H, m), 3.50-3.40 (2H, m), 2.00 (3H, s) | 458 |
| 200 | 2-pyridyl |  | 409 |

-continued

| Example | R² | ¹H NMR δ | MS m/e MH⁺ |
|---|---|---|---|
| 201 | 4-(ethoxycarbonyl)phenyl | 11.40 (1H, s), 10.97 (1H, s), 8.5 (1H, s), 8.0-7.95 (3H, t), 7.70 (2H, d), 6.95 (1H, d), 4.30 (2H, q), 3.60 (6H, m), 3.50-3.40 (2H, m), 2.00 (3H, s), 1.30 (3H, t) | 480 |
| 202 | benzo[1,3]dioxol-5-yl | 10.90 (1H, s), 10.79 (1H, s), 8.5 (1H, s), 7.95 (1H, t), 7.20 (1H, s), 7.05-6.95 (3H, m), 6.0 (2H, s), 3.60 (6H, m), 3.50-3.40 (2H, m), 2.00 (3H, s) | 452 |
| 203 | 2,4-difluorophenyl | 10.92 (1H, s), 10.71 (1H, s), 8.5 (1H, s), 8.01-7.90 (2H, m), 7.40 (1H, t), 7.20 (1H, t), 6.95 (1H, d), 3.60 (6H, m), 3.30-3.20 (2H, m), 2.00 (3H, s) | 444 |
| 204 | 3-(ethoxycarbonyl)phenyl | 11.17 (1H, s), 10.94 (1H, s), 8.50 (1H, s), 8.25 (1H, s), 7.95 (1H, d), 7.85 (1H, d), 7.65 (1H, d), 7.50 (1H, t), 6.95 (1H, d), 4.30 (2H, q), 3.60 (6H, m), 3.50-3.40 (2H, m), 2.00 (3H, s), 1.30 (3H, t) | 480 |
| 205 | 4-tert-butylphenyl | 10.90 (1H, s), 10.81 (1H, s), 8.5 (1H, s), 7.95 (1H, d), 7.45 (2H, d), 7.40 (2H, d), 6.95 (1H, d), 3.60 (6H, m), 3.50-3.40 (2H, m), 2.00 (3H, s), 1.15 (9H, s) | 464 |
| 206 | 3,4-difluorophenyl | 11.20 (1H, s), 10.95 (1H, s), 8.5 (1H, s), 7.95 (1H, d), 7.70-7.60 (1H, m), 7.45 (1H, q), 7.40-7.30 (1H, m), 6.95 (1H, d), 3.60 (6H, m), 3.50-3.40 (2H, m), 2.00 (3H, s) | 444 |
| 207 | 2,3-difluorophenyl | 11.05 (1H, s), 10.95 (1H, s), 8.5 (1H, s), 7.95 (1H, d), 7.90 (1H, d), 7.30 (1H, q), 7.20 (1H, q), 6.95 (1H, d), 3.60 (6H, m), 3.50-3.40 (2H, m), 2.00 (3H, s) | 444 |
| 208 | 3-methylphenyl | 10.90 (1H, s), 10.85 (1H, s), 8.5 (1H, s), 7.95 (1H, d), 7.45 (1H, d), 7.39 (1H, s), 7.25 (1H, t), 6.95 (1H, d), 3.60 (6H, m), 3.50-3.40 (2H, m), 2.30 (3H, s), 2.00 (3H, s) | 422 |

-continued
| Example | R² | ¹H NMR δ | MS m/e MH⁺ |
|---|---|---|---|
| 209 | 3-(benzyloxy)phenyl | 10.95 (1H, s), 10.93 (1H, s), 8.5 (1H, s), 7.95 (1H, d), 7.45-7.25 (7H, m), 7.15 (1H, d), 6.95 (1H, d), 6.85 (1H, d), 5.10 (2H, s), 3.60 (6H, m), 3.50-3.40 (2H, m), 2.00 (3H, s) | 514 |
| 210 | 3,5-difluorophenyl | 11.45 (1H, s), 10.98 (1H, s), 8.5 (1H, s), 7.95 (1H, d), 7.30 (2H, d), 6.95 (2H, t), 3.60 (6H, m), 3.50-3.40 (2H, m), 2.00 (3H, s) | 444 |
| 211 | naphthalen-1-yl | 10.93 (1H, s), 10.75 (1H, s), 8.5 (1H, s), 8.30-8.20(1H, m), 8.0-7.90 (3H, m), 7.80 (1H, d), 7.60-7.50 (3H, m), 6.95 (1H, d), 3.60 (6H, m), 3.50-3.40 (2H, m), 2.00 (3H, s) | 458 |
| 212 | 3,4,5-trifluorophenyl | 11.04 (1H, s), 10.96 (1H, s), 8.5 (1H, s), 8.20-8.10 (1H, m), 7.95 (1H, d), 7.7 (1H, q), 6.95 (2H, t), 3.60 (6H, m), 3.50-3.40 (2H, m), 2.00 (3H, s) | 462 |
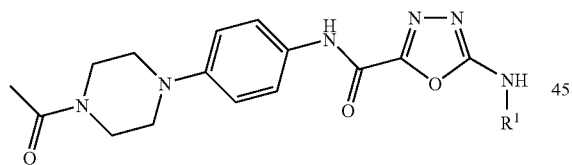
Starting material=Intermediate 21
| Example | R¹ | ¹H NMR δ | MS m/e MH⁺ |
|---|---|---|---|
| 213 | 4-fluorophenyl | 10.95 (1H, s), 10.80 (1H, s), 8.7-8.5 (4H, m), 7.20 (2H, t), 6.95 (2H, d), 3.60 (4H, s), 3.10 (4H, d), 2.00 (3H, s) | 425 |
| 214 | 3-chlorophenyl | 11.18 (1H, s), 10.84 (1H, s), 7.70 (1H, s), 7.60 (2H, d), 7.50 (1H, d), 7.40 (1H, t), 7.10 (1H, d), 6.95 (1H, d), 3.60 (4H, s), 3.10 (4H, d), 2.00 (3H, s) | 441 |

-continued
| Example | R¹ | ¹H NMR δ | MS m/e MH⁺ |
|---|---|---|---|
| 215 | 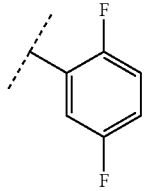 | 10.85(1H, s), 8.05-7.95 (1H, m), 7.65 (2H, d), 7.40-7.30 (1H, m), 6.95 (3H, d), 3.60 (4H, s), 3.10 (4H, d), 2.00 (3H, s) | 443 |
| 216 | 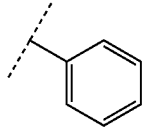 | 10.91 (2H, d), 10.80 (1H, s), 8.65-8.55 (4H, m), 7.40 (2H, t), 7.05 (1H, t), 6.95 (2H, d), 3.60 (4H, s), 3.10 (4H, d), 2.00 (3H, s) | 407 |
| 217 | 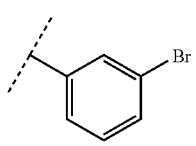 | 11.17 (1H, s), 10.83 (1H, s), 7.85 (1H, s), 7.65 (2H, d), 7.55 (1H, d), 7.35(1H, t), 7.20 (1H, d), 6.95 (2H, d), 3.60 (4H, s), 3.10 (4H, d), 2.00 (3H, s) | 487 |
| 218 | 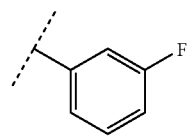 | 11.21 (1H, s), 10.83 (1H, s), 7.65 (2H, d), 7.55-7.30 (3H, m), 6.95 (2H, d), 6.90-6.80 (1H, m), 3.60 (4H, s), 3.10 (4H, d), 2.00 (3H, s) | 425 |
| 219 | 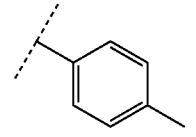 | 10.79 (1H, s), 10.77 (1H, s), 7.65 (2H, d), 7.45 (2H, d), 7.20(2H, d), 6.95 (2H, d), 3.60 (4H, s), 3.10 (4H, d), 2.20 (3H, s), 2.00 (3H, s) | 421 |
| 220 | 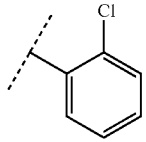 | 10.80 (1H, d), 10.34 (1H, s), 7.95 (1H, d), 7.65 (2H, d), 7.55 (1H, d), 7.40 (1H, t), 7.20 (1H, t), 6.95 (2H, d), 3.60 (4H, s), 3.10 (4H, d), 2.00 (3H, s) | 441 |
| 221 | 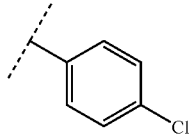 | 11.10 (1H, s), 10.84 (1H, s), 7.65-7.55 (4H, m), 7.40 (2H, d), 6.95 (2H, d), 3.60 (4H, s), 3.10 (4H, d), 2.00 (3H, s) | 441 |
| 222 | 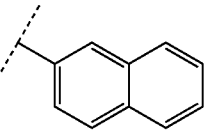 | 11.15 (1H, s), 10.82 (1H, s), 8.20 (1H, s), 7.95 (1H, d), 7.85 (2H, d), 7.70-7.60 (3H, m), 7.50 (1H, t), 7.40 (1H, t), 6.95 (2H, d), 3.60 (4H, s), 3.10 (4H, d), 2.00 (3H, s) | 457 |
| 223 | 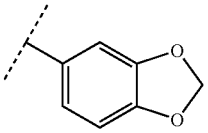 | 10.77 (1H, s), 7.65 (2H, d), 7.20 (1H, s), 7.05-6.95 (4H, m), 6.0 (2H, s), 3.60 (4H, s), 3.10 (4H, d), 2.00 (3H, s) | 451 |
| 224 | 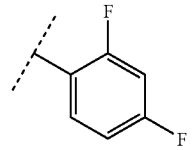 | 10.80 (1H, s), 10.65 (1H, s), 8.01-7.95 (1H, m), 7.60 (2H, d), 7.40 (1H, t), 7.20(1H, t), 6.95 (2H, d), 3.60 (4H, s), 3.10 (4H, d), 2.00 (3H, s) | 443 |

| Example | R¹ | ¹H NMR δ | MS m/e MH⁺ |
|---|---|---|---|
| 225 | ethyl 3-benzoate group | 11.17(1H, s), 10.94 (1H, s), 8.30(1H, s), 7.90 (1H, d), 7.80 (3H, t), 7.50 (1H, t), 6.95 (2H, d), 4.30 (2H, q), 3.60 (4H, s), 3.10 (4H, d), 2.00 (3H, s), 1.30 (3H, t) | 479 |
| 226 | 4-tert-butylphenyl | 10.79 (1H, s), 10.77 (1H, s), 7.65 (2H, d), 7.50 (2H, d), 7.40(2H, d), 6.95 (2H, d), 3.60 (4H, s), 3.10 (4H, d), 2.00 (3H, s), 1.20 (9H, s) | 463 |
| 227 | 3,4-difluorophenyl | 11.20 (1H, s), 10.83 (1H, s), 7.70-7.60 (3H, m), 7.45(1H, q), 7.40-7.30 (1H, m), 6.95 (2H, d), 3.60 (4H, s), 3.10 (4H, d), 2.00 (3H, s) | 443 |
| 228 | 2,3-difluorophenyl | 10.83 (1H, s), 7.95 (1H, t), 7.60 (1H, d), 7.20 (2H, q), 7.10 (1H, q), 6.95 (2H, d), 3.60 (4H, s), 3.10 (4H, d), 2.00 (3H, s) | 443 |
| 229 | 3-(benzyloxy)phenyl | 10.93 (1H, s), 10.80 (1H, s), 7.60 (2H, d), 7.50-7.25 (7H, m), 7.15 (1H, d), 6.95 (2H, d), 6.85 (1H, d), 5.10 (2H, t), 3.60 (4H, s), 3.10 (4H, m), 2.00 (3H, s) | 513 |
| 230 | 3,5-difluorophenyl | 11.45 (1H, s), 10.85 (1H, s), 7.65 (2H, d), 7.30 (2H, d), 7.0-6.90 (3H, m), 3.60 (4H, s), 3.10 (4H, d), 2.00 (3H, s) | 443 |
| 231 | 2,3,5-trifluorophenyl | 11.00 (1H, s), 10.84 (1H, s), 8.20-8.10 (1H, m), 7.75-7.60 (3H, m), 6.95 (2H, d), 3.60 (4H, s), 3.10 (4H, m), 2.00 (3H, s) | 461 |
| 232 | 3-methoxyphenyl | 10.90 (1H, s), 10.78 (1H, s), 7.65 (2H, d), 7.30-7.20 (2H, m), 7.10 (1H, t), 6.95 (2H, d), 6.60 (1H, d), 3.75 (3H, s), 3.60 (4H, s), 3.10 (4H, d), 2.00 (3H, s) | 437 |

| Example | R¹ | ¹H NMR δ | MS m/e MH⁺ |
|---|---|---|---|
| 233 | 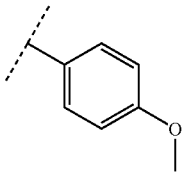 | 10.76 (1H, s), 10.68 (1H, s), 7.65 (2H, d), 7.45 (2H, d), 7.00-6.95 (4H, m), 3.70 (3H, s), 3.60 (4H, s), 3.10 (4H, d), 2.00 (3H, s) | 437 |
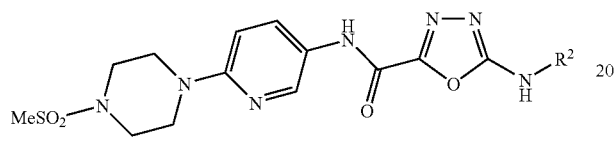
Starting material=Intermediate 63
| Example | R² | ¹H NMR δ | MS m/e MH⁺ |
|---|---|---|---|
| 234 | 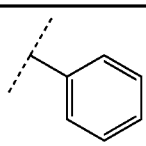 | 10.97 (1H, s), 10.93 (1H, s), 8.50 (1H, s), 8.00 (1H, d), 7.60 (2H, d), 7.40(2H, t), 7.05 (1 h, t), 6.95 (1H, d), 3.60-3.50 (4H, m), 3.10-3.05 (4H, m), 2.80 (3H, s) | 444 |
| 235 | 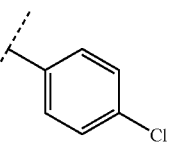 | 11.15 (1H, s), 10.95 (1H, s), 8.50 (1H, s), 8.00 (1H, d), 7.60 (2H, d), 7.40 (2H, t), 6.95 (1H, d), 3.60-3.55 (4H, m), 3.10-3.05 (4H, m), 2.85 (3H, s) | 478 |
| 236 | 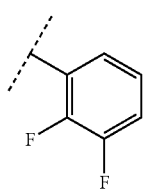 | 11.05 (1H, s), 10.95 (1H, s), 8.50 (1H, s), 8.00 (1H, d), 7.90 (1H, t), 7.30-7.10 (2H, m), 6.95 (1H, d), 3.60-3.55 (4H, m), 3.10-3.05 (4H, m), 2.85 (3H, s) | 480 |
| 237 | 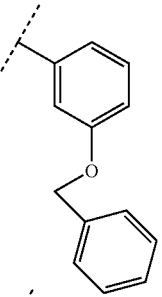 | 10.94 (1H, s), 8.50 (1H, s), 7.95 (1H, d), 7.60 (1H, d), 7.50-7.30 (7H, m), 7.10 (1H, d), 6.95 (1H, d), 6.7 (1H, d), 3.60-3.55 (4H, m), 3.10-3.05 (4H, m), 2.85 (3H, s) | 550 |
| 238 | 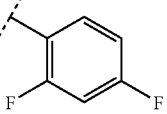 | 10.95 (1H, s), 10.70 (1H, s), 8.50 (1H, s), 8.00-7.90 (2H, m), 7.40-7.30 (1H, m), 7.20-7.10 (1H, m), 6.95 (1H, d), 3.60-3.55 (4H, m), 3.20-3.10 (4H, m), 2.85 (3H, s) | 480 |

-continued
| Example | R² | ¹H NMR δ | MS m/e MH⁺ |
|---|---|---|---|
| 239 | 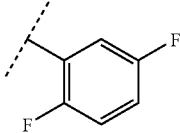 | 11.07 (1H, s), 11.00 (1H, s), 8.50 (1H, s), 8.00-7.90 (2H, m), 7.40-7.30 (1H, m), 7.00-6.95 (2H, m), 3.60-3.55 (4H, m), 3.20-3.10 (4H, m), 2.85 (3H, s) | 480 |
| 240 | 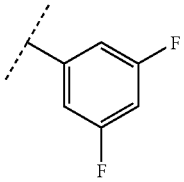 | 11.45 (1H, s), 11.00 (1H, s), 8.50 (1H, s), 8.00 (1H, d), 7.30 (2H, d), 7.0-6.95 (2H, m), 3.60-3.55 (4H, m), 3.20-3.10 (4H, m), 2.85 (3H, s) | 480 |
| 241 | 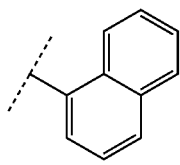 | 10.97 (1H, s), 10.75 (1H, s), 8.50 (1H, s), 8.30-8.20 (1H, m), 8.00-7.90 (3H, m), 7.80 (2H, d), 7.60-7.50 (3H, m), 6.95 (1H, d), 3.60-3.50 (4H, m), 3.10-3.05 (4H, m), 2.85 (3H, s) | 494 |
| 242 | 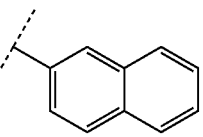 | 11.18 (1H, s), 10.98 (1H, s), 8.50 (1H, s), 8.20 (1H, s), 8.00 (1H, d), 7.95 (1H, d), 7.80 (2H, d), 7.60 (1H, d), 7.5 (1H, t), 7.40 (1H, t), 6.95 (1H, d), 3.60-3.50 (4H, m), 3.10-3.05 (4H, m), 2.85 (3H, s) | 494 |
| 243 | 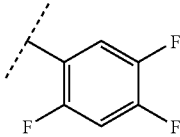 | 11.04 (1H, s), 10.98 (1H, s), 8.50 (1H, s), 8.10-8.00 (1H, m), 7.95 (1H, d), 7.70 (1H, q), 6.95 (1H, d), 3.60-3.55 (4H, m), 3.20-3.10 (4H, m), 2.85 (3H, s) | 498 |
| 244 | 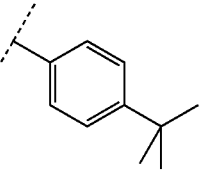 | 10.94 (1H, s), 10.81 (1H, s), 8.50 (1H, s), 8.00 (1H, d), 7.50 (2H, d), 7.40 (2H, t), 6.95 (1H, d), 3.60-3.50 (4H, m), 3.20-3.10 (4H, m), 2.85 (3H, s), 1.20 (9H, m) | 500 |
| 245 | 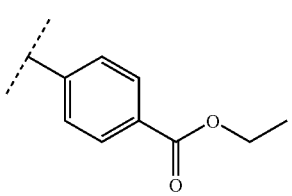 | 11.17 (1H, s), 10.97 (1H, s), 8.50 (1H, s), 8.25 (1H, s), 8.00 (1H, d), 7.85 (1H, d), 7.60 (1H, d), 7.50 (1H, t), 6.95 (1H, d), 4.30 (2H, q), 3.60-3.50 (4H, m), 3.20-3.10 (4H, m), 2.85 (3H, s), 1.30 (3H, t) | 516 |
| 246 | 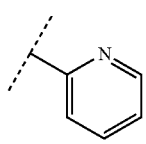 | No nmr data | 445 |
| 247 | 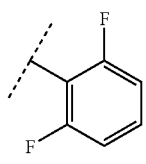 | 10.91 (1H, s), 8.50 (1H, s), 7.90 (1H, d), 7.55-7.45 (1H, m), 7.25 (1H, t), 6.95 (1H, d), 3.60-3.55 (4H, m), 3.20-3.10 (4H, m), 2.85 (3H, s) | 480 |

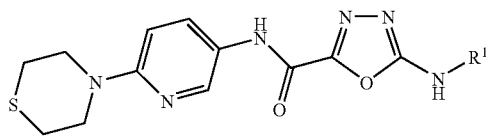
Starting material=Intermediate 64
| Example | R¹ | ¹H NMR δ | MS m/e MH⁺ |
|---|---|---|---|
| 248 | phenyl | 10.93 (1H, s), 10.88 (1H, s), 8.50 (1H, s), 7.90 (1H, d), 7.60 (2H, d), 7.40 (2H, t), 7.05 (1H, t), 6.95 (1H, d), 3.90-3.80 (4H, m), 2.60-2.50 (4H, m) | 383 |
| 249 | 2-methylphenyl | 10.85 (1H, s), 9.95 (1H, s), 8.50 (1H, s), 7.90 (1H, d), 7.70 (1H, d), 7.25-7.2 (2H, m), 7.05 (1H, t), 6.90 (1H, d), 3.90-3.80 (4H, m), 2.60-2.50 (4H, m), 2.3 (3H, s) | 397 |
| 250 | 4-methylphenyl | 10.86 (1H, s), 10.80 (1H, s), 8.50 (1H, s), 7.90 (1H, d), 7.50 (2H, d), 7.20 (2H, d), 6.95 (1H, d), 3.90-3.80 (4H, m), 2.60-2.50 (4H, m), 2.2 (3H, s) | 397 |
| 251 | 3-fluorophenyl | 11.20 (1H, s), 10.91 (1H, s), 8.50 (1H, s), 7.90 (1H, d), 7.60 (1H, d), 7.50-7.30 (2H, m), 6.95-6.90 (2H, m), 3.90-3.80 (4H, m), 2.60-2.50 (4H, m) | 401 |
| 252 | 4-fluorophenyl | 10.96 (1H, s), 10.88 (1H, s), 8.50 (1H, s), 7.90 (1H, d), 7.65-7.55 (2H, m), 7.20 (2H, t), 6.95 (1H, d), 3.90-3.80 (4H, m), 2.60-2.50 (4H, m) | 401 |
| 253 | 2-methoxyphenyl | 10.85 (1H, s), 10.02 (1H, s), 8.50 (1H, s), 7.95-7.90 (2H, m), 7.10-7.00 (2H, m), 7.05-6.95 (1H, m), 6.90 (1H, d), 3.90-3.80 (7H, m), 2.60-2.50 (4H, m) | 413 |
| 254 | 3-methoxyphenyl | 10.92 (1H, s), 10.88 (1H, s), 8.50 (1H, s), 7.90 (1H, d), 7.30-7.20 (2H, m), 7.10 (1H, d), 6.90 (1H, d), 6.80 (1H, d), 3.90-3.80 (4H, m), 3.70 (3H, s), 2.60-2.50 (4H, m) | 413 |

| Example | R¹ | ¹H NMR δ | MS m/e MH⁺ |
|---|---|---|---|
| 255 | 4-methoxyphenyl | 10.85 (1H, s), 10.68 (1H, s), 8.50 (1H, s), 7.90 (1H, d), 7.50 (2H, d), 6.95 (2H, d), 6.95 (1H, d), 3.90-3.80 (4H, m), 3.7 (3H, s), 2.60-2.50 (4H, m) | 413 |
| 256 | 2-chlorophenyl | 10.88 (1H, s), 10.36 (1H, s), 8.50 (1H, s), 8.00-7.85 (2H, m), 7.60 (1H, d), 7.40 (1H, t), 7.20 (1H, t), 6.95 (1H, d), 3.90-3.80 (4H, m), 2.60-2.50 (4H, m) | 417 |
| 257 | 3-chlorophenyl | 11.18 (1H, s), 10.91 (1H, s), 8.50 (1H, s), 7.90 (1H, d), 7.70 (1H, s), 7.50 (1H, d), 7.40 (1H, t), 7.10 (1H, d), 6.90 (1H, d), 3.90-3.80 (4H, m), 2.60-2.50 (4H, m) | 417 |
| 258 | 4-chlorophenyl | 11.10 (1H, s), 10.90 (1H, s), 8.50 (1H, s), 7.95 (1H, d), 7.60 (2H, d), 7.40 (2H, d), 6.95 (1H, d), 3.90-3.80 (4H, m), 3.60-3.40 (4H, m) | 417 |
| 259 | 2,3-difluorophenyl | 10.91 (1H, s), 8.50 (1H, s), 7.90-7.80 (2H, m), 7.30-7.10 (2H, m), 6.95 (1H, d), 3.90-3.80 (4H, m), 3.60-3.50 (4H, m) | 419 |
| 260 | 2,4-difluorophenyl | 10.88 (1H, s), 10.68 (1H, s), 8.50 (1H, s), 8.05-7.95 (1H, m), 7.90 (1H, d), 7.40-7.30 (1H, m), 7.20-7.10 (1H, m), 6.95 (1H, d), 3.90-3.80 (4H, m), 3.60-3.50 (4H, m) | 419 |
| 261 | 2,5-difluorophenyl | 10.94 (1H, s), 8.50 (1H, s), 8.00-7.90 (2H, m), 7.40-7.30 (1H, m), 7.0-6.95 (1H, m), 6.90 (1H, d), 3.90-3.80 (4H, m), 3.60-3.50 (4H, m) | 419 |
| 262 | 3,5-difluorophenyl | 11.45 (1H, s), 10.95 (1H, s), 8.50 (1H, s), 7.95-7.90 (1H, m), 7.30 (2H, d), 6.95-6.90 (2H, m), 3.90-3.80 (4H, m), 3.60-3.50 (4H, m) | 419 |
| 263 | benzo[1,3]dioxol-5-yl | 10.86 (1H, s), 10.78 (1H, s), 8.50 (1H, s), 7.90 (1H, d), 7.30 (1H, s), 7.05-6.80 (3H, m), 6.00 (2H, s), 3.90-3.80 (4H, m), 3.60-3.50 (4H, m) | 427 |

-continued
| Example | R¹ | ¹H NMR δ | MS m/e MH⁺ |
|---|---|---|---|
| 264 | 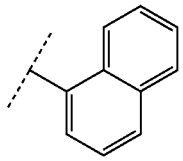 | 10.90 (1H, s), 10.75 (1H, s), 8.50 (1H, s), 8.30-8.20 (1H, m), 8.00-7.90 (3H, m), 7.80 (1H, d), 7.60-7.50 (3H, m), 6.90 (1H, d), 3.90-3.80 (4H, m), 3.60-3.50 (4H, m) | 433 |
| 265 | 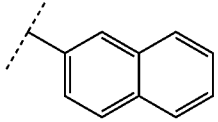 | 11.16 (1H, s), 10.91 (1H, s), 8.50 (1H, s), 8.20 (1H, s), 7.95-7.80 (2H, m), 7.80 (1H, d), 7.50 (1H, t), 7.40 (1H, t), 6.95 (1H, d), 3.90-3.80 (4H, m), 3.60-3.50 (4H, m) | 433 |
| 266 | 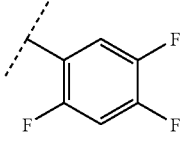 | 10.92 (1H, s), 8.50 (1H, s), 8.20-8.10 (1H, m), 7.90 (1H, d), 7.70 (1H, q), 6.90 (1H, d), 3.90-3.80 (4H, m), 3.60-3.50 (4H, m) | 437 |
| 267 | 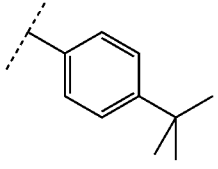 | 10.86 (1H, s), 10.80 (1H, s), 8.50 (1H, s), 7.95 (1H, d), 7.50 (2H, d), 7.40 (2H, d), 6.95 (1H, d), 3.90-3.80 (4H, m), 3.60-3.50 (4H, m) | 439 |
| 268 | 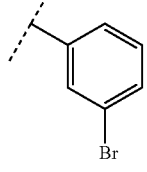 | 11.15 (1H, s), 10.91 (1H, s), 8.50 (1H, s), 7.90 (1H, d), 7.80 (1H, s), 7.55 (1H, d), 7.30 (1H, t), 7.25 (1H, d), 6.90 (1H, d), 3.90-3.80 (4H, m), 2.60-2.50 (4H, m) | 463 |
| 269 | 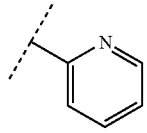 | 10.90 (1H, s), 8.50 (1H, s), 8.30 (1H, d), 7.95-7.90 (3H, m), 7.05-7.00 (1H, m), 6.95 (1H, d), 3.90-3.80 (4H, m), 2.60-2.50 (4H, m) | 384 |
| 270 | 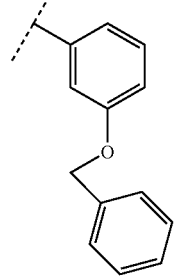 |  | 489 |
| 271 | 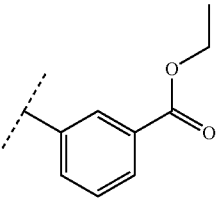 | 11.16 (1H, s), 10.90 (1H, s), 8.50 (1H, s), 8.15 (1H, s), 7.9-7.80 (2H, m), 7.60 (1H, d), 7.50 (1H, t), 6.95 (1H, d), 4.30 (2H, q), 3.90-3.80 (4H, m), 2.60-2.50 (4H, m), 1.3 (3H, t) | 455 |

-continued
| Example | R¹ | ¹H NMR δ | MS m/e MH⁺ |
|---|---|---|---|
| 272 | (2-fluorophenyl) | 10.99 (1H, s), 10.75 (1H, s), 8.50 (1H, s), 8.05-7.90 (2H, m), 7.30-7.20 (2H, m), 7.20-7.10 (1H, m), 6.95 (1H, d), 3.90-3.80 (4H, m), 2.60-2.50 (4H, m) | 401 |
| 273 | (3,4-difluorophenyl) | 11.20 (1H, s), 10.92 (1H, s), 8.50 (1H, s), 7.90 (1H, d), 7.7-7.60 (1H, m), 7.50 (1H, q), 7.40-7.30 (1H, m), 6.95 (1H, d), 3.90-3.80 (4H, m), 2.60-2.50 (4H, m) | 419 |
| 274 | (3-methylphenyl) | 10.94 (1H, s), 10.86 (1H, s), 8.50 (1H, s), 7.90 (1H, d), 7.44 (2H, d), 7.35 (1H, s), 7.25 (1H, t), 6.90 (1H, dd), 3.90-3.80 (4H, m), 2.60-2.50 (4H, m), 2.3 (3H, s) | 397 |
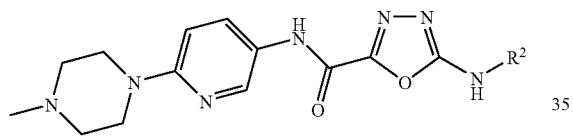
30
35
Starting material=Intermediate 31
| Example | R² | ¹H NMR δ | MS m/e MH⁺ |
|---|---|---|---|
| 275 | (4-fluorophenyl) | | 398 |
| 276 | (3-chlorophenyl) | | 415 |
| 277 | (2-methoxyphenyl) | | 410 |

-continued
| Example | R² | ¹H NMR δ | MS m/e MH⁺ |
|---|---|---|---|
| 278 | 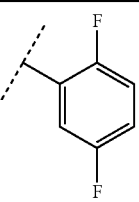 | | 416 |
| 279 | 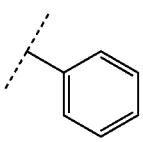 | 10.93 (1H, s), 10.88 (1H, s), 8.50 (1H, s), 7.90 (1H, d), 7.60 (2H, d), 7.40 (2H, t), 7.05 (1H, t), 6.95 (1H, d), 3.50-3.40 (4H, m), 2.40-2.30 (4H, m), 2.20 (3H, s) | 380 |
| 280 | 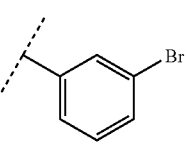 | | 459 |
| 281 | 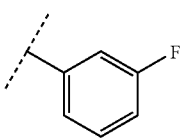 | | 398 |
| 282 | 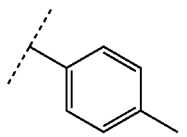 | 10.90 (1H, s), 10.81 (1H, s), 8.5 (1H, s), 7.95 (1H, d), 7.50 (2H, d), 7.20(2H, d), 6.90 (1H, d), 3.5-3.40 (4H, s), 2.50-2.40 (4H, m), 2.25 (3H, s), 2.20 (3H, s) | 394 |
| 283 | 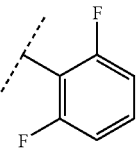 | | 416 |
| 284 | 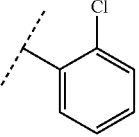 | | 415 |
| 285 | 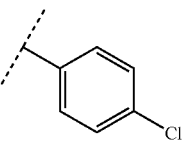 | 11.10 (1H, s), 10.90 (1H, s), 8.50 (1H, s), 7.95 (1H, d), 7.60 (2H, d), 7.40(2H, d), 6.95 (1H, d), 3.50-3.40 (4H, m), 2.50-2.40 (4H, m) | 415 |
| 286 | 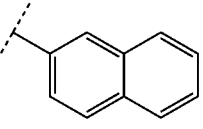 | 11.18 (1H, s), 10.92 (1H, s), 8.50 (1H, s), 8.20 (1H, s), 7.95-7.90 (1H, m), 7.90 (1H, d), 7.65 (1H, d), 7.50 (1H, t), 7.4 (1H, t), 6.90 (1H, d), 3.50-3.40 (4H, m), 2.40-2.30 (4H, m), 2.20 (3H, s) | 430 |
| 287 | 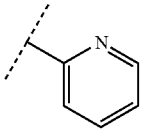 | | 381 |

-continued
| Example | R² | ¹H NMR δ | MS m/e MH⁺ |
|---|---|---|---|
| 288 | 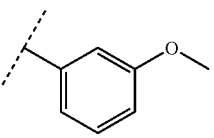 | 10.92 (1H, s), 10.88 (1H, s), 8.50 (1H, s), 7.90 (1H, d), 7.30-7.20 (2H, m), 7.10 (1H, d), 6.85 (1H, d), 6.60 (1H, d), 3.70 (3H, s), 3.50-3.40 (4H, m), 2.50-2.40 (4H, m), 2.2 (3H, s) | 410 |
| 289 | 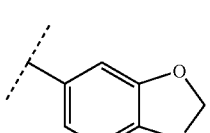 | 10.88 (1H, s), 10.78 (1H, s), 8.50 (1H, s), 7.90 (1H, d), 7.25 (1H, s), 7.00 (1H, d), 6.95 (1H, d), 6.90 (1H, d), 6.00 (2H, s), 3.50-3.40 (4H, m), 3.40-3.30 (4H, m), 2.2 (3H, s) | 424 |
| 290 | 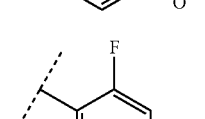 | | 416 |
| 291 | 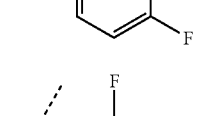 | | 416 |
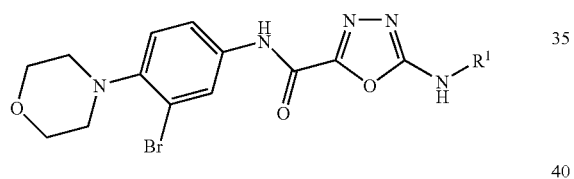
35
40
Starting material=Intermediate 65
| Example | R¹ | ¹H NMR δ | MS m/e MH⁺ |
|---|---|---|---|
| 292 | 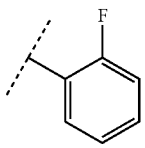 | 11.08 (1H, s), 10.76 (1H, s), 8.10 (1H, s), 8.00 (1H, t), 7.75 (1H, d), 7.35-7.10 (4H, m), 3.80-3.70 (4H, m), 3.00-2.90 (4H, m) | 464 |
| 293 | 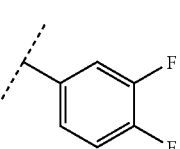 | 11.25 (1H, s), 11.11 (1H, s), 8.10 (1H, s), 7.75 (1H, d), 7.70-7.60 (1H, m), 7.50 (1H, q), 7.40-7.30 (1H, m), 7.20 (1H, s), 3.80-3.70 (4H, m), 3.00-2.90 (4H, m) | 482 |
| 294 | 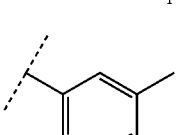 | 11.06 (1H, s), 10.88 (1H, s), 8.10 (1H, s), 7.80 (1H, d), 7.40 (1H, d), 7.35 (1H, s), 7.25-7.20 (2H, m), 3.80-3.70 (4H, m), 3.00-2.90 (4H, m), 2.30 (3H, s) | 460 |

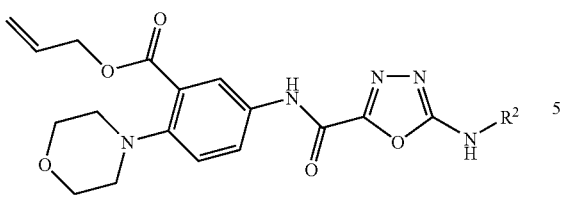

Starting material=Intermediate 66

| Example | R² | ¹H NMR δ | MS m/e MH⁺ |
|---|---|---|---|
| 295 | 2-F-phenyl | 11.08 (1H, s), 10.76 (1H, s), 8.10 (1H, s), 8.00 (1H, t), 7.80 (1H, d), 7.35-7.10 (4H, m), 6.10-5.95 (1H, m), 5.45 (1H, d), 5.30 (1H, d), 4.80 (2H, d), 3.80-3.70 (4H, m), 3.00-2.90 (4H, m) | 468 |
| 296 | 3,4-diF-phenyl | 11.24 (1H, s), 11.11 (1H, s), 8.10 (1H, s), 7.90 (1H, d), 7.70-7.60 (1H, m), 7.50 (1H, q), 7.40-7.30 (1H, m), 7.20 (1H, s), 6.10-5.95 (1H, m), 5.45 (1H, d), 5.30 (1H, d), 4.80 (2H, d), 3.80-3.70 (4H, m), 3.00-2.90 (4H, m) | 486 |

Example 297-304

The following examples were prepared by the general procedure of Example 87, using Intermediate 41 and commercially available acid chlorides.

| Example | R¹ | ¹H NMR δ | MS m/e MH⁺ |
|---|---|---|---|
| 297 | CH₂OCH₃ | 10.93 (1H, s), 10.73 (1H, s), 8.50 (1H, s), 8.05 (1H, t), 7.95 (1H, d), 7.35-7.10 (3H, m), 6.90 (1H, d), 4.10 (2H, s), 3.30 (8H, s) | 456 |
| 298 | CH₂CH₂Ph | 10.98 (1H, s), 10.93 (1H, s), 8.50 (1H, s), 8.05 (1H, t), 7.95 (1H, d), 7.35-7.10 (8H, m), 6.90 (1H, d), 3.70-3.65 (1H, m), 3.60-3.50 (3H, m), 3.45-3.40 (3H, m), 3.20-3.10 (1H, m), 2.80 (2H, q), 2.70 (2H, q) | 516 |
| 299 | 2-F-phenyl | 10.94 (1H, s), 10.73 (1H, s), 8.50 (1H, s), 8.05 (1H, t), 7.95 (1H, d), 7.55-7.40 (2H, m), 7.35-7.20 (5H, m), 7.20-7.10 (1H, m), 6.90 (1H, d), 3.80-3.75 (2H, m), 3.60-3.50 (2H, m), 3.50-3.40 (2H, m), 3.30-3.20 (2H, m) | 506 |

-continued

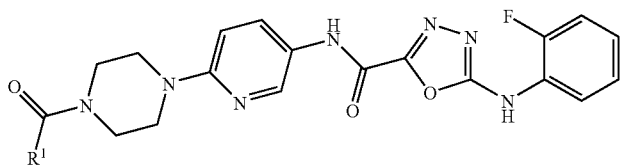

| Example | R¹ | ¹H NMR δ | MS m/e MH⁺ |
|---|---|---|---|
| 300 | 4-cyanophenyl | 10.96 (1H, s), 10.74 (1H, s), 8.50 (1H, s), 8.05-7.90 (5H, m), 7.60 (2H, d), 7.30-7.10 (3H, m), 6.90 (1H, d), 3.80-3.75 (2H, m), 3.60-3.50(2H, m), 3.50-3.40 (2H, m), 3.30-3.20 (2H, m) | 513 |
| 301 | 4-methylphenyl | 10.94 (1H, s), 10.74 (1H, s), 8.50 (1H, s), 8.05-7.90 (2H, m), 7.40-7.10 (7H, m), 6.90 (1H, d), 3.60-3.40 (8H, m), 2.30 (3H, s) | 502 |
| 302 | 2-methylphenyl | 10.94 (1H, s), 10.73 (1H, s), 8.50 (1H, s), 8.05 (1H, t), 7.95 (1H, d), 7.35-7.10(8H, m), 6.90 (1H, d), 3.80-3.75 (2H, m), 3.60-3.50 (2H, m), 3.50-3.40 (2H, m), 3.30-3.20 (2H, m), 2.10 (3H, s) | 502 |
| 303 | 3-methylphenyl | 10.94 (1H, s), 10.74 (1H, s), 8.50 (1H, s), 8.05 (1H, t), 7.95 (1H, d), 7.40-7.10 (8H, m), 6.90 (1H, d), 3.60-3.40 (8H, m), 2.30 (3H, s) | 502 |
| 304 | pyridin-3-yl | 10.94 (1H, s), 10.74 (1H, s), 8.65 (2H, s), 8.50 (1H, s), 8.05-7.85 (3H, m), 7.55-7.45 (1H, m), 7.30-7.10 (3H, m), 6.90 (1H, d), 3.60-3.40 (8H, m) | 489 |

Example 305

5-[(2-Fluorophenyl)amino]-N-[6-(4-glycoloylpiperazin-1-yl)pyridin-3-yl]-1,3,4-oxadiazole-2-carboxamide

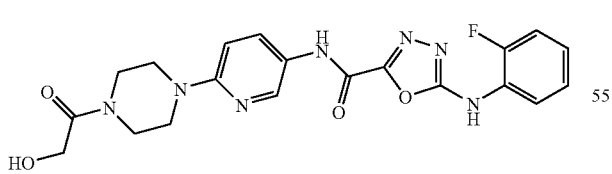

EDAC (60 mg, 0.31 mmol) was added to a stirred mixture of 5-[(2-fluorophenyl)amino]-N-(6-piperazin-1-ylpyridin-3-yl)-1,3,4-oxadiazole-2-carboxamide (Intermediate 41, 100 mg, 0.26 mmol), glycolic acid (20 mg 0.26 mmol) and HOBt (42 mg, 0.31 mmol) in 3 mL of DMF and stirring was continued for 16 h. Water (10 mL) was added and the resultant precipitate was collected by filtration, washed with water then ether and dried in vacuo to give the title compound (75 mg, 65%) as a solid; ¹H NMR δ 10.94 (1H, s), 10.70 (1H, s), 8.50 (1H, s), 8.05 (1H, t), 7.90 (1H, d), 7.35-7.20 (2H, m), 7.20-7.10 (1H, m), 6.90 (1H, d), 4.60 (1H, t), 4.10 (2H, d), 3.60-3.4 (8H, m); MS m/e MH⁺ 442.

Example 306

4-{5-[({5-[(2-Fluorophenyl)amino]-1,3,4-oxadiazol-2-yl}carbonyl)amino]pyridin-2-yl}piperazine-1-carboxamide

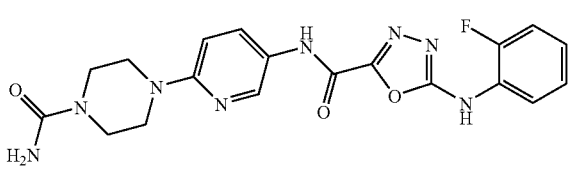

Sodium cyanate 34 mg (0.52 mmol) was added to a mixture of 5-[(2-fluorophenyl)amino]-N-(6-piperazin-1-ylpyridin-3-yl)-1,3,4-oxadiazole-2-carboxamide (Intermediate 41, 100 mg, 0.26 mmol) and glacial acetic acid (0.2 mL) in 0.6 mL of water (0.6 mL) and THF (0.3 mL). The mixture was stirred for 16 h then sodium cyanate (34 mg), glacial acetic acid (0.2 mL), dioxan (0.5 mL) and water (0.2 mL) were added. The mixture was stirred for another 2 h then directly purified by reverse phase HPLC, eluting with a gradient of acetonitrile/water containing 0.2% TFA, to give the title compound (90 mg, 82%) as a solid; $^1$H NMR δ 11.02 (1H, s), 10.74 (1H, s), 8.50 (1H, s), 8.05-7.95 (2H, m), 7.35-7.20 (2H, m), 7.20-7.10 (1H, m), 6.90 (1H, d), 3.60-3.4 (8H, m); MS m/e MH$^+$ 427.

Example 307

4-{5-[({5-[(2-Fluorophenyl)amino]-1,3,4-oxadiazol-2-yl}carbonyl)amino]pyridin-2-yl}-N-phenylpiperazine-1-carboxamide

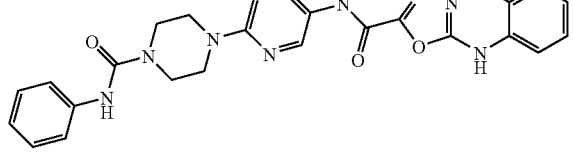

Phenyl isocyanate (0.032 mL, 0.29 mmol) was added to a stirred mixture of 5-[(2-fluorophenyl)amino]-N-(6-piperazin-1-ylpyridin-3-yl)-1,3,4-oxadiazole-2-carboxamide (Intermediate 41, 100 mg, 0.26 mmol) and DMF (1.5 mL). After 2 h the crude reaction mixture was directly purified by reverse phase HPLC eluting with a gradient of acetonitrile/water containing 0.2% TFA to give the title compound (28 mg, 20%) as a solid; $^1$H NMR δ 11.00 (1H, s), 10.74 (1H, s), 8.55 (1H, s), 8.50 (1H, s), 8.05-7.95 (2H, m), 7.45 (2H, d), 7.35-7.10 (4H, m), 7.00 (1H, d), 6.90 (1H, t), 3.80-3.60 (8H, m); MS m/e MH$^+$ 503.

Example 308

The following example was prepared by the general procedure of Example 307 using Intermediate 41 and the appropriate isocyanate.

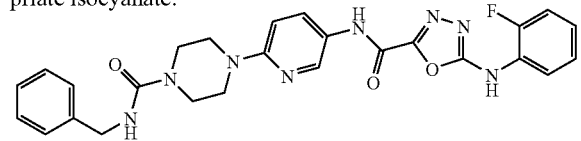

$^1$H NMR δ 10.98 (1H, s), 10.74 (1H, s), 8.5 (1H, s), 8.05-7.95 (2H, m), 7.30-7.10 (8H, m), 6.95 (1H, d), 4.20 (2H, d), 3.50 (8H, s); MS m/e MH$^+$ 517.

Example 309

Phenyl 4-{5-[({5-[(2-fluorophenyl)amino]-1,3,4-oxadiazol-2-yl}carbonyl)amino]pyridin-2-yl}piperazine-1-carboxylate

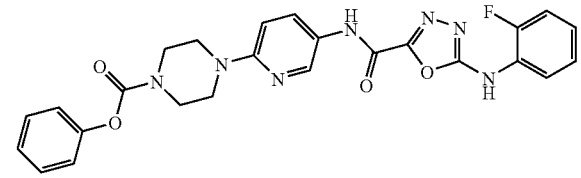

Phenyl chloroformate (0.036 mL, 0.29 mmol) was added to a mixture of 5-[(2-fluorophenyl)amino]-N-(6-piperazin-1-ylpyridin-3-yl)-1,3,4-oxadiazole-2-carboxamide (Intermediate 41, 100 mg, 0.26 mmol) and triethylamine (0.07 mL, 0.52 mmol) in DMF (1.5 mL). The mixture was stirred for 2 h then directly purified by reverse phase HPLC eluting with a gradient of acetonitrile/water containing 0.2% TFA to give the title compound (40 mg, 31%) as a solid; $^1$H NMR δ 10.95 (1H, s), 10.73 (1H, s), 8.50 (1H, s), 8.05-7.95 (2H, m), 7.45-7.10 (8H, m), 6.90 (1H, d), 3.80-3.60 (8H, m); MS m/e MH$^+$ 504.

Examples 310-312

The following Examples were prepared by the general procedure of Example 309 using Intermediate 73 in place of Intermediate 41 and using the appropriate commercially available chloroformate.

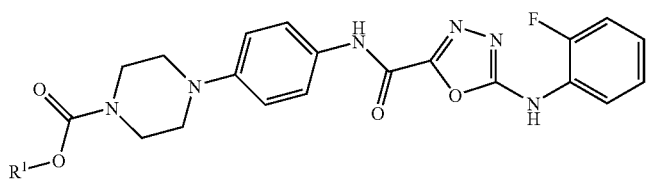

| Example | R$^1$ | $^1$H NMR δ | MS m/e MH$^+$ |
|---|---|---|---|
| 310 | Ethyl | 10.95 (1H, s), 1.73 (1H, s), 8.5 (1H, s), 8.05-7.95 (2H, m), 7.30-7.10 (3H, m), 6.95 (1H, d), 4.10 (3H, q), 3.50 (8H, s), 1.20 (2H, t) | 456 |

-continued

| Example | R¹ | ¹H NMR δ | MS m/e MH⁺ |
|---|---|---|---|
| 311 | (benzyl-CMe2-) | 10.93 (1H, s), 10.72 (1H, s), 8.5 (1H, s), 8.05 (1H, t), 7.95 (1H, d), 7.40-7.20 (7H, m), 7.20-7.10 (1H, m), 6.95 (1H, d), 5.10 (2H, s), 3.50 (8H, s) | 518 |
| 312 | Ethyl | 10.81 (1H, s), 10.70 (1H, s), 8.0 (1H, t), 7.60 (2H, d), 7.30-7.10 (3H, m), 6.95 (2H, d), 4.10 (3H, q), 3.50-3.40 (4H, m), 3.10-3.00 (4H, m), 1.20 (2H, t) | 455 |

Examples 313-318

The following examples were prepared by the general procedure of Example 72 (method B) using Intermediate 40 and the appropriate aniline.

| Example | R⁴ | ¹H NMR δ | MS m/e MH⁺ |
|---|---|---|---|
| 313[1] | butyl-S-C(Me)2- | 11.02 (1H, s), 10.74 (1H, s), 8.0 (3H, t), 7.75 (2H, d), 7.35-7.20 (4H, m), 7.20-7.10 (1H, m), 2.90 (2H, t), 1.50 (2H, m), 1.40 (2H, m), 0.85 (3H, t) | 387 |
| 314[2] | 5-methoxy-1,3,4-thiadiazol-2-yl-NHSO2-C(Me)2- |  | 492 |
| 315[3] | 2,4-difluorophenoxy-C(Me)2- | 11.10 (1H, s), 10.75 (1H, s), 8.10 (1H, t), 7.80-7.70 (2H, m), 7.50-7.40 (1H, m), 7.35-7.20 (3H, m), 7.20-7.10 (2H, m), 6.90 (1H, d) | 427 |

-continued

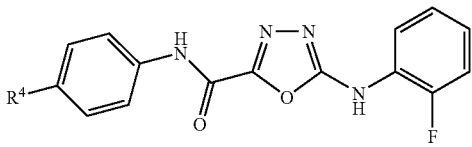

| Example | R⁴ | ¹H NMR δ | MS m/e MH⁺ |
|---|---|---|---|
| 316[4] | (structure: 4-methyl-3-oxo-pyridazine with methyl group) | 11.20 (1H, s), 10.75 (1H, s), 8.10 (1H, t), 7.90 (2H, d), 7.85 (2H, d), 7.35-7.20 (2H, m), 7.20-7.10 (1H, m), 3.45 (1H, qn), 3.30 (3H, s), 2.75 (1H, dd), 2.35 (1H, d), 1.10 (3H, d) | 423 |
| 317[5] | (structure: thiazinone ring) | 11.65 (1H, s), 11.20 (1H, s), 10.75 (1H, s), 8.10 (1H, t), 7.90 (2H, d), 7.85 (2H, d), 7.35-7.20 (2H, m), 7.20-7.10 (1H, m), 4.75 (1H, q), 1.10 (3H, d) | 427 |
| 318[6] | (structure: 4-chlorobenzyl) | 11.12 (1H, s), 10.75 (1H, s), 8.05 (1H, t), 7.90 (1H, d), 7.70-7.60 (4H, m), 7.50 (2H, d), 7.10-7.30 (7H, m) | MH⁻ 407 |

[1] Starting material (SM) prepared as described in Farmaco 2004, 59(6), 443.
[2] SM prepared as described in J. Chem. Soc. C (Organic), 1967, 24, 2700.
[3] SM prepared as described in WO 2001056990
[4] SM prepared as described in US 3746712
[5] SM prepared as described in EP 52442.
[6] SM prepared as described in WO 2001055110

Example 319

Methyl (1-{5-[({5-[(2,4,5-trifluorophenyl)amino]-1,3,4-oxadiazol-2-yl}carbonyl)amino]pyridin-2-yl}piperidin-4-yl)acetate

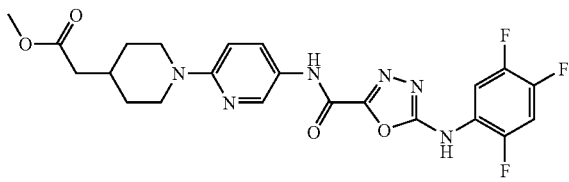

Methyl [1-(5-{[hydrazine(oxo)acetyl]amino}pyridin-2-yl)piperidin-4-yl]acetate (Intermediate 77, 215 mg, 0.64 mmol) was dissolved in DMA (4 mL) and treated with 2,4,5-trifluorophenylisothiocyanate (146 mg, 0.77 mmol). The reaction mixture was heated at 45° C. for 30 minutes then EDAC (148 mg, 0.77 mmol) was added and the mixture was heated to 85° C. for 1 h. The mixture was cooled and diluted with water (4 mL). The resulting precipitate was filtered off, washed with water and dried under high vacuum to give the title compound (277 mg, 89%) as a solid; ¹H NMR δ 1.04-1.20 (2H, m), 1.64 (2H, d), 1.78-1.95 (1H, m), 2.19 (2H, d), 2.63-2.78 (2H, m), 3.52 (3H, s), 4.16 (2H, d), 6.77 (1H, d), 7.57-7.69 (1H, m), 7.76-7.86 (1H, m), 8.01-8.17 (1H, m), 8.34-8.43 (1H, m), 10.85 (1H, s), 10.97 (1H, s); MS m/e MH⁺ 491.

Example 320

(1-{5-[({5-[(2,4,5-Trifluorophenyl)amino]-1,3,4-oxadiazol-2-yl}carbonyl)amino]pyridin-2-yl}piperidin-4-yl)acetic acid hydrochloride

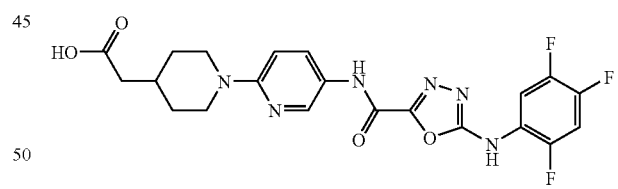

Methyl (1-{5-[({5-[(2,4,5-trifluorophenyl)amino]-1,3,4-oxadiazol-2-yl}carbonyl)-amino]pyridin-2-yl}piperidin-4-yl)acetate (Example 319, 216 mg, 0.44 mmol) was suspended in a mixture of MeOH (4 ml) and THF (8 mL). Lithium hydroxide (4.4 mL of a 1M aqueous solution) was added. The resulting clear solution was heated at 45° C. for 15 minutes then cooled and acidified to pH ~2 with dropwise addition of concentrated aqueous HCl. Volatile material was removed by evaporation and the residue was washed with water then dried to give the title compound (182 mg, 87%) as a solid; ¹H NMR δ 1.16-1.45 (2H, m), 1.76-1.93 (2H, m), 1.98-2.13 (1H, m), 2.28 (2H, d), 3.12 (2H, t), 4.28 (2H, d), 7.25-7.41 (1H, m), 7.70-7.88 (1H, m), 8.13-8.32 (2H, m), 8.55 (1H, d), 11.16 (1H, s), 11.29 (1H, s); MS m/e MH⁺ 477.

Examples 321-337
The following Examples were prepared by the general procedure of Example 1, using Intermediate 43 and commercially available isothiocyanates.
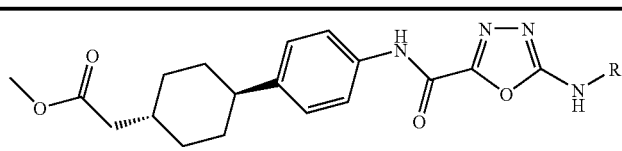
| Example | R | HPLC Retention Time (minutes) | MS m/e MH+ |
|---|---|---|---|
| 321 | 4-ethylphenyl | 2.98 | 463 |
| 322 | 4-methoxyphenyl | 2.68 | 465 |
| 323 | 3-trifluoromethylphenyl | 2.99 | 503 |
| 324 | 3-cyanophenyl | 2.71 | 460 |
| 325 | 2-ethylphenyl | 2.86 | 463 |
| 326 | 2-isopropylphenyl | 2.94 | 477 |
| 327 | 4-benzyloxyphenyl | 3.10 | 541 |
| 328 | 3-methylphenyl | 2.84 | 449 |

-continued

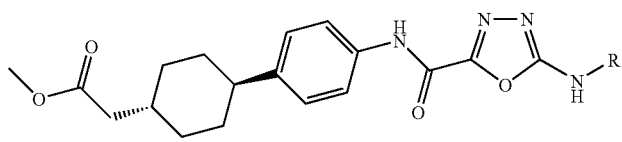

| Example | R | HPLC Retention Time (minutes) | MS m/e MH+ |
|---|---|---|---|
| 329 | 4-isopropylphenyl (gem-dimethyl) | 3.10 | 477 |
| 330 | 2-CF₃-phenyl (gem-dimethyl) | 2.80 | 503 |
| 331 | 4-CF₃-phenyl (gem-dimethyl) | 3.00 | 503 |
| 332 | 4-CN-phenyl (gem-dimethyl) | 2.69 | 460 |
| 333 | 4-OCF₃-phenyl (gem-dimethyl) | 3.04 | 519 |
| 334 | 2-OCF₃-phenyl (gem-dimethyl) | 2.96 | 519 |
| 335 | 3-ethylphenyl (gem-dimethyl) | 2.97 | 463 |
| 336 | 2-OMe-phenyl (gem-dimethyl) | 2.83 | 465 |
| 337[1] | 2-NC-phenyl (gem-dimethyl) | 2.52 | 460 |

[1] The commercially available isocyanate was used in place of isothiocyanate

Example 338

Methyl [trans-4-(4-{[(5-{[3-(aminocarbonyl)phenyl]amino}-1,3,4-oxadiazol-2-yl)carbonyl]amino}phenyl)cyclohexyl]acetate

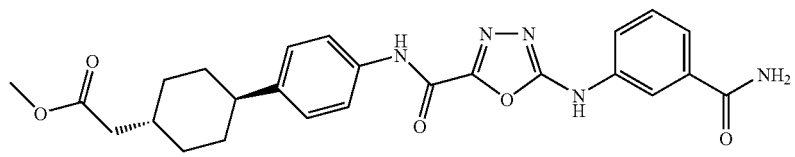

3-Aminobenzamide (54 mg, 0.39 mmol) was added to a solution of thiocarbonyldiimidazole (71 mg, 0.39 mmol) in CH$_3$CN (5 mL) and the mixture was stirred for 16 h. Methyl [trans-4-(4-{[hydrazino(oxo)acetyl]amino}phenyl)cyclohexyl]acetate (Intermediate 43) (110 mg, 0.33 mmol) and DMF (5 mL) was added and the mixture was stirred at 50° C. until a clear solution was obtained. PS-CDI (527 mg) was added and the temperature raised to 80° C. for 16 h. The mixture was filtered whilst hot and the polymer washed with DMF (2×5 mL). The filtrates were concentrated by evaporation to give the title compound as a solid; MS m/e (M+Na)$^+$ 500; HPLC retention time=2.26 minutes.

Examples 339-352

The following examples were prepared by the general procedure of Example 338 using the appropriate aniline (commercially available unless indicated otherwise) in place of 3-aminobenzamide.

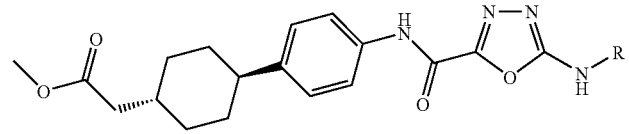

| Example | R | HPLC Retention Time (min) | MS m/e MH$^+$ |
|---|---|---|---|
| 339 | 3-benzoylphenyl | 2.98 | 561 |
| 340 | 3-(trifluoromethoxy)phenyl | 3.03 | 519 |
| 341 | 3-phenoxyphenyl | 3.13 | 527 |
| 342 | 2-(benzyloxy)phenyl | 3.12 | 541 |

-continued
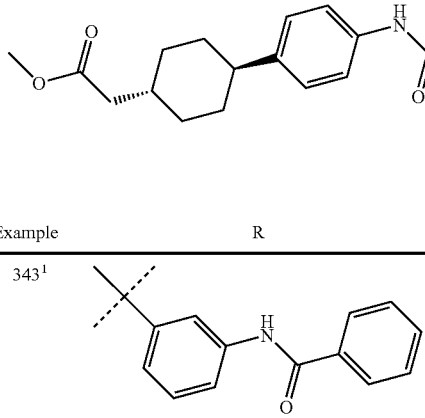
| Example | R | HPLC Retention Time (min) | MS m/e MH+ |
|---|---|---|---|
| 343[1] | 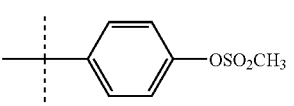 | 2.82 | 552 (M −H)− |
| 344[2] | 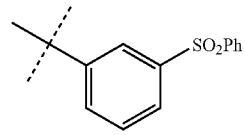 | 2.65 | 529 |
| 345 | 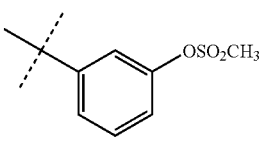 | 2.86 | 575 |
| 346[3] | 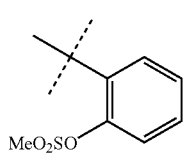 | 2.69 | 527 (M −H)− |
| 347[4] | 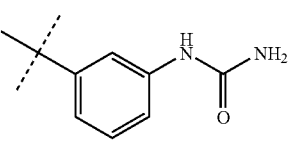 | 2.71 | 529 |
| 348 | 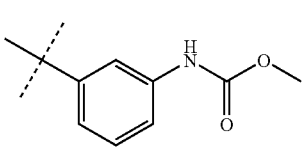 | 2.32 | 515 (M + Na)+ |
| 349[5] | 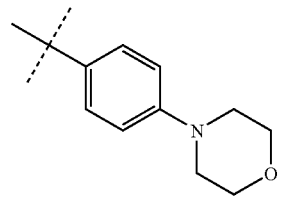 | 2.64 | 508 |
| 350 | 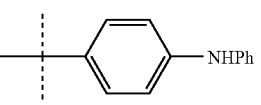 | 2.90 | 520 |
| 351 | —⟨C₆H₄⟩—NHPh | 3.08 | 526 |

-continued

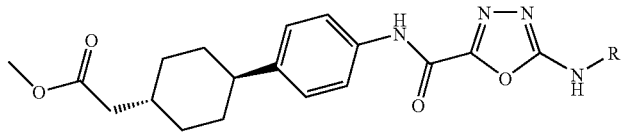

| Example | R | HPLC Retention Time (min) | MS m/e MH+ |
|---|---|---|---|
| 352 | ![NHPh substituent] | 3.14 | 526 |

The following footnotes refer to preparation of the aniline starting materials:
[1]For preparative details: CAS Reg. No. 16091-26-2.
[2]Prepared as described in J. Am. Chem. Soc., 2003, 125(22), 6630.
[3]Prepared as described in U.S. patent application No. US 3687998 (1972).
[4]Prepared as described in Tetrahedron, 1988, 54(1/2), 45.
[5]For preparative details: CAS Reg. No. 6464-98-8

Examples 353-355

The following examples were prepared by the general procedure of Example 338 but using O,O-dipyridin-2-yl thiocarbonate in place of thiocarbonyldiimidazole and using the appropriate commercially available aniline.

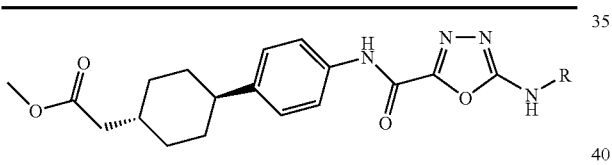

| Example | R | HPLC Retention Time (min) | MS m/e MH+ |
|---|---|---|---|
| 353 | -C6H4-SO2Ph (para) | 2.87 | 575 |
| 354[1] | -C6H4-SO2Ph (ortho) | 3.11 | 575 |
| 355 | -C6H4-SO2Et (para) | 2.64 | 527 |

[1]Heated at 80° C. for 24 hours when O,O-dipyridin-2-yl thiocarbonate and aniline mixed. DMF was also used in place of CH3CN.

Example 356

(trans-4-{4-[({5-[(4-Ethylphenyl)amino]-1,3,4-oxa-diazol-2-yl}carbonyl)amino]phenyl}cyclohexyl) acetic acid

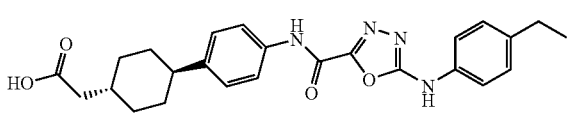

A solution of lithium hydroxide monohydrate (110 mg, 2.64 mmol.) in water (1.4 mL) was added to a suspension of methyl (trans-4-{4-[({5-[(4-ethylphenyl)amino]-1,3,4-oxa-diazol-2-yl}carbonyl)amino]phenyl}cyclohexyl)acetate (152 mg, 0.33 mmol) in THF (1.6 mL) and MeOH (2.6 mL). After 24 h, 1M aqueous HCl (5 mL) was added followed by water (10 mL). The solid was filtered off and washed with water (2×5 mL), Et2O (2×5 mL) then hexane (2×5 mL) to give the title compound as a solid (105 mg, 71%); $^1$H NMR δ 1.04-1.19 (5H, m), 1.37-1.51 (2H, m), 1.65-1.85 (5H, m), 2.11-2.15 (2H, m), 2.39-2.47 (1H, m), 2.57 (2H, q), 7.21 (4H, m), 7.49 (2H, d), 7.68 (2H, d), 10.84 (1H, s), 10.91 (1H, s), 11.99 (1H, s); MS m/e MH+ 449.

Examples 357-390

The following examples were prepared by the general procedure of Example 356 using the appropriate ester as starting material selected from Examples 321-355.

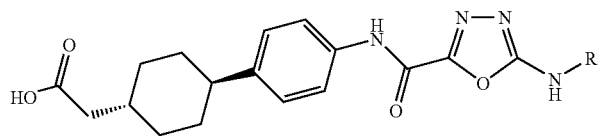

| Example | R | ¹H NMR δ | MS m/e MH⁺ |
|---|---|---|---|
| 357 | 4-methoxyphenyl-C(CH₃)– | 1.11-1.18 (2H, m), 1.42-1.50 (2H, m), 1.72-1.85 (5H, m), 2.15 (2H, d), 2.42-2.48 (1H, m), 3.75 (3H, s), 6.97-6.99 (2H, m), 7.22 (2H, d), 7.50-7.54 (2H, m), 7.68-7.70 (2H, m), 10.71 (1H, s), 10.87 (1H, s), 11.96 (1H, s) | 451 |
| 358 | 3-(CF₃)phenyl-C(CH₃)– | 1.14-1.18 (2H, m), 1.42-1.51 (2H, m), 1.71-1.85 (5H, m), 2.15 (2H, d), 2.39-2.47 (1H, m), 7.23 (2H, d), 7.42 (1H, d), 7.63-7.71 (3H, m), 7.85-7.87 (1H, m), 8.01 (1H, s), 10.94 (1H, s), 11.35 (1H, s), 11.97 (1H, s) | 489 |
| 359 | 3-cyanophenyl-C(CH₃)– | 1.05-1.20 (2H, m), 1.40-1.55 (2H, m), 1.70-1.95 (5H, m), 2.14-2.16 (2H, m), 2.46-2.55 (1H, m), 7.23 (2H, d), 7.53 (1H, d), 7.63 (1H, t), 7.70 (2H, d), 7.87 (1H, d), 8.02 (1H, s), 10.97 (1H, s), 11.43 (1H, s), 11.97 (1H, s) | 446 |
| 360 | 2-ethylphenyl-C(CH₃)– | 1.08-1.18 (5H, m), 1.41-1.51 (2H, m), 1.71-1.84 (5H, m), 2.14-2.16 (2H, m), 2.45 (1H, t), 2.70 (2H, q), 7.15-7.30 (5H, m), 7.67-7.70 (1H, m), 7.69-7.69 (2H, m), 10.00 (1H, s), 10.86 (1H, s), 11.97 (1H, s) | 449 |
| 361 | 2-isopropylphenyl-C(CH₃)– | 1.05-1.20 (8H, m), 1.41-1.50 (2H, m), 1.70-1.84 (5H, m), 2.15 (2H, d), 2.40-2.50 (1H, m), 3.25-3.35 (1H, m), 7.21-7.28 (4H, m), 7.36-7.40 (1H, m), 7.55-7.60 (1H, m), 7.66-7.69 (2H, m), 10.01 (1H, s), 10.83 (1H, s), 11.97 (1H, s) | 463 |

-continued

| Example | R | ¹H NMR δ | MS m/e MH⁺ |
|---|---|---|---|
| 362 | 4-(benzyloxy)phenyl-C(CH₃)₂– | 1.11-1.17 (2H, m), 1.42-1.50 (2H, m), 1.72-1.85 (5H, m), 2.14-2.16 (2H, m), 2.46-2.55 (1H, m), 5.10 (2H, s), 7.06 (2H, d), 7.22 (2H, d), 7.32-7.53 (7H, m), 7.68-7.71 (2H, m), 10.72 (1H, s), 10.89 (1H, s), 11.97 (1H, s) | 527 |
| 363 | 3-methylphenyl-C(CH₃)₂– | 1.08-1.18 (2H, m), 1.42-1.50 (2H, m), 1.71-1.85 (5H, m), 2.15 (2H, d), 2.33 (2H, s), 2.46-2.55 (1H, m), 6.89 (1H, d), 7.22-7.29 (3H, m), 7.39 (1H, s), 7.44 (1H, d), 7.68-7.71 (2H, m), 10.90 (1H, s), 11.97 (1H, s) | 435 |
| 364 | 4-isopropylphenyl-C(CH₃)₂– | 1.08-1.18 (2H, m), 1.21 (6H, d), 1.41-1.51 (2H, m), 1.71-1.85 (5H, m), 2.15 (2H, d), 2.42-2.47 (1H, m), 2.84-2.91 (1H, m), 7.22-7.27 (4H, m), 7.50-7.53 (2H, m), 7.68-7.71 (2H, m), 10.82 (1H, s), 10.89 (1H, s), 11.96 (1H, s) | 463 |
| 365 | 2-(trifluoromethyl)phenyl-C(CH₃)₂– | 1.10-1.17 (2H, m), 1.41-1.50 (2H, m), 1.70-1.84 (5H, m), 2.15 (2H, d), 2.45 (1H, t), 7.22 (2H, d), 7.50 (1H, t), 7.66-7.68 (2H, m), 7.75-7.86 (3H, m), 10.33 (1H, s), 10.87 (1H, s), 11.97 (1H, s) | 489 |
| 366 | 4-(trifluoromethyl)phenyl-C(CH₃)₂– | 1.11-1.18 (2H, m), 1.42-1.51 (2H, m), 1.73-1.85 (5H, m), 2.14-2.16 (2H, m), 2.42-2.53 (1H, m), 7.23 (2H, d), 7.69-7.72 (2H, m), 7.76-7.82 (4H, m), 10.96 (1H, s), 11.49 (1H, s), 12.00 (1H, s) | 489 |
| 367 | 4-cyanophenyl-C(CH₃)₂– | 1.11-1.18 (2H, m), 1.42-1.50 (2H, m), 1.73-1.85 (5H, m), 2.15 (2H, d), 2.42-2.53 (1H, m), 7.23 (2H, d), 7.69-7.72 (2H, m), 7.76-7.78 (2H, m), 7.86-7.89 (2H, m), 10.98 (1H, s), 11.57 (1H, s), 11.97 (1H, s) | 446 |

| Example | R | $^1$H NMR δ | MS m/e MH$^+$ |
|---|---|---|---|
| 368 | 4-(OCF$_3$)-phenyl (via C(CH$_3$)) | 1.11-1.18 (2H, m), 1.42-1.50 (2H, m), 1.71-1.85 (5H, m), 2.14-2.16 (2H, m), 2.42-2.54 (1H, m), 7.23 (2H, d), 7.42 (2H, d), 7.68-7.73 (4H, m), 10.94 (1H, s), 11.18 (1H, s), 11.97 (1H, s) | 505 |
| 369 | 2-(OCF$_3$)-phenyl (via C(CH$_3$)) | 1.11-1.15 (2H, m), 1.44-1.48 (2H, m), 1.74-1.85 (5H, m), 2.14-2.16 (2H, m), 2.42-2.48 (1H, m), 7.22-7.26 (3H, m), 7.44-7.50 (2H, m), 7.68-7.71 (2H, m), 8.20-8.22 (1H, m), 10.87 (1H, s), 10.93 (1H, s), 11.94 (1H, s) | 505 |
| 370 | 3-ethyl-phenyl (via C(CH$_3$)) | 1.11-1.15 (2H, m), 1.20 (3H, q), 1.42-1.50 (2H, m), 1.71-1.85 (5H, m), 2.14-2.16 (2H, m), 2.42-2.48 (1H, m), 2.63 (2H, q), 6.92 (1H, d), 7.23 (2H, d), 7.30 (1H, t), 7.43-7.48 (2H, m), 7.68-7.71 (2H, m), 10.88 (1H, s), 10.93 (1H, s), 11.98 (1H, s) | 449 |
| 371 | 3-(CONH$_2$)-phenyl (via C(CH$_3$)) | 1.12-1.17 (2H, m), 1.44-1.48 (2H, m), 1.74-1.85 (5H, m), 2.14-2.16 (2H, m), 2.42-2.48 (1H, m), 7.23 (2H, d), 7.36 (1H, s), 7.47 (1H, t), 7.55 (1H, d), 7.69-7.71 (2H, m), 7.79-7.82 (1H, m), 7.94 (1H, s), 8.04 (1H, t), 10.92 (1H, s), 11.06 (1H, s), 11.97 91H, s) | 464 |
| 372 | 3-benzoyl-phenyl (via C(CH$_3$)) | 1.11-1.18 (2H, m), 1.42-1.50 (2H, m), 1.71-1.85 (5H, m), 2.14-2.16 (2H, m), 2.42-2.48 (1H, m), 7.23 (2H, d), 7.41-7.43 (1H, m), 7.57-7.61 (3H, m), 7.68-7.73 (4H, m), 7.78-7.80 (2H, m), 7.88-7.91 (1H, m), 8.08 (1H, t), 10.92 (1H, s), 11.22 (1H, s), 11.99 (1H, s) | 525 |
| 373 | 3-(OCF$_3$)-phenyl (via C(CH$_3$)) | 1.12-1.17 (2H, m), 1.44-1.48 (2H, m), 1.74-1.85 (5H, m), 2.14-2.16 (2H, m), 2.42-2.48 (1H, m), 7.04-7.06 (1H, m), 7.23 (2H, d), 7.53-7.57 (2H, m), 7.68-7.71 (3H, m), 10.94 (1H, s), 11.33 (1H, s), 11.91 (1H, s) | 505 |

-continued

| Example | R | $^1$H NMR δ | MS m/e MH$^+$ |
|---|---|---|---|
| 374 | 1-(3-phenoxyphenyl)-1-methylethyl | 1.11-1.17 (2H, m), 1.44-1.48 (2H, m), 1.73-1.84 (5H, m), 2.14-2.16 (2H, m), 2.48-2.56 (1H, m), 6.67-6.70 (1H, m), 7.06-7.08 (2H, m), 7.16-7.23 (3H, m), 7.31-7.44 (5H, m), 7.67-7.70 (2H, m), 10.91 (1H, s), 11.06 (1H, s), 11.97 (1H, s) | 513 |
| 375 | 1-(2-benzyloxyphenyl)-1-methylethyl | 1.11-1.18 (2H, m), 1.44-1.48 (2H, m), 1.73-1.85 (5H, m), 2.15 (2H, d), 2.48-2.56 (1H, m), 5.21 (2H, s), 6.99-7.03 (1H, m), 7.08-7.12 (1H, m), 7.15-7.17 (1H, m), 7.22 (2H, d), 7.29-7.39 (3H, m), 7.50 (2H, d), 7.67-7.70 (2H, m), 7.86-7.88 (1H, m), 10.06 (1H, s), 10.87 (1H, s), 11.97 (1H, s) | 527 |
| 376 | 1-(3-benzamidophenyl)-1-methylethyl | δ1.13 (2H, d), 1.44-1.48 (2H, m), 1.65-1.87 (5H, m), 2.14-2.16 (2H, m), 2.48-2.56 (1H, m), 7.23 (2H, d), 7.36 (1H, t), 7.43-7.46 (2H, m), 7.52-7.61 (3H, m), 7.69 (2H, d), 7.97-7.99 (2H, m), 8.07 (1H, t), 10.35 (1H, s), 10.89 (1H, s), 10.97 (1H, s), 11.98 (1H, s) | 540 |
| 377 | 1-(4-methanesulfonyloxyphenyl)-1-methylethyl | 1.11-1.17 (2H, m), 1.44-1.48 (2H, m), 1.74-1.85 (5H, m), 2.15 (2H, d), 2.48-2.56 (1H, m), 3.35 (3H, s), 7.23 (2H, d), 7.39-7.41 (2H, m), 7.68-7.70 (4H, m), 10.93 (1H, s), 11.16 (1H, s), 11.98 (1H, s) | 515 |
| 378 | 1-(3-phenylsulfonylphenyl)-1-methylethyl | δ1.12-1.17 (2H, m), 1.44-1.48 (2H, m), 1.74-1.85 (5H, m), 2.15 (2H, d), 2.46-2.53 (1H, m), 7.22-7.25 (2H, m), 7.61-7.74 (7H, m), 7.82-7.84 (1H, m), 7.95-7.97 (2H, m), 8.28 (1H, d), 10.94 (1H, s), 11.39 (1H, s), 11.98 (1H, s) | 561 |

-continued

| Example | R | ¹H NMR δ | MS m/e MH⁺ |
|---|---|---|---|
| 379 | 3-(OSO₂CH₃)phenyl, gem-dimethyl | 1.08-1.18 (2H, m), 1.41-1.51 (2H, m), 1.72-1.85 (5H, m), 2.15 (2H, d), 2.42-2.48 (1H, m), 3.40 (3H, s), 7.05-7.08 (1H, m), 7.23 (2H, d), 7.51 (1H, t), 7.56-7.59 (1H, m), 7.66 (1H, t), 7.68 (1H, s), 7.71 (1H, s), 10.94 (1H, s), 11.27 (1H, s), 11.98 (1H, s) | 515 |
| 380 | 2-(OSO₂CH₃)phenyl, gem-dimethyl | 1.07-1.17 (2H, m), 1.42-1.50 (2H, m), 1.72-1.85 (5H, m), 2.14-2.16 (2H, m), 2.42-2.48 (1H, m), 3.50 (3H, s), 7.19-7.24 (3H, m), 7.42-7.48 (2H, m), 7.69 (2H, d), 8.18-8.21 (1H, m), 10.64 (1H, s), 10.95 (1H, s), 11.97 (1H, s) | 515 |
| 381 | 2-(OMe)phenyl, gem-dimethyl | 1.08-1.17 (2H, m), 1.42-1.50 (2H, m), 1.73-1.85 (5H, m), 2.15 (2H, d), 2.42-2.48 (1H, m), 3.85 (3H, s), 6.99-7.03 (1H, m), 7.09-7.15 (2H, m), 7.22 (2H, d), 7.68 (2H, d), 7.92-7.94 (1H, m), 10.04 (1H, s), 10.88 (1H, s), 11.97 (1H, s) | 451 |
| 382 | 3-(NHC(O)NH₂)phenyl, gem-dimethyl | 1.08-1.17 (2H, m), 1.42-1.50 (2H, m), 1.72-1.85 (5H, m), 2.15 (2H, d), 2.42-2.48 (1H, m), 5.82 (2H, s), 7.17-7.24 (5H, m), 7.61-7.61 (1H, m), 7.68-7.70 (2H, m), 8.61 (1H, s), 10.84 (1H, s), 10.88 (1H, s), 11.97 (1H, s) | 479 |
| 383 | 3-(NHC(O)OMe)phenyl, gem-dimethyl | 1.08-1.14 (2H, m), 1.42-1.50 (2H, m), 1.71-1.85 (5H, m), 2.15 (2H, d), 2.42-2.48 (1H, m), 3.68 (3H, s), 7.14 (1H, d), 7.22-7.34 (4H, m), 7.69 (2H, d), 7.75 (1H, t), 9.70 (1H, s), 10.88-10.91 (2H, m), 11.97 (1H, s) | 494 |
| 384 | 4-(morpholino)phenyl, gem-dimethyl | 1.08-1.17 (2H, m), 1.41-1.50 (2H, m), 1.71-1.84 (5H, m), 2.15 (2H, d), 2.42-2.48 (1H, m), 3.53-5.30 (8H, m), 7.22 (4H, d), 7.54 (2H, d), 7.69 (2H, d), 10.82 (1H, s), 10.89 (1H, s) | 506 |

-continued
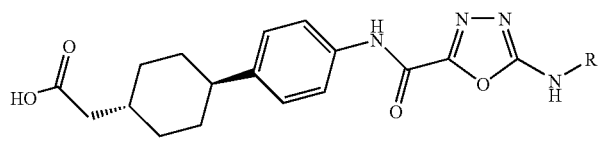
| Example | R | ¹H NMR δ | MS m/e MH⁺ |
|---|---|---|---|
| 385 | (4-SO₂Ph-phenyl) | 1.11-1.17 (2H, m), 1.41-1.50 (2H, m), 1.79-1.82 (5H, m), 2.15 (2H, d), 2.42-2.50 (1H, m), 7.23 (2H, d), 7.60-7.70 (5H, m), 7.80 (2H, d), 7.93-7.95 (2H, m), 8.00 (2H, d), 10.96 (1H, s), 11.55 (1H, s), 11.97 (1H, s) | 559 |
| 386 | (2-S(O)Ph-phenyl, gem-dimethyl) | 1.11-1.15 (2H, m), 1.44-1.48 (2H, m), 1.74-1.85 (5H, m), 2.15 (2H, d), 2.42-2.53 (1H, m), 7.23 (2H, d), 7.35-7.50 (1H, m), 7.53-7.57 (2H, m), 7.61-7.69 (3H, m), 7.70-7.80 (1H, m), 7.93-7.95 (3H, m), 8.12 (1H, d), 10.11 (1H, s), 10.84 (1H, s), 11.97 (1H, s) | 561 |
| 387 | (2-CN-phenyl, gem-dimethyl) | 1.13-1.18 (2H, m), 1.43-1.54 (2H, m), 1.74-1.85 (5H, m), 2.16 (2H, d), 2.43-2.51 (1H, m), 7.25 (2H, d), 7.45 (1H, d), 7.50 (1H, d), 7.76-7.78 (3H, m), 8.26-8.28 (1H, m), 10.67 (1H, s), 11.98 (1H, s), 12.47 (1H, s) | 446 |
| 388 | (4-NHPh-phenyl) | 1.10-1.20 (2H, m), 1.40-1.52 (2H, m), 1.74-1.90 (5H, m), 2.15 (2H, d), 2.43-2.51 (1H, m), 6.77 (1H, t), 6.97-7.04 (2H, m), 7.13 (2H, d), 7.18-7.24 (4H, m), 7.33 (2H, d), 7.48-7.50 (2H, m), 7.69 (2H, d), 8.03 (1H, s), 10.72 (1H, s), 10.88 (1H, s), 11.97 (1H, s) | 512 |
| 389 | (3-NHPh-phenyl, gem-dimethyl) | 1.08-1.18 (2H, m), 1.41-1.51 (2H, m), 1.71-1.85 (5H, m), 2.15 (2H, d), 2.41-2.52 (1H, m), 6.74-6.76 (1H, m), 6.85 (1H, t), 7.02-7.04 (1H, m), 7.12-7.15 (2H, m), 7.19-7.27 (5H, m), 7.48 (1H, t), 7.69 (2H, d), 8.27 (1H, s), 10.82 (1H, s), 10.89 (1H, s), 11.97 (1H, s) | 512 |
| 390 | (4-SO₂Et-phenyl) | 1.10-1.15 (5H, m), 1.44-1.48 (2H, m), 1.74-1.85 (5H, m), 2.15 (2H, d), 2.42-2.51 (1H, m), 3.25 (2H, q), 7.24 (2H, d), 7.70 (2H, d), 7.82-7.85 (2H, m), 7.90-7.92 (2H, m), 10.98 (1H, s), 11.56 (1H, s), 11.97 (1H, s) | 513 |

Example 391

Methyl 1-[(trans-4-{4-[({5-[(2-fluorophenyl)amino]-1,3,4-oxadiazol-2-yl}carbonyl)amino]phenyl}cyclohexyl)acetyl]piperidine-4-carboxylate

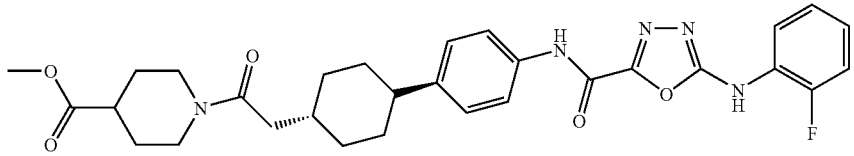

To a solution of (trans-4-{4-[({5-[(2-fluorophenyl)amino]-1,3,4-oxadiazol-2-yl}carbonyl)amino]phenyl}cyclohexyl)acetic acid (Example 112, 300 mg, 0.68 mmol) in DMF (3 mL) was added HATU (286 mg, 0.75 mmol), diisopropylethylamine (0.14 mL, 0.75 mmol) followed by methyl isonipecotate (0.15 mL, 0.75 mmol). The reaction mixture was allowed to stir at ambient temperature overnight. The DMF was evaporated and the residue re-dissolved in DMSO/MeCN/H$_2$O (7:2:1); a suspension formed which was filtered, washed with ether (2×10 mL) and dried to leave the title compound (137 mg). The filtrate was purified on an acidic reverse phase HPLC system eluting 5-95% MeCN 0.2% TFA, isolated 112 mg of the title compound (249 mg, 65%) as a solid; $^1$H NMR δ 1.07-1.16 (m, 2H), 1.36-1.53 (m, 4H), 1.75-1.88 (m, 7H), 2.24 (d, 2H), 2.41-2.47 (m, 1H), 2.59-2.65 (m, 2H), 3.11 (t, 1H), 3.62 (s, 3H), 3.85 (d, 1H), 4.26 (d, 1H), 7.14-7.34 (m, 5H), 7.68 (d, 2H), 8.04 (t, 1H), 10.75 (s, 1H), 10.93 (s, 1H); MS m/e MH$^+$ 564.

Examples 392-400

The following examples were prepared by the general procedure of Example 391 using the appropriate amine in place of methyl isonipecotate:

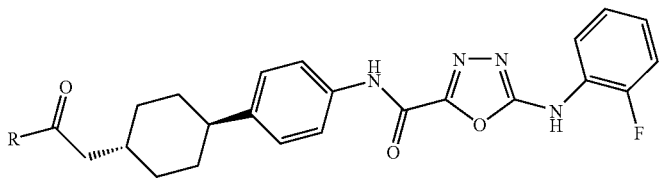

| Example | R | $^1$H NMR δ | MS m/e MH$^+$ |
|---|---|---|---|
| 392 | ![R group with methyl ester, gem-dimethyl, NH] | 1.04-1.13 (m, 2H), 1.34 (s, 6H), 1.39-1.48 (m, 2H), 1.72-1.81 (m, 5H), 1.99 (d, 2H), 2.41-2.46 (m, 1H), 3.55 (s, 3H), 7.14-7.34 (m, 5H), 7.68 (d, 2H), 8.04 (t, 1H), 8.13 (s, 1H), 10.75 (s, 1H), 10.93 (s, 1H) | 560 (M + Na)$^+$ |
| 393 | ![pyrrolidine methyl ester] | 1.07-1.17 (m, 2H), 1.40-1.49 (m, 2H), 1.77-1.93 (m, 8H), 2.12-2.28 (m, 3H), 2.41-2.46 (m, 1H), 3.53-3.58 (m, 2H), 3.61 (s, 3H), 4.28-4.31 (m, 1H), 7.13-7.34 (m, 5H), 7.69 (d, 2H), 8.06 (t, 1H), 10.75 (s, 1H), 10.99 (s, 1H) | 550 |
| 394 | ![pyrrolidine methyl ester] | 1.07-1.17 (m, 2H), 1.40-1.49 (m, 2H), 1.76-1.93 (m, 8H), 2.12-2.28 (m, 3H), 2.44-2.46 (m, 1H), 3.53-3.58 (m, 2H), 3.61 (s, 3H), 4.28-4.30 (m, 1H), 7.13-7.35 (m, 5H), 7.69 (d, 2H), 8.06 (t, 1H), 10.75 (s, 1H), 11.00 (s, 1H) | 572 (M + Na)$^+$ |

-continued

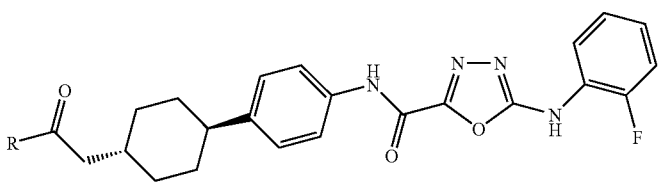

| Example | R | ¹H NMR δ | MS m/e MH⁺ |
|---|---|---|---|
| 395 | methyl (4-hydroxypyrrolidine-2-carboxylate) | 1.05-1.17 (m, 2H), 1.39-1.49 (m, 2H), 1.76-1.92 (m, 6H), 2.08-2.24 (m, 3H), 2.41-2.46 (m, 1H), 3.43-3.65 (m, 6H inc s, 3H 3.61), 4.30 (t, 1H), 4.34 (s, 1H), 7.14-7.35 (m, 5H), 7.69 (d, 2H), 8.06 (t, 1H), 10.82 (s, 1H), 11.00 (s, 1H) | 566 |
| 396 | 2-amino-2-methyl-1-propanol | 1.04-1.12 (m, 2H), 1.18 (s, 6H), 1.39-1.48 (m, 2H), 1.71-1.80 (m, 5H), 1.98 (d, 2H), 2.40-2.46 (m, 1H), 3.39 (s, 2H), 4.88 (s, 1H), 7.14-7.34 (m, 6H), 7.68 (d, 2H), 8.04 (t, 1H), 10.75 (s, 1H), 10.93 (s, 1H) | 532 M + Na |
| 397 | dioxolane-fused pyrrolidine | 1.08-1.17 (m, 2H), 1.24-1.27 (m, 1H), 1.40-1.49 (m, 2H), 1.78-1.84 (m, 5H), 2.11-2.23 (m, 2H), 2.41-2.47 (m, 1H), 3.53-3.57 (m, 1H), 3.70-3.76 (m, 2H), 4.64-4.67 (m, 1H), 4.70-4.73 (m, 1H), 4.79 (s, 1H), 4.99 (s, 1H), 7.14-7.34 (m, 5H), 7.67 (d, 2H), 8.04 (t, 1H), 10.75 (s, 1H), 10.93 (s, 1H) | 536 |
| 398 | dimethylamino | 1.07-1.15 (m, 2H), 1.40-1.49 (m, 2H), 1.77-1.84 (m, 5H), 2.22 (d, 2H), 2.42-2.48 (m, 1H), 2.82 (s, 3H), 2.98 (s, 3H), 7.14-7.34 (m, 5H), 7.68 (d, 2H), 8.04 (t, 1H), 10.75 (s, 1H), 10.93 (s, 1H) | 466 |
| 399 | N-methyl-N-(2-hydroxyethyl)amino | 1.11 (m, 2H), 1.45 (m, 2H), 1.81 (m, 5H), 2.24 (m, 2H), 2.43 (m, 1H), 3.02 (s, 1.5H, NCH3), 3.02 (s, 1.5H, NCH3), 3.33-3.38 (m, 2H), 3.45-3.55 (m, 2H), 4.60 (t, 0.5H, OH), 4.77 (t, 0.5H, OH), 7.14-7.34 (m, 5H), 7.68 (d, 2H), 8.04 (t, 1H), 10.75 (s, 1H), 10.93 (s, 1H)(rotamers detected) | 496 |
| 400 | 3-amino-1,2-propanediol | 1.05-1.13 (m, 2H), 1.39-1.48 (m, 2H), 1.71-1.80 (m, 5H), 2.04 (d, 2H), 2.41-2.47 (m, 1H), 2.97-3.04 (m, 1H), 3.17-3.23 (m, 2H), 3.46-3.51 (m, 1H), 4.39-4.78 (m, 1H), 7.14-7.34 (m, 5H), 7.68 (d, 2H), 7.77 (t, 1H), 8.04 (t, 1H), 10.75 (s, 1H), 10.93 (s, 1H) | 533 (M + Na)⁺ |

Examples 401-405

The following examples were prepared by the general procedure of Example 112 using the appropriate starting material selected from Examples 391-395

| Example | Name | $^1$H NMR δ | MS m/e MH$^+$ |
|---|---|---|---|
| 401 | 1-[(trans-4-{4-[({5-[(2-fluorophenyl)amino]-1,3,4-oxadiazol-2-yl}carbonyl)amino]phenyl}-cyclohexyl)acetyl]piperidine-4-carboxylic acid | 1.10-1.16 (m, 2H), 1.34-1.49 (m, 4H), 1.74-1.83 (m, 7H), 2.24 (d, 2H), 2.68-2.75 (m, 1H), 3.10 (t, 3H), 3.84 (d, 1H), 4.25 (d, 1H), 7.14-7.34 (m, 5H), 7.68 (d, 2H), 8.04 (t, 1H), 10.75 (s, 1H), 10.93 (s, 1H), 12.22 (s, 1H) | 550 |
| 402 | N-[(trans-4-{4-[({5-[(2-fluorophenyl)amino]-1,3,4-oxadiazol-2-yl}carbonyl)amino]phenyl}-cyclohexyl)acetyl]-2-methylalanine | 1.04-1.13 (m, 2H), 1.33 (s, 6H), 1.38-1.47 (m, 2H), 1.72-1.83 (m, 5H), 1.99 (d, 2H), 2.41-2.47 (m, 1H), 7.14-7.34 (m, 5H), 7.68 (d, 2H), 7.96 (s, 1H), 8.04 (t, 1H), 10.75 (s, 1H), 10.93 (s, 1H), 12.00 (s, 1H) | 524 |
| 403 | 1-[(trans-4-{4-[({5-[(2-fluorophenyl)amino]-1,3,4-oxadiazol-2-yl}carbonyl)amino]phenyl}-cyclohexyl)acetyl]-D-proline | 1.05-1.16 (m, 2H), 1.39-1.49 (m, 2H), 1.76-1.93 (m, 8H), 2.12-2.26 (m, 3H), 2.41-2.46 (m, 1H), 3.51-3.56 (m, 2H), 4.21-4.24 (m, 1H), 7.13-7.34 (m, 5H), 7.69 (d, 2H), 8.06 (t, 1H), 10.82 (s, 1H), 11.00 (s, 1H). CO$_2$H not seen | 536 |
| 404 | 1-[(trans-4-{4-[({5-[(2-fluorophenyl)amino]-1,3,4-oxadiazol-2-yl}carbonyl)amino]phenyl}-cyclohexyl)acetyl]-L-proline | 1.07-1.17 (m, 2H), 1.40-1.49 (m, 2H), 1.76-1.93 (m, 8H), 2.12-2.26 (m, 3H), 2.41-2.47 (m, 1H), 3.51-3.56 (m, 2H), 4.21-4.24 (m, 1H), 7.14-7.35 (m, 5H), 7.69 (d, 2H), 8.06 (t, 1H), 10.82 (s, 1H), 11.00 (s, 1H), 12.36 (s, 1H) CO2H not seen | 534 (M − H)$^-$ |
| 405 | (4R)-1-[(trans-4-{4-[({5-[(2-fluorophenyl)amino]-1,3,4-oxadiazol-2-yl}carbonyl)amino]phenyl}-cyclohexyl)acetyl]-4-hydroxy-L-proline | 1.04-1.18 (m, 2H), 1.39-1.48 (m, 2H), 1.76-1.92 (m, 6H), 2.07-2.19 (m, 3H), 2.41-2.47 (m, 1H), 3.60-3.64 (m, 2H), 4.23 (t, 1H), 4.99 (s, 1H), 4.99 (s, 1H), 5.15 (s, 1H), 7.13-7.34 (m, 5H), 7.69 (d, 2H), 8.06 (t, 1H), 11.00 (s, 1H) CO2H not seen | 552 |

Example 406

Methyl (trans-4-{5-[({5-[(2,4,5-trifluorophenyl-amino]-1,3,4-oxadiazol-2-yl}carbonyl)amino]pyridin-2-yl}cyclohexyl)acetate

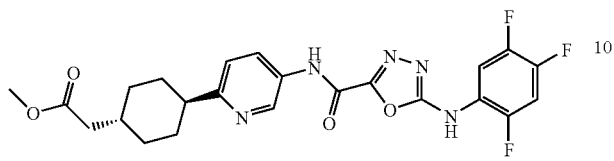

Following the procedure described in Example 105 except using methyl [trans-4-(5-{[hydrazino(oxo)acetyl]amino}pyridin-2-yl)cyclohexyl]acetate (Intermediate 78) and 2,4,5-trifluorophenylisothiocyanate as starting materials, the title compound was isolated in 79% yield; $^1$H NMR δ 1.10-1.19 (m, 2H), 1.48-1.58 (m, 2H), 1.72-1.89 (m, 5H), 2.25 (d, 2H), 2.57-2.66 (m, 1H), 3.61 (s, 3H), 7.29 (d, 1H), 7.67-7.74 (m, 1H), 8.08 (d, 1H), 8.12-8.20 (m, 1H), 8.84 (d, 1H), 11.07 (s, 1H), 11.20 (s, 1H); MS m/e MH$^+$ 490.

Example 407

(trans-4-{5-[({5-[(2,4,5-Trifluorophenyl)amino]-1,3,4-oxadiazol-2-yl}carbonyl)amino]pyridin-2-yl}cyclohexyl)acetic acid

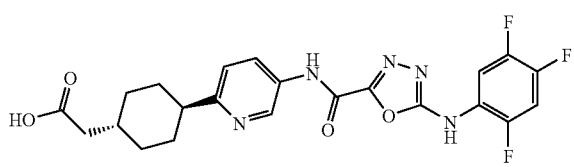

To a solution of methyl (trans-4-{5-[({5-[(2,4,5-trifluorophenyl)amino]-1,3,4-oxadiazol-2-yl}carbonyl)amino]pyridin-2-yl}cyclohexyl)acetate (Example 406, 355 mg, 0.725 mmol) in THF (5 mL) and MeOH (25 mL) was added a 2M solution of NaOH (1.8 mL). The resulting yellow solution was allowed to stir at ambient temperature for 16 hr then a further 1.8 mL of 2M NaOH was added and stirring was continued at ambient temperature for 16 hr. The volatile organics were removed by evaporation and residue adjusted to pH ~1 with 2M HCl and the suspension was filtered and dried to leave 410 mg of a solid. This was suspended in acetic acid (4 mL) and heated to 120° C., giving an incomplete solution. This was allowed to cool, filtered and washed with water then dried overnight, to give the title compound (167 mg, 48%) as a solid; $^1$H NMR (CDCl$_3$) δ 1.10-1.19 (m, 2H), 1.56-1.65 (m, 2H), 1.72-1.79 (m, 1H), 1.85-1.94 (m, 4H), 2.17 (d, 2H), 2.79-2.85 (m, 1H), 7.67-7.76 (m, 2H), 8:12-8.19 (m, 1H), 8.44 (d, 1H), 9.01 (s, 1H), 11.14 (s, 1H), 11.58 (s, 1H), CO$_2$H not seen; MS m/e MH$^+$ 476.

Example 408

[trans-4-(4-{[(5-{[4-(2-Hydroxyethyl)phenyl]amino}-1,3,4-oxadiazol-2-yl)carbonyl]amino}phenyl)cyclohexyl]acetic acid

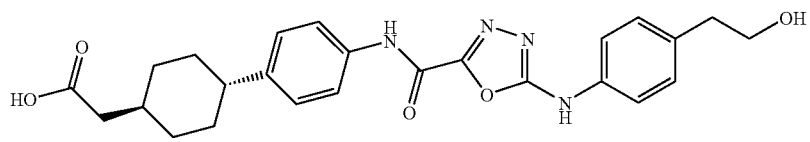

Thiocarbonyl diimidazole (117 mg, 0.65 mmol) was added in one portion to a stirred solution of 4-aminophenethyl alcohol (89 mg, 0.65 mmol) in DMA (2.5 mL) and the mixture was stirred at room temperature under an argon atmosphere for 2 h. Methyl [trans-4-(4-{[hydrazino(oxo)acetyl]amino}phenyl)cyclohexyl]acetate (Intermediate 43, 167 mg, 0.50 mmol) was added and the mixture was stirred at 80° C. for 10 minutes in a microwave. EDCI (125 mg, 0.65 mmol) was then added in one portion and the reaction mixture was heated at 90° C. for 10 minutes in a microwave. The reaction mixture was poured onto water, stirred for 30 minutes and then filtered to leave the crude oxadiazole methyl ester intermediate as a brown solid (230 mg) that was used with no further purification; MS m/e MH$^+$ 479.

A solution of lithium hydroxide (170 mg, 4.0 mmol) in H$_2$O (3 mL) was added in one portion to a solution of the crude oxadiazole product (230 mg) in a mixture of THF:MeOH (1:1, 10 mL) and the reaction mixture was stirred for 20 h. Citric acid (15 mL) was added and the mixture was stirred for 30 minutes and then filtered. The solid was washed twice with water, twice with diethylether and once with isohexane to give the title compound (150 mg, 67%) as a solid; $^1$H NMR δ 1.04-1.2 (2H, m), 1.38-1.55 (2H, m), 1.65-1.9 (5H, m), 2.15 (2H, d), 2.38-2.55 (1H, m), 2.71 (2H, t), 3.523.67 (2H, m), 4.6 (1H, t), 7.21 (2H, d), 7.22 (2H, d), 7.51 (2H, d), 7.7 (2H, d), 10.8 (1H, s), 10.9 (1H, s), 12.0 (1H, s); MS m/e MH$^+$ 465. -

Examples 409-423

The following Examples were prepared by the general procedure of Example 408, using methyl [trans-4-(4-{[hydrazino(oxo)acetyl]amino}phenyl)cyclohexyl]acetate (Intermediate 43) and the appropriate commercially available aniline, RNH$_2$.

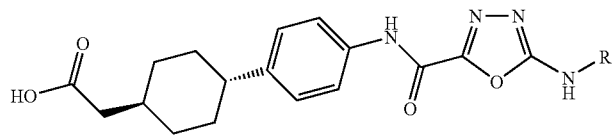

| Example | R | ¹H NMR δ | MS m/e MH⁺ |
|---|---|---|---|
| 409 | (3-ethynylphenyl)methyl | 1.04-1.2 (2H, m), 1.38-1.55 (2H, m), 1.65-1.9 (5H, m), 2.15 (2H, d), 2.38-2.55 (1H, m), 4.2 (1H, s), 7.18 (1H, dd), 7.23 (2H, d), 7.42 (1H, dd), 7.53 (1H, dd), 7.7 (1H, d), 7.77 (1H, s), 10.9 (1H, s), 11.15 (1H, s), 12.0 (1H, s) | 445 |
| 410 | (4-cyanomethylphenyl)methyl | 1.04-1.2 (2H, m), 1.38-1.55 (2H, m), 1.65-1.9 (5H, m), 2.15 (2H, d), 2.38-2.55 (1H, m), 4.0 (2H, s), 7.24 (2H, d), 7.4 (2H, d), 7.62 (2H, d), 7.7 (2H, d), 10.9 (1H, s), 11.1 (1H, s), 12.0 (1H, s) | 460 |
| 411 | (biphenyl-2-yl)methyl | 1.04-1.2 (2H, m), 1.38-1.55 (2H, m), 1.65-1.9 (5H, m), 2.15 (2H, d), 2.38-2.55 (1H, m), 7.2 (2H, d), 7.3-7.5 (8H, m), 7.65 (2H, d), 7.75 (1H, dd), 10.1 (1H, s), 10.85 (1H, s), 12.05 (1H, s) | 497 |
| 412 | (4-tert-butoxyphenyl)methyl | 1.04-1.2 (2H, m), 1.29 (9H, s), 1.38-1.55 (2H, m), 1.65-1.9 (5H, m), 2.15 (2H, d), 2.38-2.55 (1H, m), 7.01 (2H, d), 7.24 (2H, d), 7.52 (2H, d), 7.7 (2H, d), 10.8 (1H, s), 10.9 (1H, s), 12.0 (1H, s) | 493 |
| 413 | (4-phenoxyphenyl)methyl | 1.04-1.2 (2H, m), 1.38-1.55 (2H, m), 1.65-1.9 (5H, m), 2.15 (2H, d), 2.38-2.55 (1H, m), 7.0 (2H, d), 7.1 (2H, d), 7.11 (1H, dd), 7.22 (2H, d), 7.36 (2H, dd), 7.61 (2H, d), 7.7 (2H, d), 10.9 (1H, s), 10.95 (1H, s), 12.0 (1H, s) | 513 |
| 414 | [4-(1,2,4-triazol-1-yl)phenyl]methyl | 1.04-1.2 (2H, m), 1.38-1.55 (2H, m), 1.65-1.9 (5H, m), 2.15 (2H, d), 2.38-2.55 (1H, m), 7.23 (2H, d), 7.7 (2H, d), 7.79 (2H, d), 7.9 (2H, d), 8.23 (1H, s), 9.2 (1H, s), 10.9 (1H, s), 11.2 (1H, s) | 488 |
| 415 | (4-benzylphenyl)methyl | 1.04-1.2 (2H, m), 1.38-1.55 (2H, m), 1.65-1.9 (5H, m), 2.15 (2H, d), 2.38-2.55 (1H, m), 3.94 (2H, s), 7.25 (9H, m), 7.53 (2H, d), 7.7 (2H, d), 10.85 (1H, s), 10.89 (1H, s), 11.95 (1H, s) | 511 |
| 416 | (3-acetamidophenyl)methyl | 1.04-1.2 (2H, m), 1.38-1.55 (2H, m), 1.65-1.9 (5H, m), 2.05 (3H, s), 2.15 (2H, d), 2.38-2.55 (1H, m), 7.22 (2H, d), 7.32 (3H, m), 7.7 (2H, d), 7.84 (1H, s), 10.0 (1H, s), 10.87 (1H, s), 10.92 (1H, s), 12.0 (1H, s) | 478 |

-continued

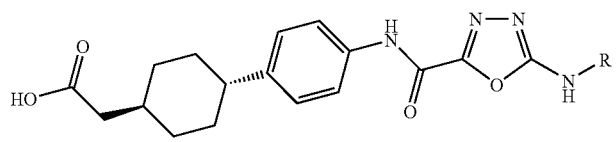

| Example | R | ¹H NMR δ | MS m/e MH⁺ |
|---|---|---|---|
| 417 | 3-Cl-phenyl | 1.04-1.2 (2H, m), 1.38-1.55 (2H, m), 1.65-1.9 (5H, m), 2.15 (2H, d), 2.38-2.55 (1H, m), 7.13 (1H, dd), 7.22 (2H, d), 7.44 (1H, dd), 7.54 (1H, dd), 7.7 (2H, d), 7.75 (1H, d), 10.94 (1H, s), 11.2 (1H, s), 12.0 (1H, s) | 455 |
| 418 | 4-ethynyl-phenyl | 1.04-1.2 (2H, m), 1.38-1.55 (2H, m), 1.65-1.9 (5H, m), 2.15 (2H, d), 2.38-2.55 (1H, m), 4.11 (1H, s), 7.25 (2H, d), 7.54 (2H, d), 7.64 (2H, d), 7.7 (2H, d), 11.0 (1H, s), 11.28 (1H, s), 12.05 (1H, s) | 445 |
| 419 | 3-Br-phenyl | 1.04-1.2 (2H, m), 1.38-1.55 (2H, m), 1.65-1.9 (5H, m), 2.15 (2H, d), 2.38-2.55 (1H, m), 7.22 (2H, d), 7.24 (1H, dd), 7.36 (2H, dd), 7.58 (2H, dd), 7.7 (2H, d), 7.98 (1H, d), 10.95 (1H, s), 11.19 (1H, s), 11.95 (1H, s) | 499 |
| 420 | 3-OCHF₂-phenyl | 1.04-1.2 (2H, m), 1.38-1.55 (2H, m), 1.65-1.9 (5H, m), 2.15 (2H, d), 2.38-2.55 (1H, m), 6.85-6.95 (1H, m), 7.2 (1H, t), 7.22 (2H, d), 7.42 (2H, dd), 7.5 (1H, s), 7.7 (2H, d), 10.92 (1H, s), 11.19 (1H, s), 11.96 (1H, s) | 487 |
| 421 | 3-(CH₂OCH₃)-phenyl | 1.04-1.2 (2H, m), 1.38-1.55 (2H, m), 1.65-1.9 (5H, m), 2.15 (2H, d), 2.38-2.55 (1H, m), 3.3 (3H, s), 4.54 (2H, s), 7.21 (1H, dd), 7.23 (2H, d), 7.38 (1H, dd), 7.4 (1H, dd), 7.7 (2H, d), 7.81 (1H, dd), 9.88 (1H, s), 10.9 (1H, s), 12.0 (1H, s) | 465 |
| 422 | 3-(2-methylpyrimidin-4-yl)-phenyl | 1.04-1.2 (2H, m), 1.38-1.55 (2H, m), 1.65-1.9 (5H, m), 2.15 (2H, d), 2.38-2.55 (1H, m), 2.72 (3H, s), 7.23 (2H, d), 7.58 (1H, dd), 7.7 (2H, d), 7.8-7.9 (3H, m), 8.47 (1H, s), 8.79 (1H, d), 10.9 (1H, s), 11.15 (1H, s), 12.0 (1H, s) | 513 |
| 423 | 4-cyclohexyl-phenyl | 1.0-1.55 (10H, m), 1.62-1.9 (9H, m), 2.15 (2H, d), 2.36-2.6 (2H, m), 7.21 (2H, d), 7.23 (2H, d), 7.52 (2H, d), 7.7 (2H, d), 10.8 (1H, s), 10.9 (1H, s), 11.9 (1H, s) | 503 |

Example 424

Methyl {trans-4-[4-({[5-(pyrimidin-4-ylamino)-1,3,4-oxadiazol-2-yl]carbonyl}amino)-phenyl]cyclohexyl}acetate

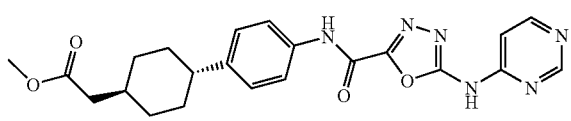

Di-2-pyridyl thionocarbonate (367 mg, 1.58 mmol) was added in one portion to a stirred solution of 4-aminopyrimidine (150 mg, 1.58 mmol) in DCM (3 mL) and the reaction mixture was heated at 100° C. for 20 minutes in the microwave and then cooled to room temperature. This solution was added to a suspension of methyl [trans-4-(4-{[hydrazino(oxo)acetyl]amino}-phenyl)cyclohexyl]acetate (Intermediate 43, 421 mg, 1.26 mmol) in DCM (5 mL) and the mixture stirred at room temperature for 5 minutes. DMF (8 mL) was added and the DCM was removed under reduced pressure. The solution was heated at 85° C. for 40 minutes in the microwave and then cooled to room temperature. EDCI (303 mg, 1.58 mmol) was added in one portion and the reaction mixture was heated at 85° C. for 60 minutes in the microwave. The reaction was quenched by the addition of H$_2$O (200 mL) and EtOAc (250 mL) was added. The layers were separated and the aqueous layer was extracted with EtOAc (2×150 mL). The combined organic layer was washed with brine (100 mL), dried (MgSO$_4$) and concentrated in vacuo to leave a dark brown gummy solid. MeOH (40 mL) was added and the mixture was heated to reflux for 2 minutes and then cooled to room temperature to leave a white suspension. The solid was filtered to give the title compound (110 mg, 20%) as a solid; $^1$H NMR δ 1.10-1.17 (2H, m), 1.43-1.47 (2H, m), 1.75-1.81 (5H, m), 2.24-2.26 (2H, d), 2.44 (1H, t), 3.61 (3H, s), 7.24 (2H, d), 7.69-7.73 (2H, m), 7.92 (1H, d), 8.69 (1H, d), 8.87 (1H, s), 11.02 (1H, s); MS m/e MH$^+$ 437.

Example 425

Methyl (trans-4-{4-({5-[(1-methyl-1H-pyrazol-3-yl)amino]-1,3,4-oxadiazol-2-yl}-carbonyl)amino]phenyl}cyclohexyl)acetate

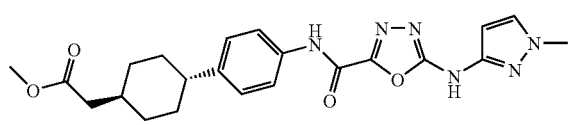

Di-2-pyridyl thionocarbonate (359 mg, 1.54 mmol) was added in one portion to a stirred solution of 3-amino-1-methylpyrazole (150 mg, 1.54 mmol) in CH$_3$CN (8 mL) and the reaction mixture was heated at 80° C. for 10 minutes in the microwave and then cooled to room temperature. Methyl [trans-4-(4-{[hydrazino(oxo)acetyl]amino}-phenyl)cyclohexyl]acetate (Intermediate 43, 412 mg, 1.24 mmol) in DCM (5 mL) was added in one portion and the mixture was heated at 85° C. for 20 minutes and then cooled to room temperature. EDCI (297 mg, 1.54 mmol) was added in one portion and the reaction mixture was heated to 85° C. for 30 minutes. The mixture was cooled to room temperature and filtered to leave a solid. The solid was washed with CH$_3$CN (5 mL) to give the title compound (373 mg, 69%) as a solid; $^1$H NMR δ 1.09-1.18 (2H, m), 1.41-1.50 (2H, m), 1.73-1.81 (5H, m), 2.24-2.26 (2H, d), 2.41-2.47 (1H, m), 3.61 (3H, s), 3.77 (3H, s), 6.41 (1H, d), 7.21-7.23 (2H, d), 7.64 (1H, d), 7.66-7.69 (2H, d), 10.84 (1H, s), 11.13 (1H, s);

MS m/e MH$^+$ 439.

Example 426

Methyl {trans-4-[4-({[5-(pyridin-3-ylamino)-1,3,4-oxadiazol-2-yl]carbonyl}amino)-phenyl]cyclohexyl}acetate

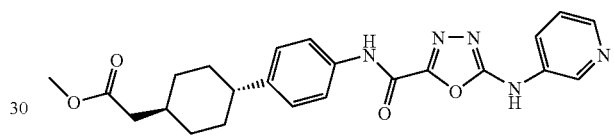

3-Pyridyl isothiocyanate (41 mg, 0.3 mmol) was added in one portion to a suspension of methyl [trans-4-(4-{[hydrazino(oxo)acetyl]amino}-phenyl)cyclohexyl]acetate (Intermediate 43, 100 mg, 0.3 mmol) in CH$_3$CN (5 mL) and the reaction mixture was heated at 80° C. for 10 minutes in the microwave and then cooled to room temperature. EDCI (58 mg, 0.3 mmol) was added in one portion and the reaction mixture was heated to 90° C. for 20 minutes. The mixture was cooled to room temperature and filtered to leave a solid. The solid was washed with CH$_3$CN (5 mL) to give the title compound (90 mg, 69%) as a solid; $^1$H NMR δ 1.12-1.18 (2H, m), 1.45 (2H, q), 1.80 (5H, m), 2.24-2.26 (2H, d), 2.42-2.48 (1H, m), 3.61 (3H, s), 7.23 (2H, d), 7.43-7.46 (1H, m), 7.69-7.71 (2H, m), 8.06-8.09 (1H, m), 8.28-8.29 (1H, m), 8.78 (1H, d), 10.95 (1H, s), 11.22 (1H, s); MS m/e MH$^+$ 436.

Example 427

Methyl {trans-4-[4-({[5-(Pyridin-4-ylamino)-1,3,4-oxadiazol-2-yl]carbonyl}amino)-phenyl]cyclohexyl}acetate

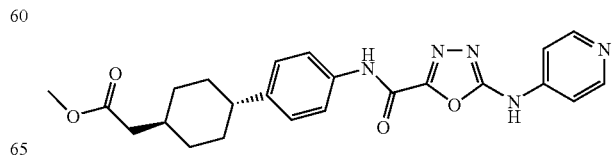

Thiocarbonyl diimidazole (190 mg, 1.06 mmol) was added in one portion to a solution of 4-aminopyridine (100 mg, 1.06 mmol) in DMA (8 mL) and the solution was stirred at room temperature for 3 h. Methyl [trans-4-(4-{[hydrazino(oxo) acetyl]amino}phenyl)cyclohexyl]-acetate (Intermediate 43, 284 mg, 0.85 mmol) was added in one portion and the reaction mixture was stirred at room temperature for 30 minutes and then heated at 80° C. for 10 minutes in the microwave. The solution was cooled to room temperature and EDCI (205 mg, 1.06 mmol) was added in one portion and the reaction mixture was heated to 90° C. for 20 minutes in the microwave. The reaction mixture was cooled to room temperature and poured into water (200 mL). The mixture was filtered and the resulting solid was recrystallised (CH$_3$CN) to give the title compound (93 mg, 20%) as a solid; $^1$H NMR δ 1.15 (2H, t), 1.42-1.51 (2H, m), 1.74-1.82 (5H, m), 2.24-2.26 (2H, d), 3.61 (3H, s), 7.23 (2H, d), 7.54-7.55 (2H, m), 7.69-7.71 (2H, m), 8.43 (2H, s) MS m/e MH$^+$ 436.

Example 428

Methyl {trans-4-[4-({[5-(pyrazin-2-ylamino)-1,3,4-oxadiazol-2-yl]carbonyl}amino)-phenyl]cyclohexyl}acetate

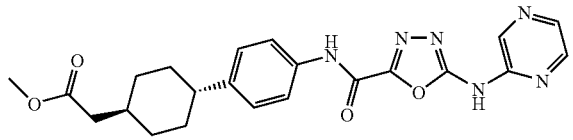

Thiocarbonyl diimidazole (179 mg, 1.00 mmol) was added in one portion to a solution of aminopyrazine (96 mg, 1.00 mmol) in DMA (5 mL) and the solution was stirred at room temperature for 6 h. Methyl [trans-4-(4-{[hydrazino(oxo) acetyl]amino}phenyl)cyclohexyl]-acetate (Intermediate 43, 267 mg, 0.80 mmol) was added in one portion and the reaction mixture was stirred at room temperature for 20 h and then heated at 80° C. for 10 minutes in the microwave. The solution was cooled to room temperature and EDCI (192 mg, 1.00 mmol) was added in one portion and the reaction mixture was heated to 90° C. for 15 minutes in the microwave. The reaction mixture was cooled to room temperature and poured into water (200 mL). The mixture was filtered and the resulting solid was recrystallised (CH$_3$CN) to give the title compound as an off white solid (35 mg, 8%); $^1$H NMR δ 1.15 (2H, m), 1.45-1.48 (2H, m), 1.79 (6H, m), 2.26 (2H, d), 2.45-2.49 (1H, m), 3.61 (3H, s), 7.23-7.25 (2H, d), 7.69-7.71 (2H, d), 8.36 (1H, d), 8.42 (1H, t), 9.19 (1H, s), 11.01 (1H, s); MS m/e MH$^+$ 437.

Example 429

Methyl {trans-4-[4-({[5-(1,3-thiazol-2-ylamino)-1,3,4-oxadiazol-2-yl]carbonyl}-amino)phenyl]cyclohexyl}acetate

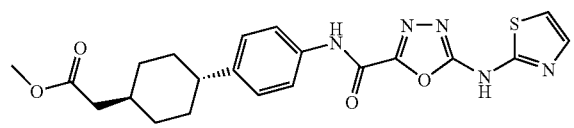

Thiocarbonyl diimidazole (179 mg, 1.00 mmol) was added in one portion to a solution of 2-aminothiazole (100 mg, 1.00 mmol) in DMA (5 mL) and the solution was stirred at room temperature for 6 h. Methyl [trans-4-(4-{[hydrazino(oxo) acetyl]amino}phenyl)cyclohexyl]-acetate (Intermediate 43, 267 mg, 0.80 mmol) was added in one portion and the reaction mixture was stirred at room temperature for 20 h and then heated at 80° C. for 10 minutes in the microwave. The solution was cooled to room temperature and EDCI (192 mg, 1.00 mmol) was added in one portion and the reaction mixture was heated to 90° C. for 15 minutes in the microwave. The reaction mixture was cooled to room temperature and poured into water (200 mL). The mixture was filtered and the resulting solid was recrystallised (CH$_3$CN) to give the title compound (130 mg, 29%) as a solid; $^1$H NMR δ 1.09-1.18 (2H, m), 1.42-1.47 (2H, m), 1.79 (5H, m), 2.24-2.26 (2H, d), 2.45 (1H, t), 3.61 (3H, s), 6.99 (1H, d), 7.22 (2H, d), 7.38 (1H, d), 7.67-7.70 (2H, m), 10.78 (1H, s);

MS m/e MH$^+$ 442.

Example 430

{trans-4-[4-({[5-(Pyrimidin-4-ylamino)-1,3,4-oxadiazol-2-yl]carbonyl}amino)-phenyl]cyclohexyl}acetic acid

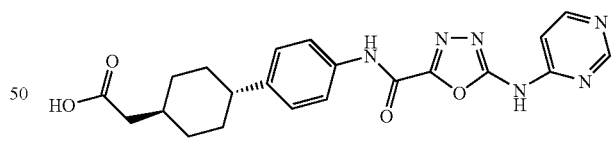

A solution of lithium hydroxide (101 mg, 2.41 mmol) in H$_2$O (1.5 mL) was added in one portion to a solution of methyl {trans-4-[4-({[5-(pyrimidin-4-ylamino)-1,3,4-oxadiazol-2-yl]-carbonyl}amino)phenyl]cyclohexyl}acetate (Example 416, 105 mg, 0.24 mmol) in a mixture of THF (1.8 mL) and MeOH (3 mL) and the reaction mixture was stirred at 35° C. for 2 h. Citric acid (50 mL) and EtOAc (50 mL) were added and the layers were separated and the aqueous layer was filtered to leave a solid. The solid was washed with water (10 mL) to give the title compound as a yellow brown solid (60 mg, 59%); $^1$H NMR δ 1.07-1.18 (2H, m), 1.41-1.51 (2H, m), 1.69-1.85 (5H, m), 2.14-2.16 (2H, d), 7.24 (2H, d), 7.71 (2H, d), 7.92 (1H, d), 8.69 (1H, d), 8.87 (1H, s), 11.00 (1H, s), 12.06 (2H, s); MS m/e MH$^+$ 423.

Examples 431-435

The following examples were prepared by the general procedure of Example 430 using the appropriate ester as starting material selected from Examples 425-429.

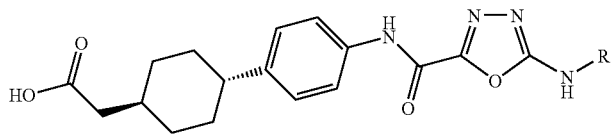

| Example | R | ¹H NMR δ | MS m/e MH⁺ |
|---|---|---|---|
| 431 | 1-methylpyrazol-5-yl | 1.07-1.17 (2H, m), 1.41-1.51 (2H, m), 1.70-1.84 (6H, m), 2.14-2.16 (2H, d), 3.77 (3H, s), 6.41-6.41 (1H, m), 7.21-7.23 (2H, d), 7.63-7.64 (1H, m), 7.66-7.69 (2H, d), 10.84 (1H, s), 11.13 (1H, s), 11.97 (1H, s) | 425 |
| 432 | pyridin-3-yl | 1.07-1.18 (2H, m), 1.41-1.51 (2H, m), 1.70-1.85 (5H, m), 2.14-2.16 (2H, d), 7.23 (2H, d), 7.43-7.46 (1H, m), 7.69-7.71 (2H, d), 8.06-8.09 (1H, m), 8.28-8.29 (1H, m), 8.78 (1H, d), 10.94 (1H, s), 11.22 (1H, s), 11.97 (1H, s) | 422 |
| 433 | pyridin-4-yl | 1.11-1.15 (2H, m), 1.45-1.49 (2H, m), 1.74-1.85 (5H, m), 2.15-2.16 (2H, d), 7.24 (2H, d), 7.54-7.55 (2H, m), 7.70 (2H, d), 8.42 (2H, s), 10.95 (1H, s) | 422 |
| 434 | pyrazin-2-yl | 1.12-1.15 (2H, m), 1.45-1.49 (2H, m), 1.82 (6H, m), 2.15-2.16 (2H, d), 7.24 (2H, d), 7.70 (2H, d), 8.36 (1H, d), 8.42-8.43 (1H, m), 9.19 (1H, s), 11.01 (1H, s) | 423 |
| 435 | thiazol-2-yl | 1.07-1.17 (2H, m), 1.41-1.51 (2H, m), 1.69-1.84 (6H, m), 2.15 (2H, d), 2.42-2.53 (1H, m), 6.99 (1H, d), 7.22 (2H, d), 7.38 (1H, d), 7.68 (2H, d), 10.78 (1H, s) | 428 |

Example 436

(trans-4-{4-[({5-[(1-Methyl-1H-pyrazol-5-yl)amino]-1,3,4-oxadiazol-2-yl}carbonyl)-amino]phenyl}cyclohexyl)acetic acid

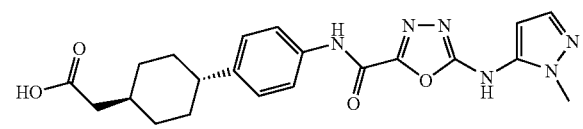

Thiocarbonyl diimidazole (179 mg, 1.00 mmol) was added in one portion to a solution of 5-amino-1-methylpyrazole (98 mg, 1.00 mmol) in DMA (5 mL) and the solution was stirred at room temperature for 6 h. Methyl [trans-4-(4-{[hydrazino(oxo)acetyl]amino}phenyl)-cyclohexyl]acetate (Intermediate 43, 267 mg, 0.80 mmol) was added in one portion and the reaction mixture was stirred at room temperature for 20 h and then heated at 80° C. for 10 minutes in the microwave. The solution was cooled to room temperature and EDCI (192 mg, 1.00 mmol) was added in one portion and the reaction mixture was heated to 90° C. for 15 minutes in the microwave. The reaction mixture was cooled to room temperature and poured into water (200 mL). The mixture was concentrated in vacuo to leave a gum, which was recrystallised (CH₃CN) to leave a gummy solid. Filtration followed by concentration in vacuo of the filtrate gave the crude oxadiazole methyl ester intermediate that was used with no further purification; MS m/e MH⁺ 439. Lithium hydroxide (420 mg, 10.0 mmol) was added in one portion to a solution of the crude oxadiazole methyl ester intermediate in a mixture of THF (4 mL), MeOH (8 mL) and water (4 mL) and the reaction mixture was stirred at 35° C. for 4 h. Citric acid (30 mL) was added and the mixture was filtered to leave a solid that was recrystallised (MeOH) to give the title compound (87 mg, 26%) as a solid; ¹H NMR δ 1.07-1.17 (2H, m), 1.41-1.51 (2H, m), 1.70-1.84 (5H, m), 2.14-2.16 (2H, d), 3.75 (3H, s), 6.70 (1H, s), 7.21-7.24 (2H, m), 7.40 (1H, s), 7.67-7.74 (2H, m); MS m/e MH⁺ 425.

Example 437

{trans-4-[4-({[5-(Pyrimidin-2-ylamino)-1,3,4-oxadiazol-2-yl]carbonyl}amino)-phenyl]cyclohexyl}acetic acid

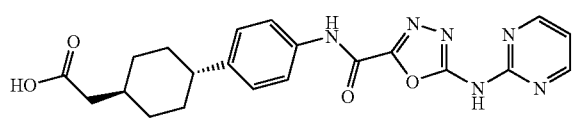

A suspension of 2-aminopyrimidine (100 mg, 1.05 mmol) in DCM (2 mL) was added to a solution of thiophosgene (81 μL, 1.05 mmol) in DCM (3 mL) and then triethylamine (294 μL, 2.10 mmol) was added in one portion. The reaction mixture was stirred for 1 h 30 minutes and then methyl [trans-4-(4-{[hydrazino(oxo)acetyl]amino}phenyl)cyclohexyl]acetate (Intermediate 43, 300 mg, 0.90 mmol) was added in one portion, the reaction mixture was stirred at room temperature for 1 h and then heated at 80° C. for 10 minutes in the microwave. The solution was cooled to room temperature and EDCI (150 mg, 0.80 mmol) was added in one portion and the reaction mixture was heated to 90° C. for 20 minutes in the microwave. The reaction mixture was cooled to room temperature and filtered. The filtrate was concentrated in vacuo to leave a brown solid, which was purified by column chromatography, using 0-20% MeOH and EtOAc as eluent to give the crude oxadiazole methyl ester intermediate that was used with no further purification; MS m/e MH⁺ 437.

A solution of lithium hydroxide (35 mg, 0.8 mmol) in H₂O (4 mL) was added in one portion to a solution of the crude oxadiazole methyl ester intermediate in a mixture of THF (2 mL) and MeOH (2 mL) and the reaction mixture was stirred at 35° C. for 2 h. Citric acid (15 mL) was added and the mixture was filtered to leave a solid that was recrystallised (MeOH) to give the title compound (5 mg, 1%) as a solid; ¹H NMR δ 1.12 (2H, m), 1.45-1.48 (2H, m), 1.80 (6H, m), 2.15-2.16 (2H, d), 7.17 (1H, t), 7.22 (2H, d), 7.70 (2H, d), 8.68 (2H, d), 11.00 (1H, s); MS m/e MH⁺ 423.

Example 438 trans-4-{4-[({5-[(2-Methoxyphenyl)amino]-1,3,4-oxadiazol-2-yl}carbonyl)amino]phenyl}-cyclohexanecarboxylic acid

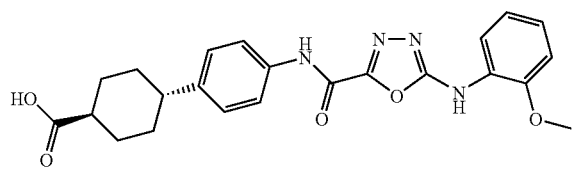

A solution of 2-methoxyphenyl isothiocyanate (59 mg, 0.36 mmol) in DMA (2 mL) was added to tert-butyl trans-4-(4-{[hydrazino(oxo)acetyl]amino}phenyl) cyclohexanecarboxylate (Intermediate 79, 108 mg, 0.30 mmol) and the mixture was stirred at 50° C. for 2 h. EDCI (86 mg, 0.45 mmol) was then added in one portion and the reaction mixture was heated at 90° C. for 10 minutes in a microwave. The reaction mixture was poured onto water (20 mL), stirred for 10 minutes and then filtered to leave the crude oxadiazole tert-butyl ester intermediate as a solid (145 mg) that was used with no further purification; MS m/e (M−H)⁻ 491.

The crude oxadiazole tert-butyl ester intermediate (145 mg) was dissolved in TFA (2.5 mL) and stirred for 6 h. The reaction mixture was concentrated in vacuo to leave a solid, which was purified by recrystallisation from a mixture of DMSO:CH₃CN:H₂O (7:2:1) to give the title compound (50 mg, 39%) as a solid; ¹H NMR δ 1.4-1.58 (4H, m), 1.8-1.9 (2H, m), 1.94-2.1 (2H, m), 2.2-2.32 (1H, m), 2.43-2.6 (1H, m), 3.85 (3H, s), 7.0 (1H, ddd), 7.14 (2H, m), 7.22 (2H, d), 7.7 (2H, d), 7.95 (1H, dd), 10.05 (1H, s), 10.9 (1H, s), 12.0 (1H, s); MS m/e (M−H)⁻ 435.

Example 439 trans-4-(4-{[(5-{[3-(Hydroxymethyl)phenyl]amino}-1,3,4-oxadiazol-2-yl)carbonyl]-amino}phenyl)cyclohexanecarboxylic acid

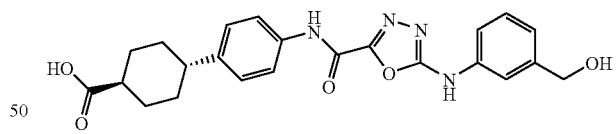

A solution of (3-hydroxymethyl)phenyl isothiocyanate (59 mg, 0.36 mmol) in DMA (2 mL) was added to tert-butyl trans-4-(4-{[hydrazino(oxo)acetyl]amino}phenyl)-cyclohexanecarboxylate (Intermediate 79, 108 mg, 0.30 mmol) and the mixture was stirred at 50° C. for 2 h. EDCI (86 mg, 0.45 mmol) was then added in one portion and the reaction mixture was heated at 90° C. for 10 minutes in a microwave. The reaction mixture was poured onto water (20 mL), stirred for 10 minutes and then filtered to leave the crude oxadiazole tert-butyl ester intermediate as a solid (160 mg) that was used with no further purification; MS m/e (M−H)⁻ 491.

The crude oxadiazole tert-butyl ester intermediate (160 mg) was dissolved in TFA (2.5 mL) and stirred for 6 h. The reaction mixture was concentrated in vacuo to leave an oil, which was stirred with a mixture of MeOH:H₂O:triethylamine (4:1:1, 6 mL) for 10 minutes. Concentration in vacuo left a brown solid, which was purified by recrystallisation from a mixture of DMSO:CH₃CN:H₂O (7:2:1) to give the title compound (67 mg, 47%) as a solid; ¹H NMR δ 1.4-1.58 (4H, m), 1.8-1.9 (2H, m), 1.94-2.1 (2H, m), 2.2-2.32 (1H, m), 2.43-2.6 (1H, m), 4.5 (2H, d), 5.2 (1H, t), 7.0 (1H, d), 7.25 (2IH, d), 7.35 (1H, dd), 7.55 (2H, m), 7.7 (2H, d), 10.9 (2H, s), 12.0 (1H, s); MS m/e (M−H)⁻ 435.

Examples 440-445

The following Examples were prepared by the general procedure of Example 431, using tert-butyl trans-4-(4-{[hydrazino(oxo)acetyl]amino}phenyl)cyclohexane-carboxylate (Intermediate 79) and commercially available isothiocyanates, R—NCS.

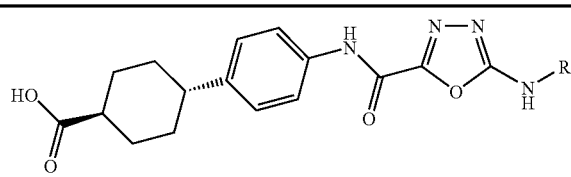

| Example | R | ¹H NMR δ | MS m/e MH⁺ |
|---|---|---|---|
| 440 | (2-trifluoromethylphenyl) | 1.4-1.58 (4H, m), 1.8-1.9 (2H, m), 1.94-2.1 (2H, m), 2.2-2.32 (1H, m), 2.43-2.6 (1H, m), 7.2 (2H, d), 7.5 (1H, dd), 7.7 (2H, d), 7.7-7.9 (3H, m), 10.4 (1H, s), 10.9 (1H, s), 12.0 (1H, s) | 473 |
| 441 | (2-trifluoromethoxyphenyl) | 1.4-1.58 (4H, m), 1.8-1.9 (2H, m), 1.94-2.1 (2H, m), 2.2-2.32 (1H, m), 2.43-2.6 (1H, m), 7.2-7.3 (3H, m), 7.4-7.5 (2H, m), 7.7 (2H, d), 8.2 (1H, dd), 10.9 (1H, s), 11.0 (1H, s), 12.0 (1H, s) | 489 |
| 442 | (3-trifluoromethylphenyl) | 1.4-1.58 (4H, m), 1.8-1.9 (2H, m), 1.94-2.1 (2H, m), 2.2-2.32 (1H, m), 2.43-2.6 (1H, m), 7.2 (2H, d), 7.4 (1H, d), 7.65 (1H, dd), 7.7 (2H, d), 7.85 (1H, dd), 8.0 (1H, s), 10.9 (1H, s), 11.3-12.3 (2H, m) | 473 |
| 443 | (4-methoxyphenyl) | 1.4-1.58 (4H, m), 1.8-1.9 (2H, m), 1.94-2.1 (2H, m), 2.2-2.32 (1H, m), 2.43-2.6 (1H, m), 3.75 (3H, s), 7.0 (2H, d), 7.2 (2H, d), 7.5 (2H, d), 7.7 (2H, d), 10.7 (1H, s), 10.9 (1H, s), 12.0 (1H, s) | 435 |
| 444 | (4-trifluoromethoxyphenyl) | 1.4-1.58 (4H, m), 1.8-1.9 (2H, m), 1.94-2.1 (2H, m), 2.2-2.32 (1H, m), 2.43-2.6 (1H, m), 7.23 (2H, d), 7.45 (1H, dd), 7.65-7.75 (4H, m), 10.9 (1H, s), 11.2 (1H, s), 12.0 (1H, s) | 489 |
| 445 | (4-trifluoromethylphenyl) | 1.4-1.58 (4H, m), 1.8-1.9 (2H, m), 1.94-2.1 (2H, m), 2.2-2.32 (1H, m), 2.43-2.6 (1H, m), 7.22 (2H, d), 7.5 (1H, dd), 7.7 (2H, d), 7.75-7.9 (4H, m), 10.95 (1H, s), 11.5 (1H, s), 12.0 (1H, s) | 473 |

Example 446 trans-4-(4-{[(5-{[2-(Benzyloxy)phenyl]amino}-1,3,4-oxadiazol-2-yl)carbonyl]amino}-phenyl)cyclohexanecarboxylic acid

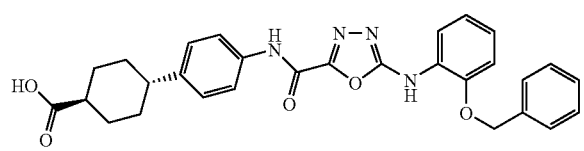

Thiocarbonyl diimidazole (64 mg, 0.36 mmol) was added in one portion to a stirred solution of 2-benzyloxyaniline (72 mg, 0.36 mmol) in DMA (2 mL) and the mixture was stirred at room temperature under an argon atmosphere for 2 h. tert-Butyl trans-4-(4-{[hydrazino-(oxo)acetyl]amino}phenyl)cyclohexanecarboxylate (Intermediate 79, 108 mg, 0.30 mmol) was added and the mixture was stirred at 80° C. for 10 minutes in a microwave. EDCI (69 mg, 0.36 mmol) was then added in one portion and the reaction mixture was heated at 90° C. for 10 minutes in a microwave. The reaction mixture was poured onto water (20 mL), stirred for 10 minutes and then filtered to leave the crude oxadiazole tert-butyl ester intermediate as a brown solid (130 mg) that was used with no further purification; MS m/e (M−H)⁻ 567.

The crude oxadiazole tert-butyl ester intermediate (130 mg) was dissolved in TFA (2 mL) and stirred for 2 h. The reaction mixture was concentrated in vacuo to leave a brown solid, which was purified by recrystallisation from a mixture of DMSO:CH₃CN:H₂O (7:2:1) to give the title compound (35 mg, 30%) as a solid; ¹H NMR δ 1.4-1.58 (4H, m), 1.8-1.9 (2H, m), 1.94-2.1 (2H, m), 2.2-2.32 (1H, m), 2.43-2.6 (1H, m), 5.22 (2H, s), 7.02 (1H, dd), 7.1 (1H, dd), 7.17 (1H, d), 7.22 (2H, d), 7.35 (3H, m), 7.5 (1H, d), 7.5 (1H, dd), 7.7 (2H, d), 7.88 (1H, dd), 10.0 (1H, s), 10.9 (1H, s), 12.0 (1H, s); MS m/e (M−H)⁻ 511.

Examples 447-449

The following Examples were prepared by the general procedure of Example 446, using tert-butyl trans-4-(4-{[hydrazino(oxo)acetyl]amino}phenyl)cyclohexane-carboxylate (Intermediate 79) and the appropriate commercially available aniline, RNH₂.

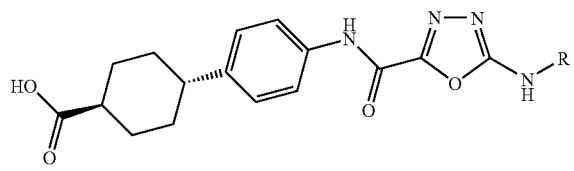

| Example | R | ¹H NMR δ | MS m/e M−H⁻ |
|---|---|---|---|
| 447 | 3-(trifluoromethoxy)phenyl | 1.4-1.58 (4H, m), 1.8-1.9 (2H, m), 1.94-2.1 (2H, m), 2.2-2.32 (1H, m), 2.43-2.6 (1H, m), 7.05 (1H, dd), 7.22 (2H, d), 7.5-7.6 (2H, m), 7.7 (2H, d), 7.65-7.75 (1H, m), 10.95 (1H, s), 11.35 (1H, s), 12.0 (1H, s) | 489 |
| 448 | 3-(methoxymethyl)phenyl | 1.4-1.58 (4H, m), 1.8-1.9 (2H, m), 1.94-2.1 (2H, m), 2.2-2.32 (1H, m), 2.43-2.6 (1H, m), 4.55 (2H, s), 7.15-7.25 (1H, m), 7.22 (2H, d), 7.38 (1H, dd), 7.4 (1H, dd), 7.5 (1H, dd), 7.7 (2H, d), 7.82 (1H, d), 9.95 (1H, s), 10.9 (1H, s), 12.0 (1H, s) | 449 |
| 449 | 3-(phenylsulfonyl)phenyl | 1.4-1.58 (4H, m), 1.8-1.9 (2H, m), 1.94-2.1 (2H, m), 2.2-2.32 (1H, m), 2.43-2.6 (1H, m), 7.24 (2H, d), 7.6-7.7 (7H, m), 7.8 (1H, dd), 7.95 (2H, dd), 8.3 (1H, s), 10.95 (1H, s), 11.4 (1H, s), 12.0 (1H, s) | 545 |

Example 450 trans-4-{4-[({5-[(3-Anilinophenyl)amino]-1,3,4-oxadiazol-2-yl}carbonyl)amino]phenyl}-cyclohexanecarboxylic acid

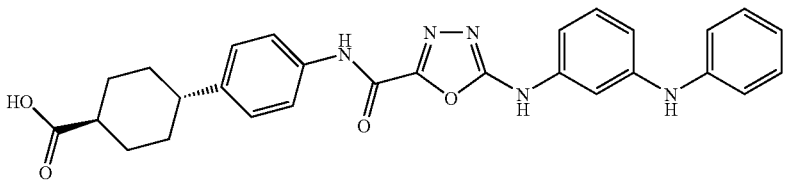

Thiocarbonyl diimidazole (64 mg, 0.36 mmol) was added in one portion to a stirred solution of 3-aminodiphenylamine (66 mg, 0.36 mmol) in DMA (2 mL) and the mixture was stirred at room temperature under an argon atmosphere for 2 h. tert-Butyl trans-4-(4-{[hydrazino(oxo)-acetyl]amino}phenyl)cyclohexanecarboxylate (Intermediate 79, 108 mg, 0.30 mmol) was added and the mixture was stirred at 80° C. for 10 minutes in a microwave. EDCI (69 mg, 0.36 mmol) was then added in one portion and the reaction mixture was heated at 90° C. for 10 minutes in a microwave. The reaction mixture was poured onto water (20 mL), stirred for 10 minutes and then filtered to leave the crude oxadiazole tert-butyl ester intermediate as a brown solid (130 mg) that was used with no further purification; MS m/e (M−H)⁻ 552.

The crude oxadiazole tert-butyl ester intermediate (130 mg) was dissolved in TFA (2 mL) and stirred for 2 h. The reaction mixture was concentrated in vacuo to leave a brown solid, which was triturated with MeOH and filtered to give the title compound (65 mg, 51%) as a solid; ¹H NMR δ 1.4-1.58 (4H, m), 1.8-1.9 (2H, m), 1.94-2.1 (2H, m), 2.2-2.32 (1H, m), 2.43-2.6 (1H, m), 6.75 (1H, dd), 6.85 (1H, dd), 7.05 (1H, dd), 7.1-7.35 (6H, m), 7.5 (1H, s), 7.7 (2H, d), 8.3 (1H, s), 10.8 (1H, s), 10.9 (1H, s), 12.0 (1H, s); MS m/e (M−H)⁻ 496.

Example 451 trans-4-{4-[({5-[(4-Anilinophenyl)amino]-1,34-oxadiazol-2-yl}carbonyl)amino]phenyl}-cyclohexanecarboxylic acid

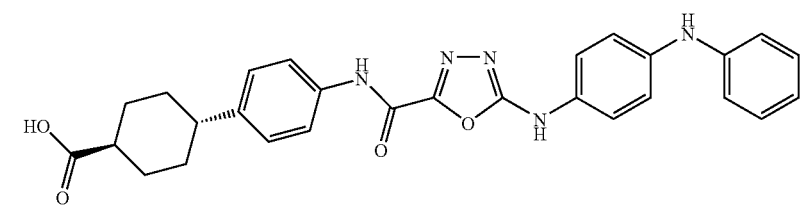

Example 451 was prepared using the procedure of Example 450, using tert-butyl trans-4-(4-{[hydrazino(oxo)acetyl]amino}phenyl)cyclohexanecarboxylate (Intermediate 79) and 4-aminodiphenylamine, to give the title compound (38 mg, 26%) as a solid; ¹H NMR δ 1.4-1.58 (4H, m), 1.8-1.9 (2H, m), 1.94-2.1 (2H, m), 2.2-2.32 (1H, m), 2.43-2.6 (1H, m), 6.78 (1H, dd), 7.0 (2H, d), 7.15 (2H, d), 7.15-7.3 (3H, m), 7.5 (2H, d), 7.7 (2H, d), 8.0 (1H, s), 10.7 (1H, s), 10.9 (1H, s), 12.0 (1H, s); MS m/e (M−H)⁻ 496.

Example 452 trans-4-[4-({[5-({2-[(Methylsulfonyl)oxy]phenyl}amino)-1,3,4-oxadiazol-2-yl]carbonyl}-amino)phenyl]cyclohexanecarboxylic acid

Thiocarbonyl diimidazole (64 mg, 0.36 mmol) was added in one portion to a stirred solution of 2-aminophenyl methanesulfonate (67 mg, 0.36 mmol) in DMA (2 mL) and the mixture was stirred at room temperature under an argon atmosphere for 2 h. tert-Butyl trans-4-(4-{[hydrazino(oxo)-acetyl]amino}phenyl)cyclohexanecarboxylate (Intermediate 79, 108 mg, 0.30 mmol) was added and the mixture was stirred at 80° C. for 10 minutes in a microwave. EDCI (69 mg, 0.36 mmol) was then added in one portion and the reaction mixture was heated at 90° C. for 10 minutes in a microwave. The reaction mixture was poured onto water (20 mL), stirred for 10 minutes and then filtered to leave the crude oxadiazole tert-butyl ester intermediate as a solid (210 mg) that was used with no further purification; MS m/e (M−H)⁻ 555.

The crude oxadiazole tert-butyl ester intermediate (210 mg) was dissolved in TFA (2 mL) and stirred for 2 h. The reaction mixture was concentrated in vacuo to leave a brown solid, which was purified by recrystallisation from a mixture of DMSO:CH$_3$CN:H$_2$O (7:2:1) and then recrystallisation from AcOH to give the title compound (21 mg, 14%) as a solid; $^1$H NMR δ 1.3-1.5 (4H, m), 1.8-1.9 (2H, m), 1.94-2.1 (2H, m), 2.2-2.32 (1H, m), 2.43-2.6 (1H, m), 3.45 (3H, s), 7.1-7.2 (1H, m), 7.2 (2H, d), 7.4 (2H, dd), 7.65 (2H, d), 8.3 (1H, d), 10.7 (1H, s), 10.9 (1H, s), 12.0 (1H, s); MS m/e MH$^+$ 501.

Example 453 trans-4-[4-({[5-({3-[(Methylsulfonyl)oxy]phenyl}amino)-1,3,4-oxadiazol-2-yl]carbonyl}-amino)phenyl]cyclohexanecarboxylic acid

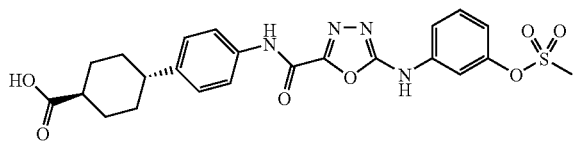

Thiocarbonyl diimidazole (64 mg, 0.36 mmol) was added in one portion to a stirred solution of 3-aminophenyl methanesulfonate (67 mg, 0.36 mmol) in DMA (2 mL) and the mixture was stirred at room temperature under an argon atmosphere for 2 h. tert-Butyl trans-4-(4-{[hydrazino-(oxo)acetyl]amino}phenyl)cyclohexanecarboxylate (Intermediate 79, 108 mg, 0.30 mmol) was added and the mixture was stirred at 80° C. for 10 minutes in a microwave. EDCI (69 mg, 0.36 mmol) was then added in one portion and the reaction mixture was heated at 90° C. for 10 minutes in a microwave. The reaction mixture was poured onto water (20 mL), stirred for 10 minutes and then filtered to leave the crude oxadiazole tert-butyl ester intermediate as a solid (195 mg) that was used with no further purification; MS m/e (M−H)$^-$ 555.

The crude oxadiazole tert-butyl ester intermediate (195 mg) was dissolved in TFA (2 mL) and stirred for 2 h. The reaction mixture was concentrated in vacuo to leave a brown solid, which was purified by recrystallisation from a mixture of DMSO:CH$_3$CN:H$_2$O (7:2:1) and then washed with AcOH to give the title compound (60 mg, 40%) as a solid; $^1$H NMR δ 1.3-1.5 (4H, m), 1.8-1.9 (2H, m), 1.94-2.1 (2H, m), 2.2-2.32 (1H, m), 2.43-2.6 (1H, m), 3.35 (3H, s), 7.0 (1H, d), 7.15 (2H, d), 7.43 (1H, dd), 7.50 (1H, d), 7.58 (1H, s), 7.65 (2H, d), 10.9 (1H, s), 11.2 (1H, s), 12.0 (1H, s); MS m/e M$^+$ 501.

Example 454 trans-4-[4-({[5-({4-[(Methylsulfonyl)oxy]phenyl}amino)-1,3,4-oxadiazol-2-yl]carbonyl}-amino)phenyl]cyclohexanecarboxylic acid

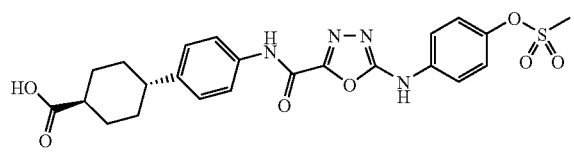

Thiocarbonyl diimidazole (64 mg, 0.36 mmol) was added in one portion to a stirred solution of 4-aminophenyl methanesulfonate (67 mg, 0.36 mmol) in DMA (2 mL) and the mixture was stirred at room temperature under an argon atmosphere for 2 h. tert-Butyl trans-4-(4-{[hydrazino(oxo)-acetyl]amino}phenyl)cyclohexanecarboxylate (Intermediate 79, 108 mg, 0.30 mmol) was added and the mixture was stirred at 80° C. for 10 minutes in a microwave. EDCI (69 mg, 0.36 mmol) was then added in one portion and the reaction mixture was heated at 90° C. for 10 minutes in a microwave. The reaction mixture was poured onto water (20 mL), stirred for 10 minutes and then filtered to leave the crude oxadiazole tert-butyl ester intermediate as a brown solid (200 mg) that was used with no further purification; MS m/e (M−H)$^-$ 555.

The crude oxadiazole tert-butyl ester intermediate (200 mg) was dissolved in TFA (2 mL) and stirred for 2 h. The reaction mixture was concentrated in vacuo to leave a brown solid, which was purified by recrystallisation from a mixture of DMSO:CH$_3$CN:H$_2$O (7:2:1) and then washed with AcOH to give the title compound (80 mg, 53%) as a solid; $^1$H NMR δ 1.3-1.5 (4H, m), 1.7-1.85 (2H, m), 1.94-2.1 (2H, m), 2.2-2.32 (1H, m), 2.43-2.6 (1H, m), 3.25 (3H, s), 7.18 (1H, d), 7.24 (2H, d), 7.6-7.75 (3H, m), 10.9 (1H, s), 11.2 (1H, s), 12.0 (1H, s); MS m/e MH$^+$ 501.

Example 455

Ethyl trans-4-{4-[({5-[(2,4,5-trifluorophenyl)amino]-1,3,4-oxadiazol-2-yl}carbonyl)-amino]phenoxy}cyclohexanecarboxylate

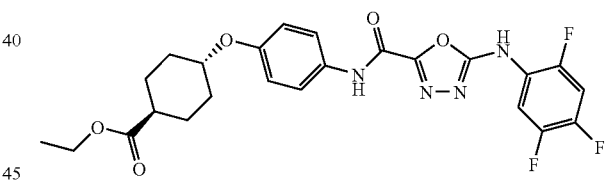

A solution of 2,4,5-trifluorophenyl isothiocyanate (70 mg, 0.37 mmol) in DMA (1 mL) was added in one portion to a stirred solution of ethyl trans-4-(4-{[hydrazino(oxo)acetyl]amino}-phenoxy)cyclohexanecarboxylate (Intermediate 80, 129 mg, 0.37 mmol) in DMA (3 mL) and the reaction mixture was stirred at room temperature for 1 h. EDCI (71 mg, 0.37 mmol) was added in one portion and the reaction mixture was heated to 85° C. for 20 minutes in a microwave. The mixture was cooled to room temperature and a further portion of EDCI (7.1 mg, 0.04 mmol) was added and the reaction mixture stirred at 85° C. for 10 minutes in a microwave. The reaction mixture was concentrated in vacuo to leave a solid, which was recrystallised (CH$_3$CN) to give the title compound (125 mg, 69%) as a solid; $^1$H NMR δ1.33 (3H, t), 1.48-1.58 (2H, m), 1.68-1.72 (2H, m), 2.06-2.10 (2H, m), 2.18-2.22 (2H, m), 2.45-2.53 (1H, m), 4.21 (2H, q), 4.39-4.46 (1H, m), 7.07-7.11 (2H, d), 7.81-7.84 (2H, d), 7.80-7.91 (1H, m), 8.29-8.36 (1H, m), 11.12-11.25 (1H, m); MS m/e MH$^+$ 505.

Example 456 trans-4-{4-[({5-[(2,4,5-Trifluorophenyl)amino]-1,3,4-oxadiazol-2-yl}carbonyl)amino]-phenoxy}cyclohexanecarboxylic acid

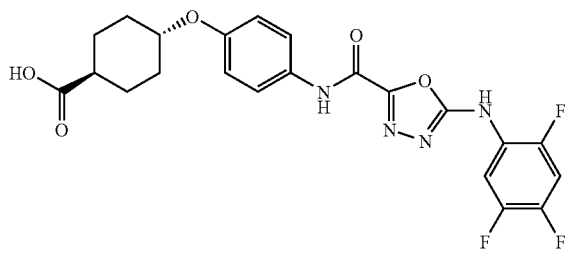

Lithium hydroxide monohydrate (104 mg, 2.48 mmol) was added in one portion to a solution of methyl trans-4-{4-[({5-[(2,4,5-trifluorophenyl)amino]-1,3,4-oxadiazol-2-yl}carbonyl)-amino]phenoxy}cyclohexanecarboxylate (Example 449, 125 mg, 0.25 mmol) in a mixture of THF (2 mL), H$_2$O (2 mL) and MeOH (4 mL) and the reaction mixture was stirred at 35° C. for 1 h. The reaction mixture was concentrated in vacuo and citric acid (15 mL) was added. The resulting mixture was filtered, washed with H$_2$O and the white solid was then triturated with hot MeOH and filtered to give the title compound (93 mg, 79%) as a solid. The compound may be recrystallised from a 4:6:1 mixture of EtOH:MeOH:H$_2$O; melting point 263-265° C.

$^1$H NMR δ 1.34-1.44 (2H, m), 1.46-1.56 (2H, m), 1.93-1.97 (2H, m), 2.05-2.09 (2H, m), 2.23-2.30 (1H, m), 4.24-4.31 (1H, m), 6.94-6.96 (2H, d), 7.67-7.69 (2H, d), 7.71 (1H, m), 8.13-8.20 (1H, m), 10.90 (1H, s), 11.03 (1H, s), 12.06 (1H, s); MS m/e (M–H)$^-$ 475.

Examples 457-463

The following Examples were prepared by the general procedure of Example 105 except that DMA was used as solvent in place of DMF, and using the appropriate commercially available arylisothiocyanates, R-NCS.

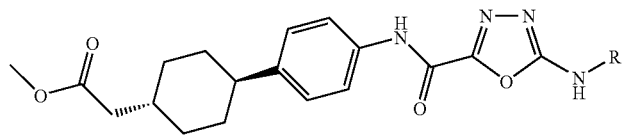

| Example | Name | $^1$H NMR δ | MS m/e MH$^+$ |
|---|---|---|---|
| 457 | Methyl (trans-4-{4-[({5-[(3-fluorophenyl)amino]-1,3,4-oxadiazol-2-yl}carbonyl)amino]phenyl}cyclohexyl)acetate | 1.01-1.23 (m, 2H), 1.36-1.56 (m, 2H), 1.66-1.87 (m, 5H), 2.25 (d, 2H), 2.37-2.46 (m, 1H), 3.60 (s, 3H), 6.89 (t, 1H), 7.21 (d, 2H), 7.36 (d, 1H), 7.43 (q, 1H), 7.51-7.57 (m, 1H), 7.70 (d, 2H), 11.01 (s, 1H), 11.28 (s, 1H) | 453 |
| 458 | Methyl (trans-4-{4-[({5-[(4-fluorophenyl)amino]-1,3,4-oxadiazol-2-yl}carbonyl)ainino]phenyl}cyclohexyl)acetate | 1.01-1.22 (m, 2H), 1.35-1.56 (m, 2H), 1.66-1.88 (m, 5H), 2.25 (d, 2H), 2.39-2.47 (m, 1H), 3.60 (s, 3H), 7.17-7.31 (m, 4H), 7.56-7.66 (m, 2H), 7.66-7.75 (m, 2H), 10.98 (s, 1H), 11.04 (s, 1H) | 453 |
| 459 | Methyl (trans-4-{4-[({5-[(2,4-difluorophenyl)amino]-1,3,4-oxadiazol-2-yl}carbonyl)amino]phenyl}cyclohexyl)acetate | 1.00-1.23 (m, 2H), 1.34-1.59 (m, 2H), 1.66-1.89 (m, 5H), 2.25 (d, 2H), 2.37-2.46 (m, 1H), 3.60 (s, 3H), 7.11-7.31 (m, 3H), 7.30-7.49 (m, 1H), 7.68 (d, 2H), 7.95-8.13 (m, 1H), 10.77 (s, 1H), 10.98 (s, 1H) | 471 |
| 460 | Methyl (trans-4-{4-[({5-[(2,6-difluorophenyl)amino]-1,3,4-oxadiazol-2-yl}carbonyl)amino]phenyl}cyclohexyl)acetate | 1.01-1.21 (m, 2H), 1.36-1.56 (m, 2H), 1.69-1.86 (m, 5H), 2.25 (d, 2H), 2.38-2.47 (m, 1H), 3.60 (s, 3H), 7.21 (d, 2H), 7.28 (t, 2H), 7.36-7.50 (m, 1H), 7.66 (d, 2H), 10.55 (s, 1H), 10.93 (s, 1H) | 471 |
| 461 | Methyl (trans-4-{4-[({5-[(2,5-difluorophenyl)amino]-1,3,4-oxadiazol-2-yl}carbonyl)amino]phenyl}cyclohexyl)acetate | 1.01-1.24 (m, 2H), 1.37-1.54 (m, 2H), 1.67-1.87 (m, 5H), 2.25 (d, 2H), 2.39-2.48 (m, 1H), 3.60 (s, 3H), 6.92-7.04 (m, 1H), 7.23 (d, 2H), 7.32-7.43 (m, 1H), 7.70 (d, 2H), 7.95-8.10 (m, 1H), 11.03 (s, 1H), 11.12 (s, 1H) | 471 |
| 462 | Methyl (trans-4-{4-[({S-[(2,3-difluorophenyl)amino]-1,3,4-oxadiazol-2-yl}carbonyl)amino]phenyl}cyclohexyl)acetate | 1.01-1.22 (m, 2H), 1.37-1.56 (m, 2H), 1.66-1.88 (m, 5H), 2.25 (d, 2H), 2.37-2.48 (m, 1H), 3.60 (s, 3H), 7.09-7.40 (m, 4H), 7.69 (d, 2H), 7.90 (s, 1H), 11.01 (s, 1H), 11.10 (s, 1H) | 471 |

-continued

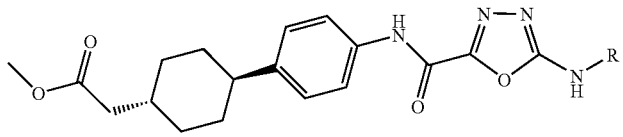

| Example | Name | ¹H NMR δ | MS m/e MH⁺ |
|---|---|---|---|
| 463 | Methyl (trans-4-{4-[({5-[(2,4,6-trifluorophenyl)amino]-1,3,4-oxadiazol-2-yl}carbonyl)amino]phenyl}cyclohexyl)acetate | 1.03-1.19 (m, 2H), 1.37-1.54 (m, 2H), 1.66-1.88 (m, 5H), 2.25 (d, 2H), 2.38-2.48 (m, 1H), 3.60 (s, 3H), 7.21 (d, 2H), 7.43 (t, 2H), 7.60-7.72 (m, 2H), 10.50 (s, 1H), 10.93 (s, 1H) | 489 |

Example 464

Methyl (trans-4-{4-[({5-[(3,4-dimethoxyhenyl)amino]-1,3,4-oxadiazol-2-yl}carbonyl)amino]phenyl}cyclohexyl)acetate

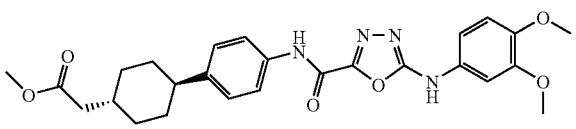

Di-2-pyridyl thionocarbonate (233 mg, 1.00 mmol) was added to 3,4-dimethoxyaniline (154 mg, 1.00 mmol) in DCM (3 mL) and the mixture was stirred for 1 h. Methyl [trans-4-(4-{[hydrazino(oxo)acetyl]amino}phenyl)cyclohexyl]acetate (Intermediate 43) (267 mg; 0.80 mmol) was added, followed by DMA. The resultant solution was heated at 85° C. for 30 minutes (DCM was allowed to boil off) then EDAC (192 mg, 1.00 mmol) was added. After a further 30 minutes the mixture was allowed to cool with stirring and was then diluted with water (7 mL). Stirring was continued and the resultant solid was collected by filtration, washed with water and dried at 60° C. under vacuum to give the title compound (288 mg, 73%); ¹H NMR δ 1.04-1.20 (m, 2H), 1.38-1.54 (m, 2H), 1.69-1.89 (m, 5H), 2.25 (d, 2H), 2.38-2.48 (m, 1H), 3.61 (s, 3H), 3.66-3.73 (m, 1H), 3.74 (s, 3H), 3.78 (s, 3H), 6.99 (d, 1H), 7.11-7.17 (m, 1H), 7.19-7.28 (m, 3H), 7.65-7.74 (m, 2H), 10.72 (s, 1H), 10.87 (s, 1H); MS m/e MH⁺ 495.

Examples 465-467

The following Examples were prepared by the general procedure of Example 464 using the appropriate aniline as starting material in place of 3,4-dimethoxyaniline.

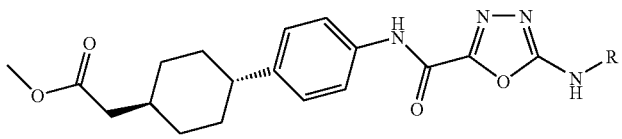

| Example | Name | ¹H NMR δ | MS m/e MH⁺ |
|---|---|---|---|
| 465[1] | Methyl (trans-4-{4-[({5-[(3-{[(1R)-2-methoxy-1-methylethyl]oxy}phenyl)amino]-1,3,4-oxadiazol-2-yl}carbonyl)ainino]phenyl}cyclohexyl)acetate | 1.05-1.20 (m, 2H), 1.25 (d, 3H), 1.38-1.54 (m, 2H), 1.70-1.87 (m, 5H), 2.25 (d, 2H), 2.37-2.47 (m, 1H), 3.22-3.33 (m, 3H), 3.42-3.55 (m, 2H), 3.61 (s, 3H), 4.51-4.68 (m, 1H), 6.67 (d, 1H), 7.11 (d, 1H), 7.17-7.34 (m, 4H), 7.63-7.77 (m, 2H), 10.93 (s, 2H) | 523 |
| 466[2] | Methyl (trans-4-{4-[({5-[(3-{[(1S)-2-methoxy-1-methylethyl]oxy}phenyl)amino]-1,3,4-oxadiazol-2-yl}carbonyl)amino]phenyl}cyclohexyl)acetate | 1.05-1.20 (m, 2H), 1.25 (d, 3H), 1.38-1.54 (m, 2H), 1.70-1.87 (m, 5H), 2.25 (d, 2H), 2.37-2.47 (m, 1H), 3.22-3.33 (m, 3H), 3.42-3.55 (m, 2H), 3.61 (s, 3H), 4.51-4.68 (m, 1H), 6.67 (d, 1H), 7.11 (d, 1H), 7.17-7.34 (m, 4H), 7.63-7.77 (m, 2H), 10.93 (s, 2H) | 523 |
| 467 | Methyl (trans-4-{4-[({5-[(4-fluoro-3-methoxyphenyl)amino]-1,3,4-oxadiazol-2-yl}carbonyl)amino]phenyl}cyclohexyl)acetate | 1.04-1.22 (m, 2H), 1.36-1.55 (m, 2H), 1.70-1.87 (m, 5H), 2.25 (d, 2H), 2.38-2.48 (m, 1H), 3.60 (s, 3H), 3.85 (s, 3H), 7.12-7.20 (m, 1H), 7.20-7.31 (m, 3H), 7.41 (d, 1H), 7.69 (d, 2H), 10.96 (s, 1H), 11.01 (s, 1H) | 483 |

[1]Preparation of the aniline starting material: Intermediate 81
[2]Preparation of the aniline starting material: Intermediate 82

Examples 468-478

The following Examples were prepared by the general procedure of Example 357, using the appropriate ester selected from Examples 457-467 as starting material, except that the crude product was recrystallised from acetic acid.

| Example | Name | $^1$H NMR δ | MS m/e MH$^+$ |
|---|---|---|---|
| 468 | (trans-4-{4-[({5-[(3-Fluoropheny)amino]-1,3,4-oxadiazol-2-yl}-carbonyl)amino]phenyl}-cyclohexyl)acetic acid | 1.12 (q, 2H), 1.46 (q, 2H), 1.67-1.88 (m, 5H), 2.15 (d, 2H), 2.44 (t, 1H), 6.82-6.98 (m, 1H), 7.23 (d, 2H), 7.31-7.39 (m, 1H), 7.39-7.50 (m, 1H), 7.49-7.59 (m, 1H), 7.70 (d, 2H), 11.01 (s, 1H), 11.28 (s, 1H), 12.03 (s, 1H) | 453 |
| 469 | (trans-4-{4-[({5-[(4-Fluorophenyl)amino]-1,3,4-oxadiazol-2-yl}carbonyl)amino]phenyl}-cyclohexyl)acetic acid | 1.11 (q, 2H), 1.45 (q, 2H), 1.64-1.88 (m, 5H), 2.15 (d, 2H), 2.44 (t, 1H), 7.17-7.31 (m, 4H), 7.58-7.66 (m, 2H), 7.66-7.77 (m, 2H), 10.98 (s, 1H), 11.04 (s, 1H), 12.03 (s, 1H) | 439 |
| 470 | (trans-4-{4-[({5-[(2,4-Difluorophenyl)amino]-1,3,4-oxadiazol-2-yl}carbonyl)amino]phenyl}-cyclohexyl)acetic acid | 1.11 (q, 2H), 1.45 (q, 2H), 1.66-1.89 (m, 5H), 2.15 (d, 2H), 2.37-2.45 (m, 1H), 7.10-7.29 (m, 3H), 7.36-7.48 (m, 1H), 7.69 (d, 2H), 7.95-8.11 (m, 1H), 10.78 (s, 1H), 10.98 (s, 1H), 12.03 (s, 1H) | 457 |
| 471 | (trans-4-{4-[({5-[(2,6-Difluorophenyl)amino]-1,3,4-oxadiazol-2-yl}carbonyl)amino]phenyl}-cyclohexyl)acetic acid | 1.11 (q, 2H), 1.45 (q, 2H), 1.64-1.88 (m, 5H), 2.14 (d, 2H), 2.36-2.48 (m, 1H), 7.22 (t, 2H), 7.28 (t, 2H), 7.37-7.49 (m, 1H), 7.67 (d, 2H), 10.56 (s, 1H), 10.93 (s, 1H), 12.03 (s, 1H) | 457 |
| 472 | (trans-4-{4-[({5-[(2,5-Difluorophenyl)amino]-1,3,4-oxadiazol-2-yl}carbonyl)amino]phenyl}-cyclohexyl)acetic acid | 1.12 (q, 2H), 1.46 (q, 2H), 1.66-1.89 (m, 5H), 2.15 (d, 2H), 2.44 (t, 1H), 6.92-7.03 (m, 1H), 7.23 (d, 2H), 7.32-7.45 (m, 1H), 7.70 (d, 2H), 7.95-8.09 (m, 1H), 11.03 (s, 1H), 11.14 (s, 1H), 12.03 (s, 1H) | 457 |
| 473 | (trans-4-{4-[({5-[(2,3-Difluorophenyl)amino]-1,3,4-oxadiazol-2-yl}carbonyl)amino]phenyl}-cyclohexyl)acetic acid | 1.11 (q, 2H), 1.46 (q, 2H), 1.66-1.87 (m, 5H), 2.15 (d, 2H), 2.38-2.47 (m, 1H), 7.12-7.35 (m, 4H), 7.69 (d, 2H), 7.92 (t, 1H), 11.01 (s, 1H), 11.11 (s, 1H), 12.04 (s, 1H) | 457 |
| 474 | (trans-4-{4-[({5-[(2,4,6-Trifluorophenyl)amino]-1,3,4-oxadiazol-2-yl}carbonyl)amino]phenyl}-cyclohexyl)acetate | 1.02-1.21 (m, 2H), 1.37-1.54 (m, 2H), 1.64-1.89 (m, 5H), 2.14 (d, 2H), 2.37-2.49 (m, 1H), 7.22 (d, 2H), 7.37-7.50 (m, 2H), 7.66 (d, 2H), 10.51 (s, 1H), 10.93 (s, 1H), 12.04 (s, 1H) | 475 |
| 475 | (trans-4-{4-[({5-[(3,4-Dimethoxyphenyl)amino]-1,3,4-oxadiazol-2-yl}carbonyl)amino]phenyl}-cyclohexyl)acetic acid | 1.04-1.19 (m, 2H), 1.38-1.54 (m, 2H), 1.66-1.90 (m, 5H), 2.15 (d, 2H), 2.38-2.48 (m, 1H), 3.74 (s, 3H), 3.78 (s, 3H), 6.99 (d, 1H), 7.11-7.18 (m, 1H), 7.20-7.27 (m, 3H), 7.65-7.74 (m, 2H), 10.72 (s, 1H), 10.87 (s, 1H), 11.98 (s, 1H) | 481 |
| 476 | (trans-4-{4-[({5-[(3-{[(1R)-2-methoxy-1-methylethyl]oxy}phenyl)amino]-1,3,4-oxadiazol-2-yl}carbonyl)amino]phenyl}-cyclohexyl)acetic acid | 1.07-1.26 (m, 2H), 1.30 (d, 3H), 1.42-1.59 (m, 2H), 1.72-1.97 (m, 5H), 2.21 (d, 2H), 2.44-2.54 (m, 1H), 3.36 (s, 3H), 3.46-3.63 (m, 2H), 4.58-4.71 (m, 1H), 6.72 (d, 1H), 7.12-7.20 (m, 1H), 7.23-7.39 (m, 4H), 7.75 (d, 2H), 11.04 (s, 2H), 12.10 (s, 1H) | 509 |
| 477 | (trans-4-{4-[({5-[(3-{[(1S)-2-methoxy-1-methylethyl]oxy}phenyl)amino]-1,3,4-oxadiazol-2-yl}carbonyl)amino]phenyl}-cyclohexyl)acetic acid | 1.07-1.26 (m, 2H), 1.30 (d, 3H), 1.42-1.59 (m, 2H), 1.72-1.97 (m, 5H), 2.21 (d, 2H), 2.44-2.54 (m, 1H), 3.36 (s, 3H), 3.46-3.63 (m, 2H), 4.58-4.71 (m, 1H), 6.72 (d, 1H), 7.12-7.20 (m, 1H), 7.23-7.39 (m, 4H), 7.75 (d, 2H), 11.04 (s, 2H), 12.10 (s, 1H) | 509 |

| Example | Name | ¹H NMR δ | MS m/e MH⁺ |
|---|---|---|---|
| 478 | (trans-4-{4-[({5-[(4-fluoro-3-methoxyphenyl)amino]-1,3,4-oxadiazol-2-yl}carbonyl)amino]phenyl}-cyclohexyl)acetic acid | 1.03-1.21 (m, 2H), 1.38-1.55 (m, 2H), 1.64-1.88 (m, 5H), 2.15 (d, 2H), 2.38-2.49 (m, 1H), 3.85 (s, 3H), 7.13-7.19 (m, 1H), 7.20-7.29 (m, 3H), 7.38-7.45 (m, 1H), 7.66-7.73 (m, 2H), 10.96 (s, 1H), 11.01 (s, 1H), 12.04 (s, 1H) | 469 |

Example 479

1-{5-[({5-[(2-Fluorophenyl)amino]-1,3,4-oxadiazol-2-yl}carbonyl)amino]pyridin-2-yl}piperidine-4-carboxylic acid hydrochloride

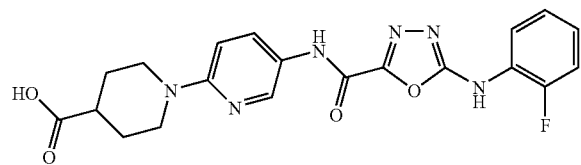

i) Following the procedure of Example 319 except that Intermediate 83 was used in place of Intermediate 77 and 2-fluorophenylisothiocyanate in place of 2,4,5-trifluorophenylisothiocyanate, there was obtained (in quantitative yield) tert-butyl 1-{5-[({5-[(2-fluorophenyl)amino]-1,3,4-oxadiazol-2-yl}carbonyl)amino]pyridin-2-yl}piperidine-4-carboxylate as a solid; ¹H NMR δ 1.41 (s, 9H), 1.44-1.60 (m, 2H), 1.83 (d, 2H), 2.92 (t, 1H), 3.33 (d, 2H), 4.09-4.20 (m, 2H), 6.88 (d, 1H), 7.12-7.22 (m, 1H), 7.27 (q, 1H), 7.33 (d, 1H), 7.86-7.96 (m, 1H), 8.06 (t, 1H), 8.44-8.52 (m, 1H), 10.80 (s, 1H), 10.96 (s, 1H); MS m/e MH⁺ 483.

ii) TFA (0.307 mL; 4.0 mmol) was added to a suspension of tert-Butyl 1-{5-[({5-[(2-fluorophenyl)amino]-1,3,4-oxadiazol-2-yl}carbonyl)amino]pyridin-2-yl}piperidine-4-carboxylate (483 mg; 1.0 mmol) in DCM (5 mL). After 3 days more TFA was added in aliquots (0.31 mL) over 2 days then HCl (1 mL of a 4M solution in 1,4-dioxan) was added. After 24 h the mixture was filtered and the solid was washed with ether and dried under vacuum at 60° C. to give the title compound (193 mg, 42%) as a solid; ¹H NMR δ 1.55-1.74 (m, 2H), 1.88-2.06 (m, 2H), 2.56-2.69 (m, 1H), 2.69-2.81 (m, 1H), 3.18-3.35 (m, 2H), 4.17 (d, 2H), 7.13-7.22 (m, 1H), 7.24-7.31 (m, 1H), 7.31-7.37 (m, 1H), 7.44 (d, 1H), 7.98-8.09 (m, 1H), 8.19-8.28 (m, 1H), 8.51-8.59 (m, 1H), 10.87 (s, 1H), 11.37 (s, 1H); MS m/e MH⁺ 427.

Example 480-482

The following Examples were prepared by the general procedure of Example 479, using the appropriate isothiocyanate in place of 2-fluorophenylisothiocyanate

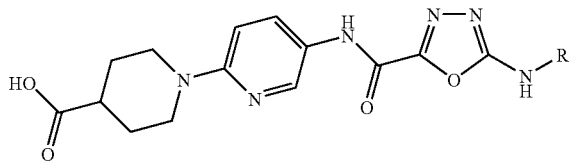

| Example | Name | ¹H NMR δ | MS m/e MH⁺ |
|---|---|---|---|
| 480 | 1-{5-[({5-[(2,4,5-trifluorophenyl)amino]-1,3,4-oxadiazol-2-yl}carbonyl)amino]pyridin-2yl}piperidine-4-carboxylic acid hydrochloride | 1.54-1.69 (m, 2H), 1.87-2.05 (m, 2H), 2.41-2.50 (m, 1H), 2.53-2.66 (m, 1H), 3.10-3.30 (m, 2H), 4.15 (d, 2H), 7.18-7.41 (m, 1H), 7.66-7.81 (m, 1H), 8.08-8.25 (m, 2H), 8.51 (s, 1H), 11.15 (s, 1H), 11.30 (s, 1H) | 463 |
| 481 | 1-{5-[({5-[(3,4-difluorophenyl)amino]-1,3,4-oxadiazol-2-yl}carbonyl)amino]pyridin-2yl}piperidine-4-carboxylic acid hydrochloride | 1.55-1.70 (m, 2H), 1.87-2.02 (m, 2H), 2.57-2.71 (m, 1H), 3.22 (t, 2H), 4.16 (d, 2H), 7.23-7.43 (m, 3H), 7.50 (q, 1H), 7.65-7.78 (m, 1H), 8.17 (d, 1H), 8.53 (d, 1H), 11.32 (s, 1H), 11.37 (s, 1H) | 445 |
| 482 | 1-{5-[({5-[(4-fluorophenyl)amino}-1,3,4-oxadiazol-2-yl}carbonyl)amino]pyridin-2yl}piperidine-4-carboxylic acid hydrochloride | 1.50-1.71 (m, 2H), 1.86-2.02 (m, 2H), 2.54-2.67 (m, 1H), 3.07-3.30 (m, 2H), 4.14 (d, 2H),7.19-7.40 (m, 3H), 7.56-7.70 (m, 2H), 8.15 (d, 1H) 8.51 (s, 1H), 11.10 (s, 1H), 11.26 (s, 1H) | 427 |

Example 483

Methyl 4-{4-[({5-[(2-fluorophenyl)amino]-1,3,4-oxadiazol-2-yl}carbonyl)amino]phenyl}butanoate

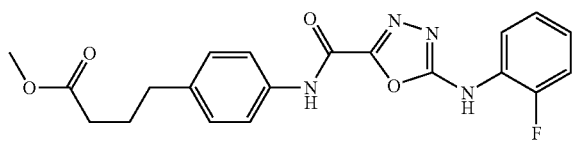

Methyl 4-(4-aminophenyl)butanoate (Journal of Medicinal Chemistry (1990), 33(11), 3014-19) (193 mg, 1 mmol) was stirred in dry DCM (9 mL) and PS-di-isopropylethylamine (750 mg, 3 mmol) was added. Methyl chloro(oxo)acetate (101 μl, 1.1 mmol) was added to the reaction mixture which was then stirred at room temperature for 2 h. The polymer supported base (HCl salt) was filtered off and washed with DCM (3 mL). Hydrazine monohydrate (53 μL, 1.1 mmol) was added to the stirred filtrate and a white precipitate formed after 2 h. The reaction mixture was stirred at room temperature overnight then DMF (5 mL) was added to dissolve the solid. 2-Fluorophenylisothiocyanate (0.135 mL, 1.1 mmol) was added via a pipette and the mixture stirred at room temperature for 2.5 h before adding EDAC (230 mg, 1.2 mmol). After stirring at room temperature for a further 2.5 h the mixture was heated to 50° C. and the DCM was allowed to evaporate. After 2 h the reaction had gone to completion and the mixture was concentrated in vacuo. The orange solid obtained was crystallised from water and then filtered. The solid was then washed with Et$_2$O, EtOAc and then MeCN (1 mL) to give the title compound (174 mg, 44%) as a solid; $^1$H NMR δ 1.79-1.87 (2H, m), 2.31 (2H, t), 2.58 (2H, t), 3.59 (3H, s), 7.15-7.20 (3H, m), 7.25-7.34 (2H, m), 7.71 (2H, d), 8.02-8.07 (1H, m), 10.76 (1H, s), 10.95 (1H, s); MS m/e MH$^+$ 399.

Examples 484-497

The following examples were prepared by the general procedure of Example 483, using the appropriate amine R$^1$NH$_2$ and isothiocyanate R$^2$—NCS.

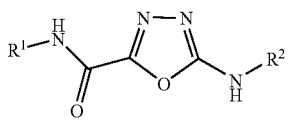

| Ex | SM | R$^1$ | R$^2$ | $^1$H NMR δ | MS m/e MH$^+$ |
|---|---|---|---|---|---|
| 484[1] | Lit.[2] | ![R1 structure with methyl ester-SCH2-phenyl] | ![2-fluorophenyl] | 3.63 (3H, s), 3.86 (2H, s), 7.16-7.20 (1H, m), 7.26-7.28 (1H, m), 7.29-7.34 (1H, m), 7.37-7.41 (2H, m), 7.76-7.80 (2H, m), 8.02-8.06 (1H, m), 10.78 (1H, s), 11.09 (1H, s) | 403 |
| 485 | Int 84 | ![adamantane-phenyl with methyl ester] | ![2-fluorophenyl] | 1.70 (2H, s), 1.85 (9H, s), 1.93 (2H, s), 2.18 (2H, s), 3.61 (3H, s), 7.16-7.19 (1H, m), 7.25-7.38 (4H, m), 7.71-7.74 (2H, m), 8.02-8.07 (1H, m), 10.76 (1H, s), 10.95 (1H, s) | 491 |

-continued
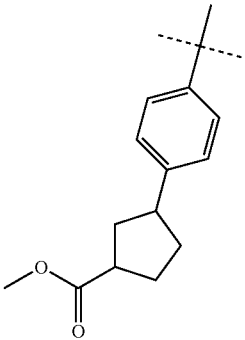
| Ex | SM | R[1] | R[2] | $^1$H NMR δ | MS m/e MH[+] |
|---|---|---|---|---|---|
| 486 | Int 85 | 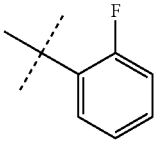 | 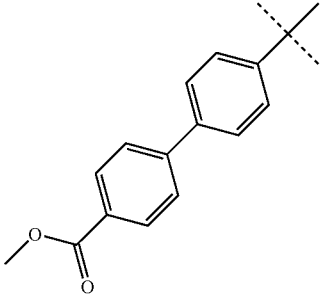 | 1.56-1.66 (1H, m), 1.74-1.89 (2H, m), 1.94-2.03 (1H, m), 2.07-2.11 (1H, m), 2.23-2.33 (1H, m), 3.01-3.14 (2H, m), 3.63 (3H, d), 7.14-7.19 (1H, m), 7.25-7.34 (3H, m), 7.71 (2H, d), 8.02-8.07 (1H, m), 10.75 (1H, s), 10.95 (1H, s) | 425 |
| 487 | Lit.[3] | 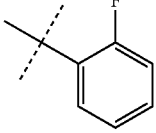 | 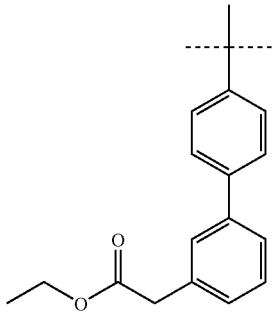 | 3.89 (3H, s), 7.17-7.20 (1H, m), 7.26-7.35 (2H, m), 7.79 (2H, d), 7.84-7.86 (2H, m), 7.96 (2H, d), 8.05 (3H, t), 10.80 (1H, s), 11.19 (1H, s) | 433 |
| 488 | Int 86 | 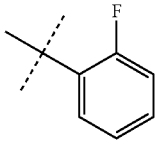 | 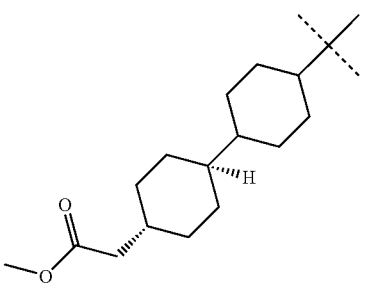 | 1.21 (3H, t), 3.75 (2H, s), 4.11 (2H, q), 7.18 (1H, s), 7.25-7.33 (3H, m), 7.41 (1H, d), 7.58 (2H, s), 7.68 (2H, d), 7.93 (2H, d), 8.08 (1H, s), 10.85 (1H, s), 11.20 (1H, s) | 461 |
| 489 | Int 87 | 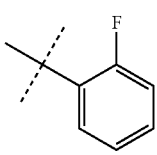 | | 0.82-1.30 (m, 6H), 1.34-1.85 (m, 12H), 2.14-2.23 (m, 2H), 3.58 (s, 3H), 3.93 (s, 1H), 4.38 (s, 1H), 7.11-7.18 (m, 1H), 7.21-7.34 (m, 2H), 8.03 (t, 1H), 8.72 (d, 1H), 8.96 (d, 1H) | 459 |

-continued
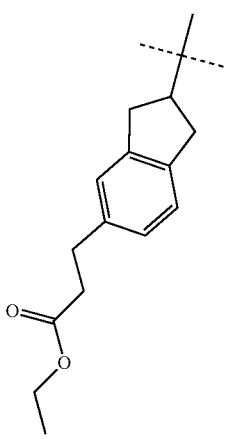
| Ex | SM | R¹ | R² | ¹H NMR δ | MS m/e MH⁺ |
|---|---|---|---|---|---|
| 490 | Int 88 | 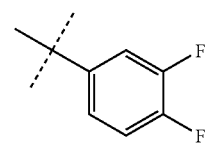 | 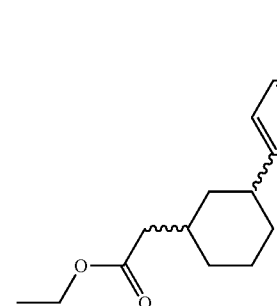 | | 457 |
| 491 | Int 89 | 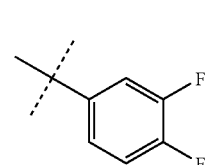 | 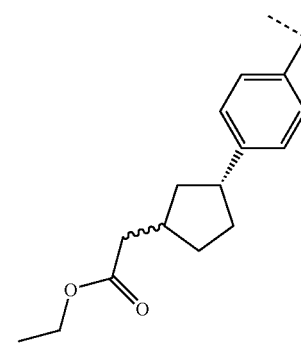 | | 485 |
| 492 | Int 90 | 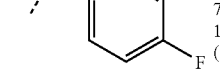 | | 1.19 (t, 3H), 1.22-2.44 (m, 9H), 2.97-3.17 (m, 1H), 4.06 (q, 2H), 7.20-7.27 (m, 2H), 7.32-7.39 (m, 1H), 7.45-7.55 (m, 1H), 7.66-7.76 (m, 3H), 11.02 (s, 1H), 11.02 (s, 1H) | 471 |

-continued

| Ex | SM | R¹ | R² | ¹H NMR δ | MS m/e MH⁺ |
|---|---|---|---|---|---|
| 493 | Int 91 | (ethyl 2-(3-(4-substituted-phenyl)cyclopentyl)acetate group) | (3,4-difluorophenyl group) | 1.19 (t, 3H), 1.22-2.44 (m, 9H), 2.97-3.17 (m, 1H), 4.06 (q, 2H), 7.20-7.27 (m, 2H), 7.32-7.39 (m, 1H), 7.45-7.55 (m, 1H), 7.66-7.76 (m, 3H), 11.02 (s, 1H), 11.02 (s, 1H) | 471 |
| 494 | Lit.⁴ | (methyl 4-(3-substituted-propoxy)benzoate group) | (3,4-difluorophenyl group) | 2.04 (2H, t), 3.46 (2H q), 3.84 (3H, s), 4.14 (2H, t), 7.06-7.08 (2H, m), 7.36 (1H, t), 7.47-7.54 (1H, m), 7.68-7.73 (1H, m), 7.92-7.96 (2H, m), 9.26 (1H, t), 11.21 (1H, s) | 433 |
| 495 | Int 92 | (methyl 3-(3-substituted-propoxy)benzoate group) | (3,4-difluorophenyl group) | 1.97-2.04 (2H, m), 3.44 (2H, q), 3.84 (3H, s), 4.09 (2H, t), 7.21-7.24 (1H, m), 7.31-7.34 (1H, m), 7.44 (1H, s), 7.42-7.49 (2H, m), 7.53-7.56 (1H, m), 7.65-7.70 (1H, m), 9.23 (1H, t), 11.18 (1H, s) | 433 |

-continued

| Ex | SM | R¹ | R² | ¹H NMR δ | MS m/e MH⁺ |
|---|---|---|---|---|---|
| 496 | Lit.⁵ | 4-tert-butylphenyl-cyclobutyl methyl ester | 3,4-difluorophenyl | 2.19-2.27 (1H, m), 2.34-2.41 (1H, m), 2.54-2.60 (2H, m), 3.13-3.22 (1H, m), 3.42 (1H, m), 3.59 (1.5H, s), 3.67 (1.5H, s), 7.22-7.32 (2H, m), 7.36 (1H, d), 7.48 (1H, d), 7.67-7.75 (3H, m), 10.98 (1H, s), 11.23 (1H, s) | 429 |
| 497 | Int 94 | 4-((cyclobutyl ethyl ester)methyl)phenyl | 3,4-difluorophenyl | 1.10-1.23 (3H, m), 1.83-2.03 (2H, m), 2.18-2.24 (2H, m), 2.56 (1H, m), 2.63 (1H, d), 2.72 (1H, d), 2.90-3.16 (1H, m), 4.03-4.07 (2H, m), 7.17 (2H, t), 7.35 (1H, d), 7.45-7.52 (1H, m), 7.64-7.73 (3H, m), 10.95 (1H, s), 11.22 (1H, s) | 457 |

¹Purified by preparativeHPLC eluting with a gradient of water-MeCN containing formic acid modifier
²Aniline prepared according to J. Pharm. Sci., 1974, 63(8), 1333
³Aniline prepared according to J. Combinatorial Chem., 2003, 5(3), 205
⁴Amine prepared according toHelv. Chin. Acta, 1983, 66(2), 489
⁵Aniline prepared according to German Patent application DE 2626287 (1976)

Example 498

4-{4-[({5-[(2-Fluorophenyl)amino]-1,3,4-oxadiazol-2-yl}carbonyl)amino]phenyl}butanoic acid

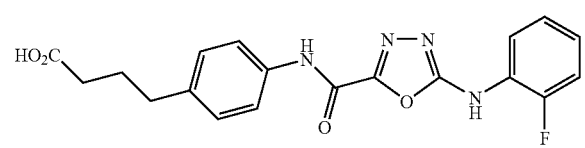

Methyl 4-{4-[({5-[(2-fluorophenyl)amino]-1,3,4-oxadiazol-2-yl}carbonyl)amino]phenyl}butanoate (Example 483) (174 mg, 0.44 mmol) was stirred in THF: MeOH (8 mL of a 1:1 mixture) and NaOH (2.5 mL of 2M aqueous solution) was added. The mixture was stirred for 8.5 h then acidified (2M HCl), allowed to stand overnight, then concentrated in vacuo. The precipitate was filtered and washed with water and then Et₂O to give the title compound (94 mg, 56%) as a solid; ¹H NMR δ 1.77-1.84 (2H, m), 2.22 (2H, t), 2.59 (2H, t), 7.14-7.21 (3H, m), 7.25-7.34 (2H, m), 7.70-7.72 (2H, m), 8.02-8.07 (1H, m), 10.74 (1H, s), 10.94 (1H, s), 11.98 (1H, s); MS m/e MH⁺ 385.

Examples 499-514

The following examples were prepared by the general procedure of Example 498, using the appropriate ester as starting material (SM).

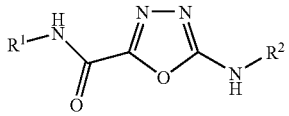

| Example | SM | R¹ | R² | ¹H NMR δ | MS m/e MH⁺ |
|---|---|---|---|---|---|
| 499 | Ex 485 | (3-phenyl adamantane carboxylic acid group) | 2-fluorophenyl | 1.70 (2H, s), 1.83 (8H, d), 1.91 (2H, s), 2.17 (2H, s), 7.16-7.20 (1H, m), 7.26-7.38 (4H, m), 7.71-7.74 (2H, m), 8.02-8.06 (1H, m), 10.74 (1H, s), 10.94 (1H, s), 12.04 (1H, s) | 477 |
| 500 | Ex 486 | (4-phenyl cyclopentane carboxylic acid group) | 2-fluorophenyl | 1.28 (0H, s), 1.52-2.38 (5H, q), 2.85-3.11 (2H, m), 3.59-3.64 (1H, m), 7.14-7.22 (1H, m), 7.25-7.34 (4H, m), 7.70 (2H, d), 8.04 (1H, t), 10.74 (1H, s), 10.94 (1H, s), 12.02 (1H, s) | 411 |
| 501 | Ex 487 | (biphenyl carboxylic acid group) | 2-fluorophenyl | 7.17-7.21 (1H, m), 7.26-7.35 (2H, m), 7.77-7.83 (4H, m), 7.95 (2H, d), 8.01-8.06 (3H, m), 10.78 (1H, s), 11.16 (1H, s) | 419 |

-continued
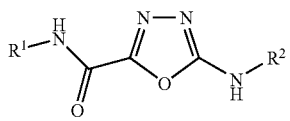
| Example | SM | R¹ | R² | ¹H NMR δ | MS m/e MH⁺ |
|---|---|---|---|---|---|
| 502 | Int 94 | (4-biphenyl-CH₂-COOH) | (2-fluorophenyl) | 3.59-3.63 (2H, s), 7.15-7.20 (1H, m), 7.26-7.36 (4H, m), 7.62-7.64 (2H, m), 7.67-7.70 (2H, m), 7.90-7.92 (2H, m), 8.03-8.08 (1H, m), 10.79 (1H, s), 11.13 (1H, s), 12.32 (1H, s) | 433 |
| 503 | Ex 488 | (3-biphenyl-CH₂-COOH) | (2-fluorophenyl) | 3.66 (2H, s), 7.18 (1H, t), 7.24-7.35 (3H, m), 7.41 (1H, t), 7.56 (2H, d), 7.68 (2H, d), 7.92 (2H, d), 8.07 (1H, t), 10.84 (1H, s), 11.18 (1H, s), 12.38 (1H, s) | 433 |
| 504¹ | Ex 489 | (bicyclohexyl-CH₂-COOH) | (2-fluorophenyl) | 0.81-1.08 (m, 2H), 1.09-1.28 (m, 4H), 1.32-1.47 (m, 2H), 1.48-1.63 (m, 3H), 1.65-1.86 (m, 6H), 2.08 (t, 2H), 2.51-2.55 (m, 1H), 3.60-3.74 (m, 1H), 3.87-3.99 (m, 1H), 7.10-7.18 (m, 1H), 7.22-7.34 (m, 2H), 7.99-8.06 (m, 1H), 8.67-8.97 (m, 1H), 10.68 (s, 1H), 10.68 (s, 1H) | 445 |

-continued
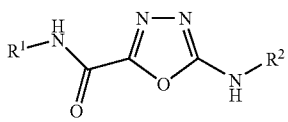
| Example | SM | R[1] | R[2] | $^1$H NMR δ | MS m/e MH[+] |
|---|---|---|---|---|---|
| 505[2] | Ex 490 | | | 2.76 (2H, t), 3.07 (2H, t), 3.14-3.19 (2H, m), 3.49-3.50 (2H, m), 4.95 (1H, m), 7.22 (1H, d), 7.32 (2H, m), 7.42-7.45 (2H, m), 7.79-7.84 (1H, m) | 429 |
| 506[2] | Int 95 | | | 1.58 (2H, m), 1.73 (2H, m), 2.57 (2H, m), 3.24 (1H, m), 7.18 (2H, d), 7.34-7.37 (1H, m), 7.48 (1H, d), 7.68-7.73 (3H, m), 10.96 (1H, s), 11.23 (1H, s). 12.60 (2H, s) | 461 |
| 507[1,3] | Int 96 | | | (d₄ MeOH) 1.41-1.62 (m, 4H), 1.71-2.05 (m, 4H), 2.14-2.21 (m, 1H), 2.42-2.54 (m, 1H), 3.46 (s, 1H), 3.57 (s, 1H), 6.97-7.28 (m, 6H), 7.92-8.02 (m, 2H) | 439 |

-continued

[Structure: R¹-NH-C(=O)-[1,3,4-oxadiazole]-NH-R²]

| Example | SM | R¹ | R² | ¹H NMR δ | MS m/e MH⁺ |
|---|---|---|---|---|---|
| 508 | Ex 491 | [cyclohexyl-CH₂-COOH with 4-phenyl substituent] | [3,4-difluorophenyl] | (d₄ MeOH) 0.87-1.91 (m, 8H), 2.13 (d, 1H), 2.24-2.32 (m, 0.5H), 2.38 (d, 1H), 2.45-2.54 (m, 1H), 2.67-2.78 (m, 0.5H), 7.09-7.24 (m, 4H), 7.48-7.62 (m, 3H) | 457 |
| 509 | Ex 492 | [cyclopentyl-CH₂-COOH with 4-phenyl substituent] | [3,4-difluorophenyl] | δ1.24-1.43 (2H, m), 1.56-1.82 (2H, m), 1.98-2.06 (2H, m), 2.17 (0.5H, m), 2.30-2.35 (2H, m), 2.44-2.45 (0.5H, m), 3.03-3.14 (1H, m), 7.23-7.26 (2H, m), 7.35-7.37 (1H, m), 7.46-7.52 (1H, m), 7.68-7.73 (3H, m), 10.97 (1H, s), 11.24 (1H, s), 11.98 (1H, s) | 443 |
| 510 | Ex 493 | [cyclopentyl-CH₂-COOH with 4-phenyl substituent] | [3,4-difluorophenyl] | 1.24-1.43 (2H, m), 1.56-1.82 (2H, m), 1.98-2.06 (2H, m), 2.17 (0.5H, m), 2.30-2.35 (2H, m), 2.44-2.45 (0.5H, m), 3.03-3.14 (1H, m), 7.23-7.26 (2H, m), 7.35-7.37 (1H, m), 7.46-7.52 (1H, m), 7.68-7.73 (3H, m), 10.97 (1H, s), 11.24 (1H, s), 11.98 (1H, s) | 443 |

-continued

| Example | SM | R¹ | R² | ¹H NMR δ | MS m/e MH⁺ |
|---|---|---|---|---|---|
| 511 | Ex 494 | 4-(HOOC)-C₆H₄-O-(CH₂)₃- | 3,4-difluorophenyl | 1.99-2.05 (2H, m), 3.40-3.46 (2H, m), 4.12 (2H, t), 7.00-7.03 (2H, m), 7.32-7.36 (1H, m), 7.42-7.47 (1H, m), 7.65-7.71 (1H, m), 7.87-7.91 (2H, m), 9.16 (1H, t), 11.15 (1H, s) | 419 |
| 512 | Ex 495 | 3-(HOOC)-C₆H₄-O-(CH₂)₃- | 3,4-difluorophenyl | 1.98-2.04 (2H, m), 3.44 (2H, q), 4.09 (2H, t), 7.17-7.20 (1H, m), 7.32-7.35 (1H, m), 7.39-7.47 (3H, m), 7.52-7.54 (1H, m), 7.65-7.70 (1H, m), 9.16 (1H, t), 11.13 (1H, s) | 419 |
| 513 | Ex 496 | 3-(4-substituted phenyl)cyclobutane-1-carboxylic acid | 3,4-difluorophenyl | 2.17-2.25 (1H, m), 2.30-2.38 (1H, m), 2.53-2.58 (2H, m), 3.03-3.09 (1H, m), 3.39-3.44 (0.5H, m), 3.62 (0.5H, m), 7.22-7.37 (3H, m), 7.45-7.52 (1H, m), 7.67-7.75 (3H, m), 10.98 (1H, s), 12.00 (1H, s) | 415 |
| 514 | Ex 497 | 3-(4-substituted benzyl)cyclobutane-1-carboxylic acid | 3,4-difluorophenyl | 1.77-1.96 (2H, m), 2.15-2.24 (2H, m), 2.43-2.46 (0.5H, m), 2.54 (0.5H, m), 2.63 (1H, d), 2.70-2.72 (1H, d), 2.87-3.04 (1H, m), 7.17 (2H, t), 7.35-7.37 (1H, m), 7.45-7.52 (1H, m), 7.68-7.73 (3H, m), 10.95 (1H, s), 11.23 (1H, s), 11.96 (1H, s) | 429 |

¹20 equivalents of 2 M NaOH was used
²10 equivalents of 2 M NaOH was used
³Purified by preparativeHPLC eluting with a gradient of water-MeCN containing formic acid modifier

Example 515

5-{4-[({5-[(3,4-Difluorophenyl)amino]-1,3,4-oxadiazol-2-yl}carbonyl)amino]-phenyl}pentanoic acid

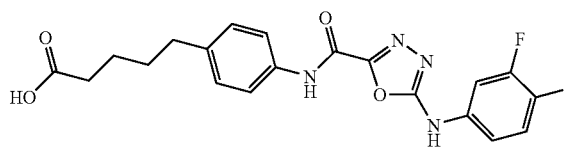

A solution of (3-{4-[({5-[(3,4-difluorophenyl)amino]-1,3,4-oxadiazol-2-yl}carbonyl)amino]phenyl}propyl)malonic acid (Example 506) (40 mg, 0.087 mmol) in AcOH (4 mL) was heated under reflux with stirring for 4 h. The reaction mixture was concentrated in vacuo and the solid filtered and washed with water then Et$_2$O to give the title compound (20 mg, 55%) as a solid; $^1$H NMR δ 1.50-1.60 (4H, m), 2.24 (2H, t), 2.55 (2H, t), 7.15-7.20 (2H, m), 7.35-7.37 (1H, m), 7.48-7.52 (1H, m), 7.68-7.73 (3H, m), 10.97 (1H, s); MS m/e MH$^+$ 417.

Example 516

N-{4-[trans-4-(2-Amino-2-oxoethyl)cyclohexyl]phenyl}-5-[(2-fluorophenyl)-amino]-1,3,4-oxadiazole-2-carboxamide

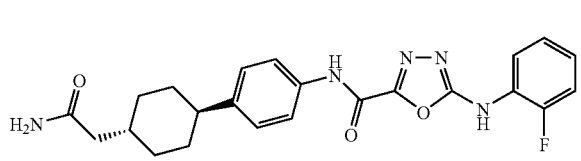

Ethyl chloroformate (0.056 mL, 0.58 mmol) was added dropwise to a stirred solution of (trans-4-{4-[({5-[(2-fluorophenyl)amino]-1,3,4-oxadiazol-2-yl}carbonyl)amino]-phenyl}cyclohexyl)acetic acid (Example 118) (170 mg, 0.39 mmol) and N-methyl morpholine (0.064 mL, 0.58 mmol) in DCM (5 mL) at 0° C. The mixture was stirred for 40 minutes then ammonia (2 mL of a 7M solution in MeOH) was added and stirring was continued for 16 h whilst warming to ambient temperature. Volatile material was removed by evaporation and the residue was triturated with water and washed with 10% ammonium hydroxide solution (10 mL) followed by ether (10 mL) and dried under reduced pressure to give the title compound (121 mg, 71%) as a solid; $^1$H NMR δ 0.98-1.15 (m, 2H), 1.33-1.50 (m, 2H), 1.63-1.85 (m, 5H), 1.95 (d, 2H), 2.37-2.44 (m, 1H), 6.75 (s, 1H), 7.10-7.35 (m, 5H), 7.66 (d, 2H), 8.03 (t, 1H), 10.78 (s, 1H), 10.99 (s, 1H); MS m/e MH$^+$ 438.

Example 517

N-{4-[trans-4-(Cyanomethyl)cyclohexyl]phenyl}-5-[(2-fluorophenyl)amino]-1,3,4-oxadiazole-2-carboxamide

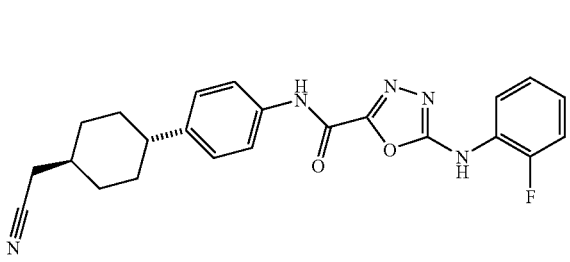

Trifluoroacetic anhydride 0.042 mL, 0.05 mmol) was added to a stirred solution of N-{4-[trans-4-(2-amino-2-oxoethyl)cyclohexyl]phenyl}-5-[(2-fluorophenyl)amino]-1,3,4-oxadiazole-2-carboxamide (Example 516) (20 mg, 0.05 mmol) and pyridine (90 uL, 0.11 mmol) in DCM (2 mL). After 15 minutes DCM (10 mL) was added and the reaction mixture was washed sequentially with 1M HCl (5 mL), water (10 mL) and 10% ammonium hydroxide solution (5 mL) then dried and concentrated under reduced pressure to give the title compound (18 mg, 95%) as a solid; $^1$H NMR δ 1.13-1.30 (m, 3H), 1.40-1.54 (m, 2H), 1.60-1.75 (m, 1H), 1.76-1.92 (m, 5H), 2.40-2.50 (m, 1H), 7.10-7.19 (m, 1H), 7.20-7.35 (m, 4H), 7.68 (d, 2H), 8.03 (t, 1H), 10.75 (s, 1H), 10.93 (s, 1H); MS m/e MH$^+$ 420.

Example 518

5-[(2-Fluorophenyl)amino]-N-[4-(propylsulfonyl)phenyl]-1,3,4-oxadiazole-2-carboxamide Following the general procedure of Example 105 but using 2-hydrazino-2-oxo-N-[4-(propylsulfonyl)phenyl]acetamide (Intermediate 97) as starting material in place of methyl [trans-4-(4-{[hydrazino(oxo)acetyl]amino}phenyl)cyclohexyl]acetate and using 2-fluorophenylisothiocyanate in place of 2-isothiocyanatopyridine the title compound was obtained as a solid; $^1$H NMR δ 0.90 (t, 3H), 1.46-1.62 (m, 2H), 3.18-3.27 (m, 2H), 7.12-7.20 (m, 1H), 7.22-7.35 (m, 2H), 7.87 (d, 2H), 7.99-8.10 (m, 3H), 10.90 (s, 1H), 11.50 (s, 1H); MS m/e MH$^+$ 405.

Examples 519-522

The following examples were prepared by the general procedure of Example 127 using Intermediate 21 and the appropriate commercially available aniline as starting materials

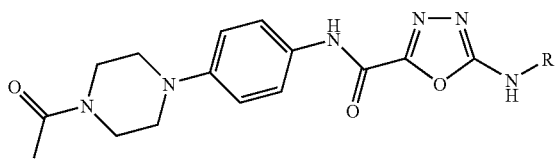

| Example | Name | ¹H NMR δ | MS m/e MH⁺ |
|---|---|---|---|
| 519 | Methyl 4'-{[5-({[4-(4-acetylpiperazin-1-yl)phenyl]amino}carbonyl)-1,3,4-oxadiazol-2-yl]amino}biphenyl-4-carboxylate | 2.07 (s, 3H), 3.05-3.11 (m, 2H), 3.12-3.19 (m, 2H), 3.54-3.63 (m, 4H), 3.93 (s, 3H), 6.97 (d, 2H), 7.64-7.88 (m, 8H), 8.03 (d, 2H), 10.90 (s, 1H), 11.20 (s, 1H) | 541 |
| 520 | N-[4-(4-acetylpiperazin-1-yl)phenyl]-5-[(4-chloro-2-fluoro-5-hydroxyphenyl)amino]-1,3,4-oxadiazole-2-carboxamide | 2.08 (s, 3H), 3.02-3.20 (m, 4H), 3.53-3.62 (m, 4H), 6.97 (d, 2H), 7.39 (d, 1H), 7.65 (d, 2H), 7.84 (d, 1H), 10.35 (s, 1H), 10.80 (s, 1H), 10.84 (s, 1H) | 475 |
| 521 | Ethyl (5-{[5-({[4-(4-acetylpiperazin-1-yl)phenyl]amino}carbonyl)-1,3,4-oxadiazol-2-yl]amino}-2-chloro-4-fluorophenoxy)acetate | 1.22 (t, 3H), 2.08 (s, 3H), 3.04-3.19 (m, 4H), 3.53-3.63 (m, 4H), 4.20 (q, 2H), 4.92 (s, 2H), 6.97 (d, 2H), 7.56 (d, 1H), 7.65 (d, 2H), 7.85 (d, 1H), 10.85 (s, 1H), 11.00 (s, 1H) | 561 |
| 522 | Methyl 3'-{[5-({[4-(4-acetylpiperazin-1-yl)phenyl]amino}carbonyl)-1,3,4-oxadiazol-2-yl]amino}biphenyl-4-carboxylate | 2.07 (s, 3H), 3.04-3.20 (m, 4H), 3.53-3.64 (m, 4H), 3.94 (s, 3H), 6.97 (d, 2H), 7.43 (d, 1H), 7.54 (t, 1H), 7.67 (d, 3H), 7.81 (d, 2H), 7.96-8.00 (m, 1H), 8.09 (d, 2H), 10.89 (s, 1H), 11.16 (s, 1H) | 541 |

Example 523

3'-{[5-({[-4-(4-Acetylpiperazin-1-yl)phenyl]amino}carbonyl)-1,3,4-oxadiazol-2-yl]amino}biphenyl-4-carboxylic acid

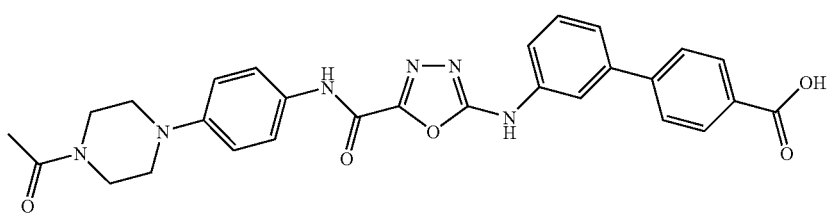

Following the procedure of Example 357 but using methyl 3'-{[5-({[4-(4-acetylpiperazin-1-yl)phenyl]amino}carbonyl)-1,3,4-oxadiazol-2-yl]amino}biphenyl-4-carboxylate as starting material in place of methyl (trans-4-{4-[({5-[(4-ethylphenyl)amino]-1,3,4-oxadiazol-2-yl}carbonyl)amino]phenyl}cyclohexyl)acetate the title compound was obtained as a solid; ¹H NMR δ 2.09 (s, 3H), 3.01-3.20 (m, 4H), 3.52-3.67 (m, 4H), 6.98 (d, 2H), 7.41 (d, 1H), 7.53 (t, 1H), 7.61-7.71 (m, 3H), 7.78 (d, 2H), 8.00 (s, 1H), 8.07 (d, 2H), 10.87 (s, 1H), 11.18 (s, 1H), 13.37 (s, 1H); MS m/e MH⁺ 527.

Example 524

2-({4-[({5-[(2-fluorophenyl)amino]-1,3,4-oxadiazol-2-yl}carbonyl)amino]phenyl}sulfonyl)-2-methylpropanoic acid

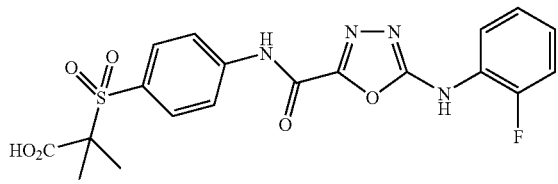

Following the general procedure described in Example 357 except using ethyl 2-({4-[({5-[(2-fluorophenyl)amino]-1,3,4-oxadiazol-2-yl}carbonyl)amino]phenyl}sulfonyl)-2-methylpropanoate (Intermediate 98) as the ester starting material the title compound was obtained as a solid; $^1$H NMR δ 1.50 (s, 6H), 7.12-7.20 (m, 1H), 7.23-7.36 (m, 2H), 7.79 (d, 2H), 7.98-8.12 (m, 3H), 10.90 (s, 1H), 11.56 (s, 1H); MS m/e MH$^+$ 449.

Example 525

(trans-4-{4-[({5-[(3-Methylisoxazol-5-yl)amino]-1,3,4-oxadiazol-2-yl}carbonyl)amino]phenyl}cyclohexyl)acetic acid

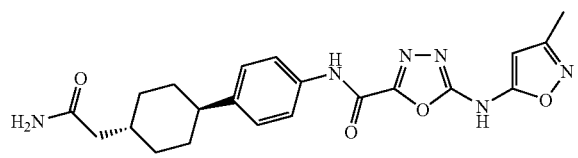

Sodium hydride (50 mg of a 60% dispersion in mineral oil, 1.25 mmol) was added to a stirred solution of 5-amino-3-methylisoxazole in THF. After 5 minutes di-2-pyridyl thionocarbonate (290 mg, 1.25 mmol) was added. Stirring was continued for a further 10 minutes then methyl [trans-4-(4-{[hydrazino(oxo)acetyl]amino}phenyl)cyclo-hexyl]acetate (Intermediate 43) (333 mg, 1.00 mmol) was added followed by DMF (5 mL). The mixture heated to 85° C. for 15 minutes then EDAC (240 mg, 1.25 mmol) was added. After a further 1 h at 85° C. volatile material was removed by evaporation and the residue was redissolved in MeOH (5 mL), THF (2.5 mL) and NaOH (3 mL of a 2M aqueous solution) and stirred for 16 h. The reaction mixture was concentrated under reduced pressure then redissolved in water (10 mL) and acidified with HCl (2M aqueous solution) to ca pH 5. The resulting precipitate was centrifuged, washed with water, dried under reduced pressure and triturated with ether to give the title compound (83 mg, 20%) as a solid; $^1$H NMR δ 1.02-1.20 (m, 2H), 1.36-1.54 (m, 2H), 1.65-1.88 (m, 5H), 2.13 (d, 2H), 2.24 (s, 3H), 2.39-2.48 (m, 1H), 6.10 (s, 1H), 7.24 (d, 2H), 7.69 (d, 2H), 11.00 (s, 1H), 12.11 (s, 1H); MS m/e MH$^+$ 426.

Examples 526-539

The following examples were prepared by the general procedure of Example 525 using the appropriate commercially available amino-heterocycle in place of 5-amino-3-methylisoxazole.

| Example | Name | $^1$H NMR δ | MS m/e MH$^+$ |
| --- | --- | --- | --- |
| 526 | {trans-4-[4-({[5-(1,3,4-thiadiazol-2-ylamino)-1,3,4-oxadiazol-2-yl]carbonyl}amino)phenyl]cyclohexyl}-acetic acid | 1.03-1.19 (m, 2H), 1.34-1.54 (m, 2H), 1.65-1.91 (m, 5H), 2.13 (d, 2H), 2.38-2.48 (m, 1H), 7.20 (d, 2H), 7.68 (d, 2H), 8.90 (s, 1H), 10.86 (s, 1H) | 428 |
| 527 | (trans-4-{4-[({5-[(2,5-dimethylpyridin-4-yl)amino]-1,3,4-oxadiazol-2-yl}carbonyl)amino]phenyl}cyclohexyl)-acetic acid | 1.03-1.21 (m, 2H), 1.36-1.53 (m, 2H), 1.67-1.89 (m, 5H), 2.14 (d, 2H), 2.22 (s, 3H), 2.41-2.48 (m, 4H), 7.21 (d, 2H), 7.70 (d, 2H), 7.95-8.06 (m, 2H) | |
| 528 | (trans-4-{4-[({5-[(5,6-dimethylpyrazin-2-yl)amino]-1,3,4-oxadiazol-2-yl}carbonyl)amino]phenyl}cyclohexyl)-acetic acid | 1.02-1.20 (m, 2H), 1.37-1.53 (m, 2H), 1.65-1.88 (m, 5H), 2.36-2.47 (m, 7H), 7.20 (d, 2H), 7.66 (d, 2H), 8.91 (s, 1H), 10.94 (s, 1H) | 451 |
| 529 | (trans-4-{4-[({5-[(3-methylpyrazin-2-yl)amino]-1,3,4-oxadiazol-2-yl}carbonyl)amino]phenyl}cyclohexyl)-acetic acid | 0.99-1.22 (m, 2H), 1.30-1.53 (m, 2H), 1.64-1.89 (m, 5H), 2.07-2.18 (m, 2H), 2.38-2.47 (m, 1H), 2.58 (s, 3H), 6.67 (d, 1H), 6.98 (d, 1H), 7.20 (d, 2H), 7.65 (d, 2H) | 437 |
| 530 | (trans-4-{4-[({5-[(5-bromopyrazin-2-yl)amino]-1,3,4-oxadiazol-2- | 1.02-1.20 (m, 2H), 1.36-1.54 (m, 2H), 1.63-1.90 (m, 5H), 2.14 (d, 2H), 2.38-2.48 (m, 1H), 7.22 (d, | 502 |

| Example | Name | ¹H NMR δ | MS m/e MH⁺ |
|---|---|---|---|
| | yl}carbonyl)amino]phenyl}cyclohexyl)-acetic acid | 2H), 7.68 (d, 2H), 8.48 (s, 1H), 8.91 (s, 1H), 10.85 (s, 1H) | |
| 531 | (trans-4-{4-[({5-[(2-methoxypyrimidin-5-yl)amino]-1,3,4-oxadiazol-2-yl}carbonyl)amino]phenyl}cyclohexyl)-acetic acid | 0.93-1.12 (m, 2H), 1.30-1.46 (m, 2H), 1.55-1.81 (m, 5H), 2.00-2.11 (m, 2H), 2.32-2.41 (m, 1H), 3.86 (s, 3H), 7.12 (d, 2H), 7.60 (d, 2H), 8.70 (s, 2H) | 453 |
| 532 | (trans-4-{4-[({5-[(5-benzyl-1,3,4-oxadiazol-2-yl)amino]-1,3,4-oxadiazol-2-yl}carbonyl)amino]phenyl}cyclohexyl)-acetic acid | 7.67 (d, 2H), 7.10-7.44 (m, 7H), 4.02 (s, 2H), 2.38-2.48 (m, 1H), 2.14 (d, 2H), 1.61-1.93 (m, 5H), 1.34-1.54 (m, 2H), 1.02-1.27 (m, 2H) | 503 |
| 533 | (trans-4-{4-[({5-[(3-methyl-1,2,4-thiadiazol-5-yl)amino]-1,3,4-oxadiazol-2-yl}carbonyl)amino]phenyl}cyclohexyl)-acetic acid | 0.99-1.20 (m, 2H), 1.35-1.55 (m, 2H), 1.63-1.92 (m, 5H), 2.14 (d, 2H), 2.35-2.47 (m, 4H), 7.22 (d, 2H), 7.67 (d, 2H), 10.87 (s, 1H) | 443 |
| 534 | (trans-4-{4-[({5-[(3-ethyl-1,2,4-thiadiazol-5-yl)amino]-1,3,4-oxadiazol-2-yl}carbonyl)amino]phenyl}cyclohexyl)-acetic acid | 1.04-1.19 (m, 2H), 1.23 (t, 3H), 1.37-1.55 (m, 2H), 1.65-1.94 (m, 5H), 2.15 (d, 2H), 2.37-2.49 (m, 1H), 2.67 (q, 2H), 7.21 (d, 2H), 7.68 (d, 2H), 10.72 (s, 1H) | 457 |
| 535 | (trans-4-{4-[({5-[(2,4-dimethylpyrimidin-5-yl)amino]-1,3,4-oxadiazol-2-yl}carbonyl)amino]phenyl}cyclohexyl)-acetic acid | 1.03-1.20 (m, 2H), 1.36-1.53 (m, 2H), 1.65-1.89 (m, 5H), 2.14 (d, 2H), 2.36-2.53 (m, 7H), 7.24 (d, 2H), 7.56-7.76 (m, 3H), 10.98 (s, 1H), 11.97 (s, 1H) | 451 |
| 536 | (trans-4-{4-[({5-[(1,3-dimethyl-1H-pyrazol-5-yl)amino]-1,3,4-oxadiazol-2-yl}carbonyl)amino]phenyl}cyclohexyl)-acetic acid | 1.03-1.20 (m, 2H), 1.38-1.53 (m, 2H), 1.67-1.88 (m, 5H), 2.09-2.17 (m, 5H), 2.36-2.48 (m, 1H), 3.68 (s, 3H), 6.14 (s, 1H), 7.22 (d, 2H), 7.67 (d, 2H), 10.91 (s, 1H) | 439 |
| 537 | (trans-4-{4-[({5-[(6-chloropyrazin-2-yl)amino]-1,3,4-oxadiazol-2-yl}carbonyl)amino]phenyl}cyclohexyl)-acetic acid | 1.03-1.20 (m, 2H), 1.36-1.54 (m, 2H), 1.65-1.91 (m, 5H), 2.15 (d, 2H), 2.40-2.49 (m, 1H), 7.25 (d, 2H), 7.69 (d, 2H), 8.48 (s, 1H), 9.20 (s, 1H), 11.05 (s, 1H), 11.86 (s, 1H) | 457 |
| 538 | (trans-4-{4-[({5-[(3,5-dimethylpyrazin-2-yl)amino]-1,3,4-oxadiazol-2-yl}carbonyl)amino]phenyl}cyclohexyl)-acetic acid | 1.23-1.41 (m, 2H), 1.56-1.75 (m, 2H), 1.85-2.10 (m, 5H), 2.34 (d, 2H), 2.56-2.74 (m, 7H), 7.43 (d, 2H), 7.87 (d, 2H), 8.35 (s, 1H), 11.12 (s, 1H), 12.14 (s, 1H) | 451 |
| 539 | [trans-4-(4-{[(5-{[4-(trifluoromethyl)-1,3-thiazol-2-yl]amino}-1,3,4-oxadiazol-2-yl)carbonyl]amino}phenyl)cyclohexyl]-acetic acid | 1.02-1.20 (m, 2H), 1.36-1.55 (m, 2H), 1.66-1.93 (m, 5H), 2.14 (d, 2H), 2.38-2.49 (m, 1H), 7.21 (d, 2H), 7.68 (d, 2H), 7.89 (s, 1H), 10.93 (s, 1H), 11.98 (s, 1H) | 496 |

Example 540

Methyl (trans-4-{4-[({5-[(3,4-difluorophenyl)amino]-1,3,4-oxadiazol-2-yl}carbonyl)amino]phenyl}cyclohexyl)acetate

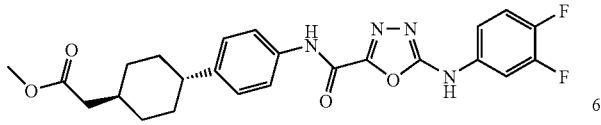

Following the general procedure of Example 457, except that 3,4-difluorophenyl-isothiocyanate was used in place of 3-fluorophenylisothiocyanate, the title compound was obtained in 90% yield as a solid; ¹H NMR δ 1.04-1.21 (m, 2H), 1.37-1.54 (m, 2H), 1.69-1.87 (m, 5H), 2.25 (d, 2H), 2.38-2.48 (m, 1H), 3.61 (s, 3H), 7.22 (d, 2H), 7.31-7.40 (m, 1H), 7.48 (q, 1H), 7.65-7.76 (m, 3H), 10.96 (s, 1H), 11.24 (s, 1H); MS m/e (M–H)⁻ 469.

Example 541

(trans-4-{4-[({5-[(3,4-Difluorophenyl)amino]-1,3,4-oxadiazol-2-yl}carbonyl)amino]phenyl}cyclohexyl)acetic acid

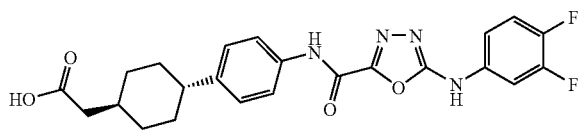

Following the procedure of Example 468 except the starting material was methyl (trans-4-{4-[({5-[(3,4-difluorophenyl)amino]-1,3,4-oxadiazol-2-yl}carbonyl)amino]phenyl}cyclohexyl)acetate, the title compound was obtained in 56% yield as a solid; $^1$H NMR δ 1.12 (q, 2H), 1.46 (q, 2H), 1.65-1.75 (m, 1H), 1.79 (t, 4H), 2.15 (d, 2H), 2.37-2.48 (m, 1H), 7.23 (d, 2H), 7.31-7.39 (m, 1H), 7.49 (q, 1H), 7.70 (d, 2H), 7.71-7.75 (m, 1H); MS m/e MH$^+$ 457.

Examples 542-546

The following Examples were prepared by the procedure of Example 525 with Intermediate 43 and the appropriate commercially available aniline RNH$_2$.

| Example | R | HPLC Retention Time (minutes) (in LCMS system) | MS m/e MH$^+$ |
|---|---|---|---|
| 542 | 3-Cl, 4-CN phenyl | 2.92 | 494 |
| 543 | 4-CN, 3-CF$_3$ phenyl | 2.99 | 567 |
| 544 | 3-CN, 4-CN phenyl | 2.78 | 483 |
| 545 | 3-CH$_3$, 4-CN phenyl | 2.85 | 474 |
| 546 | 3-SCH$_3$, 4-CN phenyl | 2.92 | 506 |

Examples 547-551

The following Examples were prepared by the procedure of Example 357 starting with the appropriate ester selected from Examples 542-546 to give the illustrated acid.

| Example | R | $^1$H NMR δ | MS m/e MH$^+$ |
|---|---|---|---|
| 547 | 3-Cl, 4-CN phenyl | 1.11-1.14 (2H, m), 1.44-1.48 (2H, m), 1.73-1.85 (5H, m), 2.14-2.16 (2H, m), 2.41-2.50 (1H, m), 7.23 (2H, d), 7.70 (3H, d), 7.93 (1H, d), 7.99 (1H, d), 11.01 (1H, s), 11.81 (1H, s), 11.97 (1H, s) | 480 |
| 548 | 4-CN, 3-CF$_3$ phenyl | 1.11-1.18 (2H, m), 1.42-1.51 (2H, m), 1.73-1.85 (5H, m), 2.15 (2H, d), 2.41-2.50 (1H, m), 7.24 (2H, d), 7.70 (2H, d), 8.01-8.04 (1H, m), 8.17-8.20 (2H, m), 11.01 (1H, s), 11.97 (2H, s) | 514 |

-continued

| Example | R | $^1$H NMR δ | MS m/e MH$^+$ |
|---|---|---|---|
| 549 | 3,4-dicyanophenyl | 1.08-1.18 (2H, m), 1.44-1.48 (2H, m), 1.72-1.33 (5H, m), 2.14-2.16 (2H, m), 2.41-2.50 (1H, m), 7.24 (2H, d), 7.70 (2H, d), 8.00-8.03 (1H, m), 8.15-8.17 (2H, m), 11.03 (1H, s), 12.02 (1H, s) | 471 |
| 550 | 4-cyano-3-methylphenyl | 1.11-1.18 (1H, m), 1.42-1.50 (2H, m), 1.71-1.85 (5H, m), 2.15 (2H, d), 2.41-2.50 (1H, m), 7.23 (2H, d), 7.60-7.64 (2H, m), 7.69 (2H, d), 7.80 (1H, d), 10.96 (1H, s), 11.47 (1H, s), 11.97 (1H, s) | 460 |
| 551 | 4-cyano-3-(methylthio)phenyl | 1.08-1.12 (2H, m), 1.42-1.50 (2H, m), 1.71-1.85 (5H, m), 2.14-2.16 (2H, m), 2.41-2.50 (1H, m), 2.60 (3H, s), 7.23 (2H, d), 7.48-7.50 (1H, m), 7.70 (2H, d), 7.74 (1H, d), 7.81 (1H, d), 10.97 (1H, s), 11.60 (1H, s), 11.97 (1H, s) | 492 |

Examples 552-569

The following Examples were prepared in two steps: (i) oxadiazole ring synthesis by the procedure of Example 354 with Intermediate 43 and the appropriate commercially available aniline RNH$_2$ then (ii) ester hydrolysis by the procedure of Example 357 to give the illustrated acid.

| Example | R | $^1$H NMR δ | MS m/e MH$^+$ |
|---|---|---|---|
| 552 | 3-chloro-4-fluorophenyl | 1.08-1.17 (2H, m), 1.39-1.53 (2H, m), 1.74-1.85 (5H, m), 2.15 (2H, d), 2.42-2.51 (1H, m), 7.23 (2H, d), 7.47 (1H, t), 7.52-7.56 (1H, m), 7.69 (2H, d), 7.82-7.85 (1H, m), 10.94 (1H, s), 11.20 (1H, s), 11.96 (1H, s) | 473 |
| 553 | 3,5-dimethylphenyl | 1.08-1.14 (2H, m), 1.44-1.48 (2H, m), 1.74-1.82 (5H, m), 2.15 (2H, d), 2.28 (6H, s), 2.41-2.50 (1H, m), 6.71 (1H, s), 7.22-7.26 (4H, m), 7.68-7.70 (2H, m), 10.77 (1H, s), 10.88 (1H, s), 11.97 (1H, s) | 449 |

-continued
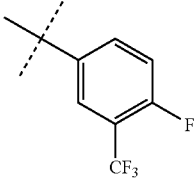
| Example | R | ¹H NMR δ | MS m/e MH⁺ |
|---|---|---|---|
| 554 | 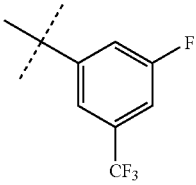 | 1.08-1.14 (2H, m), 1.42-1.50 (2H, m), 1.72-1.85 (5H, m), 2.15 (2H, d), 2.41-2.50 (1H, m), 7.23 (2H, d), 7.59 (1H, t), 7.69 (2H, d), 7.88-7.92 (1H, m), 8.01-8.03 (1H, m), 10.94 (1H, s), 11.34 (1H, s), 11.97 (1H, s) | 507 |
| 555 | 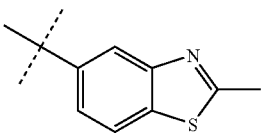 | 1.08-1.17 (2H, m), 1.42-1.51 (2H, m), 1.71-1.85 (5H, m), 2.15 (2H, d), 2.41-2.50 (1H, m), 7.24 (2H, d), 7.35 (1H, d), 7.70 (2H, d), 7.76-7.79 (2H, ni.), 10.98 (1H, s), 11.62 (1H, s), 11.97 (1H, s) | 507 |
| 556 | 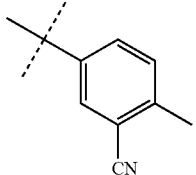 | 1.08-1.17 (2H, m), 1.42-1.51 (2H, m), 1.71-1.85 (5H, m), 2.14-2.16 (2H, m), 2.41-2.50 (1H, m), 2.78 (3H, s), 7.23 (2H, d), 7.60-7.62 (1H, m), 7.70 (2H, d), 7.92 (1H, d), 8.31 (1H, d), 10.93 (1H, s), 11.19 (1H, s), 11.97 (1H, s) | 492 |
| 557 | 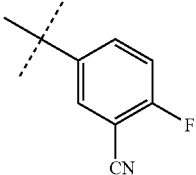 | 1.11-1.18 (2H, m), 1.42-1.50 (2H, m), 1.71-1.85 (5H, m), 2.15 (2H, d), 2.41-2.50 (1H, m), 2.46 (3H, s), 7.23 (2H, d), 7.50 (1H, d), 7.69 (2H, d), 7.73-7.76 (1H, m), 7.96 (1H, d), 10.95 (1H, s), 11.27 (1H, s), 11.97 (1H, s | 458 |
| 558 | 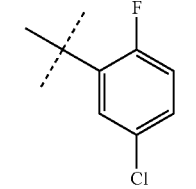 | 1.11-1.18 (2H, m), 1.42-1.50 (2H, m), 1.71-1.85 (5H, m), 2.15 (2H, d), 2.41-2.50 (1H, m), 2.46 (3H, s), 7.23 (2H, d), 7.50 (1H, d), 7.69 (2H, d), 7.73-7.76 (1H, m), 7.96 (1H, d), 10.95 (1H, s), 11.27 (1H, s), 11.97 (1H, s | 464 |
| 559 | 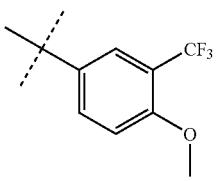 | 1.08-1.17 (2H, m), 1.41-1.48 (2H, m), 1.71-1.85 (5H, m), 2.15 (2H, d), 2.41-2.50 (1H, m), 7.18-7.24 (3H, m), 7.35-7.40 (1H, m), 7.64-7.70 (2H, m), 8.20-8.22 (1H, m), 10.96 (1H, s), 11.07 (1H, s), 11.97 (1H, s) | 473 |
| 560 | | 1.11-1.17 (2H, m), 1.42-1.50 (2H, m), 1.71-1.85 (5H, m), 2.14-2.16 (2H, m), 2.41-2.50 (1H, m), 3.88 (3H, s), 7.23 (2H, d), 7.35 (1H, d), 7.69 (2H, d), 7.82-7.84 (1H, m), 7.90 (1H, d), 10.90 (1H, s), 11.01 (1H, s), 11.97 (1H, s) | 519 |

-continued

| Example | R | ¹H NMR δ | MS m/e MH⁺ |
|---|---|---|---|
| 561 | 4-Cl-3-CN-phenyl | 1.11-1.18 (2H, m), 1.42-1.50 (2H, m), 1.73-1.85 (5H, m), 2.15 (2H, d), 2.41-2.50 (1H, m), 7.23 (2H, d), 7.70 (2H, d), 7.78 (1H, d), 7.86-7.89 (1H, m), 8.09 (1H, d), 10.98 (1H, s), 11.55 (1H, s), 11.97 (1H, s) | 478 |
| 562 | 4-Cl-3-OMe-phenyl | 1.08-1.18 (2H, m), 1.42-1.50 (2H, m), 1.71-1.85 (5H, m), 2.15 (2H, d), 2.41-2.50 (1H, m), 3.88 (3H, s), 7.20-7.24 (3H, m), 7.42-7.44 (2H, m), 7.69 (2H, d), 10.91 (1H, s), 11.11 (1H, s), 11.97 (1H, s) | 485 |
| 563 | 3-CF₃-5-OMe-phenyl | 1.11-1.17 (2H, m), 1.42-1.50 (2H, m), 1.72-1.85 (5H, m), 2.14-2.16 (2H, m), 2.41-2.50 (1H, m), 3.86 (3H, s), 6.95 (1H, s), 7.23 (2H, d), 7.52 (2H, d), 7.69 (2H, d), 10.94 (1H, s), 11.33 (1H, s), 11.97 (1H, s) | 519 |
| 564 | 4-Cl-3-F-phenyl | δ1.07-1.17 (2H, m), 1.42-1.50 (2H, m), 1.71-1.85 (5H, m), 2.14-2.16 (2H, m), 2.42-2.48 (1H, m), 7.23 (2H, d), 7.38-7.41 (1H, m), 7.61 (1H, t), 7.68-7.72 (3H, m), 10.96 (1H, s), 11.38 (1H, s), 11.97 (1H, s) | 473 |
| 565 | 3-F-4-CN-phenyl | 1.08-1.18 (2H, m), 1.41-1.50 (2H, m), 1.71-1.85 (5H, m), 2.15 (2H, d), 2.42-2.53 (1H, m), 7.24 (2H, d), 7.67 (2H, d), 7.79-7.81 (1H, m), 7.92-7.95 (1H, m), 8.38 (1H, t), 11.01 (1H, s), 11.44 (1H, s), 11.97 (1H, s) | 464 |
| 566 | 3-F-4-OMe-phenyl | 1.30-1.39 (2H, m), 1.63-1.72 (2H, m), 1.93-2.06 (5H, m), 2.36 (2H, d), 2.41-2.50 (1H, m), 4.04 (3H, s), 7.43 (3H, t), 7.51-7.54 (1H, m), 7.72-7.76 (1H, m), 7.90 (2H, d), 11.12-11.15 (2H, m), 12.18 (1H, s) | 469 |
| 567 | 2-methylbenzothiazol-5-yl | 1.11-1.18 (2H, m), 1.42-1.51 (2H, m), 1.72-1.85 (5H, m), 2.14-2.16 (2H, m), 2.41-2.50 (1H, m), 2.81 (3H, s), 7.23 (2H, d), 7.53-7.56 (1H, m), 7.71 (2H, d), 8.01 (1H, d), 8.31 (1H, d), 10.95 (1H, s), 11.17 (1H, s), 11.97 (1H, s) | 492 |
| 568 | 2-oxo-2,3-dihydro-1H-benzimidazol-5-yl | 1.11-1.18 (2H, m), 1.42-1.50 (2H, m), 1.72-1.85 (5H, m), 2.14-2.16 (2H, m), 2.41-2.50 (1H, m), 6.92 (1H, d), 7.08-7.11 (1H, m), 7.22 (2H, d), 7.37 (1H, d), 7.69 (2H, d), 10.49 (1H, s), 10.58 (1H, s), 10.73 (1H, s), 10.87 (1H, s), 11.97 (1H, s) | 477 |

-continued

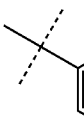

| Example | R | ¹H NMR δ | MS m/e MH⁺ |
|---|---|---|---|
| 569 | 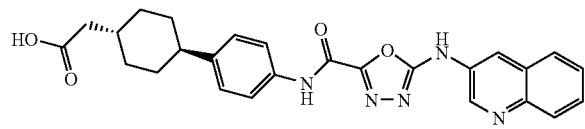 | 1.13 (2H, d), 1.44-1.48 (2H, m), 1.82 (5H, m), 2.14-2.16 (2H, m), 2.41-2.50 (1H, m), 2.55 (3H, s), 7.24 (2H, d), 7.50-7.53 (1H, m), 7.69-7.75 (3H, m), 8.14 (1H, d), 10.94 (1H, s), 11.26 (1H, s), 11.97 (1H, m) | 475 |

Example 570

{trans-4-[4-({[5-(Quinolin-3-ylamino)-1,3,4-oxadiazol-2-yl]carbonyl}amino)-phenyl]cyclohexyl}acetic acid Thiocarbonyl diimidazole (178 mg, 1.00 mmol) was added in one portion to a solution of 3-aminoquinoline (144 mg, 1.00 mmol) in DMA (5 mL) and the solution was stirred at room temperature for 40 h. Methyl [trans-4-(4-{[hydrazino (oxo)acetyl]amino}phenyl)cyclohexyl]acetate (Intermediate 43, 333 mg, 1.00 mmol) was added in one portion and the reaction mixture was stirred at room temperature for 20 h and then heated at 80° C. for 15 mins in the microwave. The solution was cooled to room temperature and EDCI (192 mg, 1.00 mmol) was added in one portion and the reaction mixture was heated to 90° C. for 20 mins in the microwave. The reaction mixture was concentrated in vacuo to give a gum, which was recrystallised (CH₃CN) to give the crude oxadiazole methyl ester intermediate as a gummy solid that was used with no further purification.

Lithium hydroxide (420 mg, 10.0 mmol) was added in one portion to a solution of the crude oxadiazole methyl ester intermediate in a mixture of THF (4 mL), MeOH (8 mL) and H₂O (4 mL) and the reaction mixture was stirred at 35° C. for 3 h. Citric acid (30 mL) was added and the mixture was filtered to leave a solid that was triturated (MeOH). The resulting solid was recrystallised using DMSO:H₂O:CH₃CN (7:1:2) to give the title compound (216 mg, 46%) as a solid; ¹H NMR δ1.08-1.18 (2H, m), 1.42-1.52 (2H, m), 1.71-1.85 (6H, m), 2.15 (2H, d), 7.24 (2H, d), 7.59-7.68 (2H, m), 7.70-7.73 (2H, m), 7.99 (2H, t), 8.62 (1H, d), 8.99 (1H, d), 10.96 (1H, s); MS m/e (M−H)⁻ 471.

Examples 571-581

The following examples were prepared by the general procedure of Example 570 using the appropriate commercially available amino-heterocycle as starting material except where stated otherwise.

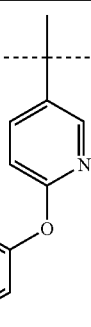

| Example | R | ¹H NMR δ | MS m/e (M −H)⁻ |
|---|---|---|---|
| 571 | | 1.07-1.17 (2H, m), 1.41-1.51 (2H, m), 1.69-1.84 (6H, m), 2.14-2.16 (2H, d), 7.14-7.18 (3H, m), 7.22 (2H, d), 7.44-7.47 (2H, m), 7.68-7.71 (2H, m), 8.10-8.13 (1H, m), 8.40 (1H, d), 10.92 (1H, s) | 547 |

-continued
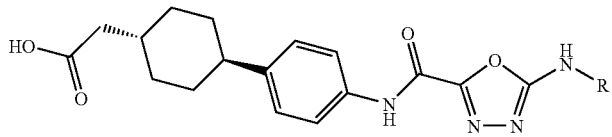
| Example | R | ¹H NMR δ | MS m/e (M −H)⁻ |
|---|---|---|---|
| 572 | 5-(6-methoxypyridyl) | 1.07-1.17 (2H, m), 1.41-1.50 (2H, m), 1.70-1.75 (1H, m), 1.78-1.85 (5H, m), 2.13 (2H, d), 3.61 (2H, s), 3.84 (3H, s), 6.88 (1H, d), 7.22 (2H, d), 7.69 (2H, d), 7.92-7.95 (1H, m), 8.39 (1H, d), 10.85 (1H, s) | 451 |
| 573 | 2-(4-methylpyridyl) | 1.07-1.18 (2H, m), 1.42-1.50 (2H, m), 1.71-1.85 (7H, m), 2.15 (2H, d), 2.37 (3H, s), 6.89 (1H, d), 7.21-7.24 (2H, m), 7.68-7.73 (3H, m), 8.14 (1H, d), 10.87 (1H, s), 11.84 (2H, s) | 435 |
| 574 | 2-(5-methylpyridyl) | 1.08-1.18 (2H, m), 1.41-1.50 (2H, m), 1.71-1.85 (6H, m), 2.14-2.16 (2H, d), 2.27 (3H, s), 7.21-7.24 (2H, m), 7.68-7.72 (3H, m), 7.82 (1H, d), 8.15 (1H, s) | 435 |
| 575 | 3-(2-methoxypyridyl) | 1.07-1.17 (2H, m), 1.41-1.50 (2H, m), 1.71-1.84 (6H, m), 2.14-2.16 (2H, d), 3.96 (3H, s), 7.06-7.09 (1H, m), 7.23 (2H, d), 7.67-7.70 (2H, d), 7.90-7.91 (1H, m), 8.30-8.33 (1H, m), 10.40 (1H, s), 10.91 (1H, s), 11.97 (1H, s) | 451 |
| 576 | 2-(5-fluoropyridyl) | 1.07-1.17 (2H, m), 1.41-1.51 (2H, m), 1.69-1.84 (6H, m), 2.15 (2H, d), 2.45-2.48 (1H, m), 7.23 (2H, d), 7.69 (2H, d), 7.82-7.90 (1H, m), 7.96-8.00 (1H, m), 8.36 (1H, d), 10.95 (1H, s) | 439 |

-continued
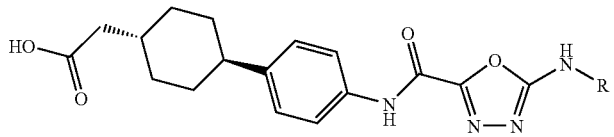
| Example | R | ¹H NMR δ | MS m/e (M −H)⁻ |
|---|---|---|---|
| 577 | (5-pyridyl with 6-O-(4-methoxyphenyl)) | 1.11-1.17 (2H, m), 1.41-1.51 (2H, m), 1.71-1.84 (6H, m), 2.15 (2H, d), 3.77 (3H, s), 6.94-6.98 (2H, m), 7.04-7.08 (3H, m), 7.22 (2H, d), 7.68-7.70 (2H, m), 8.04-8.07 (1H, m), 8.36 (1H, d), 10.91 (1H, s) | 543 |
| 578[1] | (5-pyridyl with 6-O-CH₂-(3-chlorophenyl)) | 1.06-1.17 (2H, m), 1.41-1.51 (2H, m), 1.69-1.84 (5H, m), 2.15 (2H, d), 5.36 (2H, d), 6.99-7.01 (1H, m), 7.22 (2H, d), 7.37-7.44 (4H, m), 7.51 (1H, s), 7.68-7.70 (2H, d), 7.96-7.99 (1H, m), 8.40-8.41 (1H, m), 10.90 (1H, s) | 561 |
| 579 | (7-azaindol-5-yl) | 1.08-1.17 (2H, m), 1.42-1.50 (2H, m), 1.72-1.85 (6H, m), 2.14-2.16 (2H, d), 6.48 (1H, d), 7.23 (2H, d), 7.49 (1H, d), 7.70 (2H, d), 8.27 (1H, d), 8.36 (1H, d), 10.84 (1H, s), 10.89 (1H, s), 11.61 (1H, s) | 460 |
| 580[2] | (6-cyanopyridin-3-yl) | 1.14 (2H, m), 1.46 (2H, m), 1.82 (5H, m), 2.14-2.16 (2H, d), 7.24 (2H, d), 7.69-7.72 (2H, d), 8.08 (1H, d), 8.26-8.29 (1H, m), 8.84 (1H, d), 11.97 (1H, s) | 447 |

-continued

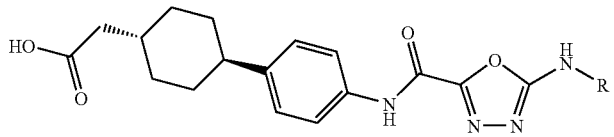

| Example | R | $^1$H NMR δ | MS m/e (M −H)$^-$ |
|---|---|---|---|
| 581[2] | 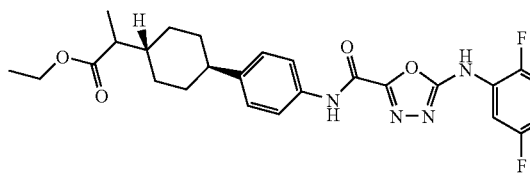 | | 447 |

[1] The amino-heterocycle was synthesised as described as in WO2001021597
[2] Purified by reverse phase preparative HPLC, eluting with a gradient of CH$_3$CN and H$_2$O containing 0.2% TFA

Example 582 rac-trans-Ethyl 2-(4-{4-[({5-[(2,4,5-trifluorophenyl)amino]-1,3,4-oxadiazol-2-yl}carbonyl)-amino]phenyl}cyclohexyl)propanoate 2,4,5-Trifluorophenyl isothiocyanate (252 mg, 1.33 mmol) was added in one portion to a suspension of trans-ethyl 2-[4-(4-{[hydrazino(oxo)acetyl]amino}phenyl)cyclo-hexyl]propanoate (Intermediate 99, 400 mg, 1.11 mmol) in DMA (6 mL) and the reaction mixture was stirred at room temperature for 2 h. EDCI (319 mg, 1.66 mmol) was added in one portion and the reaction mixture was heated to 90° C. for 10 mins in the microwave. The mixture was then cooled to room temperature and H$_2$O (20 mL) was added. The mixture was filtered to leave a solid, which was washed with H$_2$O (10 mL) to give the title compound (550 mg, 95%) as a solid; $^1$H NMR δ 1.1 (3H, d), 1.12-1.28 (2H, m), 1.2 (3H, t), 1.35-1.51 (2H, m), 1.52-1.64 (1H, m), 1.65-1.75 (1H, m), 1.77-1.9 (3H, m), 2.22-2.32 (1H, m), 2.38-2.51 (1H, m), 4.01-4.16 (2H, m), 7.2 (2H, d), 7.65-7.78 (1H, m), 7.69 (2H, d), 8.1-8.25 (1H, m), 10.95 (1H, s), 11.05 (1H, s); MS m/e MH$^+$ 517.

Examples 583-584

The following examples were prepared by the general procedure of Example 582 using the appropriate commercially available isothiocyanate as starting material.

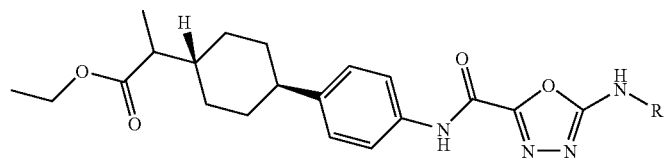

| Example | R | $^1$H NMR δ | MS m/e (M −H)$^-$ |
|---|---|---|---|
| 583 | (4-cyanophenyl) | 1.08 (3H, d), 1.1-1.28 (2H, m), 1.2 (3H, t), 1.35-1.5 (2H, m), 1.51-1.64 (1H, m), 1.65-1.74 (1H, m), 1.75-1.9 (3H, m), 2.22-2.34 (1H, m), 2.39-2.5 (1H, m), 4.01-4.16 (2H, m), 7.21 (2H, d), 7.7 (2H, d), 7.78 (2H, d), 7.89 (2H, d), 11.0 (1H, s), 11.55 (1H, s) | 488 |

-continued

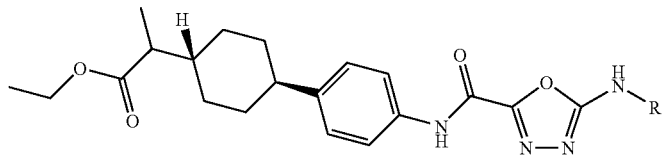

| Example | R | ¹H NMR δ | MS m/e (M −H)⁻ |
|---|---|---|---|
| 584 | (3,4-difluorophenyl, attached via isopropyl-like linker) | 1.1 (3H, d), 1.12-1.28 (2H, m), 1.2 (3H, t), 1.37-1.51 (2H, m), 1.52-1.64 (1H, m), 1.65-1.75 (1H, m), 1.77-1.9 (3H, m), 2.22-2.34 (1H, m), 2.39-2.5 (1H, m), 4.03-4.17 (2H, m), 7.22 (2H, d), 7.32-7.4 (1H, m), 7.44-7.55 (1H, m), 7.65-7.75 (1H, m), 7.7 (2H, d), 10.95 (1H, s), 11.25 (1H, s) | 499 |

Example 585 rac-2-(trans-4-{4-[([{5-(2,4,5-trifluorophenyl)amino]-1,3,4-oxadiazol-2-yl}carbonyl)amino]phenyl}cyclohexyl)propanoic acid

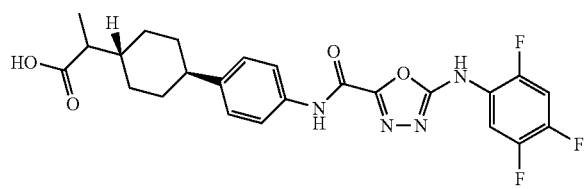

A solution of lithium hydroxide (17 mg, 0.39 mmol) in H₂O (1.0 mL) was added in one portion to a solution of trans-ethyl 2-(4-{4-[({5-[(2,4,5-trifluorophenyl)amino]-1,3,4-oxadiazol-2-yl}carbonyl)-amino]phenyl}cyclohexyl)propanoate (Example 582, 25 mg, 0.05 mmol) in a mixture of THF (1.5 mL) and MeOH (1.5 mL) and the reaction mixture was stirred at room temperature for 24 h. A 1M aqueous solution of citric acid (10 mL) was added and the mixture was filtered to leave a solid. The solid was washed with H₂O (2 mL) and purified by reverse phase preparative HPLC, eluting with a gradient of CH₃CN and H₂O containing 0.2% TFA to give the title compound (10 mg, 42%) as a solid. The individual isomers may be separated by chiral chromatography under standard conditions and purified by recrystallisation from EtOH to give:

(2R)-2-(trans-4-{4-[({5-[(2,4,5-Trifluorophenyl)amino]-1,3,4-oxadiazol-2-yl}carbonyl)amino]phenyl}cyclohexyl)-propanoic acid ¹H NMR δ 1.01-1.1 (5H, m), 1.1-1.28 (2H, m), 1.37-1.5 (2H, m), 1.51-1.63 (1H, m), 1.71-1.9 (4H, m), 2.14-2.22 (1H, m), 2.4-2.5 (1H, m), 3.45 (2H, dq), 4.32 (1H, t), 7.21 (2H, d), 7.62-7.75 (m, 1H), 7.7 (2H, d), 8.1-8.22 (m, 1H), 10.95 (1H, s), 11.03 (1H, s), 12.0 (1H, s); MS m/e MH⁺ 489.

(2S)-2-(trans-4-{4-[(5-[(2,4,5-Trifluorophenyl)amino]-1,3,4-oxadiazol-2-yl}carbonyl)amino]phenyl}cyclohexyl)propanoic acid ¹H NMR δ1.01-1.1 (5H, m), 1.1-1.28 (2H, m), 1.37-1.5 (2H, m), 1.51-1.63 (1H, m), 1.71-1.9 (4H, m), 2.14-2.22 (1H, m), 2.4-2.5 (1H, m), 3.45 (2H, dq), 4.32 (1H, t), 7.21 (2H, d), 7.62-7.75 (m, 1H), 7.7 (2H, d), 8.1-8.22 (m, 1H), 10.95 (1H, s), 11.03 (1H, s), 12.0 (1H, s); MS m/e MH⁺ 489.

Example 586 rac-trans-2-(4-{4-[({5-[(3,4-Difluorophenyl)amino]-1,3,4-oxadiazol-2-yl}carbonyl)amino]-phenyl}cyclohexyl)propanoic acid

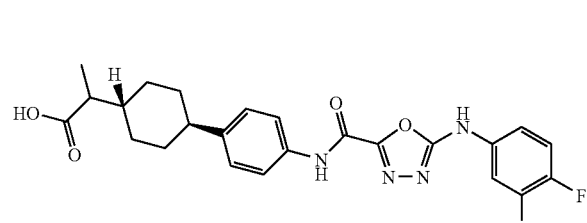

The following example was prepared using the method described for Example 585 but using Example 584 as starting material to give the title compound (9.5 mg, 40%) as a solid. The individual isomers may be separated by chiral chromatography under standard conditions and purified by recrystallisation from EtOH to give:

(2R)-2-(trans-4-{4-[({5-[(3,4-difluorophenyl)amino]-1,3,4-oxadiazol-2-yl}carbonyl)amino]phenyl}cyclohexyl)propanoic acid ¹H NMR δ 1.05 (3H, d), 1.1-1.26 (2H, m), 1.35-1.5 (2H, m), 1.51-1.62 (1H, m), 1.7-1.9 (4H, m), 2.12-2.23 (1H, m), 2.38-2.5 (1H, m), 7.21 (2H, d), 7.29-7.38 (1H, m), 7.41-7.51 (1H, m), 7.64-7.76 (1H, m), 7.69 (2H, d), 11.0 (1H, s); MS m/e MH⁺ 471.

(2S)-2-(trans-4-{4-[({5-[(3,4-difluorophenyl)amino]-1,3,4-oxadiazol-2-yl}carbonyl)amino]-phenyl}cyclohexyl)propanoic acid ¹H NMR δ1H NMR δ: 1.05 (3H, d), 1.1-1.26 (2H, m), 1.35-1.5 (2H, m), 1.51-1.62 (1H, m), 1.7-1.9 (4H, m), 2.12-2.23 (1H, m), 2.38-2.5 (1H, m), 7.21 (2H, d), 7.29-7.38 (1H, m), 7.41-7.51 (1H, m), 7.64-7.76 (1H, m), 7.69 (2H, d), 11.0 (1H, s), 11.7 (1H, s); MS m/e MH⁺ 471.

Example 587 rac-trans-2-(4-{4-[({5-[(4-Cyanophenyl)amino]-1,3,4-oxadiazol-2-yl}carbonyl)amino]-phenyl}cyclohexyl)propanoic acid

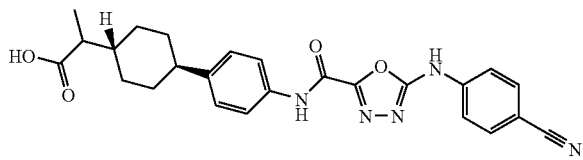

Potassium trimethylsilanolate (65 mg, 0.51 mmol) was added in one portion to a solution of trans-ethyl 2-(4-{4-[({5-[(4-cyanophenyl)amino]-1,3,4-oxadiazol-2-yl}carbonyl)amino]-phenyl}cyclohexyl)propanoate (Example 583, 25 mg, 0.051 mmol) in THF (2 mL) and the reaction mixture was stirred at room temperature for 48 h. A 1M aqueous solution of citric acid (10 mL) was added and the mixture was filtered to leave a solid. The solid was washed with H₂O (2 mL) and purified by reverse phase preparative HPLC, eluting with a gradient of CH₃CN and H₂O containing 0.2% TFA, to give the title compound (11 mg, 47%) as a solid; ¹H NMR δ 1.05 (3H, t), 1.1-1.3 (2H, m), 1.38-1.51 (2H, m), 1.52-1.63 (1H, m), 1.7-1.9 (4H, m), 2.13-2.25 (1H, m), 2.4-2.5 (1H, m), 7.22 (2H, d), 7.7 (2H, d), 7.76 (2H, d), 7.85 (2H, d), 11.0 (1H, s); MS m/e MH⁺ 460.

Examples 588-597

The following Examples were prepared in two steps: (i) oxadiazole ring synthesis by the procedure of Example 1 with Intermediate 43 and the appropriate commercially available isothiocyanate R—NCS then (ii) hydrolysis of the crude ester product by the procedure of Example 357 to give the indicated acid.

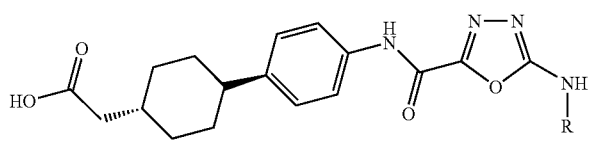

| Example | R | ¹H NMR δ | MS m/e MH⁺ |
|---|---|---|---|
| 588 | (4-methylphenyl) | 1.07-1.17 (2H, m), 1.41-1.51 (2H, m), 1.70-1.85 (6H, m), 2.15 (2H, d), 2.28 (3H, s), 7.19-7.24 (4H, m), 7.48-7.50 (2H, m), 7.69 (2H, d), 10.81-10.89 (2H, m), 11.97 (1H, s) | 433 (M−H)⁻ |
| 589 | (4-bromophenyl) | 1.11-1.14 (2H, m), 1.44-1.48 (2H, m), 1.82 (6H, t), 2.14-2.16 (2H, m), 7.23 (2H, d), 7.58 (4H, s), 7.69 (2H, d), 10.94 (1H, s), 11.13 (1H, s), 11.98 (1H, s) | 499 |
| 590 | (4-ethoxyphenyl) | 1.14 (2H, d), 1.33 (3H, t), 1.44-1.48 (2H, m), 1.82 (6H, t), 2.15 (2H, d), 4.01 (2H, q), 6.95-6.98 (2H, m), 7.22 (2H, d), 7.49-7.51 (2H, m), 7.69 (2H, d), 10.71 (1H, s), 10.88 (1H, s), 11.97 (1H, s) | 465 |
| 591 | (4-tert-butylphenyl) | 1.08-1.18 (2H, m), 1.29 (9H, s), 1.42-1.50 (2H, m), 1.70-1.85 (6H, m), 2.15 (2H, d), 7.23 (2H, d), 7.39-7.43 (2H, m), 7.51-7.53 (2H, m), 7.69 (2H, d), 10.83 (1H, s), 10.89 (1H, s), 11.98-11.99 (1H, m) | 477 |

-continued
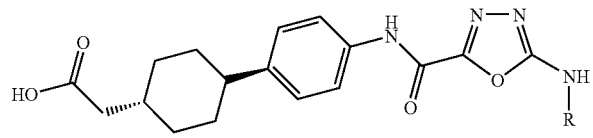
| Example | R | ¹H NMR δ | MS m/e MH⁺ |
|---|---|---|---|
| 592 | 2-ethoxyphenyl (CMe₂) | 1.13 (2H, d), 1.37 (3H, t), 1.44-1.48 (2H, m), 1.82 (6H, m), 2.15 (2H, d), 4.11 (2H, q), 6.97-7.02 (1H, m), 7.08-7.10 (2H, m), 7.23 (2H, d), 7.68 (2H, d), 7.92-7.94 (1H, m), 9.96 (1H, s), 10.89 (1H, s), 11.97 (1H, s) | 465 |
| 593 | 2-methylphenyl (CMe₂) | 1.07-1.17 (2H, m), 1.40-1.51 (2H, m), 1.68-1.84 (6H, m), 2.16 (2H, m), 2.30 (3H, s), 7.08-7.15 (1H, m), 7.17-7.37 (4H, m), 7.67-7.74 (3H, m), 10.02 (1H, s), 10.89 (1H, s), 12.00 (1H, s) | 435 |
| 594 | 4-sulfamoylphenyl (CMe₂) | 1.07-1.17 (2H, m), 1.41-1.51 (2H, m), 1.70-1.84 (6H, m), 2.15 (2H, d), 7.22-7.26 (4H, m), 7.68-7.71 (2H, m), 7.73-7.75 (2H, m), 7.84-7.86 (2H, m), 10.96 (1H, s), 11.41 (1H, s), 11.99 (1H, s) | 498 (M−H)⁻ |
| 595 | 2-chlorophenyl (CMe₂) | 1.10-1.14 (2H, m), 1.44-1.48 (2H, m), 1.73-1.84 (6H, m), 2.14-2.16 (2H, m), 7.20-7.24 (3H, m), 7.41-7.45 (1H, m), 7.54-7.57 (1H, m), 7.68 (2H, d), 7.95-7.98 (1H, m), 10.41 (1H, s), 10.93 (1H, s) 12.00 (1H, s) | 453 (M−H)⁻ |
| 596 | 3-methoxyphenyl (CMe₂) | 1.08-1.15 (2H, m), 1.44-1.48 (2H, m), 1.74-1.85 (6H, m), 2.14-2.16 (2H, m), 3.74-3.78 (3H, m), 6.65-6.67 (1H, m), 7.14-7.32 (5H, m), 7.68-7.71 (2H, m), 10.91-10.94 (2H, m), 11.97 (1H, s) | 451 |
| 597 | 4-(trifluoromethylthio)phenyl (CMe₂) | 1.10-1.14 (2H, m), 1.44-1.48 (2H, m), 1.82 (6H, t), 2.15 (2H, q), 7.23 (2H, d), 7.70 (2H, d), 7.76 (4H, s), 10.96 (1H, s), 11.40 (1H, s), 12.00 (1H, s) | 519 (M−H)⁻ |

Examples 598-601

The following examples were prepared by the general procedure of Example 483, using the appropriate aniline (commercially available unless indicated otherwise) and 3,4-difluorophenylisothiocyanate.

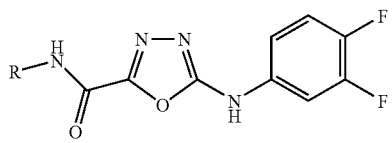

| Example | R | $^1$H NMR δ | MS m/e MH$^+$ |
|---|---|---|---|
| 598 | 3-phenoxyphenyl | 6.99-7.07 (4H, m), 7.12-7.16 (1H, m), 7.34-7.42 (3H, m), 7.45-7.52 (1H, m), 7.68-7.73 (1H, m), 7.81-7.83 (2H, m), 11.07 (1H, s), 11.23 (1H, s) | 407 (M−H)$^-$ |
| 599[1] | 3-(2-methoxyphenoxy)phenyl | 3.76 (3H, s), 6.85-6.87 (2H, m), 6.96-6.99 (1H, m), 7.00-7.04 (1H, m), 7.17-7.21 (2H, m), 7.35 (1H, t), 7.45-7.52 (1H, m), 7.67-7.73 (3H, m), 10.98 (1H, s), 11.22 (1H, s) | 439 |
| 600[2] | 3-(4-methylphenoxy)phenyl | 2.30 (3H, s), 6.90-6.93 (2H, m), 6.99-7.01 (2H, m), 7.19-7.21 (2H, m), 7.35 (1H, d), 7.44-7.49 (1H, m), 7.67-7.73 (1H, m), 7.78-7.80 (2H, m), 11.04 (2H, s) | 423 |

-continued

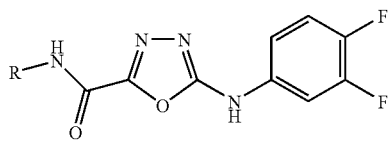

| Example | R | ¹H NMR δ | MS m/e MH⁺ |
|---|---|---|---|
| 601 | (3-methoxyphenoxy)phenyl-isopropyl group | 3.75 (3H, s), 6.53-6.58 (2H, m), 6.70-6.73 (1H, m), 7.04-7.08 (2H, m), 7.28 (1H, t), 7.34-7.38 (1H, m), 7.45-7.52 (1H, m), 7.68-7.73 (1H, m), 7.80-7.84 (2H, m), 11.08 (1H, s), 11.24 (1H, s) | 439 |

[1] Preparation of aniline starting material described in Patent Application WO 2001056990
[2] Preparation of aniline starting material described in Patent Application WO 9521815

Example 602

N-(3,5-Dichloro-4-morpholin-4-ylphenyl)-5-[(3-methylphenyl)amino]-1,3,4-oxadiazole-2-carboxamide

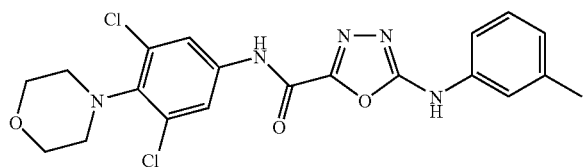

Following the general procedure of Example 1, using Intermediate 100 and 3-methylphenylisothiocyanate as starting materials, the title compound was obtained; ¹H NMR δ 2.30 (3H, s), 3.11 (4H, t), 3.67-3.69 (4H, m), 6.87 (1H, d), 7.25 (1H, t), 7.36 (1H, s), 7.42 (1H, d), 7.91 (2H, s), 10.94 (1H, broad s), 11.17 (1H, broad s); MS m/e MH⁺ 448.

Example 603

N-{6-[4-(Cyclopropylmethyl)piperazin-1-yl]pyridin-3-yl}-5-[(2-fluorophenyl)amino]-1,3,4-oxadiazole-2-carboxamide

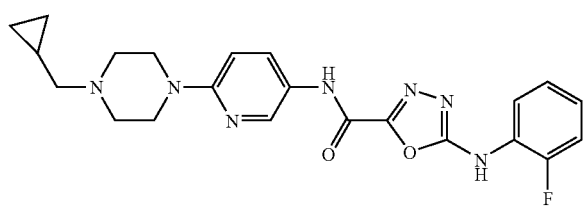

5-[(2-Fluorophenyl)amino]-N-(6-piperazin-1-ylpyridin-3-yl)-1,3,4-oxadiazole-2-carboxamide (Intermediate 41) (120 mg, 0.31 mmol) in DMA (2 mL) was placed in a microwave tube with cyclopropylmethyl bromide (88 mg, 0.62 mmol), and triethylamine (64 mg, 0.62 mmol). The mixture was heated with stirring in the microwave at 110° C. for 60 minutes then transferred directly onto a reverse phase HPLC column and eluted with a gradient of acetonitrile/water containing 0.2%/TFA to give the title compound (125 mg, 91%) as a solid; ¹H NMR δ 10.65 (1H, s), 10.40 (1H, bs), 8.20 (1H, s), 7.65 (2H, m), 6.90 (2H, m), 6.80 (1H, m), 6.65 (1H, d), 4.00 (2H, d), 3.25 (2H, d), 2.80 (6H, m), 0.75 (1H, m), 0.30 (2H, m), 0.00 (2H, m); MS m/e MH⁺ 438.

Example 604

5-[(2-Fluorophenyl)amino]-N-{6-[4-(2-methoxyethyl)piperazin-1-yl]pyridin-3-yl}-1,3,4-oxadiazole-2-carboxamide

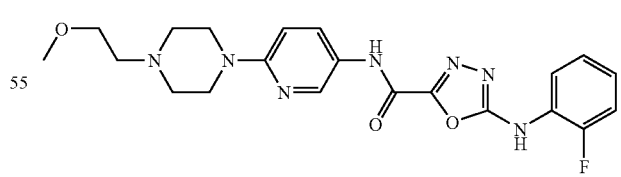

Following the procedure of Example 603 except that 1-bromo-2-methoxyethane was used in place of cyclopropylmethyl bromide, the title compound was obtained; ¹H NMR δ 10.98 (1H, s), 10.73 (1H, bs), 8.55 (1H, s), 8.00 (2H, m), 7.30 (2H, m), 7.15 (1H, m), 6.95 (1H, d), 4.30 (2H, bd), 3.70 (2H, m), 3.55 (2H, m), 3.35 (5H, m), 3.15 (4H, m); MS m/e MH⁺ 442.

Examples 605-609

The following examples were prepared by the general procedure of Example 72 using Intermediate 40 and the appropriate aniline.

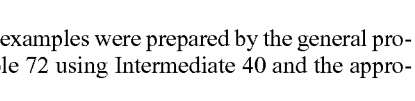

| Example | R | $^1$H NMR δ | MS m/e MH$^+$ |
|---|---|---|---|
| 605 | ![morpholinoethoxy]  (2-morpholin-4-ylethoxy) | 10.90 (1H, s), 10.75 (1H, s), 8.05 (1H, t), 7.70 (1H, d), 7.30 (2H, m), 7.15 (1H, m), 7.00 (2H, d), 4.20 (2H, m), 3.70 (4H, bs), 3.25 (4H, bs), 2.70 (2H, m) | 428 |
| 606 | ![3-hydroxypropoxy]  (3-hydroxypropoxy) | 10.90 (1H, s), 10.85 (1H, s), 8.05 (1H, t), 7.70 (2H, d), 7.30 (2H, d), 7.20 (1H, m), 6.95 (2H, d), 4.00 (2H, t), 3.55 (2H, t), 1.85 (2H, q) | 394 (M + Na)$^+$ |
| 607 | ![2-ethoxyethoxy]  (2-ethoxyethoxy) | 10.85 (1H, s), 10.75 (1H, s), 8.05 (1H, t), 7.70 (2H, d), 7.30 (2H, m), 7.15 (1H, m), 6.95 (2H, d), 4.05 (2H, t), 3.70 (2H, t), 3.50 (2H, q), 1.15 (3H, t) | 385 (M −H)$^-$ |
| 608 | ![N,N-diethyl-2-methylpropanamide]  (N,N-diethyl-2-methylpropanamide) | 10.95 (1H, s), 10.70 (1H, bs), 8.05 (1H, t), 7.65 (2H, d), 7.30 (2H, m), 7.15 (1H, m), 6.80 (2H, d), 3.65 (2H, q), 3.06 (2H, q), 1.55 (6H, s), 1.05 (3H, t), 0.90 (3H, t) | 456 |
| 609 | ![pyrrolidin-1-yl]  (pyrrolidin-1-yl) | | 368 |

The aniline starting materials are described in the following references:
[1] PCT Patent Application WO2004005282 (4-(2-morpholin-4-ylethoxy)aniline)
[2] PCT Patent Application WO9515952 (3-(4-aminophenoxy)propan-1-ol)
[3] German Patent Application DE2732384 (4-(2-ethoxyethoxy)aniline)
[4] Indian Journal of chemistry, Section B, 1986, 25B(12), 1277 (2-(4-aminophenoxy)-N,N-diethyl-2-methylpropanamide)
[5] PCT Patent Application WO2004073634A2)(4-pyrrolidin-1-ylaniline)

Example 610

Methyl trans-4-{4-[({5-[(2,4,5-trifluorophenyl)amino]-1,3,4-oxadiazol-2-yl}carbonyl)amino]phenyl}cyclohexanecarboxylate

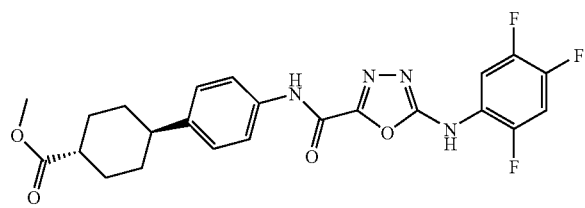

Following the procedure of Example 105 except that methyl trans-4-(4-{[hydrazino(oxo) acetyl]amino}phenyl)cyclohexanecarboxylate (Intermediate 44) and 2,4,5-trifluorophenylisothiocyanate were used as starting materials the title compound was obtained as solid; $^1$H NMR δ 1.47 (1H, s), 1.49 (2H, d), 1.52 (1H, s), 1.85 (2H, d), 2.01 (2H, d), 2.45 (1H+DMSO, m), 2.53-2.56 (1H, m), 3.62 (3H, s), 7.22-7.24 (2H, m), 7.68 (1H, s), 7.71 (2H, q), 8.15-8.18 (1H, m), 10.96 (1H, s), 11.04 (1H, s) MS m/e MH$^+$ 475.

Example 611 trans-4-{4-[({5-[(2,4,5-Trifluorophenyl)amino]-1,3,4-oxadiazol-2-yl}carbonyl)-amino]phenyl}cyclohexanecarboxylic acid

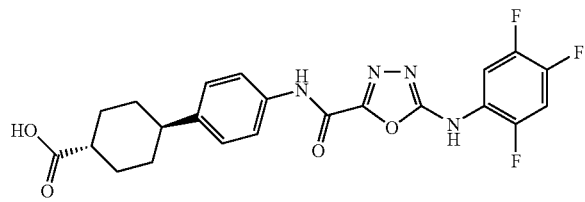

Following the procedure of Example 112 except that the starting material was methyl trans-4-{4-[({5-[(2,4,5-trifluorophenyl)amino]-1,3,4-oxadiazol-2-yl}carbonyl)amino]phenyl}cyclohexanecarboxylate (Example 610) and purification was by trituration with MeCN the title compound was obtained as a solid; $^1$H NMR δ 1.44 (1H, s), 1.48 (3H, d), 1.52 (1H, s), 1.84 (2H, d), 2.00 (2H, d), 2.25 (2H, d), 2.45 (1H+DMSO, m), 2.53-2.56 (1H, m), 7.23 (2H, d), 7.68 (1H, s), 7.69 (2H, d), 8.15 (1H, s); MS m/e MH$^+$ 461.

Example 612

Methyl 6-{4-[({5-[(2-fluorophenyl)amino]-1,3,4-oxadiazol-2-yl}carbonyl)amino]-piperidin-1-yl}nicotinate

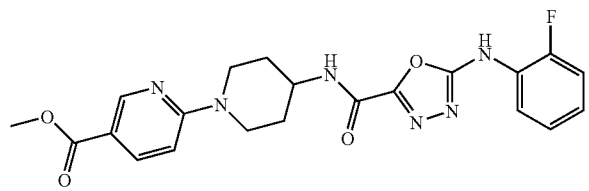

A solution of 5-[(2-fluorophenyl)amino]-N-piperidin-4-yl-1,3,4-oxadiazole-2-carboxamide (Intermediate 101) (100 mg, 0.33 mmol) and methyl 6-chloronicotinate (56 mg, 0.33 mmol) in dry DMF (3 mL) was heated in the microwave at 120° C. for 1 h. The reaction mixture was filtered and the filtrate was purified by preparative HPLC to give the title compound (17 mg, 12%) as a solid; $^1$H NMR δ 1.66-1.53 (m, 2H), 1.92-1.82 (m, 2H), 3.12-2.99 (m, 2H), 3.80 (s, 3H), 4.16-4.04 (m, 1H), 4.54-4.42 (m, 2H), 6.92 (d, 1H), 7.18-7.10 (m, 1H), 7.33-7.21 (m, 2H), 7.97-7.92 (m, 1H), 8.04-7.98 (m, 1H), 8.65 (d, 1H), 9.03 (d, 1H), 10.62 (s, 1H); MS m/e MH$^+$ 441.

Example 613

6-{4-[({5-[(2-Fluorophenyl)amino]-1,3,4-oxadiazol-2-yl}carbonyl)amino]-piperidin-1-yl}nicotinic acid

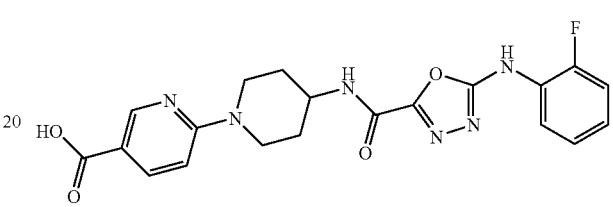

A mixture of 2M NaOH (2 mL, 4 mmol) and methyl 6-{4-[({5-[(2-fluorophenyl)amino]-1,3,4-oxadiazol-2-yl}carbonyl)amino]piperidin-1-yl}nicotinate (17 mg, 0.04 mmol) (Example 612) in MeOH (10 mL) was stirred for 16 h then taken to pH 7 by addition of 2M HCl. The solution was concentrated by evaporation to give a cloudy aqueous mixture that was cooled on an ice bath. The precipitate was collected by filtration, washed with water and Et$_2$O and dried to give the title compound (13 mg, 88%) as a solid; $^1$H NMR (CD$_3$OD) δ 8.61 (s, 1H), 8.02-7.88 (m, 2H), 7.16-7.05 (m, 2H), 7.05-6.97 (m, 1H), 6.75 (d, 1H), 4.47-4.37 (m, 2H), 4.17-4.06 (m, 1H), 3.08-2.97 (m, 2H), 1.99-1.89 (m, 2H), 1.63-1.50 (m, 2H); MS m/e MH$^+$ 427.

Example 614

6-{4-[({5-[(2-Fluorophenyl)amino]-1,3,4-oxadiazol-2-yl}carbonyl)amino]-piperidin-1-yl}nicotinamide

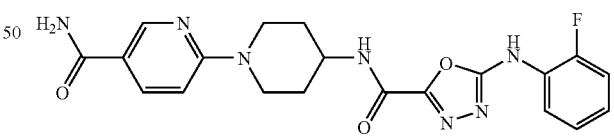

A solution of 5-[(2-fluorophenyl)amino]-N-piperidin-4-yl-1,3,4-oxadiazole-2-carboxamide (Intermediate 101) (200 mg, 0.66 mmol) and 6-chloronicotinamide (103 mg, 0.66 mmol) in dry DMF (4 mL) was heated in the microwave at 125° C. for 20 minutes and then for a further 10 minutes at 135° C. The mixture was filtered and purified by preparative HPLC to give the title compound (7 mg, 2.5%) as a solid; $^1$H NMR δ 1.55-1.65 (2H, m), 1.83-1.86 (2H, m), 2.99 (2H, t), 4.04-4.12 (1H, m), 4.42-4.46 (2H, m), 6.87 (1H, d), 7.11 (2H, m), 7.21-7.30 (2H, m), 7.72 (1H, s), 7.94-8.03 (2H, m), 8.62 (1H, d), 8.99 (1H, d), 10.61 (1H, s); MS m/e MH$^+$ 426.

Example 615

(6-{4-[({5-[(2-Fluorophenyl)amino]-1,3,4-oxadiazol-2-yl}carbonyl)amino]-piperidin-1-yl}pyridin-3-yl)acetic acid

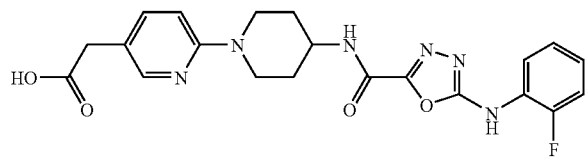

A mixture of 2M NaOH (0.09 mL, 0.18 mmol) and methyl (6-{4-[({5-[(2-fluorophenyl)amino]-1,3,4-oxadiazol-2-yl}carbonyl)amino]piperidin-1-yl}pyridin-3-yl)acetate (Intermediate 102) (41 mg, 0.09 mmol) in MeOH (1 mL) was stirred for 16 h then acidified with 2M HCl and concentrated by evaporation. The residue purified by preparative HPLC to give the title compound (1 mg) as a gum; $^1$H NMR (CD$_3$OD) δ 1.78-1.63 (m, 3H), 2.11-2.00 (m, 2H), 3.35-3.25 (m, 2H), 3.55 (s, 2H), 4.23-4.07 (m, 3H), 7.07-6.99 (m, 1H), 7.15-7.07 (m, 2H), 7.30-7.23 (m, 1H), 7.79 (s, 1H), 7.89-7.83 (m, 1H), 7.99-7.91 (m, 1H); MS m/e MH$^+$ 441.

Example 616

5-{[3-(Anilinocarbonyl)phenyl]amino}-N-(6-morpholin-4-ylpyridin-3-yl)-1,3,4-oxadiazole-2-carboxamide

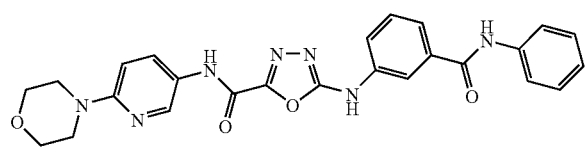

EDCI (77 mg, 0.40 mmol) was added to a suspension of 3-[(5-{[(6-morpholin-4-ylpyridin-3-yl)amino]carbonyl}-1,3,4-oxadiazol-2-yl)amino]benzoic acid (Intermediate 103) (150 mg, 0.37 mmol), aniline (0.043 mL, 0.44 mmol) and HOBt (54 mg, 0.40 mmol) in DMF (4.5 mL). After 72 hours the mixture was diluted with H$_2$O (20 mL) and the solid filtered. Purification by reverse phase preparative HPLC (2 injections of 55 mg in 2 mL DMF) gave the title compound (as a trifluoroacetate salt) (6.8 mg, 3%) as a solid; $^1$H NMR δ 3.45 (4H, t), 3.72 (4H, t), 6.96 (1H, d), 7.12 (1H, t), 7.37 (2H, t), 7.56 (1H, t), 7.65 (1H, d), 7.77 (1H, s), 7.79-7.79 (1H, m), 7.84-7.86 (1H, m), 8.00-8.03 (1H, m), 8.11 (1H, d), 8.53 (1H, d), 10.29 (1H, s), 11.03 (1H, s), 11.17 (1H, s); MS m/e (MH)$^+$ 486.

Example 617

N-{4-[trans-4-(Aminomethyl)cyclohexyl]phenyl}-5-[(2-fluorophenyl)amino]-1,3,4-oxadiazole-2-carboxamide

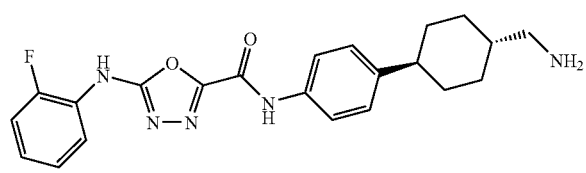

4M HCl in 1,4-dioxane (1 mL) was added to tert-butyl [(trans-4-{4-[({5-[(2-fluorophenyl)amino]-1,3,4-oxadiazol-2-yl}carbonyl)amino]phenyl}cyclohexyl)-methyl]carbamate (Example 618) (50 mg, 0.10 mmol) and the suspension stirred for 18 hours. All volatiles were removed in vacuo and the residue triturated with Et$_2$O (3 mL), the solid filtered, washed with Et$_2$O (2×5 mL), isohexane (2×5 mL) to give the title compound (as a hydrochloride salt) (44 mg, 99%) as a white solid; $^1$H NMR δ 1.07-1.16 (2H, m), 1.39-1.47 (2H, m), 1.57-1.69 (1H, m), 1.87 (4H, t), 2.41-2.52 (1H, m), 2.71 (2H, d), 7.14-7.20 (1H, m), 7.23 (1H, s), 7.25-7.27 (2H, m), 7.29-7.34 (1H, m), 7.70 (2H, d), 7.87 (3H, s), 8.01-8.06 (1H, m), 10.76 (1H, s), 10.94 (1H, s); MS m/e (MH)$^+$ 410.

Example 618 tert-Butyl [(trans-4-{4-[({5-[(2-fluorophenyl)amino]-1,3,4-oxadiazol-2-yl}carbonyl)amino]phenyl}cyclohexyl)methyl]carbamate

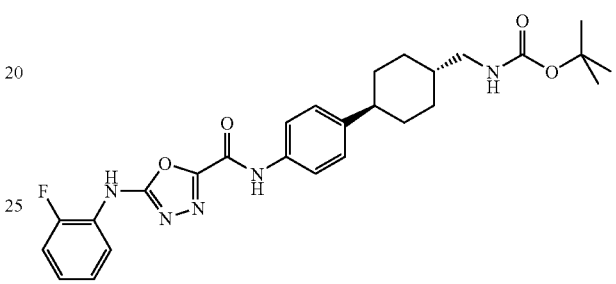

The following example was prepared according to the procedure of Example 141 using Intermediate 104 and 2-fluorophenyl isothiocyanate to give the title compound as a solid; $^1$H NMR δ 1.00-1.06 (2H, m), 1.35-1.39 (2H, m), 1.79-1.81 (4H, m), 2.44 (1H, t), 2.82 (2H, t), 6.81 (1H, t), 7.13-7.34 (5H, m), 7.68 (2H, d), 8.02-8.07 (1H, m), 10.75 (1H, s), 10.92 (1H, s); MS m/e (MH)$^+$ 510.

Example 619

Methyl (1-{5-[({5-[(3,4-difluorophenyl)amino]-1,3,4-oxadiazol-2-yl}carbonyl)amino]pyridin-2-yl}piperidin-4-yl)acetate

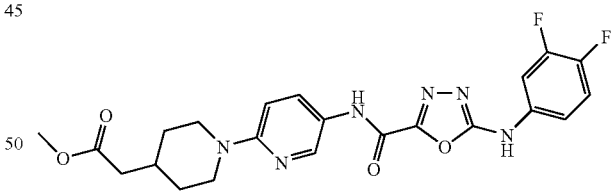

To a suspension methyl [1-(5-{[hydrazino(oxo)acetyl]amino}pyridin-2-yl)piperidin-4-yl]acetate (Intermediate 77) (250 mg, 0.745 mmol) in anhydrous DMF (3 mL) was added 3,4-difluoroisothiocyanate (155 mg, 0.894 mmol) in anhydrous DMF (1 mL) and the suspension heated to 45° C. A clear solution quickly formed and heating and stirring continued for a further ~1 hr. EDAC.HCl (175 mg, 0.913 mmol) was added and the reaction mixture heated to 85° C. for 2.5 hrs, and allowed to cool to ambient temperature overnight. Water was added to the reaction mixture and a yellow suspension formed which was filtered and dried. This material was suspended in absolute EtOH and heated to 80° C., after ~5 mins the suspension was filtered and dried to provide the title compound as a yellow solid (189 mg, 0.727 mmol; 79%);

¹H NMR δ 1.14-1.24 (m, 2H), 1.70-1.73 (m, 2H), 1.89-1.98 (m, 1H), 2.28 (d, 2H), 2.76-2.83 (m, 2H), 3.61 (s, 3H), 4.22-4.25 (m, 2H), 6.85 (d, 1H), 7.34-7.37 (m, 1H), 7.45-7.52 (m, 1H), 7.67-7.73 (m, 1H), 7.89 (d, 1H), 8.46 (d, 1H), 10.90 (s, 1H), 11.21 (s, 1H); MS m/e MH⁺ 473.

1H), 11.01 (s, 1H), 11.23 (s, 1H); CO₂H not seen; MS m/e MH⁺ 459.

Example 621

Methyl [1-(5-{[(5-{[4-(trifluoromethoxy)phenyl]amino}-1,3,4-oxadiazol-2-yl)carbonyl]amino}pyridin-2-yl)piperidin-4-yl]acetate

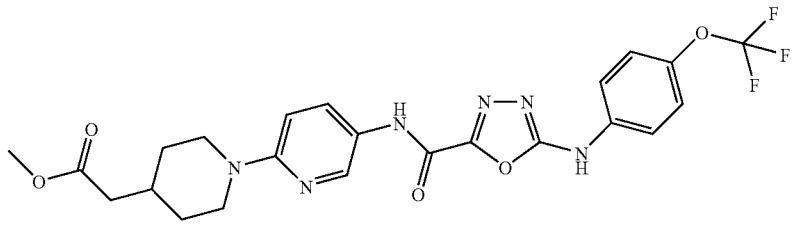

Prepared as described for Example 619 except 4-(trifluoromethoxy)phenylisothiocyanate (197 mg, 0.89 mmol) was used as starting material. The title compound was obtained as a yellow solid (270 mg, 0.519 mmol; 69%); ¹H NMR δ 1.14-1.24 (m, 2H), 1.71 (d, 2H), 1.89-1.98 (m, 1H), 2.28 (d, 2H), 2.79 (t, 2H), 3.60 (s, 3H), 4.23 (d, 2H), 6.84 (d, 1H), 7.42 (d, 2H), 7.71 (d, 2H), 7.89 (d, 1H), 8.46 (s, 1H), 10.89 (s, 1H), 11.17 (s, 1H); MS m/e MH⁺ 521.

Example 620

(1-{5-[({5-[(3,4-Difluorophenyl)amino]-1,3,4-oxadiazol-2-yl}carbonyl)amino]pyridin-2-yl}piperidin-4-yl)acetic acid

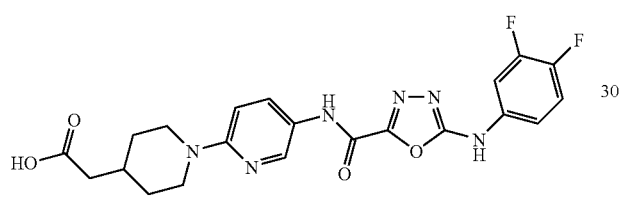

To a solution of methyl (1-{5-[({5-[(3,4-difluorophenyl)amino]-1,3,4-oxadiazol-2-yl}carbonyl)amino]pyridin-2-yl}piperidin-4-yl)acetate (Example 619, 189 mg, 0.40 mmol) in MeOH (10 mL) was added a 2M solution of NaOH (1 mL). The resulting yellow solution was allowed to stir at ambient temperature overnight. The volatile organics were removed by evaporation and residue adjusted to pH ~1 with 2M HCl and the suspension was filtered and dried to leave a solid which was dissolved in DMSO/MeCN/water(7:2:1) and purified on a reverse phase preparative HPLC column eluting 5-95% MeCN 0.2% TFA. The title compound was isolated as a yellow solid (108 mg, 0.235 mmol; 58.9%); ¹H NMR δ 1.16-1.27 (m, 2H), 1.76 (d, 2H), 1.91-1.99 (m, 1H), 2.19 (d, 2H), 2.90 (t, 2H), 4.21 (d, 2H), 7.00 (br d, 1H), 7.34-7.37 (m, 1H), 7.49 (q, 1H), 7.67-7.73 (m, 1H), 7.98 (d, 1H), 8.46 (s,

Example 622

[1-(5-{[(5-{[4-(Trifluoromethoxy)phenyl]amino}-1,3,4-oxadiazol-2-yl)carbonyl]amino}pyridin-2-yl)piperidin-4-yl]acetic acid

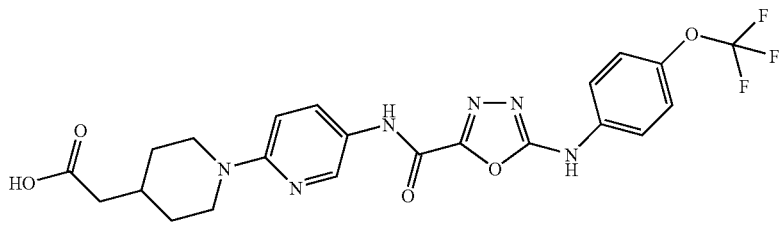

Prepared as described for Example 620 except Example 621 was used as starting material. The title compound was isolated as a yellow solid, (172 mg, 0.361 mmol; 69.4%).

¹H NMR δ 1.16-1.26 (m, 2H), 1.76 (d, 2H), 1.89-1.98 (m, 1H), 2.19 (d, 2H), 2.90 (t, 2H), 4.21 (d, 2H), 7.01 (d, 1H), 7.42 (d, 2H), 7.71 (d, 2H), 7.98 (d, 1H), 8.46 (s, 1H), 11.00 (s, 1H), 11.19 (s, 1H); CO₂H not seen; MS m/e MH⁺ 507.

Example 623

Methyl 2-methyl-2-(trans-4-{4-[({5-[(2,4,5-trifluorophenyl)amino]-1,3,4-oxadiazol-2-yl}carbonyl)amino]phenyl}cyclohexyl)propanoate

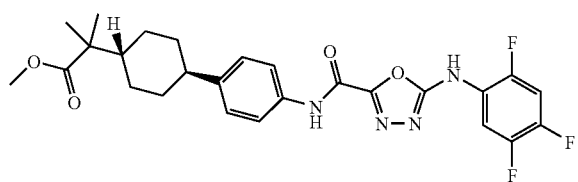

A solution of 2,4,5-trifluorophenyl isothiocyanate (183 mg, 0.96 mmol) in DMA (1 mL) was added in one portion to a suspension of methyl 2-[trans-4-(4-{[hydrazino(oxo)acetyl]amino}-phenyl)cyclohexyl]-2-methylpropanoate (Intermediate 105, 290 mg, 0.80 mmol) in DMA (3 mL) and the reaction mixture was stirred at room temperature for 1 h 30 mins. EDCI (230 mg, 1.20 mmol) was added in one portion and the reaction mixture was heated to 90° C. for 10 mins in the microwave. The mixture was then cooled to room temperature, poured into $H_2O$ (20 mL) and stirred for 5 mins. The mixture was centrifuged and the aqueous layer decanted off to leave a solid residue. The solid residue was taken up in $H_2O$ (5 mL), stirred for 5 mins and then centrifuged and the aqueous layer decanted off to leave a solid residue. $H_2O$ (5 mL) was added and the mixture was filtered to give the title compound (398 mg, 96%) as a solid; $^1$H NMR δ 1.1 (6H, s), 1.12-1.26 (2H, m), 1.36-1.5 (2H, m), 1.57-1.7 (3H, m), 1.78-1.89 (2H, m), 2.39-2.49 (1H, m), 3.6 (3H, s), 7.2 (2H, d), 7.65-7.78 (1H, m), 7.68 (2H, d), 8.12-8.24 (1H, m), 11.0 (1H, s), 11.1 (1H, s); MS m/e MH$^+$ 517.

Example 624

2-Methyl-2-(trans-4-{4-[({5-[(2,4,5-trifluorophenyl)amino]-1,3,4-oxadiazol-2-yl}carbonyl)amino]phenyl}cyclohexyl)propanoic acid

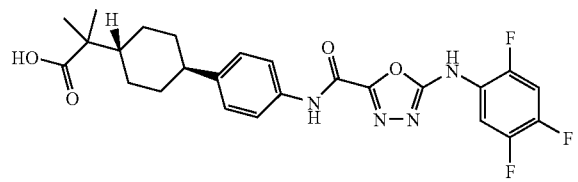

Potassium trimethylsilanolate (970 mg, 7.6 mmol) was added in one portion in a stirred solution of methyl 2-methyl-2-(trans-4-{4-[({5-[(2,4,5-trifluorophenyl)amino]-1,3,4-oxadiazol-2-yl}carbonyl)amino]phenyl}cyclohexyl)propanoate (Example 623, 390 mg, 0.76 mmol) in THF (10 mL) and the reaction mixture was heated in the microwave at 90° C. for 20 min, then 100° C. for 1 h and finally at 120° C. for 30 min. The reaction mixture was concentrated in vacuo to leave a yellow solid and then a 1M aqueous solution of citric acid (40 mL) was added and the mixture was stirred for 30 mins. The mixture was filtered to leave a solid. The solid was washed with $H_2O$ (20 mL) and purified by recrystallisation, using ethanol as solvent, to give the title compound (219 mg, 57%) as a white solid; $^1$H NMR δ 1.06 (6H, s), 1.12-1.27 (2H, m), 1.37-1.5 (2H, m), 1.58-1.75 (3H, m), 1.8-1.9 (2H, m), 2.39-2.5 (1H, m), 7.22 (2H, m), 7.65 (2H, m), 7.68-7.78 (1H, m), 8.14-8.24 (1H, m), 11.0 (1H, s), 11.13 (1H, s), 12.1 (1H, s); MS m/e MH$^+$ 502.

Example 625

1-{5-[({5-[(3,4-Difluorophenyl)amino]-1,3,4-oxadiazol-2-yl}carbonyl)amino]pyridin-2-yl}-4-methylpiperidine-4-carboxylic acid

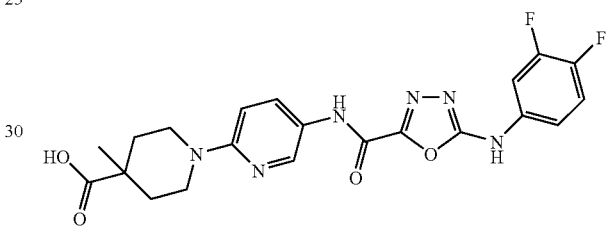

To a solution of methyl 1-{5-[({5-[(3,4-difluorophenyl)amino]-1,3,4-oxadiazol-2-yl}carbonyl)amino]pyridin-2-yl}-4-methylpiperidine-4-carboxylate (Example 631; 282 mg, 0.60 mmol) in MeOH (10 mL) was added a 2M solution of NaOH (1.5 mL). The resulting yellow solution was allowed to stir at ambient temperature overnight. The reaction mixture was then heated to 50° C. for 8 hours and allowed to stir at ambient temperature overnight. The volatile organics were removed by evaporation, the aqueous residue was washed with ether (50 mL) and aqueous phase adjusted to pH ~1 with 2M HCl. The resultant suspension was filtered and dried under vacuum at ambient temperature to give the title compound (230 mg, 0.502 mmol, 84%); $^1$H NMR δ 1.21 (s, 3H), 1.47-1.54 (m, 2H), 2.03-2.08 (m, 2H), 3.29-3.36 (m, 2H), 3.95-4.00 (m, 2H), 7.30 (d, 1H), 7.37-7.41 (m, 1H), 7.48 (q, 1H), 7.69-7.75 (m, 1H), 8.15 (d, 1H), 8.54 (s, 1H), 11.25 (s, 1H), 11.37 (s, 1H); $CO_2\underline{H}$ not seen; MS m/e MH$^+$ 459.

The following examples were prepared by the general procedure described above using the appropriate starting esters (Examples 632-636).

| Example | Name | $^1$H NMR δ | MS m/e M + H$^+$ |
|---|---|---|---|
| 626 | 1-{5-[({5-[(4-ethylphenyl)amino]-1,3,4-oxadiazol-2- | 1.16-1.20 (m, 6H), 1.42-1.49 (m, 2H), 2.00-2.05 (m, 2H), 2.58 (q, 2H), 3.18-3.24 (m, | 451 |

| Example | Name | ¹H NMR δ | MS m/e M + H⁺ |
|---------|------|----------|---------------|
|  | yl}carbonyl)amino]pyridin-2-yl}-4-methylpiperidine-4-carboxylic acid | 2H), 3.86-3.89 (m, 2H), 7.03-7.07 (m, 1H), 7.23 (d, 2H), 7.51 (d, 2H), 8.01 (d, 1H), 8.47 (s, 1H), 10.83 (s, 1H), 11.00 (s, 1H); $CO_2\underline{H}$ seen. |  |
| 627 | 4-methyl-1-(5-{[(5-{[4-(trifluoromethoxy)phenyl]amino}-1,3,4-oxadiazol-2-yl)carbonyl]amino}pyridin-2-yl)piperidine-4-carboxylic acid | 1.41 (s, 3H), 1.66 (t, 2H), 2.22-2.26 (m, 2H), 3.41 (t, 2H), 4.06-4.11 (m, 2H), 7.21 (d, 1H), 7.64 (d, 2H), 7.93 (d, 2H), 8.20 (d, 1H), 8.69 (s, 1H), 11.21 (s, 1H), 11.41 (s, 1H); $CO_2\underline{H}$ seen. | 507 |
| 628 | 4-methyl-1-{5-[({5-[(2,4,5-trifluorophenyl)amino]-1,3,4-oxadiazol-2-yl}carbonyl)amino]pyridin-2-yl}piperidine-4-carboxylic acid | 1.20 (s, 3H), 1.46-1.53 (m, 2H), 2.02-2.08 (m, 2H), 3.25-3.33 (m, 2H), 3.91-3.94 (m, 2H), 7.23 (d, 1H), 7.65-7.75 (m, 1H), 8.09-8.20 (m, 2H), 8.50 (s, 1H), 11.08 (s, 1H), 11.19 (s, 1H); $CO_2\underline{H}$ seen. | 477 |
| 629 | 4-methyl-1-(5-{[(5-{[4-(trifluoromethyl)phenyl]amino}-1,3,4-oxadiazol-2-yl)carbonyl]amino}pyridin-2-yl)piperidine-4-carboxylic acid | 1.19 (s, 3H), 1.40-1.47 (m, 2H), 2.00-2.04 (m, 2H), 3.15-3.22 (m, 2H), 3.83-3.88 (m, 2H), 6.98 (d, 1H), 7.76-7.82 (m, 4H), 7.98 (d, 1H), 8.48 (s, 1H), 11.01 (s, 1H), 11.43 (s, 1H); $CO_2\underline{H}$ seen. | 491 |
| 630 | 1-(5-{[(5-{[4-(4-chlorophenoxy)phenyl]amino}-1,3,4-oxadiazol-2-yl)carbonyl]amino}pyridin-2-yl)-4-methylpiperidine-4-carboxylic acid | 1.25 (s, 3H), 1.49-1.55 (m, 2H), 2.06-2.11 (m, 2H), 3.27-3.33 (m, 2H), 3.93-3.98 (m, 2H), 7.05 (d, 2H), 7.17-7.21 (m, 3H), 7.47 (d, 2H), 7.70 (d, 2H), 8.10 (d, 1H), 8.55 (s, 1H), 11.08 (s, 1H), 11.13 (s, 1H); $CO_2\underline{H}$ not seen. | 549 |

Example 631

Methyl 1-{5-[({5-[(3,4-difluorophenyl)amino]-1,3,4-oxadiazol-2-yl}carbonyl)amino]pyridin-2-yl}-4-methylpiperidine-4-carboxylate

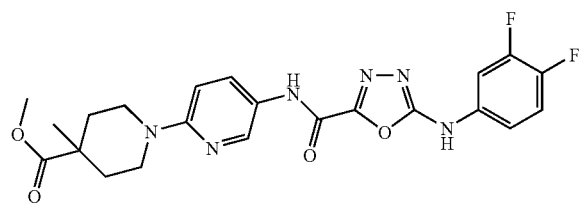

To a suspension of methyl 1-(5-{[hydrazino(oxo)acetyl]amino}pyridin-2-yl)-4-methylpiperidine-4-carboxylate (Intermediate 109; 250 mg, 0.75 mmol) in anhydrous DMF (3 mL) was added 3,4-difluorophenylisothiocyanate (154 mg, 0.89 mmol) in anhydrous DMF (1 mL) and the resulting suspension heated to 45° C. for 1 hr. EDAC.HCl (172 mg, 0.89 mmol) was added and the reaction mixture heated to 85° C. for 2 hrs and then allowed to cool to ambient temperature. Water (15 mL) was added and the suspension was filtered, washed with water (2×10 mL) and ether (15 mL) then dried to give the title product as a yellow solid (282 mg, 0.597 mmol, 79.6%);

¹H NMR δ 1.12 (s, 3H), 1.34-1.42 (m, 2H), 1.92-1.97 (m, 2H), 3.02-3.08 (m, 2H), 3.59 (s, 3H), 3.76-3.81 (m, 2H), 6.79 (d, 1H), 7.27-7.30 (m, 1H), 7.40 (q, 1H), 7.60-7.66 (m, 1H), 7.83 (d, 1H), 8.40 (s, 1H), 10.84 (s, 1H), 11.13 (s, 1H); MS m/e MH⁺ 473.

The following examples were prepared by the general procedure described above using the appropriate isothiocyanates, which were commercially available except 1-chloro-4-(4-isothiocyanatophenoxy)benzene which was made from 4-(4-chlorophenoxy)aniline and 1,1'-carbonothioylbis(1H-imidazole) as described in Barclay, Tristin K.; Santillan, Alejandro, Jr.; Tang, Liu Y.; Venkatesan, Hariharan; Wolin, Ronald L. PCT Int. Appl. (2005) WO 2005044810.

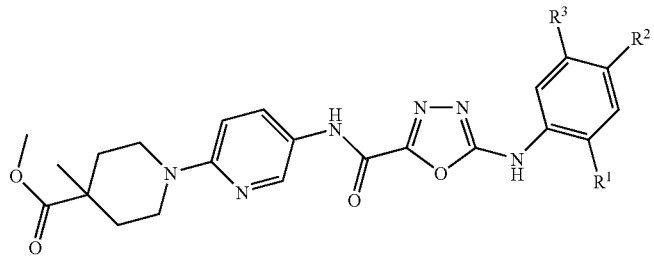

| Example | R | ¹H NMR δ | MS m/e MH⁺ |
|---|---|---|---|
| 632 | $R^1$, $R^3$ = H, $R^2$ = Et, methyl 1-{5-[({5-[(4-ethylphenyl)amino]-1,3,4-oxadiazol-2-yl}carbonyl)amino]pyridin-2-yl}-4-methylpiperidine-4-carboxylate | 1.16-1.20 (m, 6H), 1.42-1.49 (m, 2H), 1.99-2.04 (m, 2H), 2.59 (q, 2H), 3.10-3.16 (m, 2H), 3.67 (s, 3H), 3.82-3.88 (m, 2H), 6.86 (d, 1H), 7.23 (d, 2H), 7.51 (d, 2H), 7.90 (d, 1H), 8.47 (s, 1H), 10.81 (s, 1H), 10.85 (s, 1H) | 465 |
| 633 | $R^1$, $R^3$ = H, $R^2$ = OCF₃, methyl 4-methyl-1-(5-{[(5-{[4-(trifluoromethoxy)phenyl]amino}-1,3,4-oxadiazol-2-yl)carbonyl]amino}pyridin-2-yl)piperidine-4-carboxylate | 1.19 (s, 3H), 1.42-1.48 (m, 2H), 2.00-2.04 (m, 2H), 3.10-3.17 (m, 2H), 3.66 (s, 3H), 3.83-3.88 (m, 2H), 6.86 (d, 1H), 7.42 (d, 2H), 7.71 (d, 2H), 7.90 (d, 1H), 8.47 (s, 1H), 10.90 (s, 1H), 11.17 (s, 1H) | 521 |
| 634 | $R^1$, $R^2$, $R^3$ = F, methyl 4-methyl-1-{5-[({5-[(2,4,5-trifluorophenyl)amino]-1,3,4-oxadiazol-2-yl}carbonyl)amino]pyridin-2-yl}piperidine-4-carboxylate | 1.19 (s, 3H), 1.42-1.49 (m, 2H), 1.99-2.04 (m, 2H), 3.10-3.16 (m, 2H), 3.66 (s, 3H), 3.83-3.88 (m, 2H), 6.87 (d, 1H), 7.70 (q, 1H), 7.89 (d, 1H), 8.13-8.19 (m, 1H), 8.47 (s, 1H), 10.91 (s, 1H), 11.02 (s, 1H) | 491 |
| 635 | $R^1$, $R^3$ = H, $R^2$ = CF₃, methyl 4-methyl-1-(5-{[(5-{[4-(trifluoromethyl)phenyl]amino}-1,3,4-oxadiazol-2-yl)carbonyl]amino}pyridin-2-yl)piperidine-4-carboxylate | 1.20 (s, 3H), 1.41-1.49 (m, 2H), 2.00-2.05 (m, 2H), 3.09-3.17 (m, 2H), 3.66 (s, 3H), 3.82-3.88 (m, 2H), 6.86 (d, 1H), 7.76-7.82 (m, 4H), 7.90 (d, 1H), 8.47 (s, 1H), 10.93 (s, 1H), 11.41 (s, 1H) | 505 |
| 636 | $R^1$, $R^3$ = H, $R^2$ = 4-chlorophenoxy, methyl 1-(5-{[(5-{[4-(4-chlorophenoxy)phenyl]amino}-1,3,4-oxadiazol-2-yl)carbonyl]amino}pyridin-2-yl)-4-methylpiperidine-4-carboxylate | 1.20 (s, 3H), 1.41-1.49 (m, 2H), 1.99-2.05 (m, 2H), 3.10-3.16 (m, 2H), 3.66 (s, 3H), 3.82-3.88 (m, 2H), 6.86 (d, 1H), 7.00 (d, 2H), 7.13 (d, 2H), 7.41 (d, 2H), 7.64 (d, 2H), 7.90 (d, 1H), 8.47 (s, 1H), 10.88 (s, 1H), 10.97 (s, 1H) | 563 |

Example 637

1-(5-{[(5-{[4-(4-Chlorophenoxy)phenyl]amino}-1,3,4-oxadiazol-2-yl)carbonyl]amino}pyridin-2-yl)piperidine-4-carboxylic acid To a stirred solution of methyl 1-(5-{[(5-{[4-(4-chlorophenoxy)phenyl]amino}-1,3,4-oxadiazol-2-yl)carbonyl]amino}pyridin-2-yl)piperidine-4-carboxylate (Example 638; 340 mg, 0.62 mmol) in MeOH (5 mL) was added 2M NaOH (1.5 mL, 3.10 mmol) and the reaction mixture was allowed to stir at ambient temperature overnight. The solvent was evapo-

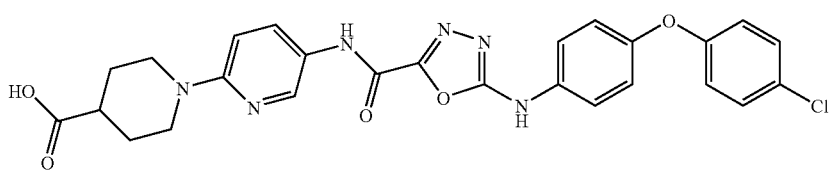

rated and the aqueous residue adjusted to pH ~1-2 with 2M HCl, the solid was filtered and dried to give the title compound (284 mg, 0.531 mmol, 86%); $^1$H NMR δ 1.79-1.90 (m, 2H), 2.14-2.19 (m, 2H), 2.78-2.84 (m, 1H), 3.33-3.40 (m, 2H), 4.35-4.39 (m, 2H), 7.23 (d, 2H), 7.37 (d, 2H), 7.43 (d, 1H), 7.64 (d, 2H), 7.88 (d, 2H), 8.33 (d, 1H), 8.73 (s, 1H), 11.26 (s, 1H), 11.36 (s, 1H); $CO_2H$ not seen; MS m/e MH$^+$ 535.

Example 638

Methyl 1-(5-{[(5-{[4-(4-chlorophenoxy)phenyl]amino}-1,3,4-oxadiazol-2-yl)carbonyl]amino}pyridin-2-yl)piperidine-4-carboxylate

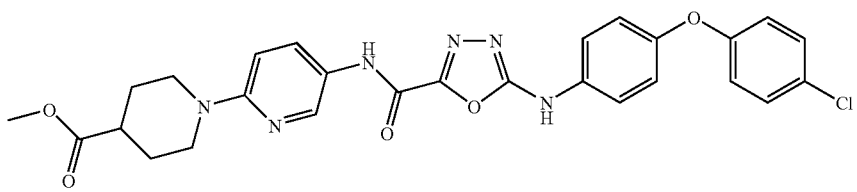

Prepared using the procedures described above for Example 631 except starting from methyl 1-(5-{[hydrazino(oxo)acetyl]amino}pyridin-2-yl)piperidine-4-carboxylate (Intermediate 83) and 1-chloro-4-(4-isothiocyanatophenoxy)benzene. $^1$H NMR δ 1.51-1.61 (m, 2H), 1.86-1.91 (m, 2H), 2.59-2.66 (m, 1H), 2.91-2.98 (m, 2H), 3.63 (s, 3H), 4.14-4.19 (m, 2H), 6.87 (d, 1H), 7.00 (d, 2H), 7.13 (d, 2H), 7.41 (d, 2H), 7.64 (d, 2H), 7.90 (d, 1H), 8.47 (s, 1H), 10.88 (s, 1H), 10.97 (s, 1H); MS m/e MH$^+$ 549.

Example 639

[1-(5-{[(5-{[4-(4-Chlorophenoxy)phenyl]amino}-1,3,4-oxadiazol-2-yl)carbonyl]amino}pyridin-2-yl)piperidin-4-yl]acetic acid

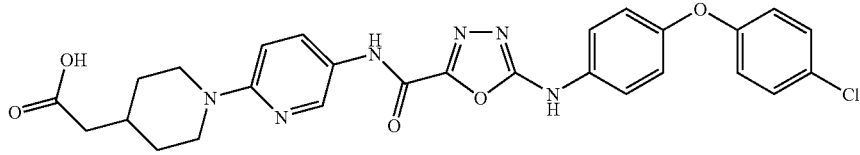

Prepared by the procedure described for 1-(5-{[(5-{[4-(4-Chlorophenoxy)phenyl]amino}-1,3,4-oxadiazol-2-yl)carbonyl]amino}pyridin-2-yl)piperidine-4-carboxylic acid (Example 637) except starting with methyl [1-(5-{[(5-{[4-(4-chlorophenoxy)phenyl]amino}-1,3,4-oxadiazol-2-yl)carbonyl]amino}pyridin-2-yl)piperidin-4-yl]acetate (Example 640).

$^1$H NMR δ 1.44-1.54 (m, 2H), 2.03 (d, 2H), 2.18-2.28 (m, 1H), 2.44 (d, 2H), 3.31 (t, 2H), 4.47 (d, 2H), 7.22 (d, 2H), 7.36 (d, 2H), 7.49-7.52 (m, 1H), 7.64 (d, 2H), 7.88 (d, 2H), 8.37 (d, 1H), 8.74 (s, 1H), 11.28 (s, 1H), 11.42 (s, 1H); $CO_2\underline{H}$ not seen; MS m/e MH$^+$ 549.

Example 640

Methyl [1-(5-{[(5-{[4-(4-chlorophenoxy)phenyl]amino}-1,3,4-oxadiazol-2-yl)carbonyl]amino}pyridin-2-yl)piperidin-4-yl]acetate

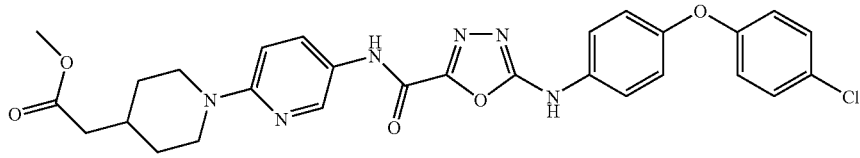

Prepared using the procedures described above for Example 631 except using methyl [1-(5-{[hydrazino(oxo)acetyl]amino}pyridin-2-yl)piperidin-4-yl]acetate (Intermediate 77) and 1-chloro-4-(4-isothiocyanatophenoxy)benzene.

$^1$H NMR δ 1.20-1.30 (m, 2H), 1.77 (d, 2H), 1.97-2.05 (m, 1H), 2.32 (d, 2H), 2.98 (t, 2H), 3.63 (s, 3H), 4.20 (d, 2H), 7.01 (d, 2H), 7.11-7.16 (m, 3H), 7.43 (d, 2H), 7.66 (d, 2H), 8.06 (d, 1H), 8.48 (s, 1H), 11.01 (s, 1H), 11.07 (s, 1H); MS m/e MH$^+$ 563.

Example 641 rac-Ethyl 2-(trans-4-{2-chloro-4-[({5-[(2,4,5-trifluorophenyl)amino]-1,3,4-oxadiazol-2-yl}carbonyl)amino]phenyl}cyclohexyl)propanoate Following the general procedure of Example 623, except that ethyl 2-[trans-4-(2-chloro-4-{[hydrazino(oxo)acetyl]amino}phenyl)-cyclohexyl]propanoate (Intermediate 106) was used in place of methyl 2-[trans-4-(4-{[hydrazino(oxo)acetyl]amino}-phenyl)cyclohexyl]-2-methylpropanoate (Intermediate 105), the title compound was obtained in 88% yield as a solid; $^1$H NMR δ 1.05 (3H, d), 1.1-1.27 (2H, m), 1.18 (3H, t), 1.38-1.51 (2H, m), 1.52-1.65 (1H, m), 1.66-1.87 (4H, m), 2.22-2.35 (1H, m), 2.78-2.9 (1H, m), 4.09 (2H, dq), 7.39 (1H, d), 7.68-7.79 (1H, m), 7.72 (1H, dd), 7.93 (1H, d), 8.13-8.27 (1H, m), 11.18 (1H, s), 11.24 (1H, s); MS m/e MH$^+$ 551.

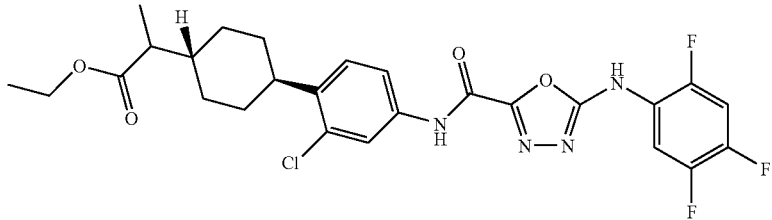

Example 642 rac-Ethyl 2-(trans-4-{3-chloro-4-[({5-[(2,4,5-trifluorophenyl)amino]-1,3,4-oxadiazol-2-yl}carbonyl)amino]phenyl}cyclohexyl)propanoate

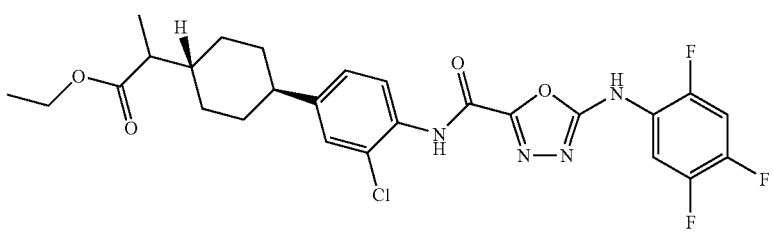

Following the general procedure of Example 623, except that ethyl 2-[trans-4-(3-chloro-4-{[hydrazino(oxo)acetyl]amino}phenyl)-cyclohexyl]propanoate (Intermediate 107) was used in place of methyl 2-[trans-4-(4-{[hydrazino(oxo)acetyl]amino}-phenyl)cyclohexyl]-2-methylpropanoate (Intermediate 105), the title compound was obtained in 92% yield as a solid; ¹H NMR δ 1.05 (3H, d), 1.1-1.27 (2H, m), 1.18 (3H, t), 1.38-1.51 (2H, m), 1.52-1.65 (1H, m), 1.66-1.87 (4H, m), 2.22-2.35 (1H, m), 2.78-2.9 (1H, m), 4.09 (2H, dq), 7.2 (1H, dd), 7.38 (1H, d), 7.47 (1H, d), 7.62-7.75 (1H, m), 8.07-8.19 (1H, m), 11.2 (1H, s), 11.25 (1H, s); MS m/e MH⁺ 4551.

Example 643 rac-2-(trans-4-{2-Chloro-4-[({5-[(2,4,5-trifluorophenyl)amino]-1,3,4-oxadiazol-2-yl}carbonyl)amino]phenyl}cyclohexyl)propanoic acid

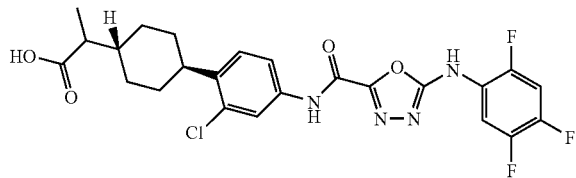

Potassium trimethylsilanolate (1.29 g, 9.98 mmol) was added in one portion to a stirred solution of rac-ethyl 2-(trans-4-{2-chloro-4-[({5-[(2,4,5-trifluorophenyl)amino]-1,3,4-oxadiazol-2-yl}carbonyl)amino]phenyl}cyclohexyl)propanoate (Example 641, 550 mg, 1.0 mmol) in THF (10 mL) and the reaction mixture was heated in the microwave at 90° C. for 20 min. The reaction mixture was concentrated in vacuo to leave a yellow solid and then a 1M aqueous solution of citric acid (40 mL) was added and the mixture was stirred for 30 mins. The mixture was filtered to leave a solid, which was washed with H₂O (20 mL) to give the title compound (570 mg, 97%) as an off-white solid. The individual isomers may be separated by chiral chromatography under standard conditions and recrystallised from EtOH/water to give (2R)-2-(trans-4-{2-chloro-4-[({5-[(2,4,5-trifluorophenyl)amino]-1,3,4-oxadiazol-2-yl}carbonyl)amino]phenyl}cyclohexyl)-propanoic acid ¹H NMR δ 1.07 (3H, d), 1.1-1.31 (2H, m), 1.37-1.53 (2H, m), 1.54-1.67 (1H, m), 1.71-1.9 (4H, m), 2.15-2.27 (1H, m), 2.79-2.91 (1H, m), 7.39 (1H, d), 7.64-7.76 (1H, m), 7.69 (1H, dd), 7.94 (1H, d), 8.13-8.24 (1H, m), 11.5 (1H, s), 11.2 (1H, s), 12.1 (1H, s); MS m/e MH⁺ 523;

and (2S)-2-(trans-4-{2-chloro-4-[({5-[(2,4,5-trifluorophenyl)amino]-1,3,4-oxadiazol-2-yl}carbonyl)amino]phenyl}cyclohexyl)propanoic acid ¹H NMR δ 1.07 (3H, d), 1.1-1.31 (2H, m), 1.37-1.53 (2H, m), 1.54-1.67 (1H, m), 1.71-1.9 (4H, m), 2.15-2.27 (1H, m), 2.79-2.91 (1H, m), 7.39 (1H, d), 7.64-7.76 (1H, m), 7.69 (1H, dd), 7.94 (1H, d), 8.13-8.24 (1H, m), 11.5 (1H, s), 11.2 (1H, s), 12.1 (1H, s); MS m/e MH⁺ 523.

Example 644 rac-2-(trans-4-{3-Chloro-4-[({5-[(2,4,5-trifluorophenyl)amino]-1,3,4-oxadiazol-2-yl}carbonyl)amino]phenyl}cyclohexyl)propanoic acid

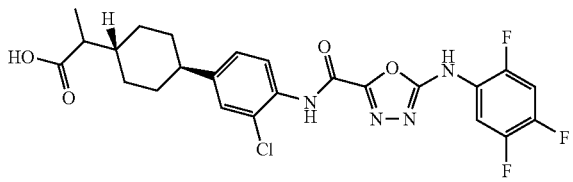

Following the general procedure of Example 643, except that rac-ethyl 2-(trans-4-{3-chloro-4-[({5-[(2,4,5-trifluorophenyl)amino]-1,3,4-oxadiazol-2-yl}carbonyl)amino]phenyl}cyclo-hexyl)propanoate (Example 642) was used in place of rac-ethyl 2-(trans-4-{2-chloro-4-[({5-[(2,4,5-trifluorophenyl)amino]-1,3,4-oxadiazol-2-yl}carbonyl)amino]phenyl}cyclohexyl)-propanoate (Example 641), the title compound was obtained in 95% yield as an off-white solid; ¹H NMR δ 1.0 (3H, d), 1.02-1.22 (2H, m), 1.32-1.6 (3H, m), 1.63-1.84 (4H, m), 2.06-2.18 (1H, m), 2.4-2.53 (1H, m), 7.21 (1H, dd), 7.38 (1H, d), 7.47 (1H, d), 7.62-7.75 (1H, m), 8.07-8.19 (1H, m), 10.58 (1H, s), 11.1 (1H, s), 12.02 (1H, s); MS m/e MH⁺ 523. The individual isomers may be separated by chiral chromatography under standard conditions to give (2R)-2-(trans-4-{3-chloro-4-[({5-[(2,4,5-trifluorophenyl)amino]-1,3,4-oxadiazol-2-yl}-carbonyl)amino]phenyl}cyclo-hexyl)propanoic acid and (2S)-2-(trans-4-{3-chloro-4-[({5-[(2,4,5-trifluorophenyl)amino]-1,3,4-oxadiazol-2-yl}carbonyl)amino]phenyl}cyclohexyl)-propanoic acid.

Example 645

Ethyl cis-4-{4-[({5-[(2,4,5-trifluorophenyl)amino]-1,3,4-oxadiazol-2-yl}carbonyl)amino]-phenoxy}cyclohexanecarboxylate

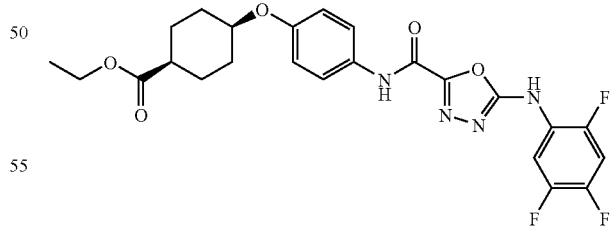

Hydrazine monohydrate (32 µL, 0.65 mmol) was added in one portion to a stirred solution of ethyl cis-4-(4-{[methoxy(oxo)acetyl]amino}phenoxy)cyclohexanecarboxylate (Intermediate 108) (188 mg, 0.54 mmol) in EtOH (3 mL) and the reaction mixture was stirred at room temperature for 10 mins. EtOH (40 mL) and hydrazine monohydrate (9.0 µL, 0.18 mmol) were added and the reaction mixture was stirred for a further 20 mins. Diethylether (50 mL) was added and the mixture was filtered to leave a solid. The filtrate was concentrated in vacuo to leave a gum. The solid and the gum were combined to give the crude hydrazide that was used with no further purification; MS m/e (M–H)⁻ 348. A solution of 2,4,5-trifluorophenyl isothiocyanate (103 mg, 0.54 mmol) in DMA (1 mL) was added in one portion to a stirred solution of the crude hydrazide (189 mg, 0.54 mmol) in DMA (4 mL) and the reaction mixture was stirred at room temperature for 1 h. EDCI (125 mg, 0.65 mmol) was added in one portion and the reaction mixture was heated to 60° C. for 2 mins and then stirred at room temperature for 60 h. The reaction mixture was concentrated in vacuo to leave an oil. Hot water was added and the residue was stirred for 5 min to give a precipitate, which was filtered to give the title compound as a light brown solid (221 mg, 81%); ¹H NMR δ 1.20 (3H, t), 1.65-1.71 (4H, m), 1.76-1.85 (4H, m), 2.52 (1H, m), 4.09 (2H, q), 4.51 (1H, s), 6.96 (2H, d), 7.67-7.74 (3H, m), 8.15-8.18 (1H, m), 10.95 (1H, s), 11.05 (1H, s); MS m/e (M–H)⁻ 503.

amino]-phenoxy}cyclohexanlecarboxylate (Example 645, 221 mg, 0.44 mmol) in a mixture of THF (4 mL), H₂O (4 mL) and MeOH (8 mL) and the reaction mixture was stirred at 35° C. for 3 h. The reaction mixture was concentrated in vacuo and citric acid (40 mL) was added. The resulting mixture was filtered, washed with H₂O and recrystallised from ethanol/H₂O to give the title compound as a pale yellow solid (118 mg, 56%); ¹H NMR δ 1.66-1.70 (4H, m), 1.75-1.83 (4H, m), 2.33-2.40 (1H, m), 4.50 (1H, s), 6.96 (2H, d), 7.67-7.74 (3H, m), 8.17 (1H, q), 10.95 (1H, s), 11.10 (1H, s), 12.05 (1H, s); MS m/e (M–H)⁻ 475. The compound may be further recrystallised from EtOH, melting point 251-253° C.

The following examples were prepared by the general procedure as described for (1-{5-[({5-[(3,4-difluorophenyl)amino]-1,3,4-oxadiazol-2-yl}carbonyl)amino]pyridin-2-yl}piperidin-4-yl)acetic acid (Example 619) using the appropriate starting material selected from Examples 649 and 650.

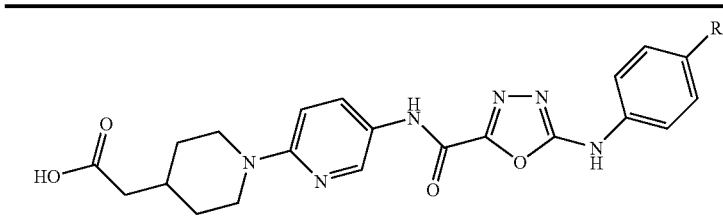

| Example | R | Name | ¹H NMR δ | MS m/e M+H⁺ |
|---|---|---|---|---|
| 647 | Et | (1-{5-[({5-[(4-ethylphenyl)amino]-1,3,4-oxadiazol-2-yl}carbonyl)amino]pyridin-2-yl}piperidin-4-yl)acetic acid | 1.17-1.27 (m, 5H), 1.77 (d, H), 1.90-2.00 (m, 1H), 2.20 (d, 2H), 2.56-2.62 (m, 2H), 2.92 (t, 2H), 4.20 (d, 2H), 7.04 (d, 1H), 7.23 (d, 2H), 7.51 (d, 2H), 8.00 (d, 1H), 8.46 (s, 1H), 10.83 (s, 1H), 10.99 (s, 1H); CO₂H not seen. | 451 |
| 648 | CF₃ | [1-(5-{[(5-{[4-(trifluoromethyl)phenyl]amino}-1,3,4-oxadiazol-2-yl)carbonyl]amino}pyridin-2-yl)piperidin-4-yl]acetic acid | 1.17-1.26 (m, 2H), 1.77 (d, 2H), 1.90-2.00 (m, 1H), 2.19 (d, 2H), 2.91 (t, 2H), 4.21 (d, 2H), 7.03 (d, 1H), 7.76-7.83 (m, 4H), 8.00 (d, 1H), 8.46 (s, 1H), 11.04 (s, 1H), 11.43 (s, 1H); CO₂H not seen | 491 |

Example 646 cis-4-{4-[({5-[(2,4,5-Trifluorophenyl)amino]-1,3,4-oxadiazol-2-yl}carbonyl)amino]-phenoxy}cyclohexanecarboxylic acid

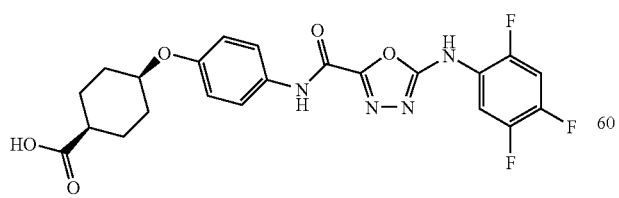

Lithium hydroxide monohydrate (184 mg, 4.38 mmol) was added in one portion to a solution of ethyl cis-4-{4-[({5-[(2,4,5-trifluorophenyl)amino]-1,3,4-oxadiazol-2-yl}carbonyl)

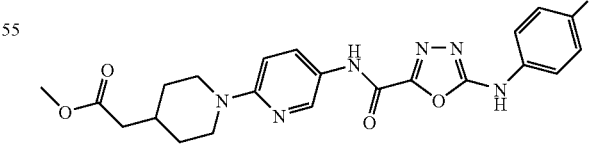

The following examples were prepared by the general procedure as described for methyl (1-{5-[({5-[(3,4-difluorophenyl)amino]-1,3,4-oxadiazol-2-yl}carbonyl)amino]pyridin-2-yl}piperidin-4-yl)acetate (Example 620) using the appropriate isothiocyanate:

| Example | R | Name | ¹H NMR δ | MS m/e M + H⁺ |
|---|---|---|---|---|
| 649 | Et | methyl (1-{5-[({5-[(4-ethylphenyl)amino]-1,3,4-oxadiazol-2-yl}carbonyl)amino]pyridin-2-yl}piperidin-4-yl)acetate | 1.16-1.21 (m, 5H), 1.69-1.73 (m, 2H), 1.89-1.98 (m, 1H), 2.28 (d, 2H), 2.76-2.83 (m, 2H), 3.61 (s, 3H), 4.22-4.25 (m, 2H), 4.31 (t, 2H), 6.84 (d, 1H), 7.23 (d, 2H), 7.51 (d, 2H), 7.89 (d, 1H), 8.46 (d, 1H), 10.81 (s, 1H), 10.85 (s, 1H) | 465 |
| 650 | CF₃ | methyl [1-(5-{[(5-{[4-(trifluoromethyl)phenyl]amino}-1,3,4-oxadiazol-2-yl)carbonyl]amino}pyridin-2-yl)piperidin-4-yl]acetate | 1.14-1.25 (m, 2H), 1.71 (d, 2H), 1.89-1.99 (m, 1H), 2.28 (d, 2H), 2.77-2.84 (m, 2H), 3.61 (s, 3H), 4.24 (d, 2H), 6.85 (d, 1H), 7.76-7.82 (m, 4H), 7.89 (d, 1H), 8.46 (s, 1H), 10.92 (s, 1H), 11.42 (s, 1H) | 505 |

The following examples were prepared by the general procedure as described previously as in Example 480:

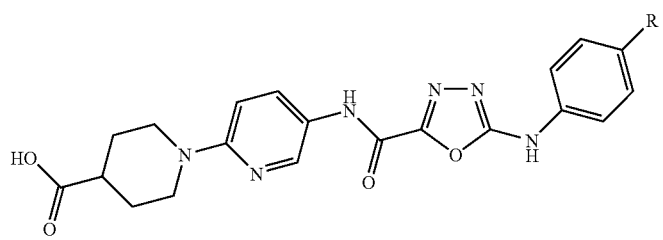

| Example | R | Name | ¹H NMR δ | MS m/e M+H⁺ |
|---|---|---|---|---|
| 651 | Et | 1-{5-[({5-[(4-ethylphenyl)amino]-1,3,4-oxadiazol-2-yl}carbonyl)amino]pyridin-2-yl}piperidine-4-carboxylic acid | 1.39 (t, 3H), 1.74-1.84 (m, 2H), 2.09-2.13 (m, 2H), 2.75-2.82 (m, 3H), 3.25 (t, 2H), 4.31-4.36 (m, 2H), 7.25 (d, 1H), 7.43 (d, 2H), 7.72 (d, 2H), 8.22 (d, 1H), 8.68 (d, 1H), 11.04 (s, 1H), 11.20 (s, 1H); CO₂H not seen | 437 |
| 652 | OCF₃ | 1-(5-{[(5-{[4-(trifluoromethoxy)phenyl]amino}-1,3,4-oxadiazol-2-yl)carbonyl]amino}pyridin-2-yl)piperidine-4-carboxylic acid | 1.61-1.70 (m, 2H), 1.96-2.00 (m, 2H), 2.62-2.64 (m, 1H), 3.11 (t, 2H), 4.18-4.23 (m, 2H), 7.10 (d, 1H), 7.50 (d, 2H), 7.79 (d, 2H), 8.08 (d, 1H), 8.56 (d, 1H), 11.10 (s, 1H), 11.26 (s, 1H); CO2H not seen. | 493 |
| 653 | CF₃ | 1-(5-{[(5-{[4-(trifluoromethyl)phenyl]amino}-1,3,4-oxadiazol-2-yl)carbonyl]amino}pyridin-2-yl)piperidine-4-carboxylic acid | 1.52-1.62 (m, 2H), 1.88-1.92 (m, 2H), 2.54-2.56 (m, 1H), 2.98-3.05 (m, 2H), 4.11-4.16 (m, 2H), 6.99 (d, 1H), 7.76-7.82 (m, 4H), 7.98 (d, 1H), 8.48 (d, 1H), 11.02 (s, 1H), 11.43 (s, 1H); CO₂H not seen | 477 |

The following examples were prepared by the general procedure as described previously, as in Example 620, using the appropriate isothiocyanate:

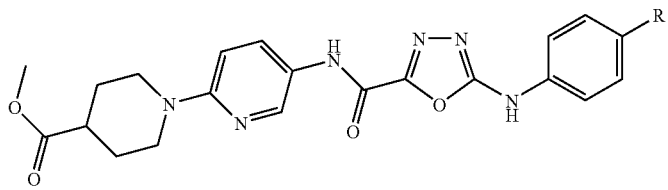

| Example | R | Name | $^1$H NMR δ | MS m/e M+H$^+$ |
|---|---|---|---|---|
| 654 | Et | methyl 1-{5-[({5-[(4-ethylphenyl)amino]-1,3,4-oxadiazol-2-yl}carbonyl)amino]pyridin-2-yl}piperidine-4-carboxylate | 1.18 (t, 3H), 1.51-1.61 (m, 2H), 1.86-1.91 (m, 2H), 2.56-2.62 (m, 3H), 2.91-2.98 (m, 2H), 3.63 (s, 3H), 4.14-4.18 (m, 2H), 6.87 (d, 1H), 7.23 (d, 2H), 7.51 (d, 2H), 7.91 (dd, 1H), 8.48 (d, 1H), 10.81 (s, 1H), 10.86 (s, 1H) | 451 |
| 655 | OCF$_3$ | methyl 1-(5-{[(5-{[4-(trifluoromethoxy)phenyl]amino}-1,3,4-oxadiazol-2-yl)carbonyl]amino}pyridin-2-yl)piperidine-4-carboxylate | 1.51-1.61 (m, 2H), 1.86-1.91 (m, 2H), 2.59-2.65 (m, 1H), 2.91-2.98 (m, 2H), 3.63 (s, 3H), 4.14-4.18 (m, 2H), 6.88 (d, 1H), 7.42 (d, 2H), 7.71 (d, 2H), 7.91 (dd, 1H), 8.48 (d, 1H), 10.91 (s, 1H), 11.17 (s, 1H) | 507 |
| 656 | CF$_3$ | methyl 1-(5-{[(5-{[4-(trifluoromethyl)phenyl]amino}-1,3,4-oxadiazol-2-yl)carbonyl]amino}pyridin-2-yl)piperidine-4-carboxylate | 1.51-1.61 (m, 2H), 1.87-1.91 (m, 2H), 2.59-2.66 (m, 1H), 2.91-2.98 (m, 2H), 3.63 (s, 3H), 4.14-4.18 (m, 2H), 6.88 (d, 1H), 7.76-7.82 (m, 4H) 7.91 (dd, 1H), 8.49 (d, 1H), 10.94 (s, 1H), 11.41 (s, 1H) | 491 |

Examples 657-679

The following examples were prepared by the general procedure of Example 525 using the appropriate commercially available aniline in place of 5-amino-3-methylisoxazole

| Example | Name | $^1$H NMR δ | MS m/e MH$^+$ |
|---|---|---|---|
| 657[1] | (trans-4-{4-[({5-[(2-chloro-4-methylphenyl)amino]-1,3,4-oxadiazol-2-yl}carbonyl)amino]phenyl}-cyclohexyl)acetic acid | 0.97-1.12 (m, 2H), 1.29-1.46 (m, 2H), 1.60-1.80 (m, 5H), 2.07 (d, 2H), 2.24 (s, 3H), 2.31-2.41 (m, 1H), 7.15 (m, 3H), 7.31 (s, 1H), 7.60 (d, 2H), 7.69 (d, 1H), 10.20 (s, 1H), 11.51 (s, 1H), 11.82 (s, 1H) | 469 |
| 658[1] | (trans-4-{4-[({5-[(4-methoxy-2-methylphenyl)amino]-1,3,4-oxadiazol-2-yl}carbonyl)amino]phenyl}-cyclohexyl)acetic acid | 1.04-1.19 (m, 2H), 1.39-1.52 (m, 2H), 1.66-1.87 (m, 5H), 2.14 (d, 2H), 2.25 (s, 3H), 2.38-2.48 (m, 1H), 3.76 (s, 3H), 6.80-6.84 (m, 1H), 6.85-6.88 (m, 1H), 7.22 (d, 2H), 7.47 (d, 1H), 7.67 (d, 2H), 9.82 (s, 1H), 11.61 (s, 1H), 11.95 (s, 1H) | 465 |
| 659[1] | (trans-4-{4-[({5-[(4-fluoro-2-methylphenyl)amino]-1,3,4-oxadiazol-2-yl}carbonyl)amino]phenyl}-cyclohexyl)acetic acid | 0.97-1.11 (m, 2H), 1.30-1.44 (m, 2H), 1.60-1.79 (m, 5H), 2.07 (d, 2H), 2.22 (s, 3H), 2.31-2.41 (m, 1H), 6.97-7.11 (m, 2H), 7.15 (d, 2H), 7.56-7.65 (m, 3H), 9.93 (s, 1H), 10.78 (s, 1H), 11.88 (s, 1H) | 453 |

-continued

| Example | Name | ¹H NMR δ | MS m/e MH⁺ |
|---|---|---|---|
| 660[1] | [trans-4-(4-{[(5-{[4-fluoro-2-(trifluoromethyl)phenyl]amino}-1,3,4-oxadiazol-2-yl)carbonyl]amino}phenyl)-cyclohexyl]acetic acid | 1.04-1.20 (m, 2H), 1.38-1.54 (m, 2H), 1.66-1.88 (m, 5H), 2.14 (d, 2H), 2.38-2.49 (m, 1H), 7.21 (d, 2H), 7.61-7.75 (m, 4H), 7.84-7.94 (m, 1H), 10.35 (s, 1H), 10.87 (s, 1H), 11.95 (s, 1H) | 507 |
| 661[1] | (trans-4-{4-[({5-[(2,4-dichlorophenyl)amino]-1,3,4-oxadiazol-2-yl}carbonyl)amino]phenyl}-cyclohexyl)acetic acid | 0.97-1.12 (m, 2H), 1.30-1.44 (m, 2H), 1.59-1.81 (m, 5H), 2.07 (d, 2H), 2.31-2.41 (m, 1H), 7.15 (d, 2H), 7.44 (d, 1H), 7.57-7.66 (m, 3H), 7.95 (d, 1H), 10.45 (s, 1H), 10.85 (s, 1H), 11.89 (s, 1H) | 489 |
| 662[1] | (trans-4-{4-[({5-[(2-chloro-4-cyanophenyl)amino]-1,3,4-oxadiazol-2-yl}carbonyl)amino]phenyl}-cyclohexyl)acetic acid | 1.04-1.21 (m, 2H), 1.37-1.53 (m, 2H), 1.65-1.89 (m, 5H), 2.15 (d, 2H), 2.40-2.49 (m, 1H), 7.23 (d, 2H), 7.69 (d, 2H), 7.89-7.95 (m, 1H), 8.12 (d, 1H), 8.36 (d, 1H), 10.89 (s, 1H), 11.00 (s, 1H), 11.94 (s, 1H) | 480 |
| 663[1] | (trans-4-{4-[({5-[(4-cyano-2-methylphenyl)amino]-1,3,4-oxadiazol-2-yl}carbonyl)amino]phenyl}-cyclohexyl)acetic acid | 1.02-1.20 (m, 2H), 1.37-1.54 (m, 2H), 1.66-1.88 (m, 5H), 2.13 (d, 2H), 2.31-2.44 (m, 1H), 7.23 (d, 2H), 7.64-7.81 (m, 4H), 8.18 (d, 1H), 10.46 (s, 1H), 10.99 (s, 1H), 11.99 (s, 1H) | 460 |
| 664[1] | (trans-4-{4-[({5-[(4-chloro-2,5-dimethylphenyl)amino]-1,3,4-oxadiazol-2-yl}carbonyl)amino]phenyl}-cyclohexyl)acetic acid | 0.96-1.12 (m, 2H), 1.30-1.45 (m, 2H), 1.59-1.80 (m, 5H), 2.06 (d, 2H), 2.18 (s, 3H), 2.24 (s, 3H), 2.32-2.40 (m, 1H), 7.14 (d, 2H), 7.25 (s, 1H), 7.57-7.65 (m, 3H), 9.97 (s, 1H), 10.78 (s, 1H), 11.87 (s, 1H) | 483 |
| 665[1] | (trans-4-{4-[({5-[(4-cyano-2-ethylphenyl)amino]-1,3,4-oxadiazol-2-yl}carbonyl)amino]phenyl}-cyclohexyl)acetic acid | 1.03-1.24 (m, 5H), 1.37-1.54 (m, 2H), 1.66-1.89 (m, 5H), 2.15 (d, 2H), 2.39-2.48 (m, 1H), 2.80 (q, 2H), 7.23 (d, 2H), 7.65-7.79 (m, 4H), 8.18 (d, 1H), 10.45 (s, 1H), 10.97 (s, 1H), 11.96 (s, 1H) | 474 |
| 666[1] | (trans-4-{4-[({5-[(2-chloro-4-fluorophenyl)amino]-1,3,4-oxadiazol-2-yl}carbonyl)amino]phenyl}-cyclohexyl)acetic acid | 1.01-1.22 (m, 2H), 1.34-1.55 (m, 2H), 1.63-1.89 (m, 5H), 2.14 (d, 2H), 2.38-2.48 (m, 1H), 7.22 (d, 2H), 7.30-7.41 (m, 1H), 7.54-7.63 (m, 1H), 7.70 (d, 2H), 7.90-8.01 (m, 1H), 10.47 (s, 1H), 10.97 (s, 1H), 12.04 (s, 1H) | 473 |
| 667[1] | (trans-4-{4-[({5-[(4-chloro-2-methylphenyl)amino]-1,3,4-oxadiazol-2-yl}carbonyl)amino]phenyl}-cyclohexyl)acetic acid | 0.97-1.13 (m, 2H), 1.31-1.47 (m, 2H), 1.60-1.81 (m, 5H), 2.08 (d, 2H), 2.23 (s, 3H), 2.32-2.41 (m, 1H), 7.16 (d, 2H), 7.23-7.36 (m, 2H), 7.62 (d, 2H), 7.76 (d, 1H), 10.09 (s, 1H), 10.90 (s, 1H), 11.97 (s, 1H) | 469 |
| 668 | (trans-4-{4-[({5-[(2,3-dichlorophenyl)amino]-1,3,4-oxadiazol-2-yl}carbonyl)amino]phenyl}-cyclohexyl)acetic acid | 1.02-1.19 (m, 2H), 1.35-1.54 (m, 2H), 1.65-1.88 (m, 5H), 2.14 (d, 2H), 2.38-2.48 (m, 1H), 7.22 (d, 2H), 7.40-7.50 (m, 2H), 7.69 (d, 2H), 7.97-8.04 (m, 1H), 10.68 (s, 1H), 11.01 (s, 1H), 12.05 (s, 1H) | 489 |
| 669 | (trans-4-{4-[({5-[(2,5-dichlorophenyl)amino]-1,3,4-oxadiazol-2-yl}carbonyl)amino]phenyl}-cyclohexyl)acetic acid | 1.03-1.18 (m, 2H), 1.38-1.53 (m, 2H), 1.65-1.87 (m, 5H), 2.14 (d, 2H), 2.38-2.48 (m, 1H), 7.19-7.30 (m, 3H), 7.58 (d, 1H), 7.69 (d, 2H), 8.16-8.21 (m, 1H), 10.69 (s, 1H), 11.02 (s, 1H), 12.05 (s, 1H) | 489 |
| 670 | (trans-4-{4-[({5-[(2-bromo-4-methylphenyl)amino]-1,3,4-oxadiazol-2-yl}carbonyl)amino]phenyl}-cyclohexyl)acetic acid | 1.03-1.18 (m, 2H), 1.38-1.51 (m, 2H), 1.66-1.87 (m, 5H), 2.14 (d, 2H), 2.32 (s, 3H), 2.38-2.48 (m, 1H), 7.21 (d, 2H), 7.28 (d, 1H), 7.56 (s, 1H), 7.63-7.72 (m, 3H), 10.24 (s, 1H), 10.94 (s, 1H), 12.04 (s, 1H) | 515 |
| 671 | [trans-4-(4-{[(5-{[2-chloro-5-(trifluoromethyl)phenyl]amino}-1,3,4-oxadiazol-2-yl)carbonyl]amino}phenyl)-cyclohexyl]acetic acid | 1.02-1.19 (m, 2H), 1.37-1.53 (m, 2H), 1.66-1.88 (m, 5H), 2.14 (d, 2H), 2.38-2.49 (m, 1H), 7.24 (d, 2H), 7.55 (d, 1H), 7.70 (d, 2H), 7.81 (d, 1H), 8.51 (s, 1H), 10.84 (s, 1H), 11.01 (s, 1H), 12.04 (s, 1H) | 523 |
| 672 | [trans-4-(4-{[(5-{[2-bromo-4-(trifluoromethyl)phenyl]amino}- | 0.96-1.11 (m, 2H), 1.29-1.46 (m, 2H), 1.57-1.81 (m, 5H), 2.07 (d, 2H), 2.30-2.41 (m, 1H), 7.16 (d, 2H), 7.63 (d, | 567 |

| Example | Name | $^1$H NMR δ | MS m/e MH$^+$ |
|---|---|---|---|
| | 1,3,4-oxadiazol-2-yl)carbonyl]amino}phenyl)-cyclohexyl]acetic acid | 2H), 7.80 (d, 1H), 8.02 (s, 1H), 8.17 (d, 1H), 10.96 (s, 1H), 10.96 (s, 1H), 11.97 (s, 1H) | |
| 673 | [trans-4-(4-{[(5-{[2-chloro-4-(trifluoromethyl)phenyl]amino}-1,3,4-oxadiazol-2-yl)carbonyl]amino}phenyl)-cyclohexyl]acetic acid | 1.01-1.20 (m, 2H), 1.34-1.53 (m, 2H), 1.64-1.89 (m, 5H), 2.14 (d, 2H), 2.36-2.48 (m, 1H), 7.23 (d, 2H), 7.70 (d, 2H), 7.84 (d, 1H), 7.96 (s, 1H), 8.37 (d, 1H), 10.81 (s, 1H), 11.05 (s, 1H), 12.04 (s, 1H) | 523 |
| 674 | (trans-4-{4-[({5-[(4-bromo-2-chlorophenyl)amino]-1,3,4-oxadiazol-2-yl}carbonyl)amino]phenyl}-cyclohexyl)acetic acid | 1.03-1.20 (m, 2H), 1.37-1.53 (m, 2H), 1.65-1.88 (m, 5H), 2.14 (d, 2H), 2.37-2.48 (m, 1H), 7.23 (d, 2H), 7.62-7.73 (m, 3H), 7.83 (s, 1H), 7.99 (d, 1H), 10.58 (s, 1H), 11.00 (s, 1H), 12.04 (s, 1H) | 535 |
| 675 | (trans-4-{4-[({5-[(3-chloro-2-methylphenyl)amino]-1,3,4-oxadiazol-2-yl}carbonyl)amino]phenyl}-cyclohexyl)acetic acid | 1.03-1.18 (m, 2H), 1.37-1.52 (m, 2H), 1.66-1.86 (m, 5H), 2.14 (d, 2H), 2.34 (s, 3H), 2.39-2.49 (m, 1H), 7.11-7.25 (m, 3H), 7.27-7.34 (m, 1H), 7.65-7.75 (m, 3H), 10.31 (s, 1H), 10.96 (s, 1H), 12.03 (s, 1H) | 469 |
| 676 | (trans-4-{4-[({5-[(5-bromo-2-methylphenyl)amino]-1,3,4-oxadiazol-2-yl}carbonyl)amino]phenyl}-cyclohexyl)acetic acid | 1.03-1.19 (m, 2H), 1.37-1.51 (m, 2H), 1.65-1.88 (m, 5H), 2.14 (d, 2H), 2.28 (s, 3H), 2.37-2.48 (m, 1H), 7.17-7.30 (m, 4H), 7.69 (d, 2H), 8.08 (s, 1H), 10.24 (s, 1H), 10.98 (s, 1H), 12.02 (s, 1H) | 513 |
| 677 | (trans-4-{4-[({5-[(2-chloro-5-fluorophenyl)amino]-1,3,4-oxadiazol-2-yl}carbonyl)amino]phenyl}-cyclohexyl)acetic acid | 1.03-1.20 (m, 2H), 1.38-1.53 (m, 2H), 1.64-1.87 (m, 5H), 2.15 (d, 2H), 2.37-2.49 (m, 1H), 7.03-7.10 (m, 1H), 7.23 (d, 2H), 7.56-7.63 (m, 1H), 7.69 (d, 2H), 7.97-8.05 (m, 1H), 10.69 (s, 1H), 11.03 (s, 1H), 12.07 (s, 1H) | 473 |
| 678[1] | (trans-4-{4-[({5-[(2-chloro-5-methylphenyl)amino]-1,3,4-oxadiazol-2-yl}carbonyl)amino]phenyl}-cyclohexyl)acetic acid | 1.04-1.20 (m, 2H), 1.38-1.52 (m, 2H), 1.67-1.87 (m, 5H), 2.14 (d, 2H), 2.34 (s, 3H), 2.39-2.49 (m, 1H), 7.05 (d, 1H), 7.23 (d, 2H), 7.42 (d, 1H), 7.68 (d, 2H), 7.75 (s, 1H), 10.37 (s, 1H), 10.95 (s, 1H), 12.02 (s, 1H) | 469 |
| 679[1] | (trans-4-{4-[({5-[(5-chloro-2-methylphenyl)amino]-1,3,4-oxadiazol-2-yl}carbonyl)amino]phenyl}-cyclohexyl)acetic acid | 1.03-1.19 (m, 2H), 1.37-1.52 (m, 2H), 1.67-1.87 (m, 5H), 2.14 (d, 2H), 2.29 (s, 3H), 2.38-2.48 (m, 1H), 7.13 (d, 1H), 7.22 (d, 2H), 7.28 (d, 1H), 7.69 (d, 2H), 7.97 (s, 1H), 10.25 (s, 1H), 10.99 (s, 1H), 12.02 (s, 1H) | 469 |

[1] The product was recrystallised from acetic acid

Example 680

The following example was prepared by the general procedure of Example 483 using the appropriate aniline $R^1NH_2$ and isothiocyanate $R^2$—NCS.

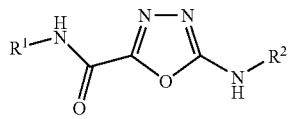

| Example | SM | R¹ | R² | ¹H NMR δ | MS m/e MH⁺ |
|---------|-----|-----|-----|----------|------------|
| 680 | Int 110 | | | 1.02-1.10 (3H, m), 1.17-1.22 (3H, m), 2.16-2.22 (3H, m), 2.33-2.68 (3H, m), 3.50 (1H, m), 4.06-4.11 (2H, m), 7.21-7.28 (2H, m), 7.36 (1H, d), 7.47-7.50 (1H, m), 7.68-7.75 (3H, m), 10.95-10.97 (1H, m), 11.23 (1H, s) | 471 |

Example 681

The following example was prepared by the general procedure of Example 498, using Example 680 as starting material (SM).

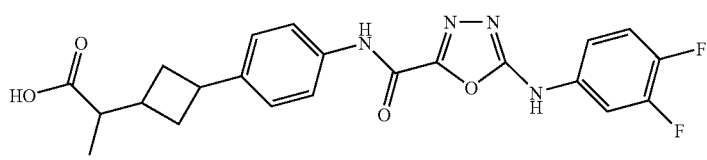

| Example | ¹H NMR δ | MS m/e MH⁺ |
|---------|----------|------------|
| 681 | 0.98-1.12 (3H, m), 1.71-1.92 (1H, m), 2.13-2.24 (3H, m), 2.28-2.44 (2H, m), 3.42-3.53 (1H, m), 7.21-7.28 (2H, m), 7.35-7.40 (1H, m), 7.45-7.50 (1H, m), 7.65-7.75 (3H, m), 10.96 (1H, d), 11.23 (1H, s), 12.01 (1H, s) | 443 |

Example 682

Methyl 1-{5-[({5-[(3,4-difluorophenyl)amino]-1,3,4-oxadiazol-2-yl}carbonyl)amino]-3-methylpyridin-2-yl}piperidine-4-carboxylate

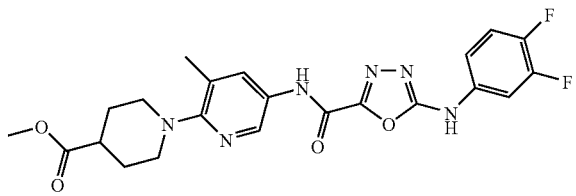

To a stirred suspension of methyl 1-(5-{[hydrazino(oxo)acetyl]amino}-3-methylpyridin-2-yl)piperidine-4-carboxylate (Intermediate 111) (336 mg; 1.00 mmol) in anhydrous DMA (5 mL) was added 3,4-difluorophenylisothiocyanate (206 mg; 1.20 mmol) and the clear solution, obtained on warming, was heated to 45° C. for 1 hr. EDAC (231 mg) was added and the reaction heated at 85° C. for 1 hr. The reaction mixture was cooled and water (~5 mL) was added. The precipitated solid was filtered off and dried under vacuum at 60° C. to leave the title compounds as a yellow powder (381 mg, 81% yield). $^1$H NMR δ 1.62-1.81 (m, 2H), 1.83-2.00 (m, 2H), 2.16 (s, 3H), 2.51-2.59 (m, 1H), 2.65-2.84 (m, 2H), 3.23-3.41 (m, 2H), 3.70 (s, 3H), 7.28-7.40 (m, 1H), 7.39-7.57 (m, 1H), 7.59-7.76 (m, 1H), 7.90 (d, 1H), 8.44 (d, 1H), 10.97 (s, 1H), 11.16 (s, 1H). MS m/e MH$^+$=473.

In a similar manner, from the appropriate hydrazides (Intermediates 111 to 113) and the commercially available isothiocyanates, the following example were synthesised.

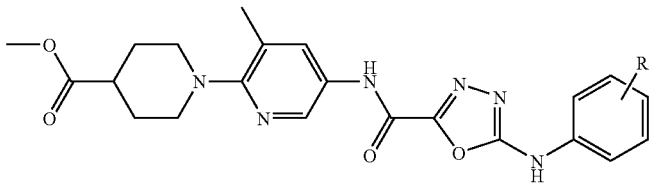

| Example | Name | $^1$H NMR δ | MS m/e M +H$^+$ |
|---|---|---|---|
| 683 R = 4-OCF$_3$ | Methyl 1-(3-methyl-5-{[(5-{[4-trifluoromethoxy)phenyl]amino}-1,3,4-oxadiazol-2-yl)carbonyl]amino}pyridin-2-yl)piperidine-4-carboxylate | 1.62-1.79 (m, 2H), 1.83-1.97 (m, 2H), 2.25 (s, 3H), 2.44-2.52 (m, 1H), 2.66-2.81 (m, 2H), 3.19-3.37 (m, 2H), 3.66 (s, 3H), 7.40 (d, 2H), 7.69 (d, 2H), 7.90 (d, 1H), 8.43 (d, 1H), 10.98 (s, 1H), 11.16 (s, 1H) | 521 |
| 684 R = 4-CF$_3$ | Methyl 1-(3-methyl-5-{[(5-{[4-trifluoromethyl)phenyl]amino}-1,3,4-oxadiazol-2-yl)carbonyl]amino}pyridin-2-yl)piperidine-4-carboxylate | 1.61-1.82 (m, 2H), 1.85-1.99 (m, 2H), 2.18 (s, 3H), 2.52-2.58 (m, 1H), 2.68-2.83 (m, 2H), 3.24-3.42 (m, 2H), 3.58 (s, 3H), 7.62-7.88 (m, 4H), 7.92 (d, 1H), 8.45 (d, 1H), 11.00 (s, 1H), 11.39 (s, 1H) | 505 |
| 685 R = 4-Et | Methyl 1-{5-[({5-[(4-ethylphenyl)amino]-1,3,4-oxadiazol-2-yl}carbonyl)amino]-3-methylpyridin-2-yl}piperidine-4-carboxylate | 1.16 (t, 3H), 1.59-1.80 (m, 2H), 1.86-1.99 (m, 2H), 2.19 (s, 3H), 2.51-2.64 (m, 3H), 2.68-2.83 (m, 2H), 3.31 (d, 2H), 3.58 (s, 3H), 7.22 (d, 2H), 7.50 (d, 2H), 7.90 (d, 1H), 8.44 (d, 1H), 10.83 (s, 1H), 10.95 (s, 1H) | 465 |

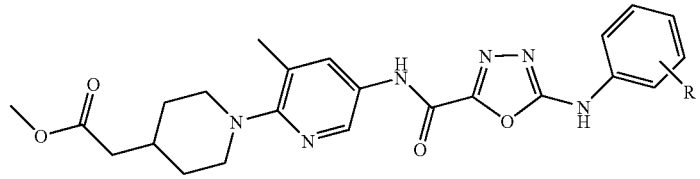

| Example | Name | $^1$H NMR δ | MS m/e M +H$^+$ |
|---|---|---|---|
| 686 R = 3,4-diF | Methyl (1-{5-[({5-[(3,4-difluorophenyl)amino]-1,3,4-oxadiazol-2-yl}carbonyl)amino]-3-methylpyridin-2-yl}piperidin-4-yl)acetate | 1.24-1.45 (m, 2H), 1.66-1.78 (m, 2H), 1.78-1.92 (m, 1H), 2.18 (s, 3H), 2.31 (d, 2H), 2.60-2.75 (m, 2H), 3.25-3.39 (m, 2H), 3.56 (s, 3H), 7.28-7.39 (m, 1H), 7.39-7.53 (m, 1H), | 487 |

-continued

| Example | Name | $^1$H NMR δ | MS m/e M+H$^+$ |
|---|---|---|---|
| | | 7.62-7.74 (m, 1H), 7.89 (d, 1H), 8.43 (d, 1H), 11.06 (s, 1H), 11.30 (s, 1H) | |
| 687 R = 4-OCF$_3$ | Methyl [1-(3-methyl-5-{[(5-{[4-trifluoromethyl)phenyl]amino}-1,3,4-oxadiazol-2-yl)carbonyl]amino}pyridin-2-yl)piperidin-4-yl]acetate | 1.24-1.43 (m, 2H), 1.63-1.79 (m, 2H), 1.79-1.92 (m, 1H) 2.25 (s, 3H), 2.32 (d, 2H), 2.61-2.75 (m, 2H), 3.22-3.39 (m, 2H), 3.65 (s, 3H), 7.40 (d, 2H), 7.69 (d, 2H), 7.90 (d, 1H), 8.43 (d, 1H), 10.98 (s, 1H), 11.23 (s, 1H) | 535 |
| 688 R = 4-CF$_3$ | Methyl [1-(3-methyl-5-{[(5-{[4-trifluoromethyl)phenyl]amino}-1,3,4-oxadiazol-2-yl)carbonyl]amino}pyridin-2-yl)piperidin-4-yl]acetate | 1.23-1.48 (m, 2H), 1.66-1.79 (m, 2H), 1.78-1.93 (m, 1H), 2.17 (s, 3H), 2.32 (d, 2H), 2.59-2.75 (m, 2H), 3.24-3.41 (m, 2H), 3.70 (s, 3H), 7.61-7.84 (m, 4H), 7.90 (d, 1H), 8.43 (d, 1H), 10.98 (s, 1H), 11.48 (s, 1H) | 519 |
| 689 R = 4-Et | Methyl (1-{5-[({5-[(4-ethylphenyl)amino]-1,3,4-oxadiazol-2-yl}carbonyl)amino]-3-methylpyridin-2-yl}piperidin-4-yl)acetate | 1.17 (t, 3H), 1.24-1.44 (m, 2H), 1.67-1.78 (m, 2H), 1.79-1.90 (m, 1H), 2.16 (s, 3H), 2.31 (d, 2H), 2.57 (q, 2H), 2.62-2.75 (m, 2H), 3.22-3.39 (m, 2H), 3.67 (s, 3H), 7.21 (d, 2H), 7.49 (d, 2H), 7.89 (d, 1H), 8.43 (d, 1H), 10.81 (s, 1H), 11.02 (s, 1H) | 479 |

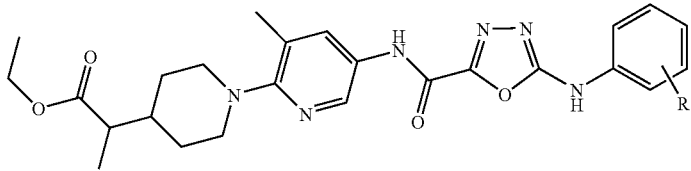

| Example | Name | $^1$H NMR δ | MS m/e M+H$^+$ |
|---|---|---|---|
| 690 R = 3,4-diF | Ethyl 2-(1-{5-[({5-[(3,4-difluorophenyl)amino]-1,3,4-oxadiazol-2-yl}carbonyl)amino]-3-methylpyridin-2-yl}piperidin-4-yl)propanoate | 1.08 (d, 3H), 1.19 (t, 3H), 1.29-1.45 (m, 2H), 1.55-1.67 (m, 2H), 1.67-1.79 (m, 1H), 1.92 (s, 3H), 2.10-2.23 (m, 2H), 2.24-2.34 (m, 1H), 2.56-2.73 (m, 2H), 3.21-3.46 (m, 3H), 4.02-4.13 (m, 2H), 7.27-7.38 (m, 1H), 7.38-7.53 (m, 1H), 7.61-7.75 (m, 1H), 7.89 (d, 1H), 8.43 (d, 1H), 11.37 (s, 1H). | 515 |
| 691 R = 4-OCF$_3$ | Ethyl 2-[1-(3-methyl-5-{[(5-{[4-trifluoromethyl)phenyl]amino}-1,3,4-oxadizol-2-yl)carbonyl]amino}pyridin-2-yl)piperidin-4-yl]propanoate | 1.08 (d, 3H), 1.19 (t, 3H), 1.29-1.47 (m, 2H), 1.51-1.68 (m, 2H), 1.67-1.79 (m, 1H), 2.24 (s, 3H), 2.23-2.35 (m, 1H), 2.55-2.76 (m, 2H), 3.22-3.44 (m, 3H), 4.07 (q, 2H), 7.39 (d, 2H), 7.67 (d, 2H), 7.87 (d, 1H), 8.40 (d, 1H), 11.05 (s, 1H) | 563 |
| 692 R = 2,4,5-triF | Ethyl 2-(1-{3-methyl-5-[({5-[(2,4,5-trifluorophenyl)amino]-1,3,4-oxadiazol-2-yl}carbonyl)amino]pyridine-2-yl}piperidin-4-yl)propanoate | 1.06 (d, 3H), 1.20 (q, 3H), 1.25-1.48 (m, 2H), 1.51-1.67 (m, 2H), 1.68-1.78 (m, 1H), 2.14 (s, 3H), 2.24-2.38 (m, 1H), 2.53-2.73 (m, 2H), 3.20-3.45 (m, 3H), 4.08 (q, 2H), 7.67 (q, 1H), 7.88 (d, 1H), 8.15 (q, 1H), 8.43 (d, 1H), 10.98 (s, 1H) | 533 |
| 693 R = 4-Et | Ethyl 2-(1-{5-[({5-[(4-ethylphenyl)amino]-1,3,4-oxadiazol-2-yl}carbonyl)amino]-3-methylpyridin-2-yl}piperidin-4-yl)propanoate | 1.08 (d, 3H), 1.19 (q, 6H), 1.35 (m, 2H), 1.60 (m, 2H), 1.73 (m, 1H), 2.20 (s, 3H) 2.30 (m, 1H), 2.58 (q, 2H), 2.60 (m, 2H), 3.37 (m, 2H), 4.07 (q, 2H), 7.20 (d, 2H), 7.48 (d, 2H), 7.85 (d, 1H), 8.42 (d, 2H), 10.84 (s, 1H), 10.97 (s, 1H) | 507 |

The following examples were prepared from the appropriate esters (Examples 682-689) by hydrolysis following the method of Example 320.

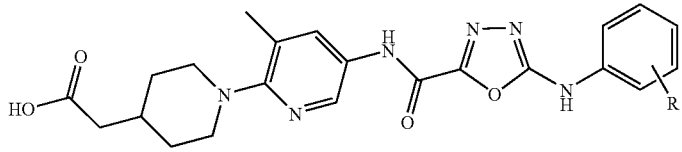

| Example | Name | $^1$NMR δ | MS m/e M +H$^+$ |
|---|---|---|---|
| 694 R = 3,4-diF | (1-{5-[({5-[(3,4-difluorophenyl)amino]-1,3,4-oxadiazol-2-yl}carbonyl)amino]-3-methylpyridin-2-yl}piperidin-4-yl)acetic acid | 1.18-1.41 (m, 2H), 1.61-1.77 (m, 2H), 1.75-1.89 (m, 1H), 2.13 (d, 2H), 2.28 (s, 3H), 2.69-2.91 (m, 2H), 3.31-3.48 (m, 2H), 7.22-7.32 (m, 1H), 7.32-7.47 (m, 1H), 7.56-7.68 (m, 1H), 7.97 (s, 1H), 8.43 (d, 1H), 11.13 (s, 1H), 11.31 (s, 1H) | 473 |
| 695 R = 4-OCF$_3$ | [1-(3-methyl-5-{[(5-{[4-(trifluoromethoxy)phenyl]amino}-1,3,4-oxadiazol-2-yl)carbonyl]amino}pyridin-2-yl)piperidin-4-yl] acetic acid | 1.27-1.48 (m, 2H), 1.70-1.85 (m, 2H), 1.84-1.99 (m, 1H), 2.21 (d, 2H), 2.35 (s, 3H), 2.79-3.02 (m, 2H), 3.42-3.54 (m, 2H), 7.41 (d, 2H), 7.70 (d, 2H), 8.05 (s, 1H), 8.44 (s, 1H), 8.44 (s, 1H), 11.14 (s, 2H). | 521 |
| 696 R = CF$_3$ | [1-(3-methyl-5-{[(5-{[4-(trifluoromethyl)phenyl]amino}-1,3,4-oxadiazol-2-yl)carbonyl]amino}pyridin-2-yl)piperidin-4-yl] acetic acid | 1.27-1.49 (m, 2H), 1.71-1.85 (m, 2H), 1.85-1.98 (m, 1H), 2.22 (d, 2H), 2.34 (s, 3H), 2.81-3.00 (m, 2H), 3.43-3.54 (m, 2H), 7.78 (q, 4H), 8.06 (s, 1H), 8.51 (d, 1H), 11.23 (s, 1H), 11.55 (s, 1H) | 505 |
| 697 R = 4-Et | (1-{5-[({5-[(4-ethylphenyl)amino]-1,3,4-oxadiazol-2-yl}carbonyl)amino]-3-methylpyridin-2-yl}piperidin-4-yl)acetic acid | 1.16 (t, 3H), 1.27-1.46 (m, 2H), 1.72-1.85 (m, 2H), 1.85-1.94 (m, 1H), 2.21 (d, 2H), 2.35 (s, 3H), 2.57 (q, 2H), 2.80-2.96 (m, 2H), 3.43-3.54 (m, 2H), 7.21 (d, 2H), 7.51 (d, 2H), 8.03 (s, 1H), 8.50 (d, 1H) 10.86 (s, 1H), 11.26 (s, 1H) | 465 |

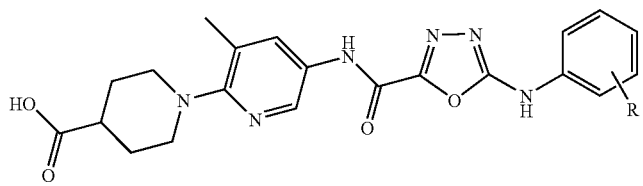

| Example | Name | $^1$NMR δ | MS m/e M +H$^+$ |
|---|---|---|---|
| 698 R = 3,4-diF | 1-{5-[({5-[(3,4-difluorophenyl)amino]-1,3,4-oxadiazol-2-yl}carbonyl)amino]-3-methylpyridin-2-yl} | 1.55-1.73 (m, 2H), 1.78-1.92 (m, 2H), 2.25 (s, 3H), 2.30-2.39 (m, 1H), 2.73-2.92 (m, 2H), 3.29-3.43 (m, 2H), 7.19-7.32 (m, | 459 |

| | | | |
|---|---|---|---|
| | piperidine-4-carboxylic acid | 1H), 7.32-7.45 (m, 1H), 7.54-7.71 (m, 1H), 8.01 (s, 1H), 8.41 (d, 1H), 11.08 (s, 1H), 11.18 (s, 1H), 11.30 (s, 1H) | |
| 699 R = OCF$_3$ | 1-(3-methyl-5-{[(5-{[4-(trifluoromethoxy)phenyl]amino}-1,3,4-oxadiazol-2-yl)carbonyl]amino}pyridin-2-yl)piperidine-4-carboxylic acid | 1.64-1.82 (m, 2H), 1.86-2.01 (m, 2H), 2.32 (s, 3H), 2.38-2.45 (m, 1H), 2.77-2.97 (m, 2H), 3.32-3.48 (m, 2H), 7.38 (d, 2H), 7.65-7.77 (m, 2H), 8.09 (s, 1H), 8.49 (d, 1H), 11.14 (s, 1H), 11.26 (s, 1H), 11.31 (s, 1H) | 507 |
| 700 R = CF$_3$ | 1-(3-methyl-5-{[(5-{[4-(trifluoromethyl)phenyl]amino}-1,3,4-oxadiazol-2-yl)carbonyl]amino}pyridin-2-yl)piperidine-4-carboxylic acid | 1.55-1.74 (m, 2H), 1.80-1.93 (m, 2H), 2.16 (s, 3H), 2.33-2.39 (m, 1H), 2.76-2.92 (m, 2H), 3.28-3.43 (m, 2H), 7.62-7.79 (m, 4H), 7.95 (s, 1H), 8.44 (d, 1H), 11.12 (s, 1H), 11.38 (s, 1H), 11.51 (s, 1H) | 491 |
| 701 R = 4-Et | 1-{5-[({5-[(4-ethylphenyl)amino]-1,3,4-oxadiazol-2-yl}carbonyl)amino]-3-methylpyridin-2-yl}piperidine-4-carboxylic acid | 1.17 (t, 3H), 1.59-1.82 (m, 2H), 1.87-1.99 (m, 2H), 2.23-2.33 (m, 3H), 2.37-2.47 (m, 1H), 2.59 (q, 2H), 2.79-2.93 (m, 2H), 3.34-3.47 (m, 2H), 3.54 (m, 2H), 7.21 (d, 2H), 7.45-7.55 (m, 2H), 7.97 (s, 1H), 8.44 (s, 1H), 10.84 (s, 1H), 10.94 (s, 1H), 11.16 (s, 1H) | 451 |

Example 702

1-(5-{[(5-{[4-(4-Fluorophenoxy)phenyl]amino}-1,3,4-oxadiazol-2-yl)carbonyl]amino}pyridin-2-yl)piperidine-4-carboxylic acid

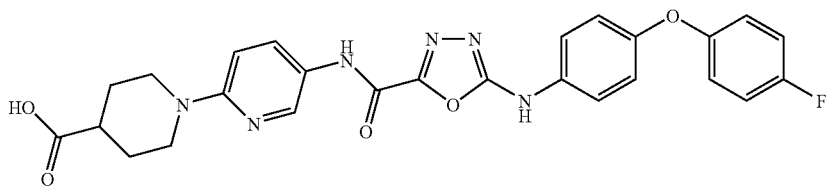

To a stirred solution of methyl 1-(5-{[(5-{[4-(4-fluorophenoxy)phenyl]amino}-1,3,4-oxadiazol-2-yl)carbonyl]amino}pyridin-2-yl)piperidine-4-carboxylate (Example 705, 415 mg, 0.78 mmol) in MeOH (5 mL) was added 2M NaOH (2 mL, 4 mmol) and the reaction mixture was allowed to stir at ambient temperature overnight. The solvent was evaporated and the aqueous residue adjusted to pH ~1-2 with 2M HCl, the solid was filtered and dried to leave a cream solid (284 mg). Glacial AcOH (~40 mL) was added and the suspension heated to 150° C., a small amount of material still didn't dissolve so the suspension was filtered and allowed to cool. The resulting solid was filtered and dried under vacuum at 40° C. to leave a white solid, 106 mg.

$^1$H NMR δ 1.57-1.66 (m, 2H), 1.91-1.95 (m, 2H), 2.56-2.62 (m, 1H), 3.14-3.20 (m, 2H), 4.14 (d, 2H), 7.01-7.04 (m, 2H), 7.11 (d, 2H), 7.22 (t, 2H), 7.26-7.31 (m, 1H), 7.63 (d, 2H), 8.14 (d, 1H), 8.51 (s, 1H), 11.06 (s, 1H), 11.24 (s, 1H); MS m/e MH$^+$ 519.

Examples 703 and 704 were prepared using the procedure described above, from Examples 707 and 706 respectively.

Example 703

1-(5-{[(5-{[4-(4-Fluorophenoxy)phenyl]amino}-1,3,4-oxadiazol-2-yl)carbonyl]amino}pyridin-2-3l)-4-methylpiperidine-4-carboxylic acid

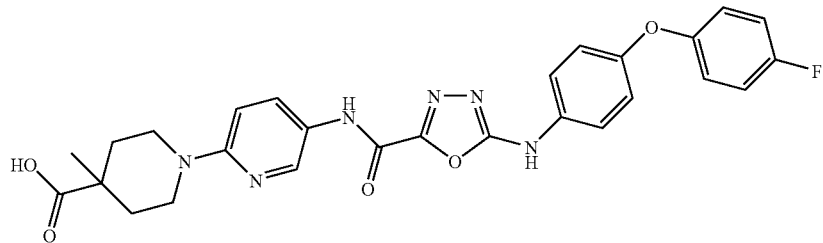

$^1$H NMR δ 1.17 (s, 3H), 1.37-1.43 (m, 2H), 1.97-2.00 (m, 2H), 3.11 (t, 2H), 3.86-3.89 (m, 2H), 6.87 (d, 1H), 7.01-7.04 (m, 2H), 7.09 (d, 2H), 7.22 (t, 2H), 7.62 (d, 2H), 7.90 (d, 1H), 8.47 (s, 1H), 10.94 (s, 1H), 11.00 (s, 1H), 12.41 (s, 1H); MS m/e MH$^+$ 533.

Example 704

[1-(5-{[(5-{[4-(4-Fluorophenoxy)phenyl]amino}-1,3,4-oxadiazol-2-yl)carbonyl]amino}pyridin-2-yl)piperidin-4-yl]acetic acid

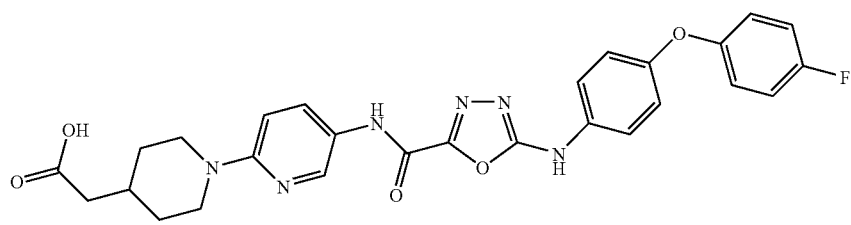

$^1$H NMR δ 1.15-1.24 (m, 2H), 1.73-1.76 (m, 2H), 1.90-1.94 (m, 1H), 2.19 (d, 2H), 2.83-2.89 (m, 2H), 4.20-4.24 (m, 2H), 6.93-7.04 (m, 3H), 7.11 (d, 2H), 7.19-7.24 (m, 2H), 7.62 (d, 2H), 7.96 (d, 1H), 8.46 (s, 1H), 11.01 (s, 2H); MS m/e MH$^+$ 533.

Example 705

Methyl 1-(5-{[(5-{[4-(4-fluorophenoxy)phenyl]amino}-1,3,4-oxadiazol-2-yl)carbonyl]amino}pyridin-2-yl)piperidine-4-carboxylate

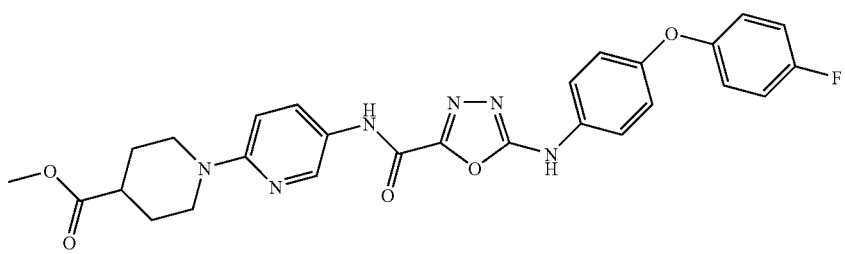

To a stirred solution of 4-(4-fluorophenoxy)aniline (190 mg, 0.93 mmol) in anhydrous DMA (4 mL) was added 1,1'-carbonothioylbis(1H-imidazole) (167 mg, 0.93 mmol) and the mixture stirred at ambient temperature for 1 hr. Methyl 1-(5-{[hydrazino(oxo)acetyl]amino}pyridin-2-yl)piperidine-4-carboxylate (250 mg, 0.78 mmol) was added and the reaction mixture was heated to 50° C. for 1 hr. EDCI.HCl (180 mg, 0.93 mmol) was added and the reaction mixture heated to 85° C. overnight and then allowed to cool to ambient temperature. Water (~20 mL) was added and the suspension filtered, washed with ether (~15 mL) and dried to leave the title compound as a pale yellow solid (415 mg, 0.780 mmol, 100%). $^1$H NMR δ 1.50-1.58 (m, 2H), 1.87-1.90 (m, 2H), 2.61-2.67 (m, 1H), 2.90-2.94 (m, 2H), 3.62 (s, 3H), 4.17 (d, 2H), 6.87-6.89 (m, 1H), 7.00-7.10 (m, 4H), 7.19-7.23 (m, 2H), 7.60-7.63 (m, 2H), 7.90-7.92 (m, 1H), 8.48 (s, 1H), 10.95 (s, 1H), 10.99 (s, 1H); MS m/e MH$^+$ 533.

Examples 706 and 707 were prepared using the procedure described above.

Methyl [1-(5-{[hydrazino(oxo)acetyl]amino}pyridin-2-yl)piperidin-4-yl]acetate (262 mg, 0.78 mmol) was used instead of ethyl 1-(5-{[hydrazino(oxo)acetyl]amino}pyridin-2-yl)piperidine-4-carboxylate. The title compound was isolated as a pale yellow solid (379 mg, 0.694 mmol, 89%). $^1$H NMR δ 1.14-1.20 (m, 2H), 1.68-1.73 (m, 2H), 1.91-1.95 (m, 1H), 2.28 (d, 2H), 2.76-2.82 (m, 2H), 3.60 (s, 3H), 4.22-4.25 (m, 2H), 6.84-6.86 (m, 1H), 7.00-7.10 (m, 4H), 7.19-7.23 (m, 2H), 7.60-7.63 (m, 2H), 7.88-7.90 (m, 1H), 8.46 (s, 1H), 10.93 (s, 1H), 10.99 (s, 1H); MS m/e MH$^+$ 548.

Example 706

Methyl [1-(5-{[(5-{[4-(4-fluorophenoxy)phenyl]amino}-1,3,4-oxadiazol-2-yl)carbonyl]amino}pyridin-2-yl)piperidin-4-yl]acetate

Example 707

Methyl 1-(5-{[(5-{[4-(4-fluorophenoxy)phenyl]amino}-1,3,4-oxadiazol-2-yl)carbonyl]amino}pyridin-2-yl)-4-methylpiperidine-4-carboxylate

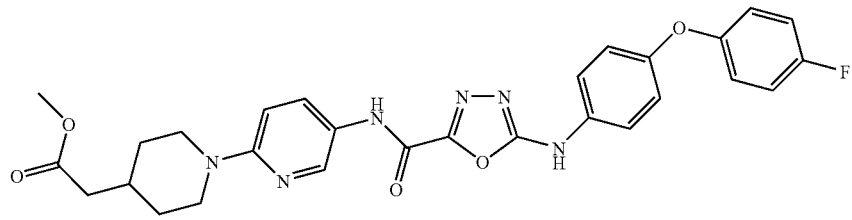

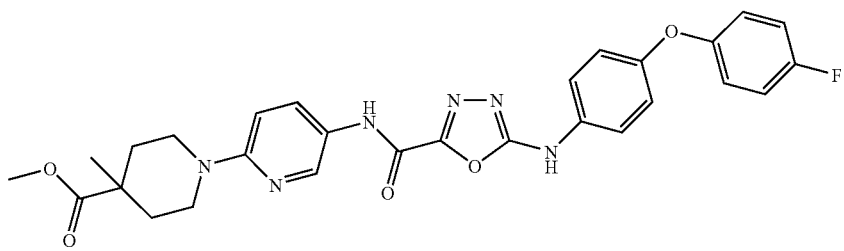

Methyl 1-(5-{[hydrazino(oxo)acetyl]amino}pyridin-2-yl)-4-methylpiperidine-4-carboxylate (262 mg, 0.78 mmol) was used instead of ethyl 1-(5-{[hydrazino(oxo)acetyl]amino}pyridin-2-yl)piperidine-4-carboxylate. The title compound was isolated as a pale brown solid (410 mg, 0.75 mmol, 96%). $^1$H NMR δ 1.18 (s, 3H), 1.41-1.47 (m, 2H), 1.96-2.02 (m, 2H), 3.08-3.13 (m, 2H), 3.65 (s, 3H), 3.84-3.88 (m, 2H), 6.86-6.88 (m, 1H), 7.00-7.10 (m, 4H), 7.19-7.23 (m, 2H), 7.60-7.63 (m, 2H), 7.89-7.91 (m, 1H), 8.47 (s, 1H), 10.94 (s, 1H), 10.99 (s, 1H); MS m/e MH$^+$ 548.

Example 708

(1-{5-[({5-[(3,4-difluorophenyl)amino]-1,3,4-oxadiazol-2-yl}carbonyl)amino]pyridin-2-yl}-4-methylpiperidin-4-yl)acetic acid

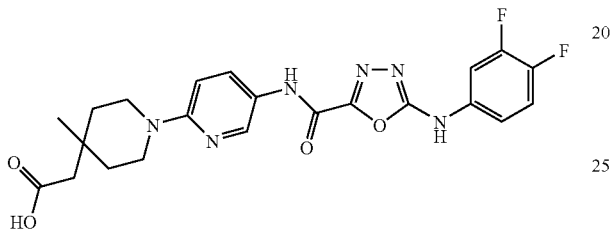

Prepared from Intermediate 114 by hydrolysis using 5 equivalents of 2M NaOH in MeOH followed by purification on a reverse phase system eluting 5-95% water (0.2% TFA)-MeCN (0.2% TFA). $^1$H NMR δ 1.07 (s, 3H), 1.42-1.46 (m, 2H), 1.56-1.61 (m, 2H), 2.24 (s, 2H), 3.40-3.47 (m, 2H), 3.58-3.62 (m, 2H), 6.88 (d, 1H), 7.34-7.36 (m, 1H), 7.50 (q, 1H), 7.68-7.73 (m, 1H), 7.91 (d, 1H), 8.46 (s, 1H), 10.98 (s, 1H), 11.27 (s, 1H), 12.04 (s, 1H); MS m/e MH$^+$ 473.

The following compounds were prepared from the appropriate esters (Intermediates 115-117) in the same manner as described above:

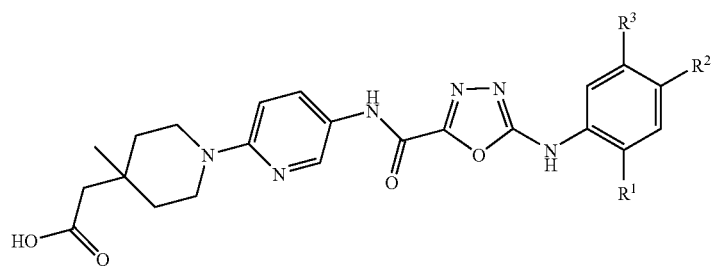

| Example | Name | $^1$H NMR (400 MHz, DMSO)δ | MS m/e M +H$^+$ |
|---|---|---|---|
| 709<br>$R^1 = R^2 = R^3 = F$ | (4-methyl-1-{5-[({5-[(2,4,5-trifluorophenyl)amino]-1,3,4-oxadiazol-2-yl}carbonyl)amino]pyridin-2-yl}piperidin-4-yl)acetic acid | 1.02 (s, 3H), 1.37-1.41 (m, 2H), 1.51-1.56 (m, 2H), 2.19 (s, 2H), 3.34-3.39 (m, 2H), 3.53-3.56 (m, 2H), 6.82 (d, 1H), 7.65-7.72 (m, 1H), 7.84 (d, 1H), 8.10-8.17 (m, 1H), 8.41 (s, 1H), 10.94 (s, 1H), 11.05 (s, 1H), 11.99 (s, 1H) | 491 |

-continued

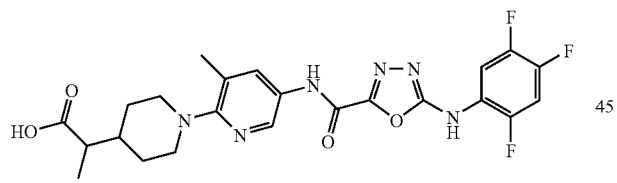

| Example | Name | $^1$H NMR (400 MHz, DMSO)δ | MS m/e M +H$^+$ |
|---|---|---|---|
| 710 R$^1$ = R$^3$ =H, R$^2$ = CF$_3$ | [4-methyl-1-(5-{[(5-{[4-(trifluoromethyl)phenyl]amino}-1,3,4-oxadiazol-2-yl)carbonyl]amino}pyridin-2-yl)piperidin-4-yl]acetic acid | 11.50 (s, 1H), 11.19 (s, 1H), 8.48 (s, 1H), 8.06 (d, 1H), 7.82-7.77 (m, 4H), 7.16-7.11 (m, 1H), 3.66-3.62 (m, 2H), 3.51-3.47 (m, 2H), 2.27 (s, 2H), 1.66-1.62 (m, 2H), 1.52-1.46 (m, 2H), 1.09 (s, 3H); CO$_2$H not seen. | 505 |
| 711 R$^1$ = R$^3$ =H, R$^2$ = O(4-F—C$_6$H$_4$) | [1-(5-{[(5-{[4-(4-fluorophenoxy)phenyl]amino}-1,3,4-oxadiazol-2-yl)carbonyl]amino}pyridin-2-yl)-4-methylpiperidin-4-acetic acid | 1.07 (s, 3H), 1.41-1.46 (m, 2H), 1.56-1.62 (m, 2H), 2.24 (s, 2H), 3.41-3.45 (m, 2H), 3.57-3.63 (m, 2H), 6.84 (d, H), 7.00-7.04 (m, 2H), 7.09 (d, 2H), 7.21 (t, 2H), 7.62 (d, 2H), 7.91 (d, 1H), 8.46 (s, 1H); 10.95 (s, 1H), 11.00 (s, 1H), 12.05 (s, 1H) | 547 |

Example 712

2-(1-{3-Methyl-5-[({5-[(2,4,5-trifluorophenyl)amino]-1,3,4-oxadiazol-2-yl}carbonyl)amino]pyridin-2-yl}piperidin-4-yl)propanoic acid

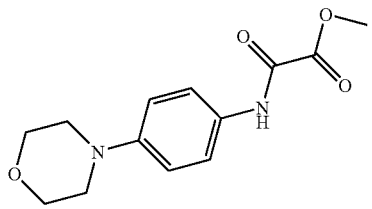

Ethyl 2-(1-{3-methyl-5-[({5-[(2,4,5-trifluorophenyl)amino]-1,3,4-oxadiazol-2-yl}carbonyl)amino]pyridine-2-yl}piperidin-4-yl)propanoate (Example 692) (70 mg; 0.13 mmol) was dissolved in dry THF (2.0 mL), treated with potassium trimethylsilanolate (167 mg; 1.30 mmol) and placed in a Biotage 'Initiator' microwave. The reaction was heated at 90° C. for 35 mins., monitoring by LCMS, as a yellow precipitate formed. The reaction was incomplete (~9% ester remained). A further portion of potassium trimethylsilanolate (17 mg) was added and the reaction was returned to the microwave for 15 mins. Very little more reaction was seen (ie ~5% of starting ester remained). The resulting yellow suspension was treated with water (3 mL) and acidified, to about pH 2, with dropwise addition of aq. 1M HCl. With vigorous stirring for ~15 mins, a white precipitate formed which was filtered, washed with water and dried under vacuum at 60° C. to give the title compound (45 mg; 79% yield).

$^1$H NMR δ 1.08 (d, 3H), 1.29-1.53 (m, 2H), 1.58-1.83 (m, 3H), 2.16-2.28 (m, 1H), 2.34 (s, 3H), 2.74-2.94 (m, 2H), 3.43-3.56 (m, 2H), 7.64-7.78 (m, 1H), 8.01 (s, 1H), 8.08-8.21 (m, 1H), 8.44 (s, 1H), 11.02 (s, 1H), 11.26 (s, 1H). MH$^+$=505.53.

Preparation of Starting Materials

Intermediate 1: Methyl [(4-morpholin-4-yl phenyl)amino](oxo)acetate

Methyl chlorooxaacetate (4.64 mL, 50 mmol) was added dropwise to an ice cooled solution of 4-morpholinoaniline (8.91 g, 50 mmol) and ethyldiisopropylamine (9.4 mL, 55 mmol) in DCM (125 mL). The reaction was stirred for 2 h at room temperature then quenched with water (100 mL). The organic layer was removed, dried (MgSO$_4$), filtered and evaporated to give the title compound (11.7 g, 89%): $^1$H NMR δ10.63 (1H, s), 7.61 (2H, d), 6.92 (2H, d), 3.88 (3H, s), 3.78-3.68 (4H, m), 3.15-3.04 (4H, m); MS m/e MH$^+$ 265.

The following intermediates were prepared by the general procedure of intermediate 1 (method D1) using intermediates 36 and 38, known anilines [tert-butyl 4-(4-amino-2-fluorophenyl)piperazine-1-carboxylate (WO 2004018439), 5-amino-2-morpholin-4-ylbenzonitrile (WO 2000047558), (3-methyl-4-morpholin-4-ylphenyl)amine (DE 1020048), (3-fluoro-4-morpholin-4-ylphenyl)amine (J. Med. Chem. 1996, 39, 673-679)] and commercially available anilines. In method D2 triethylamine was used as the base instead of ethyldiisopropylamine and in Method D3 pyridine was used:

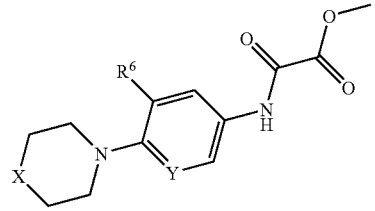

| Inter | X | Y | $R^6$ | $^1$H NMR δ | MS m/e $MH^+$ | Method |
|---|---|---|---|---|---|---|
| 2 | $CH_2$ | CH | H | | 263 | D2 |
| 3 | NMe | CH | H | | 278 | D2 |
| 4 | NAc | CH | H | | 306 | D2 |
| 5 | NBoc | CH | H | 10.58 (1H, s), 7.80 (1H, d), 6.95 (1H, d), 3.80 (3H, s), 3.40-3.45 (4H, m), 3.00-3.10 (4H, m), 1.40 (9H, s) | 308 | D2 |
| 6 | O | CCl | H | 10.85 (1H, s), 7.89 (1H, d), 7.68 (1H, d), 7.17 (1H, d), 3.85 (3H, s), 3.76-3.70 (4H, m), 2.98-2.90 (4H, m) | 299 | D1 |
| 7 | O | CF | H | 10.74 (1H, s), 7.65-6.97 (3H, m), 3.86-3.69 (7H, m), 3.31-2.46 (4H, m) | 283 | D3 |
| 8 | O | CCN | H | 10.91 (1H, s), 8.07-7.64 (2H, m), 7.21 (1H, t), 3.86-3.71 (7H, m), 3.28-3.06 (4H, m) | 290 | D3 |
| 9 | O | CMe | H | 10.58 (1H, s), 7.55-7.46 (2H, m), 7.00 (1H, d), 3.83 (3H, s), 3.75-3.68 (4H, m), 2.82-2.76 (4H, m), 2.23 (3H, s) | 279 | D3 |
| 10 | O | N | H | 10.74 (1H, s), 8.48 (1H, d), 7.91 (1H, dd), 6.88 (1H, d), 3.85 (3H, s), 3.74-3.66 (4H, m), 3.45-3.37 (4H, m) | 266 | D1 |
| 11 | O | N | Cl | 11.01 (1H, s), 8.57 (1H, d), 8.19 (1H, d), 3.85 (3H, s), 3.72 (4H, t), 3.23-3.17 (4H, m) | 300 | D3 |
| 12 | NMe | N | H | | 279 | D2 |
| 13 | NAc | CMe | H | 10.59 (1H, s), 7.56-7.46 (2H, m), 6.98 (1H, d), 3.83 (3H, s), 3.60-3.50 (4H, m), 2.84-2.69 (4H, m), 2.25 (3H, s), 2.02 (3H, s) | 320 | D3 |
| 14 | NBoc | CF | H | 10.82 (1H, s), 7.61 (1H, dd), 7.48 (1H, d), 7.03 (1H, t), 3.83 (3H, s), 3.50-3.41 (4H, m), 2.96-2.87 (4H, m), 1.41 (9H, s) | 326 $[MH - C_4H_8]^+$ | D3 |
| 15 | NAc | N | H | | 307 | |
| 16 | NBoc | N | H | 10.69 (1H, s), 8.45 (1H, s), 7.85 (1H, d), 5.75 (2H, s), 3.80 (3H, s), 3.40 (8H, s), 1.40 (9H, s) | 365 | |

Intermediate 17: Methyl [(4-iodophenyl)amino](oxo)acetate

The title compound was prepared by the general procedure of intermediate 1 using triethylamine as base and 4-iodo-aniline. This yielded the title compound as a pale brown solid; MS m/e MH+ 306.

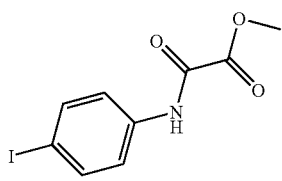

Intermediate 18: 2-Hydrazino-N-(4-morpholin-4-ylphenyl)-2-oxoacetamide

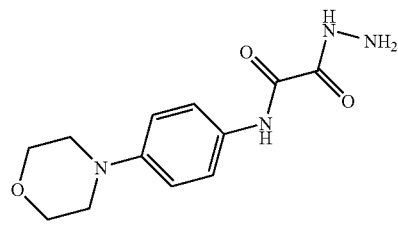

Hydrazine hydrate (1.25 mL, 25 mmol) was added to a stirred suspension of methyl [(4-morpholin-4-ylphenyl)amino](oxo)acetate (intermediate 1, 6.6 g, 25 mmol) in methanol (150 mL). The reaction was heated to 75° C. for 2 h during which time the precipitate thickened. After cooling the precipitate was filtered and washed with diethyl ether (50 mL) and dried to give the title compound (6.32 g, 94%):
$^1$H NMR δ 10.38 (1H, s), 10.15 (1H, s), 7.69 (2H, d), 6.91 (2H, d), 3.75 (4H, m), 3.08 (4H, m); MS m/e MH+ 265.

Intermediates 19-33 were prepared by the general procedure of intermediate 18 using intermediates 2-16 and either methanol or ethanol as solvent.

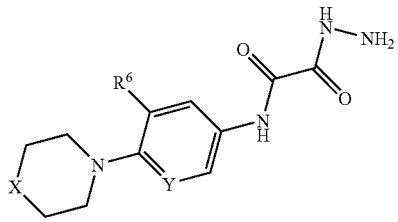

| Intermediate | X | Y | R$^6$ | $^1$H NMR (DMSO-d$_6$)δ | MS m/e MH+ |
|---|---|---|---|---|---|
| 19 | CH$_2$ | CH | H | | 263 |
| 20 | NMe | CH | H | | 278 |
| 21 | NAc | CH | H | | 306 |
| 22 | NBoc | CH | H | | 308 |
| 23 | O | CCl | H | 10.68 (1H, s), 10.22 (1H, bs), 7.97 (1H, s), 7.75 (1H, dd), 7.17 (1H, d), 4.60 (2H, bs), 3.78-3.71 (4H, m), 2.98-2.91 (4H, m) | 299 |
| 24 | O | CF | H | 7.67 (1H, dd), 7.60-7.54 (1H, m), 7.00 (1H, t), 4.78-4.24 (3H, m), 3.71 (4H, t), 2.95 (4H, t) | 283 |
| 25 | O | CCN | H | 10.78 (1H, s), 10.27 (1H, s), 8.15-8.11 (1H, m), 8.01 (1H, dd), 7.18 (1H, d), 4.55 (2H, bs), 3.74 (4H, t), 3.09 (4H, t) | 290 |
| 26 | O | CMe | H | 10.34 (1H, bs), 7.65-7.53 (2H, m), 6.98 (1H, d), 4.57 (2H, bs), 3.71 (4H, t), 2.78 (4H, t), 2.22 (3H, s) | 279 |
| 27 | O | N | H | 10.54 (1H, s), 10.20 (1H, bs), 8.54 (1H, s), 7.95 (1H, d), 6.84 (1H, d), 4.60 (2H, bs), 3.73-3.66 (4H, m), 3.44-3.36 (4H, m) | 266 |

-continued

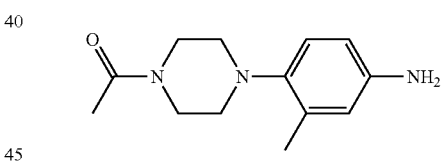

| Intermediate | X | Y | R⁶ | ¹H NMR (DMSO-d₆)δ | MS m/e MH⁺ |
|---|---|---|---|---|---|
| 28 | O | N | Cl | 10.85 (1H, bs), 10.29 (1H, bs), 8.65 (1H, d), 8.25 (1H, d), 4.62 (2H, bs), 3.71 (4H, t), 3.18 (4H, t) | 300 |
| 29 | NAc | CMe | H | 10.45 (1H, s), 7.65-7.53 (2H, m), 6.97 (1H, d), 4.57 (2H, bs), 3.59-3.50 (4H, m), 2.82-2.69 (4H, m), 2.24 (3H, s), 2.02 (3H, s) | 320 |
| 30 | NBoc | CF | H | 10.62 (1H, s), 10.22 (1H, s), 7.68 (1H, dd), 7.56 (1H, d), 7.01 (1H, t), 4.59 (2H, bs), 3.49-3.41 (4H, m), 2.94-2.86 (4H, m), 1.41 (9H, s) | 326 [MH − C₄H₈]⁺ |
| 31 | NMe | N | H |  | 279 |
| 32 | NAc | N | H | 10.45 (1H, s), 10.16 (1H, s), 8.50 (1H, d), 7.90 (1H, dd), 6.90 (1H, d), 4.60 (2H, bs), 3.50 (6H, m), 3.40 (2H, m), 2.00 (3H, s) | 307 |
| 33 | NBOC | N | H | 10.45 (1H, s), 10.16 (1H, s), 8.50 (1H, d), 7.90 (1H, dd), 6.90 (1H, d), 4.60 (2H, bs), 3.00 (8H, s), 2.00 (9H, s) | 309 [MH − C₄H₈]⁺ |

Intermediate 34:
N-(4-Iodophenyl)-2-hydrazino-2-oxoacetamide

The title compound was prepared by the general procedure of intermediate 18 using Intermediate 17.

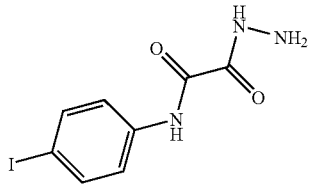

MS m/e MH⁺ 306.

Intermediate 35: N-(4-Iodophenyl)-5-[(2-fluorophenyl)amino]-1,3,4-oxadiazole-2-carboxamide The title compound was prepared by the general procedure of Example 1 using methyl [(4-iodophenyl)amino](oxo)acetate.

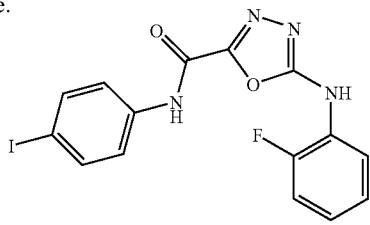

MS m/e MH⁺ 425.

This compound is a compound of formula (I) and so forms part of the invention.

Intermediate 36:
1-Acetyl-4-(4-amino-2-methylphenyl)-piperazine

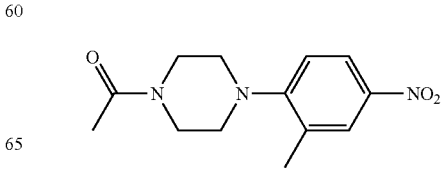

Palldium on carbon catalyst (2.0 g) was added to a solution of intermediate 37 (19.5 g, 74.1 mmol) in EtOAc/EtOH (1:1) (250 mL). The reaction was allowed to stir under a balloon atmosphere of hydrogen fro 18 h. The reaction was filtered through a pad of Celite® and the resulting clear solution evaporated under reduced pressure. The resulting white solid was triturated with ether and dried in vacuo at 60° C.; ¹H NMR δ 6.74 (1H, d), 6.41 (1H, d), 6.36 (1H, dd), 4.67 (2H, broad s), 3.56-3.48 (4H, m), 2.72-2.60 (4H, m), 2.15 (3H, s), 2.02 (3H, s); MS m/e MH⁺ 234.

Intermediate 37:
1-Acetyl-4-(2-methyl-4-nitrophenyl)piperazine

1-Butyl-3-methylimidazolium hexafluorophosphate (1.75 g, 7.7 mmol) and acetyl piperazine (39.7 g, 309.4 mmol) was added to a stirred solution of 2-fluoro-5-nitrotoluene (12 g, 77.4 mmol) in MeCN (3 mL) and heated to 85° C. for 2 h. The reaction was cooled and concentrated in vacuo. Water (100 mL) was added to the resulting residue and the reaction extracted with EtOAc (3×100 mL). The solvent was dried (MgSO$_4$), filtered, and concentrated in vacuo to yield the product as a yellow solid which was triturated with isohexane and dried in vacuo at 60° C.; $^1$H NMR δ 8.05 (2H, m), 7.14 (1H, d), 3.64-3.58 (4H, m), 3.05-2.94 (4H, m), 2.37 (3H, s), 2.37 (3H, s); MS m/e MH$^+$ 264.

Intermediate 38: 5-Chloro-6-morpholin-4-ylpyridin-3-amine

The title compound was prepared by the general procedure of Intermediate 36 using 4-(3-chloro-5-nitro-pyridin-2-yl)-morpholine.

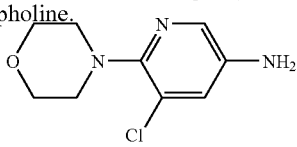

$^1$H NMR (300 MHz, DMSO-d$_6$) δ 7.64-7.60 (1H, m), 7.06-7.03 (1H, m), 5.15 (2H, broad s), 3.68 (4H, t, J=4.5 Hz), 2.98-2.92 (4H, m); MS m/e MH$^+$ 214.

Intermediate 39: 4-(3-Chloro-5-nitropyridin-2-yl)morpholine

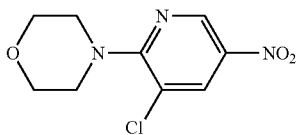

2,3-Dichloro-5-nitropyridine (Synthesis, 1990, 6, 499-501) (20 g, 104 mmol) was added portionwise to morpholine (40 mL) at 0° C. and heated at 120° C. for 1 h. The reaction was cooled to room temperature, water (100 mL) added and the reaction extracted with DCM (3×150 mL). The organics were dried (MgSO$_4$), filtered, and the solvent removed under reduced pressure to give the product as a yellow solid, which was triturated with isohexane and allowed to dry under vacuum at 60° C. $^1$H NMR δ 8.98 (1H, d), 8.47 (1H, d), 3.74-3.69 (4H, m), 3.67-3.62 (4H, m); MS m/e MH$^+$ 244.

Intermediate 40: Ethyl 5-[(2-fluorophenyl)amino]-1,3,4-oxadiazole-2-carboxylate

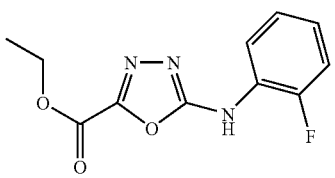

Hydrazine monohydrate (834 mg, 16.6 mmol) was in DCM (70 mL), and cooled in a dry ice/acetone bath to −60° C. 2-Fluoroisocyanate (2.28 g, 16.6 mmol) was dissolved in DCM (5 mL) and added dropwise to the hydrazine solution, which was then stirred at −60° C. for 2 h. The reaction mixture was allowed to warm to room temperature and stirred for 18 h. The solid formed was filtered and washed with DCM (2×20 mL). The filtrate was concentrated in vacuo to quantitatively afford N-(2-fluorophenyl)hydrazinecarboxamide as a white solid (MS m/e MW$^+$ 170) which was used without further purification. This solid was stirred in ethanol-water (1:1, 50 mL). Ethyl glycoxylate (50% solution in toluene, 2.55 g, 24.9 mmol), was added and the reaction allowed to stir for 18 h. The ethanol was evaporated off from the reaction mixture in vacuo, and the resulting precipitate was filtered and washed with water (2×20 mL), then dried in vacuo to afford ethyl (2E)-({[(2-fluorophenyl)amino]carbonyl}hydrazono)acetate as a white solid (2.93 g, 70%, MS m/e MH$^+$ 254). This solid (3.55 g, 14.0 mmol), and sodium acetate (4.58 g, 14.7 mmol), were mixed together and suspended with stirring in glacial acetic acid (20 mL). A solution of bromine (2.37 g, 14.7 mmol) in glacial acetic acid (6 mL), was added dropwise to the reaction and left to stir at room temperature for 30 min. The reaction was then heated in an oil bath at 130° C. for 1 h and poured into water (50 mL). The resulting solid was filtered and washed with water (2×20 mL), dissolved in DCM (50 mL), washed with water (2×20 mL), then the organics were dried (MgSO$_4$), filtered and concentrated in vacuo to afford the title compound as an off white solid (2.92 g, 82%); $^1$H NMR (CDCl$_3$) δ 8.18(1H, t), 7.72 (1H, s), 7.05-7.26 (3H, m), 4.48 (2H, q), 1.45 (3H, t); MS m/e MH$^+$ 252.

Intermediate 41: 5-[(2-fluorophenyl)amino]-N-(6-piperazin-1-ylpyridin-3-yl)-1,3,4-oxadiazole-2-carboxamide

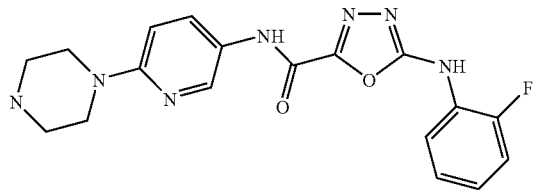

Example 78 (9.8 g, 20.3 mmol) was stirred in DCM (20 mL). 4N HCl in Dioxan (30 mL) was added and the reaction stirred for 2 h. The reaction was concentrated in vacuo, EtOAc (30 mL), water (30 mL) and triethylamine (10 mL) added, and stirred for 5 min. The resulting solid was filtered and washed with water (10 mL) then EtOAc (10 mL), then dried in vacuo to afford the title compound as a pale pink solid (7.4 g, 95%);

$^1$H NMR δ8.50 (1H, s), 8.05 (1H, t), 7.95 (1H, d), 7.2-7.35 (2H, m), 7.10-7.20 (1H, m), 3.45 (4H, s), 2.95 (4H, s); MS m/e MH$^+$ 384.

This compound is a compound of formula (I) and so forms part of the invention.

Intermediate 42: 4-(5-Aminopyridine-2-yl)butan-1-ol

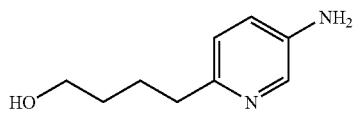

A mixture of 2-bromo-5-nitro pyridine (2.03 g, 10 mmol), 3-butyn-1-ol (1.05 g, 15 mmol), copper(I) iodide (19 mg, 0.1 mmol), dichlorobis(triphenylphosphine)palladium (II) (140 mg, 0.02 mmol), triethylamine (5.06 g, 50 mmol) in acetonitrile (30 mL) was stirred for 4 h. The reaction mixture was evaporated to dryness and loaded onto a Biotage KPSil60A cartridge, and purified by flash chromatography using Et$_2$O-DCM (1:9) as eluent to afford 4-(5-nitropyridin-2-yl)but-3-yn-1-ol as an oil (1.42 g, MS m/e MH$^+$ 193). This oil (1 g, 5.21 mmol) was stirred in methanol (50 mL) and 10% palladium on carbon (0.2 g) was added and the reaction stirred under an atmosphere of hydrogen. The reaction was filtered through Celite® and concentrated in vacuo to afford the title compound as an oil (0.87 g). $^1$H NMR δ 7.99 (1H, s), 6.93 (2H, s), 3.86 (2H, t), 3.55 (2H, s), 2.73 (2H, t), 1.70-1.74 (2H, m), 1.60-1.62 (2H, m); MS m/e MH$^+$ 167.

Intermediate 43: Methyl [trans-4-(4-{[hydrazino(oxo)acetyl]amino}phenyl)cyclohexyl]acetate

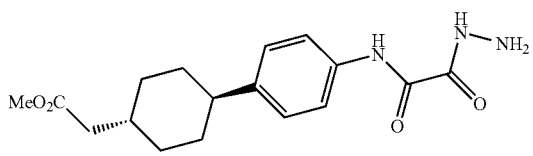

i) Methyl (trans-4-phenylcyclohexyl)acetate

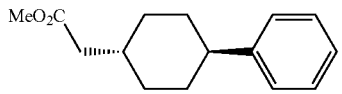

10% Pd/C (4520 mg) was added to a solution of methyl [trans-4-(4-{[(trifluoromethyl)sulfonyl]oxy}phenyl)cyclohexyl]acetate (prepared as described in Patent Application WO2004/047755) (8100 mg) in MeOH (150 mL). The resulting suspension was stirred for 16 h under an atmosphere of Hydrogen. The suspension was filtered through diatomaceous earth and concentrated in vacuo to give a slurry. This was extracted into EtOAc (300 mL). The organic extract was washed with saturated aqueous sodium hydrogen carbonate solution (75 mL) and then brine (75 mL). The organic layer was dried and concentrated in vacuo to give the title compound (4720 mg) as an oil; $^1$H NMR δ 7.28-7.11 (5H, m), 3.58 (3H, s), 2.43 (1H+DMSO, m), 2.22 (2H, d), 1.83-1.67 (5H, m), 1.44 (2H, m), 1.13 (2H, m); MS m/e MH$^+$ 233.

ii) Methyl [trans-4-(4-aminophenyl)cyclohexyl]acetate

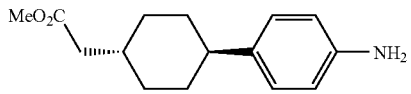

A mixture of 65% nitric acid (3.95 mL) and 95% sulphuric acid (4.97 mL) was added dropwise to a stirred solution of methyl (trans-4-phenylcyclohexyl)acetate (4710 mg) in CCl$_4$ (20 mL) at 5° C. and the solution was allowed to warm to ambient temperature and stirred for 16 hours. Ice/water (50 mL) was added and the mixture was extracted with DCM (2×40 mL). The organic extracts were combined, washed with brine (50 mL), dried, and concentrated in vacuo to give an oil. This oil was purified by flash chromatography on a 80 g Biotage™ silica column, using a gradient of 0-20% EtOAc in hexane as the eluent to give crude methyl [trans-4-(4-nitrophenyl)cyclohexyl]acetate which was dissolved in ethyl acetate (30 mL). 10% palladium on carbon (0.400 g) was added and the resulting suspension was stirred at ambient temperature for 16 hours under an atmosphere of hydrogen. The suspension was filtered through diatomaceous earth and concentrated in vacuo to give a solid. This was purified by flash chromatography on a 40 g Biotage™ silica column using a gradient of 20-45% EtOAc/hexane as eluent to give the title compound (1740 mg) as a solid; $^1$H NMR δ 6.83 (2H, d), 6.46 (2H, d), 4.72 (2H, s), 3.59 (3H, s), 2.23 (3H, m), 1.72 (5H, m), 1.35 (2H, m), 1.09 (2H, m); MS m/e MH$^+$ 248.

iii) Methyl ({4-[trans-4-(2-methoxy-2-oxoethyl)cyclohexyl]phenyl}amino)(oxo)acetate

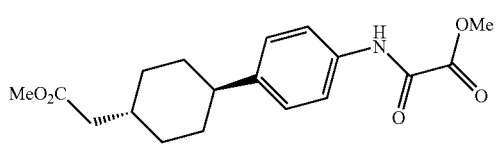

Methyl chloro(oxo)acetate (0.842 mL) was added to a stirred solution of methyl [trans-4-(4-aminophenyl)cyclohexyl]acetate (1740 mg) and pyridine (0.689 mL) in DCM (50 mL) at 0° C. After the addition was complete the mixture was allowed to warm to ambient temperature and stirred for 64 hours. The solution was diluted with DCM (100 mL), washed with water (50 mL) and brine (50 mL), then dried and concentrated in vacuo to give the title compound (2267 mg) as a solid; $^1$H NMR δ 7.60 (2H, d), 7.18 (2H, d), 3.83 (3H, s), 3.58 (3H, s), 2.58-35 (1H+DMSO, m), 2.21 (2H, d), 1.75 (5H, m), 1.43 (2H, m), 1.12 (2H, m); MS m/e MH$^-$ 332.

iv) Hydrazine hydrate (0.361 mL) was added to a stirred solution of methyl ({4-[trans-4-(2-methoxy-2-oxoethyl)cyclohexyl]phenyl}amino)(oxo)acetate (2260 mg) in EtOH (50 mL). The mixture was stirred for 1 hour. The precipitate was filtered off, washed with Et$_2$O, and dried under vacuum overnight to give the title compound (Intermediate 43, 1845 mg) as a solid; $^1$H NMR δ 10.44 (1H, s), 10.20 (1H, s), 7.70 (2H, d), 7.21 (2H, d), 4.60 (2H, s), 3.60 (3H, s), 2.42 (1H, m), 1.79 (5H, m), 1.45 (2H, m), 1.11 (2H, m); MS m/e MH$^+$ 334.

Intermediate 43': This refers to material prepared by exactly the same procedure as for Intermediate 43 except that ethanol was used as solvent in step (i), giving rise to a small proportion of ethyl ester in the final product.

Intermediate 44: Methyl trans-4-(4-{[hydrazino(oxo)acetyl]amino}phenyl)cyclohexanecarboxnlate

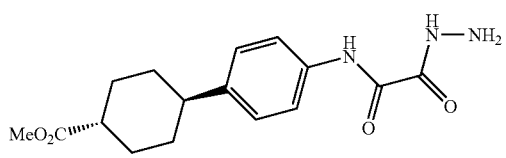

i) Methyl trans-4-phenylcyclohexanecarboxylate

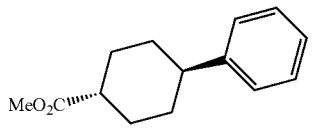

10% Palladium on carbon (1800 mg) was added to a solution of methyl trans-4-(4-chlorophenyl)cyclohexanecarboxylate (8670 mg) in EtOH (100 mL). The resulting suspension was stirred for 16 h under an atmosphere of hydrogen at 25 bar in a high pressure cell then was filtered through diatomaceous earth and concentrated in vacuo to give the title compound (6940 mg) as a solid; $^1$H NMR δ 7.30-7.11 (5H, m), 3.59 (3H, s), 2.53-2.30 (2H+ DMSO, m), 1.98 (2H, m), 1.82 (2H, m), 1.47 (4H, m); MS m/e M$^{-+}$ 218.

ii) Methyl trans-4-(4-{[methoxy(oxo)acetyl]amino}phenyl)cyclohexanecarboxylate

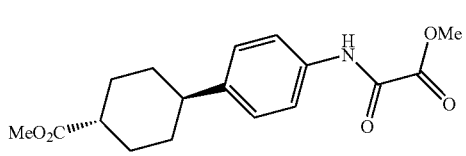

A mixture of 65% nitric acid (6.2 mL) and 95% sulphuric acid (7.8 mL) in carbon tetrachloride (10 mL) was added dropwise to a solution of methyl trans-4-phenylcyclohexanecarboxylate (6940 mg) keeping the internal temperature below 5° C. The mixture was allowed to warm and stirred for 16 h. Ice/water (50 mL) was added and the mixture was extracted with DCM (2×75 mL). The extracts were combined, washed with brine (50 mL), dried and concentrated in vacuo to give an oil. This oil was chromatographed on an 80 g Biotage™ silica column, using a gradient of 0-20% EtOAc/hexane as the eluent to give crude methyl trans-4-(4-nitrophenyl)cyclohexanecarboxylate (4445 mg); MS m/e MH$^+$ 264.10% Pd/C (450 mg) was added to a solution of this material (4440 mg) in EtOAc (50 mL) and the suspension was stirred for 16 hours under an atmosphere of hydrogen then filtered through diatomaceous earth and concentrated in vacuo. The residue was purified by chromatography on an 80 g Biotage™ silica column using a gradient of 0-50% EtOAc/hexane as eluent to give crude methyl trans-4-(4-aminophenyl)cyclohexanecarboxylate (2900 mg). A solution of this material (2890 mg) and pyridine (1.67 mL) in DCM (50 mL) was cooled to 5° C. Methyl chloro(oxo)acetate (1.48 mL) was added and the solution was allowed to warm up with stirring for 16 h. Water (75 mL) was added and the mixture was extracted with DCM (2×75 mL). The extracts were combined, dried, and concentrated in vacuo to give a solid. This solid was purified by flash chromatography on 80 g Biotage™ silica column eluting with a gradient of 0-50% EtOAc/hexane to give the title compound (919 mg) as a solid; $^1$H NMR δ 10.66 (1H, s), 7.60 (2H, d), 7.20 (2H, d), 3.83 (3H, s), 3.60 (3H, s), 2.56-2.30 (2H+DMSO, m), 2.00 (2H, m), 1.80 (2H, m), 1.46 (4H, m); MS m/e MH$^+$ 320.

iii) Hydrazine hydrate (0.152 mL) was added to a stirred solution of methyl trans-4-(4-{[methoxy(oxo)acetyl]amino}phenyl)cyclohexanecarboxylate (913 mg) in EtOH (25 mL). The mixture was stirred for 2 hours. The precipitate was filtered off, washed with EtOH, and dried under vacuum to give the title compound (Intermediate 44, 277 mg) as a solid; $^1$HNMR δ 10.43 (1H, s), 7.67 (2H, d), 7.17 (2H, d), 4.52 (2H, s), 3.59 (3H, s), 2.53-2.33 (2H+DMSO, m), 1.97 (2H, m), 1.81 (2H, m), 1.46 (4H, m); MS m/e MH$^+$ 320.

Intermediate 45: (4-{4-[({5-[(2-Fluorophenyl)amino]-1,3,4-oxadiazol-2-yl}carbonyl)amino]phenyl}cyclohexyl)acetic acid The starting material (4-{4-[({5-[(2-fluorophenyl)amino]-1,3,4-oxadiazol-2-yl}carbonyl)amino]phenyl}cyclohexyl)acetic acid for Example 119 was a ca. 2:1 trans:cis isomeric mixture and it was prepared in an analogous manner to that described for the pure trans isomer (Example 118) except that the starting material was ethyl (4-phenylcyclohexyl)acetate and it was a mixture of cis/trans isomers, prepared as described in Patent Application WO2004/047755.

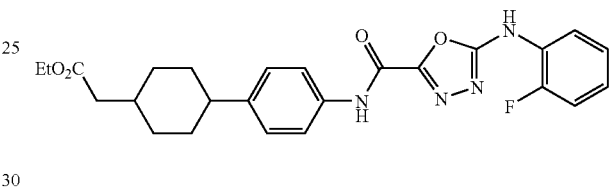

Intermediate 46: 2-Hydrazino-2-oxo-N-(3-phenoxypropyl)acetamide

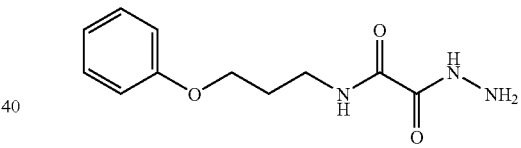

i) Methyl chloro(oxo)acetate (1.77 mL) was added to a stirred solution of (3-phenoxypropyl)amine hydrochloride (3000 mg) and pyridine (2.98 mL) in DCM (100 mL) at 0° C. After the addition was complete the solution was allowed to warm to ambient temperature and stirred for 16 hours. Water (50 mL) was added and the mixture was extracted with DCM (2×75 mL). The organic extracts were combined, washed with brine (50 mL), dried and concentrated in vacuo to give an oil. This was purified by flash chromatography on a 90 g Biotage™ silica column using a gradient of 10-60% EtOAc in hexane as the eluent to give methyl oxo[(3-phenoxypropyl)amino]acetate (3212 mg) as a solid; $^1$H NMR δ (CDCl$_3$) 7.60 (1H, bs), 7.28 (2H+CHCl$_3$, m), 6.94 (3H, m), 4.07 (2H, t), 3.90 (3H, s), 3.58 (2H, quartet), 2.08 (2H, m), +0.1 mole of EtOAc; MS m/e MH$^+$ 238.

ii) Hydrazine monohydrate (6.3 mL) was added to a stirred suspension of methyl oxo[(3-phenoxypropyl)amino]acetate (3080 mg) in ethanol (50 mL). The reaction mixture was heated to 85° C. for 3 hours then allowed to cool. The precipitate was filtered off, washed with Et$_2$O and dried under vacuum, to give the title compound (Intermediate 46, 2.269 g) as a solid; $^1$H NMR δ 9.95 (1H, s), 8.77 (1H, s), 7.28 (2H, m), 6.92 (3H, m), 4.50 (2H, s), 3.99 (2H, t), 3.30 (2H+H$_2$O, m), 1.94 (2H, t); MS m/e MNa$^+$ 260.

Intermediate 47:
N-(4-Cyclohexylphenyl)-2-hydrazino-2-oxoacetamide

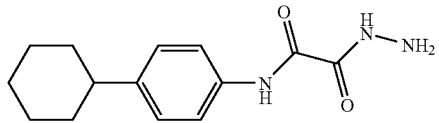

i) Methyl chloro(oxo)acetate (1.88 mL) was added to a stirred solution of 4-cyclohexylaniline (2980 mg) and pyridine (1.80 mL) in DCM (100 mL) at 0° C. After the addition was complete allowed to warm to ambient temperature and stirred for 16 hours. Water (50 mL) added. Extracted with DCM (2×75 mL). The organics were combined washed with brine (50 mL), dried over MgSO$_4$ and concentrated in vacuo to give methyl [(4-cyclohexylphenyl)amino](oxo)acetate (4133 mg) as a solid; $^1$H NMR δ 10.66 (1H, s), 7.60 (2H, d), 7.19 (2H, d), 3.84 (3H, s), 2.50 (1H+DMSO, m), 1.84-2.65 (5H, m), 1.46-1.14 (5H, m); MS m/e M–H$^-$ 260.

ii) Hydrazine monohydrate (7.40 mL) was added to a stirred suspension of methyl [(4-cyclohexylphenyl)amino] (oxo)acetate (3990 mg) in ethanol (50 mL) at ambient temperature. The reaction was heated to 85° C. and allowed to stir for a further 3 hours. Allowed to cool to ambient temperature overnight. The precipitate was filtered off, washed with Et$_2$O and dried under vacuum, to give the title compound (Intermediate 47, 3750 mg) as a solid; $^1$H NMR δ10.42 (1H, s), 10.17 (1H, s), 7.68 (2H, d), 7.16 (2H, d), 4.58 (1H, s), 2.48 (1H+DMSO, m), 1.89-1.65 (5H, m), 1.46-1.13 (5H, m); MS m/e M–H$^-$ 260.

Intermediate 48:
O-(Pentafluorophenyl)(3-ethoxyphenyl)thiocarbamate

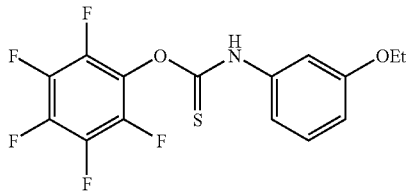

A solution of pentafluorophenylchlorothioformate (4.0 mL 24.9 mmol) in dichloromethane (10 mL) was added dropwise to a stirred, ice-cooled solution of 3-ethoxyaniline (3.02 mL, 22.65 mmol) and pyridine (1.33 mL, 37.4 mmol) in dichloromethane (250 mL). The mixture was allowed to reach room temperature and stirred for a further 14 h. The mixture was washed with 1M aqueous citric acid (100 mL), saturated aqueous NaHCO$_3$ (100 mL) and water (100 mL) then dried. Volatile material was removed by evaporation to give an oil that was purified by flash chromatography on SiO$_2$ eluting with isohexane to give the title compound (6.2 g) as an oil; $^1$H NMR (CDCl$_3$) δ 7.28-7.17 (1H, m), 6.84-6.76 (2H, m), 6.75-6.69 (1H, m), 4.01 (2H, q), 1.41 (3H, t).

Intermediate 49: 5-(Biphenyl-3-yl{[2-(trimethylsilyl)ethoxy]methyl}amino)-N-(6-morpholin-4-ylpyridin-3-yl)-N-{[2-(trimethylsilyl)ethoxy]methyl}-1,3,4-oxadiazole-2-carboxamide

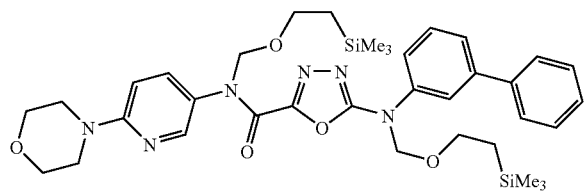

(i) 5-((3-Iodophenyl){[2-(trimethylsilyl)ethoxy]methyl}amino)-N-(6-morpholin-4-ylpyridin-3-yl)-N-{[2-(trimethylsilyl)ethoxy]methyl}-1,3,4-oxadiazole-2-carboxamide

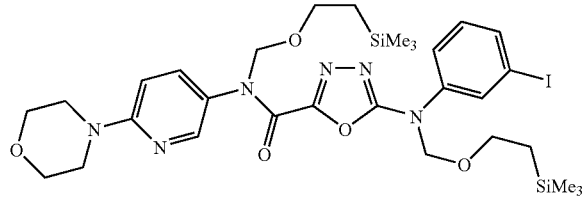

5-[(3-Iodophenyl)amino]-N-(6-morpholin-4-ylpyridin-3-yl)-1,3,4-oxadiazole-2-carboxamide (Example 146) (610 mg, 1.24 mmol) was added portionwise to an ice-cooled suspension of sodium hydride (60% dispersion in oil) (119 mg, 2.97 mmol) in anhydrous DMF (5 mL) in dry glassware. The mixture was stirred at 0° C. for 10 minutes and ambient temperature for 30 minutes then recooled in an ice bath and [2-(chloromethoxy)ethyl](trimethyl)silane (0.482 mL, 2.73 mmol) was added dropwise. The mixture was allowed to warm up and stirred for 16 h. ether (60 mL) was added, and the mixture was washed with water (3×20 mL) and the aqueous extracts were re-extracted with ether (20 mL). The organic extracts were combined, dried and concentrated by evaporation and the residue was purified by chromatography, eluting with 0-20% ether/DCM to give the title compound (610 mg, 65%) as gum; $^1$H NMR δ 8.09 (1H, s), 7.94 (1H, s), 7.74 (1H, d), 7.59-7.40 (2H, m), 7.28 (1H, t), 6.86 (1H, d), 5.24-5.11 (1H, m), 3.80-3.48 (12H, m), 0.98-0.84 (4H, m), 0.10-0.05 (18H, m).

(ii) Potassium phosphate (214 mg, 1.01 mmol) was added to 5-((3-iodophenyl){[2-(trimethylsilyl)ethoxy]methyl}amino)-N-(6-morpholin-4-ylpyridin-3-yl)-N-{[2-(trimethylsilyl)ethoxy]methyl}-1,3,4-oxadiazole-2-carboxamide (190 mg, 0.25 mmol) and phenylboronic acid (37 mg, 0.30 mmol) in DMF (3 mL) and the mixture was degassed. Tetrakis(triphenylphosphine)palladium (29 mg, 0.03 mmol) was added and the mixture was heated to 80° C. for 90 minutes. Phenylboronic acid (8 mg, 0.06 mmol) and tetrakis(triphenylphosphine)palladium (10 mg, 0.01 mmol) was added, the mixture degassed and heated to 80° C. for 240 minutes. The mixture was cooled, diluted with ether (60 mL) and washed with water (3×20 mL). The aqueous layers were re-extracted with ether (20 mL) and the organic layers were combined, dried and concentrated by evaporation. The residue was purified by chromatography, eluting with 0-20% ether/DCM to give the title compound (Intermediate 49, 149 mg, 84%) as a gum; $^1$H NMR δ 8.09 (1H, s), 7.83-7.66 (4H, m), 7.66-7.37 (6H, m), 6.86 (1H, d), 5.37 (2H, s), 5.19 (2H, s), 3.79-3.62 (8H, m), 3.55-3.49 (4H, m), 0.93 (4H, t), 0.06 (9H, s), 0.01 (9H, s).

Intermediates 50-57

The following intermediates were prepared by the general procedure of intermediate 1 (Method D3) using intermediates as indicated in the table, anilines known in the literature as referenced or commercially available anilines.

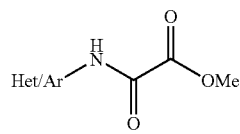

| Int. | Het/Ar | $^1$H NMR δ | MS m/e MH$^+$ | SM |
|---|---|---|---|---|
| 50 | 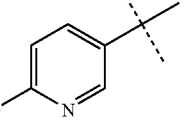 | 8.48 (1H, d), 8.0 (1H, dd), 6.8 (1H, d), 3.81 (3H, s), 3.83 (3H, s). | 211 | Purchased |
| 51 |  | 10.55 (1H, s), 7.57 (2H, d), 6.90 (2H, d), 3.82 (3H, s), 3.72-3.60 (2H, m), 3.56-3.48 (2H, m), 2.20 (2H, t), 1.13 (6H, d) | 293 | Int. 67 |
| 52 |  | 10.45 (1H, s), 7.51 (2H, dd), 6.75-6.66 (2H, m), 3.81 (3H, s), 3.67-3.42 (6H, m), 3.36-3.23 (2H, m), 1.98-1.71 (5H, m) | 320 | Int. 69 |
| 53 | 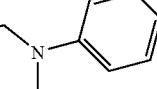 | | MH$^+$ – C$_4$H$_8$: 365 | Int. 72 |
| 54 | 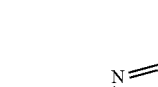 | | 251 | Purchased |
| 55 | 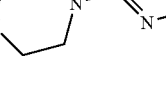 | 10.68 (1H, s), 8.40 (1H, s), 7.80 (1H, d), 6.80 (1H, d), 3.85 (3H, s), 3.90-3.80 (4H, m), 2.60-2.50 (4H, m) | 282 | Lit.[1] |

-continued

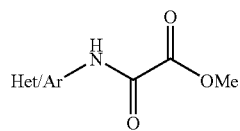

| Int. | Het/Ar | ¹H NMR δ | MS m/e MH⁺ | SM |
|---|---|---|---|---|
| 56 | (2-bromo-4-morpholinophenyl) | 10.08 (1H, s), 8.10 (1H, s), 7.70 (1H, d), 7.20 (1H, d), 3.85 (3H, s), 3.80-3.70 (4H, m), 2.95-2.85 (4H, m) | 345 | Int. 75 |
| 57 | (2-allyloxycarbonyl-4-morpholinophenyl) | 10.82 (1H, s), 8.10 (1H, s), 7.80 (1H, d), 7.10 (1H, d), 6.10-5.95 (1H, m), 5.40 (1H, d), 5.30 (1H, d), 4.70 (2H, d), 3.85 (3H, s), 3.80-3.70 (4H, m), 2.95-2.85 (4H, m) | 349 | Int. 76 |

¹6-Thiomorpholin-4-ylpyridin-3-amine, prepared as described in Patent Application WO02081-453.

Intermediates 58-66

The following intermediates were prepared by the general procedure of Intermediate 18 using Intermediates 50-57 or 74 and either methanol or ethanol as solvent.

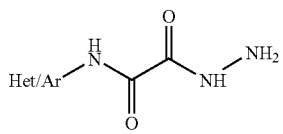

| Int. | Het/Ar | ¹H NMR δ | MS m/e MH⁺ | SM Int. |
|---|---|---|---|---|
| 58 | (6-methoxypyridin-3-yl) | 10.48 (1H, s), 8.50 (1H, s), 7.90 (1H, d), 6.90 (1H, d), 3.90-3.80 4H, m), 2.60-2.50 (1H, m) | 211 | 50 |
| 59 | (4-(2,6-dimethylmorpholino)phenyl) | 10.32 (1H, s), 7.63 (2H, d), 6.89 (2H, d), 4.65-4.39 (2H, m), 3.72-3.60 (3H, m), 3.52 (2H, d), 2.19 (2H, t), 1.13 (6H, d) | 293 | 51 |
| 60 | (4-(4-acetyl-1,4-diazepan-1-yl)phenyl) | 10.21 (1H, s), 10.07 (1H, s), 7.62-7.54 (2H, m), 6.69 (2H, dd), 4.54 (2H, s), 3.66-3.42 (6H, m), 3.34-3.24 (2H, m), 1.97-1.71 (5H, m) | 320 | 52 |

-continued
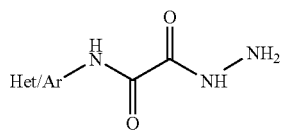
| Int. | Het/Ar | ¹H NMR δ | MS m/e MH⁺ | SM Int. |
|---|---|---|---|---|
| 61 | acetyl-piperazinyl-pyrimidine | 8.71 (2H, s), 3.76-3.62 (4H, m), 3.53-3.46 (4H, m), 2.02 (3H, s) | 308 | 71 |
| 62 | 2-methyl-benzothiazole | | 251 | 54 |
| 63 | methylsulfonyl-piperazinyl-pyridine | | 343 | 74 |
| 64 | thiomorpholinyl-pyridine | 10.48 (1H, s), 8.50 (1H, s), 7.90 (1H, d), 6.90 (1H, d), 3.90-3.80 4H, m), 2.60-2.50 (1H, m) | 282 | 55 |
| 65 | bromo-morpholinyl-phenyl | 10.65 (1H, s), 10.22 (1H, s), 8.10 (1H, s), 7.80 (1H, d), 7.20 (1H, d), 4.6 (2H, s), 3.80-3.70 (4H, m), 2.95-2.85 (4H, m) | 345 | 56 |
| 66 | allyloxycarbonyl-morpholinyl-pyridine | 10.65 (1H, s), 10.20 (1H, s), 8.20 (1H, s), 7.85 (1H, d), 7.10 (1H, d), 6.10-5.95 (1H, m), 5.40 (1H, d), 5.30 (1H, d), 4.70 (2H, d), 4.60-4.55 (2H, m), 3.80-3.70 (4H, m), 2.95-2.85 (4H, m) | 349 | 57 |

Intermediate 67:
4-[cis-2,6-dimethylmorpholin-4-yl]aniline

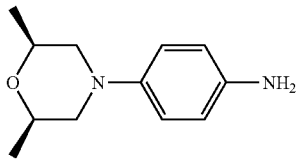

A mixture of cis-2,6-dimethyl-4-(4-nitrophenyl)morpholine (Intermediate 68, 8.0 g) and 10% palladium on carbon (800 mg) in ethanol (100 mL) was stirred under an atmosphere of hydrogen at 50° C. for 6 h. The mixture was filtered and the filtrate was concentrated by evaporation to give the title compound (4.3 g, 100%) as an oil which subsequently solidified; $^1$H NMR δ (CDCl$_3$): 6.79 (2H, d), 6.65 (2H, d), 3.81 (2H, m), 3.25 (2H, d), 2.33, (2H, t), 1.23 (6H, d); MS m/e MH$^+$: 207.

Intermediate 68:
cis-2,6-Dimethyl-4-(4-nitrophenyl)morpholine

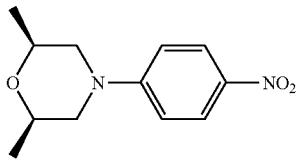

1-Fluoro-4-nitrobenzene (4.9 g, 34.75 mmol) was added to a stirred mixture of cis-2,6-dimethylmorpholine (44.4 g, 38.26 mmol) and anhydrous potassium carbonate (2.5 g, 18.12 mmol) in acetonitrile (50 mL). The mixture was heated under reflux for 19 h, cooled, filtered and the solid washed with acetonitrile. The filtrate was concentrated by evaporation to give the title compound (8.1 g, 99%) as a solid; $^1$H NMR δ (CDCl$_3$): 8.13 (2H, d), 6.82 (2H, d), 3.76 (2H, m), 3.66 (2H, dt), 2.61 (2H, t), 1.28 (6H, d); MS m/e MH$^+$: 237.

Intermediate 69:
[4-(4-acetyl-1,4-diazepan-1-yl)phenyl]amine

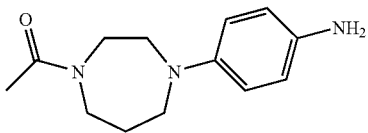

Following the general procedure of Intermediate 36 but using 1-acetyl-4-(4-nitrophenyl)-1,4-diazepane (Intermediate 70) as starting material there was thus obtained the title compound in 97% yield; $^1$H NMR δ: 6.55-6.46 (4H, m), 4.30 (2H, br s), 3.59-3.48 (3H, m), 3.41-3.26 (5H, m), 1.99-1.72 (5H, m); MS m/e MH$^+$: 234.

Intermediate 70:
1-Acetyl-4-(4-nitrophenyl)-1,4-diazepane

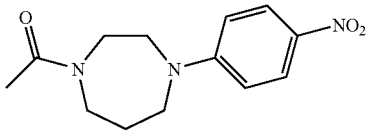

N-Acetylhomopiperazine (7.2 mL, 54.6 mmol) and DIPEA (12.3 mL, 74.4 mmol) were added to a stirred solution of 4-fluoronitrobenzene (7.0 g, 49.6 mmol) acetonitrile (100 mL) and the mixture was heated to 80° C. under nitrogen with stirring for 16 h. Volatile material was removed by evaporation and the residue was dissolved in EtOAc (150 mL) and water (150 mL) was added. The organic layer was separated and the aqueous layer was extracted again with EtOAc (2×150 mL). The organic layers were combined and dried, concentrated by evaporation then the residue was triturated with isohexane to give the title compound (5.6 g, 53%) as a solid; $^1$H NMR δ 8.01 (2H, qd), 6.92-6.82 (2H, m), 3.80 (1H, t), 3.70-3.56 (5H, m), 3.35 (2H, dt), 1.97-1.71 (5H, m); MS m/e MH$^+$: 264.

Intermediate 71: Methyl {[2-(4-acetylpiperazin-1-yl)pyrimidin-5-yl]amino}(oxo)acetate

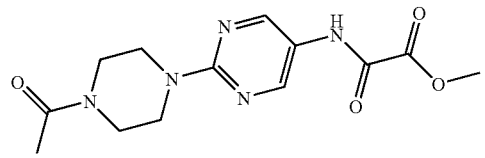

A solution of tert-Butyl-4-(5-{[methoxy(oxo)acetyl]amino}pyrimidin-2-yl)piperazine 1-carboxylate (Intermediate 53; 4.14 g, 11.33 mmol) in a 4M solution of HCl in dioxane (40 mL) was stirred for 16 h. The precipitate was collected by filtration and washed with ether to give N-(5-{[methoxy(oxo)acetyl]amino}pyrimidin-2-yl)piperazine hydrochloride as a solid. Pyridine (9.16 mL, 113.30 mmol), followed by acetyl chloride (0.97 mL, 13.60 mmol) were added to an ice-cooled suspension of this solid (3.4 g) in DCM (100 mL) and the mixture was allowed to warm to ambient temperature and stirred for 1 h. Water (100 mL) was added and the mixture was extracted with DCM (3×100 mL). The organic extracts were combined, dried and concentrated by evaporation. The residue was triturated with isohexane to give the title compound (2.45 g, 70%) as a solid; $^1$H NMR δ: 10.79 (1H, s), 8.65 (2H, s), 3.84 (3H, s), 3.75-3.65 (4H, m), 3.52-3.45 (4H, m), 2.04 (3H, s); MS m/e MH$^+$: 308.

Intermediate 72: tert-Butyl 4-(5-aminopyrimidin-2-yl)piperazine-1-carboxylate

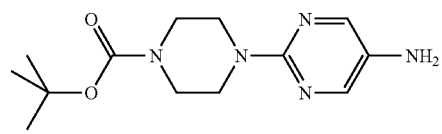

Bis(dibenzylideneacetone)palladium (0.17 g, 0.29 mmol) was added to a mixture of tert-butyl 4-(5-bromopyrimidin-2-yl)piperazine-1-carboxylate (6.15 g, 17.92 mmol, prepared as described in Patent Application WO 2001087870), sodium tert-butoxide (2.41 g, 25.09 mmol), benzophenone imine (3.61 g, 21.50 mmol), and BINAP (0.34 g, 21.5 mmol) in anhydrous toluene (150 mL). The mixture was heated to 80° C. and stirred for 16 h under an atmosphere of nitrogen. The mixture was diluted with EtOAc (100 mL) and filtered through diatomaceous earth then concentrated by evaporation to give an oil. This intermediate was stirred together with THF (150 mL) and 2N 1HCl (100 mL) for 2 h. The mixture was then neutralised by the addition of saturated aqueous sodium hydrogen carbonate solution and the mixture was extracted with EtOAc (3×100 mL). The organic extracts were dried, filtered, concentrated by evaporation and triturated with hexane to give the title compound as a solid (4.6 g, 92%); $^1$H NMR δ: 7.90 (2H, s), 4.61 (2H, s), 3.51-3.45 (4H, m), 3.40-3.30 (4H, m), 1.20 (9H, s); MS m/e MH$^+$: 280.

Intermediate 73: 5-[(2-Fluorophenyl)amino]-N-(4-piperazin-1-Ylphenyl)-1,3,4-oxadiazole-2-carboxamide

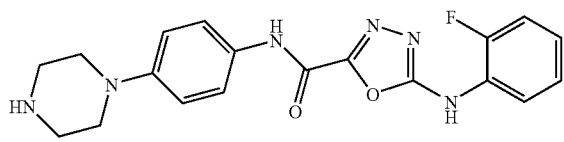

Following the general procedure of Intermediate 41 but using Example 80 as starting material in place of Example 78 there was thus obtained the title compound in 69% yield; $^1$H NMR δ 10.88 (1H, s), 9.40 (1H, s), 8.00 (1H, t), 7.60 (2H, d), 7.35-7.10 (3H, m), 7.00 (2H, d), 3.40-3.30 (4H, m), 3.20-3.10 (4H, m); MS m/e MH$^+$ 383.

This compound is a compound of formula (I) and so forms part of the invention.

Intermediate 74: Methyl ({6-[4-(methylsulfonyl)piperazin-1-yl]pyridin-3-yl}amino)(oxo)acetate

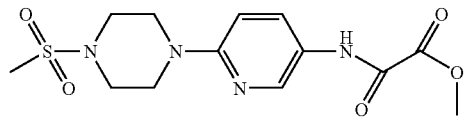

A solution of tert-butyl 4-(5-{[methoxy(oxo)acetyl]amino}pyridin-2-yl)piperazine-1-carboxylate (Intermediate 16, 4 g, 11 mmol) in 4N HCl/dioxan (25 mL) was stood for 16 h then concentrated by evaporation. The residue was dissolved in a mixture of DMF (20 mL) and pyridine (7 mL) then methanesulphonyl chloride (1.28 mL, 16.48 mmol) was added. The mixture was stirred for 3 hours then was diluted with water (50 mL) and extracted with dichloromethane (2×100 mL). The organic extracts were dried and concentrated by evaporation to give the title compound as a solid that was used without further purification; MS m/e MH$^+$ 343.

Intermediate 75: (3-bromo-4-morpholin-4-ylphenyl)amine

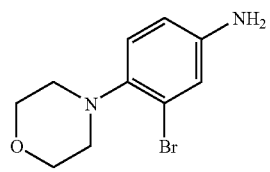

i) 4-(2-bromo-4-nitrophenyl)morpholine

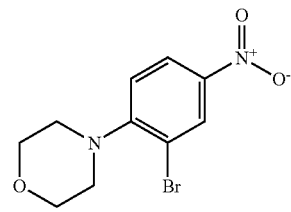

Morpholine (7.92 mL, 90.9 mmol) was added to a solution of 2-bromo-1-fluoro-4-nitrobenzene (10 g, 45.5 mmol) in acetonitrile (100 mL) and the mixture was heated under reflux for 6 h. Volatile material was removed by evaporation and the residue was diluted with water (100 mL) then extracted with ethyl acetate (2×100 mL). The organic extracts were combined, dried and concentrated to give the title compound (12.9 g, 99%) as a solid; $^1$H NMR δ 8.40 (1H, s), 8.20 (1H, d), 7.10 (1H, d), 3.80-3.70 (4H, m), 3.20-3.10 (4H, m); MS m/e MH$^+$ 287.

ii) Following the general procedure of Intermediate 36 but using 4-(2-bromo-4-nitrophenyl)morpholine as starting material and allowing 5 h for hydrogenation and subsequently purifying by chromatography eluting with EtOAc/isohexane there was thus obtained the title compound (Intermediate 75) in 24% yield; $^1$H NMR δ 6.90 (1H, d), 6.80 (1H, s), 6.50 (1H, dd), 5.00 (2H, s), 5.40 (1H, d), 3.70-3.60 (4H, m), 2.80-2.70 (4H, m); MS m/e MH$^+$ 258.

Intermediate 76: Allyl 5-amino-2-morpholin-4-ylbenzoate

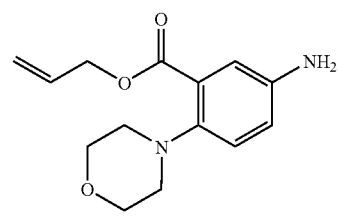

i) Allyl 2-morpholin-4-yl-5-nitrobenzoate

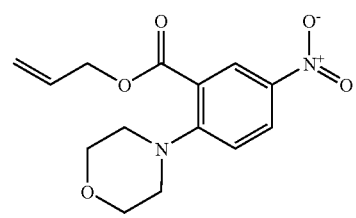

Morpholine (7.78 mL, 88.9 mmol) was added to a solution of 2-fluoro-5-nitrobenzoic acid allyl ester (prepared as described in WO 9315078; 10 g, 44.4 mmol) in acetonitrile (100 mL) and the mixture was heated under reflux for 6 h. Volatile material was removed by evaporation and the residue was diluted with water (100 mL) and extracted with EtOAc (2×100 mL). The organic layers were dried and concentrated by evaporation to give the title compound (12.87 g, 99%) as a viscous liquid; $^1$H NMR δ: 8.40(1H, s), 8.20 (1H, d), 7.10 (1H, d), 6.10-5.95 (1H, m), 5.40 (1H, d), 5.30 (1H, d), 4.80 (2H, s), 3.70-3.60 (4H, m), 3.20-3.10 (4H, m); MS m/e MH 293.

ii) Tin(II) chloride dihydrate (17.37 g, 77 mmol) was added to a solution of allyl 2-morpholin-4-yl-5-nitrobenzoate (11.24 g, 38.5 mmol) in EtOAc (250 mL) and the mixture was stirred and heated under reflux for 4 h. Ethanol (150 mL) was added, followed by another portion of Tin(II) chloride dihydrate (17.4 g) and the mixture was heated for another 2 h. The mixture was cooled and filtered then the filtrate was washed repeatedly with aqueous ammonium hydroxide and re-filtered. The organic layer was dried and concentrated by evaporation to give the title compound (Intermediate 76, 5.42 g, 54%) as a solid; $^1$H NMR δ 6.90 (1H, d), 6.80 (1H, s), 6.70 (1H, d), 6.10-5.95 (1H, m), 5.40 (1H, d), 5.30 (1H, d), 5.00 (2H, s), 4.80 (2H, s), 3.70-3.60 (4H, m), 3.20-3.10 (4H, m); MS m/e MH$^+$ 263.

Intermediate 77: Methyl [1-(5-{[hydrazine(oxo)acetyl]amino}pyridin-2-yl)piperidin-4-yl]acetate

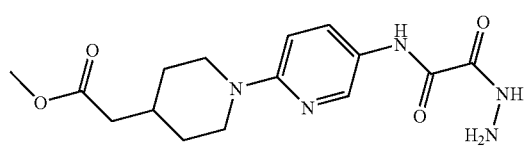

i) Methyl [1-(5-nitropyridin-2-yl)piperidin-4-yl]acetate

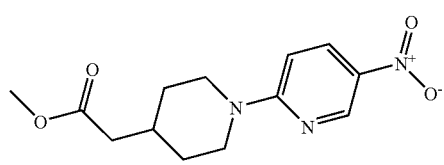

A mixture of 2-Chloro-5-nitropyridine (1.59 g, 10 mmol) and methyl piperidin-4-ylacetate hydrochloride (1.8 g, 10 mmol) (prepared as described in Patent Application WO 2000029407) in DMA (50 mL) was treated with 2-tert-butyl-imino-2-diethylamino-1,3-dimethyl-perhydro-1,3,2-diaza-phosphorine (BEMP) (15 g of a 2.2 mmol/g loading on polystyrene support, 33 mmol). The resulting mixture was stirred for 2.5 h then filtered through diatomaceous earth. Volatile material was removed by evaporation to give the title compound (740 mg, 21%) as a solid; $^1$H NMR δ 1.08-1.28 (2H, m), 1.77 (2H, d), 1.99-2.12 (1H, m), 2.29 (2H, d), 3.07 (2H, t), 3.60 (3H, s), 4.51 (2H, d), 6.94 (1H, d), 8.13-8.25 (1H, m), 8.95 (d, 1H); MS m/e MH$^+$ 280.

ii) Methyl [1-(5-aminopyridin-2-yl)piperidine-4-yl]acetate

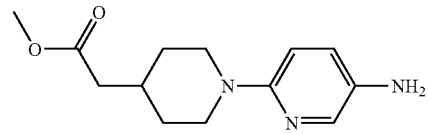

A solution of methyl [1-(5-nitropyridin-2-yl)piperidin-4-yl]acetate (710 mg, 2.60 mmol) in EtOH (26 mL) was treated with 10% Pd on charcoal (71 mg), and stirred vigorously under an atmosphere of hydrogen for 4 h. The reaction mixture was filtered through diatomaceous earth and the filtrate was evaporated to dryness to give the title compound (556 mg, 70%) as an oil; $^1$H NMR δ 1.12-1.27 (2H, m), 1.67 (2H, d), 1.75-1.89 (1H, m), 2.25 (2H, d), 2.56 (2H, t), 3.33 (2H, s), 3.58 (3H, s), 4.52 (2H, s), 6.61 (1H, d), 6.86-6.93 (1H, m), 7.58 (1H, d); MS m/e MH$^+$ 250.

iii) Following the general procedure described for Intermediate 47 there was thus obtained, from the first step following chromatography eluting with 0-50% EtOAc/isohexane, ({6-[4-(2-Methoxy-2-oxoethyl)piperidin-1-yl]pyridin-3-yl}amino)(oxo)acetate (in 97% yield) as a solid; $^1$H NMR δ 1.09-1.26 (2H, m), 1.69 (2H, d), 1.84-2.00 (1H, m), 2.29 (2H, d), 2.71-2.86 (2H, m), 3.58 (3H, s), 3.80 (3H, s), 4.14-4.28 (2H, m), 6.84 (1H, d), 7.79-7.91 (1H, m), 8.42 (1H, d), 10.71 (1H, s); MS m/e MH$^+$ 336; and from the second step, the title compound (Intermediate 77, in 33% yield) as a solid; $^1$H NMR δ 1.11-1.23 (2H, m), 1.69 (2H, d), 1.84-2.00 (1H, m), 2.28 (2H, d), 2.70-2.85 (2H, m), 3.60 (3H, s), 4.22 (2H, d), 4.60 (2H, s), 6.82 (1H, d), 7.85-7.94 (1H, m), 8.49 (1H, d), 10.22 (1H, s), 10.51 (1H, s); MS m/e MH$^+$ 336.

Intermediate 78: Methyl [trans-4-(5-{[hydrazino(oxo)acetyl]amino}pyridin-2-yl)cyclohexyl]acetate

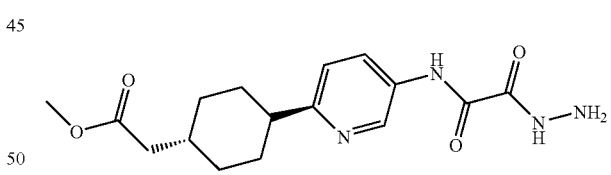

i) 1,4-Dioxaspiro[4.5]dec-7-en-8-yl trifluoromethanesulphonate

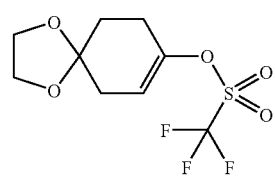

To a solution of diisopropylamine (10 mL, 67.61 mmol) in anhydrous THF (100 mL) cooled to −78° C. was added nBuLi (34 mL, 67.6 mmol, 2M solution in cyclohexane) and the reaction mixture was allowed to stir at −78° C. for 10 minutes. 1,4-Dioxaspiro[4.5]decan-8-one (9.60 g, 61.46 mmol) in anhydrous THF (100 mL) was added and the reaction mixture allowed to stir for 90 minutes at −78° C. A solution of N-phenyltrifluoromethanesulphonimide (25 g, 76.83 mmol) in anhydrous THF (100 mL) was added and the reaction mixture was allowed to warm slowly to ambient temperature overnight. The solvent was concentrated under reduced pressure and the residue was redissolved in ether (500 mL) and washed with 1M HCl (2×200 mL), 1M NaOH (2×200 mL) brine (200 mL). The organic phase was separated, dried (MgSO$_4$) and concentrated to leave crude product. The residue was columned on a 300 g silica Biotage cartridge loading in isohexane and eluting a gradient of isohexane—DCM 0-50% to leave a clear oil, 11.86 g (41.14 mmol, 67%): $^1$H NMR (CDCl$_3$) δ 1.89-1.91 (m, 2H), 1.90 (t, 2H), 2.52-2.56 (m, 2H), 3.99 (s, 4H), 5.66 (s, 1H)

ii) 8-(4,4,5,5-Tetramethyl-1,3,2-dioxaborolan-2-yl)-1,4-dioxaspiro[4.5]dec-7-ene

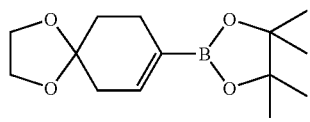

To a stirred solution of 1,4-dioxaspiro[4.5]dec-7-en-8-yl trifluoromethanesulphonate prepared as above (11.18 g, 38.79 mmol) in dry dioxane (200 mL) was added bis(pinacolato)diboron (10.8 g, 42.67 mmol), Pd(dppf)$_2$Cl$_2$DCM ([1,1'-bis(diphenylphosphino(ferrocene)]dichloropalladium(II), complex with DCM (1:1) (951 mg, 1.16 mmol), bis(diphenylphosphino)ferrocene (646 mg, 1.16 mmol) and potassium acetate (11.4 g, 0.116 mol). The reaction mixture was degassed by bubbling nitrogen through it for 15 minutes then heated to 80° C. for 3 hours. The reaction mixture was allowed to cool, the solvent removed and the residue was partitioned between EtOAc (200 mL) and water (200 mL), the organic phase was washed with brine (200 mL) and aqueous extracts were combined and reextracted with EtOAc (200 mL). The organic washings were combined, dried (MgSO$_4$) and concentrated under reduced pressure to leave an oil. This was dissolved in DCM-isohexane (1:1, 20 mL) and the filtrate purified on a 120 g SiliCycle cartridge, eluting with 50%-100% DCM/isohexane to give the title compound (8.4 g, 81%); $^1$H NMR (CDCl$_3$) δ 1.25 (s, 12H), 1.71-1.75 (m, 2H), 2.34-2.37 (m, 4H), 3.98 (s, 4H), 6.48 (s, 1H); GCMS EI 266 M+.

iii) 2-(1,4-Dioxaspiro[4.5]dec-7-en-8-yl)-5-nitropyridine

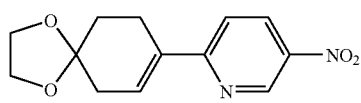

A stirred solution of 8-(4,4,5,5-tetramethyl-1,3,2-dioxaborolan-2-yl)-1,4-dioxaspiro[4.5]dec-7-ene prepared as above (8.40 g, 31.56 mmol), 2-bromo-5-nitropyridine (6.0 g, 29.55 mmol) in DME (200 mL), degassed 2M potassium carbonate (40 mL) was added palladium tetrakis(triphenylphosphine) (Pd(PPh$_3$)$_4$; 1.8 g, 1.58 mmol). The reaction mixture was evacuated with nitrogen (3 cycles) and allowed to stir under vacuum for 5 minutes, then heated to 80° C. overnight. The reaction mixture was allowed to cool to ambient temperature, EtOAc (200 mL) was added followed by water (200 mL), the suspension was filtered and the organic phase was separated and the aqueous layer re-extracted into EtOAc (200 mL). The organic extracts were combined, washed with brine (200 mL), dried (MgSO$_4$) and concentrated to leave crude product. DCM was added and the suspension was filtered and dried to leave the title compound (1.64 g). The filtrate was concentrated after the addition of DCM a further 1.51 g of product was obtained, the filtrate was purified on a 120 g SiliCycle cartridge eluting 20-50-70% EtOAc in isohexane to provide 1.72 g of product. Total yield is 4.85 g (18.51 mmol, 58%);
$^1$H NMR (CDCl$_3$) δ 1.96 (t, 2H), 2.57-2.58 (m, 2H), 2.79-2.83 (m, 2H), 4.03 (s, 4H), 6.85-6.88 (m, 1H), 7.53 (d, 1H), 8.39 (d, 1H), 9.35 (s, 1H); GCMS 263 MH+.

iv) 6-(1,4-Dioxaspiro[4.5]dec-8-yl)pyridin-3-amine

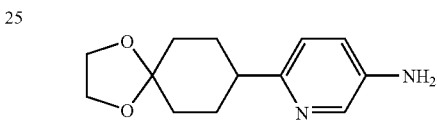

Wet 50% palladium on carbon (750 mg) was added to a solution of 2-(1,4-dioxaspiro[4.5]dec-7-en-8-yl)-5-nitropyridine (3.96 g, 15.11 mmol), prepared as above, in MeOH (500 mL). The reaction mixture was deoxygenated by evacuation and placed under an atmosphere of hydrogen (5 cycles) then stirred for 16 h. The mixture was filtered, and the filtrate concentrated to give the title compound (3.10 g, 87%) as a solid;
$^1$H NMR (CDCl$_3$) δ 1.68-1.96 (m, 8H), 2.63-2.70 (m, 1H), 3.97 (s, 4H), 3.97 (s, 2H), 6.93-7.00 (m, 2H), 8.03 (s, 1H); MS m/e MH+ 235.

v) Benzyl [6-(1,4-dioxaspiro[4.5]dec-8-yl)pyridin-3-yl]carbamate

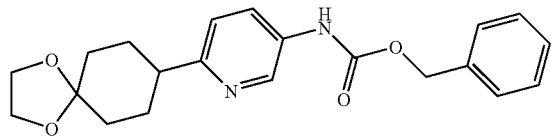

To an ice water cooled solution of 6-(1,4-dioxaspiro[4.5]dec-8-yl)pyridin-3-amine (3.08 g, 13.15 mmol), prepared as above, in THF (50 mL) was added pyridine (3.19 mL, 39.44 mmol) followed by benzyl chloroformate (1.9 mL, 13.15 mmol). The resulting suspension was allowed to stir at 0° C., then after 2 hrs a further 0.5 mL of benzyl chloroformate was added and reaction mixture was allowed to stir at ambient temperature overnight. It was partitioned between EtOAc (100 mL) and water (50 mL), the organic phase was separated and the aqueous phase re extracted into EtOAc (200 mL). The organic extracts were combined, dried and concentrated to leave crude product. This was purified on a 120 g silica SiliCycle cartridge, eluting with 30-50% EtOAc/isohexane using an Isco Companion, to provide the title compound (4.94 g, 100%); $^1$H NMR (CDCl$_3$) δ 1.66-1.97 (m, 8H), 2.70-2.77 (m, 1H), 3.97 (s, 4H), 5.21 (s, 2H), 6.71 (s, 1H), 7.16 (d, 1H), 7.35-7.41 (m, 5H), 7.91 (s, 1H), 8.37 (s, 1H); MS m/e MH$^+$ 369.

vi) Benzyl [6-(4-oxocyclohexyl)pyridin-3-yl]carbamate

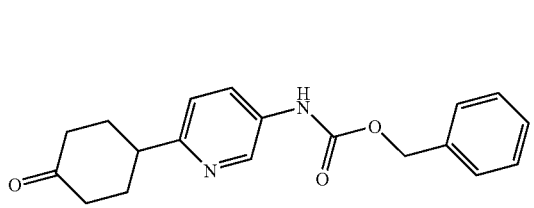

To an ice water cooled solution of benzyl [6-(1,4-dioxaspiro[4.5]dec-8-yl)pyridin-3-yl]carbamate, prepared as above, (4.94 g, 13.41 mmol) was added TFA (20 mL) followed by water (1.1 mL). The reaction mixture was allowed to stir at ambient temperature for 2 hours. It was treated with 2M NaOH to adjust the pH to 10 and then the mixture was extracted into EtOAc (3×200 mL), the organic phase was separated, dried (MgSO$_4$) and concentrated to leave a gum, 4.05 g (12.26 mmol, 93%) which was used directly in the next stage; $^1$H NMR (CDCl$_3$) δ 1.97-2.10 (m, 2H), 2.24-2.29 (m, 2H), 2.49-2.53 (m, 4H), 3.13-3.21 (m, 1H), 5.22 (s, 2H), 6.82 (s, 1H), 7.18 (d, 1H), 7.36-7.40 (m, 5H), 7.96 (s, 1H), 8.41 (s, 1H); MS m/e MH$^+$ 325.

vii) Methyl [4-(5-{[(benzyloxy)carbonyl]amino}pyridin-2-yl)cyclohexylidene]acetate

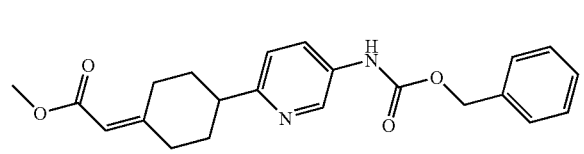

To an ice water cooled suspension of a 60% mineral oil dispersion of sodium hydride (585 mg, 24.35 mmol) in anhydrous THF (60 mL) was added trimethylphosphonoacetate (3.1 mL, 18.73 mmol). After 10 minutes a solution of benzyl [6-(4-oxocyclohexyl)pyridin-3-yl]carbamate, prepared as above, (4.05 g, 12.49 mmol) in THF (40 mL) was added and the reaction mixture allowed to warm to ambient temperature over the weekend. Water (100 mL) was added and the volatile material was removed under reduced pressure and the mixture extracted into EtOAc (4×200 mL) the organic extracts were combined, washed with brine (50 mL), dried (MgSO$_4$) and concentrated under reduced pressure to leave crude product. This was purified on a 120 g silica SiliCycle cartridge, loading in and eluting 30-50% EtOAc/isohexane to provide the title compound (3.17 g, 66.7%); $^1$H NMR (CDCl$_3$) δ 1.63-1.76 (m, 2H), 2.03-2.15 (m, 3H), 2.31-2.44 (m, 2H), 2.92-2.97 (m, 1H), 3.69 (s, 3H), 3.92-3.96 (m, 1H), 5.21 (s, 2H), 5.68 (s, 1H), 6.71 (s, 1H), 7.12 (d, 1H), 7.35-7.40 (m, 5H), 8.37 (s, 1H), 8.37 (s, 1H); MS m/e MH$^+$ 381.

viii) Methyl [trans-4-(5-aminopyridin-2-yl)cyclohexyl]acetate hydrochloride salt

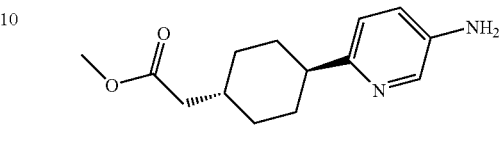

To a stirred solution of methyl [4-(5-{[(benzyloxy)carbonyl]amino}pyridin-2-yl)cyclohexylidene]acetate, prepared as above, (3.17 g, 8.33 mmol) in methanol (200 mL) was added 50% wet Palladium on carbon (1.0 g), deoxygenated by evacuation and placed under an atmosphere of hydrogen (5 cycles) then stirred for 16 h. The mixture was filtered and the filtrate concentrated to give a gum (2.05 g). The residue was dissolved in DCM/ether (40 mL of a 1:1 mixture) and HCl (8.5 mL of a 2M solution in ether) was added with stirring. The suspension was allowed to stir at ambient temperature and concentrated to provide the salt as a white solid. This was recrystallised from absolute ethanol-ether to provide the title compound (1.10 g, 54%) as a solid; $^1$H NMR δ 1.07-1.21 (m, 2H), 1.52-1.62 (m, 2H), 1.72-1.88 (m, 5H), 2.27 (d, 2H), 2.74-2.81 (m, 1H), 3.61 (s, 3H), 7.59-7.59 (m, 2H), 7.87 (d, 1H); MS m/e MH$^+$ 249.

ix) Methyl ({6-[trans-4-(2-methoxy-2-oxoethyl)cyclohexyl]pyridin-3-yl}amino)(oxo)acetate

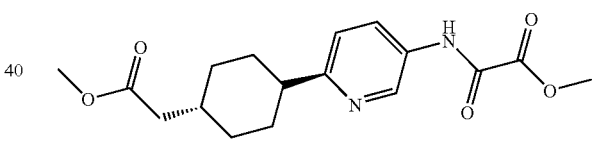

To an ice water cooled solution of methyl [trans-4-(5-aminopyridin-2-yl)cyclohexyl]acetate hydrochloride, prepared as above, (831 mg, 2.59 mmol) in DCM (50 mL) was added triethylamine (1.3 mL, 9.31 mmol) followed by methyl chlorooxoacetate (0.31 mL, 3.36 mmol) and the reaction mixture was allowed to stir at O—C for 2 hrs. The reaction mixture was diluted with DCM (100 mL) and washed with water (80 mL) then brine (80 mL) and the aqueous layer was re extracted with DCM (50 mL). The organic washings were combined, dried and concentrated to give the title compound, 865 mg (2.59 mmol, 100%) which was taken through to the next stage; $^1$H NMR (CDCl$_3$) δ 1.13-1.27 (m, 1H), 1.57-1.64 (m, 3H), 1.84-2.00 (m, 5H), 2.26 (d, 2H), 2.62-2.70 (m, 1H), 3.68 (s, 3H), 3.98 (s, 3H), 7.18 (d, 1H), 8.13 (d, 1H), 8.60 (s, 1H), 8.82 (brs, 1H); MS m/e MH$^+$ 335.

x) To a suspension of methyl ({6-[4-(2-methoxy-2-oxoethyl)cyclohexyl]pyridin-3-yl}amino)(oxo)acetate, prepared as above, (865 mg, 2.59 mmol) in absolute ethanol (50 mL) was added hydrazine monohydrate (0.15 mL, 3.09 mmol). A thick white suspension formed which was then allowed to stir at ambient temperature for ~1.5 hrs, filtered, washed with ether (2×20 mL) and then dried to give the title compound (Intermediate 78), 610 mg (1.82 mmol, 70%) as a solid; $^1$H NMR δ 1.09-1.21 (m, 2H), 1.47-1.56 (m, 2H), 1.71-1.87 (m, 5H), 2.25 (d, 2H), 2.54-2.63 (m, 1H), 3.60 (s, 3H), 4.62 (s, 2H), 7.24 (d, 1H), 8.07 (d, 1H), 8.85 (s, 1H), 10.27 (s, 1H) (not all NH protons seen); MS m/e MH+ 335.

Intermediate 79: tert-Butyl trans-4-(4-{[hydrazino(oxo)acetyl]amino}phenyl)cyclohexanecarboxylate

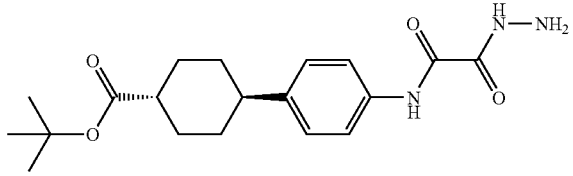

i) trans-4-Phenylcyclohexanecarboxylic acid

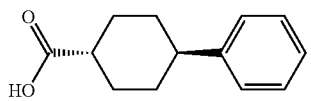

Palladium (10 wt. %) on carbon (50 g) and triethylamine (90 mL, 0.65 mol) were added sequentially, each in one portion, to a stirred solution of 4-(4-chlorophenyl)cyclohexanecarboxylic acid (150 g, 0.63 mol) in MeOH (1.5 L). The reaction mixture was stirred under a hydrogen atmosphere for 4 h at 50° C. at a pressure of 5 bar then cooled, filtered and then concentrated in vacuo to give the title compound (160 g, 83%) as a solid, which was contaminated with triethylamine hydrochloride (0.65 mol) and used with no further purification; $^1$H NMR δ 1.23 (9H, t), 1.44-1.53 (4H, m), 1.8-1.9 (2H, m), 1.96-2:05 (2H, m), 2.22-2.32 (1H, m), 2.45-2.58 (1H, m), 3.05 (6H, q), 7.1-7.35 (5H, m).

ii) trans-4-(4-Nitrophenyl)cyclohexanecarboxylic acid

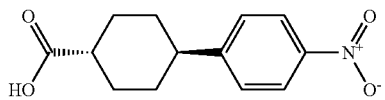

A mixture of concentrated sulphuric acid (1.5 mL) and concentrated nitric acid (0.9 mL) was added dropwise to a vigorously stirred solution of trans-4-phenylcyclohexanecarboxylic acid (1.7 g. 8.3 mmol) in nitrobenzene (4 mL) at 5° C. The reaction mixture was warmed to room temperature and stirred for 2.5 h and then poured onto ice. The aqueous mixture was extracted with DCM and the organic layer was concentrated in vacuo to leave a yellow oil, which crystallised to a white solid upon standing. The solid was triturated with toluene and filtered to give the title compound (600 mg, 60%) as a solid; $^1$H NMR δ 1.4-1.6 (4H, m), 1.75-1.9 (2H, m), 1.95-2.1 (2H, m), 2.2-2.38 (1H, m), 2.64-2.77 (1H, m), 7.52 (2H, d), 8.15 (2H, d); MS m/e (M–H)⁻ 248.

iii) tert-Butyl trans-4-(4-nitrophenyl)cyclohexanecarboxylate

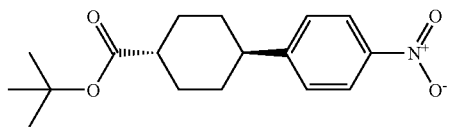

4-(Dimethylamino)pyridine (9.7 g, 80.2 mmol) and a solution of di-tert-butyl dicarbonate (17.5 g, 80.2 mmol) in DCM (5 mL) were added sequentially, each in one portion, to a mixture of trans-4-(4-nitrophenyl)cyclohexanecarboxylic acid (10 g, 40.1 mmol) in DCM (45 mL) at room temperature. The reaction was stirred for 16 h and then evaporated to leave a yellow oil. The oil was triturated with a mixture of isohexane:EtOAc (4:1) and filtered. The filtrate was concentrated in vacuo and purified by chromatography, eluting with 20-33% EtOAc in isohexane, to give the title compound as a waxy solid (4.3 g, 35%); $^1$H NMR δ 1.4 (9H, s), 1.4-1.6 (4H, m), 1.8-1.9 (2H, m), 1.95-2.05 (2H, m), 2.2-2.35 (1H, m), 2.65-2.75 (1H, m), 7.55 (2H, d), 8.18 (2H, d).

iv) tert-Butyl trans-4-(4-aminophenyl)cyclolhexancearboxylate

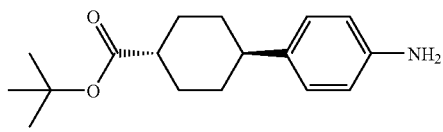

10% Palladium on charcoal (500 mg) was added in one portion to a stirred solution of tert-butyl trans-4-(4-nitrophenyl)cyclohexanecarboxylate (4.3 g, 14.1 mmol) in EtOAc (75 mL) and the mixture was stirred under a hydrogen atmosphere for 20 h. The mixture was filtered through a pad of diatomaceous earth and the filtrate was concentrated in vacuo to give the title compound (3.8 g, 98%) as a waxy solid; $^1$H NMR δ 1.4 (9H, s), 1.3-1.5 (4H, m), 1.7-1.8 (2H, m), 1.9-2.0 (2H, m), 2.15-2.25 (1H, m), 2.25-2.35 (1H, m), 4.75 (2H, s), 6.5 (2H, d), 6.85 (2H, d); MS m/e MH+ 276.

v) tert-Butyl trans-4-(4-{[methoxy(oxo)acetyl]amino}phenyl)cyclohexanecarboxylate

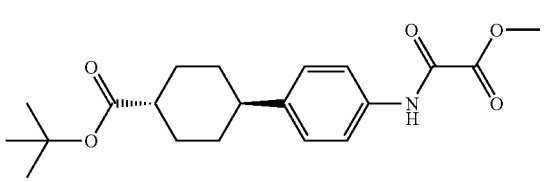

Methyl chlorooxoacetate (2.5 g, 20.7 mmol) was added dropwise to a mixture of tert-butyl trans-4-(4-aminophenyl) cyclohexanecarboxylate (3.8 g, 13.8 mmol) and pyridine (2.2 mL, 27.6 mmol) in DCM (40 mL) at 10° C. The reaction mixture was warmed to room temperature and stirred for 16 h and then quenched with water. The layers were separated and the organic layer was washed with brine. The organic layer was dried and concentrated in vacuo and the residue was purified by chromatography, eluting with 10-50% ethyl acetate in isohexane, to give the title compound (4.0 g, 80%) as an oil; ¹H NMR δ 1.4 (9H, s), 1.4-1.55 (4H, m), 1.8-1.9 (2H, m), 1.9-2.05 (2H, m), 2.2-2.3 (1H, m), 2.4-2.6 (1H, m), 3.75 (3H, s), 7.2 (2H, d), 7.65 (2H, d); MS m/e (M−H)⁻ 360.

vi) Hydrazine hydrate (0.59 mL, 12.2 mmol) was added in one portion to a stirred mixture of tert-butyl trans-4-(4-{[methoxy(oxo)acetyl]amino}phenyl)cyclohexanecarboxylate (4.0 g, 11.1 mmol) in EtOH (50 mL) and the reaction mixture was stirred at room temperature for 3 h. EtOH (25 mL) was added and the mixture was filtered to give the title compound (Intermediate 79) (3.7 g, 92%) as a solid; ¹H NMR δ 1.4 (9H, s), 1.4-1.5 (4H, m), 1.8-1.9 (2H, m), 1.9-2.0 (2H, m), 2.15-2.3 (1H, m), 2.4-2.55 (1H, m), 4.5 (1H, s), 4.6 (2H, s), 7.2 (2H, d), 7.7 (2H, d), 10.45 (1H, s); MS m/e (M−H)⁻ 360.

Intermediate 80: Ethyl trans-4-(4-{[hydrazino(oxo)acetyl]amino}phenoxy)cyclo-hexanecarboxylate

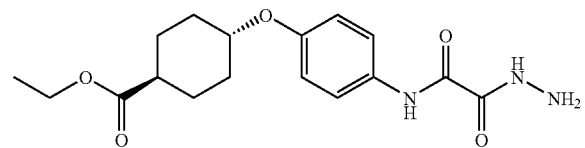

i) Ethyl trans-4-(4-aminophenoxy)cyclohexanecarboxylate

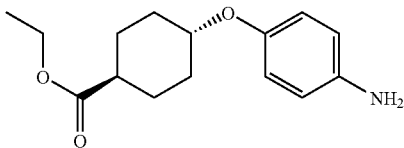

A solution of ethyl 4-hydroxycyclohexanecarboxylate (2.0 g, 11.6 mmol) in DMF (3 ml) was added in one portion to a stirred suspension of sodium hydride (60% dispersion in mineral oil, 490 mg, 12.2 mmol) in DMF (15 mL) at 0° C. under an argon atmosphere. The mixture was stirred at 0° C. for 10 minutes and then warmed to room temperature and stirred for 20 minutes and then a solution of 1-fluoro-4-nitrobenzene (1.24 mL, 11.6 mmol) in DMF (2 mL) was added in one portion. The reaction mixture was stirred at room temperature for 2 h and then heated at 110° C. for 24 h. The solution was concentrated in vacuo to leave a residue that was taken up in EtOAc (250 mL) and water (150 mL) was added. The layers were separated and the organic layer was washed with H₂O (2×100 mL) and brine (50 mL) and then dried (MgSO₄) and concentrated in vacuo to leave an oil. The oil was taken up in a mixture of hot EtOAc and isohexane (1:1) and left for 20 h. Filtration, followed by concentration in vacuo of the filtrate left an oil, which was purified by column chromatography, using 10-40% EtOAc in isohexane as eluent, to give crude ethyl 4-(4-nitrophenoxy)cyclohexanecarboxylate as an off white solid that was used without further purification.

Palladium (10 wt. %) on carbon (50 mg) was added in one portion to a solution of crude ethyl 4-(4-nitrophenoxy)cyclohexanecarboxylate in a mixture of EtOH (15 mL) and THF (10 mL). The reaction mixture was stirred under a hydrogen atmosphere at room temperature for 16 h then filtered and concentrated in vacuo to give a solid that was purified by chromatography, using 30-60% EtOAc in isohexane as eluent, to give the title compound (127 mg, 4% over 2 steps) as a solid; ¹H NMR (CDCl₃) δ1.16-1.20 (3H, t), 1.31-1.42 (2H, m), 1.43-1.52 (2H, m), 1.96-2.01 (2H, m), 2.05-2.10 (2H, m), 2.20-2.28 (1H, m), 3.35 (2H, br s), 3.89-3.96 (1H, m), 4.05 (2H, q), 6.53-6.57 (2H, d), 6.65-6.69 (2H, d); MS m/e MH⁺ 264.

ii) Ethyl trans-4-(4-{[methoxy(oxo)acetyl]amino}phenoxy)cyclohexanecarboxylate

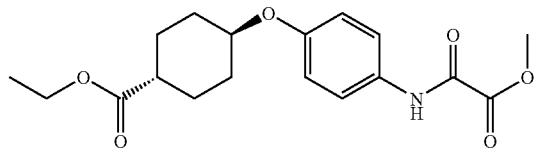

Methyl chlorooxoacetate (45 μL, 0.48 mmol) was added in one portion to a stirred solution of ethyl 4-(4-aminophenoxy)cyclohexanecarboxylate (127 mg, 0.48 mmol) and pyridine (47 μL, 0.58 mmol) in DCM (5 mL) and the reaction mixture was stirred for 30 minutes. Volatile material was removed by evaporation and the residue was taken up in EtOAc (40 mL) and an aqueous solution of hydrochloric acid (1M, 20 mL) was added. The layers were separated and the organic layer was washed with brine (10 mL), dried and concentrated in vacuo to give the title compound (152 mg, 91%) as a solid; ¹H NMR (CDCl₃) δ1.19 (3H, t), 1.39-1.45 (2H, m), 1.48-1.56 (2H, m), 1.97-2.03 (2H, m), 2.08-2.12 (2H, m), 2.23-2.31 (1H, m), 3.89 (3H, s), 4.07 (2H, q), 4.11-4.14 (1H, m), 6.80-6.84 (2H, d), 7.44-7.48 (2H, d), 8.66 (1H, s); MS m/e MR⁺ 350.

iii) Hydrazine monohydrate (0.15 mL, 3.34 mmol) was added in one portion to a stirred solution of ethyl trans-4-(4-{[methoxy(oxo)acetyl]amino}phenoxy)cyclohexanecarboxylate (150 mg, 3.04 mmol) in EtOH (3 mL) and the reaction mixture was stirred for 20 minutes. Ether (10 mL) was added and the mixture was cooled to 5° C. The mixture was filtered to give the title compound (Intermediate 80) (129 mg, 85%) as a solid that was used without further purification; MS m/e MH⁺ 350.

Intermediate 81: 3-{[(1R)-2-Methoxy-1-methyl-ethyl]oxy}aniline

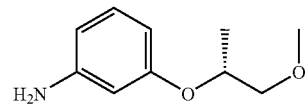

i) 1-{[(1R)-2-Methoxy-1-methylethyl]oxy}-3-nitrobenzene

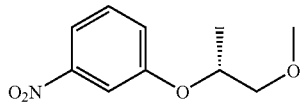

DEAD (1.97 mL, 10.8 mmol) was added dropwise to a stirred mixture of 3-nitrophenol (2.50 g, 18 mmol), (2S)-1-methoxypropan-2-ol (648 mg, 7.2 mmol) and triphenylphosphine (2.84 g, 10.8 mmol) in DCM (10 ml). The reaction mixture was stirred for 16 h then treated with saturated aqueous sodium hydrogen carbonate solution. The resultant mixture was partitioned and the organics were washed with 1M NaOH, dried and concentrated by evaporation. The residue was triturated with 1:1 EtOAC/hexanes. and filtered. The filtrate was concentrated by evaporation and the residue was purified by chromatography eluting with 25% EtOAc/hexane to give the title compound (1 g) as an oil; $^1$H NMR (400 MHz, DMSO) δ1.24 (d, 3H), 3.24 (s, 3H), 3.44-3.60 (m, 2H), 4.71-4.89 (m, 1H), 7.38-7.48 (m, 1H), 7.57 (t, 1H), 7.70-7.76 (m, 1H), 7.76-7.86 (m, 1H).

ii) 1-{[(1R)-2-methoxy-1-methylethyl]oxy}-3-nitrobenzene (1.00 g; 4.74 mmol) was dissolved in MeOH (20 ml) and treated with 10% palladium on carbon then placed under an atmosphere of hydrogen and stirred for 24 h. The reaction mixture was filtered then concentrated by evaporation to give the title compound (Intermediate 81) (0.88 g) as an oil; $^1$H NMR δ 1.18 (d, 3H), 3.24 (s, 3H), 3.34-3.42 (m, 1H), 3.42-3.52 (m, 1H), 4.37-4.49 (m, 1H), 4.90 (s, 2H), 6.04-6.11 (m, 1H), 6.10-6.18 (m, 2H), 6.83-6.91 (m, 1H); MH$^+$ 182.

Intermediate 82: 3-{[(1S)-2-Methoxy-1-methylethyl]oxy}aniline

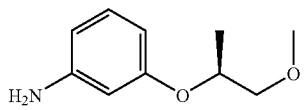

i) 1-{[(1S)-2-Methoxy-1-methylethyl]oxy}-3-nitrobenzene

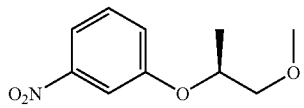

Following the procedure described for Intermediate 81 part (i) except that (2R)-1-methoxypropan-2-ol was used in place of (2S)-1-methoxypropan-2-ol, the title compound was obtained as an oil; $^1$H NMR δ 1.25 (d, 3H), 3.26 (s, 3H), 3.43-3.61 (m, 2H), 4.69-4.88 (m, 1H), 7.40-7.47 (m, 1H), 7.57 (t, 1H), 7.69-7.75 (m, 1H), 7.76-7.83 (m, 1H).

ii) Reduction of 1-{[(1S)-2-Methoxy-1-methylethyl]oxy}-3-nitrobenzene following the procedure described for Intermediate 81 part (ii) gave the title compound (Intermediate 82) as oil; $^1$H NMR δ 1.17 (d, 3H), 3.26 (s, 3H), 3.35-3.42 (m, 1H), 3.42-3.51 (m, 1H), 4.37-4.49 (m, 1H), 4.90 (s, 2H), 6.03-6.11 (m, 1H), 6.10-6.19 (m, 2H), 6.81-6.94 (m, 1H); MS m/e MH$^+$ 182.

Intermediate 83: tert-Butyl 1-(5-{[hydrazino(oxo)acetyl]amino}pyridin-2-yl)piperidine-4-carboxylate

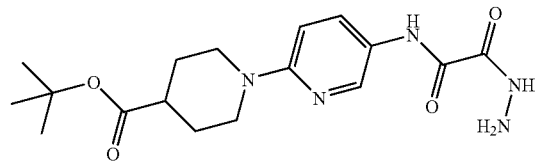

i) tert-Butyl 1-(5-nitropyridin-2-yl)piperidine-4-carboxylate

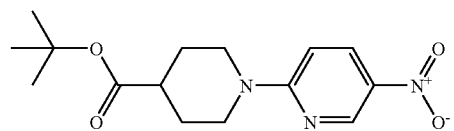

Following the procedure described for Intermediate 77 part (i), but using tert-butylpiperidine-4-carboxylate hydrochloride in place of methyl piperidin-4-ylacetate hydrochloride, the title compound was obtained in 91% yield; $^1$H NMR δ1.35 (s, 9H), 1.51 (q, 2H), 1.90 (d, 2H), 2.55-2.69 (m, 1H), 3.20 (t, 2H), 4.39 (d, 2H), 6.96 (d, 1H), 8.20 (d, 1H), 8.95 (d, 1H); MS m/e MH$^+$ 252.

ii) tert-Butyl 1-(5-aminopyridin-2-yl)piperidine-4-carboxylate

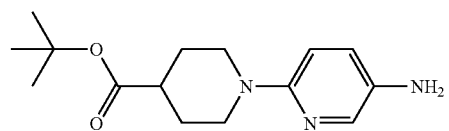

Following the procedure described for Intermediate 77 part (ii), the title compound was obtained in 95% yield as a solid; $^1$H NMR (CDCl$_3$) δ1.41 (s, 9H), 1.68-1.85 (m, 2H), 1.89-2.02 (m, 2H), 2.28-2.44 (m, 1H), 2.74-2.87 (m, 2H), 3.91-4.06 (m, 2H), 6.64 (d, 1H), 6.98 (d, 1H), 7.79 (d, 1H); MS m/e MH$^+$ 252.

iii) Following the procedure described for Intermediate 77 part (iii), the first intermediate, tert-Butyl 1-(5-{[methoxy(oxo)acetyl]amino}pyridin-2-yl)piperidine-4-carboxylate, was obtained in 97% yield as a solid; $^1$H NMR (CDCl$_3$) δ1.39 (s, 9H), 1.64-1.82 (m, 2H), 1.96 (d, 2H), 2.36-2.52 (m, 1H), 2.98 (t, 2H), 3.95 (s, 3H), 4.10-4.26 (m, 2H), 6.68 (d, 1H), 7.94 (d, 1H), 8.29 (d, 1H), 8.69 (s, 1H); MS m/e MH$^+$ 364; then condensation with hydrazine gave the title compound (Intermediate 83) in 72% yield as a solid; $^1$H NMR δ1.35 (s, 9H), 1.44-1.61 (m, 2H), 1.75-1.88 (m, 2H), 2.38-2.49 (m, 1H), 2.90 (t, 2H), 4.12 (d, 2H), 4.62 (s, 2H), 6.84 (d, 1H), 7.91 (d, 1H), 8.51 (d, 1H), 10.23 (s, 1H), 10.53 (s, 1H); MS m/e MH+ 364.

Intermediate 84: Methyl 3-(4-aminophenyl)cyclopentanecarboxylate

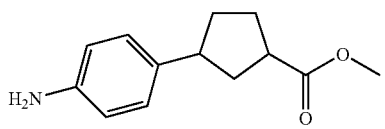

i) Methyl 3-(4-nitrophenyl)cyclopentanecarboxylate

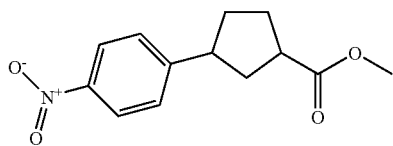

A mixture of 65% nitric acid (0.95 mL) and 95% sulphuric acid (1.2 mL) in carbon tetrachloride (2.5 mL) was added dropwise to a solution of methyl 3-phenylcyclopentanecarboxylate (Journal of Organic Chemistry, 1988, 53(17), 4021) (1 g, 4.9 mmol) and the mixture was stirred at 5-10° C. for 2 h. Ice/water (30 mL) was added and the mixture was extracted with DCM (2×50 mL). The extracts were combined, washed with water and dried. The residue was adsorbed onto silica and purified by chromatography eluting with 0-30% EtOAc in hexane to give the title compound (782 mg, 64%) as an oil; $^1$H NMR δ3.90 (3H, s), 7.94-7.97 (2H, m), 8.03-8.06 (2H, m), 8.09-8.12 (2H, m), 8.33-8.36 (2H, m).

ii) 10% palladium on carbon (78 mg) was added to a stirred solution of methyl 3-(4-nitrophenyl)cyclopentanecarboxylate (782 mg, 3.14 mmol) in EtOH (40 mL). The mixture was stirred under an atmosphere of hydrogen for 16 h then filtered through diatomaceous earth and the filter washed with EtOAc. Volatile material was removed by evaporation to give the title compound (Intermediate 84) (608 mg, 88%) as an oil; $^1$H NMR δ 2.24-1.45 (m, 6H), 3.03-2.83 (m, 2H), 3.62 (s, 3H), 4.80 (s, 2H), 6.53-6.46 (m, 2H), 6.92-6.86 (m, 2H); MS m/e MH+ 220.

Intermediate 85: Methyl 3-(4-aminophenyl)adamantane-1-carboxylate

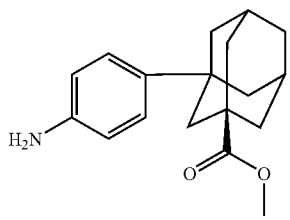

i) Methyl 3-(4-Nitrophenyl)adamantane-1-carboxylate

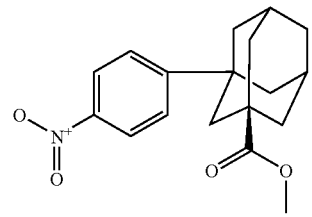

3-(4-Nitrophenyl)adamantane-1-carboxylic acid (500 mg, 1.66 mmol) was stirred in MeOH (8 mL) and concentrated sulphuric acid (0.1 mL) was added. After stirring at room temperature overnight the reaction mixture was basified with aqueous potassium carbonate (30 mL of a saturated solution) and then concentrated in vacuo. The residue was extracted with EtOAc (2×250 mL) and washed with water and brine. The organics were dried and solvent removed in vacuo to give a white solid (554 mg, 100%); $^1$H NMR δ 8.18 (d, 2H), 7.68 (d, 2H), 3.61 (s, 3H), 2.23-2.17 (m, 2H), 2.01-1.97 (m, 2H), 1.91-1.84 (m, 8H), 1.74-1.69 (m, 2H); MS m/e M+MeCN 357.

ii) Methyl 3-(4-Nitrophenyl)adamantane-1-carboxylate was reduced by the method of Intermediate 84, step (ii), to give the title compound (Intermediate 85); $^1$H NMR δ 6.99 (d, 2H), 6.51 (d, 2H), 4.80 (s, 2H), 3.59 (s, 3H), 2.17-2.10 (m, 2H), 1.87-1.79 (m, 6H), 1.77-1.72 (m, 4H), 1.69-1.63 (m, 2H); MS m/e M+MeCN 327.

Intermediate 86: Ethyl 4'-aminobiphenyl-3-yl)acetate

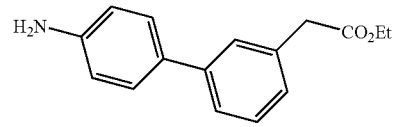

i) Ethyl [4'-(dibenzylamino)biphenyl-3-yl]acetate

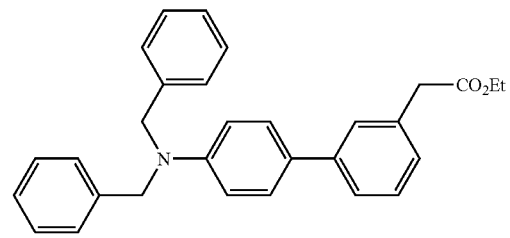

[4-(Dibenzylamino)phenyl]boronic acid (UK Patent Application No. GB 2276161 (1994)) (400 mL, 1.26 mmol) was stirred in 5 mL dry toluene and potassium carbonate was added followed by ethyl (3-bromophenyl)acetate (338 mg, 1.39 mmol) as a solution in toluene (1 mL). The reaction vessel was evacuated and refilled with nitrogen (5 times). Pd(PPh$_3$)$_4$ (73 mg, 0.06 mmol) was added as a solution in toluene (1 mL) and the vessel was deoxygenated as before.

The reaction mixture was heated at 90° C. for 16 h then cooled and filtered through diatomaceous earth. Volatile material was removed by evaporation, the residue was adsorbed onto silica and purified by chromatography eluting with 10-50% EtOAc/isohexane to give the title compound (175 mg, 32%) as a gum; $^1$H NMR δ 1.18 (t, 3H), 3.67 (s, 2H), 4.07 (q, 2H), 4.76 (s, 4H), 6.76 (d, 2H), 7.11 (d, 2H), 7.44-7.20 (m, 14H); MS m/e MH$^+$ 436.

ii) Nitrogen was bubbled through a solution of ethyl [4'-(dibenzylamino)biphenyl-3-yl]acetate (170 mg, 0.39 mmol) in EtOH (15 mL) and EtOAc (15 mL) then 10% palladium on carbon (30 mg) was added and the mixture was stirred under an atmosphere of hydrogen for 16 h. The mixture was filtered through diatomaceous earth and concentrated by evaporation to give the title compound (Intermediate 86) (98 mg) as a gum; $^1$H NMR δ 1.19 (t, 3H), 3.69 (s, 2H), 4.09 (q, 2H), 5.24 (s, 2H), 6.64 (d, 2H), 7.11 (d, 1H), 7.37-7.30 (m, 3H), 7.42 (d, 2H); MS m/e M+MeCN 297.

Intermediate 87: Methyl [(1R,4R)-4'-amino-1,1'-bi(cyclohexyl)-4-yl]acetate

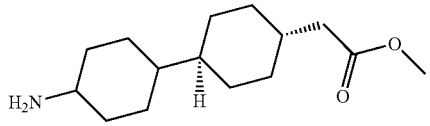

A mixture of methyl [trans-4-(4-aminophenyl)cyclohexyl]acetate (from Intermediate 43, step (ii)) (200 mg, 0.81 mmol) and Rhodium (5% on alumina; 15 mg) in EtOH/water (6 mL of a 1:2 mixture) was stirred under an atmosphere of hydrogen at 48 bar, 65° C. for 3 h then filtered. The filtrate was concentrated by evaporation to give the title compound as a gum.

Intermediate 88: Ethyl 3-(2-amino-2,3-dihydro-1H-inden-5-yl)propanoate

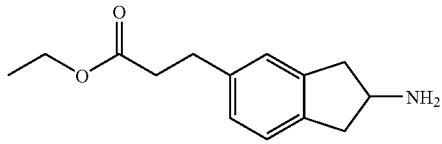

i) Benzyl (5-bromo-2,3-dihydro-1H-inden-2-yl)carbamate

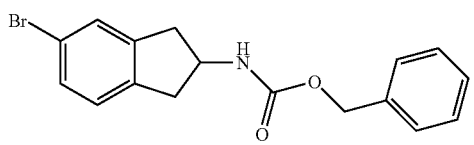

Benzyl chloroformate (0.804 mL, 5.63 mmol) was added slowly with stirring to a mixture of 5-bromoindan-2-amine hydrobromide (Advanced Synth. & Catalysis 343(5), 461-472, 2001) (1.5 g, 5.12 mmol) and triethylamine (1.57 mL, 11.3 mmol) in DCM (20 mL) at 0° C.

The reaction mixture was allowed to warm to room temperature and stirred for 16 h. DCM (150 mL) was added and the solution was washed with 0.5M aqueous HCl (100 mL) then saturated aqueous sodium hydrogencarbonate solution (100 mL). MeOH (10 mL) was added as cosolvent and the solution was dried and concentrated by evaporation. The residue was purified by chromatography to give the title compound (804 mg, 45%) as a solid; $^1$H NMR δ 2.59-2.87 (m, 2H), 3.03-3.23 (m, 2H), 4.23-4.39 (m, 1H), 4.50 (d, 1H), 5.04 (s, 2H), 7.14-7.44 (m, 8H); MS m/e MH$^+$ 214.

ii) Ethyl (2E)-3-(2-{[(benzyloxy)carbonyl]amino}-2,3-dihydro-1H-inden-5-yl)acrylate

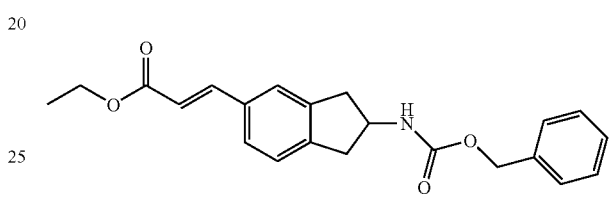

A mixture of palladium(II) acetate (3 mg, 0.01 mmol), Tri-o-tolylphosphine (7 mg, 0.02 mmol) and DIPEA (0.088 mL, 0.5 mmol) was stirred in MeCN (2 mL) at 60° C. under a nitrogen atmosphere for 20 minutes in a 5 mL microwave vial. Benzyl(5-bromo-2,3-dihydro-1H-inden-2-yl)carbamate (174 mg, 0.5 mmol) and ethyl acrylate (28 μL, 0.25 mmol) were added and the mixture was heated in the microwave at 180° C. for 0.5 h. The mixture was adsorbed onto silica and purified by chromatography with 0-40% EtOAc/isohexane as eluent to give the title compound (105 mg, 57%) as a gum; $^1$H NMR (CDCl$_3$) δ 1.32 (t, 3H), 2.62-2.88 (m, 2H), 3.12-3.36 (m, 2H), 4.18-4.29 (m, 2H), 4.46-4.62 (m, 1H), 4.76 (d, 1H), 5.09 (s, 2H), 6.32-6.41 (m, 1H), 7.10-7.44 (m, 8H), 7.57-7.68 (m, 1H); MS m/e MH$^+$ 366.

iii) Ethyl (2E)-3-(2-{[(benzyloxy)carbonyl]amino}-2,3-dihydro-1H-inden-5-yl)acrylate was reduced by the general procedure of Intermediate 84, step (ii), to give the title compound (Intermediate 88); $^1$H NMR (CD$_3$OD) δ 1.01-1.18 (m, 3H), 2.44-2.70 (m, 2H), 2.73-2.96 (m, 2H), 3.02-3.35 (m, 4H), 3.92-4.05 (m, 2H), 4.30-4.42 (m, 1H), 6.84-7.23 (m, 3H); MS m/e MH$^+$ 234.

Intermediate 89: Ethyl [3-(4-aminophenyl)cyclohexyl]acetate

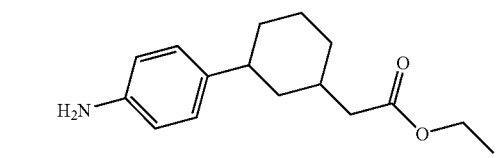

i) 3-[4-(Benzyloxy)phenyl]cyclohexanone

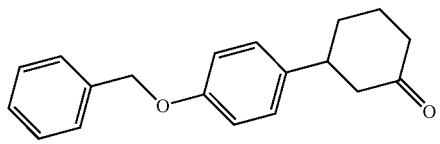

[4-(Benzyloxy)phenyl]boronic acid (2 g, 8.77 mmol) was dissolved in dioxane/water (50 mL/5 mL) and Rh(acac)(C$_2$H$_4$)$_2$ (68 mg, 0.26 mmol) and racemic BINAP (164 mg, 0.26 mmol) were added. The mixture was degassed 3 times and put under a nitrogen atmosphere. Cyclohexenone (1.02 mL, 10.52 mmol) was added to the yellow solution and the mixture heated at reflux overnight. The reaction mixture was cooled, saturated aqueous sodium hydrogen carbonate solution (50 mL) added, then extracted with EtOAc (2×100 mL). The organic extracts were washed with water (100 mL) and dried. Volatile material was removed by evaporation and purification by chromatography gave the title compound (565 mg, 23%) as a solid; $^1$H NMR δ1.65-1.69 (1H, m), 1.78-1.93 (2H, m), 1.99-2.04 (1H, m), 2.22-2.35 (2H, m), 2.39-2.43 (1H, m), 2.65 (1H, m), 2.90-2.96 (1H, m), 5.08 (2H, s), 6.96 (2H, d), 7.20 (2H, d), 7.31-7.45 (5H, m); MS m/e MH$^+$ 281.

ii) Ethyl {3-[4-(benzyloxy)phenyl]cyclohexylidene}acetate

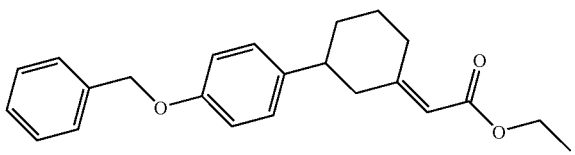

Triethylphosphonoacetate (0.48 mL, 2.42 mmol) was added to a stirred suspension of sodium hydride (97 mg of a 60% dispersion in oil, 2.42 mmol) in THF (10 mL) at 0° C. The mixture was allowed to warm to ambient temperature and stirred for 15 minutes then 3-[4-(benzyloxy)phenyl]cyclohexanone (565 mg, 2.02 mmol) was added as a solution in THF (10 mL). After 3 h saturated aqueous ammonium chloride solution (50 mL) was added and the mixture was extracted with EtOAc (2×50 mL). The organic layers were washed with water (50 mL) then dried and concentrated by evaporation to give the title compound as an oil that was used directly in the next step; MS m/e MH$^+$ 351.

iii) Ethyl [3-(4-hydroxyphenyl)cyclohexyl]acetate

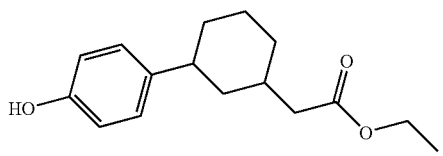

Ethyl {3-[4-(benzyloxy)phenyl]cyclohexylidene}acetate was reduced following the general procedure described for Intermediate 84, part (ii), to give the title compound; $^1$H NMR δ 1.12-1.19 (3H, m), 0.93-1.82 (8H, m), 2.18 (1H, d), 2.45 (1H, d), 2.65 (1H, m), 2.99 (1H, m), 4.04 (2H, q), 6.65-6.67 (2H, m), 7.00 (2H, t), 9.12 (1H, s); MS m/e (M−H)$^-$ 261.

iv) Ethyl [3-(4-{[(trifluoromethyl)sulphonyl]oxy}phenyl)cyclohexyl]acetate

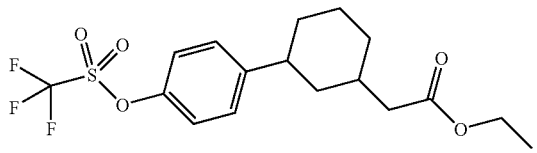

Ethyl [3-(4-hydroxyphenyl)cyclohexyl]acetate (329 mg, 1.25 mmol) was stirred in dry DCM (15 mL) under nitrogen. The mixture was cooled with an ice bath and trifluoromethanesulphonic anhydride (0.264 mL, 1.57 mmol) was added. Triethylamine (0.263 mL, 1.88 mmol) was then added dropwise over 5 minutes, keeping the temperature below 10° C. and the mixture was stirred for 2 h. Saturated aqueous sodium hydrogen carbonate solution (10 mL) was added, the layers were separated and the aqueous phase was extracted with DCM (20 mL). The organic layers were dried and concentrated by evaporation to give an oil that was purified by chromatography eluting with 0-40% EtOAc/isohexane to give the title compound (345 mg, 70%) as an oil; $^1$H NMR δ 0.94-2.00 (9H, s), 1.16 (3H, m), 2.23 (1H, d), 2.47 (1H, d), 2.62-2.85 (1H, m), 4.01-4.09 (2H, m), 7.41-7.44 (4H, m); MS m/e (M−H)$^-$ 393.

v) Ethyl (3-{4-[(diphenylmethylene)amino]phenyl}cyclohexyl)acetate

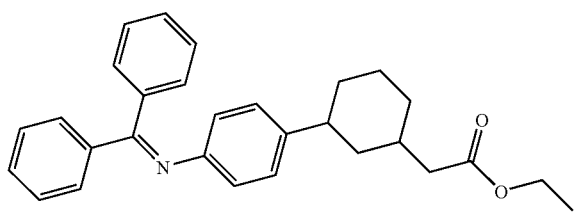

Ethyl [3-(4-{[(trifluoromethyl)sulphonyl]oxy}phenyl)cyclohexyl]acetate (322 mg, 0.85 mmol) was stirred in dry THF (8 mL) under a nitrogen atmosphere and caesium carbonate (387 mg, 1.19 mmol), palladium(II) acetate (12 mg, 0.05 mmol) and BINAP (32 mg, 0.05 mmol) were added followed by benzophenone imine (0.214 mL, 1.27 mmol). The reaction vessel was degassed 6 times and stirred under reflux for 16 h. The mixture was extracted with ether (2×100 mL) and washed with water (100 mL). The organic extracts were dried and concentrated by evaporation to give an oil that was purified by chromatography eluting with 0-30% EtOAc/isohexane to give the title compound (137 mg, 38%) as an oil; $^1$H NMR δ 0.81-2.48 (m, 9H), 1.12-1.21 (m, 3H), 2.58-2.72 (m, 1H), 3.97-4.12 (m, 2H), 6.57-6.65 (m, 1H), 6.94-7.04 (m, 1H), 7.10-7.18 (m, 1H), 7.29-7.36 (m, 1H), 7.37-7.78 (m, 10H); MS m/e MH$^+$ 426.

vi)

Aqueous HCl (1 mL of a 1M solution) was added to ethyl (3-{4-[(diphenylmethylene)amino]phenyl}cyclohexyl)acetate (137 mg, 0.32 mmol) in EtOH (10 mL) with stirring. After 1 h the reaction mixture was basified with aqueous potassium carbonate (10 mL of a saturated solution and the mixture was extracted with Et$_2$O (2×15 mL), washed with water (15 mL) and dried. Volatile material was removed by evaporation and the residue was purified by chromatography eluting with 0-35% EtOAc/isohexane to give the title compound (Intermediate 89) (40 mg, 48%) as a gum; MS m/e MH$^+$ 262.

Intermediate 90: Ethyl [(3R)-3-(4-aminophenyl)cyclopentyl]acetate

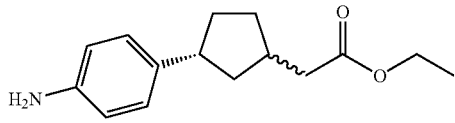

i) (3R)-3-(4-Bromophenyl)cyclopentanone

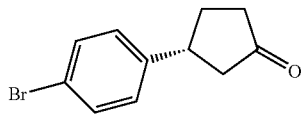

4-Bromophenylboronic acid (4 g, 19.92 mmol), Rh(acac)(C$_2$H$_4$)$_2$ (acetylacetonatobis(ethylene)Rhodium (I); 103 mg, 0.4 mmol) and (R)-BINAP (249 mg, 0.4 mmol) were placed in a 100 mL 3-necked round bottomed flask and 1,4-dioxane (40 mL) was added. The reaction vessel was degassed several times before putting under a nitrogen atmosphere. Water (4 mL) was added followed by cyclopent-2-en-1-one (1.185 mL, 14.14 mmol). The reaction mixture was then heated at 100° C. overnight before cooling and washing with saturated aqueous sodium hydrogen carbonate solution (50 mL). The mixture was extracted with EtOAc (2×100 mL) and the organics dried then purified by chromatography eluting with 0-40% EtOAc/isohexane) to give the title compound (1.62 g, 48%) as an oil that crystallised upon standing; $^1$H NMR δ1.86-1.93 (1H, m), 2.23-2.36 (3H, m), 2.53-2.57 (1H, m), 3.34-3.43 (1H, m), 7.29-7.32 (2H, m), 7.50-7.53 (2H, m); α$_D$=+20° (MeOH, c=1, L=1)

ii) Ethyl [(3R)-3-(4-bromophenyl)cyclopentylidene]acetate

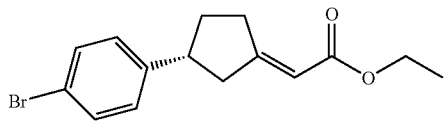

Following the general procedure described for ethyl {3-[4-(benzyloxy)phenyl]cyclohexylidene}acetate (Intermediate 89 (ii)), replacing 3-[4-(benzyloxy)phenyl]cyclohexanone with (3R)-3-(4-bromophenyl)cyclopentanone the title compound was obtained; $^1$H NMR δ1.18-1.23 (3H, m), 1.61-1.78 (1H, m), 2.06-2.20 (1H, m), 2.53-2.67 (3H, m), 2.84-3.04 (1H, m), 3.08-3.24 (1H, m), 4.01-4.10 (2H, m), 5.82-5.85 (1H, m), 7.24-7.28 (2H, m), 7.47-7.51 (2H, m); MS m/e MH$^+$ 310.

iii) Ethyl ((3R)-3-{4-[(diphenylmethylene)amino]phenyl}cyclopentylidene)acetate

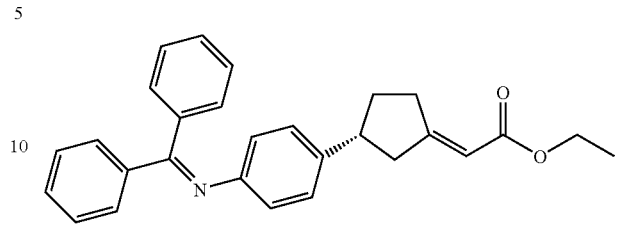

Following the procedure described for ethyl (3-{4-[(diphenylmethylene)amino]phenyl}cyclohexyl)acetate (Intermediate 89(iii)), replacing ethyl [3-(4-{[(trifluoromethyl)sulphonyl]oxy}phenyl)cyclohexyl]acetate with ethyl [(3R)-3-(4-bromophenyl)cyclopentylidene]acetate, the title compound was obtained; MS m/e MH$^+$ 410.

iv) Ethyl [(3R)-3-(4-aminophenyl)cyclopentylidene]acetate

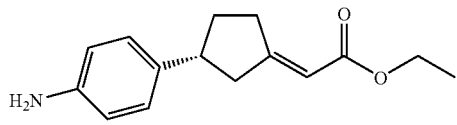

Following the procedure described for ethyl [3-(4-aminophenyl)cyclohexyl]acetate (Intermediate 89Iv), replacing ethyl (3-{4[(diphenylmethylene)amino]phenyl}cyclohexyl)acetate with ethyl ((3R)-3-{4-[(diphenylmethylene)amino]phenyl}cyclopentylidene)acetate the title compound was obtained; $^1$H NMR δ 1.17-1.22 (3H, m), 1.57-1.68 (1H, m), 2.27-2.48 (2H, m), 2.53 (OH, s), 2.56-2.68 (1H, m), 2.74-2.76 (1H, m), 2.93-3.00 (1H, m), 3.15-3.24 (0.5H, m), 3.69-3.71 (0.5H, m), 4.01-4.12 (2H, m), 4.79-4.83 (2H, m), 5.49-5.53 (1H, m), 5.78-5.82 (1H, m), 6.47-6.52 (2H, m), 6.80-6.93 (2H, m); MS m/e M+MeCN 287.07 v) Ethyl [(3R)-3-(4-aminophenyl)cyclopentyl]acetate

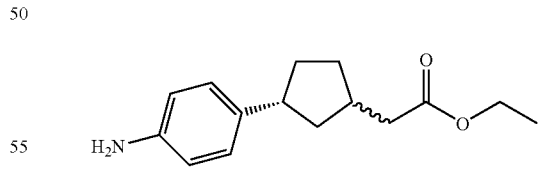

Following the procedure described for methyl 3-(4-aminophenyl)cyclopentanecarboxylate, replacing methyl 3-(4-nitrophenyl)cyclopentanecarboxylate (Intermediate 84(ii)) with ethyl [(3R)-3-(4-aminophenyl)cyclopentylidene]acetate, the title compound was obtained; $^1$H NMR δ 1.18 (t, 3H), 1.21-1.76 (m, 2H), 1.80-2.12 (m, 2H), 2.23-2.48 (m, 2H), 2.80-3.01 (m, 1H), 3.16-3.30 (m, 2H), 4.06 (q, 2H), 4.79 (s, 2H), 6.45-6.51 (m, 2H), 6.84-6.91 (m, 2H); MS m/e M+MeCN 289.

Intermediate 91: Ethyl [(3S)-3-(4-aminophenyl)cyclopentyl]acetate

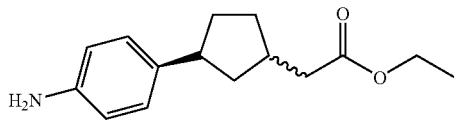

i) (3S)-3-(4-Bromophenyl)cyclopentanone

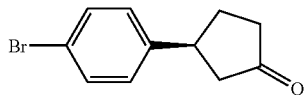

Following the procedure described for (3S)-3-(4-Bromophenyl)cyclopentanone (Intermediate 90(i)), replacing (R)-BINAP with (S)-BINAP, the title compound was obtained; $^1$H NMR δ 1.86-1.93 (1H, m), 2.23-2.36 (3H, m), 2.53-2.57 (1H, m), 3.34-3.43 (1H, m), 7.29-7.32 (2H, m), 7.50-7.53 (2H, m); $α_D$=−18° (MeOH, c=1, L=1)

ii) Ethyl [(3S)-3-(4-bromophenyl)cyclopentylidene]acetate

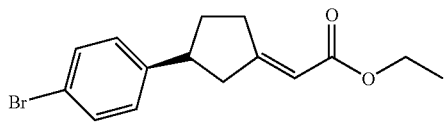

Following the procedure described for ethyl {3-[4-(benzyloxy)phenyl]cyclahexylidene}acetate (Intermediate 89(ii)), replacing 3-[4-(benzyloxy)phenyl]cyclohexanone with (3S)-3-(4-bromophenyl)cyclopentanone the title compound was obtained; $^1$H NMR δ1.18-1.23 (3H, m), 1.61-1.78 (1H, m), 2.06-2.20 (1H, m), 2.53-2.67 (3H, m), 2.84-3.04 (1H, m), 3.08-3.24 (1H, m), 4.01-4.10 (2H, m), 5.82-5.85 (1H, m), 7.24-7.28 (2H, m), 7.47-7.51 (2H, m); MS m/e MH⁺ 309.

iii) Ethyl ((3S)-3-{4-[(diphenylmethylene)amino]phenyl}cyclopentylidene)acetate

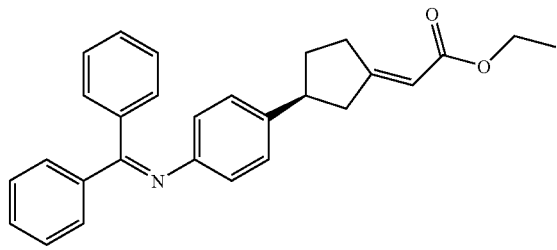

Following the procedure described for ethyl (3-{4-[(diphenylmethylene)amino]phenyl}cyclohexyl)acetate (Intermediate 89(iii)), replacing ethyl [3-(4-{[(trifluoromethyl)sulphonyl]oxy}phenyl)cyclohexyl]acetate with ethyl [(3S)-3-(4-bromophenyl)cyclopentylidene]acetate the title compound was obtained; MS m/e MH⁺ 410.

iv) Ethyl [(3S)-3-(4-aminophenyl)cyclopentylidene]acetate

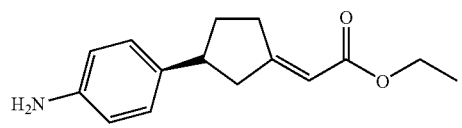

Following the procedure described for ethyl [3-(4-aminophenyl)cyclohexyl]acetate (Intermediate 89(iv)), replacing ethyl (3-{4-[(diphenylmethylene)amino]phenyl}cyclohexyl)acetate with ethyl ((3S)-3-{4-[(diphenylmethylene)amino]phenyl}cyclopentylidene)acetate the title compound was obtained; $^1$H NMR δ 1.17-1.22 (3H, m), 1.57-1.68 (1H, m), 2.27-2.48 (2H, m), 2.53 (OH, s), 2.56-2.68 (1H, m), 2.74-2.76 (1H, m), 2.93-3.00 (1H, m), 3.15-3.24 (0.5H, m), 3.69-3.71 (0.5H, m), 4.01-4.12 (2H, m), 4.79-4.83 (2H, m), 5.49-5.53 (1H, m), 5.78-5.82 (1H, m), 6.47-6.52 (2H, m), 6.80-6.93 (2H, m); MS m/e M+MeCN 287.

v) Ethyl [(3S)-3-(4-aminophenyl)cyclopentyl]acetate

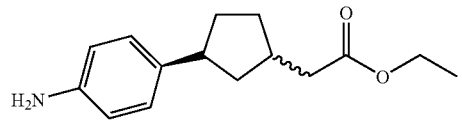

Following the procedure described for methyl 3-(4-aminophenyl)cyclopentanecarboxylate, replacing methyl 3-(4-nitrophenyl)cyclopentanecarboxylate (Intermediate 84(ii)) with ethyl [(3S)-3-(4-aminophenyl)cyclopentylidene]acetate the title compound was obtained; $^1$H NMR δ1.18 (t, 3H), 1.21-1.76 (m, 2H), 1.80-2.12 (m, 2H), 2.23-2.48 (m, 2H), 2.80-3.01 (m, 1H), 3.16-3.30 (m, 2H), 4.06 (q, 2H), 4.79 (s, 2H), 6.45-6.51 (m, 2H), 6.84-6.91 (m, 2H); MS m/e M+MeCN 289.

Intermediate 92: Methyl 3-(3-aminopropoxy)benzoate

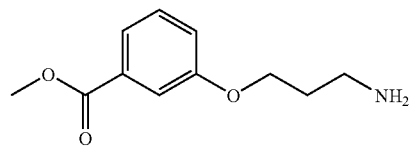

i) Methyl 3-(3-{[(benzyloxy)carbonyl]amino}propoxy)benzoate

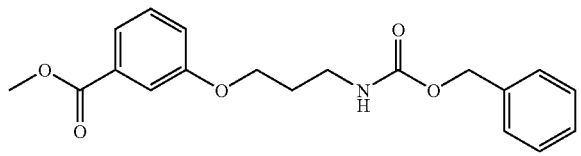

A mixture of methyl 3-hydroxybenzoate (609 mg, 4 mmol), benzyl N-(3-hydroxypropyl)carbamate (754 mg, 3.6 mmol) and polymer supported triphenylphosphine (PS—PPh₃) (4 g, 12 mmol) in THF (40 mL) was stirred and diethyl azodicarboxylate (948 mg, 5.44 mmol) was added as a solution in THF (4 mL). The mixture was stirred for 16 h then was filtered and washed with DCM and concentrated by evaporation. The residue was purified by chromatography eluting with DCM to give the title compound (481 mg, 35%) as an oil; $^1$H NMR δ 1.85-1.92 (2H, m), 3.19 (2H, q), 3.86 (3H, s), 4.05 (2H, t), 5.02 (2H, s), 7.20-7.22 (1H, m), 7.29-7.38 (5H, m), 7.42-7.45 (2H, m), 7.53-7.56 (1H, m).

ii) Following the procedure described for methyl 3-(4-aminophenyl)cyclopentanecarboxylate, replacing methyl 3-(4-nitrophenyl)cyclopentanecarboxylate (Intermediate 84 (i)) with methyl 3-(3-{[(benzyloxy)carbonyl]amino}propoxy)benzoate and using EtOAc as solvent instead of EtOH the title compound was obtained; $^1$H NMR δ 1.77-1.83 (2H, m), 2.70 (2H, t), 3.86 (3H, s), 4.09 (2H, t), 7.21-7.23 (1H, m), 7.43 (2H, t), 7.54 (1H, d); MS m/e MH⁺ 210.

Intermediate 93: Ethyl 3-(4-aminobenzyl)cyclobutanecarboxylate

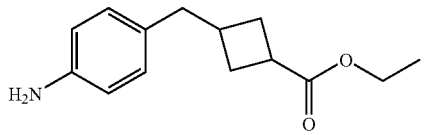

i) Ethyl 3-(4-nitrobenzyl)cyclobutanecarboxylate

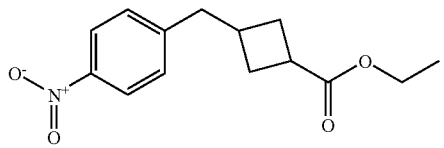

A mixture of concentrated nitric acid (0.5 mL) and concentrated sulphuric acid (0.8 mL) was added slowly with stirring to an ice-cooled solution of ethyl 3-benzylcyclobutanecarboxylate (German Patent DE 2626287) (876 mmol, 4.02 mmol) in nitrobenzene (2 mL). The reaction mixture was warmed to ambient temperature and stirred for 1.5 h then poured onto ice/water. DCM (5 mL) was added and the mixture was stirred before passing through a phase separation cartridge. Solvent was removed by evaporation to give the title compound that was used directly in the next step.

ii) Ethyl 3-(4-nitrobenzyl)cyclobutanecarboxylate (4.02 mmol) was stirred in EtOAc (20 mL) at room temperature and nitrogen was bubbled through. 10% Palladium on carbon (160 mg) was added and the reaction vessel was put under an atmosphere of hydrogen. The mixture was stirred overnight then filtered through diatomaceous earth and concentrated by evaporation under reduced pressure. The residue was purified by chromatography eluting with 0-55% EtOAc/isohexane to give the title compound (466 mg, 50%) as an oil; $^1$H NMR δ 1.15-1.20 (3H, m), 1.77-1.94 (2H, m), 2.13-2.20 (2H, m), 2.33-2.37 (2H, m), 2.43-2.46 (1H, m), 2.53-2.56 (1H, m), 2.92-3.07 (1H, m), 4.01-4.08 (2H, m), 4.77 (2H, d), 6.46-6.49 (2H, m), 6.78-6.82 (2H, m); MS m/e M+MeCN 275.

Intermediate 94: Diethyl {-4'-[({5-[(2-fluorophenyl)amino]-1,3,4-oxadiazol-2-yl}carbonyl)amino]biphenyl-4-yl}malonate

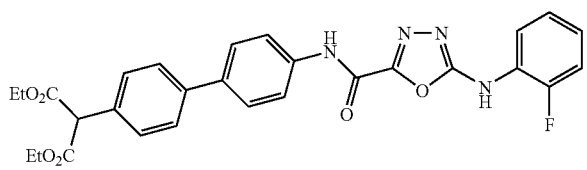

i) Diethyl (4'-nitrobiphenyl-4-yl)malonate

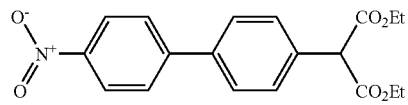

A mixture of 4-(4-bromophenyl)nitrobenzene (Journal of Organic Chemistry, 2005, 70(9), 3730) (800 mg, 2.88 mmol), 2-dicyclohexylphosphino-2',4',6'-triisopropylbiphenyl (Xphos) (69 mg) and caesium carbonate (2.81 g, 8.63 mmol) in toluene (40 mL) was deoxygenated then palladium(II) acetate (13 mg, 0.06 mmol) and diethyl malonate (0.480 mL, 3.2 mmol) were added. The reaction mixture was heated under reflux for 2 h, cooled and then filtered through diatomaceous earth and the filter washed with EtOAc. The filtrate was concentrated by evaporation and adsorbed onto silica then purified by chromatography, eluting with 0-25% EtOAc in isohexane, to give the title compound (1.047 g) as a solid.

ii) Diethyl (4'-aminobiphenyl-4-yl)malonate

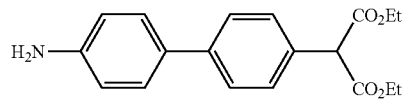

Diethyl (4'-nitrobiphenyl-4-yl)malonate was reduced by the method of Intermediate 84, step (ii), to give the title compound; $^1$H NMR δ 1.17-1.22 (6H, m), 4.10-4.22 (4H, m), 4.92 (1H, s), 5.22 (2H, s), 6.63-6.66 (2H, m), 7.35-7.38 (4H, m), 7.52-7.54 (2H, m); MS m/e MH⁺ 328.

iii) Following the procedure of Example 483 except that diethyl (4'-aminobiphenyl-4-yl)malonate was used as starting material in place of methyl 4-(4-aminophenyl)butanoate, the title compound (Intermediate 94) was obtained as a solid; $^1$H NMR δ 1.20 (6H, t), 4.15-4.22 (4H, m), 5.00 (1H, s), 7.17-7.20 (1H, m), 7.26-7.35 (2H, m), 7.47 (2H, d), 7.68-7.73 (4H, m), 7.92 (2H, d), 8.03-8.08 (1H, m), 10.79 (1H, s), 11.14 (1H, s); MS m/e MH⁺ 533.

Intermediate 95:Diethyl (3-{4'-[({5-[(3,4-difluorophenyl)amino]-1,3,4-oxadiazol-2-yl}carbonyl)amino]biphenyl-4-yl}propyl)malonate

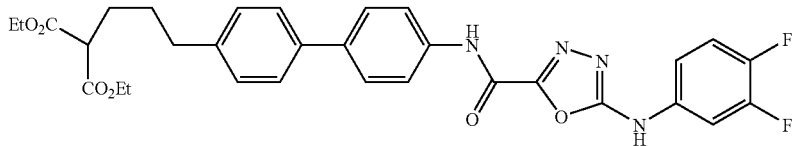

i) Diethyl [3-(4-aminophenyl)propyl]malonate

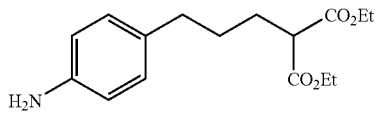

Following the general procedure of Intermediate 84 except that diethyl (3-phenylpropyl)malonate (J. Med. Chem., 2004, 47(12), 3282) was used in place of methyl 3-phenylcyclopentanecarboxylate, nitration and reduction (using EtOAc as solvent in place of EtOH) gave the title compound (purified by chromatography, eluting with 10-50% EtOAc/Isohexane); $^1$H NMR δ 1.17 (t, 6H), 1.42-1.53 (m, 2H), 1.69-1.78 (m, 2H), 2.40 (t, 2H), 3.45 (t, 1H), 4.07-4.16 (m, 4H), 4.81 (s, 2H), 6.48 (d, 2H), 6.81 (d, 2H); MS m/e MH$^+$ 294.

ii) Following the procedure of Example 483 except that diethyl [3-(4-aminophenyl)propyl]malonate was used as starting material in place of methyl 4-(4-aminophenyl)butanoate, the title compound (Intermediate 95) was obtained; MS m/e MH$^+$ 517.

Intermediate 96: Diisopropyl (4-{4-[({5-[(2-fluorophenyl)amino]-1,3,4-oxadiazol-2-yl}carbonyl)amino]cyclohexyl}phenyl)malonate

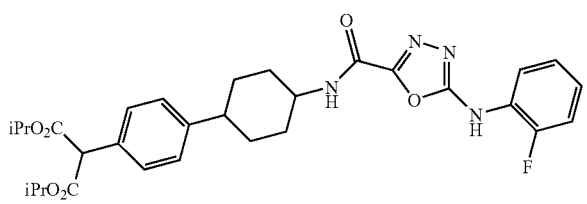

i) 4-(4-Oxocyclohexyl)phenyl 4-methylbenzenesulphonate

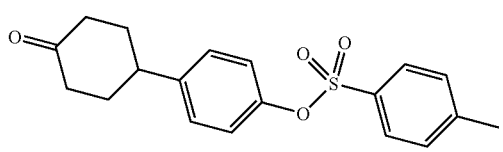

4-(4-Hydroxyphenyl)cyclohexanone (2 g, 10.51 mmol) was stirred in 10 mL acetone with potassium carbonate (1.6 g, 11.56 mmol) at room temperature. p-Toluenesulphonyl chloride (2.2 g, 11.56 mmol) was added (as a solution in 5 mL acetone) and the mixture was heated at reflux overnight and the reaction mixture was cooled and then quenched with water (20 mL). The mixture was extracted with EtOAc (2×30 mL) and the organics separated and dried (MgSO$_4$). The solvent was concentrated in vacuo to leave a colourless oil which yielded a white solid upon trituration with Et$_2$O and isohexane. The solid was filtered off and washed with isohexane. The solid was dissolved in EtOAc and passed through an Isolute NH$_2$ column. The product was isolated as a white crystalline solid (2.49 g, 69%); $^1$H NMR δ 1.78-1.88 (2H, m), 1.99-2.09 (2H, m), 2.23-2.28 (2H, m), 2.43 (3H, s), 2.53-2.58 (2H, m), 3.02-3.10 (1H, m), 6.94-6.98 (2H, m), 7.30-7.33 (2H, m), 7.48 (2H, d), 7.74-7.76 (2H, m); MS m/e M+Na$^+$ 367.

ii) 4-(1,4-Dioxaspiro[4.5]dec-8-yl)phenyl 4-methylbenzenesulphonate

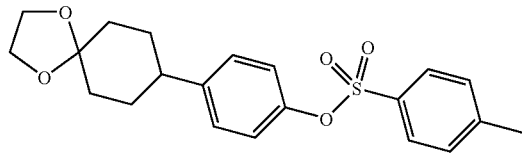

Boron trifluoride diethyletherate (3.3 mL, 26.0 mmol) was added dropwise via a syringe to a stirred solution of 4-(4-oxocyclohexyl)phenyl 4-methylbenzenesulphonate (2.49 g, 7.23 mmol) in dry DCM/ethylene glycol (15 mL/14.11 mL) cooled with an isopropanol/ice bath and stirred for 40 minutes. The mixture was poured onto water (50 mL) and extracted with DCM (2×100 mL). The organic phase was washed with 10% sodium hydrogen carbonate solution (100 mL) then dried and concentrated by evaporation to give the title compound (2.685 g, 96%) as a solid; $^1$H NMR δ 1.54-1.66 (4H, m), 1.68-1.75 (4H, m), 2.43 (3H, s), 2.54-2.60 (1H, m), 3.86-3.89 (4H, s), 6.91-6.95 (2H, m), 7.21-7.25 (2H, m), 7.46-7.48 (2H, m), 7.73-7.75 (2H, m); MS m/e M+Na$^+$ 411.

iii) Diethyl [4-(1,4-dioxaspiro[4.5]dec-8-yl)phenyl]malonate

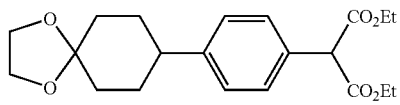

4-(1,4-Dioxaspiro[4.5]dec-8-yl)phenyl 4-methylbenzene-sulphonate (2.05 g, 5.27 mmol) was stirred with 2-dicyclohexylphosphino-2',4',6'-triisopropylbiphenyl (Xphos) (502 mg, 1.05 mmol) and caesium carbonate (5.15 g, 15.81 mmol) in toluene (40 mL) at room temperature under a nitrogen atmosphere. The reaction mixture was degassed several times then palladium(II) acetate (95 mg, 0.42 mmol) was added, followed by diethyl malonate (0.96 mL, 6.324 mmol). The mixture was heated under reflux for 40 h then was filtered through diatomaceous earth and concentrated by evaporation. The residue was adsorbed onto silica and purified by chromatography eluting with 0-40% EtOAc/isohexane to give the title compound (294 mg, 15%) as an oil; $^1$H NMR δ 1.18 (6H, t), 1.58-1.71 (4H, m), 1.75 (4H, t), 2.56 (1H, t), 3.89 (4H, q), 4.08-4.20 (4H, m), 4.88 (1H, s), 7.15-7.29 (4H, m); MS m/e MH$^+$ 377.

iv) Diethyl [4-(4-oxocyclohexyl)phenyl]malonate

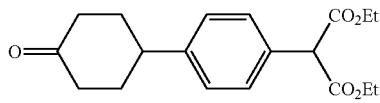

Aqueous HCl (1.15 mL of a 2M solution) was added to a stirred solution of diethyl [4-(1,4-dioxaspiro[4.5]dec-8-yl)phenyl]malonate (290 mg, 0.77 mmol) in 4 mL THF. The mixture was stirred for 64 h then was partitioned between water and EtOAc. The organic phase was separated and the aqueous further extracted with EtOAc. The organics were combined and dried then concentrated by evaporation to give the title compound (249 mg, 97%) as a gum; $^1$H NMR δ 1.18 (6H, t), 1.82-1.93 (2H, m), 2.06-2.11 (2H, m), 2.26-2.29 (2H, m), 2.54-2.63 (2H, m), 3.04-3.10 (1H, m), 4.08-4.21 (4H, m), 4.88 (1H, s), 7.31 (4H, s); MS m/e M+Na$^+$ 355.

v) Diisopropyl [4-(4-aminocyclohexyl)phenyl]malonate

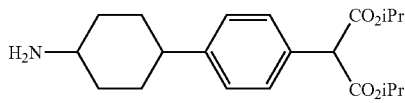

Titanium tetra(isopropoxide) (426 mg, 1.5 mmol) was added to a solution of diethyl [4-(4-oxocyclohexyl)phenyl]malonate (249 mg, 0.75 mmol) in a 2M solution of ammonia in isopropanol (1.88 mL, 3.75 mmol) and the reaction mixture was stirred for 64 h. Sodium borohydride (43 mg, 1.125 mmol) was added and the mixture was stirred for 4 h then aqueous ammonia (1 mL concentrated ammonia in 4 mL water) was added. The mixture was filtered and the filtrate was separated and the aqueous phase further extracted with EtOAc (2×20 mL). The organic phase was dried and solvent was removed by evaporation to give the title compound (116 mg, 46%) as a gum; $^1$H NMR δ 1.14-1.23 (m, 12H), 1.35-2.65 (m, 10H), 4.73-4.79 (m, 1H), 4.87-5.01 (m, 2H), 7.08-7.38 (m, 4H); MS m/e MH$^+$ 362.

vi) Following the general procedure of Example 72 except using diisopropyl [4-(4-aminocyclohexyl)phenyl]malonate as the amine in place of [4-(4-isopropylpiperazin-1-yl)phenyl]amine, the title compound (Intermediate 96) was obtained as a solid; MS m/e MH$^+$ 567.

Intermediate 97: 2-Hydrazino-2-oxo-N-[4-(propylsulphonyl)phenyl]acetamide

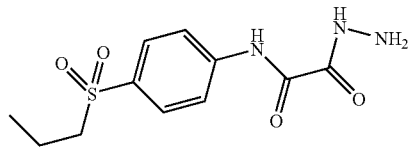

i) Methyl oxo[{4-(propylsulphonyl)phenyl]amino}acetate

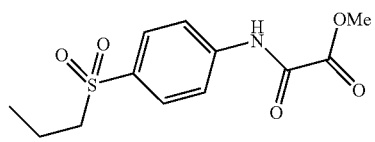

The procedure described for Intermediate 43 (part iii) was followed except that the aniline used was 4-(propylsulphonyl)aniline (prepared as described in Helv. Chim. Acta 1983, 66(4), 1046), to give the title compound; $^1$H NMR δ 11.27 (s, 1H), 8.02 (d, 2H), 7.87 (d, 2H), 3.93 (s, 3H), 3.19-3.27 (m, 2H), 1.48-1.63 (m, 2H), 0.85-0.97 (m, 3H); MS m/e MH$^+$ 286.

ii) The procedure described for Intermediate 43 (part iv) was followed starting with methyl oxo{[4-(propylsulphonyl)phenyl]amino}acetate to give the title compound (Intermediate 97); $^1$H NMR δ 0.85-0.97 (m, 3H), 1.46-1.65 (m, 2H), 3.18-3.27 (m, 2H), 4.77 (s, 2H), 7.85 (d, 2H), 8.10 (d, 2H), 10.44 (s, 1H), 11.09 (s, 1H); MS m/e MH$^+$ 286.

Intermediate 98: Methyl 2-({4-[({5-[(2-fluorophenyl)amino]-1,3,4-oxadiazol-2-yl}carbonyl)amino]phenyl}sulphonyl)-2-methylpropanoate

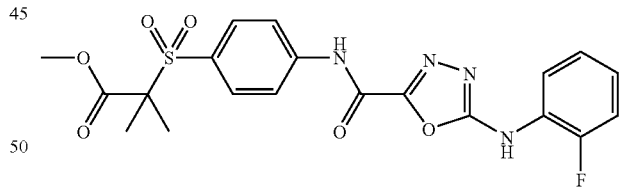

i) Methyl 2-[(4-aminophenyl)sulphonyl]-2-methylpropanoate

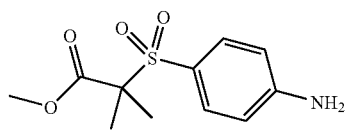

The general procedure described for Intermediate 77 (part ii) was followed, except the starting material was methyl 2-methyl-2-[(4-nitrophenyl)sulphonyl]propanoate (CAS Reg. No. 364044-08-6), to give the title compound; ¹H NMR δ 1.44 (s, 6H), 3.60 (s, 3H), 6.27 (s, 2H), 6.63 (d, 2H), 7.33 (d, 2H); MS m/e (M+Na)+281.

ii) Methyl 2-[(4-{[methoxy(oxo)acetyl]amino}phenyl)sulphonyl]-2-methylpropanoate

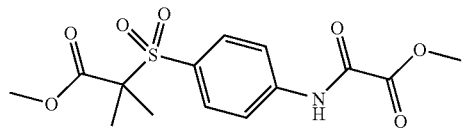

The procedure described for Intermediate 43 (part iii) was followed except that the aniline used was methyl 2-[(4-aminophenyl)sulphonyl]-2-methylpropanoate, to give the title compound; ¹H NMR δ 1.57 (s, 6H), 3.67 (s, 3H), 3.94 (s, 3H), 7.80 (d, 2H), 8.06 (d, 2H), 11.32 (s, 1H); MS m/e MH⁺ 344.

iii) Methyl 2-[(4-{[hydrazino(oxo)acetyl]amino}phenyl)sulphonyl]-2-methylpropanoate

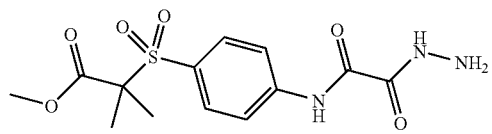

The procedure described for Intermediate 43 (part iv) was followed starting with methyl 2-[(4-{[methoxy(oxo)acetyl]amino}phenyl)sulphonyl]-2-methylpropanoate to give the title compound; ¹H NMR δ 1.56 (s, 6H), 3.67 (s, 3H), 4.77 (s, 2H), 7.77 (d, 2H), 8.11 (d, 2H); MS m/e (M+Na)⁺ 366.

iv) The procedure described for Example 105 was followed starting with methyl 2-[(4-{[hydrazino(oxo)acetyl]amino}phenyl)sulphonyl]-2-methylpropanoate to give the title compound (Intermediate 98); ¹H NMR δ 1.54 (s, 6H), 3.65 (s, 3H), 7.12-7.20 (m, 1H), 7.23-7.35 (m, 2H), 7.78 (d, 2H), 8.03 (t, 1H), 8.10 (d, 2H), 10.89 (s, 1H), 11.57 (s, 1H); MS m/e MH⁺ 463.

Intermediate 99: trans-Ethyl 2-[4-(4-{[hydrazino(oxo)acetyl]amino}phenyl)cyclohexyl]propanoate

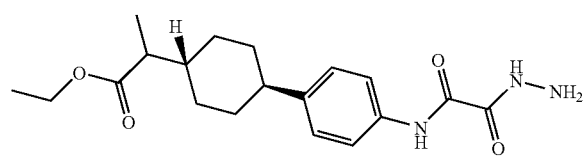

i) Ethyl 2-[4-(4-hydroxyphenyl)cyclohexylidene]propanoate

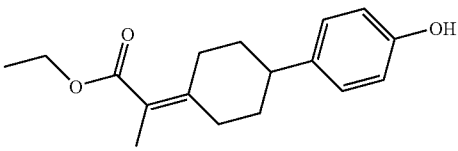

A solution of triethylphosphonopropionate (12.5 g, 52.6 mmol) in THF (10 mL) was added in one portion to a stirred mixture of sodium hydride (60% in mineral oil, 2.3 g, 57.6 mmol) in THF (75 mL) and the reaction mixture was stirred at 11° C. under an argon atmosphere for 1 h. In a separate flask tetramethylguanidine (6.61 g, 57.4 mmol) was added in one portion to a solution of 4-(4-hydroxyphenyl)cyclohexanone (9.1 g, 47.8 mmol) in THF (40 mL) at 10° C. under an argon atmosphere and the stirred mixture was warmed to room temperature over 1 h. This mixture was added in one portion to the triethylphosphonopropionate mixture at 10° C. and the combined reaction mixture was warmed to ambient temperature and stirred for 18 h under an argon atmosphere. A saturated aqueous solution of ammonium chloride (75 mL) and EtOAc (100 mL) were added. The layers were separated and the aqueous layer was extracted with EtOAc (100 mL). The combined organic layers were dried and concentrated in vacuo to leave a residue. The residue was triturated with a mixture of ether and isohexane (2:1), filtered and the filtrate was concentrated in vacuo to give the title compound (6.9 g, 53%) as a solid; ¹H NMR δ 1.21 (3H, t), 1.33-1.5 (2H, m), 1.78-2.1 (4H, m), 1.84 (3H, s), 2.6-2.78 (2H, m), 2.99-3.09 (1H, m), 4.12 (2H, q), 6.67 (2H, d), 7.02 92H, d), 9.08 (1H, s); MS m/e MH⁺ 275.

ii) trans-Ethyl 2-[4-(4-hydroxyphenyl)cyclohexyl]propanoate

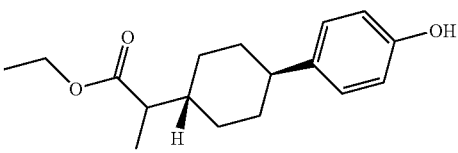

10% Palladium on carbon (250 mg) was added in one portion to a stirred solution of ethyl 2-[4-(4-hydroxyphenyl)cyclohexylidene]propanoate (6.9 g, 25.3 mmol) in EtOAc (50 mL) and the reaction mixture was stirred under a hydrogen atmosphere for 24 h. The reaction mixture was filtered and concentrated in vacuo to give a solid that was recrystallised from a mixture of isohexane and EtOAc (10:1) to give the title compound (2.2 g, 32%) as a solid; ¹H NMR δ (CDCl₃) 1.0-1.3 (2H, m), 1.08 (3H, d), 1.2 (3H, t), 1.3-1.45 (2H, m), 1.45-1.64 (2H, m), 1.65-1.75 (1H, m), 1.77-1.9 (3H, m), 2.15-2.26 (1H, m), 2.28-2.39 (1H, m), 4.1 (2H, q), 6.68 (2H, d), 7.0 (2H, d).

iii) trans-Ethyl 2-[4-(4-{[(trifluoromethyl)sulfonyl]oxy}phenyl)cyclohexyl]propanoate

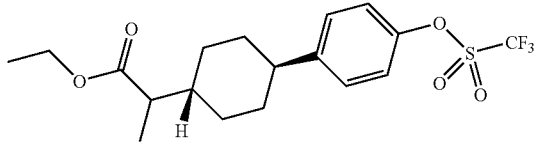

Ethyldiisopropylamine (1.6 mL) and N-phenyltrifluoromethanesulfonimide (4.12 g, 11.5 mmol) was added sequentially, each in portions over 1 minute, to a stirred solution of trans-ethyl 2-[4-(4-hydroxyphenyl)cyclohexyl]propanoate (2.6 g, 9.23 mmol) in DCM (25 mL) at 5° C. The reaction mixture was warmed to room temperature and stirred for 18 h and then an aqueous solution of sodium hydroxide (2M, 30 mL) was added. The layers were separated and the organic layer was washed with $H_2O$ (30 mL), dried and concentrated in vacuo to leave a residue. The residue was purified by column chromatography, eluting with 0-20% EtOAc in isohexane as eluent, to give the title compound (3.6 g, 96%) as an oil; $^1$H NMR δ ($CDCl_3$) 1.0-1.25 (2H, m), 1.1 (3H, d), 1.2 (3H, t), 1.3-1.45 (2H, m), 1.5-1.64 (2H, m), 1.7-1.79 (1H, m), 1.8-1.95 (3H, m), 2.17-2.28 (1H, m), 2.38-2.48 (1H, m), 4.1 (2H, q), 7.1 (2H, d), 7.2 (2H, d).

iv) trans-Ethyl 2-(4-{4-[(diphenylmethylene)amino]phenyl}cyclohexyl)propanoate

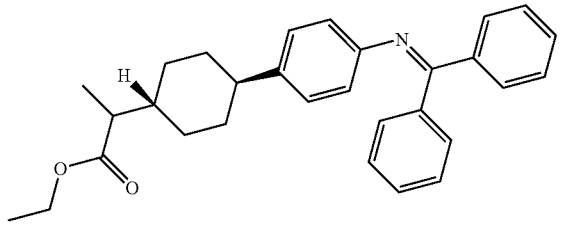

Caesium carbonate (4.0 g, 12.4 mmol), R-BINAP (330 mg, 0.53 mmol), palladium acetate (119 mg, 0.53 mmol) and benzophenone imine (2.2 mL, 13.2 mmol) were added sequentially, each in one portion, to a stirred solution of trans-ethyl 2-[4-(4-{[(trifluoromethyl)-sulfonyl]oxy}phenyl)cyclohexyl]propanoate in THF (50 mL) and the reaction mixture was heated at 65° C. for 70 h under an argon atmosphere. The reaction mixture was cooled to room temperature and concentrated in vacuo to leave a residue. The residue was taken up in EtOAc (75 mL) and $H_2O$ (25 mL) was added. The layers were separated and the organic layer was extracted with brine (25 mL), dried and concentrated in vacuo to leave a residue. The residue was purified by chromatography, eluting with 10-50% EtOAc in isohexane, to give the title compound (2.3 g, 59%) as an oil; $^1$H NMR δ ($CDCl_3$) 1.07-1.25 (2H, m), 1.15 (3H, d), 1.3 (3H, t), 1.35-1.5 (2H, m), 1.55-1.7 (2H, m), 1.72-1.8 (1H, m), 1.83-1.95 (2H, m), 2.24-2.43 (2H, m), 4.15 (2H, q), 6.7 (2H, d), 7.0 (2H, d), 7.15 (2H, d), 7.23-7.35 (1H, m), 7.4 (2H, dd), 7.47-7.55 (2H, m), 7.78 (2H, d), 7.84 (1H, d); MS m/e $MH^+$ 440.

v) trans-Ethyl 2-[4-(4-aminophenyl)cyclohexyl]propanoate

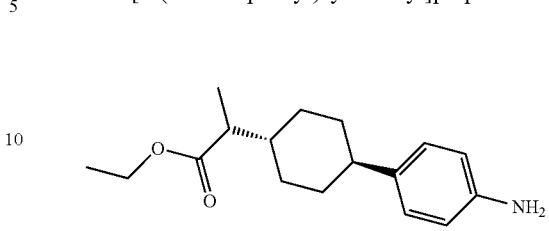

10% Palladium on carbon (500 mg) was added in one portion to a stirred solution of trans-ethyl 2-(4-{4-[(diphenylmethylene)amino]phenyl}cyclohexyl)propanoate (2.3 g, 5.23 mmol) in ethanol (50 mL) and the reaction mixture was stirred under a hydrogen atmosphere for 6 h. The reaction mixture was filtered and concentrated in vacuo to leave an oil. The oil was purified by chromatography, using 20-50% EtOAc in isohexane as eluent, to give the title compound (1.0 g, 71%) as an oil; $^1$H NMR δ ($CDCl_3$) 0.9-1.1 (2H, m), 0.95 (3H, d), 1.1 (3H, t), 1.18-1.32 (2H, m), 1.38-1.5 (1H, m), 1.54-1.64 (1H, m), 1.65-1.8 (3H, m), 2.04-2.15 (1H, m), 2.18-2.3 (1H, m), 3.98 (2H, q), 6.8 (2H, d), 6.92 (2H, d); MS m/e $MH^+$ 276.

vi) trans-Ethyl 2-[4-(4-{[methoxy(oxo)acetyl]amino}phenyl)cyclohexyl]propanoate

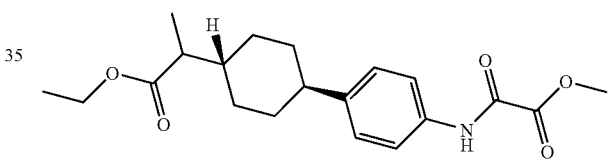

A solution of methyl chlorooxoacetate (670 mg, 5.45 mmol) in DCM (3 mL) was added in one portion to a solution of trans-ethyl 2-[4-(4-aminophenyl)cyclohexyl]propanoate (1.0 g, 3.63 mmol) and pyridine (0.59 mL, 7.26 mmol) in DCM (22 mL) at 5° C. and the mixture was warmed to room temperature and stirred for 2 h. The reaction mixture was concentrated in vacuo and EtOAc (30 mL) was added. The layers were separated and the organic layer was washed with water (25 mL) and brine (25 mL). The organic layer was dried and concentrated in vacuo to give the title compound (1.3 g, 99%) as a solid; $^1$H NMR δ ($CDCl_3$) 1.0-1.1.25 (2H, m), 1.1 (3H, d), 1.2 (3H, t), 1.3-1.47 (2H, m), 1.48-1.55 (2H, m), 1.68-1.79 (1H, m), 1.8-1.95 (2H, m), 2.18-2.28 (1H, m), 2.35-2.5 (1H, m), 3.9 (3H, t), 4.08 (2H, q), 7.12 (2H, d), 7.47 (2H, d); MS m/e $(M-H)^-$ 360.

vii) Hydrazine hydrate (229 mg, 4.57 mmol) was added in one portion to a stirred solution of trans-ethyl 2-[4-(4-{[methoxy(oxo)acetyl]amino}phenyl)cyclohexyl]propanoate (1.3 g, 3.6 mmol) in ethanol (25 mL) and the reaction mixture was stirred at room temperature for 18 h. The mixture was filtered to leave a solid, which was washed with ethanol (10 mL) to give the title compound (Intermediate 99) (1.2 g, 92%) as a solid; $^1$H NMR δ 1.07 (3H, d), 1.1-1.3 (2H, m), 1.2 (3H, t), 1.36-1.5 (2H, m), 1.5-1.63 (1H, m), 1.65-1.72 (1H, m), 1.75-1.88 (3H, m), 2.2-2.32 (1H, m), 2.35-2.49 (1H, m), 4.0-4.17 (2H, m), 4.6 (2H, s), 7.19 (2H, d), 7.7 (2H, d), 10.44 (1H, s); MS m/e $MH^+$ 362.

Intermediate 100: N-(3,5-dichloro-4-morpholin-4-ylphenyl)-2-hydrazino-2-oxoacetamide

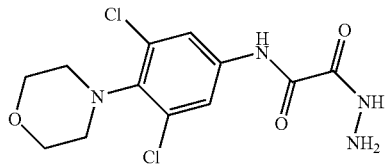

i) (3,5-Dichloro-4-morpholin-4-ylphenyl)amine

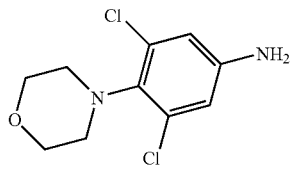

Following the general procedure of Intermediate 36 using 4-(2,6-dichloro-4-nitrophenyl)morpholine (prepared as described in J. Med. Chem., 1980, 23(10), 1083) the title compound was obtained; $^1$H NMR δ 3.01 (4H, t), 3.64 (4H, t), 5.50 (1H, broad s), 6.57 (2H, s); MS m/e MH$^+$ 247.

ii) Methyl [(3,5-dichloro-4-morpholin-4-ylphenyl)amino](oxo)acetate

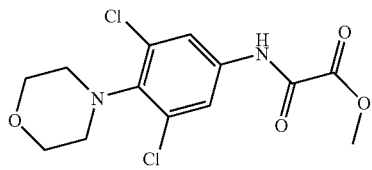

Following the general procedure of Intermediate 1, using pyridine as base and 4-(2,6-dichloro-4-nitrophenyl)morpholine, the title compound was obtained; $^1$H NMR δ 3.09 (4H, t), 3.67 (4H, t), 3.84 (3H, s), 7.85 (2H, s), 10.98 (1H, s); MS m/e MH$^+$ 333.

iii) Following the general procedure of Intermediate 18, using methyl [(3,5-dichloro-4-morpholin-4-ylphenyl)amino](oxo)acetate as starting material, the title compound (Intermediate 100) was obtained; $^1$H NMR δ 3.08 (4H, t), 3.67 (4H, t), 4.62 (2H, s), 7.93 (2H, s), 10.31 (1H, broad s), 10.83 (1H, broad s); MS m/e MH$^+$ 333.

Intermediate 101: 5-[(2-Fluorophenyl)amino]-N-piperidin-4-yl-1,3,4-oxadiazole-2-carboxamide

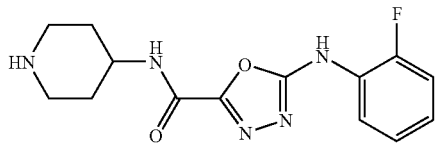

i) tert-Butyl 4-[({5-[(2-fluorophenyl)amino]-1,3,4-oxadiazol-2-yl}carbonyl)amino]piperidine-1-carboxylate

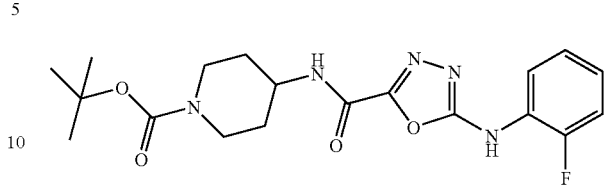

A suspension of ethyl 5-[(2-fluorophenyl)amino]-1,3,4-oxadiazole-2-carboxylate (intermediate 40) (102 mg, 0.41 mmol) and tert-butyl-4-aminopiperidine-1-carboxylate (81 mg, 0.41 mmol) was heated to 85° C. for 18 hours. Upon cooling the solid was filtered and washed with EtOH (10 mL), Et$_2$O (10 mL) then hexane (10 mL) to leave the title compound (123 mg, 74%) as a white solid; $^1$H NMR δ 1.41 (9H, s), 1.46-1.54 (2H, m), 1.73-1.76 (2H, m), 2.81 (2H, s), 3.93-3.96 (3H, m), 7.13-7.17 (1H, m), 7.23-7.32 (2H, m), 7.99-8.04 (1H, m), 9.02 (1H, d), 10.63 (1H, s); MS m/e (M−H)$^−$ 404.

ii) tert-Butyl 4-[({5-[(2-fluorophenyl)amino]-1,3,4-oxadiazol-2-yl}carbonyl)amino]piperidine-1-carboxylate (5.66 g, 13.96 mmol) was suspended in 4M HCl in 1,4-dioxane (50 ml) and stirred for 18 hours. After removal of the solvent in vacuo the residue was partitioned between MeOH:DCM (1:9) (500 mL) and 2M aqueous potassium carbonate (500 mL). The aqueous was extracted with MeOH:DCM (1:9) (7×50 mL) and the combined organics dried (Na$_2$SO$_4$), filtered and concentrated in vacuo. The solid was triturated with hot Et$_2$O (20 mL), filtered then washed with Et$_2$O (20 mL), hexane (20 mL) to leave the title product (Intermediate 101, 2.80 g, 66%) as a beige powder; $^1$H NMR δ 1.44-1.57 (2H, m), 1.66-1.74 (2H, m), 2.47-2.59 (2H, m), 2.94-3.02 (2H, m), 3.74-3.86 (1H, m), 7.04-7.11 (1H, m), 7.17-7.28 (2H, m), 7.96-8.04 (1H, m), 8.92 (1H, d); MS m/e (MH)$^+$ 306.

Intermediate 102: Methyl (6-{4-[({5-[(2-fluorophenyl)amino]-1,3,4-oxadiazol-2-yl}carbonyl)amino]piperidin-1-yl}pyridin-3-yl)acetate

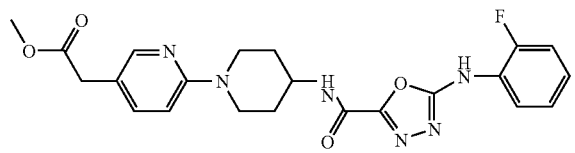

i) Methyl (6-chloro-1-oxidopyridin-3-yl)acetate

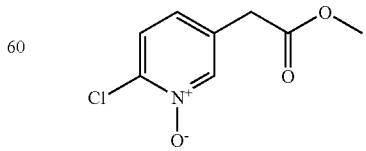

Hydrogen peroxide (0.409 mL of a 30% aqueous solution, 3.6 mmol) was added slowly to a stirred solution of trifluoroacetic anhydride (0.915 mL, 6.55 mmol) in DCM (5 mL) with heating under reflux. After 30 min, methyl (6-chloropyridin-3-yl)acetate (Indian Journal of Chemistry, Section B: Organic Chemistry Including Medicinal Chemistry (2004), 43B(4), 864) (608 mg, 3.28 mmol) was added as a solution in DCM (5 mL). The reaction mixture was stirred under reflux for 1 h and then allowed to cool with stirring for 16 h. Solid potassium carbonate was added until there was no more effervescence then the mixture was filtered, concentrated by evaporation and the resultant oil was triturated with Et$_2$O to give the title compound (291 mg, 44%) as a solid; $^1$H NMR δ 3.64 (s, 3H), 3.79 (s, 2H), 7.30 (d, 1H), 7.75 (d, 1H), 8.45 (s, 1H); MS m/e MH$^+$ 202.

ii) Methyl (6-{4-[({5-[(2-fluorophenyl)amino]-1,3,4-oxadiazol-2-yl}carbonyl)amino]piperidin-1-yl}-1-oxidopyridin-3-yl)acetate

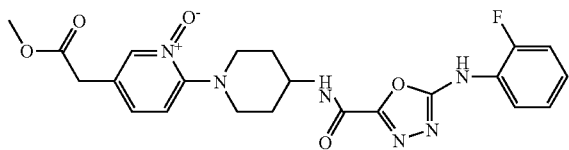

5-[(2-Fluorophenyl)amino]-N-piperidin-4-yl-1,3,4-oxadiazole-2-carboxamide (Intermediate 101) (100 mg, 0.33 mmol) and methyl (6-chloro-1-oxidopyridin-3-yl)acetate (67 mg, 0.33 mmol) were heated with sodium hydrogen carbonate (56 mg, 0.66 mmol) in 2-methyl-2-butanol (4 mL) at 100° C. for 22 h. The reaction mixture was concentrated by evaporation and the residue was dissolved in DMSO then filtered and purified by preparative HPLC to give the title compound (50 mg, 32%) as a gum; $^1$H NMR δ 1.94-1.74 (m, 4H), 2.58-2.43 (m, 2H), 2.95-2.84 (m, 2H), 3.65 (s, 3H), 4.07-3.93 (m, 3H), 7.21-7.12 (m, 2H), 7.35-7.23 (m, 2H), 7.45-7.40 (m, 1H), 8.06-7.98 (m, 1H), 8.25-8.20 (m, 1H), 9.13 (d, 1H), 10.64 (s, 1H); MS m/e MH$^+$ 471.

iii) Methyl (6-{4-[({5-[(2-fluorophenyl)amino]-1,3,4-oxadiazol-2-yl}carbonyl)amino]piperidin-1-yl}-1-oxidopyridin-3-yl)acetate (40 mg, 0.09 mmol) was stirred in THF (1.3 mL) at room temperature and water (1.3 mL) was added. Ammonium chloride (334 mg, 6.24 mmol) was added to the mixture followed by Zn dust (26 mg, 0.38 mmol). The reaction mixture was stirred overnight before diluting with 2 mL DMSO and filtering. The filtrate was purified by preparative HPLC to yield the title compound (Intermediate 102) as a gum; MS m/e MH$^+$ 455.

Intermediate 103: 3-[(5-{[(6-morpholin-4-ylpyridin-3-yl)amino]carbonyl}-1,3,4-oxadiazol-2-yl)amino]benzoic acid

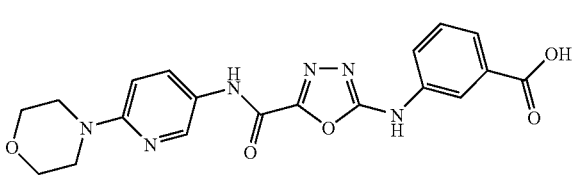

i) tert-butyl 3-[(5-{[(6-morpholin-4-ylpyridin-3-yl)amino]carbonyl}-1,3,4-oxadiazol-2-yl)amino]benzoate

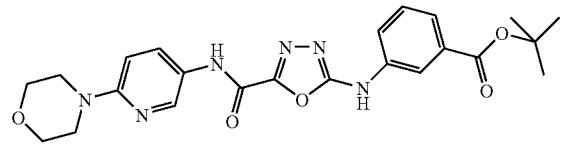

Prepared from tert-butyl 3-isothiocyanatobenzoate and Intermediate 27 by the method of Example 1. $^1$H NMR δ 1.57 (9H, s), 3.42 (4H, t), 3.71 (4H, t), 6.86-6.88 (1H, m), 7.52 (1H, t), 7.58-7.61 (1H, m), 7.82-7.85 (1H, m), 7.95-7.98 (1H, m), 8.25 (1H, t), 8.53 (1H, d), 10.97 (1H, s), 11.17 (1H, s); MS m/e (MH)$^+$ 467 ii) 3-[(5-{[(6-morpholin-4-ylpyridin-3-yl)amino]carbonyl}-1,3,4-oxadiazol-2-yl)amino]benzoic acid 4M HCl in 1,4-dioxane (70 mL) was added to tert-butyl 3-[(5-{[(6-morpholin-4-ylpyridin-3-yl)amino]carbonyl}-1,3,4-oxadiazol-2-yl)amino]benzoate (3.22 g, 6.90 mmol) and the suspension stirred for 18 hours. All volatiles were removed in vacuo and the residue triturated with Et$_2$O (20 mL), the solid filtered, washed with Et$_2$O (2×10 mL), hexane (2×10 mL) to give the title compound (2.80 g, 99%) as a cream powder; MS m/e (MH)$^+$ 411

Intermediate 104: tert-butyl {[trans-4-(4-{[hydrazino(oxo)acetyl]amino}phenyl)cyclohexyl]methyl}carbamate

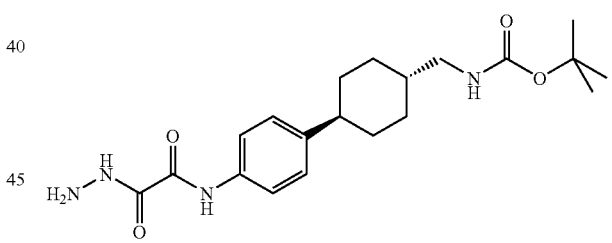

i) Methyl [trans-4-(4-{[[(benzyloxy)carbonyl]amino}phenyl)cyclohexyl]acetate

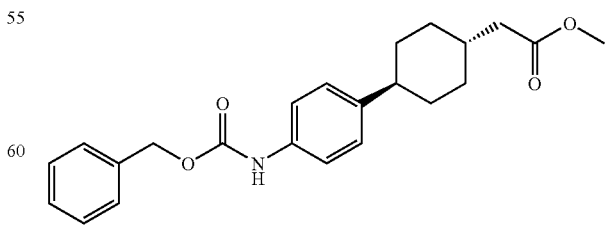

To a solution of Intermediate 43 (3.31 g, 13.40 mmol) in dry pyridine (18 mL) under an inert atmosphere at 0° C. was added benzyl chloroformate (2.30 mL, 16.08 mmol) then allowed to warm to ambient temperature and stirred for 18 hours. After concentrating in vacuo the residue was partitioned between Et₂O (150 mL) and 1M aqueous HCl (20 mL). The organic phase was dried (MgSO₄), filtered and evaporated to a yellow solid. Purification by chromatography through silica gave the title compound (3.50 g, 68%) as an off white solid; ¹H NMR (CDCl₃) δ1.03-1.12 (2H, m), 1.35-1.46 (2H, m), 1.74-1.82 (5H, m), 2.17-2.18 (2H, m), 2.33-2.39 (1H, m), 3.61 (3H, s), 5.12 (2H, s), 6.50 (1H, s), 7.06 (2H, d), 7.19-7.34 (7H, m)

ii) [trans-4-(4-{[(Benzyloxy)carbonyl]amino}phenyl)cyclohexyl]acetic acid

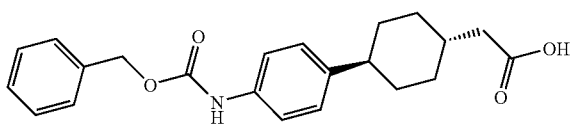

To a solution of methyl [trans-4-(4-{[(benzyloxy)carbonyl]amino}phenyl)cyclohexyl]acetate (3.34 g, 8.76 mmol) in THF (42 mL) and MeOH (42 mL) was added 0.6M aqueous lithium hydroxide (43.6 mL, 26.27 mmol) and the mixture stirred at ambient temperature for 18 hours. The mixture was partitioned between EtOAc (200 mL) and 1M HCl (100 mL). The organic phase was concentrated in vacuo and the residue partitioned between EtOAc (300 mL) and brine (20 mL). The organic phase was dried (MgSO4), filtered and evaporated to give the title compound (3.19 g, 99%) as a white solid; ¹H NMR (CDCl₃) δ 1.05-1.15 (2H, m), 1.36-1.46 (2H, m), 1.74-1.87 (5H, m), 2.22 (2H, d), 2.34-2.41 (1H, m), 5.13 (2H, s), 6.58 (1H, s), 7.07 (2H, d), 7.21 (3H, t), 7.28-7.35 (4H, m); MS m/e (MH)⁺ 368 iii) Benzyl [4-(trans-4-{[(tert-butoxycarbonyl)amino]methyl}cyclohexyl)phenyl]carbamate

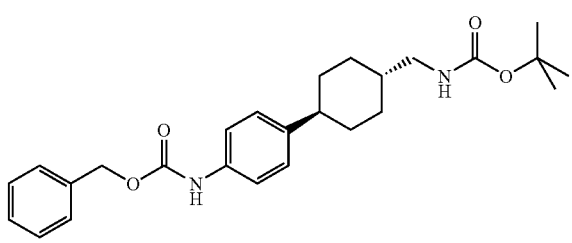

To a suspension of [trans-4-(4-{[(benzyloxy)carbonyl]amino}phenyl)cyclohexyl]acetic acid (516 mg, 1.40 mmol) in tert-butanol (3 mL) under an inert atmosphere was added triethylamine (0.45 mL, 3.23 mmol) and diphenyl phosphorylazide (0.70 mL, 3.23 mmol) and the mixture heated to 80° C. for 24 hours. Upon cooling the mixture was partitioned between EtOAc (100 mL) and H₂O (20 mL). The aqueous phase was further extracted with DCM (2×20 mL) and the combined organics dried (MgSO₄), filtered and evaporated. Purification by chromatography through silica gave the title compound (525 mg, 86%) as a white solid. ¹H NMR (CDCl₃) δ 0.96-1.07 (2H, m), 1.30-1.44 (12H, m), 1.78-1.85 (4H, m), 2.33-2.39 (1H, m), 2.94 (2H, t), 4.52 (1H, s), 5.12 (2H, s), 6.51 (1H, s), 7.04-7.07 (2H, m), 7.19-7.34 (7H, m)

iv) tert-Butyl {[trans-4-(4-aminophenyl)cyclohexyl]methyl}carbamate

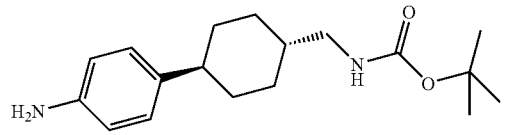

Benzyl [4-(trans-4-{[(tert-butoxycarbonyl)amino]methyl}cyclohexyl)phenyl]carbamate (0.50 g, 1.14 mmol) in EtOH (10 mL) and EtOAc (10 mL) was hydrogenated over 10% Pd/C (100 mg) at ambient pressure and 40° C. After 2 hours the catalyst was removed by filtration and the solution concentrated in vacuo to leave the title compound (320 mg, 86%) as a white solid; ¹H NMR δ 0.95-1.02 (2H, m), 1.25-1.39 (12H, m), 1.73-1.75 (4H, m), 2.22-2.25 (1H, m), 2.80 (2H, t), 4.75 (2H, s), 6.46-6.49 (2H, m), 6.78 (1H, t), 6.85 (2H, d)

v) Methyl {[4-(trans-4-{[(tert-butoxycarbonyl)amino]methyl}cyclohexyl)phenyl]amino}(oxo)acetate

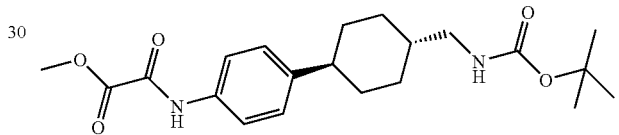

Prepared from tert-butyl {[trans-4-(4-aminophenyl)cyclohexyl]methyl}carbamate and methyl chlorooxoacetate by method described for Intermediate 1, method D3.

¹H NMR (CDCl₃) δ1.08-1.18 (2H, m), 1.41-1.52 (12H, m), 1.93 (4H, t), 2.46-2.53 (1H, m), 3.05 (2H, t), 4.00 (3H, s), 4.63 (1H, s), 7.23 (2H, d), 7.57 (2H, d), 8.81 (1H, s)

vi) tert-Butyl {[trans-4-(4-{[hydrazino(oxo)acetyl]amino}phenyl)cyclohexyl]methyl}carbamate Prepared using hydrazine hydrate in EtOH from methyl {[4-(trans-4-{[(tert-butoxycarbonyl)amino]methyl}cyclohexyl)phenyl]amino}(oxo)acetate as described for Intermediate 18.1 ¹H NMR δ 0.99-1.06 (2H, m), 1.37-1.42 (12H, m), 1.77-1.80 (4H, m), 2.39-2.49 (1H, m), 2.81 (2H, t), 4.60 (2H, s), 6.80 (1H, t), 7.19 (2H, d), 7.68 (2H, d), 10.21 (1H, s), 10.45 (1H, s)

Intermediate 105: Methyl 2-[trans-4-(4-{[hydrazino(oxo)acetyl]amino}phenyl)-cyclohexyl]-2-methylpropanoate

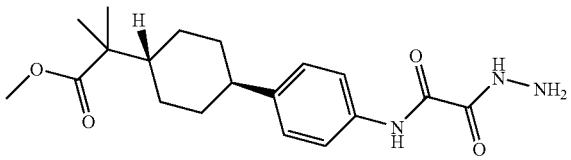

i) Methyl 2-[trans-4-(4-{[tert-butyl(dimethyl)silyl]oxy}phenyl)cyclohexyl]propanoate

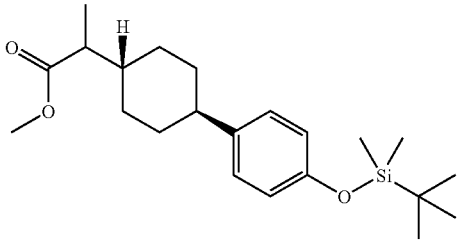

A solution of tert-butyl dimethylsilylchloride (7.29 g, 48.3 mmol) in DMA (80 mL) was added dropwise to a stirred solution of methyl [trans-4-(4-hydroxyphenyl)cyclohexyl] acetate (prepared as described in Patent Application WO2004/047755) (10.0 g, 40.3 mmol) and imidazole (6.86 g, 100.7 mmol) and the reaction mixture was stirred at room temperature for 20 h. Ethyl acetate (250 mL) was added and the mixture was washed with $H_2O$ (6×30 mL) and brine. The organic layer was dried ($MgSO_4$) and concentrated in vacuo to leave the silyl-protected phenol as a colourless oil, which was used with no further purification.

A solution of lithium diisopropylamide (14.9 mmol) in THF (10 mL) was added dropwise to a stirred solution of the crude silyl-protected phenol (5.43 g, 14.9 mmol) in THF (50 mL) at −78° C. under an argon atmosphere and the mixture was warmed to 0° C. The mixture was cooled to −78° C. and methyl iodide (0.98 mL, 15.7 mmol) was added dropwise. The reaction mixture was warmed to room temperature and stirred for 20 h. Saturated aqueous ammonium chloride (50 mL) and ethyl acetate were added sequentially, both in one portion. The organic layer was separated and washed with $H_2O$ and brine, dried ($MgSO_4$) and concentrated in vacuo to leave an oil. The oil was purified by column chromatography, using a gradient of 10-25% ethyl acetate:isohexane was eluent, to give the title compound (5.0 g, 89%) as a colourless oil; $^1$H NMR δ 0.0 (6H, s), 0.8 (9H, s), 0.9-1.08 (2H, m), 0.97 (3H, d), 1.18-1.32 (2H, m), 1.37-1.5 (2H, m), 1.52-1.62 (1H, m), 1.66-1.8 (2H, m), 2.08-2.28 (2H, m), 3.5 (3H, s), 6.57 (2H, d), 6.86 (2H, d).

ii) Methyl 2-[trans-4-(4-{[tert-butyl(dimethyl)silyl]oxy}phenyl)cyclohexyl]-2-methylpropanoate

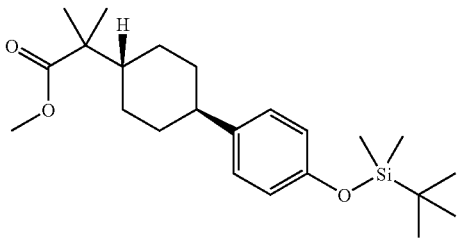

A solution of lithium diisopropylamide (12.9 mmol) in THF (20 mL) was added dropwise to a stirred solution of methyl 2-[trans-4-(4-{[tert-butyl(dimethyl)silyl]oxy}phenyl)cyclohexyl]-propanoate (4.42 g, 11.7 mmol) in THF (40 mL) at −78° C. under an argon atmosphere and the mixture was warmed to room temperature. The mixture was cooled to −78° C. and methyl iodide (0.92 mL, 14.7 mmol) was added dropwise. The reaction mixture was warmed to room temperature and stirred for 20 h. Saturated aqueous ammonium chloride (100 mL) and ethyl acetate were added sequentially, both in one portion. The organic layer was separated and washed with $H_2O$ and brine, dried ($MgSO_4$) and concentrated in vacuo to leave an oil. The oil was purified by column chromatography, using a gradient of 0-15% ethyl acetate:isohexane was eluent, to give the title compound (4.0 g, 87%) as a colourless oil; $^1$H NMR δ 0.0 (6H, s), 0.8 (9H, s), 0.98 (6H, s), 1.0-1.1 (2H, m), 1.18-1.31 (2H, m), 1.45-1.56 (3H, m), 1.7-1.8 (2H, m), 2.15-2.28 (1H, m), 3.5 (3H, s), 6.55 (2H, d), 6.85 (2H, d).

iii) Methyl 2-methyl-2-[trans-4-(4-{[(trifluoromethyl)sulfonyl]oxy}phenyl)cyclohexyl]-propanoate

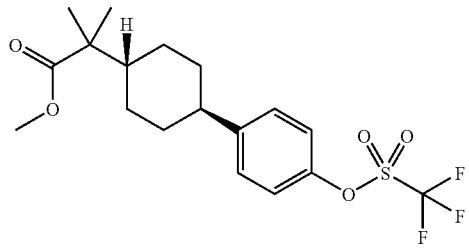

A solution of tetrabutylammonium fluoride (1M in THF, 11.3 mL, 11.3 mmol) was added in one portion to a stirred solution of methyl 2-[trans-4-(4-{[tert-butyl(dimethyl)silyl]oxy}-phenyl)cyclohexyl]-2-methylpropanoate (4.0 g, 10.2 mmol) in THF (40 mL) and the reaction mixture was stirred at room temperature for 18 h. Ethyl acetate (75 mL) was added and the mixture was washed with $H_2O$ (2×50 mL) and brine. The organic layer was dried ($MgSO_4$) and concentrated in vacuo to leave the crude phenol as an oil, which was used with no further purification.

N-Phenyltrifluoromethanesulfinimide (6.47 g, 18.1 mmol) was added portionwise over 1 min to a stirred solution of the crude phenol (4.0 g, 14.5 mmol) and DIPEA (2.52 mL, 14.5 mmol) in DCM (70 mL) at 10° C. The reaction mixture was stirred at room temperature for 18 h and then a 2N aqueous solution of NaOH (100 mL) was added. The layers were separated and the organic layer was washed with $H_2O$ and then passed through a phase separation cartridge and concentrated in vacuo to leave an oil. The oil was purified by column chromatography, eluting with 0-20% ethyl acetate in isohexane, to give the title compound (4.57 g, 77%) as a colourless oil; $^1$H NMR δ 1.15 (6H, s), 1.17-1.3 (2H, m), 1.38-1.52 (2H, m), 1.63-1.39 (3H, m), 1.9-2.0 (2H, m), 2.43-2.56 (1H, m), 3.68 (3H, s), 7.18 (2H, d), 7.27 (2H, d).

(iv) Methyl 2-[trans-4-(4-aminophenyl)cyclohexyl]-2-methylpropanoate

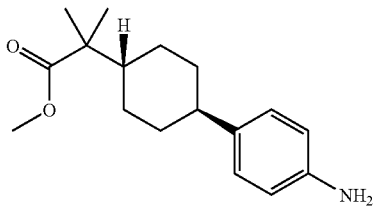

Caesium carbonate (5.11 g, 15.7 mmol), R-BINAP (420 mg, 0.67 mmol), palladium acetate (151 mg, 0.67 mmol) and benzophenone imine (2.82 mL, 16.8 mmol) were added sequentially, each in one portion, to a stirred solution of methyl 2-methyl-2-[trans-4-(4-{[(trifluoromethyl)sulfonyl]oxy}phenyl)cyclohexyl]-propanoate (4.57 g, 11.2 mmol) in THF (60 mL) and the reaction mixture was heated at 65° C. for 18 h under an argon atmosphere. The reaction mixture was cooled to room temperature and concentrated in vacuo to leave a residue. The residue was taken up in EtOAc and $H_2O$ was added. The layers were separated and the organic layer was washed with brine, dried ($MgSO_4$) and concentrated in vacuo to leave a residue. The residue was purified by column chromatography, eluting with 10-50% EtOAc in isohexane, to give the crude benzophenone imine product (1.7 g) as an oil, which was used with no further purification; MS m/e $MH^+$ 440.

10% Palladium on carbon (500 mg) was added in one portion to a stirred solution of the crude benzophenone imine (1.7 g) in a mixture of MeOH (25 mL) and THF (25 mL) and the reaction mixture was stirred under a hydrogen atmosphere for 20 h. The reaction mixture was filtered and concentrated in vacuo to leave an oil. The oil was purified by column chromatography, using a gradient of 11-50% EtOAc:isohexane as eluent, to give the title compound (250 mg, 8%) as a solid; $^1H$ NMR δ 1.14 (6H, s), 1.15-1.28 (2H, m), 1.36-1:48 (2H, m), 1.61-1.74 (3H, m), 1.86-1.95 (2H, m), 2.3-2.4 (1H, m), 3.52 (2H, s), 3.67 (3H, s), 6.61 (2H, d), 6.99 (2H, d); MS m/e $MH^+$ 276.

(v) A solution of methyl chlorooxoacetate (167 mg, 1.36 mmol) in DCM (2 mL) was added in one portion to a solution of methyl 2-[trans-4-(4-aminophenyl)cyclohexyl]-2-methyl-propanoate (250 mg, 0.91 mmol) and pyridine (0.22 mL, 2.72 mmol) in DCM (10 mL) at 10° C. and the mixture was stirred at 10° C. for 30 mins and then warmed to room temperature and stirred for 2 h. The reaction mixture was concentrated in vacuo and EtOAc was added. The mixture was washed with water and brine, dried ($MgSO_4$) and concentrated in vacuo to give the crude methyl ester (0.35 g) as a solid, which was used with no further purification; $^1H$ NMR δ 1.16 (6H, s), 1.18-1.3 (2H, m), 1.3801.52 (2H, m), 1.64-1.78 (3H, m), 1.9-2.0 (2H, m), 2.4-2.51 (1H, m), 3.68 (3H, s), 3.97 (3H, m), 7.2 (2H, d), 7.53 (2H, d), 8.76 (1H, s); MS m/e $(M–H)^-$ 360.

A solution of hydrazine hydrate (54 mg, 1.08 mmol) in ethanol (1 mL) was added dropwise to a stirred solution of the crude methyl ester (0.35 g, 0.91 mmol) in ethanol (9 mL) and the reaction mixture was stirred at room temperature for 18 h. The mixture was filtered to leave a solid, which was washed with ethanol to give the title compound (Intermediate 105) (0.30 g, 91%) as a white solid; $^1H$ NMR δ 1.13 (6H, s), 1.16-1.3 (2H, m), 1.4-1.54 (2H, m), 1.63-1.74 (3H, m), 1.82- 1.93 (2H, m), 1.9-2.54 (1H, m), 3.68 (3H, s), 4.69 (2H, s), 7.25 (2H, d), 7.75 (2H, d), 10.33 (1H, s), 10.57 (1H, s); MS m/e $MH^+$ 362.

Intermediate 106: Ethyl 2-[trans-4-(2-chloro-4-{[hydrazino(oxo)acetyl]amino}phenyl)-cyclohexyl]propanoate

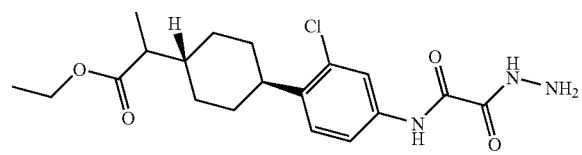

i) 3-Chloro-4-(1,4-dioxaspiro[4.5]dec-7-en-8-yl)aniline

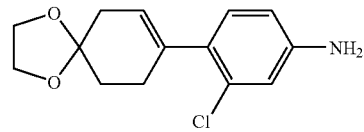

A 2N aqueous solution of potassium carbonate (26.5 mL) and tetrakis(triphenylphosphine) palladium(0) (1.23 g, 1.06 mmol) were added sequentially, each in one portion, to a stirred solution of 8-(4,4,5,5-tetramethyl-1,3,2-dioxaborolan-2-yl)-1,4-dioxaspiro[4.5]dec-7-ene (Intermediate 78ii, 5.65 g, 21.2 mmol) and 4-bromo-3-chloro aniline (4.39 g, 21.2 mmol) in dimethoxyethane (80 mL) at room temperature under an argon atmosphere. The reaction mixture was then heated at 80° C. for 24 h under an argon atmosphere. The reaction mixture was cooled to room temperature and ethyl acetate was added and then the mixture was washed twice with $H_2O$ and then brine. The organic layer was dried ($MgSO_4$) and concentrated in vacuo to leave an oil, which was purified by column chromatography, using a gradient of 20-50% ethyl acetate:isohexane as eluent, to give the title compound (3.5 g, 62%) as a solid; $^1H$ NMR δ 1.7-1.8 (2H, m), 2.26-2.43 (4H, m), 3.91 (4H, s), 5.28 (2H, s), 5.4-5.47 (1H, m), 6.45 (1H, dd), 6.59 (1H, d), 6.86 (1H, d).

ii) Benzyl [3-chloro-4-(1,4-dioxaspiro[4.5]dec-8-yl)phenyl]carbamate

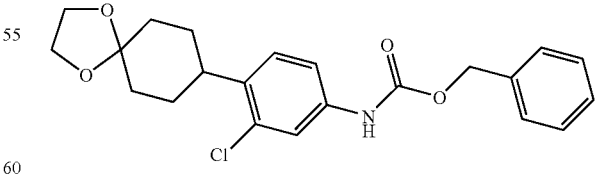

Platinum oxide (250 mg) was added in one portion to a stirred solution of 3-chloro-4-(1,4-dioxaspiro[4.5]dec-7-en-8-yl)aniline (3.4 g, 12.8 mmol) in ethyl acetate (50 mL) and the mixture was stirred at room temperature under a hydrogen atmosphere for 9 h. A further portion of platinum oxide (250 mg) was added in one portion and the mixture was stirred for 8 h at room temperature under a hydrogen atmosphere. The reaction mixture was filtered and concentrated in vacuo to leave the cyclohexane-aniline product (2.1 g) as a solid, which was used with no further purification.

Pyridine (1.91 mL, 23.5 mmol) and benzyl chloroformate (1.34 g, 7.84 mmol) were added sequentially, each in one portion, to a stirred solution of the crude cyclohexane-aniline (2.1 g, 7.84 mmol) in THF (30 mL) at 5° C. and the reaction mixture was stirred at 110° C. for 3 h. Ethyl acetate (75 mL) was added and the mixture was washed with H₂O (2×30 mL) and brine. The organic layer was dried (MgSO₄) and concentrated in vacuo to leave a solid, which was purified by column chromatography, using a gradient of 20-50% ethyl acetate:isohexane as eluent, to give the title compound (2.3 g, 74%) as a white solid; ¹H NMR δ 1.58-1.96 (8H, m), 4.0 (4H, s), 5.22 (2H, s), 6.63 (1H, s), 7.2 (1H, dd), 7.25 (1H, d), 7.33-7.45 (5H, m), 7.5 (1H, d); MS m/e MH⁺ 402.

iii) Ethyl 2-[4-(4-{[(benzyloxy)carbonyl]amino}-2-chlorophenyl)cyclohexylidene]-propanoate

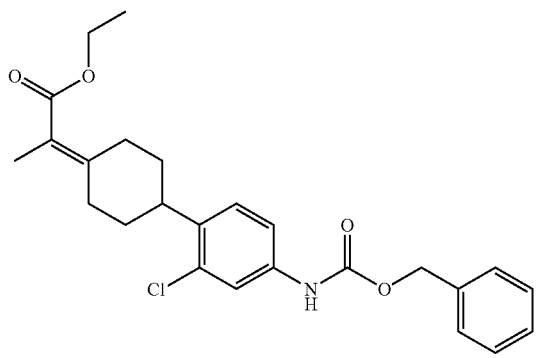

Water (1 mL) was added in one portion to a stirred solution of benzyl [3-chloro-4-(1,4-dioxaspiro[4.5]dec-8-yl)phenyl] carbamate (2.30 g, 5.72 mmol) in TFA (20 mL) and the reaction mixture was stirred at room temperature for 2 h. The mixture was cooled to 10° C. and a 2N aqueous solution of sodium hydroxide was added until the pH of the mixture was 10. Ethyl acetate (50 mL) was added and the layers were separated and the aqueous layer was extracted with ethyl acetate (50 mL). The combined organic layers were washed with H₂O and brine, dried (MgSO₄) and concentrated in vacuo to leave the crude cyclohexanone product (2.0 g), which was used with no further purification. Triethylphosphonopropionate (1.60 g, 6.71 mmol) was added dropwise to a stirred suspension of sodium hydride (60% dispersion in mineral oil, 0.29 g, 7.27 mmol) in THF (30 mL) at 10° C. under an argon atmosphere and the mixture was warmed to room temperature. The reaction mixture was cooled to 10° C. and then a solution of the crude cyclohexanone (2.0 g) in THF (10 mL) was added dropwise. The reaction mixture was warmed to room temperature and stirred for 4 h. A saturated aqueous solution of ammonium chloride (50 mL) and ethyl acetate (70 mL) were added. The layers were separated and the organic layer was washed with H₂O and brine, dried (MgSO₄) and concentrated in vacuo to leave an oil. Purification by column chromatography, using a gradient of 11-66% ethyl acetate:isohexane as eluent, gave the title compound (1.50 g, 60%) as a solid; ¹H NMR δ 1.3 (3H, t), 1.4-1.6 (2H, m), 1.9 (3H, s), 1.94-2.12 (4H, m), 2.72-2.85 (1H, m), 3.1-3.25 (2H, m), 4.2 (2H, q), 5.2 (2H, s), 6.59 (1H, s), 7.13 (1H, dd), 7.19 (1H, dd), 7.3-7.43 (5H, m), 7.5 (1H, d); MS m/e (M−H)⁻ 440.

iv) Ethyl 2-[4-(2-chloro-4-{[methoxy(oxo)acetyl]amino}phenyl)cyclohexyl]propanoate

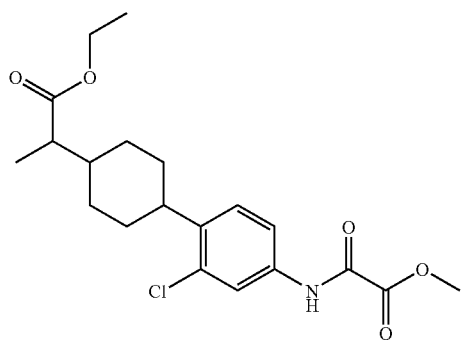

Platinum oxide (300 mg) was added in one portion to a stirred solution of ethyl 2-[4-(4-{[(benzyloxy)carbonyl]amino}-2-chlorophenyl)cyclohexylidene]propanoate (1.5 g, 3.39 mmol) in ethyl acetate (30 mL) and the mixture was stirred at room temperature under a hydrogen atmosphere for 7 h. A further portion of platinum oxide (1.0 g) was added in one portion and the mixture was stirred for 1 h at room temperature under a hydrogen atmosphere. The reaction mixture was filtered and concentrated in vacuo to leave a residue, which was purified by column chromatography, using a gradient of 11-50% ethyl acetate:isohexane as eluent, to give the aniline product as a mixture of cis- and trans-cyclohexane isomers, that was used with no further purification.

A solution of methyl chlorooxoacetate (266 mg, 2.17 mmol) in DCM (2 mL) was added in one portion to a solution of the crude aniline (500 mg, 1.44 mmol) and pyridine (0.35 mL, 4.33 mmol) in DCM (8 mL) at 10° C. and the mixture was stirred at 10° C. for 30 mins and then warmed to room temperature and stirred for 2 h. The reaction mixture was concentrated in vacuo and EtOAc was added. The mixture was washed with H₂O and brine, dried (MgSO₄) and concentrated in vacuo to leave the title compound as an oil (0.58 g, 43% over 2 steps); ¹H NMR (for major trans-isomer) δ 1.15 (3H, d), 1.19-1.33 (2H, m), 1.28 (3H, t), 1.35-1.5 (2H, m), 1.6-1.75 (1H, m), 1.76-1.85 (1H, m), 1.86-2.0 (3H, m), 2.25-2.35 (1H, m), 2.89-3.01 (1H, m), 3.99 (3H, s), 4.16 (2H, dq), 7.24 (1H, d), 7.48 (1H, dd), 7.7 (1H, d), 8.75 (1H, s); MS m/e (M−H)⁻ 394.

v) A solution of hydrazine hydrate (86 mg, 1.73 mmol) in ethanol (1 mL) was added dropwise to a stirred solution of ethyl 2-[4-(2-chloro-4-{[methoxy(oxo)acetyl]amino}phenyl)cyclo-hexyl]propanoate (0.58 g, 1.44 mmol) in ethanol (14 mL) and the reaction mixture was stirred at room temperature for 18 h. The mixture was filtered to leave a solid, which was washed with ethanol to give the title compound (Intermediate 106) (0.45 g, 81%) as a white solid; ¹H NMR δ 1.14 (3H, d), 1.16-1.28 (2H, m), 1.27 (3H, t), 1.4-1.58 (2H, m), 1.6-1.7 (1H, m), 1.71-1.93 (4H, m), 2.29-2.39 (1H, m), 2.82-2.94 (1H, m), 4.15 (2H, dq), 4.7 (2H, s), 7.4 (1H, d), 7.8 (1H, dd), 8.01 (1H, d), 10.4 (1H, s), 10.8 (1H, s); MS m/e MH⁺ 396.

Intermediate 107: Ethyl 2-[trans-4-(3-chloro-4-{[hydrazino(oxo)acetyl]amino}phenyl)-cyclohexyl]propanoate

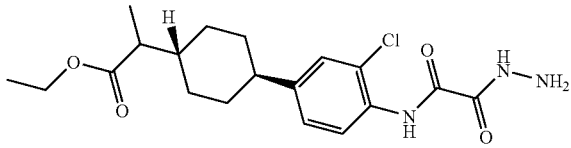

i) 2-Chloro-4-(1,4-dioxaspiro[4.5]dec-7-en-8-yl)aniline

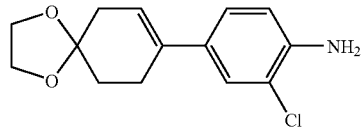

Following the general procedure of Intermediate 106i, except that 4-bromo-2-chloroaniline was used in place of 4-bromo-3-chloroaniline, the title compound was obtained in 68% yield as a solid; $^1$H NMR δ 1.75-1.82 (2H, m), 2.3-2.36 (2H, m), 2.41-2.5 (2H, m), 3.91 (4H, s), 5.3 (2H, s), 5.81-5.88 (1H, m), 6.74 (1H, d), 7.11 (1H, dd), 7.21 (1H, d).

ii) 2-Chloro-4-(1,4-dioxaspiro[4.5]dec-8-yl)aniline

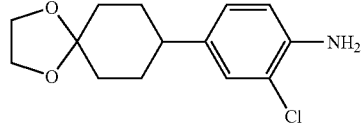

Platinum oxide (200 mg) was added in one portion to a stirred solution of 2-chloro-4-(1,4-dioxaspiro[4.5]dec-7-en-8-yl)aniline (3.8 g, 14.3 mmol) in ethyl acetate (50 mL) and the mixture was stirred at room temperature under a hydrogen atmosphere for 8 h. The reaction mixture was filtered and concentrated in vacuo to leave the title compound (2.4 g, 63%) as a solid; $^1$H NMR δ 1.5-1.65 (4H, m), 1.67-1.8 (4H, m), 2.38-2.48 (1H, m), 3.88 (4H, s), 5.1 (2H, s), 6.72 (1H, d), 6.9 (1H, dd), 7.0 (1H, d); MS m/e MH$^+$ 268.

iii) Benzyl [2-chloro-4-(1,4-dioxaspiro[4.5]dec-8-yl)phenyl]carbamate

Pyridine (2.18 mL, 26.9 mmol) and benzyl chloroformate (1.53 g, 8.96 mmol) were added sequentially, each in one portion, to a stirred solution of 2-chloro-4-(1,4-dioxaspiro[4.5]dec-8-yl)aniline (2.40 g, 8.96 mmol) in THF (30 mL) at 5° C. and the reaction mixture was stirred at 10° C. for 3 h. Ethyl acetate (75 mL) was added and the mixture was washed with H$_2$O (2×30 mL) and brine. The organic layer was dried (MgSO$_4$) and concentrated in vacuo to leave a solid, which was purified by column chromatography, using a gradient of 20-50% ethyl acetate:isohexane as eluent, to give the title compound (2.6 g, 72%) as a white solid; $^1$H NMR δ 1.65-1.93 (8H, m), 2.49-2.6 (1H, m), 4.0 (4H, s), 5.25 (2H, s), 7.12 (1H, s), 7.15 (1H, dd), 7.25 (1H, d), 7.37-7.48 (5H, m), 8.08 (1H, d); MS m/e (M–H)$^-$ 400.

iv) Benzyl [2-chloro-4-(4-oxocyclohexyl)phenyl]carbamate

Water (1 mL) was added in one portion to a stirred solution of benzyl [2-chloro-4-(1,4-dioxaspiro[4.5]dec-8-yl)phenyl]carbamate (2.60 g, 6.47 mmol) in TFA (20 mL) and the reaction mixture was stirred at room temperature for 2 h. The mixture was cooled to 10° C. and a 2N aqueous solution of sodium hydroxide was added until the pH of the mixture was 10. Ethyl acetate (50 mL) was added and the layers were separated and the aqueous layer was extracted with ethyl acetate (50 mL). The combined organic layers were washed with H$_2$O and brine, dried (MgSO$_4$) and concentrated in vacuo to leave the title compound (2.3 g, 99%) as a solid; $^1$H NMR δ 1.82-1.99 (2H, m), 2.17-2.28 (2H, m), 2.45-2.57 (4H, m), 2.94-3.07 (1H, m), 5.24 (2H, s), 7.17 (1H, dd), 7.25 (1H, d), 7.32-7.5 (5H, m), 8.13 (1H, d); MS m/e (M–H)$^-$ 356.

v) Ethyl 2-[4-(4-{[(benzyloxy)carbonyl]amino}-3-chlorophenyl)cyclohexylidene]-propanoate

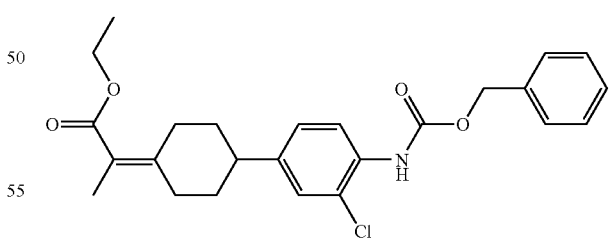

A solution of triethylphosphonopropionate (1.54 g, 6.46 mmol) in THF (10 mL) was added dropwise to a stirred suspension of sodium hydride (60% dispersion in mineral oil, 0.28 g, 7.05 mmol) in THF (30 mL) at 10° C. under an argon atmosphere and the mixture was warmed to room temperature. The reaction mixture was cooled to 10° C. and then a solution of benzyl [2-chloro-4-(4-oxocyclohexyl)phenyl]carbamate (2.36 g, 5.87 mmol) in THF (10 mL) was added dropwise. The reaction mixture was warmed to room temperature and stirred for 4 h. A saturated aqueous solution of ammonium chloride (50 mL) and ethyl acetate (70 mL) were added. The layers were separated and the organic layer was washed with H₂O and brine, dried (MgSO₄) and concentrated in vacuo to leave an oil. Purification by column chromatography, using a gradient of 11-66% ethyl acetate:isohexane as eluent, gave the title compound (1.80 g, 69%) as a solid; ¹H NMR δ 1.34 (3H, t), 1.46-1.53 (2H, m), 1.93 (3H, s), 1.95-2.1 (4H, m), 2.67-2.87 (2H, m), 3.13-3.24 (1H, m), 4.22 (2H, q), 5.24 (2H, s), 7.1-7.18 (2H, m), 7.21 (1H, d), 7.33-7.5 (5H, m), 8.08 (1H, d); MS m/e (M−H)⁻ 440.

vi) Ethyl 2-[trans-4-(4-amino-3-chlorophenyl)cyclohexyl]propanoate

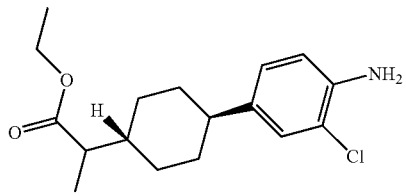

Platinum oxide (300 mg) was added in one portion to a stirred solution of ethyl 2-[4-(4-{[(benzyloxy)carbonyl]amino}-3-chlorophenyl)cyclohexylidene]propanoate (1.7 g, 3.85 mmol) in ethyl acetate (50 mL) and the mixture was stirred at room temperature under a hydrogen atmosphere for 9 h. The reaction mixture was filtered and concentrated in vacuo to leave a residue, which was purified by column chromatography, using a gradient of 11-66% ethyl acetate:isohexane as eluent, to give the aniline product as a mixture of cis- and trans-cyclohexane isomers. Recrystallisation from a mixture of ethanol and diethyl ether gave the title compound (0.37 g, 28%) as a white solid; ¹H NMR δ 1.08 (3H, d), 1.2-1.3 (1H, m), 1.27 (3H, t), 1.31-1.49 (1H, m), 1.52-1.7 (1H, m), 1.71-1.81 (1H, m), 1.81-1.97 (3H, m), 2.2-2.32 (1H, m), 2.33-2.48 (1H, m), 4.15 (2H, dq), 7.02 (1H, dd), 7.2 (1H, d), 7.22 (1H, d); MS m/e MH⁺ 310.

vii) A solution of methyl chlorooxoacetate (197 mg, 1.60 mmol) in DCM (2 mL) was added in one portion to a solution of ethyl 2-[trans-4-(4-amino-3-chlorophenyl)cyclohexyl]propanoate (370 mg, 1.07 mmol) and pyridine (0.26 mL, 3.21 mmol) in DCM (8 mL) at 10° C. and the mixture was stirred at 10° C. for 30 mins and then warmed to room temperature and stirred for 2 h. The reaction mixture was concentrated in vacuo and EtOAc was added. The mixture was washed with water and brine, dried (MgSO₄) and concentrated in vacuo to give the crude methyl ester (0.44 g) as a solid, which was used with no further purification; ¹H NMR δ 1.15 (3H, d), 1.18-1.3 (1H, m), 1.27 (3H, t), 1.36-1.5 (2H, m), 1.58-1.7 (1H, m), 1.73-1.83 (1H, m), 1.85-1.98 (3H, m), 2.23-2.34 (1H, m), 2.39-2.51 (1H, m), 4.0 (3H, s), 4.15 (2H, dq), 7.15 (1H, dd), 7.26 (1H, d), 8.3 (1H, d), 9.35 (1H, s); MS m/e MH⁺ 396.

Hydrazine hydrate (64 mg, 1.28 mmol) was added to a stirred solution of the crude methyl ester (0.44 g) in ethanol (5 mL) and the reaction mixture was stirred at room temperature for 18 h. The mixture was filtered to leave a solid, which was washed with ethanol to give the title compound (Intermediate 107) (0.35 g, 83%) as a white solid; ¹H NMR δ 1.11 (3H, d), 1.15-1.3 (2H, m), 1.24 (3H, t), 1.42-1.58 (2H, m), 1.59-1.7 (1H, m), 1.7-1.8 (1H, m), 1.81-1.95 (3H, m), 2.28-2.38 (1H, m), 2.49-2.6 (1H, m), 4.08 (2H, dq), 4.72 (2H, s), 7.32 (1H, dd), 7.47 (1H, d), 7.9 (1H, d), 10.05 (1H, s), 10.45 (1H, s); MS m/e MH⁺ 396.

Intermediate 108: Ethyl cis-4-(4-{[methoxy(oxo)acetyl]amino}phenoxy)cyclohexane-carboxylate

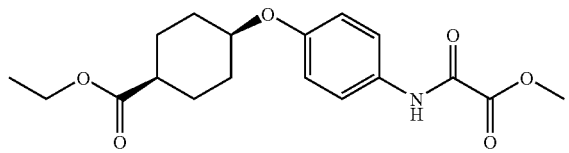

i) Ethyl cis-4-(4-nitrophenoxy)cyclohexanecarboxylate

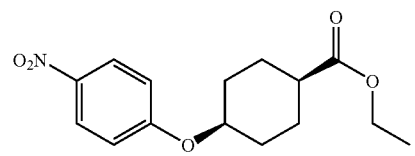

A solution of ethyl 4-hydroxycyclohexanecarboxylate (2.0 g, 11.6 mmol) in DMF (3 ml) was added in one portion to a stirred suspension of sodium hydride (60% dispersion in mineral oil, 490 mg, 12.2 mmol) in DMF (15 mL) at 0° C. under an argon atmosphere. The mixture was stirred at 0° C. for 10 mins and then warmed to room temperature and stirred for 20 mins and then a solution of 1-fluoro-4-nitrobenzene (1.24 mL, 11.6 mmol) in DMF (2 mL) was added in one portion. The reaction mixture was stirred at room temperature for 2 h and then heated at 110° C. for 24 h. The solution was concentrated in vacuo to leave a residue that was taken up in EtOAc (250 mL) and H₂O (150 mL) was added. The layers were separated and the organic layer was washed with H₂O (2×100 mL) and brine (50 mL) and then dried (MgSO₄) and concentrated in vacuo to leave an oil. The oil was taken up in a mixture of hot EtOAc and isohexane (1:1) and left for 20 h. Filtration, followed by concentration in vacuo of the filtrate left an oil, which was purified by column chromatography, using a gradient of 10-40% EtOAc:isohexane as eluent, to give the title compound (0.27 g, 16%) as an oil; ¹H NMR (CDCl₃) δ 1.24 (3H, q), 1.66-1.72 (2H, m), 1.74-1.79 (2H, m), 1.90-1.95 (2H, m), 1.98-2.04 (2H, m), 2.38-2.44 (1H, m), 4.11-4.16 (2H, q), 4.57-4.60 (1H, m), 6.90-6.93 (2H, d), 8.15-8.18 (2H, d).

ii) Ethyl cis-4-(4-aminophenoxy)cyclohexanecarboxylate

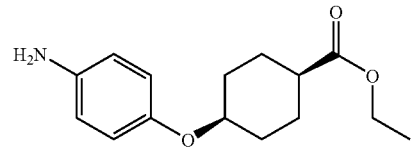

Palladium (10 wt. %) on carbon (50 mg) was added in one portion to a solution of ethyl cis-4-(4-nitrophenoxy)cyclohexanecarboxylate (0.23 g, 0.78 mmol) in a mixture of EtOH (15 mL) and THF (10 mL) and the reaction mixture was stirred under a hydrogen atmosphere at room temperature for 16 h. The reaction mixture was filtered and then concentrated in vacuo to leave the title compound (0.20 g, 100%) as an oil; $^1$H NMR (CDCl$_3$) δ 1.23-1.28 (3H, t), 1.55-1.63 (2H, m), 1.68-1.74 (2H, m), 1.93-2.03 (4H, m), 2.34-2.40 (1H, m), 4.10-4.17 (2H, q), 4.26-4.30 (1H, m), 6.60-6.63 (2H, d), 6.73-6.78 (2H, d) MS m/e MH$^+$ 264.

iii) Ethyl cis-4-(4-{[methoxy(oxo)acetyl]amino}phenoxy)cyclohexanecarboxylate

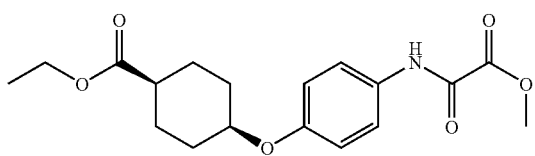

Methyl chlorooxoacetate (72 μL, 0.77 mmol) was added in one portion to a stirred solution of ethyl cis-4-(4-aminophenoxy)cyclohexanecarboxylate (204 mg, 0.77 mmol) and pyridine (76 μL, 0.93 mmol) in DCM (5 mL) and the reaction mixture was stirred at room temperature for 1 h. Concentration in vacuo left a residue which was taken up in EtOAc (50 mL) and an aqueous solution of hydrochloric acid (1M, 30 mL) was added. The layers were separated and the organic layer was washed with brine (20 mL), dried (MgSO$_4$) and concentrated in vacuo to leave an oil. The oil was purified by column chromatography, using a gradient of 10-70% ethyl acetate:isohexane as eluent, to give the title compound (Intermediate 108) (188 mg, 70%) as an oil; $^1$H NMR (CDCl$_3$) δ 1.23-1.28 (3H, t), 1.57-1.68 (2H, m), 1.71-1.78 (2H, m), 1.92-2.04 (4H, m), 2.36-2.43 (1H, m), 3.96 (3H, s), 4.14 (2H, q), 4.43-4.45 (1H, m), 6.89-6.93 (2H, d), 7.51-7.55 (2H, d), 8.76 (1H, s); MS m/e (M−H)$^-$ 348.

Intermediate 109: Methyl 1-(5-{[hydrazino(oxo)acetyl]amino}pyridin-2-yl)piperidine-4-carboxylate

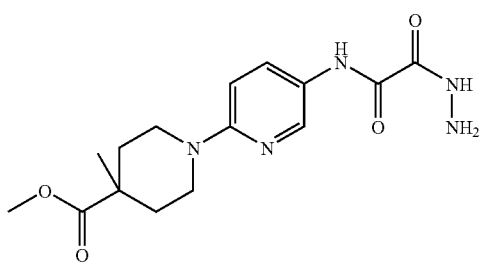

i) 1-tert-Butyl 4-methyl 4-methylpiperidine-1,4-dicarboxylate

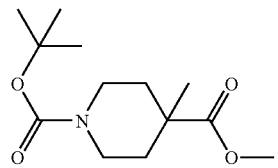

To a solution of 1(tert-butoxycarbonyl)-4-methylpiperidine-4-carboxylic acid (5.0 g, 20.55 mmol) in methanol (60 mL) and toluene (100 mL) was added a 2M solution of trimethylsilyldiazomethane (20 mL) in hexanes (the addition was accompanied by effervescence and a small exotherm). The resulting pale yellow solution was allowed to stir at ambient temperature for 1 hr. The solvent was removed under reduce pressure to give the title compound as a pale yellow oil (5.28 g 20.55 mmol, 100%); $^1$H NMR (CDCl$_3$) δ 1.20 (s, 3H), 1.34-1.39 (m, 2H), 1.44 (s, 9H), 2.03-2.07 (m, 2H), 2.96-3.03 (m, 2H), 3.70 (s, 3H), 3.72-3.77 (m, 2H); MS m/e MH$^+$ 257 ii) Methyl 4-methylpiperidine-4-carboxylate hydrochloride

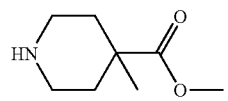

4M HCl in dioxane (25 mL) was added to 1-tert-butyl 4-methyl 4-methylpiperidine-1,4-dicarboxylate (5.28 g, 20.55 mmol) at ambient temperature. The reaction mixture was allowed to stir at ambient temperature for 5 hrs. The solvent was removed under reduced pressure and ether was added to the residue and the suspension was filtered and dried to give the title compound as a white solid (3.82 g, 19.72 mmol, 96%); $^1$H NMR δ 1.12 (s, 3H), 1.53-1.60 (m, 2H), 1.99-2.04 (m, 2H), 2.76-2.82 (m, 2H), 3.07-3.12 (m, 2H), 3.61 (s, 3H), 8.72 (s, 1H); MS m/e MH$^+$-157 iii) Methyl 4-methyl-1-(5-nitropyridin-2-yl)piperidine-4-carboxylate

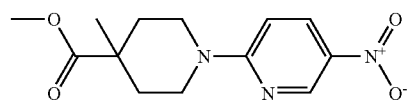

To a solution of 2-chloro-5-nitropyridine (2.0 g, 12.62 mmol) in DMSO (20 mL) was added sodium carbonate (6.70 g, 63.08 mmol) followed by methyl 4-methylpiperidine-4-carboxylate hydrochloride (2.44 g, 12.62 mmol). The reaction mixture was heated to 60° C. for 2 hours. The reaction mixture was poured onto water (100 mL) and the suspension filtered, washed with water (4×150 mL) and dried to leave the title compound as a yellow solid (3.32 g, 11.89 mmol, 94%); $^1$H NMR (CDCl$_3$) δ 1.26 (s, 3H), 1.46-1.52 (m, 2H), 2.21-2.25 (m, 2H), 3.26-3.32 (m, 2H), 3.74 (s, 3H), 4.16-4.20 (m, 2H), 6.56 (d, 1H), 8.18 (d, 1H), 9.03 (s, 1H); MS m/e MH$^+$ 280.

iv) Methyl 1-(5-aminopyridin-2-yl)-4-methylpiperidine-4-carboxylate

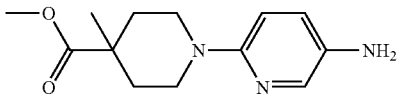

To a solution of methyl 4-methyl-1-(5-nitropyridin-2-yl)piperidine-4-carboxylate (3.32 g, 11.89 mmol) in abs EtOH (200 mL) and THF (200 mL) was added 10% Pd/C (400 mg) and then the reaction mixture was evacuated with hydrogen (5 cycles) and allowed to stir at ambient temperature overnight. The reaction mixture was filtered and then concentrated and the black residue purified on a 120 g silica Crawford silicyle cartridge loading in 40% EtOAc/isohexane with some DCM and eluting a gradient of 40-80% EtOAc using an Isco companion to provide the title compound (2.96 g, 11.89 mmol, 100%).

$^1$H NMR (CDCl$_3$) δ 1.23 (s, 3H), 1.51-1.58 (m, 2H), 2.16-2.20 (m, 2H), 2.98-3.05 (m, 2H), 3.25 (s, 2H), 3.67-3.70 (m, 2H), 3.70 (s, 3H), 6.57 (d, 1H), 6.97 (d, 1H), 7.78 (d, 1H); MS m/e MH$^+$ 250.

v) Methyl 1-(5-{[methoxy(oxo)acetyl]amino}pyridin-2-yl)-4-methylpiperidine-4-carboxylate

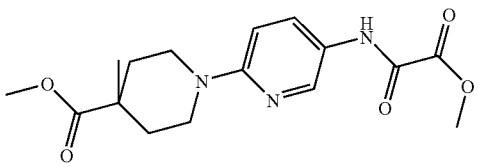

To a solution of methyl 1-(5-aminopyridin-2-yl)-4-methylpiperidine-4-carboxylate (2.96 g, 11.89 mmol) in DCM (100 mL) was added triethylamine (2.2 mL, 15.84 mmol) followed by methyl chlorooxoacetate (1.6 mL, 17.15 mmol) and the reaction mixture was allowed to stir at ambient temperature for 1.5 hrs. The reaction mixture was washed with brine (2×100 mL), the aqueous layer was re extracted with DCM (50 mL) and the organic washings were combined, dried and concentrated to leave the title compound as a brown gum (3.98 g, 11.89 mmol, 100%). $^1$H NMR (CDCl$_3$) δ 1.72-1.82 (m, 2H), 1.96-2.02 (m, 2H), 2.52-2.59 (m, 1H), 2.95-3.03 (m, 2H), 3.70 (s, 3H), 3.97 (s, 3H), 4.16-4.22 (m, 2H), 6.67 (d, 1H), 7.93 (d, 1H), 8.28 (s, 1H), 8.66 (s, 1H); MS m/e MH$^+$ 336.

vi) Methyl 1-(5-{[hydrazino(oxo)acetyl]amino}pyridin-2-yl)piperidine-4-carboxylate To a vigorously stirred suspension of methyl 1-(5-{[methoxy(oxo)acetyl]amino}pyridin-2-yl)piperidine-4-carboxylate (3.12 g, 9.71 mmol) in absolute ethanol was added hydrazine monohydrate (0.52 mL, 10.76 mmol) and the suspension was allowed to stir at ambient temperature for 2 hours. The suspension was filtered, washed with ether (4×100 mL) and dried under vacuum at ambient temperature to provide the title compound (2.62 g, 7.81 mmol, 80%). $^1$H NMR δ 1.18 (s, 3H), 1.40-1.47 (m, 2H), 1.98-2.03 (m, 2H), 3.07-3.14 (m, 3H), 3.66 (s, 3H), 3.80-3.86 (m, 2H), 4.58 (s, 1H), 6.83 (d, 1H), 7.90 (d, 1H), 8.49 (s, 1H), 10.17 (s, 1H), 10.46 (s, 1H); MS m/e MH$^+$ 336.

Intermediate 110: Ethyl 2-[3-(4-aminophenyl)cyclobutyl]propanoate

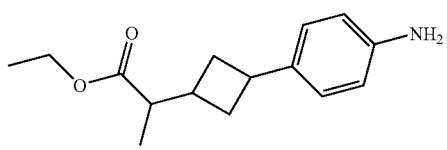

i) Ethyl 2-(3-phenylcyclobutylidene)propanoate

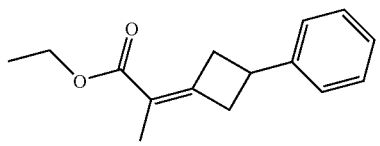

Following the general procedure described for ethyl {3-[4-(benzyloxy)phenyl]cyclohexylidene}acetate (Intermediate 891i), replacing 3-[4-(benzyloxy)phenyl]cyclohexanone with 3-phenylcyclobutanone (J. Org. Chem., 2005, 70(11), 4549-4552) and triethyl phosphonoacetate with triethyl phosphonopropionate the title compound was obtained; $^1$H NMR δ (CDCl$_3$): 1.24-1.32 (3H, m), 1.75-1.76 (3H, m), 2.87-2.91 (1H, m), 3.19-3.23 (2H, m), 3.54-3.59 (2H, m), 4.09-4.21 (2H, m), 7.19-7.36 (5H, m); MS m/e MH$^+$ 231.

ii) Ethyl 2-(3-phenylcyclobutyl)propanoate

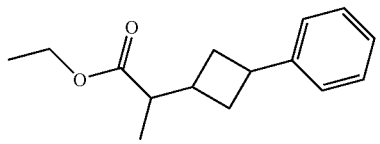

Following the general procedure described for ethyl 3-(4-aminobenzyl)cyclobutanecarboxylate (Intermediate 931i), replacing ethyl 3-(4-nitrobenzyl)cyclobutanecarboxylate with ethyl 2-(3-phenylcyclobutylidene)propanoate the title compound was obtained without chromatography; $^1$H NMR δ (CDCl$_3$): 1.08-1.10 (0.75H, d), 1.12-1.15 (3.25H, d), 1.22-

1.30 (3H, m), 2.17-2.64 (6H, m), 3.34 (0.25H, m), 3.48-3.54 (0.75H, m), 4.09-4.18 (2H, m), 7.15-7.36 (5H, m); MS m/e MH⁺ 233.

iii) Ethyl 2-[3-(4-nitrophenyl)cyclobutyl]propanoate

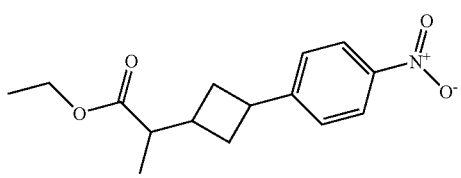

Following the general procedure described for ethyl 3-(4-nitrobenzyl)cyclobutanecarboxylate (Intermediate 93i), replacing ethyl 3-benzylcyclobutanecarboxylate with ethyl 2-(3-phenylcyclobutyl)propanoate the title compound was obtained which was used directly in the next step.

iv) Following the general procedure described for ethyl 3-(4-aminobenzyl)cyclobutanecarboxylate (Intermediate 931i), replacing ethyl 3-(4-nitrobenzyl)cyclobutanecarboxylate with ethyl 2-[3-(4-nitrophenyl)cyclobutyl]propanoate the title compound (Intermediate 110) was obtained; ¹H NMR δ (CDCl₃): 1.07-1.16 (3H, m), 1.22-1.27 (3H, m), 1.65-1.90 (1H, m), 2.11-2.62 (5H, m), 3.22-3.43 (1H, m), 4.09-4.16 (2H, m), 6.65 (2H, t), 6.98-7.07 (2H, m); MS m/e MH⁺ 248.

Intermediate 111: Methyl 1-(5-{[hydrazino(oxo)acetyl]amino}-3-methylpyridin-2-yl)piperidine-4-carboxylate

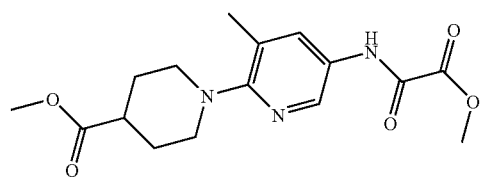

i) Methyl 1-(3-methyl-5-nitropyridin-2-yl)piperidine-4-carboxylate

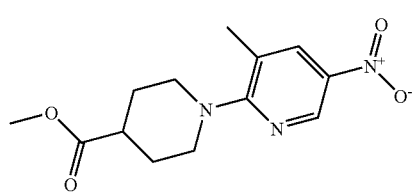

To a solution of 2-chloro-3-methyl-5-nitropyridine (1.73 g, 10.00 mmol) in DMSO (20 mL) was added sodium carbonate (5.30 g, 50.00 mmol) followed by methyl isonipecotate (1.35 mL, 10.00 mmol). The reaction mixture was heated to 60° C. for 110 minutes. The reaction mixture was left to stand at room temperature overnight. A further aliquot of methyl isonipecotate (3.33 mmol, 476 mg, 450 μL) was added and heating resumed at 60° C. for 100 mins. The reaction mixture was poured onto ice water and the suspension was filtered, washed with water (4×75 mL) and dried under vacuum to leave a yellow powder; (2.43 g, 87% yield). This was used in the next stage without further purification. ¹H NMR δ 1.61-1.74 (m, 2H), 1.91-2.10 (m, 2H), 2.31 (s, 3H), 2.61-2.73 (m, 1H), 2.94-3.09 (m, 2H), 3.61 (s, 3H), 3.83-3.98 (m, 2H), 8.19 (d, 1H), 8.86 (d, 1H). MS m/e MH⁺ 280.18.

ii) Methyl 1-(5-amino-3-methylpyridin-2-yl)piperidine-4-carboxylate

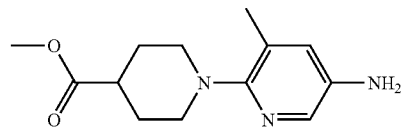

Methyl 1-(3-methyl-5-nitropyridin-2-yl)piperidine-4-carboxylate (2.40 g) was dissolved in EtOH (86 mL), treated with 10% Pd/C (860 mg) and placed under an atmosphere of hydrogen (balloon). LCMS indicated complete reaction at ~100 mins. The catalyst was filtered off and solvent removed under vacuum to leave a colourless oil (2.16 g). This was used in the next step without further purification. ¹H NMR δ 1.58-1.75 (m, 2H), 1.81-1.91 (m, 2H), 2.10 (s, 3H), 2.37-2.50 (m, 1H), 2.55-2.75 (m, 2H), 2.99-3.09 (m, 2H), 3.61 (s, 3H), 6.76 (d, 1H), 7.48 (d, 1H). MS m/e MH⁺ 250.27.

iii) Methyl 1-(5-{[methoxy(oxo)acetyl]amino}-3-methylpyridin-2-yl)piperidine-4-carboxylate To an ice-water cooled solution of methyl 1-(5-amino-3-methylpyridin-2-yl)piperidine-4-carboxylate (2.14 g; 8.59 mmol) in DCM (43 mL) was added methyl chloro(oxo)acetate (1.03 mL; 11.17 mmol) followed by pyridine (834 μL; 10.31 mmol) and the reaction mixture was allowed to stir at ~0° C. for 30 mins, then allowed to warm to room temperature. The reaction solution was washed with water (40 mL) then saturated brine (40 mL). The organics were dried over MgSO₄, filtered and evaporated under vacuum to yield a pale tan solid (2.01 g, 70% yield). This was used for the next stage without further purification. ¹H NMR δ 1.60-1.80 (m, 2H), 1.85-1.99 (m, 2H), 2.18 (s, 3H), 2.54-2.62 (m, 1H), 2.69-2.88 (m, 2H), 3.26-3.40 (m, 2H), 3.56 (s, 3H), 3.82 (s, 3H), 7.87 (d, 1H), 8.40 (d, 1H), 10.75 (s, 1H). MS m/e MH⁺ 336.20.

iv) Methyl 1-(5-{[hydrazino(oxo)acetyl]amino}-3-methylpyridin-2-yl)piperidine-4-carboxylate Methyl 1-(5-{[methoxy(oxo)acetyl]amino}-3-methylpyridin-2-yl)piperidine-4-carboxylate (2.01 g; 5.99 mmol) was dissolved in EtOH (140 mL) and treated with dropwise addition of hydrazine hydrate (320 μL; 6.59 mmol). Within a few minutes a flocculent precipitate formed. Vigorous stirring was continued for 17 hrs. A further 32 μL (0.65 mmol) hydrazine hydrate was added and stirring continued at ambient temperature for 24 hrs. The precipitated solid was filtered off, washed with ether on the filter and dried under high vacuum at 60° C. to give the title compound (1.76 g, 88% yield). This was used in the next stage without further purification. $^1$H NMR δ 1.59-1.80 (m, 2H), 1.83-1.98 (m, 2H), 2.16 (s, 3H), 2.52-2.60 (m, 1H), 2.66-2.84 (m, 2H), 3.22-3.37 (m, 2H), 3.58 (s, 3H), 4.54 (d, 2H), 7.89 (d, 1H), 8.47 (d, 1H), 10.14 (s, 1H), 10.48 (s, 1H). MS m/e MH$^+$ 336.24.

Intermediate 112: Methyl [1-(5-{[hydrazino(oxo)acetyl]amino}-3-methylpyridin-2-yl)piperidin-4-yl] acetate

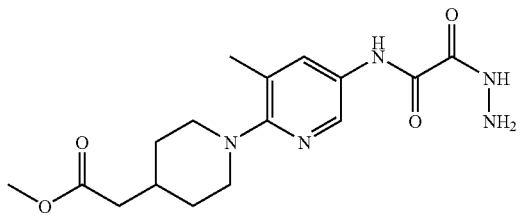

i) Methyl [1-(3-methyl-5-nitropyridin-2-yl)piperidin-4-yl]acetate

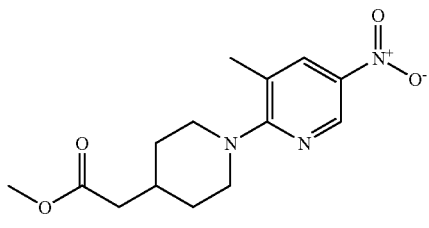

Prepared as in Intermediate 111 part 1), using methyl piperidin-4-ylacetate as starting material. $^1$H NMR δ 1.20-1.41 (m, 2H), 1.68-1.83 (m, 2H), 1.87-2.06 (m, 1H), 2.26-2.35 (m, 5H), 2.85-3.04 (m, 2H), 3.55 (s, 3H), 3.88-3.99 (m, 2H), 8.17 (d, 1H), 8.86 (d, 1H). MS m/e MH$^+$ 294.24.

ii) Methyl [1-(5-amino-3-methylpyridin-2-yl)piperidin-4-yl]acetate

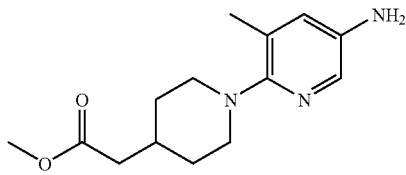

Prepared following the method of Intermediate 111 part ii). $^1$H NMR δ 1.31 (m, 2H), 1.69 (m, 2H), 1.74 (m, 1H), 2.09 (s, 3H), 2.28 (d, 2H), 2.57 (m, 2H), 3.02 (m, 2H), 3.59 (s, 3H), 4.73 (s, 2H), 6.75 (d, 1H), 7.28 (d, 1H). MS m/e MH$^+$ 264.23.

iii) Methyl ({6-[4-(2-methoxy-2-oxoethyl)piperidin-1-yl]-5-methylpyridin-3-yl}amino)(oxo)acetate

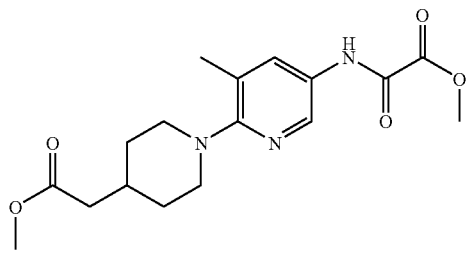

Prepared following the method of Intermediate 111 part iii). $^1$H NMR δ 1.24-1.44 (m, 2H), 1.67-1.79 (m, 2H), 1.79-1.93 (m, 1H), 2.17 (s, 3H), 2.30 (d, 2H), 2.61-2.78 (m, 2H), 3.26-3.41 (m, 2H), 3.57 (s, 3H), 3.89 (s, 3H), 7.85 (d, 1H), 8.39 (d, 1H), 10.72 (s, 1H). MS m/e MH$^+$ 350.23.

iv) Methyl [1-(5-{[hydrazino(oxo)acetyl]amino}-3-methylpyridin-2-yl)piperidin-4-yl]acetate Prepared following the method of Intermediate 111 part iv). $^1$H NMR δ 1.23-1.44 (m, 2H), 1.66-1.79 (m, 2H), 1.77-1.93 (m, 1H), 2.16 (s, 3H), 2.30 (d, 2H), 2.59-2.76 (m, 2H), 3.22-3.40 (m, 2H), 3.56 (s, 3H), 4.52 (s, 2H), 7.88 (d, 1H), 8.46 (d, 1H), 10.14 (s, 1H), 10.51 (s, 1H). MS m/e MH$^+$ 350.21.

Intermediate 113: Ethyl 2-{1-(5-{[hydrazino(oxo)acetyl]amino}-3-methylpyridin-2-yl)piperidin-4-yl] propanoate

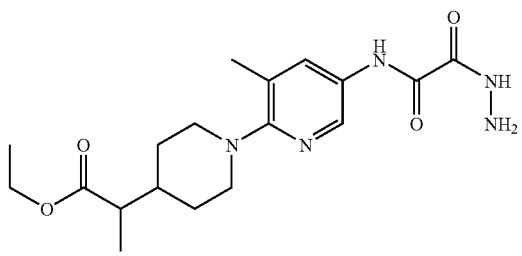

i) tert-Butyl 4-(2-methoxy-1-methyl-2-oxoethylidene)piperidine-1-carboxylate

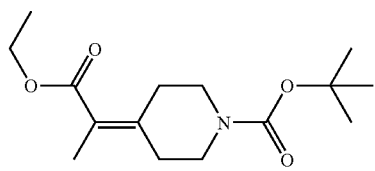

To a suspension of 60% NaH (2.005 g; 50.00 mmol) in anhydrous THF (100 mL), under an atmosphere of argon, was added triethyl 2-phosphonopropionate (10.73 mL; 50.00 mmol), at such a rate as to keep the reaction temperature below 30° C. The resulting mixture was stirred at room temperature for a further 1 hr. A solution of N-Boc-4-piperidone (9.965 g; 50.00 mmol), in anhydrous THF (50 mL), was added dropwise over five minutes. The resulting clear solution was stirred at ambient temperature for ~1 hr. The reaction was quenched by the addition of water (100 mL). The resulting mixture was partitioned, the aq layer extracted once with EtOAc and the combined organics washed with saturated brine. The organics were dried over $MgSO_4$, filtered and evaporated to a colourless oil; 14.76 g. (~quantitative yield). This was used in the next stage without further purification. $^1$H NMR δ 1.19 (t, 3H), 1.36 (s, 9H), 1.77 (s, 3H), 2.25-2.37 (m, 2H), 2.51-2.56 (m, 2H), 3.22-3.44 (m, 4H), 4.11 (q, 2H). MS m/e [MH—($CO_2$, $C_4H_8$)]$^+$=184.31.

ii) Ethyl 2-piperidin-4-ylidenepropanoate hydrochloride

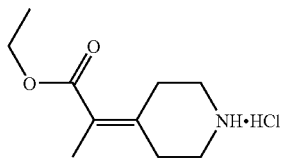

tert-Butyl 4-(2-methoxy-1-methyl-2-oxoethylidene)piperidine-1-carboxylate (2.83 g; 10 mmol) was dissolved in EtOH (50 mL) and treated with 4M HCl/1,4-dioxane solution (20 mL, 80 mmol). The resulting solution was stirred at ambient temperature for 6 hrs. The solvents were removed under vacuum to leave a syrup. This was dried under vacuum to give the title product (3.199 g, ~quantitative yield). This was used in the next stage without further purification. $^1$H NMR δ 1.22 (t, 3H), 1.78 (s, 3H), 2.44-2.57 (m, 2H), 2.65-2.77 (m, 2H), 2.98-3.15 (m, 4H), 4.14 (q, 2H), 9.52 (s, 2H). MS m/e MH$^+$=184.32.

iii) Ethyl 2-[1-(3-methyl-5-nitropyridin-2-yl)piperidin-4ylidene]propanoate

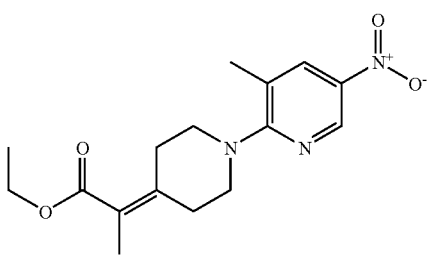

Prepared as in Intermediate 111 part i) using ethyl 2-piperidin-4-ylidenepropanoate.
$^1$H NMR δ 1.23 (t, 3H), 1.89 (s, 3H), 2.39 (s, 3H), 2.49-2.56 (m, 2H), 2.67-2.78 (m, 2H), 3.47-3.66 (m, 4H), 4.14 (q, 2H), 8.18 (d, 1H), 8.86 (d, 1H). MS m/e MH$^+$ 320.21.

iv) Ethyl 2-[1-(5-amino-3-methylpyridin-2-yl)piperidin-4-yl]propanoate

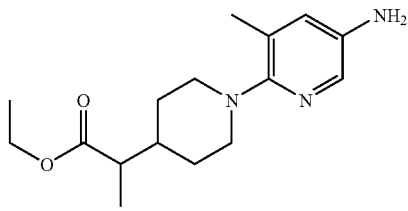

Ethyl 2-[1-(3-methyl-5-nitropyridin-2-yl)piperidin-4-ylidene]propanoate (2.30 g; 7.20 mmol) was suspended in EtOH (100 mL) and treated with 10% Pd/C (230 mg). The resulting mixture was placed under an atmosphere of hydrogen (balloon) at ambient temperature and stirred vigorously at ambient temperature for 2 hrs. LCMS indicated no reduction of alkene but reduction of the nitro-group was essentially complete. The catalyst was filtered off and the filtrate was evaporated to a gum (2.42 g). The reaction was repeated under 20 bar of hydrogen, at 30° C., for 3 hrs with 241 mg 10% Pd/C catalyst. The catalyst was filtered off (Celite) and the solvent removed under vacuum to leave a dark blue gum (2.12 g). This was used in the next step without further purification. $^1$H NMR δ 1.06 (d, 3H), 1.18 (t, 3H), 1.24-1.43 (m, 2H), 1.45-1.63 (m, 2H), 1.61-1.74 (m, 1H), 2.06 (s, 3H), 2.21-2.35 (m, 1H), 2.50-2.63 (m, 1H), 2.99-3.13 (m, 2H), 3.36-3.50 (m, 1H), 3.98-4.14 (m, 2H), 4.65 (s, 2H), 6.76 (d, 1H), 7.47 (d, 1H). MS m/e MH$^+$ 292.27.

v) Ethyl 2-[1-(5-{[methoxy(oxo)acetyl]amino}-3-methylpyridin-2-yl)piperidin-4-yl]propanoate

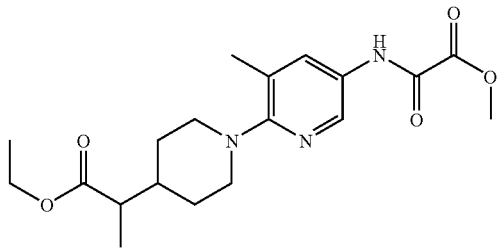

Prepared following the method described for Intermediate 111 part iii).
$^1$H NMR δ 1.07 (d, 3H), 1.18 (t, 3H), 1.28-1.45 (m, 2H), 1.54-1.67 (m, 2H), 1.67-1.80 (m, 1H), 2.17 (s, 3H), 2.24-2.36 (m, 1H), 2.59-2.78 (m, 2H), 3.31-3.47 (m, 2H), 3.82 (s, 3H), 4.01-4.15 (m, 2H), 7.86 (d, 1H), 8.39 (d, 1H), 10.76 (s, 1H). MS m/e MH$^+$ 378.17.

vi) Ethyl 2-{1-(5-{[hydrazine(oxo)acetyl]amino}-3-methylpyridin-2-yl)piperidin-4-yl]propanoate Prepared following the method described for Intermediate 111 part iv)
$^1$H NMR δ 1.06 (d, 3H), 1.19 (t, 3H), 1.24-1.46 (m, 2H), 1.52-1.67 (m, 2H), 1.66-1.81 (m, 1H), 2.15 (s, 3H), 2.24-2.36 (m, 1H), 2.53-2.75 (m, 2H), 3.30-3.40 (m, 2H), 4.07 (q, 2H), 4.36 (s, 1H), 4.70 (s, 1H), 7.87 (d, 1H), 8.46 (d, 1H), 9.80 (s, 1H), 10.51 (s, 1H). MS m/e MH$^+$ 378.22.

Intermediate 114: Methyl (1-{5-[({5-[(3,4-difluorophenyl)amino]-1,3,4-oxadiazol-2-yl}carbonyl)amino]pyridin-2-yl}-4-methylpiperidin-4-yl)acetate

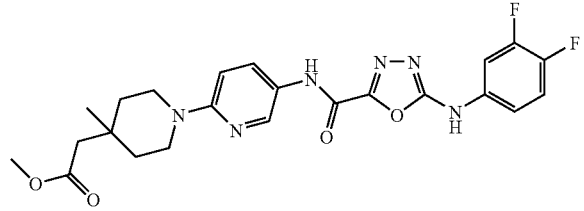

MS m/e MH⁺ 487. This intermediate is also a compound of formula (I) and is a further feature of the invention.

i) Methyl [4-methyl-1-(5-nitropyridin-2-yl)piperidin-4-yl]acetate

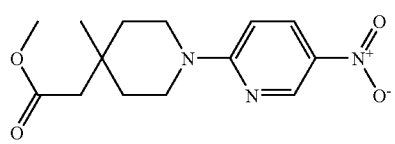

To a solution of 2-chloro-5-nitropyridine (2.97 g, 18.77 mmol) in DMSO (30 mL) was added sodium carbonate (6.4 g, 60.38 mmol) followed by methyl (4-methylpiperidin-4-yl) acetate (3.21 g, 18.77 mmol) (prepared according to the procedures described by Janet Ralbovsky, Joseph Lisko and Wei He, *Synthetic Communications*, 2005, 35 (12), 1613-1625 and Gerhard Hund, and Woldemar Schneider, *Chem Ber* 1980,113 (2), 401-7). The reaction mixture was heated to 60° C. for 1.5 hours, then allowed to cool and water (100 mL) was added. The suspension filtered, and dried to leave a yellow solid (3.70 g, 12.62 mmol, 67%). $^1$H NMR δ 1.08 (s, 3H), 1.45-1.48 (m, 2H), 1.55-1.61 (m, 2H), 2.38 (s, 2H), 3.59 (s, 3H), 3.64-3.70 (m, 2H), 3.85-3.91 (m, 2H), 6.95 (d, 1H), 8.19 (d, 1H), 8.95 (s, 1H); MS m/e MH⁺ 294.

ii) Methyl [1-(5-aminopyridin-2-yl)-4-methylpiperidin-4-yl]acetate

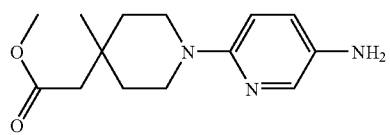

Prepared from methyl [4-methyl-1-(5-nitropyridin-2-yl) piperidin-4-yl]acetate following the method for Intermediate 77 stage ii). $^1$H NMR δ 1.01 (s, 3H), 1.41-1.45 (m, 2H), 1.52-1.58 (m, 2H), 2.30 (s, 2H), 3.12-3.19 (m, 2H), 3.34-3.38 (m, 2H), 3.58 (s, 3H), 4.52 (s, 2H), 6.62 (d, 1H), 6.89 (d, 1H), 7.58 (s, 1H); MS m/e MH⁺ 264.

iii) Methyl ({6-[4-(2-methoxy-2-oxoethyl)-4-methylpiperidin-1-yl]pyridin-3-yl}amino)(oxo)acetate

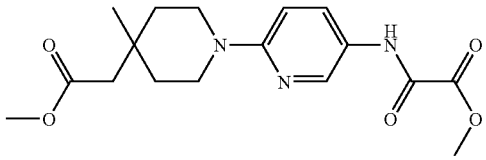

To a solution of methyl [1-(5-aminopyridin-2-yl)-4-methylpiperidin-4-yl]acetate (3.29 g, 13.20 mmol) in DCM (100 mL) was added triethylamine (2.2 mL, 15.84 mmol) followed by methyl chlorooxoacetate (1.6 mL, 17.15 mmol) and the reaction mixture was allowed to stir at ambient temperature for 1.5 hrs. The reaction mixture was washed brine (2×100 mL), the aqueous layer was re extracted with DCM (50 mL) the organic washings were combined, dried and concentrated to leave the title compound as a brown gum (4.4 g, 13.2 mmol, 100%). $^1$H NMR δ 1.06 (s, 3H), 1.40-1.46 (m, 2H), 1.53-1.57 (m, 2H), 2.36 (s, 3H), 3.46-3.52 (m, 2H), 3.59 (s, 3H), 3.67-3.73 (m, 2H), 3.78 (s, 3H), 6.90 (d, 1H), 7.56 (d, 1H), 8.06 (s, 1H); MS m/e MH⁺ 350.

iv) Methyl [1-(5-{[hydrazino(oxo)acetyl]amino}pyridin-2-yl)-4-methylpiperidin-4-yl]acetate

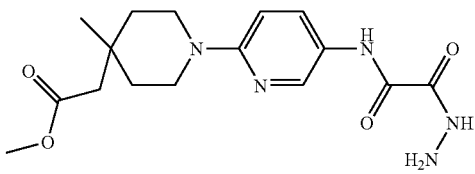

Prepared from the product of the previous reaction and hydrazine hydrate following the method of Intermediate 47 part ii).

$^1$H NMR δ 1.04 (s, 3H), 1.40-1.45 (m, 2H), 1.51-1.58 (m, 2H), 2.33 (s, 2H), 3.36-3.42 (m, 2H), 3.57-3.62 (m, 5H, inc s, 3H), 4.48 (s, 1H), 4.60 (s, 1H), 6.83 (d, 1H), 7.90 (d, 1H), 8.50 (s, 1H), 9.96 (s, 1H), 10.23 (s, 1H); MS m/e MH⁺ 350.

v) Methyl (1-{5-[({5-[(3,4-difluorophenyl)amino]-1,3,4-oxadiazol-2-yl}carbonyl)amino]pyridin-2-yl}-4-methylpiperidin-4-yl)acetate Prepared from the product of the pervious reaction and 3,4-difluorophenylisothiocyanate, following the method of Example 319, but the product was taken through directly to the hydrolysis stage; MS m/e MH⁺ 487.

The following intermediates were prepared from the hydrazide product of Intermediate A part iv) and the appropriate isothiocyanate following the method of Example 319. They were taken through crude to the hydrolysis stage without further purification or characterisation:

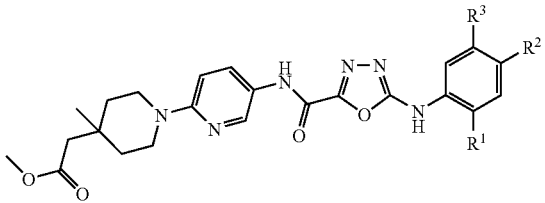

| Intermediate | Name | MS m/e M +H⁺ |
|---|---|---|
| 115 $R^1 = R^2 = R^3 = F$ | Methyl (4-methyl-1-{5-[({5-[(2,4,5-trifluorophenyl)amino]-1,3,4-oxadiazol-2-yl}carbonyl)amino]pyridin-2-yl}piperidin-4-yl)acetate | 505 |
| 116 $R^1 = R^3 = H$, $R^2 = CF_3$ | Methyl [4-methyl-1-(5-{[(5-{[4-trifluoromethyl)phenyl]amino}-1,3,4-oxadiazol-2-yl)carbonyl]amino}pyridin-2-yl)piperidin-4-yl]acetate | 519 |
| 117 $R^1 = R^3 = H$, $R^2 = O(4-F-C_6H_4)$ | Methyl [1-(5-{[(5-{[4-(4-fluorophenoxy)phenyl]amino}-1,3,4-oxadiazol-2-yl)carbonyl]amino}pyridin-2-yl)-4-methylpiperidin-4-yl]acetate | 561 |

The invention claimed is:

1. A compound of formula (I)

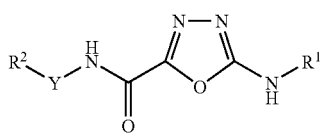

or a pharmaceutically-acceptable salt thereof,
wherein:
$R^1$ is a phenyl optionally substituted by 1, 2 or 3 substituents independently selected from halo, (1-4C)alkyl, ethynyl, (1-4C)alkoxy, hydroxy, (1-4C)alkoxy(1-4C)alkoxy, methoxymethyl, cyanomethyl, hydroxy(1-4C)alkyl, trifluoromethyl, difluoromethoxy, trifluoromethoxy, trifluoromethylthio, cyano, methylthio, methylsulfonyloxy, methylsulfonyl, ethylsulfonyl, aminocarbonylamino, methoxycarbonylamino, methylcarbonylamino, (1-4C)alkoxycarbonyl, methoxycarbonylmethoxy, benzyloxy, pyridylmethoxy, phenoxy optionally substituted by methoxy or halo, phenyl optionally substituted by methoxycarbonyl or carboxy, benzyl, aminosulfonyl, cyclohexyl, methylpyrimidinyl, triazolyl and morpholino;
Y is a direct bond;
$R^2$ is a phenyl optionally substituted by at least one group —Z and optionally one or more further substituents selected from halo, cyano, nitro, amino, hydroxy and halo(1-6C)alkyl;
Z is a hydrocarbyl group selected from (1-6C)alkyl, phenyl, cycloalkyl, cycloalkyl combined with (1-4C)alkyl, and phenyl combined with (1-4C)alkyl, wherein the hydrocarbyl group is optionally substituted on any available atom by one or more groups selected from halo, halo(1-6C)alkyl, cyano, nitro, —C(O)$_n$R$^{20}$, —OR$^{20}$, —S(O)$_m$R$^{20}$, —OS(O)$_2$R$^{20}$, —NR$^{21}$R$^{22}$, —C(O)NR$^{21}$R$^{22}$, —OC(O)NR$^{21}$R$^{22}$, —CH=NOR$^{20}$, —NR$^{21}$C(O)$_n$R$^{20}$, —NR$^{20}$CONR$^{21}$R$^{22}$, —N=CR$^{21}$R$^{22}$, —S(O)2NR$^{21}$R$^{22}$ and —NR$^{21}$S(O)$_2$R$^{22}$;
$R^{20}$, $R^{21}$ and $R^{22}$ are independently selected from hydrogen and (1-4C)alkyl;
m is independently 0, 1 or 2;
p is 1 or 2; and
n is 1 or 2.

2. The compound according to claim 1, or a pharmaceutically-acceptable salt thereof, wherein $R^2$—Y is selected from:
(1-4C)alkylphenyl;
biphenyl;
(chloro)biphenyl;
(methoxycarbonyl)biphenyl;
(ethoxycarbonylmethyl)biphenyl;
(carboxy)biphenyl;
methoxycarbonylpropylphenyl;
(carboxypropyl)phenyl;
dicarboxybutylphenyl;
carboxybutylphenyl;
(ethoxycarbonylmethyl)cyclohexylphenyl;
(methoxycarbonylmethyl)cyclohexylphenyl;
cyclohexylphenyl;
(carboxymethyl)cyclohexylphenyl;
(hydroxyethyl)cyclohexylphenyl;
(aminocarbonylmethyl)cyclohexylphenyl;
(cyanomethyl)cyclohexylphenyl;
carboxycyclohexylphenyl;
(dimethylaminocarbonylmethyl)cyclohexylphenyl;
(aminomethyl)cyclohexylphenyl;
(tertbutoxycarbonylaminomethyl)cyclohexylphenyl;
(methoxycarbonyl)cyclopentylphenyl;
(ethoxycarbonylmethyl)cyclopentylphenyl;
(carboxy)cyclopentylphenyl;
(carboxymethyl)cyclopentylphenyl;
(methoxycarbonyl)cyclobutylphenyl;
(ethoxycarbonyl)cyclobutylmethylphenyl;
(carboxy)cyclobutylphenyl;
(carboxy)cyclobutylmethylphenyl;
(carboxyethyl)cyclobutylphenyl;
(ethoxycarbonylethyl)cyclobutylphenyl;
1-(ethoxycarbonyl)ethylcyclohexylphenyl; and
1-carboxyethylcyclohexylphenyl.

3. The compound of formula (I) as claimed in claim 1, which is a compound of formula (IZA), or a pharmaceutically-acceptable salt thereof,

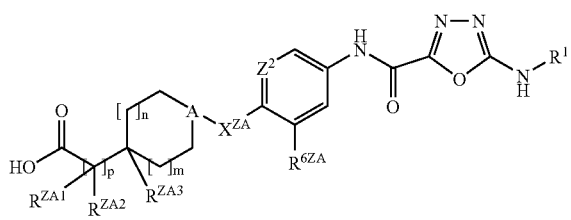

wherein
$R^1$ is phenyl optionally substituted with 1, 2 or 3 substituents independently selected from fluoro, chloro, bromo, trifluoromethyl, methoxy, difluoromethoxy, trifluoromethoxy, cyano, methyl, ethyl, ethynyl, benzyloxy, phenoxy, phenyl, and;

$Z^2$ is CH;

$R^{Z41}$ and $R^{Z42}$ are each independently hydrogen or methyl;

$R^{Z43}$ is hydrogen or methyl;

$R^{6Z4}$ is hydrogen, fluoro, chloro or methyl;

A is CH;

$X^{Z4}$ is a direct bond or —$CH_2$;

m is 0, 1 or 2;

n is 0 or 1, provided that m+n=0, 1 or 2; and p is 0 or 1.

4. A method for inhibiting DGAT1 activity in a warm-blooded animal in need of such treatment comprising administering to said animal an effective amount of a compound of formula (I) as claimed in claim 1 or a pharmaceutically-acceptable salt thereof.

5. A method of treating diabetes mellitus and obesity in a warm-blooded animal, in need of such treatment comprising administering to said animal an effective amount of a compound of formula (I) as claimed in claim 1 or a pharmaceutically-acceptable salt thereof.

6. A pharmaceutical composition comprising a compound of formula (I) as claimed in claim 1 or claim 3 a pharmaceutically-acceptable salt thereof, in association with a pharmaceutically-acceptable excipient or carrier.

* * * * *